(12) United States Patent
Ding et al.

(10) Patent No.: US 12,291,516 B2
(45) Date of Patent: May 6, 2025

(54) SUBSTITUTED 1-AMINO-1H-IMIDAZOLE-5-CARBOXAMIDE AS BRUTON'S TYROSINE KINASE INHIBITORS

(71) Applicant: Henan Zhiwei Biomedicine Co., Ltd., Xinxiang (CN)

(72) Inventors: Qingjie Ding, Xinxiang (CN); Chunhua Ma, Xinxiang (CN); Yuqin Jiang, Xinxiang (CN); Guiqing Xu, Xinxiang (CN); Wei Li, Xinxiang (CN); Minghao Zhao, Xinxiang (CN); Qingyun Li, Xinxiang (CN); Dandan Zhang, Xinxiang (CN); Guojie Fan, Xinxiang (CN); Yang Li, Xinxiang (CN); Xin Shi, Xinxiang (CN); Shouning Yang, Xinxiang (CN)

(73) Assignee: Henan Zhiwei Biomedicine Co., Ltd., Xinxiang (CN)

( * ) Notice: Subject to any disclaimer, the term of this patent is extended or adjusted under 35 U.S.C. 154(b) by 803 days.

(21) Appl. No.: 17/609,989

(22) PCT Filed: May 9, 2020

(86) PCT No.: PCT/CN2020/089407
§ 371 (c)(1),
(2) Date: Nov. 9, 2021

(87) PCT Pub. No.: WO2020/228637
PCT Pub. Date: Nov. 19, 2020

(65) Prior Publication Data
US 2022/0259181 A1    Aug. 18, 2022

(30) Foreign Application Priority Data
May 10, 2019 (CN) .......................... 201910388246.3

(51) Int. Cl.
*C07D 401/14* (2006.01)
*A61P 35/00* (2006.01)

(52) U.S. Cl.
CPC ............ *C07D 401/14* (2013.01); *A61P 35/00* (2018.01)

(58) Field of Classification Search
CPC .. C07D 401/14; C07D 417/14; C07D 409/14; A61P 35/00; A61P 35/02; A61P 29/00; A61P 37/00; A61P 37/06; A61P 37/08; A61K 31/4439; A61K 31/444
See application file for complete search history.

(56) References Cited

FOREIGN PATENT DOCUMENTS

| | | |
|---|---|---|
| AU | 2020276334 A1 | 12/2021 |
| CN | 103848810 A | 6/2014 |
| CN | 104884458 A | 9/2015 |
| CN | 106588914 A | 4/2017 |
| CN | 107056789 A | 8/2017 |
| CN | 107226805 A | 10/2017 |
| JP | 2015524480 A | 8/2015 |
| JP | 2016500119 A | 1/2016 |
| WO | 2015057992 A1 | 4/2015 |
| WO | 2016004280 A2 | 1/2016 |
| WO | 2017198050 A1 | 11/2017 |
| WO | 2018175512 A1 | 9/2018 |
| WO | 2020228637 A1 | 11/2020 |

OTHER PUBLICATIONS

Chunhua Ma et al., "Discovery of 1-Amino-1H-imidazole-5-carboxamide Derivatives as Highly Selective, Covalent Bruton's Tyrosine Kinase (BTK) Inhibitors," Journal of Medicinal Chemistry (2021); A-AC.
Office Action issued on Aug. 22, 2022 for Australian Patent Application No. 2020276334 (6 pages).
Office Action issued on May 13, 2022 for Chinese Patent Application No. 202010388187.2 (13 pages).
Office Action issued on Nov. 28, 2022 for Japanese Patent Application No. 2021-567893 (2 pages).

*Primary Examiner* — Matthew P Coughlin
*Assistant Examiner* — Anna Grace Kuckla
(74) *Attorney, Agent, or Firm* — Fox Rothschild LLP

(57) ABSTRACT

Disclosed is a compound of formula I or a pharmaceutically acceptable salt, active metabolite, tautomer, stereoisomer, or prodrug thereof as BTK (Bruton's Tyrosine Kinase) inhibitors, which is useful for the treatment of autoimmune disease, inflammatory disease, cancer and potentially allergies.

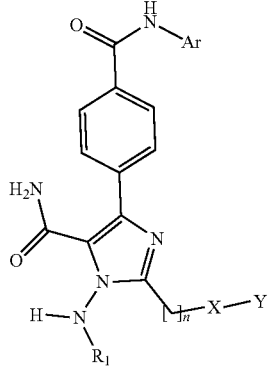

18 Claims, No Drawings

SUBSTITUTED 1-AMINO-1H-IMIDAZOLE-5-CARBOXAMIDE AS BRUTON'S TYROSINE KINASE INHIBITORS

CROSS REFERENCE TO RELATED APPLICATIONS

This application is the U.S. national phase of International Patent Application No. PCT/CN2020/089407 filed on May 9, 2020, which is based upon and claims priority to Chinese Patent Application No. 201910388246.3 filed May 10, 2019.

TECHNICAL FIELD

The invention relates to a series of 1-amino-1H-imidazole-5-carboxamide compounds of formula I as BTK (Bruton's Tyrosine Kinase) inhibitors, and the methods of making and using the same for the treatment of autoimmune disease, inflammatory disease, cancer and potentially allergies.

BACKGROUND ART

BTK (Bruton's Tyrosine Kinase) is a non-receptor tyrosine kinase of the Tec family (Bradshaw et al, Cell Signal, 2010, 22, 1175-184). It plays an important role in the maturation of B cells and the activation of mast cells. It is primarily expressed in hematopoietic cells such as B cell, mast cell and microphages and exists in tissues including bone marrow, lymph nodes and spleens. They participate in signal transduction in response to virtually all types of extracellular stimuli which are transmitted by growth factor receptors, cytokine receptors, G-protein coupled receptors, antigen-receptors and integrins (Qiu et al, *Oncogene*, 2000, 19, 5651-5661) Structurally it features a pleckstrin homology domain, a Src homology 3 domain, a Src homology 2 domain, and a Src homology 1 domain (kinase domain). The pleckstrin homology domain binds phosphatidylinositol (3,4,5)-triphosphate (PIP3) and induces BTK to phosphorylate phospholipase C gamma which then hydrolyzes phosphatidylinositol 4,5 biphosphate (PIP2) into two secondary messengers, inositol triphosphate (IP3) and diacylglycerol (DAG) which in turn modulate downstream B cell signaling. Dysfunctional BTK activation has been the culprit of autoimmune disease such as rheumatoid arthritis, osteoporosis, lupus and implicated in many cancers. Mutations of BTK gene are directly implicated in the immunodeficiency disease X-linked agammaglobulinemia (XLA). Patients with this disease have premature B cells in their bone marrow but they never mature and enter into circulation.

BTK inhibitors such as Ibrutinib (Structure A. Pan et al, *Chem Med Chem* 2007, 2:58-61; Lee A. Honigberg et al, *PNAS Jul.* 20, 2010, 107 (29), 13075-13080) and Acalabrutinib (Structure B, Barf et al, *J Pharmacol Exp Ther* 2017, 363:240-252; Robert B. Kargbo, *ACS Med Chem Lett.*, 2017 Sep. 14; 8(9): 911-913) have demonstrated their effectiveness in the treatment of various cancers.

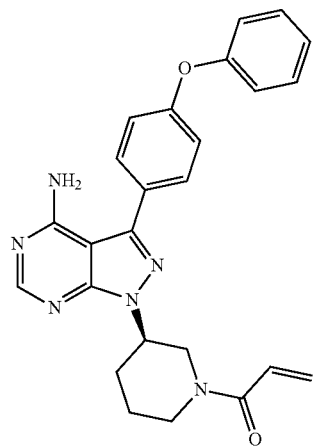

A

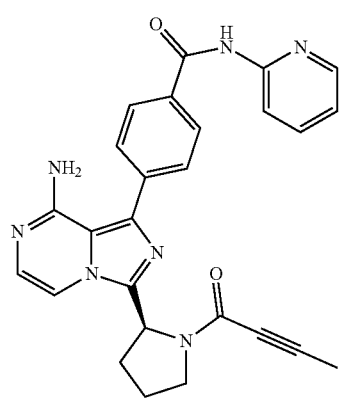

B

Several other candidates (Bradshaw et al. *Nat Chem Biol*, 2015, 11(7), 525-531; U.S. Pat. No. 9,447,106 B2; CN103848810 A1) in different stages of clinical trials are being tested for various diseases including cancer and autoimmune diseases. All these point to the potential application of BTK inhibition in the treatment of various diseases in the area of cancer, allergy and auto-immune diseases.

SUMMARY OF INVENTION

The present invention concerns compounds as protein kinase BTK (Bruton's Tyrosine Kinase) inhibitors which may be used for the treatment of autoimmune disease, inflammatory disease, cancer and potentially allergies. In one aspect, the invention provides a compound represented by Formula I, or a pharmaceutically acceptable salt, active metabolite, tautomer, stereoisomer, or prodrug thereof,

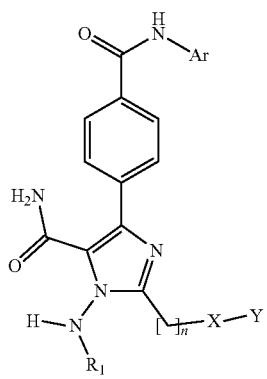

I wherein
- $R_1$ is independently selected from H, $C_{1-6}$ alkyl, and $R_5C(O)$— where $R_5$ is independently selected from the group consisting of $C_{1-6}$ alkyl and $C_{1-6}$ alkoxy;
- Ar is independently selected from heteroaryl and heteroaryl substituted with groups selected from halogen, cyano, $C_{1-6}$ alkyl, $C_{1-6}$ alkoxy, $C_{1-6}$ alkyl substituted with halogen or hydroxyl or $C_{1-6}$ alkoxy, $C_6$ or $C_{10}$ aryl, or $C_6$ or $C_{10}$ aryl substituted with halogen;
- n is selected from 0 and 1;
- X is a 4-8 membered nitrogen-containing heterocyclyl where the heterocyclyl is substituted on the nitrogen with Y, or a nitrogen-containing spiral heterocyclyl where the said nitrogen is substituted with Y; for example, the spiral heterocyclyl may have two 4-8 membered rings;
- Y is selected from the groups consisting of —CN, —C(=O)P, —S(=O)P and —S(=O)$_2$P; where P is selected from

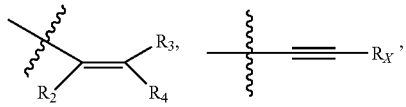

and
- Rx is selected from the group consisting of H, halogen, cyano, $C_{1-6}$ alkyl, and $C_{1-6}$ alkyl substituted with halogen, $C_{1-6}$ alkoxy, $C_{3-6}$ cycloalkyl, phenyl, —(CH$_2$)$_m$NR$_6$R$_7$;
- $R_2$ is selected from hydrogen; halogen; cyano; $C_{1-6}$ alkyl; $C_{1-6}$ alkyl substituted by substituents selected from the groups consisting of F, hydroxyl and $C_{1-6}$ alkoxy; $C_{3-6}$ cycloalkyl; $C_{3-6}$ cycloalkyl substituted with F;
- $R_3$ and $R_4$ are independently selected from hydrogen; halogen; cyano; $C_6$ or $C_{10}$ aryl; heteroaryl; $C_{1-6}$ alkyl; $C_{1-6}$ alkyl substituted with $C_{1-6}$ alkoxy, NR$_6$R$_7$, halogen, hydroxyl, $C_6$ or $C_{10}$ aryl, and heteroaryl; $C_{3-6}$ cycloalkyl; $C_{3-6}$ cycloalkyl substituted with halogen; $C_{2-6}$ alkenyl; $C_{2-6}$ alkenyl substituted with $C_{1-6}$ alkoxy, NR$_6$R$_7$, halogen, hydroxyl, $C_6$ or $C_{10}$ aryl and heteroaryl;
- $R_6$ and $R_7$ are each independently selected from hydrogen, $C_{1-6}$ alkyl or together with the nitrogen they substitute form a 4-6 membered heterocyclyl;
- m is an integer of 1 to 3;

In some embodiments, the heterocyclyl or spiral heterocyclyl defined for X has only one nitrogen as a ring atom.

In some embodiments, in Formula I, $R_1$ is H or $C_{1-6}$ alkyl. Particularly, $R_1$ is H or methyl.

In some embodiments, in Formula I, Ar is selected from the group consisting of:

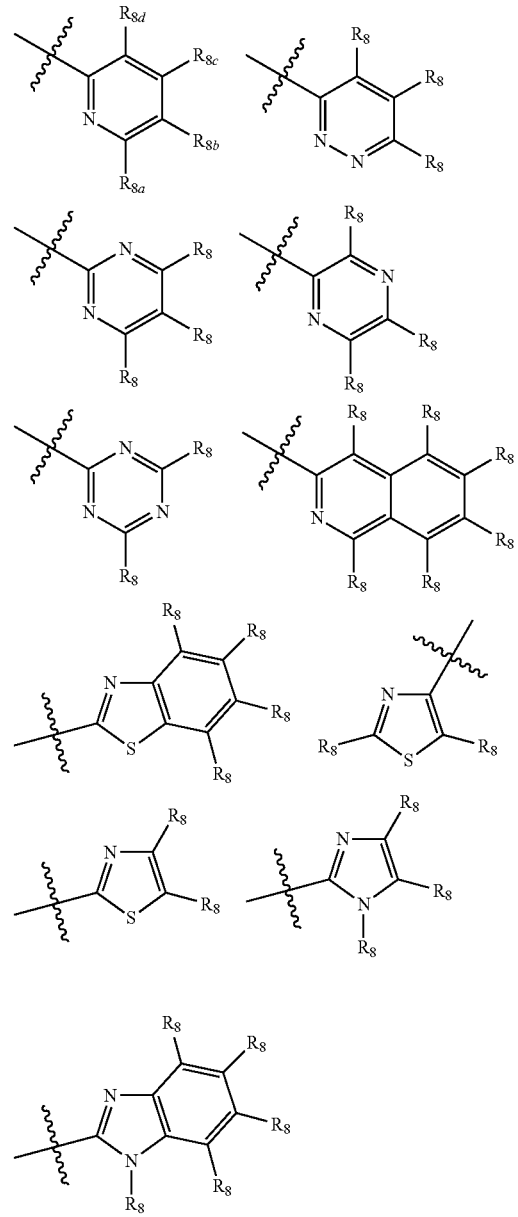

wherein $R_8$, $R_{8a}$, $R_{8b}$, $R_{8c}$ and $R_{8d}$ are independently selected from the group consisting of H; $C_{1-6}$ alkyl; $C_{1-6}$ alkyl substituted with halogen, particularly $C_{1-6}$ alkyl substituted with F, more specifically CF$_3$; $C_{1-6}$ alkoxy; halogen; $C_6$ or $C_{10}$ aryl; $C_6$ or $C_{10}$ aryl substituted independently, for example p-substituted, with halogen, $C_{1-6}$ alkyl, $C_{1-6}$ alkoxy, cyano, or trifluoromethyl; heteroaryl, particularly a five-membered or six-membered heteroaryl, or a bicycles where five-membered or six-membered fused with each other, which may have at least one heteroatom selected from O, S, or N.

For example, Ar is one of the followings:

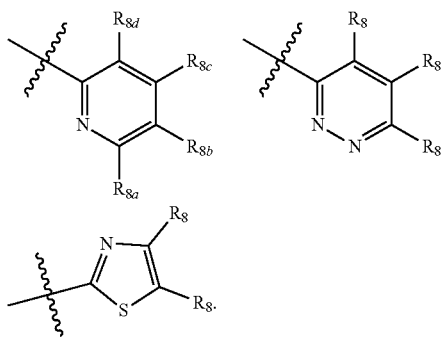

In some embodiments, in Formula I, Ar is selected from:

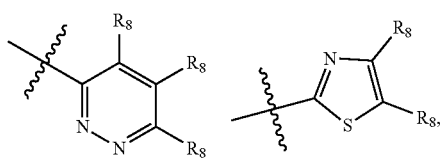

wherein, $R_8$ is hydrogen.

In some embodiments, in Formula I, Ar is represented by the following formula:

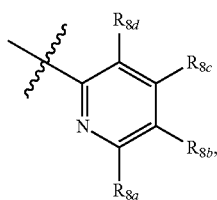

wherein,
$R_{8a}$ is H;
$R_{8b}$ is independently selected from H, halogen or $C_{1-6}$ alkyl;
$R_{8c}$ is independently selected from the group consisting of H, $C_{1-6}$ alkyl, $C_{1-6}$ alkyl substituted by halogen, halogen, cyano, $C_{1-6}$ alkoxyl, $C_6$ or $C_{10}$ aryl; $C_6$ or $C_{10}$ aryl substituted, for example p-substituted, with substituents selected from the group consisting of halogen, $C_{1-6}$ alkyl, $C_{1-6}$ alkoxyl, cyano or —$CF_3$; and
$R_{8d}$ is H.

In some embodiments, in Formula I, Ar is selected from:

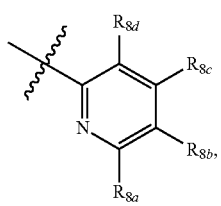

wherein,
$R_{8a}$ is H; $R_{8b}$ is independently selected from H, Cl or $CH_3$; $R_{8c}$ is independently selected from the group consisting of H, $CH_3$, $CH_2CH_3$, $OCH_3$, F, Cl, Br, I and CN, $CF_3$, isopropyl, phenyl, phenyl substituted, for example p-substituted, independently with halogen or CN; and $R_{8d}$ is H.

In some embodiments, in Formula I, X is selected from the group consisting of:

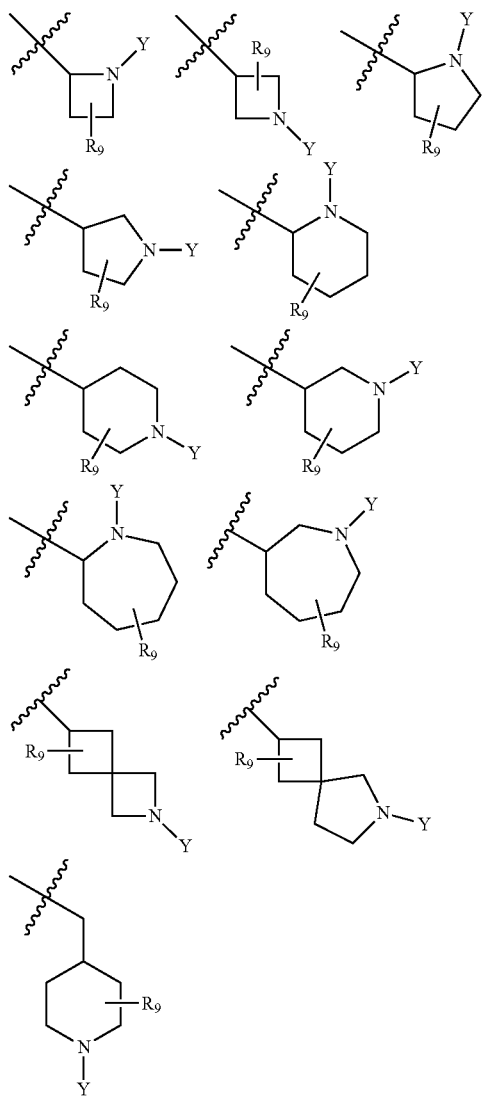

Wherein $R_9$ is independently selected from H, F, $C_{1-6}$ alkyl, $C_{1-6}$ alkyl substituted with halogen, $C_{1-6}$ alkoxy, and $NR_6R_7$; and $R_9$ substitute more than one position; or $R_9$ may form a double bond in the ring, or form a 4-6 member ring fused with the ring $R_9$ substitute.

In some embodiments, in P of Formula I, $R_2$ is selected from the group consisting of H, halogen, cyano, $C_{1-6}$ alkyl, and $C_{1-6}$ alkyl substituted with F; $R_3$ is selected from hydrogen or $C_{1-6}$ alkyl; and $R_4$ is selected from the group consisting of hydrogen, $C_6$ or $C_{10}$ aryl, $C_{3-6}$ cycloalkyl, $C_{1-6}$ alkyl, and $C_{1-6}$ alkyl substituted with F. Particularly, $R_2$ is independently selected from the group consisting of H, F, cyano, $CH_3$ and $CF_3$; $R_3$ is selected from hydrogen or methyl; $R_4$ is selected from the group consisting of hydrogen, phenyl, cyclopropyl, $C_{1-6}$ alkyl (for example, methyl, ethyl, isopropyl, tert-butyl and trifluoromethyl) and $C_{1-6}$ alkyl substituted with F.

In some embodiments, Rx is selected from the group consisting of H, $C_{3-6}$ cycloalkyl, $C_{1-6}$ alkyl, and $C_{1-6}$ alkyl substituted with F. Particularly, Rx is selected from the group consisting of H, methyl, and cyclopropyl.

In another embodiment, in formula I, X is

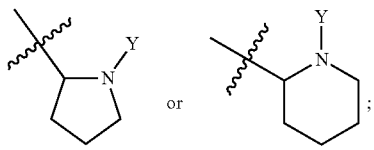

wherein Y is —C(=O)P,
P is

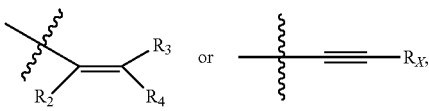

wherein,
$R_2$ is independently selected from the group consisting of H, F, cyano and $CF_3$,
$R_3$ is hydrogen;
$R_4$ is independently selected from the group consisting of H, cyclopropyl, methyl, and trifluoromethyl;
Rx is selected from the group consisting of H, methyl, and cyclopropyl;
n is 0.

In another embodiment, in formula I,
Ar is selected from

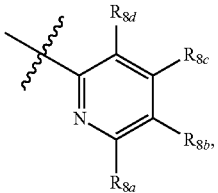

wherein,
$R_{8a}$, $R_{8b}$ and $R_{8d}$ are hydrogen;
$R_{8c}$ is independently selected from Cl, I, $CF_3$ or phenyl substituted with F, for example p-substituted with F;
X is

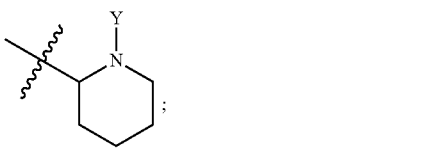

Y is —C(=O)P, P is

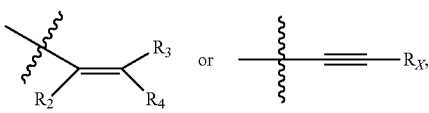

wherein,
$R_2$ is hydrogen;
$R_3$ is hydrogen;
$R_4$ is independently selected from the group consisting of H and trifluoromethyl;
Rx is selected from the group consisting of H, methyl;
n is 0; and $R_1$ is hydrogen.

All the foregoing heteroaryl may be five-membered or six-membered heteroaryl, or may have bicycles where five-membered or six-membered fused with each other, which may have at least one heteroatom selected from O, S, or N.

In some embodiments, the present invention provides the following specific compounds as follows.

(S)-2-(1-acryloylpyrrolidin-2-yl)-1-amino-4-(4-(pyridin-2-ylcarbamoyl)phenyl)-1H-imidazole-5-carboxamide (S)-1-amino-2-(1-methacryloylpyrrolidin-2-yl)-4-(4-(pyridin-2-ylcarbamoyl)phenyl)-1H-imidazole-5-carboxamide (S)-1-amino-2-(1-(3-methylbut-2-enoyl)pyrrolidin-2-yl)-4-(4-(pyridin-2-ylcarbamoyl)phenyl)-1H-imidazole-5-carboxamide (S,E)-1-amino-2-(1-(but-2-enoyl)pyrrolidin-2-yl)-4-(4-(pyridin-2-ylcarbamoyl)phenyl)-1H-imidazole-5-carboxamide (S)-1-amino-2-(1-(2-cyano-3-cyclopropylacryloyl)pyrrolidin-2-yl)-4-(4-(pyridin-2-ylcarbamoyl)phenyl)-1H-imidazole-5-carboxamide (S,E)-1-amino-2-(1-(pent-2-enoyl)pyrrolidin-2-yl)-4-(4-(pyridin-2-ylcarbamoyl)phenyl)-1H-imidazole-5-carboxamide (S)-1-amino-2-(1-propioloylpyrrolidin-2-yl)-4-(4-(pyridin-2-ylcarbamoyl)phenyl)-1H-imidazole-5-carboxamide (S)-1-amino-2-(1-(but-2-ynoyl)pyrrolidin-2-yl)-4-(4-(pyridin-2-ylcarbamoyl)phenyl)-1H-imidazole-5-carboxamide (S)-1-amino-2-(1-cyanopyrrolidin-2-yl)-4-(4-(pyridin-2-ylcarbamoyl)phenyl)-1H-imidazole-5-carboxamide (S)-2-(1-acryloylpyrrolidin-2-yl)-1-amino-4-(4-((4-methylpyridin-2-yl)carbamoyl)phenyl)-1H-imidazole-5-carboxamide (S)-1-amino-2-(1-methacryloylpyrrolidin-2-yl)-4-(4-((4-methylpyridin-2-yl)carbamoyl)phenyl)-1H-imidazole-5-carboxamide (S)-1-amino-2-(1-(3-methylbut-2-enoyl)pyrrolidin-2-yl)-4-(4-((4-methylpyridin-2-yl)carbamoyl)phenyl)-1H-imidazole-5-carboxamide (S,E)-1-amino-2-(1-(but-2-enoyl)pyrrolidin-2-yl)-4-(4-((4-methyl-pyridin-2-yl)carbamoyl)phenyl)-1H-imidazole-5-carboxamide (S, E)-1-amino-2-(1-(2-cyano-3-cyclopropylacryloyl)pyrrolidin-2-yl)-4-(4-((4-methylpyridin-2-yl)carbamoyl)phenyl)-1H-imidazole-5-carboxamide (S, E)-1-amino-2-(1-(2-cyano-4-methylpent-2-enoyl)pyrrolidin-2-yl)-4-(4-((4-methylpyridin-2-yl)carbamoyl)phenyl)-1H-imidazole-5-carboxamide (S,E)-1-amino-4-(4-((4-methylpyridin-2-yl)carbamoyl)phenyl)-2-(1-(pent-2-enoyl)pyrrolidin-2-yl)-1H-imidazole-5-carboxamide (S)-1-amino-4-(4-((4-methylpyridin-2-yl)carbamoyl)phenyl)-2-(1-propioloylpyrrolidin-2-yl)-1H-imidazole-5-carboxamide (S)-1-amino-2-(1-(but-2-ynoyl)pyrrolidin-2-yl)-4-(4-((4-methylpyridin-2-yl)carbamoyl)phenyl)-1H-imidazole-5-carboxamide (S)-2-(1-acryloylpyrrolidin-2-yl)-1-amino-4-(4-((5-methylpyridin-2-yl)carbamoyl)phenyl)-1H-imidazole-5-carboxamide (S)-1-amino-2-(1-methacryloylpyrrolidin-2-yl)-4-(4-((5-methylpyridin-2-yl)carbamoyl)phenyl)-1H-imidazole-5-carboxamide (S)-1-amino-2-(1-(3-methylbut-2-enoyl)pyrrolidin-2-yl)-4-(4-((5-methylpyridin-2-yl)carbamoyl)phenyl)-1H-imidazole-5-carboxamide (S,E)-1-amino-2-(1-(but-2-enoyl)pyrrolidin-2-yl)-4-(4-((5-methylpyridin-2-yl)carbamoyl)phenyl)-1H-imidazole-5-carboxamide (S, E)-1-amino-2-(1-(2-cyano-3-cyclopropylacryloyl)pyrrolidin-2-yl)-4-(4-((5-methylpyridin-2-yl)carbamoyl)phenyl)-1H-imidazole-5-carboxamide (S, E)-1-amino-2-(1-(2-cyano-4,4-dimethylpent-2-enoyl)pyrrolidin-2-yl)-4-(4-((5-methylpyridin-2-yl)carbamoyl)phenyl)-1H-imidazole-5-carboxamide (S,E)-1-amino-4-(4-((5-methylpyridin-2-yl)carbamoyl)phenyl)-2-(1-(pent-2-enoyl)pyrrolidin-2-yl)-1H-imidazole-5-carboxamide (S)-1-amino-4-(4-((5-methylpyridin-2-yl)carbamoyl)phenyl)-2-(1-propioloylpyrrolidin-2-yl)-1H-imidazole-5-carboxamide (S)-1-amino-2-(1-(but-2-ynoyl)pyrrolidin-2-yl)-4-(4-((5-methylpyridin-2-yl)carbamoyl)phenyl)-1H-imidazole-5-carboxamide (S)-2-(1-acryloylpyrrolidin-2-yl)-1-amino-4-(4-((4-methoxypyridin-2-yl)carbamoyl)phenyl)-1H-imidazole-5-carboxamide (S)-1-amino-2-(1-methacryloylpyrrolidin-2-yl)-4-(4-((4-methoxypyridin-2-yl)carbamoyl)phenyl)-1H-imidazole-5-carboxamide (S)-1-amino-4-(4-((4-methoxypyridin-2-yl)carbamoyl)phenyl)-2-(1-(3-methylbut-2-enoyl)pyrrolidin-2-yl)-1H-imidazole-5-carboxamide (S,E)-1-amino-2-(1-(but-2-enoyl)pyrrolidin-2-yl)-4-(4-((4-methoxypyridin-2-yl)carbamoyl)phenyl)-1H-imidazole-5-carboxamide (S,E)-1-amino-4-(4-((4-methoxypyridin-2-yl)carbamoyl)phenyl)-2-(1-(pent-2-enoyl)pyrrolidin-2-yl)-1H-imidazole-5-carboxamide (S)-1-amino-4-(4-((4-methoxypyridin-2-yl)carbamoyl)phenyl)-2-(1-propioloylpyrrolidin-2-yl)-1H-imidazole-5-carboxamide (S)-1-amino-2-(1-(but-2-ynoyl)pyrrolidin-2-yl)-4-(4-((4-methoxypyridin-2-yl)carbamoyl)phenyl)-1H-imidazole-5-carboxamide (S)-2-(1-acryloylpyrrolidin-2-yl)-1-amino-4-(4-((4-ethylpyridin-2-yl)carbamoyl)phenyl)-1H-imidazole-5-carboxamide (S)-1-amino-4-(4-((4-ethylpyridin-2-yl)carbamoyl)phenyl)-2-(1-methacryloylpyrrolidin-2-yl)-1H-imidazole-5-carboxamide (S)-1-amino-4-(4-((4-ethylpyridin-2-yl)carbamoyl)phenyl)-2-(1-(3-methylbut-2-enoyl)pyrrolidin-2-yl)-1H-imidazole-5-carboxamide (S)-1-amino-2-(1-(but-2-ynoyl)pyrrolidin-2-yl)-4-(4-((4-ethylpyridin-2-yl)carbamoyl)phenyl)-1H-imidazole-5-carboxamide (S)-1-amino-2-(1-cyanopyrrolidin-2-yl)-4-(4-((4-ethylpyridin-2-yl)carbamoyl)phenyl)-1H-imidazole-5-carboxamide (S)-2-(1-acryloylpyrrolidin-2-yl)-1-amino-4-(4-((4-fluoropyridin-2-yl)carbamoyl)phenyl)-1H-imidazole-5-carboxamide (S)-1-amino-2-(1-(but-2-ynoyl)pyrrolidin-2-yl)-4-(4-((4-fluoropyridin-2-yl)carbamoyl)phenyl)-1H-imidazole-5-carboxamide (S)-2-(1-acryloylpyrrolidin-2-yl)-1-amino-4-(4-((4-(trifluoromethyl)pyridin-2-yl)carbamoyl)phenyl)-1H-imidazole-5-carboxamide (S)-1-amino-2-(1-(but-2-ynoyl)pyrrolidin-2-yl)-4-(4-((4-(trifluoromethyl)pyridin-2-yl)carbamoyl)phenyl)-1H-imidazole-5-carboxamide (S)-2-(1-acryloylpyrrolidin-2-yl)-1-amino-4-(4-((4-isopropylpyridin-2-yl)carbamoyl)phenyl)-1H-imidazole-5-carboxamide (S)-2-(1-acryloylpyrrolidin-2-yl)-1-(methylamino)-4-(4-((4-methylpyridin-2-yl)carbamoyl)phenyl)-1H-imidazole-5-carboxamide (S)-2-(1-acryloylpiperidin-2-yl)-1-amino-4-(4-(pyridin-2-ylcarbamoyl)phenyl)-1H-imidazole-5-carboxamide (S)-1-amino-2-(1-methacryloylpiperidin-2-yl)-4-(4-(pyridin-2-ylcarbamoyl)phenyl)-1H-imidazole-5-carboxamide (S,E)-1-amino-2-(1-(but-2-enoyl)piperidin-2-yl)-4-(4-(pyridin-2-ylcarbamoyl)phenyl)-1H-imidazole-5-carboxamide (S)-1-amino-2-(1-(3-methylbut-2-enoyl)piperidin-2-yl)-4-(4-(pyridin-2-ylcarbamoyl)phenyl)-1H-imidazole-5-carboxamide (S)-1-amino-2-(1-(but-2-ynoyl)piperidin-2-yl)-4-(4-(pyridin-2-ylcarbamoyl)phenyl)-1H-imidazole-5-carboxamide (S,E)-1-amino-2-(1-(pent-2-enoyl)piperidin-2-yl)-4-(4-(pyridin-2-ylcarbamoyl)phenyl)-1H-imidazole-5-carboxamide (S,E)-1-amino-2-(1-(2-cyano-3-cyclopropylacryloyl)piperidin-2-yl)-4-(4-(pyridin-2-ylcarbamoyl)phenyl)-1H-imidazole-5-carboxamide (S)-2-(1-acryloylpiperidin-2-yl)-1-amino-4-(4-((4-methylpyridin-2-yl)carbamoyl)phenyl)-1H-imidazole-5-carboxamide (S)-1-amino-2-(1-methacryloylpiperidin-2-yl)-4-(4-((4-methylpyridin-2-yl)carbamoyl)phenyl)-1H-imidazole-5-carboxamide (S,E)-1-amino-2-(1-(but-2-enoyl)piperidin-2-yl)-4-(4-((4-methylpyridin-2-yl)carbamoyl)phenyl)-1H-imidazole-5-carboxamide (S)-1-amino-2-(1-(3-methylbut-2-enoyl)piperidin-2-yl)-4-(4-((4-methylpyridin-2-yl)carbamoyl)phenyl)-1H-imidazole-5-carboxamide (S, E)-1-amino-2-(1-cinnamoylpiperidin-2-yl)-4-(4-((4-methylpyridin-2-yl)carbamoyl)phenyl)-1H-imidazole-5-carboxamide (S)-1-amino-2-(1-(but-2-ynoyl)piperidin-2-yl)-4-(4-((4-methylpyridin-2-yl)carbamoyl)phenyl)-1H-imidazole-5-carboxamide (S)-1-amino-2-(1-(2-fluoroacryloyl)piperidin-2-yl)-4-(4-((4-methylpyridin-2-yl)carbamoyl)phenyl)-1H-imidazole-5-carboxamide (S,E)-1-amino-4-(4-((4-methylpyridin-2-yl)carbamoyl)phenyl)-2-(1-(4,4,4-trifluorobut-2-enoyl)piperidin-2-yl)-1H-imidazole-5-carboxamide (S)-2-(1-acryloylpiperidin-2-yl)-1-amino-4-(4-((5-methylpyridin-2-yl)carbamoyl)phenyl)-1H-imidazole-5-carboxamide (S)-1-amino-2-(1-methacryloylpiperidin-2-yl)-4-(4-((5-methylpyridin-2-yl)carbamoyl)phenyl)-1H-imidazole-5-carboxamide (S)-1-amino-2-(1-(3-methylbut-2-enoyl)piperidin-2-yl)-4-(4-((5-methylpyridin-2-yl)carbamoyl)phenyl)-1H-imidazole-5-carboxamide (S)-1-amino-2-(1-(but-2-ynoyl)piperidin-2-yl)-4-(4-((5-methylpyridin-2-yl)carbamoyl)phenyl)-1H-imidazole-5-carboxamide (S)-2-(1-acryloylpiperidin-2-yl)-1-amino-4-(4-((4-phenylpyridin-2-yl)carbamoyl)phenyl)-1H-imidazole-5-carboxamide (S)-1-amino-2-(1-(but-2-ynoyl)piperidin-2-yl)-4-(4-((4-phenylpyridin-2-yl)carbamoyl)phenyl)-1H-imidazole-5-carboxamide (S)-2-(1-acryloylpiperidin-2-yl)-1-amino-4-(4-((4-methoxypyridin-2-yl)carbamoyl)phenyl)-1H-imidazole-5-carboxamide (S)-1-amino-2-(1-(but-2-ynoyl)piperidin-2-yl)-4-(4-((4-methoxy-pyridin-2-yl)carbamoyl)phenyl)-1H-imidazole-5-carboxamide (S,E)-1-amino-4-(4-((4-methoxypyridin-2-yl)carbamoyl)phenyl)-2-(1-(4,4,4-trifluorobut-2-enoyl)piperidin-2-yl)-1H-imidazole-5-carboxamide (S)-1-amino-2-(1-(2-fluoroacryloyl)piperidin-2-yl)-4-(4-((4-methoxy-pyridin-2-yl)carbamoyl)phenyl)-1H-imidazole-5-carboxamide (S)-2-(1-acryloylpiperidin-2-yl)-1-amino-4-(4-((4-isopropylpyridin-2-yl)carbamoyl)phenyl)-1H-imidazole-5-carboxamide (S)-2-(1-acryloylpiperidin-2-yl)-1-amino-4-(4-((4-chloropyridin-2-yl)carbamoyl)phenyl)-1H-imidazole-5-carboxamide (S)-2-(1-acryloylpiperidin-2-yl)-1-amino-4-(4-((4-ethylpyridin-2-yl)carbamoyl)phenyl)-1H-imidazole-5-carboxamide (S)-1-amino-4-(4-((4-ethylpyridin-2-yl)carbamoyl)phenyl)-2-(1-methacryloylpiperidin-2-yl)-1H-imidazole-5-carboxamide (S,E)-1-amino-2-(1-(but-2-enoyl)piperidin-2-yl)-4-(4-((4-ethylpyridin-2-yl)carbamoyl)phenyl)-1H-imidazole-5-carboxamide (S)-1-amino-4-(4-((4-ethylpyridin-2-yl)carbamoyl)phenyl)-2-(1-(3-methylbut-2-enoyl)piperidin-2-yl)-1H-imidazole-5-carboxamide (S)-1-amino-2-(1-(but-2-ynoyl)piperidin-2-yl)-4-(4-((4-ethylpyridin-2-yl)carbamoyl)phenyl)-1H-imidazole-5-carboxamide (S,E)-1-amino-2-(1-(2-cyano-3-cyclopropylacryloyl)piperidin-2-yl)-4-(4-((4-ethylpyridin-2-yl)carbamoyl)phenyl)-1H-imidazole-5-carboxamide (S,E)-1-amino-2-(1-(2-cyano-4-methylpent-2-enoyl)piperidin-2-yl)-4-(4-((4-ethylpyridin-2-yl)carbamoyl)phenyl)-1H-imidazole-5-carboxamide (S,E)-1-amino-4-(4-((4-ethylpyridin-2-yl)carbamoyl)phenyl)-2-(1-(pent-2-enoyl)piperidin-2-yl)-1H-imidazole-5-carboxamide (S)-2-(1-acryloylpiperidin-2-yl)-4-(4-((4-ethylpyridin-2-yl)carbamoyl)phenyl)-1-(methylamino)-1H-imidazole-5-carboxamide (S)-1-amino-2-(1-(but-2-ynoyl)piperidin-2-yl)-4-(4-((4-cyanopyridin-2-yl)carbamoyl)phenyl)-1H-imidazole-5-carboxamide (S)-2-(1-acryloylpiperidin-2-yl)-1-amino-4-(4-((4-cyanopyridin-2-yl)carbamoyl)phenyl)-1H-imidazole-5-carboxamide (S)-2-(1-acryloylpiperidin-2-yl)-1-amino-4-(4-((4-(trifluoromethyl)pyridin-2-yl)carbamoyl)phenyl)-1H-imidazole-5-carboxamide (S)-1-amino-2-(1-(but-2-ynoyl)piperidin-2-yl)-4-(4-((4-(trifluoromethyl)pyridin-2-yl)carbamoyl)phenyl)-1H-imidazole-5-carboxamide (S)-2-(1-acryloylpiperidin-2-yl)-1-amino-4-(4-((5-chloropyridin-2-yl)carbamoyl)phenyl)-1H-imidazole-5-carboxamide (S)-2-(1-acryloylpiperidin-2-yl)-1-amino-4-(4-((4-bromopyridin-2-yl)carbamoyl)phenyl)-1H-imidazole-5-carboxamide (S)-1-amino-4-(4-((4-bromopyridin-2-yl)carbamoyl)phenyl)-2-(1-(but-2-ynoyl)piperidin-2-yl)-1H-imidazole-5-carboxamide (S)-2-(1-acryloylpiperidin-2-yl)-1-amino-4-(4-((4-iodopyridin-2-yl)carbamoyl)phenyl)-1H-imidazole-5-carboxamide (S)-1-amino-2-(1-(but-2-ynoyl)piperidin-2-yl)-4-(4-((4-iodopyridin-2-yl)carbamoyl)phenyl)-1H-imidazole-5-carboxamide (S)-2-(1-acryloylpiperidin-2-yl)-1-amino-4-(4-((4-(4-fluorophenyl)pyridin-2-yl)carbamoyl)phenyl)-1H-imidazole-5-carboxamide (S)-1-amino-2-(1-(but-2-ynoyl)piperidin-2-yl)-4-(4-((4-(4-fluorophenyl)pyridin-2-yl)carbamoyl)phenyl)-1H-imidazole-5-carboxamide (R)-2-(1-acryloylpiperidin-3-yl)-1-amino-4-(4-((4-ethylpyridin-2-yl)carbamoyl)phenyl)-1H-imidazole-5-carboxamide 2-(1-acryloylazepan-2-yl)-1-amino-4-(4-((4-ethylpyridin-2-yl)carbamoyl)phenyl)-1H-imidazole-5-carboxamide 2-(2-acryloyl-2-azaspiro[3.3]heptan-6-yl)-1-amino-4-(4-((4-ethylpyridin-2-yl)carbamoyl)phenyl)-1H-imidazole-5-carboxamide (S)-1-amino-4-(4-((4-methylpyridin-2-yl)carbamoyl)phenyl)-2-(1-propioloylpiperidin-2-yl)-1H-imidazole-5-carboxamide (S)-1-amino-4-(4-((4-methoxypyridin-2-yl)carbamoyl)phenyl)-2-(1-propioloylpiperidin-2-yl)-1H-imidazole-5-carboxamide (S)-1-amino-2-(1-(but-2-ynoyl)piperidin-2-yl)-4-(4-((4-chloropyridin-2-yl)carbamoyl)phenyl)-1H-imidazole-5-carboxamide (S)-1-amino-4-(4-((4-chloropyridin-2-yl)carbamoyl)phenyl)-2-(1-propioloylpiperidin-2-yl)-1H-imidazole-5-carboxamide (S)-1-amino-4-(4-((4-ethylpyridin-2-yl)carbamoyl)phenyl)-2-(1-propioloylpiperidin-2-yl)-1H-imidazole-5-carboxamide (S)-2-(1-acryloylpiperidin-2-yl)-1-amino-4-(4-(pyridazin-3-ylcarbamoyl)phenyl)-1H-imidazole-5-carboxamide (S)-1-amino-2-(1-(but-2-ynoyl)piperidin-2-yl)-4-(4-(pyridazin-3-ylcarbamoyl)phenyl)-1H-imidazole-5-carboxamide 2-((1-acryloylpiperidin-4-yl)methyl)-1-amino-4-(4-(pyridin-2-ylcarbamoyl)phenyl)-1H-imidazole-5-carboxamide 1-amino-2-((1-(but-2-ynoyl)piperidin-4-yl)methyl)-4-(4-(pyridin-2-ylcarbamoyl)phenyl)-1H-imidazole-5-carboxamide (S)-2-(1-acryloylpiperidin-2-yl)-1-amino-4-(4-(thiazol-2-ylcarbamoyl)phenyl)-1H-imidazole-5-carboxamide (S)-2-(1-acryloylpiperidin-2-yl)-1-amino-4-(4-((4-fluoropyridin-2-yl)carbamoyl)phenyl)-1H-imidazole-5-carboxamide (S)-2-(1-acryloylpiperidin-2-yl)-1-amino-4-(4-((5-fluoro-4-methylpyridin-2-yl)carbamoyl)phenyl)-1H-imidazole-5-carboxamide (S)-1-amino-2-(1-(but-2-ynoyl)piperidin-2-yl)-4-(4-((5-fluoro-4-methylpyridin-2-yl)carbamoyl)phenyl)-1H-imidazole-5-carboxamide (S)-2-(1-acryloylpiperidin-2-yl)-1-amino-4-(4-((4-(4-chlorophenyl)pyridin-2-yl)carbamoyl)phenyl)-1H-imidazole-5-carboxamide (S)-1-amino-2-(1-(but-2-ynoyl)piperidin-2-yl)-4-(4-((4-(4-chlorophenyl)pyridin-2-yl)carbamoyl)phenyl)-1H-imidazole-5-carboxamide (S)-2-(1-acryloylpiperidin-2-yl)-1-amino-4-(4-((4-(4-cyanophenyl)pyridin-2-yl)carbamoyl)phenyl)-1H-imidazole-5-carboxamide (S)-1-amino-2-(1-(but-2-ynoyl)piperidin-2-yl)-4-(4-((4-(4-cyanophenyl)pyridin-2-yl)carbamoyl)phenyl)-1H-imidazole-5-carboxamide In a further aspect, the invention provides a pharmaceutical composition which includes an effective amount of a compound of the invention, or a pharmaceutically acceptable salt, active metabolite, tautomer, stereoisomer, or prodrug thereof, and a pharmaceutically acceptable carrier.

In some embodiments, the pharmaceutical composition is in a form suitable for administration including but not limited to oral administration, parenteral administration, topical administration and rectal administration. In further or additional embodiments, the pharmaceutical composition is in the form of a tablet, capsule, pill, powder, sustained release formulation, solution and suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments the amount of compound of formula I is in the range of about 0.001 to about 1000 mg/kg body weight/day. In further or additional embodiments the amount of compound of formula I is about 0.001 to about 7 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments, the pharmaceutical composition further comprises at least one therapeutic agent.

In another aspect, the invention provides a method for preventing or treating a subject suffering from or at risk of BTK mediated disease or condition, comprising administering to said subject an effective amount of a compound of this invention or a pharmaceutically acceptable salt, active metabolite, tautomer, stereoisomer, or prodrug thereof, or a pharmaceutical composition of this invention.

In another aspect, the invention provides a method for preventing or treating a subject suffering from or at risk of a disease or disorder selected from the group consisting of an autoimmune disease, inflammatory disease, cancer, allergy, diffused large B cell lymphoma, follicular lymphoma, chronic lymphocytic leukemia, mantel cell lymphoma, splenic marginal zone lymphoma, large B cell lymphoma, lupus erythematosus, rheumatoid arthritis, Crohn's disease, psoriasis, multiple sclerosis, asthma etc., comprising administering to said subject an effective amount of a compound of this invention or a pharmaceutically acceptable salt, active metabolite, tautomer, stereoisomer, or prodrug thereof, or a pharmaceutical composition of this invention.

In a further aspect, the invention provides a use of a compound of the invention, or a pharmaceutically acceptable salt, active metabolite, tautomer, stereoisomer, or prodrug thereof, in the preparation of a medicament for inhibiting the activity of BTK (Bruton's Tyrosine Kinase).

In another aspect, the invention provides a use of a compound of the invention, or a pharmaceutically acceptable salt, active metabolite, tautomer, stereoisomer, or prodrug thereof, in the preparation of a medicament for treating a disease or disorder that may benefit from the inhibition of BTK.

In another aspect, the invention provides a use of a compound of the invention, or a pharmaceutically acceptable salt, active metabolite, tautomer, stereoisomer, or prodrug thereof, in the preparation of a medicament for treating a disease or disorder selected from the group consisting of an autoimmune disease, inflammatory disease, cancer, allergy, diffused large B cell lymphoma, follicular lymphoma, chronic lymphocytic leukemia, mantel cell lymphoma, splenic marginal zone lymphoma, large B cell lymphoma, lupus erythematosus, rheumatoid arthritis, Crohn's disease, psoriasis, multiple sclerosis, asthma etc.

In another aspect, the invention provides a compound of the invention, or a pharmaceutically acceptable salt, active metabolite, tautomer, stereoisomer, or prodrug thereof, for inhibiting BTK.

In another aspect, the invention provides a compound of the invention, or a pharmaceutically acceptable salt, active metabolite, tautomer, stereoisomer, or prodrug thereof, for the treatment of a disease or disorder that may benefit from the inhibition of BTK.

In another aspect, the invention provides a compound of the invention, or a pharmaceutically acceptable salt, active metabolite, tautomer, stereoisomer, or prodrug thereof, for treating a disease or disorder selected from the group consisting of an autoimmune disease, inflammatory disease, cancer, allergy, diffused large B cell lymphoma, follicular lymphoma, chronic lymphocytic leukemia, mantel cell lymphoma, splenic marginal zone lymphoma, large B cell lymphoma, lupus erythematosus, rheumatoid arthritis, Crohn's disease, psoriasis, multiple sclerosis, asthma etc.

In some embodiments, the subject is a mammal, such as human.

In some embodiments, the foregoing disease or condition includes but not limit to cancer, autoimmune disease, inflammatory disease and allergy. Such diseases include but not limit to diffused large B cell lymphoma, follicular lymphoma, chronic lymphocytic leukemia, mantel cell lymphoma, splenic marginal zone lymphoma, large B cell lymphoma, lupus erythematosus, rheumatoid arthritis, Crohn's disease, psoriasis, multiple sclerosis, asthma etc.

DETAILED DESCRIPTION

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

The present invention also intended to include isotopically labeled compounds. The commonly seen isotopic atoms include but not limited to $^2H$, $^3H$, $^{13}C$, $^4C$, $^{17}O$, $^{18}O$, $^5N$ etc. These atoms are the same as their naturally richest atom but have a different mass number. Applications of isotopically labeling in drug discovery are reported (Elmore, Charles S., *Annual Report of Medicinal Chemistry*, 2009, 44, 515-534).

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as though not limited to "alkyl", "aryl" are equivalent to their optionally substituted forms. For example, "alkyl" as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer should be understood to include all possible stereoisomers, including regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. A racemate (a mixture of S and R form), diastereomers and single isomers of either S or R can exist. It is the intention of the invention that compounds claimed here could be a mixture of diastereomers, a racemate or a single isomer of either S or R.

The term "optional" or "optionally" means that the subsequently described event or circumstance may or may not occur, and that the description includes instances where said event or circumstance occurs and instances in which it does not. For example, "alkyl optionally substituted with . . . " means either "alkyl" or "substituted alkyl with . . . " as defined below.

As used herein, a group designated as "$C_{1-6}$" indicates that there are one to six carbon atoms in the moiety, i.e. groups containing 1 carbon atom, 2 carbon atoms, 3 carbon atoms, 4 carbon atoms, 5 carbon atoms, and 6 carbon atoms. Thus, by way of example only, "$C_1$-$C_6$ alkyl" indicates that there are one to six carbon atoms in the alkyl group, i.e., the alkyl group is selected from among methyl, ethyl, propyl, iso-propyl, n-butyl, isobutyl, sec-butyl, and t-butyl, n-pentyl, isopentyl, neopentyl, n-hexyl and the isomers thereof.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings.

The term "fused" as used herein, alone or in combination, refers to cyclic structures in which two or more rings share one or more bonds.

The term "heterocyclyl" as used herein, alone or in combination, refers collectively to heteroalicyclyl groups. Herein, whenever the number of carbon atoms in a heterocycle is indicated (e.g., $C_3$-$C_6$ heterocycle), at least one non-carbon atom (the heteroatom) must be present in the ring. Designations such as "$C_3$-$C_6$ heterocycle" refer only to the number of carbon atoms in the ring and do not refer to the total number of atoms in the ring. Designations such as "4-8 membered heterocycle" refer to the total number of atoms that are contained in the ring (i.e., a four, five, six, seven, or eight membered ring, in which at least one atom is a carbon atom, at least one atom is a heteroatom and the remaining two to six atoms are either carbon atoms or heteroatoms). For heterocycles having two or more heteroatoms, those two or more heteroatoms can be the same or different from one another. Heterocycles can be optionally substituted. Bonding (i.e. attachment to a parent molecule or further substitution) to a heterocycle can be via a heteroatom or a carbon atom. The "heterocycle" includes heterocycloalkyl.

The term "spiral heterocyclyl" as used herein, alone or in combination, refers to a polycyclyl wherein two rings share a carbon atom and at least one ring atom is a heteroatom. The spiral heterocyclyl may have two or more cycles, each of them may be 4-8 membered cycles. Spiral heterocyclyl can be optionally substituted. Bonding (i.e. attachment to a parent molecule or further substitution) to a spiral heterocycle can be via a heteroatom or a carbon atom. The "spiral heterocycle" includes heterocycloalkyl.

The term "cycloalkyl" as used herein, alone or in combination, refers to an optionally substituted, saturated, hydrocarbon monoradical ring which may include additional, non-ring carbon atoms as substituents (e.g. methylcyclopropyl). The cycloalkyl may have three to about ten, or three to about eight, or three to about six, or three to five ring atoms. The examples include but not limited to cyclopropyl, cyclobutyl, cyclopentyl, and cyclohexyl.

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings. Moreover, the term aryl includes but not limited to monocycle, bicycle and tricycle or more cycles. The aryl (for example monocyclic aryl) contains, for example, from six to about twelve, or six to about ten, or six to about eight ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "heteroaryl" as used herein, alone or in combination, refers to optionally substituted aromatic mono-radicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms, which may contain at least one of the above mentioned heteroatoms. It may have one cycle, for example, five-membered or six-membered heteroaryl; or bi-cycle, for example, nine-membered or ten-membered heteroaryl. A heteroaryl group may be further substituted via any or all of its carbon atoms, and/or any or all of its heteroatoms.

The term "alkyl" as used herein, alone or in combination, refers to an optionally substituted straight-chain, or optionally substituted branched-chain saturated hydrocarbon monoradical having, for example, from one to about eighteen, or one to about ten carbon atoms, or one to six carbon atoms. The term "lower alkyl" as used herein, alone or in combination, refers to an alkyl having relatively less carbon atoms, for example having one to about eight carbon atoms, preferably having one to about 6, or one to about four carbon atoms. Examples of alkyl include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and the like.

The "alkyl" as used in combination includes but not limited to the "alkyl" included in "alkoxy".

The term "alkoxy" as used herein, alone or in combination, refers to an alkyl ether radical, O-alkyl. Non-limiting examples of alkoxy radicals include methoxy, ethoxy, n-propoxy, isopropoxy, n-butoxy, iso-butoxy, sec-butoxy, tertbutoxy and the like.

The term "alkenyl" as used herein, alone or in combination, refers to an optionally substituted straight-chain, or optionally substituted branched-chain hydrocarbon monoradical having one or more carbon-carbon double-bonds and having, for example, from two to about eighteen or two to about ten carbon atoms, or two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. The present definition also covers the occurrence of the term "alkenyl" where no numerical range is designated.

The terms "halogen", "halo" or "halide" as used herein, alone or in combination refer to fluoro, chloro, bromo and iodo.

Hydroxy or hydroxyl refers to a group of —OH.

Cyano refers to a group of —CN.

Either of a substituent or substituents refers to one or more substituents.

In the molecular structures shown in the invention, when asymmetric centers appear, a solid wedge means the bond is pointing to the top of the paper while a dotted wedge means the bond is pointing to the back of the paper. A solid bond line usually means all possible isomers.

Certain Pharmaceutical Terminology

The term "subject", "patient" or "individual" as used herein in reference to individuals suffering from a disease, a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical *Sciences* (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic or organic base.

The term "tautomer" as used herein refers to an isomer readily interconverted from a compound of this invention by e.g., migration of a hydrogen atom or proton.

The term "prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism.

$IC_{50}$ means the concentration of a particular compound that inhibits 50% of a specific measured activity.

EMBODIMENTS

The novel features of the invention are set forth with particularity in the appended claims. A better understanding of the features and advantages of the present invention will be obtained by reference to the following detailed description that sets forth illustrative embodiments, in which the principles of the invention are utilized.

Some embodiments of the present invention have been shown and described herein by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

EXPERIMENTAL

General Synthesis of the Compounds of the Invention

The compounds of the invention can generally be synthesized by the chemistry scheme outlined in Scheme-1. All related compounds can be similarly prepared by the general method of Scheme-1 and the synthesis of specific compound is provided in the section of compound examples described in the following text.

A standard esterification reaction of ethanol with 4-acetyl benzoic acid catalyzed by concentrated sulfuric acid gave the desired ethyl ester 2 in good yield. Condensation of ethyl 4-acetyl benzoate 2 with diethyl carbonate gave keto ester 3. Bromination of keto ester 3 with N-bromo succinimide in diethyl ether with ammonium chloride as catalyst gave bromide compound 4 which condensed with acid 5 to give compound 6. Treatment of compound 6 with excess of ammonium chloride in xylene at reflux for 2-3 hours produced desired imidazole diester 7. Selective hydrolysis of diester 7 with lithium hydroxide in a mixture of THF/$H_2O$ at room temperature gave benzoic acid analog 8 which was condensed with 2-aminopyridine derivatives to give pyridinyl benzamide 9. Next, selective N amination of the imidazole nitrogen with 0-diphenylphophinylhydroxylamine (Aldrich) gave 1-amino-1H-imidazole 10 in good yield. It is noteworthy that no other regioisomer was observed. Then, lithium hydroxide hydrolysis of compound 10 gave acid 11 which was transformed to amide 12 after stirring it with ammonium chloride, HATU, DIPEA in DMF at room temperature overnight. The final compound 14 was obtained after treating amide 12 with 30% TFA in methylene chloride to generate intermediate 13, which was reacted with crotonyl chloride (or the corresponding acid with other reagents) and DIPEA in methylene chloride.

Scheme-1

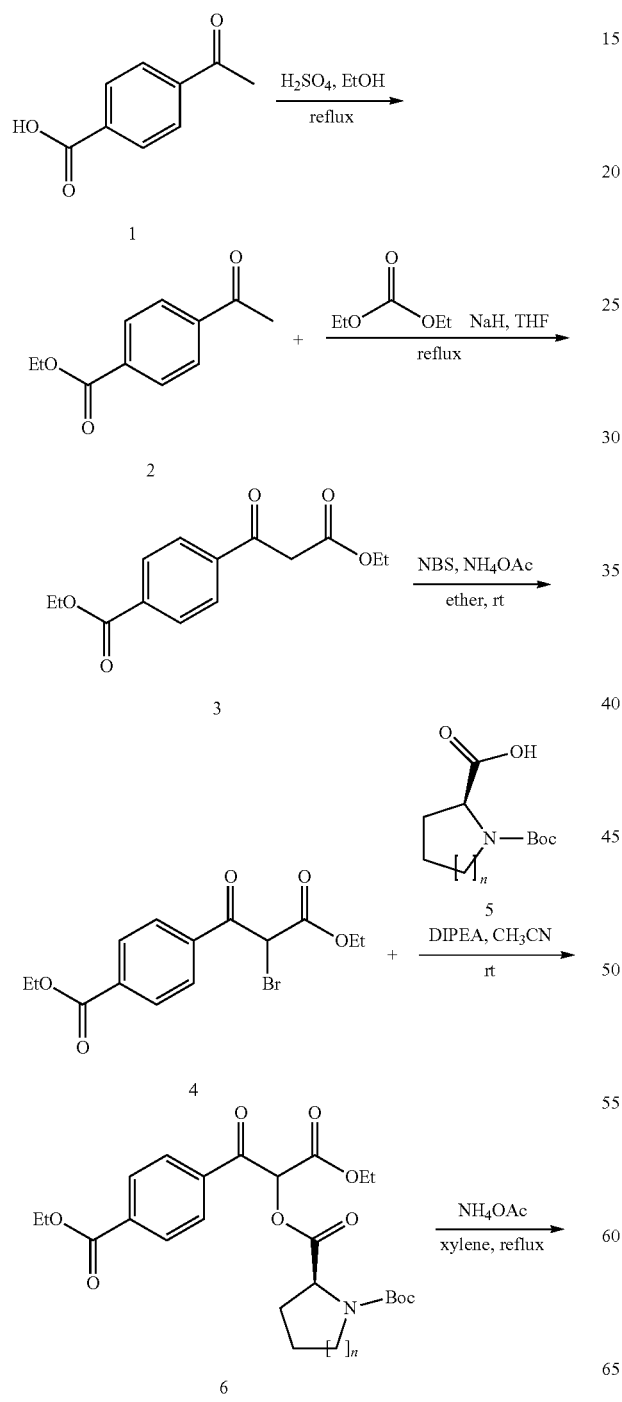

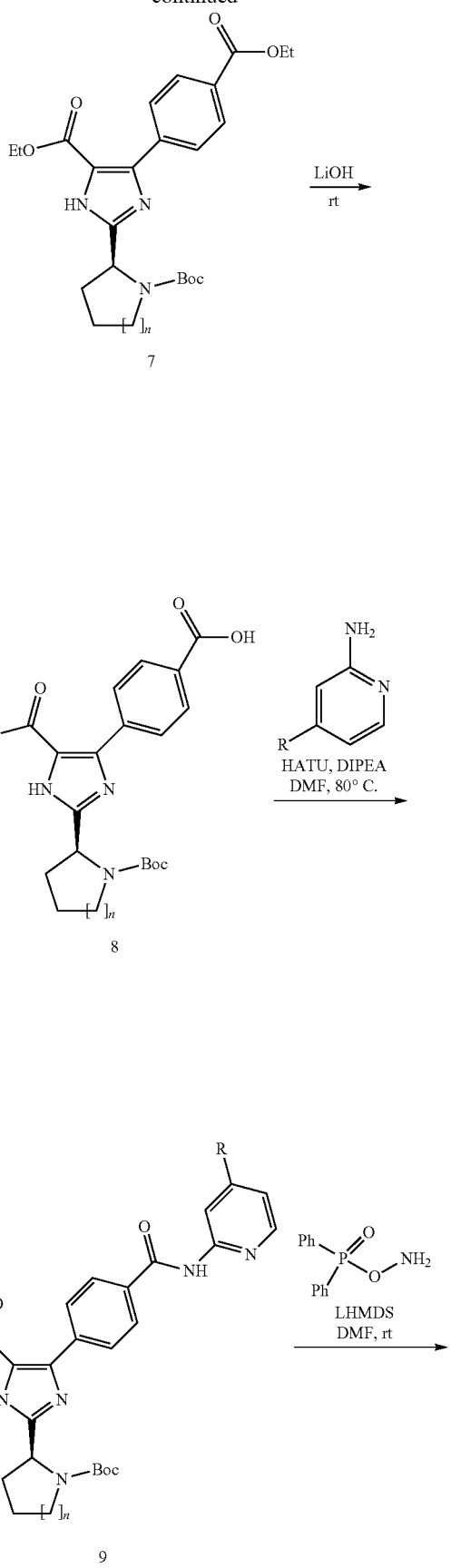

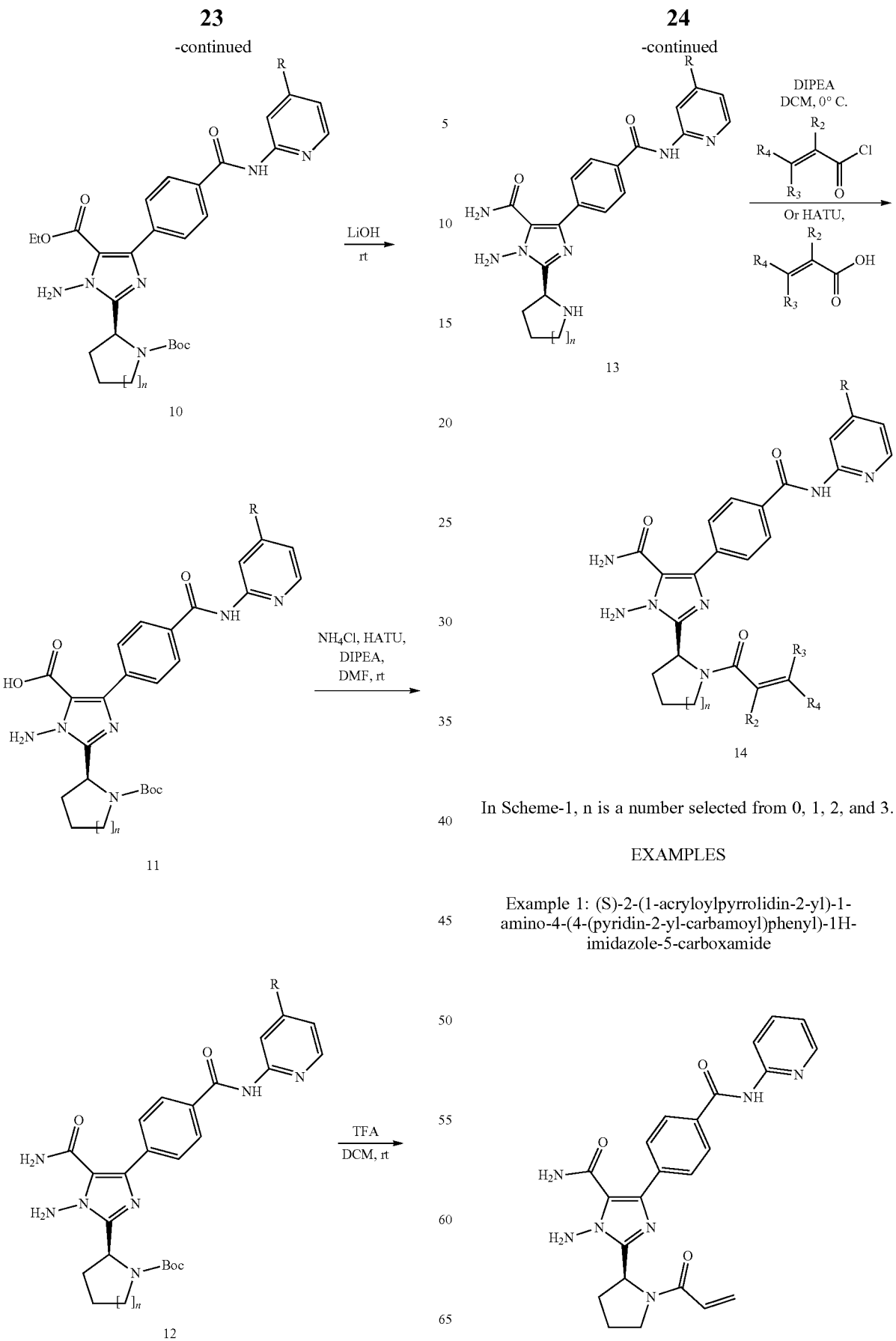
In Scheme-1, n is a number selected from 0, 1, 2, and 3.
EXAMPLES
Example 1: (S)-2-(1-acryloylpyrrolidin-2-yl)-1-amino-4-(4-(pyridin-2-yl-carbamoyl)phenyl)-1H-imidazole-5-carboxamide

Step A: Preparation of ethyl 4-acetylbenzoate

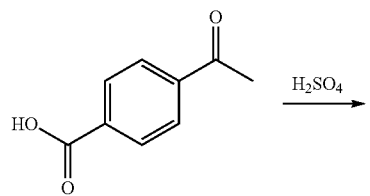

To the solution of 4-acetylbenzoic acid (1000 g, 6.1 mol) in ethanol (2 L) was slowly added H₂SO₄ (10 mL) at 0° C., and the mixture was refluxed at 80° C. for 3 h. The solvent was removed under vacuum and the residue was extracted with ethyl acetate, washed with saturated brine, dried over anhydrous Na₂SO₄, filtered and concentrated. The residue was purified by chromatography with petroleum ether and ethyl acetate (10:1) to afford ethyl 4-acetylbenzoate as a white solid (1077 g, 92%). ¹H NMR (CDCl₃, 600 MHz) δ: 8.11 (d, J=7.6 Hz, 2H), 7.99 (d, J=7.7 Hz, 2H), 4.39 (q, J=7.0 Hz, 2H), 2.63 (s, 3H), 1.40 (t, J=7.1 Hz, 3H). MS (ESI, m/z): 193.1 [M+H]⁺.

Step B: Preparation of ethyl 4-(3-ethoxy-3-oxopropanoyl)benzoate

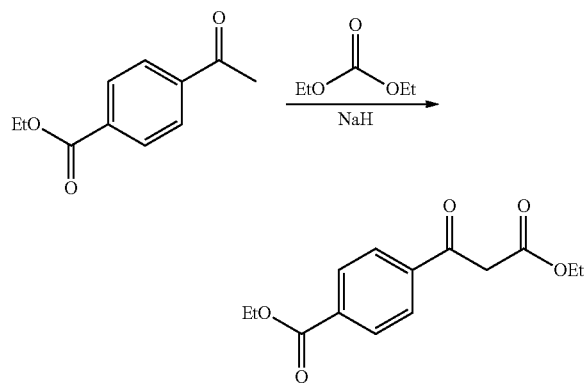

To the solution of diethyl carbonate (423 g, 3.49 mol) in anhydrous tetrahydrofuran (1 L) under N₂ atmosphere, 60% NaH (195 g, 4.88 mol) and 335 g (1.74 mol) of the product of Step A were added, and the mixture was refluxed for 3 h. After the completion of the reaction, the mixture was cooled to room temperature, and 1 mol/L cooled glacial acetic acid was added dropwise until pH 6-7. The solvent tetrahydrofuran was evaporated, and the residue was diluted with saturated brine and extracted with ethyl acetate (3×500 mL). The combined organic layer was washed with saturated brine, dried over anhydrous Na₂SO₄, filtered and concentrated. The residue was purified by chromatography with petroleum ether and ethyl acetate (12:1) to afford ethyl 4-(3-ethoxy-3-oxopropanoyl)benzoate as a yellow oil (399 g, 87%). ¹H NMR (CDCl₃, 400 MHz) δ: 12.54 (s, 0.7H), 8.13 (d, J=8.6 Hz, 0.5H), 8.07 (d, J=8.6 Hz, 1.4H), 7.98 (d, J=8.6 Hz, 0.5H), 7.82 (d, J=8.6 Hz, 1.4H), 5.72 (s, 0.7H), 4.43-4.36 (m, 2H), 4.27 (q, J=7.1 Hz, 1.4H), 4.20 (q, J=7.1 Hz, 0.5H), 4.00 (s, 0.5H), 1.42-1.38 (m, 3H), 1.33 (t, J=7.1 Hz, 2.1H), 1.24 (t, J=7.1 Hz, 0.8H). MS (ESI, m/z): 265.1 [M+H]⁺.

Step C: Preparation of ethyl 4-(2-bromo-3-ethoxy-3-oxopropanoyl) benzoate

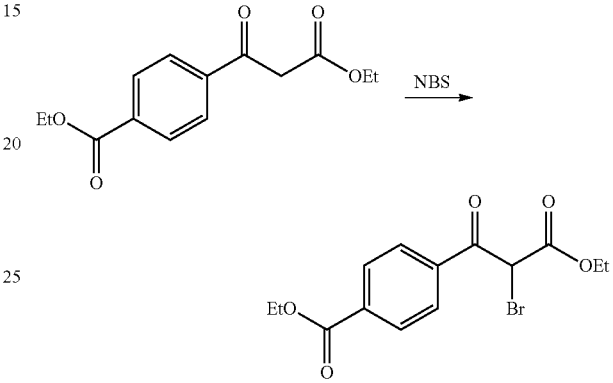

To the solution of 180 g (680 mmol) of the product of Step B, NBS (129 g, 727 mmol) and NH₄OAc (5.3 g, 68 mmol) were added and stirred in ether (1000 mL) at room temperature. The reaction was monitored by TLC. After completion, ether was evaporated and the crude mixture was diluted with water (1500 mL). The product was extracted with ethyl acetate (2×1500 mL) and the combined organic extracts were dried over anhydrous Na₂SO₄, filtered and concentrated.

The residue was purified by flash column chromatography with petroleum ether and ethyl acetate (10:1) to give ethyl 4-(2-bromo-3-ethoxy-3-oxopropanoyl)benzoate as a yellow oil (200 g, 86%). ¹H NMR (CDCl₃, 400 MHz) δ: 8.13 (d, J=8.6 Hz, 2H), 8.02 (d, J=8.6 Hz, 2H), 5.66 (s, 1H), 4.39 (q, J=7.1 Hz, 2H), 4.26 (q, J=7.1 Hz, 2H), 1.39 (t, J=7.1 Hz, 3H), 1.22 (t, J=7.1 Hz, 3H). MS (ESI, m/z): 343.1 [M+H]⁺.

Step D: Preparation of 1-(tert-butyl) 2-(1-ethoxy-3-(4-(ethoxycarbonyl) phenyl)-1,3-dioxopropan-2-yl) (2S)-pyrrolidine-1,2-dicarboxylate

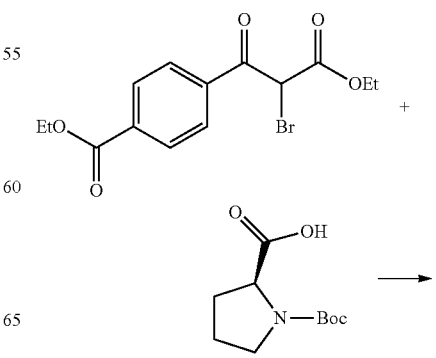

-continued

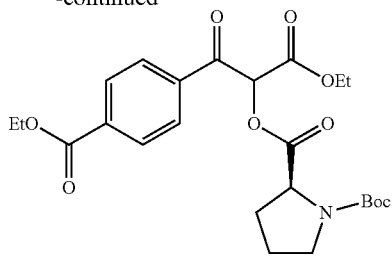

To the solution of 256 g (746 mmol) of the product of Step C in acetonitrile (2 L) was added (tert-butoxycarbonyl)-L-proline (168 g, 781 mmol) and diisopropylethylamine (141 mL, 746 mmol). The mixture was stirred at room temperature for 3 h before all volatile were evaporated. The residue was diluted with water (1000 mL) and extracted with ethyl acetate (3000 mL). The organic phase was separated, dried over anhydrous $Na_2SO_4$ and concentrated. The residue was purified by flash column chromatography with petroleum ether and ethyl acetate (7:1) to give the 1-(tert-butyl) 2-(1-ethoxy-3-(4-(ethoxycarbonyl)phenyl)-1,3-dioxopropan-2-yl)(2S)-pyrrolidine-1,2-dicarboxylate as a light yellow oil (330 g, 93%). $^1$H NMR (CDCl$_3$, 400 MHz) δ: 8.12-8.09 (m, 2H), 8.03-7.98 (m, 2H), 6.33-6.27 (m, 1H), 4.48-4.34 (m, 3H), 4.23-4.18 (m, 2H), 3.56-3.28 (m, 2H), 2.29-2.07 (m, 2H), 1.98-1.83 (m, 2H), 1.42-1.29 (m, 12H), 1.20-1.14 (m, 3H). MS (ESI, m/z): 478.2 [M+H]$^+$.

Step E: Preparation of ethyl (S)-2-(1-(tert-butoxycarbonyl)pyrrolidin-2-yl)-4-(4-(ethoxycarbonyl)phenyl)-1H-imidazole-5-carboxylate

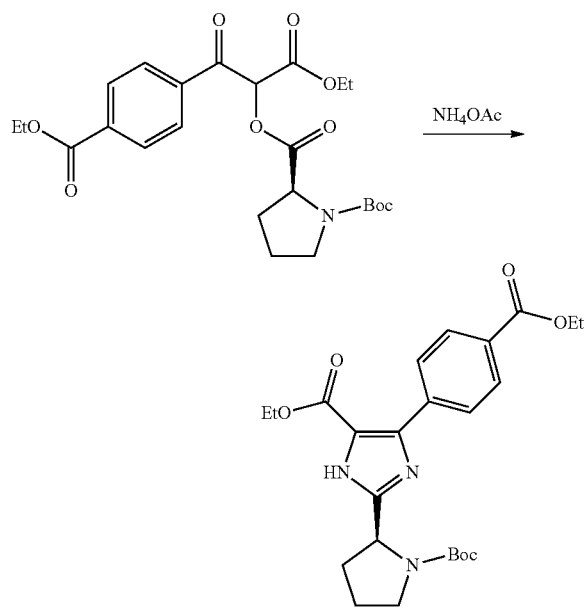

To the solution of 202 g (423 mmol) of the product of Step D in xylene (1250 mL) in a 1 L pressure bottle was added NH$_4$OAc (390 g, 5059 mmol). And the reaction was heated at 140° C. for 2.5 h. After being cooled, the solution was partition between ethyl acetate (3000 mL) and water (1000 mL). The organic layer was concentrated and the residue was purified by chromatography with petroleum ether and ethyl acetate (5:1) to afford ethyl (S)-2-(1-(tert-butoxycarbonyl)pyrrolidin-2-yl)-4-(4-(ethoxycarbonyl)phenyl)-1H-imidazole-5-carboxylate as a light yellow oil (77 g, 40%). $^1$H NMR (CDCl$_3$, 600 MHz) δ: 11.17 (s, 1H), 8.13-7.89 (m, 4H), 5.03-4.85 (m, 1H), 4.33 (q, J=6.6 Hz, 2H), 4.26-4.21 (m, 2H), 3.49-3.38 (m, 2H), 2.85-2.11 (m, 3H), 1.92-1.82 (m, 1H), 1.45-1.39 (m, 9H), 1.35 (t, J=6.8 Hz, 3H), 1.23-1.21 (m, 3H). MS (ESI, m/z): 458.2 [M+H]$^+$.

Step F: Preparation of (S)-4-(2-(1-(tert-butoxycarbonyl)pyrrolidin-2-yl)-5-(ethoxycarbonyl)-1H-imidazol-4-yl)benzoic acid

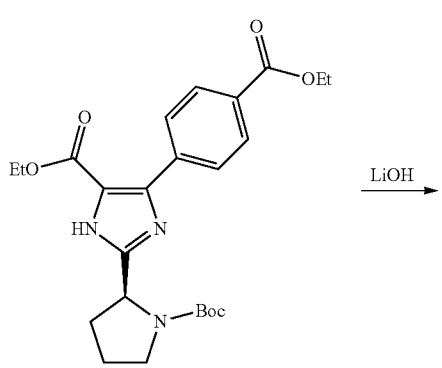

LiOH

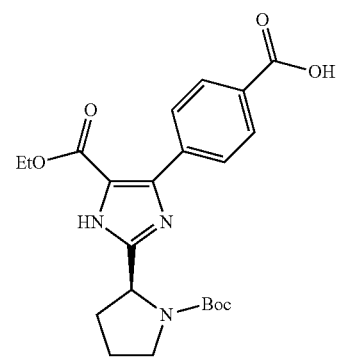

To the solution of 4.57 g (10 mmol) of the product of Step E in 1,4-dioxane (50 mL) was added aqueous lithium hydroxide (2 mol/L, 50 mL) and stirred at room temperature for 2 h. The reaction mixture was evaporated and diluted with water (100 mL) and acidified with aqueous HCl till pH 3. The white precipitate was isolated by filtration and dried to afford (S)-4-(2-(1-(tert-butoxycarbonyl)pyrrolidin-2-yl)-5-(ethoxy-carbonyl)-1H-imidazol-4-yl)benzoic acid (3.86 g, 90%).

Step G: Preparation of ethyl (S)-2-(1-(tert-butoxycarbonyl)pyrrolidin-2-yl)-4-(4-(pyridin-2-ylcarbamoyl)phenyl)-1H-imidazole-5-carboxylate

Step H: Preparation of ethyl (S)-1-amino-2-(1-(tert-butoxycarbonyl)pyrrolidin-2-yl)-4-(4-(pyridin-2-ylcarbamoyl)phenyl)-1H-imidazole-5-carboxylate

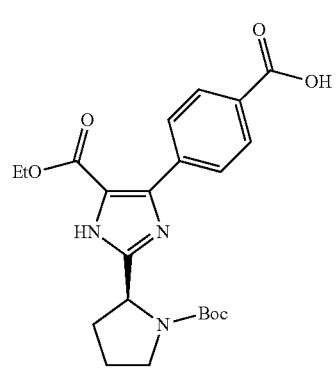
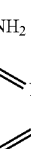
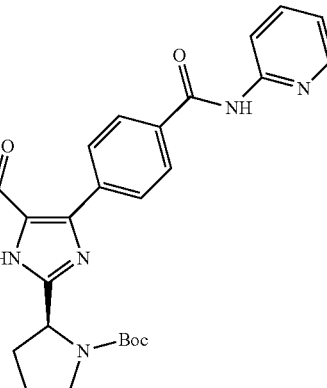
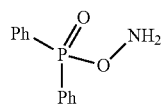
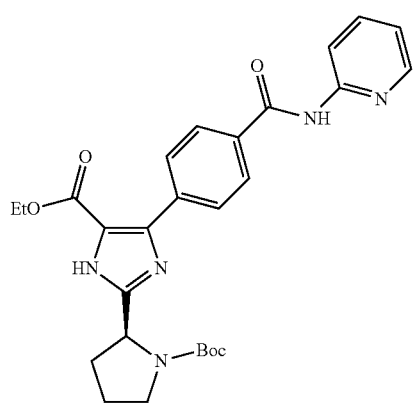
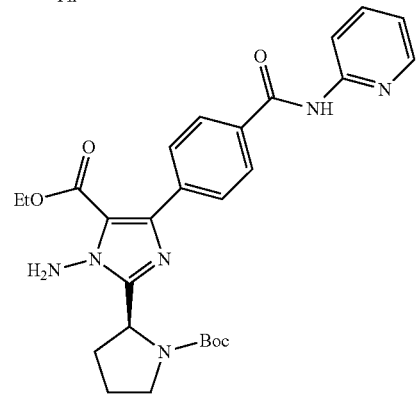

To the solution of 29.0 g (67 mmol) of the product of Step F in dry N,N-dimethylformamide (250 mL) was stirred and added HATU (30.8 g, 81 mmol), diisopropylethylamine (58 mL, 337 mmol) and pyridin-2-amine (9.5 g, 101 mmol). The reaction mixture was stirred at 80° C. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (2:1) to afford ethyl (S)-2-(1-(tert-butoxycarbonyl)pyrrolidin-2-yl)-4-(4-(pyridin-2-ylcarbamoyl)phenyl)-1H-imidazole-5-carboxylate as a white solid (29.5 g, 87%). $^1$H NMR (CDCl$_3$, 400 MHz) δ: 11.12 (s, 1H), 8.80 (s, 1H), 8.40 (d, J=8.4 Hz, 1H), 8.27-8.26 (m, 1H), 8.15 (d, J=7.7 Hz, 2H), 7.95 (d, J=8.4 Hz, 2H), 7.77-7.72 (m, 1H), 7.06-7.03 (m, 1H), 4.98-4.97 (m, 1H), 4.35-4.28 (m, 2H), 3.52-3.42 (m, 2H), 2.21-1.94 (m, 4H), 1.50 (s, 9H), 1.33-1.29 (m, 3H). MS (ESI, m/z): 506.1 [M+H]$^+$.

To the solution of 2.6 g (5.1 mmol) of the product of Step G in dry N,N-dimethylformamide (25 mL) was stirred and slowly added lithium hexamethyldisilazane (6.1 mL, 1 M solution in tetrahydrofuran) at −10° C. After the mixture was stirred for 10 min, O-(diphenylphosphinyl) hydroxylamine (1.2 g, 5.1 mmol) was added at 0° C. and the resulting suspension was stirred 2 h at room temperature (in cases where the reaction mixture became too viscous, additional N,N-dimethylformamide was added). The reaction was quenched with brine and concentrated to dryness in vacuum. The residue was washed three times with ethyl acetate (3×100 mL). The combined organic fractions were dried with anhydrous Na$_2$SO$_4$ and the solvent was removed under reduced pressure to afford the crude residue, which was subjected to column chromatography with petroleum ether and ethyl acetate (2:1) to give the desired product ethyl (S)-1-amino-2-(1-(tert-butoxycarbonyl)pyrrolidin-2-yl)-4-(4-(pyridin-2-ylcarbamoyl)phenyl)-1H-imidazole-5-carboxylate as a white solid (1.9 g, 71%). $^1$H NMR (CDCl$_3$, 600 MHz) δ: 8.93 (s, 1H), 8.39 (d, J=8.3 Hz, 1H), 8.22 (d, J=4.2 Hz, 1H), 7.92 (d, J=7.6 Hz, 2H), 7.78 (d, J=7.6 Hz, 2H), 7.73 (t, J=7.7 Hz, 1H), 7.02 (t, J=5.6 Hz, 1H), 6.64 (s, 2H), 5.22-5.13 (m, 1H), 4.25-4.22 (m, 2H), 3.56-3.55 (m, 1H), 3.46-3.43 (m, 1H), 2.39-2.36 (m, 2H), 2.23-2.18 (m, 1H), 1.92-1.91 (m, 1H), 1.39 (s, 7H), 1.24 (s, 2H), 1.20 (t, J=6.6 Hz, 3H). MS (ESI, m/z): 521.1 [M+H]$^+$.

Step I: Preparation of (S)-1-amino-2-(1-(tert-butoxycarbonyl)pyrrolidin-2-yl)-4-(4-(pyridin-2-ylcarbamoyl)phenyl)-1H-imidazole-5-carboxylic acid

Step J: Preparation of tert-butyl (S)-2-(1-amino-5-carbamoyl-4-(4-(pyridin-2-ylcarbamoyl)phenyl)-1H-imidazol-2-yl)pyrrolidine-1-carboxylate

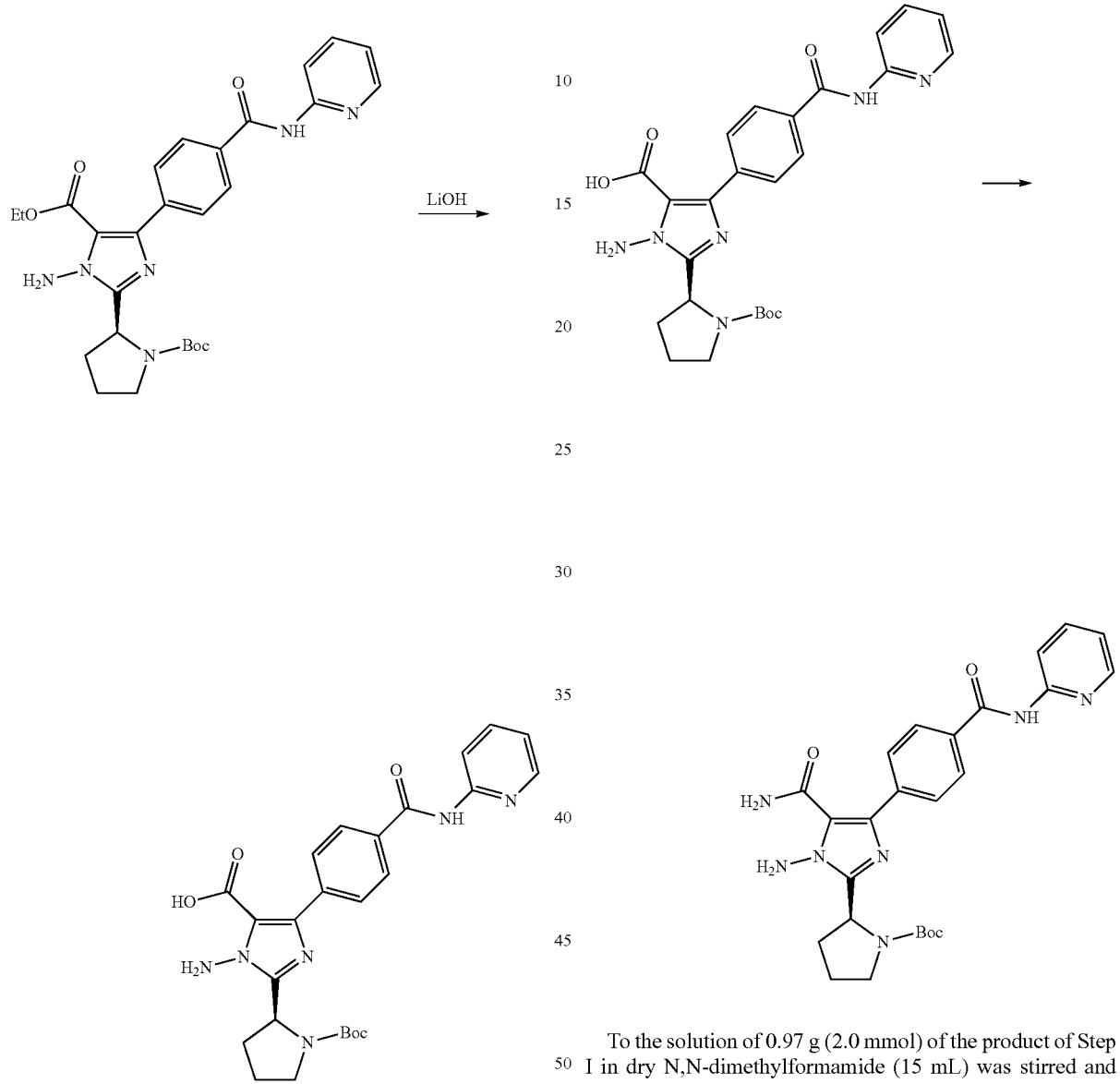

To the solution of 1.36 g (2.6 mmol) of the product of Step H in methanol (15 mL) was stirred and added aqueous lithium hydroxide (2 mol/L, 14 mL), then stirred at room temperature for 2 h. The reaction mixture was evaporated and diluted with water (100 mL) and acidified with aqueous HCl till pH 3. The mixture was washed with ethyl acetate three times (3×50 mL). The combined organic layers were concentrated under reduced pressure to afford (S)-1-amino-2-(1-(tert-butoxycarbonyl)pyrrolidin-2-yl)-4-(4-(pyridin-2-ylcarbamoyl)phenyl)-1H-imidazole-5-carboxylic acid as a white solid (1.15 g, 90%).

To the solution of 0.97 g (2.0 mmol) of the product of Step I in dry N,N-dimethylformamide (15 mL) was stirred and added HATU (1.1 g, 2.9 mmol), diisopropylethylamine (1 mL, 5.9 mmol) and NH$_4$Cl (1.1 g, 20 mmol). The reaction mixture was stirred at room temperature for 2 h. The reaction mixture was quenched with brine and washed with ethyl acetate three times (3×50 mL). The combined organic layers were concentrated under reduced pressure and purified by flash chromatography with dichloromethane and methanol (30:1) to afford tert-butyl (S)-2-(1-amino-5-carbamoyl-4-(4-(pyridin-2-ylcarbamoyl)phenyl)-1H-imidazol-2-yl)pyrrolidine-1-carboxylate as a white solid (0.8 g, 83%). $^1$H NMR (CDCl$_3$, 400 MHz) δ: 10.72 (s, 1H), 8.40-8.38 (m, 1H), 8.21 (d, J=8.4 Hz, 1H), 8.12 (s, 1H), 8.02 (d, J=8.2 Hz, 2H), 7.86-7.81 (m, 3H), 7.69 (s, 1H), 7.18-7.15 (m, 1H), 6.22 (s, 1H), 5.97 (s, 1H), 5.11-5.06 (m, 1H), 3.57-3.47 (m, 1H), 3.44-3.38 (m, 1H), 2.28-1.82 (m, 4H), 1.39 (s, 5H), 1.15 (s, 4H). MS (ESI, m/z): 492.2 [M+H]$^+$.

Step K: Preparation of (S)-1-amino-4-(4-(pyridin-2-ylcarbamoyl)phenyl)-2-(pyrrolidin-2-yl)-1H-imidazole-5-carboxamide

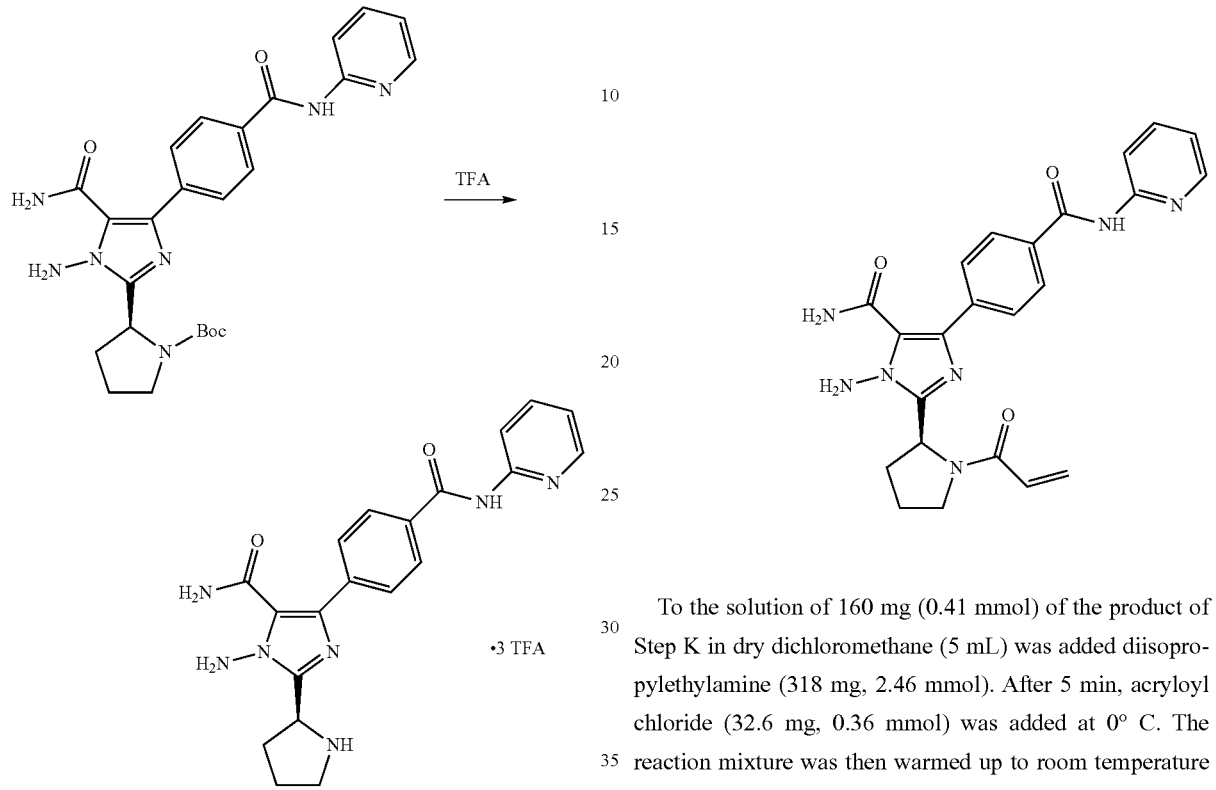

To the solution of 190 mg (0.39 mmol) of the product of Step J in dichloromethane (5 mL) was added trifluoroacetic acid (2.5 mL). The mixture was stirred at room temperature for 1 h and then concentrated to afford (S)-1-amino-4-(4-(pyridin-2-ylcarbamoyl)phenyl)-2-(pyrrolidin-2-yl)-1-H-imidazole-5-carboxamide as a light yellow oil. MS (ESI, m/z): 392.1 [M+H]$^+$.

Step L: Preparation of (S)-2-(1-acryloylpyrrolidin-2-yl)-1-amino-4-(4-(pyridin-2-ylcarbamoyl)phenyl)-1H-imidazole-5-carboxamide

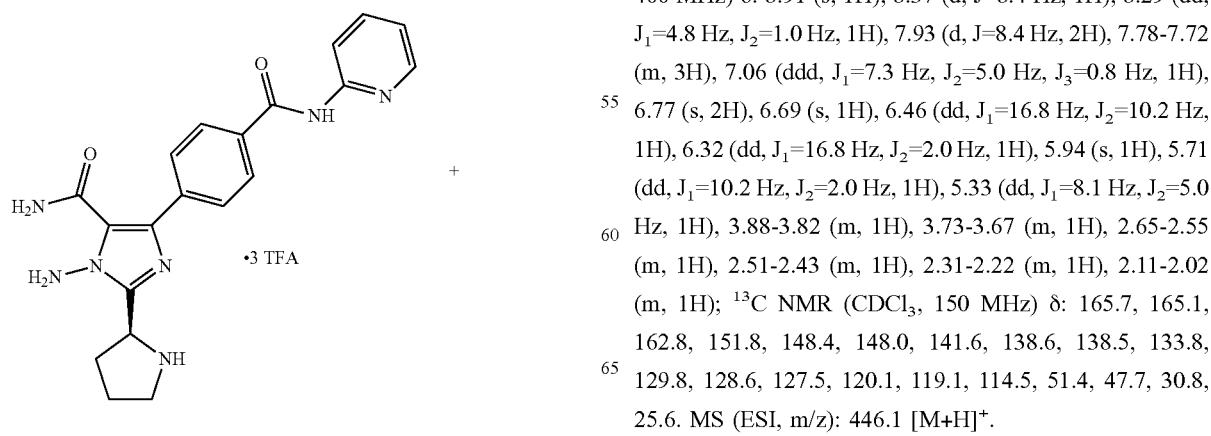

To the solution of 160 mg (0.41 mmol) of the product of Step K in dry dichloromethane (5 mL) was added diisopropylethylamine (318 mg, 2.46 mmol). After 5 min, acryloyl chloride (32.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-2-(1-acryloyl-pyrrolidin-2-yl)-1-amino-4-(4-(pyridin-2-ylcarbamoyl)phenyl)-1H-imidazole-5-carboxamide as an off-white solid (99 mg, 62%). $^1$H NMR (CDCl$_3$, 400 MHz) δ: 8.91 (s, 1H), 8.37 (d, J=8.4 Hz, 1H), 8.29 (dd, J$_1$=4.8 Hz, J$_2$=1.0 Hz, 1H), 7.93 (d, J=8.4 Hz, 2H), 7.78-7.72 (m, 3H), 7.06 (ddd, J$_1$=7.3 Hz, J$_2$=5.0 Hz, J$_3$=0.8 Hz, 1H), 6.77 (s, 2H), 6.69 (s, 1H), 6.46 (dd, J$_1$=16.8 Hz, J$_2$=10.2 Hz, 1H), 6.32 (dd, J$_1$=16.8 Hz, J$_2$=2.0 Hz, 1H), 5.94 (s, 1H), 5.71 (dd, J$_1$=10.2 Hz, J$_2$=2.0 Hz, 1H), 5.33 (dd, J$_1$=8.1 Hz, J$_2$=5.0 Hz, 1H), 3.88-3.82 (m, 1H), 3.73-3.67 (m, 1H), 2.65-2.55 (m, 1H), 2.51-2.43 (m, 1H), 2.31-2.22 (m, 1H), 2.11-2.02 (m, 1H); $^{13}$C NMR (CDCl$_3$, 150 MHz) δ: 165.7, 165.1, 162.8, 151.8, 148.4, 148.0, 141.6, 138.6, 138.5, 133.8, 129.8, 128.6, 127.5, 120.1, 119.1, 114.5, 51.4, 47.7, 30.8, 25.6. MS (ESI, m/z): 446.1 [M+H]$^+$.

Example 2: (S)-1-amino-2-(1-methacryloylpyrrolidin-2-yl)-4-(4-(pyridin-2-ylcarbamoyl)phenyl)-1H-imidazole-5-carboxamide

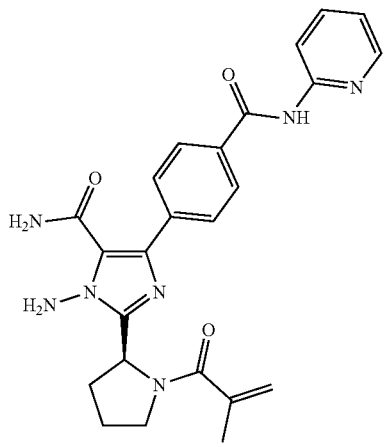 [SMILES: C=C(C)C(=O)N1CCC[C@H]1c1nc(-c2ccc(C(=O)Nc3ccccn3)cc2)c(C(N)=O)n1N]

Preparation of (S)-1-amino-2-(1-methacryloylpyrrolidin-2-yl)-4-(4-(pyridin-2-ylcarbamoyl)phenyl)-1H-imidazole-5-carboxamide

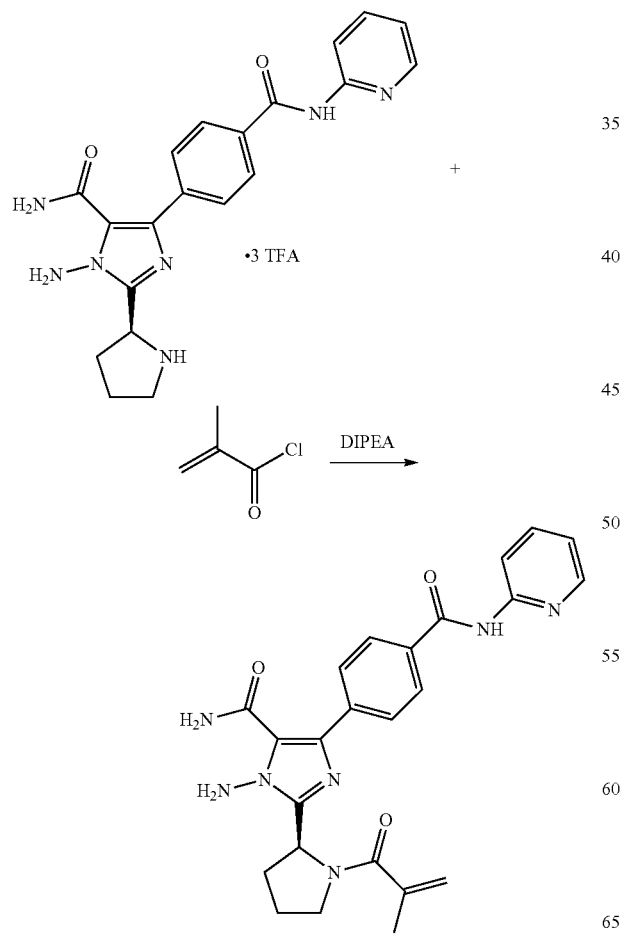

To the solution of 160 mg (0.41 mmol) of the product of Step K of example 1 in dry dichloromethane (5 mL) was added diisopropylethylamine (318 mg, 2.46 mmol). After 5 min, methacryloyl chloride (37.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-methacryloylpyrrolidin-2-yl)-4-(4-(pyridin-2-ylcarbamoyl)phenyl)-1H-imidazole-5-carboxamide as an off-white solid (110 mg, 59%). $^1$H NMR (CDCl$_3$, 600 MHz) δ: 9.26 (s, 1H), 8.31 (d, J=8.3 Hz, 1H), 8.23 (d, J=4.4 Hz, 1H), 7.85 (d, J=8.0 Hz, 2H), 7.70 (t, J=7.8 Hz, 1H), 7.66 (d, J=8.0 Hz, 2H), 7.02-7.00 (m, 1H), 6.87 (s, 1H), 6.66 (s, 2H), 6.45 (s, 1H), 5.27 (s, 1H), 5.26-5.23 (m, 1H), 5.20 (s, 1H), 3.75-3.68 (m, 2H), 2.53-2.48 (m, 2H), 2.32-2.27 (m, 2H), 1.90 (s, 3H); $^{13}$C NMR (CDCl$_3$, 150 MHz) δ: 171.2, 165.9, 162.9, 151.8, 148.6, 147.8, 141.5, 140.7, 138.5, 138.3, 133.7, 129.6, 127.5, 119.9, 119.5, 118.0, 114.6, 51.2, 50.0, 30.9, 25.8, 19.7. MS (ESI, m/z): 460.2 [M+H]$^+$.

Example 3: (S)-1-amino-2-(1-(3-methylbut-2-enoyl)pyrrolidin-2-yl)-4-(4-(pyridin-2-ylcarbamoyl)phenyl)-1H-imidazole-5-carboxamide

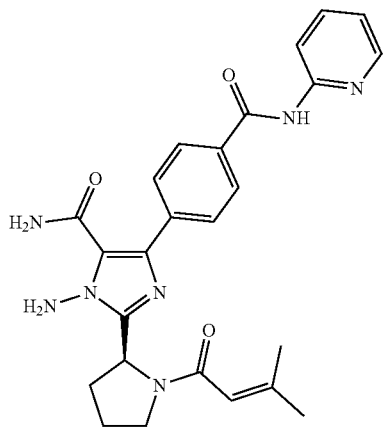 [SMILES: CC(C)=CC(=O)N1CCC[C@H]1c1nc(-c2ccc(C(=O)Nc3ccccn3)cc2)c(C(N)=O)n1N]

Preparation of (S)-1-amino-2-(1-(3-methylbut-2-enoyl)pyrrolidin-2-yl)-4-(4-(pyridin-2-ylcarbamoyl)phenyl)-1H-imidazole-5-carboxamide Example 4: (S,E)-1-amino-2-(1-(but-2-enoyl)pyrrolidin-2-yl)-4-(4-(pyridin-2-ylcarbamoyl)phenyl)-1H-imidazole-5-carboxamide

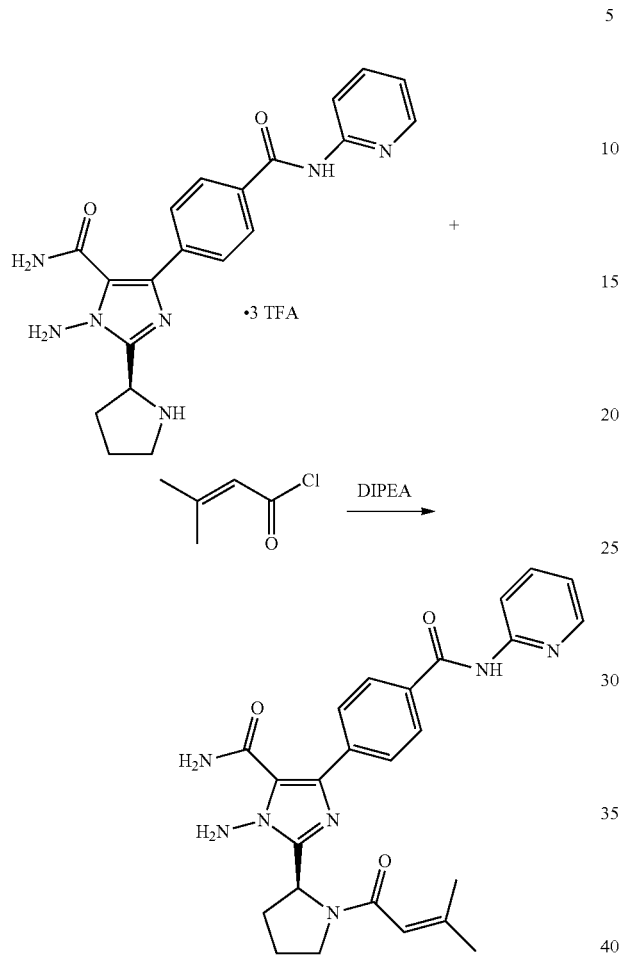

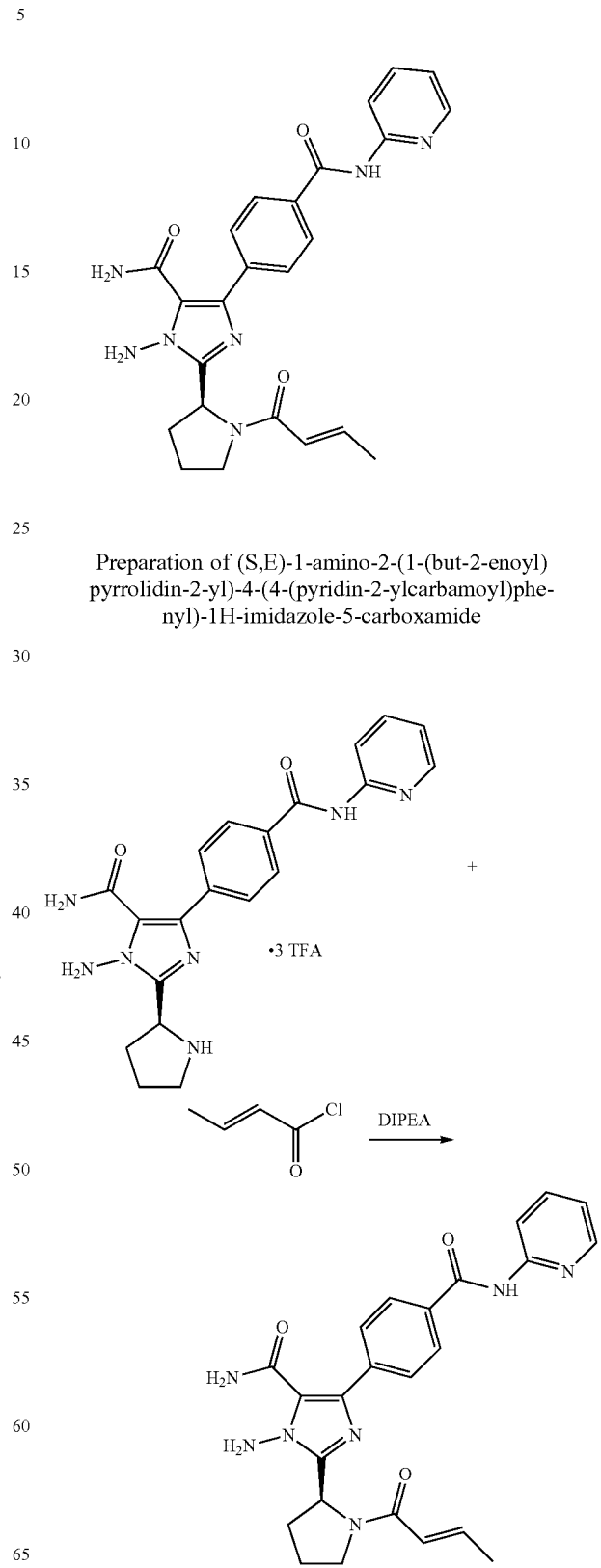

Preparation of (S,E)-1-amino-2-(1-(but-2-enoyl)pyrrolidin-2-yl)-4-(4-(pyridin-2-ylcarbamoyl)phenyl)-1H-imidazole-5-carboxamide To the solution of 160 mg (0.41 mmol) of the product of Step K of example 1 in dry dichloromethane (5 mL) was added diisopropylethylamine (318 mg, 2.46 mmol). After 5 min, 3-methylbut-2-enoyl chloride (42.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(3-methylbut-2-enoyl)pyrrolidin-2-yl)-4-(4-(pyridin-2-ylcarbamoyl)phenyl)-1H-imidazole-5-carboxamide as an off-white solid (131 mg, 67%). $^1$H NMR ($CDCl_3$, 600 MHz) δ: 8.93 (s, 1H), 8.38-8.30 (m, 2H), 7.98-7.87 (m, 2H), 7.78-7.75 (m, 3H), 7.10-7.04 (m, 1H), 6.89-6.81 (m, 3H), 5.89 (s, 1H), 5.79 (s, 1H), 5.30-5.23 (m, 1H), 3.75-3.72 (m, 1H), 3.62-3.58 (m, 1H), 2.55-2.46 (m, 2H), 2.27-2.23 (m, 1H), 2.03-1.99 (m, 4H), 1.85 (s, 3H); $^{13}$C NMR ($CDCl_3$, 150 MHz) δ: 167.0, 165.7, 162.7, 151.7, 151.0, 148.9, 147.9, 141.8, 138.7, 138.6, 133.7, 129.9, 127.5, 120.1, 119.1, 117.7, 114.6, 50.8, 48.0, 30.9, 27.2, 25.6, 20.4. MS (ESI, m/z): 474.2 [M+H]$^+$.

To the solution of 160 mg (0.41 mmol) of the product of Step K of example 1 in dry dichloromethane (5 mL) was added diisopropylethylamine (318 mg, 2.46 mmol). After 5 min, (E)-but-2-enoylchloride (37.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S,E)-1-amino-2-(1-(but-2-enoyl)pyrrolidin-2-yl)-4-(4-(pyridin-2-ylcarbamoyl)phenyl)-1H-imidazole-5-carboxamide as an off-white solid (102 mg, 54%). $^1$H NMR (CDCl$_3$, 600 MHz) δ: 9.35 (s, 1H), 8.30 (d, J=8.3 Hz, 1H), 8.22 (d, J=4.3 Hz, 1H), 7.82 (d, J=7.9 Hz, 2H), 7.69-7.66 (m, 3H), 7.15 (s, 1H), 7.01-6.99 (m, 1H), 6.85-6.79 (m, 1H), 6.70 (s, 2H), 6.56 (s, 1H), 6.08 (d, J=15.1 Hz, 1H), 5.23-5.21 (m, 1H), 3.78-3.74 (m, 1H), 3.64-3.60 (m, 1H), 2.56-2.49 (m, 1H), 2.39-2.35 (m, 1H), 2.20-2.14 (m, 1H), 2.02-1.95 (m, 1H), 1.81 (d, J=6.8 Hz, 3H); $^{13}$C NMR (CDCl$_3$, 150 MHz) δ: 166.0, 165.4, 162.9, 151.9, 148.7, 147.8, 142.4, 141.5, 138.4, 138.3, 133.5, 129.6, 127.4, 122.8, 119.9, 119.5, 114.6, 51.2, 47.5, 30.7, 25.4, 18.2. MS (ESI, m/z): 460.2 [M+H]$^+$.

Example 5: (S)-1-amino-2-(1-(2-cyano-3-cyclopropylacryloyl)pyrrolidin-2-yl)-4-(4-(pyridin-2-ylcarbamoyl)phenyl)-1H-imidazole-5-carboxamide

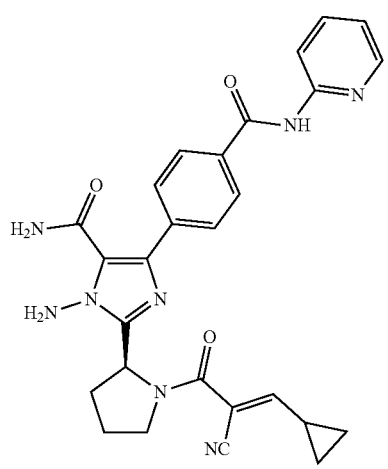 [SMILES: N#C/C(=C\C1CC1)C(=O)N1CCC[C@H]1c1nc(-c2ccc(C(=O)Nc3ccccn3)cc2)c(C(N)=O)n1N]

Step A: Preparation of (S)-1-amino-2-(1-(2-cyanoacetyl)pyrrolidin-2-yl)-4-(4-(pyridin-2-ylcarbamoyl)phenyl)-1H-imidazole-5-carboxamide

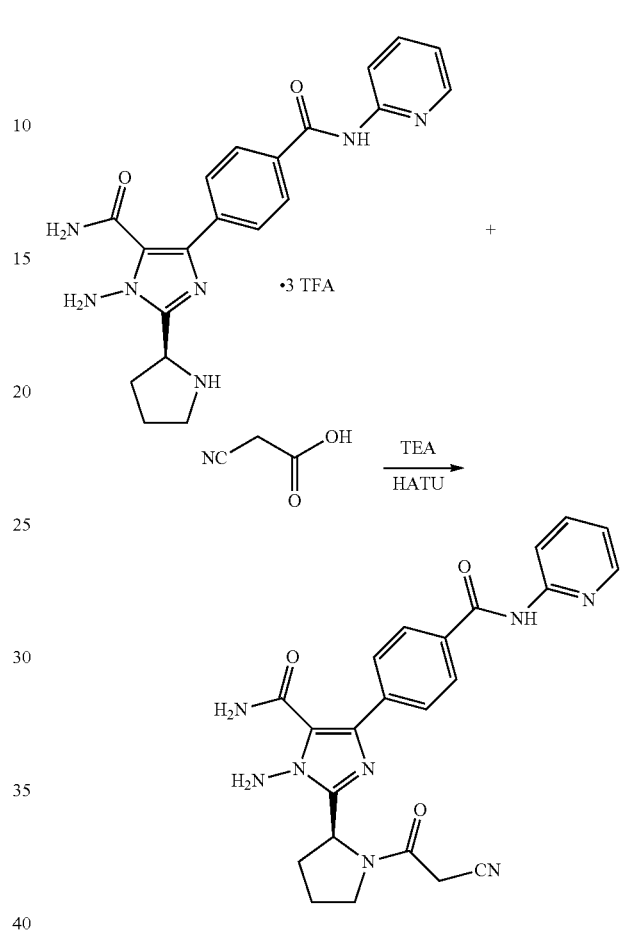

To the solution of 160 mg (0.41 mmol) of the product of Step K of example 1 in dry N,N-Dimethylformamide (5 mL) was added triethylamine (248 mg, 2.46 mmol). After 5 min, 2-cyanoacetic acid (30.6 mg, 0.36 mmol) and HATU (234 mg, 0.61 mmol) was added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (23:1) to give (S)-1-amino-2-(1-(2-cyanoacetyl)pyrrolidin-2-yl)-4-(4-(pyridin-2-ylcarbamoyl)phenyl)-1H-imidazole-5-carboxamide as an off-white solid (95 mg, 50%). $^1$H NMR (CDCl$_3$, 600 MHz) δ: 8.80 (s, 1H), 8.39 (d, J=8.3 Hz, 1H), 8.31 (d, J=4.7 Hz, 1H), 7.97 (d, J=7.8 Hz, 2H), 7.78-7.76 (m, 3H), 7.10-7.08 (m, 1H), 6.48 (s, 2H), 6.25 (s, 1H), 5.74 (s, 1H), 5.36-5.33 (m, 1H), 3.79-3.75 (m, 1H), 3.62-3.58 (m, 1H), 3.48 (dd, J$_1$=26.3 Hz, J$_2$=18.2 Hz, 2H), 2.63-2.56 (m, 1H), 2.48-2.43 (m, 1H), 2.34-2.28 (m, 1H), 2.14-2.08 (m, 1H); $^{13}$C NMR (CDCl$_3$, 150 MHz) δ: 165.4, 162.6, 160.9, 151.7, 148.0, 147.9, 141.4, 138.7, 138.2, 134.2, 129.9, 127.7, 120.2, 119.2, 114.5, 113.7, 52.2, 48.2, 31.0, 26.3, 25.5. MS (ESI, m/z): 459.1 [M+H]$^+$.

Step B: Preparation of (S)-1-amino-2-(1-(2-cyano-3-cyclopropylacryloyl)pyrrolidin-2-yl)-4-(4-(pyridin-2-ylcarbamoyl)phenyl)-1H-imidazole-5-carboxamide

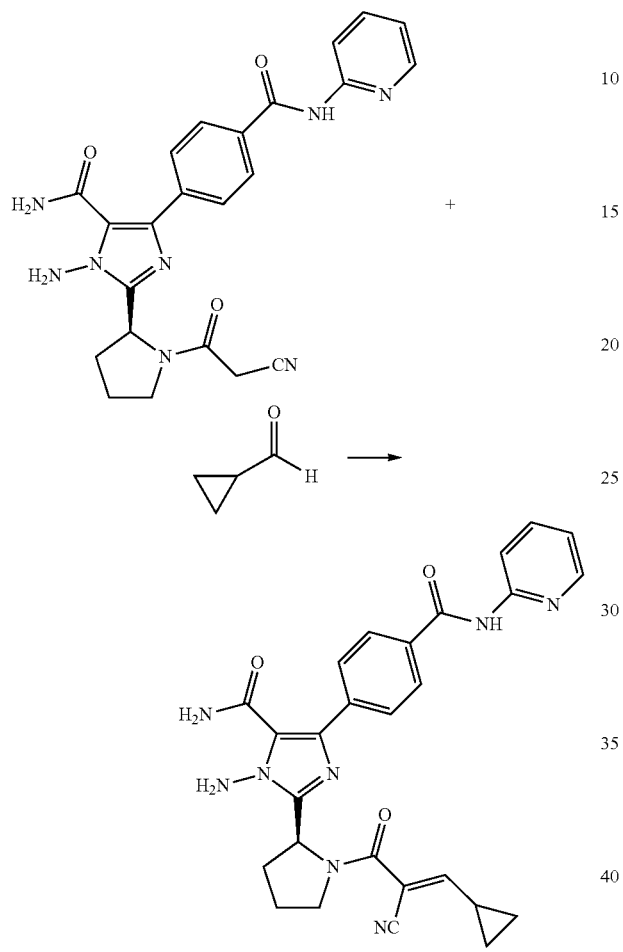

To the solution of cyclopropanecarbaldehyde (7.7 mg, 0.11 mmol) in dry dichloromethane (5 mL) at 0° C. was added pyrrolidine (45 μL, 0.55 mmol) and TMS-Cl (70 μL, 0.55 mmol). The ice bath was removed and the reaction mixture was stirred for 10 min followed by the additions of 50 mg (0.11 mmol) of the product of Step A. The reaction solution was stirred for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (27:1) to afford (S)-1-amino-2-(1-(2-cyano-3-cyclopropylacryloyl)pyrrolidin-2-yl)-4-(4-(pyridin-2-ylcarbamoyl)phenyl)-1H-imidazole-5-carboxamide as a white solid (38 mg, 67%). $^1$H NMR (CDCl$_3$, 600 MHz) δ: 9.16 (s, 1H), 8.36 (d, J=8.3 Hz, 1H), 8.27 (d, J=3.8 Hz, 1H), 7.91 (d, J=8.1 Hz, 2H), 7.76-7.62 (m, 3H), 7.07-7.05 (m, 1H), 6.79 (d, J=11.3 Hz, 1H), 6.56-6.41 (m, 3H), 6.28 (s, 1H), 5.31-5.29 (m, 1H), 4.05-4.01 (m, 1H), 3.93-3.89 (m, 1H), 2.49-2.45 (m, 2H), 2.31-2.27 (m, 1H), 2.10-1.99 (m, 2H), 1.24-1.23 (m, 2H), 0.89-0.85 (m, 2H); $^{13}$C NMR (CDCl$_3$, 150 MHz) δ: 167.8, 165.7, 162.9, 161.4, 151.7, 148.0, 147.8, 141.5, 138.7, 138.2, 133.9, 129.7, 127.7, 120.1, 119.1, 115.5, 114.6, 107.4, 53.0, 49.5, 30.7, 26.1, 15.8, 11.2, 11.1. MS (ESI, m/z): 511.2 [M+H]$^+$.

Example 6

(S,E)-1-amino-2-(1-(pent-2-enoyl)pyrrolidin-2-yl)-4-(4-(pyridin-2-ylcarbamoyl)phenyl)-1H-imidazole-5-carboxamide

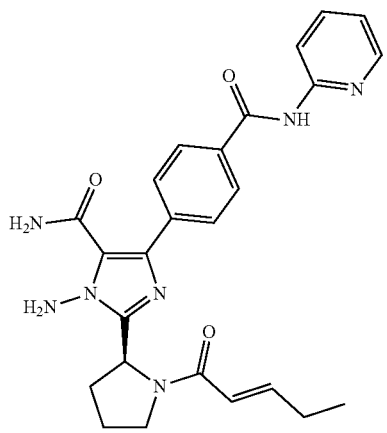 [SMILES: CC/C=C/C(=O)N1CCC[C@H]1c1nc(-c2ccc(C(=O)Nc3ccccn3)cc2)c(C(N)=O)n1N]

Preparation of (S,E)-1-amino-2-(1-(pent-2-enoyl)pyrrolidin-2-yl)-4-(4-(pyridin-2-ylcarbamoyl)phenyl)-1H-imidazole-5-carboxamide

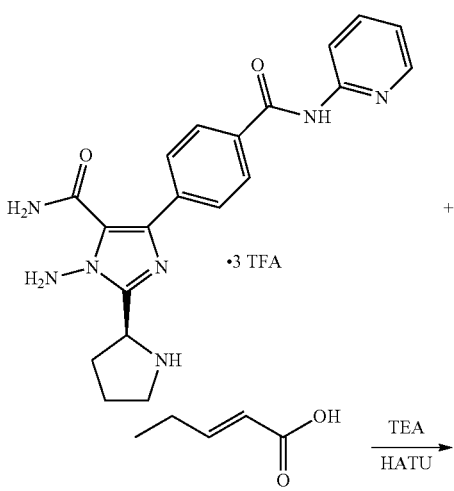

43

-continued

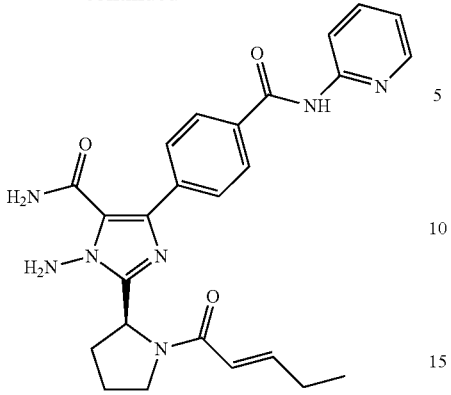

To the solution of 160 mg (0.41 mmol) of the product of Step K of example 1 in dry N,N-Dimethylformamide (5 mL) was added triethylamine (248 mg, 2.46 mmol). After 5 min, (E)-pent-2-enoic acid (36 mg, 0.36 mmol) and HATU (234 mg, 0.61 mmol) was added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S,E)-1-amino-2-(1-(pent-2-enoyl)pyrrolidin-2-yl)-4-(4-(pyridin-2-ylcarbamoyl)phenyl)-1H-imidazole-5-carboxamide as an off-white solid (124 mg, 64%). $^1$H NMR (CDCl$_3$, 600 MHz) δ: 9.21 (s, 1H), 8.32 (d, J=8.3 Hz, 1H), 8.25 (d, J=4.1 Hz, 1H), 7.86 (d, J=7.8 Hz, 2H), 7.72-7.70 (m, 3H), 7.09 (s, 1H), 7.03-7.01 (m, 1H), 6.91-6.87 (m, 1H), 6.75 (s, 2H), 6.35 (s, 1H), 6.07 (d, J=15.1 Hz, 1H), 5.25 (d, J$_1$=7.6 Hz, J$_2$=5.0 Hz, 1H), 3.81-3.78 (m, 1H), 3.67-3.63 (m, 1H), 2.60-2.53 (m, 1H), 2.44-2.39 (m, 1H), 2.24-2.17 (m, 3H), 2.05-1.99 (m, 1H), 1.02 (t, J=7.4 Hz, 3H); $^{13}$C NMR (CDCl$_3$, 150 MHz) δ: 165.9, 165.7, 162.8, 151.8, 148.8, 148.7, 147.8, 141.7, 138.5, 138.4, 133.6, 129.7, 127.4, 120.4, 119.9, 119.3, 114.6, 51.2, 47.5, 30.8, 25.6, 25.5, 12.6. MS (ESI, m/z): 474.2 [M+H]$^+$.

Example 7: (S)-1-amino-2-(1-propioloylpyrrolidin-2-yl)-4-(4-(pyridin-2-ylcarbamoyl)phenyl)-1H-imidazole-5-carboxamide

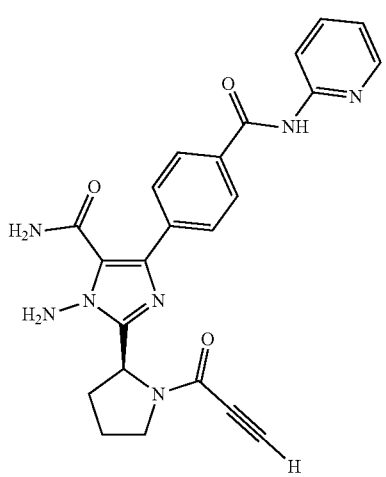 [SMILES: C#CC(=O)N1CCC[C@H]1c1nc(-c2ccc(C(=O)Nc3ccccn3)cc2)c(C(N)=O)n1N]

44

Preparation of (S)-1-amino-2-(1-propioloylpyrrolidin-2-yl)-4-(4-(pyridin-2-ylcarbamoyl)phenyl)-1H-imidazole-5-carboxamide

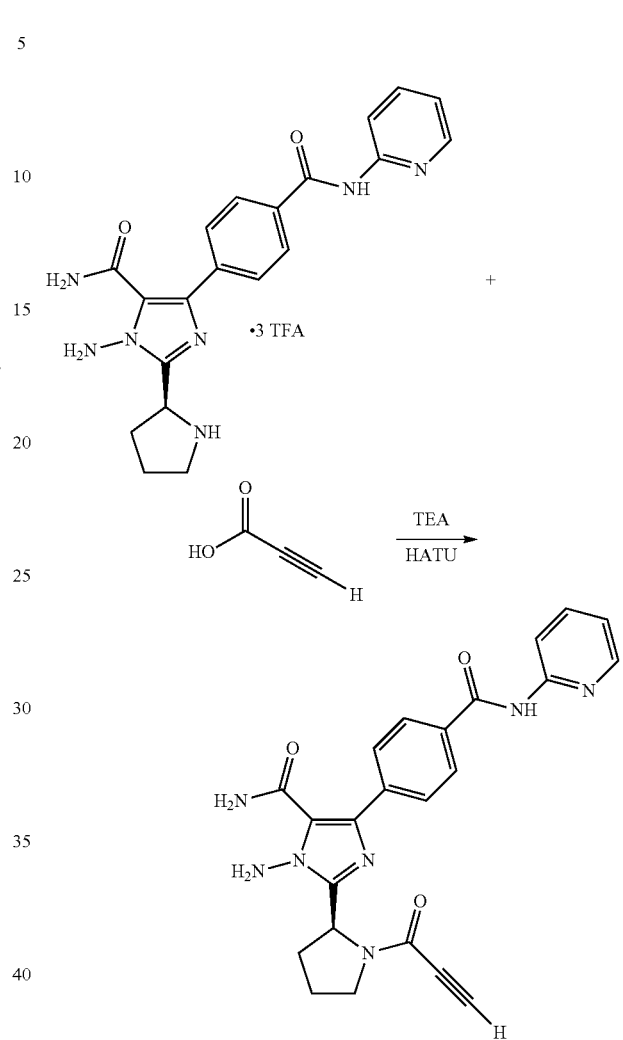

To the solution of 160 mg (0.41 mmol) of the product of Step K of example 1 in dry N,N-Dimethylformamide (5 mL) was added triethylamine (248 mg, 2.46 mmol). After 5 min, propiolic acid (25.2 mg, 0.36 mmol) and HATU (234 mg, 0.61 mmol) was added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (23:1) to give (S)-1-amino-2-(1-propioloylpyrrolidin-2-yl)-4-(4-(pyridin-2-ylcarbamoyl)phenyl)-1H-imidazole-5-carboxamide as a yellow solid (102 mg, 56%). $^1$H NMR (CDCl$_3$, 600 MHz) δ: 8.82 (s, 1H), 8.40 (d, J=8.3 Hz, 1H), 8.31 (d, J=3.8 Hz, 1H), 7.99-7.96 (m, 2H), 7.79-7.75 (m, 3H), 7.10-7.08 (m, 1H), 6.65-6.63 (m, 2H), 6.30 (s, 1H), 5.62 (s, 1H), 5.30 (dd, J$_1$=8.0 Hz, J$_2$=5.4 Hz, 1H), 3.92-3.90 (m, 2H), 3.10 (s, 1H), 2.59-2.47 (m, 2H), 2.38-2.32 (m, 1H), 2.07-2.02 (m, 1H); $^{13}$C NMR (CDCl$_3$, 150 MHz) δ: 165.4, 162.6, 152.2, 151.6, 147.9, 147.5, 141.5, 138.8, 138.4, 134.1, 129.9, 127.7, 120.2, 119.0, 114.5, 78.6, 76.4, 50.9, 49.3, 31.2, 25.0. MS (ESI, m/z): 444.1 [M+H]⁺.

Example 8: (S)-1-amino-2-(1-(but-2-ynoyl)pyrrolidin-2-yl)-4-(4-(pyridin-2-ylcarbamoyl)phenyl)-1H-imidazole-5-carboxamide

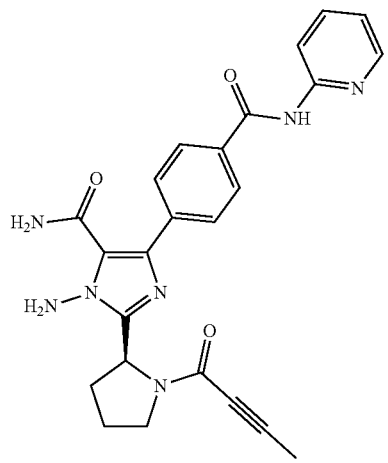 [SMILES: CC#CC(=O)N1CCC[C@H]1c1nc(-c2ccc(C(=O)Nc3ccccn3)cc2)c(C(N)=O)n1N]

Preparation of (S)-1-amino-2-(1-(but-2-ynoyl)pyrrolidin-2-yl)-4-(4-(pyridin-2-ylcarbamoyl)phenyl)-1H-imidazole-5-carboxamide

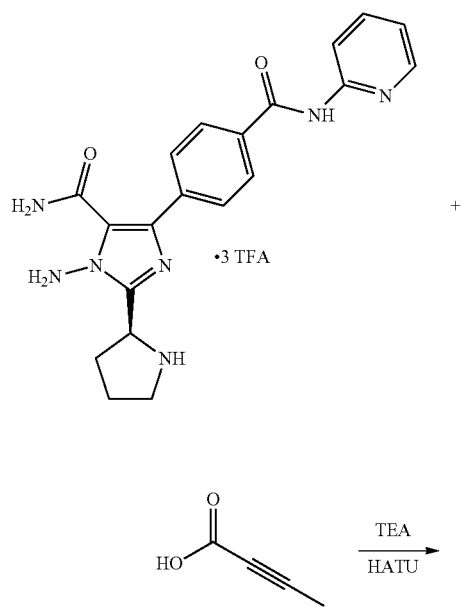

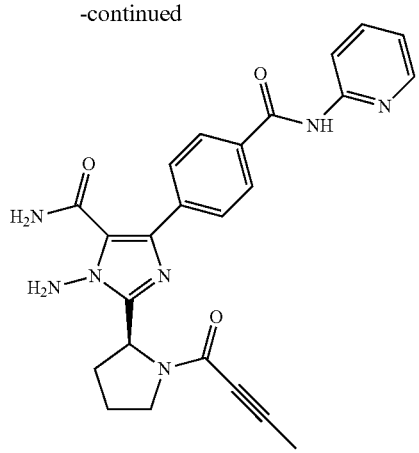

To the solution of 160 mg (0.41 mmol) of the product of Step K of example 1 in dry N,N-Dimethylformamide (5 mL) was added triethylamine (248 mg, 2.46 mmol). After 5 min, but-2-ynoic acid (30.2 mg, 0.36 mmol) and HATU (234 mg, 0.61 mmol) was added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na₂SO₄, filtered and concentrated. The residue was purified by chromatography with dichloromethane and methanol (23:1) to give (S)-1-amino-2-(1-(but-2-ynoyl)pyrrolidin-2-yl)-4-(4-(pyridin-2-ylcarbamoyl)phenyl)-1H-imidazole-5-carboxamide as an off-white solid (88 mg, 47%). ¹H NMR (CDCl₃, 400 MHz) δ: 8.66 (s, 1H), 8.40 (d, J=8.8 Hz, 1H), 8.32 (d, J=3.9 Hz, 1H), 7.97 (d, J=8.4 Hz, 2H), 7.86-7.75 (m, 3H), 7.10-7.08 (m, 1H), 6.70 (s, 2H), 6.43 (s, 1H), 5.51 (s, 1H), 5.28-5.25 (m, 1H), 3.88-3.85 (m, 2H), 2.59-2.47 (m, 2H), 2.37-2.30 (m, 1H), 2.05-2.00 (m, 4H); ¹³C NMR (DMSO, 100 MHz) δ: 165.7, 162.2, 152.3, 151.9, 148.3, 147.9, 138.1, 138.0, 136.3, 132.0, 127.7, 127.1, 124.7, 119.8, 114.7, 88.6, 74.3, 50.9, 48.5, 31.0, 23.8, 3.3. MS (ESI, m/z): 458.1 [M+H]⁺.

Example 9: (S)-1-amino-2-(1-cyanopyrrolidin-2-yl)-4-(4-(pyridin-2-ylcarbamoyl)phenyl)-1H-imidazole-5-carboxamide

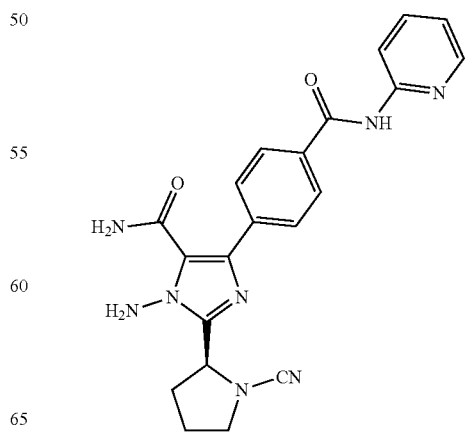

Preparation of (S)-1-amino-2-(1-cyanopyrrolidin-2-yl)-4-(4-(pyridin-2-ylcarbamoyl)phenyl)-1H-imidazole-5-carboxamide Example 10: (S)-2-(1-acryloylpyrrolidin-2-yl)-1-amino-4-(4-((4-methylpyridin-2-yl)carbamoyl)phenyl)-1H-imidazole-5-carboxamide

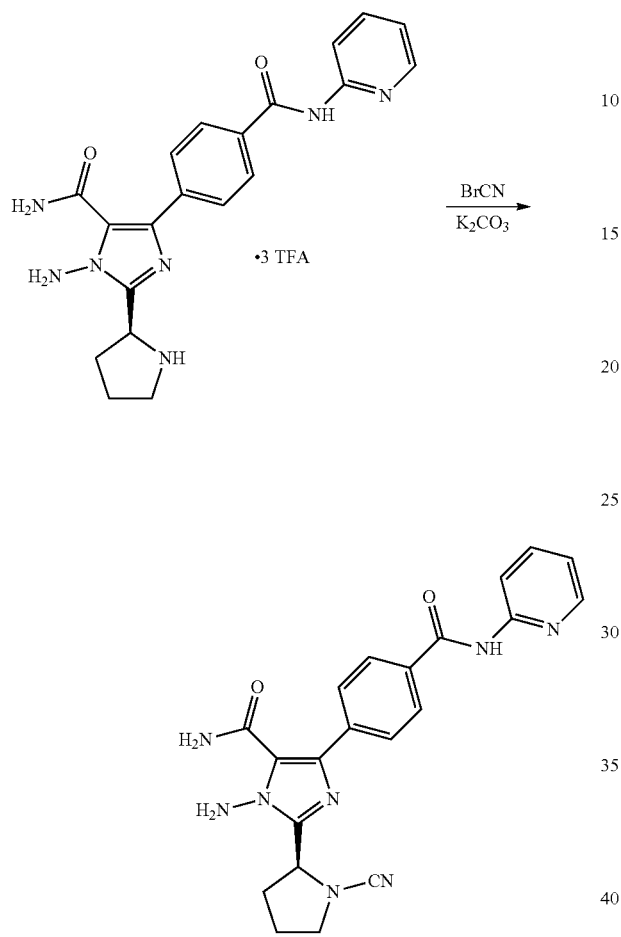

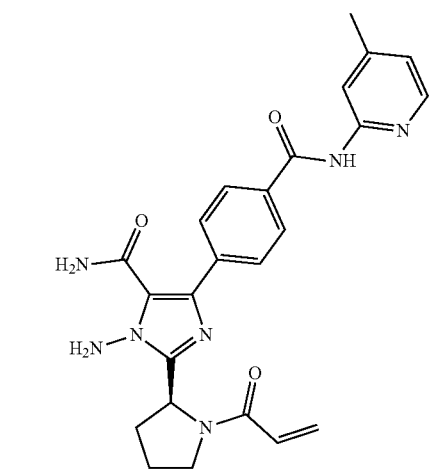 [SMILES: C=CC(=O)N1CCC[C@H]1c1nc(-c2ccc(C(=O)Nc3cc(C)ccn3)cc2)c(C(N)=O)n1N]

Step A: Preparation of (S)-ethyl 2-(1-(tert-butoxycarbonyl)pyrrolidin-2-yl)-4-(4-((4-methylpyridin-2-yl)carbamoyl)phenyl)-1H-imidazole-5-carboxylate

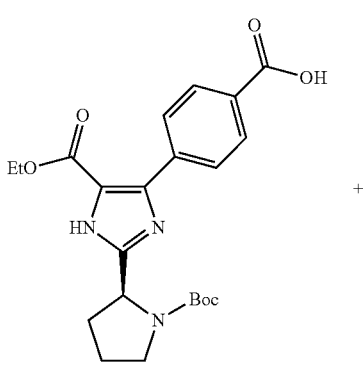

To the solution of 160 mg (0.41 mmol) of the product of Step K of example 1 in dry acetonitrile (5 mL) was added K₂CO₃ (170 mg, 1.23 mmol). After 5 min, BrCN (43.4 mg, 0.41 mmol) was added. The reaction mixture was continued to stir at room temperature for 6 h. Ethyl acetate and water were added. The layers were separated, and the aqueous phase was extracted with ethyl acetate. The combined organic phases were washed three times (3×50 mL) with brine solution. The organic phase was dried over anhydrous Na₂SO₄, filtered and concentrated. The residue was purified by chromatography with dichloromethane and methanol (25:1) to give (S)-1-amino-2-(1-cyanopyrrolidin-2-yl)-4-(4-(pyridin-2-ylcarbamoyl)phenyl)-1H-imidazole-5-carboxamide as a yellow solid (74 mg, 43%). $^1$H NMR (CDCl₃, 400 MHz) δ: 9.05 (s, 1H), 8.35 (d, J=8.4 Hz, 1H), 8.28 (d, J=4.2 Hz, 1H), 7.96 (d, J=8.2 Hz, 2H), 7.78-7.72 (m, 3H), 7.07 (dd, J₁=7.2 Hz, J₂=5.0 Hz, 1H), 6.19 (s, 1H), 5.93 (s, 1H), 5.71 (s, 2H), 5.20 (t, J=6.7 Hz, 1H), 3.69-3.64 (m, 1H), 3.56-3.51 (m, 1H), 2.54-2.46 (m, 1H), 2.32-2.22 (m, 2H), 2.07-1.99 (m, 1H); $^{13}$C NMR (CDCl₃, 150 MHz) δ: 165.4, 162.6, 151.7, 148.3, 148.0, 140.8, 138.7, 137.6, 134.4, 129.6, 128.0, 121.5, 120.2, 117.1, 114.5, 56.0, 51.3, 30.6, 25.5. MS (ESI, m/z): 417.1 [M+H]⁺.

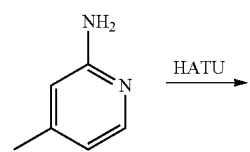

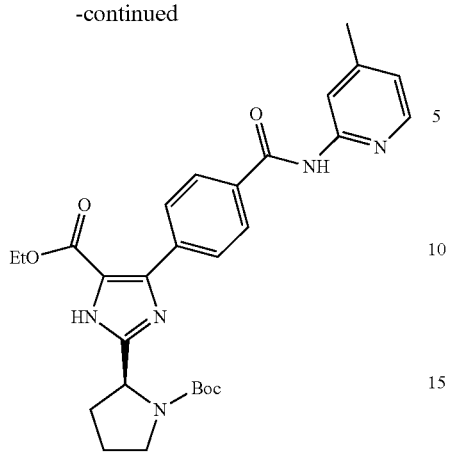
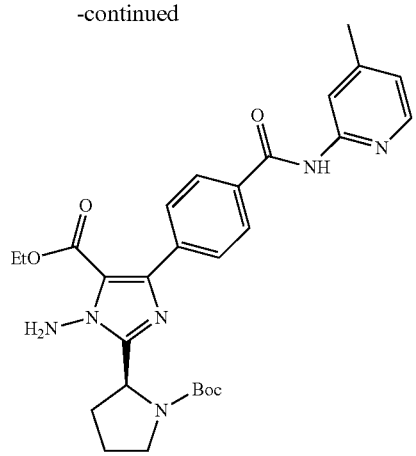

To the solution of 29.0 g (67 mmol) of the product of Step F of example 1 in dry N,N-dimethylformamide (250 mL) was stirred and added HATU (30.8 g, 81 mmol), diisopropylethylamine (58 mL, 337 mmol) and 4-methylpyridin-2-amine (10.9 g, 101 mmol). The reaction mixture was stirred at 80° C. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (2:1) to afford (S)-ethyl 2-(1-(tert-butoxycarbonyl)pyrrolidin-2-yl)-4-(4-((4-methylpyridin-2-yl)carbamoyl)phenyl)-1H-imidazole-5-carboxylate as white solid (25.0 g, 71%). $^1$H NMR (CDCl$_3$, 400 MHz) δ: 11.06 (s, 1H), 8.56 (s, 1H), 8.26 (s, 1H), 8.17-8.14 (m, 3H), 7.96 (d, J=8.3 Hz, 2H), 6.91 (d, J=4.9 Hz, 1H), 4.99-4.97 (m, 1H), 4.37-4.31 (m, 2H), 3.52-3.42 (m, 2H), 3.01-2.92 (m, 1H), 2.41 (s, 3H), 2.24-1.96 (m, 3H), 1.51 (s, 9H), 1.33 (t, J=7.0 Hz, 3H). MS (ESI, m/z): 520.2 [M+H]$^+$.

Step B: Preparation of (S)-ethyl 1-amino-2-(1-(tert-butoxycarbonyl)pyrrolidin-2-yl)-4-(4-((4-methylpyridin-2-yl)carbamoyl)phenyl)-1H-imidazole-5-carboxylate To the solution of 2.6 g (5.1 mmol) of the product of Step A in dry N,N-Dimethylformamide (25 mL) was stirred and slowly added lithium hexamethyldisilazane (6.1 mL, 1 M solution in tetrahydrofuran) at −10° C. After the mixture was stirred for 10 min, O-(diphenylphosphinyl) hydroxylamine (1.2 g, 5.1 mmol) was added at 0° C. and the resulting suspension was stirred 2 h at room temperature (in cases where the reaction mixture became too viscous, additional N,N-dimethylformamide was added). The reaction was quenched with brine and concentrated to dryness in vacuum. The residue was washed three times with ethyl acetate (3×50 mL). The combined organic fractions were dried with anhydrous Na$_2$SO$_4$ and the solvent was removed under reduced pressure to afford the crude residue, which was subjected to column chromatography with petroleum ether and ethyl acetate (2:1) to give the desired product (S)-ethyl 1-amino-2-(1-(tert-butoxycarbonyl)pyrrolidin-2-yl)-4-(4-((4-methylpyridin-2-yl)carbamoyl)phenyl)-1H-imidazole-5-carboxylate (1.5 g, 55%). $^1$H NMR (CDCl$_3$, 400 MHz) δ: 8.69 (s, 1H), 8.27 (s, 1H), 8.16 (d, J=5.1 Hz, 1H), 7.93 (d, J=8.3 Hz, 2H), 7.81 (d, J=8.4 Hz, 2H), 6.91 (d, J=4.8 Hz, 1H), 6.66 (s, 2H), 5.21-5.18 (m, 1H), 4.32-4.25 (m, 2H), 3.61-3.55 (m, 1H), 3.50-3.44 (m, 1H), 2.45-2.37 (m, 4H), 2.27-2.20 (m, 1H), 1.97-1.91 (m, 1H), 1.73-1.68 (m, 1H), 1.42 (s, 7H), 1.27-1.21 (m, 5H). MS (ESI, m/z): 535.2 [M+H]$^+$.

Step C: Preparation of (S)-1-amino-2-(1-(tert-butoxycarbonyl)pyrrolidin-2-yl)-4-(4-((4-methylpyridin-2-yl)carbamoyl)phenyl)-1H-imidazole-5-carboxylic acid

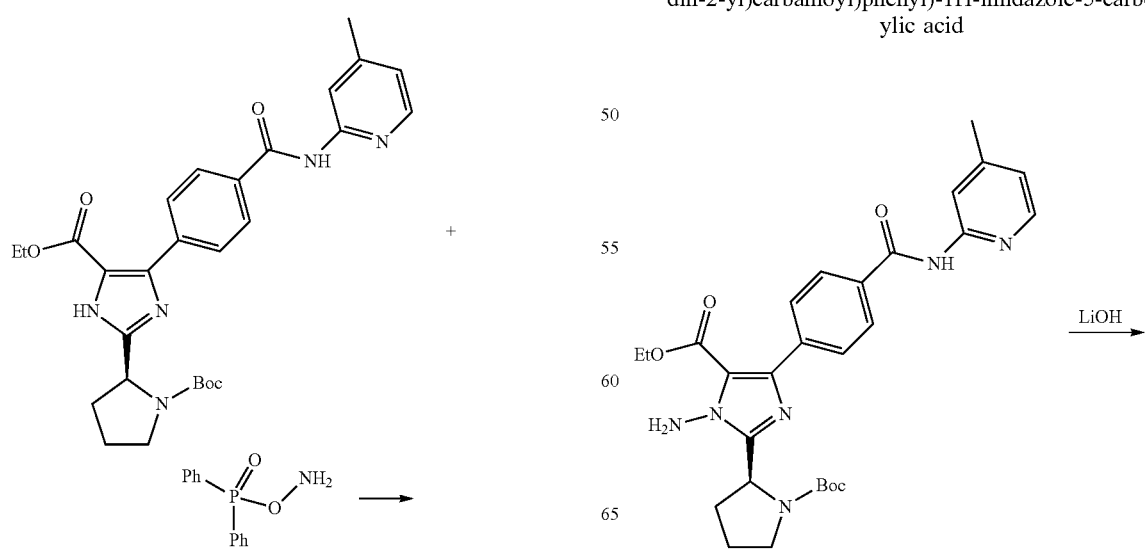

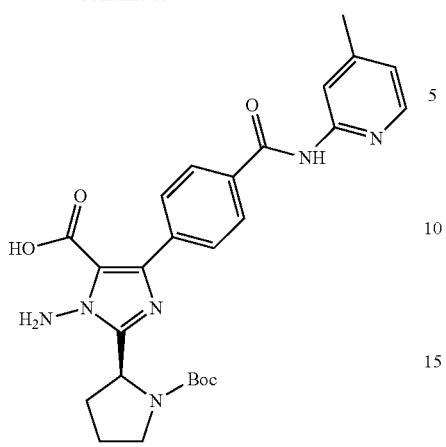

To the solution of 1.38 g (2.6 mmol) of the product of Step B in methanol (15 mL) was stirred and added aqueous lithium hydroxide (2 mol/L, 14 mL), then stirred at room temperature for 2 h. The reaction mixture was evaporated and diluted with water (100 mL) and acidified with aqueous HCl till pH 3. The mixture was washed with ethyl acetate three times (3×50 mL). The combined organic layers were concentrated under reduced pressure to afford (S)-1-amino-2-(1-(tert-butoxycarbonyl)pyrrolidin-2-yl)-4-(4-((4-methylpyridin-2-yl)carbamoyl)phenyl)-1H-imidazole-5-carboxylic acid as a white solid (1.02 g, 78%).

Step D: Preparation of (S)-tert-butyl 2-(1-amino-5-carbamoyl-4-(4-((4-methylpyridin-2-yl)carbamoyl)phenyl)-1H-imidazol-2-yl)pyrrolidine-1-carboxylate

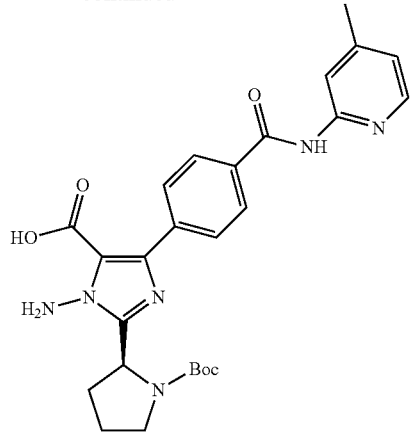

To the solution of 1.01 g (2.0 mmol) of the product of Step C in dry N,N-Dimethylformamide (15 mL) was stirred and added HATU (1.1 g, 2.9 mmol), diisopropylethylamine (1 mL, 5.9 mmol) and NH$_4$Cl (1.1 g, 20 mmol). The reaction mixture was stirred at room temperature for 2 h. The reaction mixture was quenched with brine and washed with ethyl acetate three times (3×50 mL). The combined organic layers were concentrated under reduced pressure and purified by flash chromatography with dichloromethane and methanol (30:1) to afford (S)-tert-butyl 2-(1-amino-5-carbamoyl-4-(4-((4-methylpyridin-2-yl)carbamoyl)phenyl)-1H-imidazol-2-yl)pyrrolidine-1-carboxylate as a white solid (0.91 g, 90%). $^1$H NMR (CDCl$_3$, 400 MHz) δ: 8.76 (s, 1H), 8.24 (s, 1H), 8.15 (d, J=5.0 Hz, 1H), 7.95 (d, J=8.2 Hz, 2H), 7.82 (d, J=8.1 Hz, 2H), 6.91 (d, J=4.8 Hz, 1H), 6.78 (s, 1H), 6.63 (s, 2H), 5.70 (s, 1H), 5.12-5.09 (m, 1H), 3.59-3.44 (m, 2H), 2.50-2.40 (m, 5H), 2.28-2.19 (m, 1H), 1.99-1.92 (m, 1H), 1.43 (s, 7H), 1.28 (s, 2H). MS (ESI, m/z): 506.2 [M+H]$^+$.

Step E: Preparation of (S)-1-amino-4-(4-((4-methylpyridin-2-yl)carbamoyl)phenyl)-2-(pyrrolidin-2-yl)-1H-imidazole-5-carboxamide

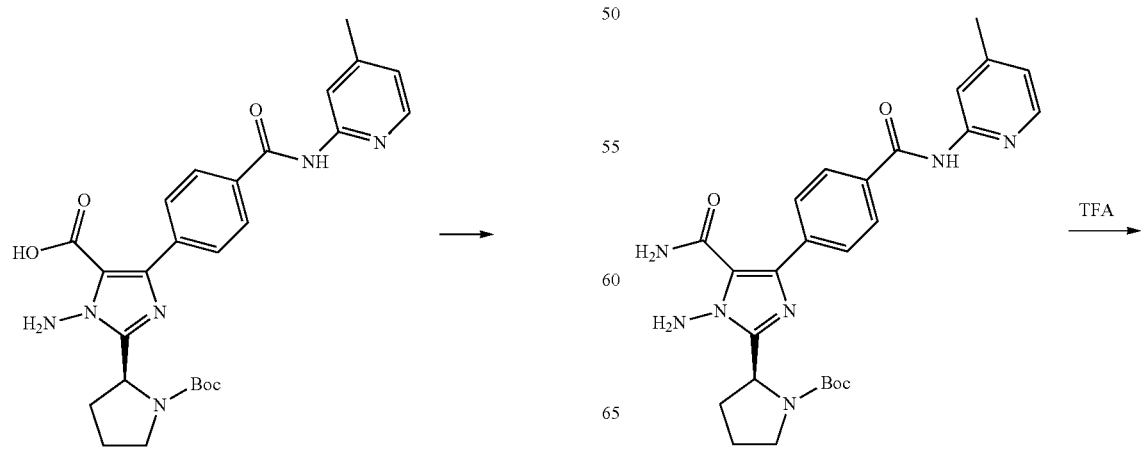

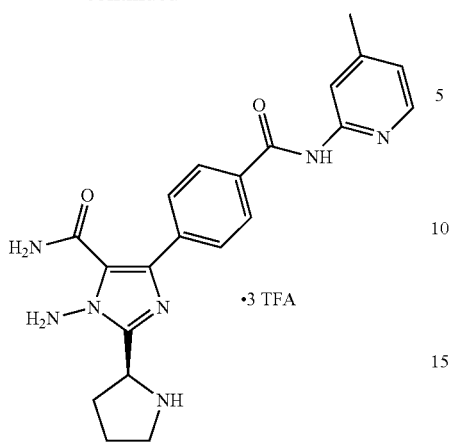

To the solution of 197 mg (0.39 mmol) of the product of Step D in dichloromethane (5 mL) was added trifluoroacetic acid (2.5 mL). The mixture was stirred at room temperature for 1 h and then concentrated to afford (S)-1-amino-4-(4-((4-methylpyridin-2-yl)carbamoyl)phenyl)-2-(pyrrolidin-2-yl)-1H-imidazole-5-carboxamide as a light yellow oil. MS (ESI, m/z): 406.1 [M+H]$^+$.

Step F: Preparation of (S)-2-(1-acryloylpyrrolidin-2-yl)-1-amino-4-(4-((4-methylpyridin-2-yl)carbamoyl)phenyl)-1H-imidazole-5-carboxamide

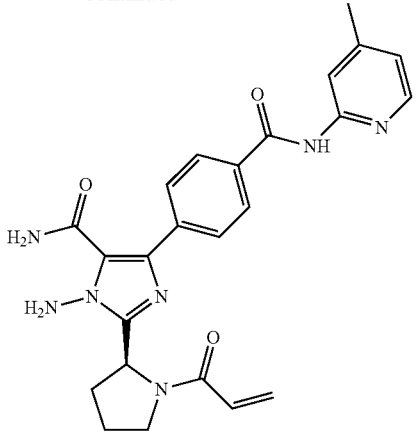

To the solution of 180 mg (0.44 mmol) of the product of Step E in dry dichloromethane (5 mL) was added diisopropylethylamine (344 mg, 2.67 mmol). After 5 min, acryloyl chloride (36.2 mg, 0.40 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by with chromatography dichloromethane and methanol (25:1) to give (S)-2-(1-acryloylpyrrolidin-2-yl)-1-amino-4-(4-((4-methylpyridin-2-yl)carbamoyl)phenyl)-1H-imidazole-5-carboxamide as an off-white solid (104 mg, 51%). $^1$H NMR (CDCl$_3$, 400 MHz) δ: 9.39 (s, 1H), 8.28 (s, 1H), 8.12 (d, J=4.8 Hz, 1H), 7.95 (d, J=8.3 Hz, 2H), 7.76 (d, J=8.3 Hz, 2H), 6.92 (d, J=4.8 Hz, 1H), 6.70 (s, 2H), 6.45 (dd, J$_1$=16.8 Hz, J$_2$=10.2 Hz, 1H), 6.31 (dd, J$_1$=16.8 Hz, J$_2$=1.9 Hz, 1H), 6.02 (s, 1H), 5.70 (dd, J$_1$=10.2 Hz, J$_2$=1.9 Hz, 1H), 5.32 (dd, J$_1$=8.0 Hz, J$_2$=5.0 Hz, 1H), 3.87-3.82 (m, 1H), 3.72-3.66 (m, 1H), 2.64-2.54 (m, 1H), 2.50-2.44 (m, 1H), 2.41 (s, 3H), 2.30-2.22 (m, 1H), 2.10-2.01 (m, 1H); $^{13}$C NMR (CDCl$_3$, 150 MHz) δ: 165.8, 165.1, 162.8, 151.5, 151.2, 148.4, 146.3, 141.6, 138.5, 133.7, 129.8, 128.6, 128.6, 127.7, 121.2, 119.1, 115.4, 51.3, 47.7, 30.8, 25.6, 21.7. MS (ESI, m/z): 460.2 [M+H]$^+$.

Example 11: (S)-1-amino-2-(1-methacryloylpyrrolidin-2-yl)-4-(4-((4-methylpyridin-2-yl)carbamoyl)phenyl)-1H-imidazole-5-carboxamide

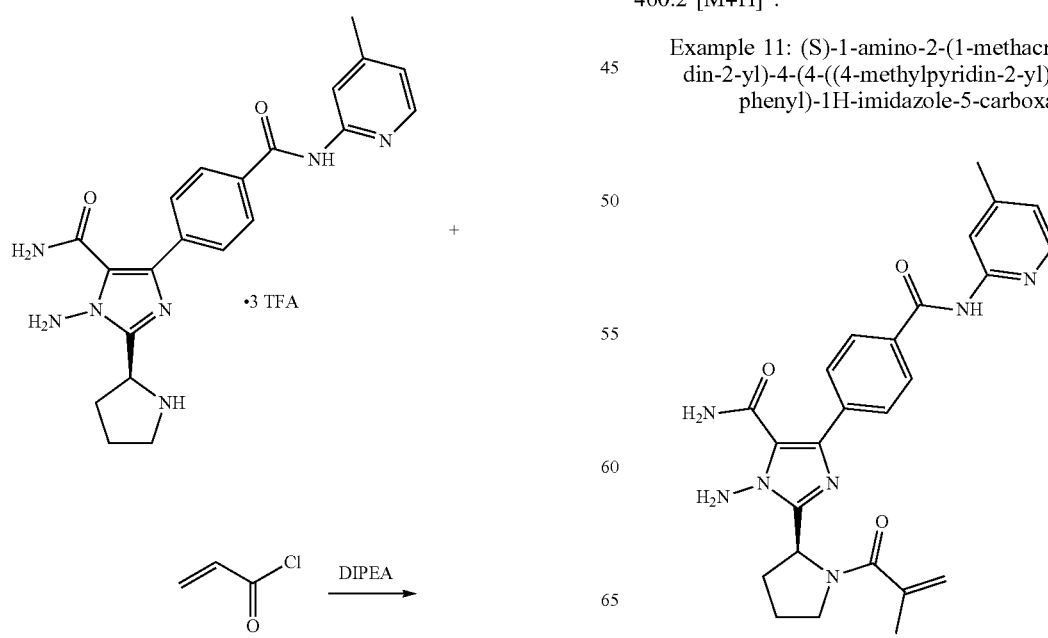

Preparation of (S)-1-amino-2-(1-methacryloylpyrrolidin-2-yl)-4-(4-((4-methylpyridin-2-yl)carbamoyl)phenyl)-1H-imidazole-5-carboxamide

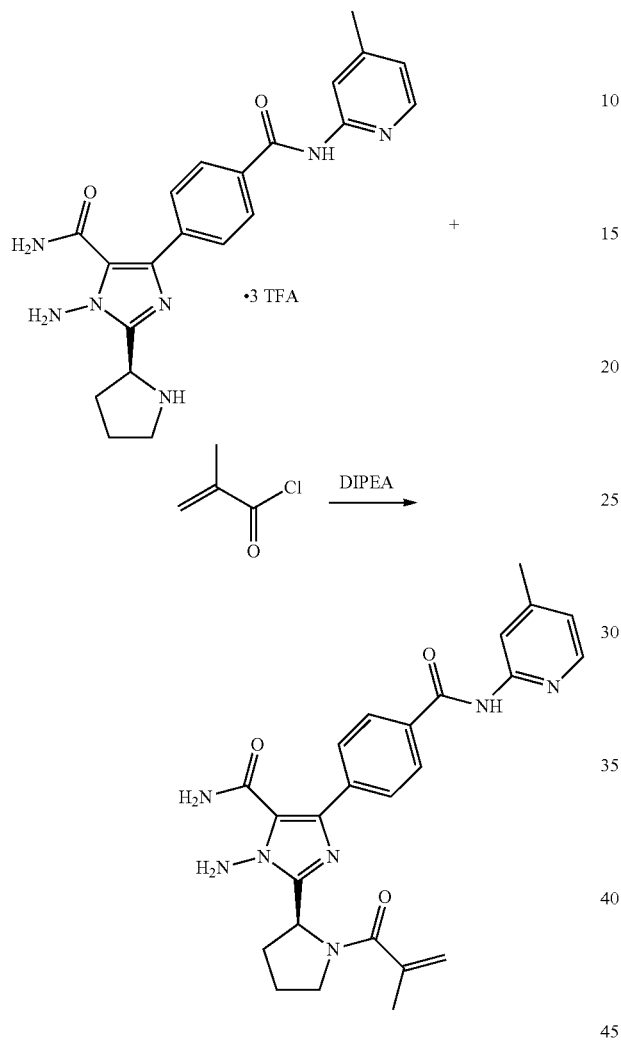

To the solution of 180 mg (0.44 mmol) of the product of Step E of example 10 in dry dichloromethane (5 mL) was added diisopropylethylamine (344 mg, 2.67 mmol). After 5 min, methacryloyl chloride (41.8 mg, 0.40 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-1-amino-2-(1-methacryloylpyrrolidin-2-yl)-4-(4-((4-methylpyridin-2-yl)carbamoyl)phenyl)-1H-imidazole-5-carboxamide as an off-white solid (110 mg, 52%). $^1$H NMR (CDCl$_3$, 600 MHz) δ: 9.09 (s, 1H), 8.21 (s, 1H), 8.11 (d, J=4.9 Hz, 1H), 7.91 (d, J=8.3 Hz, 2H), 7.71 (d, J=8.3 Hz, 2H), 6.88 (d, J=4.8 Hz, 1H), 6.72 (s, 2H), 6.67 (s, 1H), 6.24 (s, 1H), 5.29 (s, 1H), 5.26 (t, J=7.2 Hz, 1H), 5.21 (s, 1H), 3.77-3.69 (m, 2H), 2.57-2.51 (m, 1H), 2.38 (s, 3H), 2.34-2.27 (m, 2H), 1.95-1.87 (m, 4H); $^{13}$C NMR (CDCl$_3$, 150 MHz) δ: 171.2, 165.7, 162.8, 151.8, 150.1, 148.4, 147.4, 141.6, 140.7, 138.4, 133.9, 129.8, 127.6, 121.2, 119.2, 118.0, 115.1, 51.2, 50.0, 30.9, 25.9, 21.6, 19.8. MS (ESI, m/z): 474.2 [M+H]$^+$.

Example 12: (S)-1-amino-2-(1-(3-methylbut-2-enoyl)pyrrolidin-2-yl)-4-(4-((4-methylpyridin-2-yl)carbamoyl)phenyl)-1H-imidazole-5-carboxamide

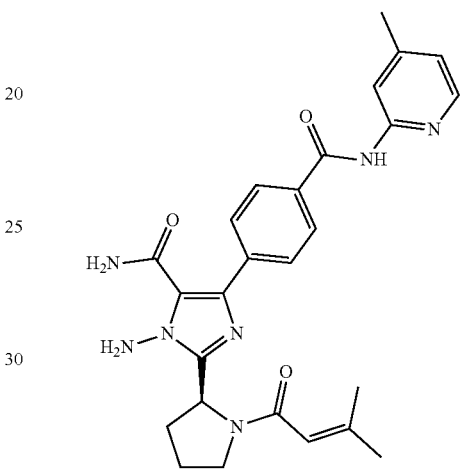

Preparation of (S)-1-amino-2-(1-(3-methylbut-2-enoyl)pyrrolidin-2-yl)-4-(4-((4-methylpyridin-2-yl)carbamoyl)phenyl)-1H-imidazole-5-carboxamide

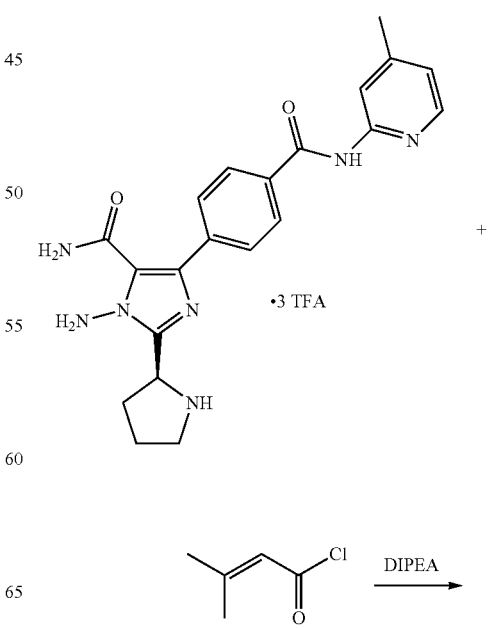

57
-continued

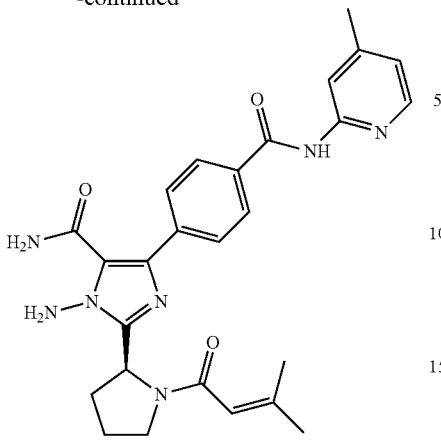

To the solution of 180 mg (0.44 mmol) of the product of Step E of example 10 in dry dichloromethane (5 mL) was added diisopropylethylamine (344 mg, 2.67 mmol). After 5 min, 3-methylbut-2-enoyl chloride (47.4 mg, 0.40 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(3-methylbut-2-enoyl)pyrrolidin-2-yl)-4-(4-((4-methylpyridin-2-yl)carbamoyl)phenyl)-1H-imidazole-5-carboxamide as an off-white solid (130 mg, 61%). $^1$H NMR (CDCl$_3$, 600 MHz) δ: 9.15 (s, 1H), 8.22 (s, 1H), 8.11 (d, J=5.1 Hz, 1H), 7.90 (d, J=8.3 Hz, 2H), 7.74 (d, J=8.3 Hz, 2H), 6.93 (s, 1H), 6.88 (d, J=4.9 Hz, 1H), 6.79 (s, 2H), 6.21 (s, 1H), 5.77 (s, 1H), 5.25 (dd, J$_1$=8.0 Hz, J$_2$=5.2 Hz, 1H), 3.74-3.70 (m, 1H), 3.61-3.57 (m, 1H), 2.54-2.42 (m, 2H), 2.38 (s, 3H), 2.26-2.20 (m, 1H), 2.03-1.98 (m, 4H), 1.83 (s, 3H); $^{13}$C NMR (CDCl$_3$, 150 MHz) δ: 166.9, 165.8, 162.8, 151.8, 150.9, 150.3, 148.8, 147.2, 141.7, 138.5, 133.7, 129.8, 127.5, 121.2, 119.1, 117.6, 115.1, 50.8, 48.0, 30.8, 27.2, 25.6, 21.6, 20.3. MS (ESI, m/z): 488.2 [M+H]$^+$.

Example 13: (S,E)-1-amino-2-(1-(but-2-enoyl)pyrrolidin-2-yl)-4-(4-((4-methyl-pyridin-2-yl)carbamoyl)phenyl)-1H-imidazole-5-carboxamide

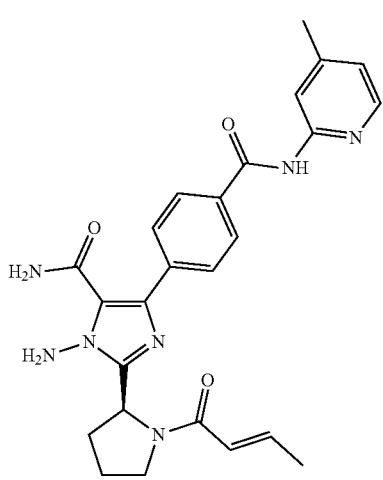 [SMILES: C/C=C/C(=O)N1CCC[C@H]1c1nc(-c2ccc(C(=O)Nc3cc(C)ccn3)cc2)c(C(N)=O)n1N]

58
Preparation of (S,E)-1-amino-2-(1-(but-2-enoyl)pyrrolidin-2-yl)-4-(4-((4-methyl-pyridin-2-yl)carbamoyl)phenyl)-1H-imidazole-5-carboxamide

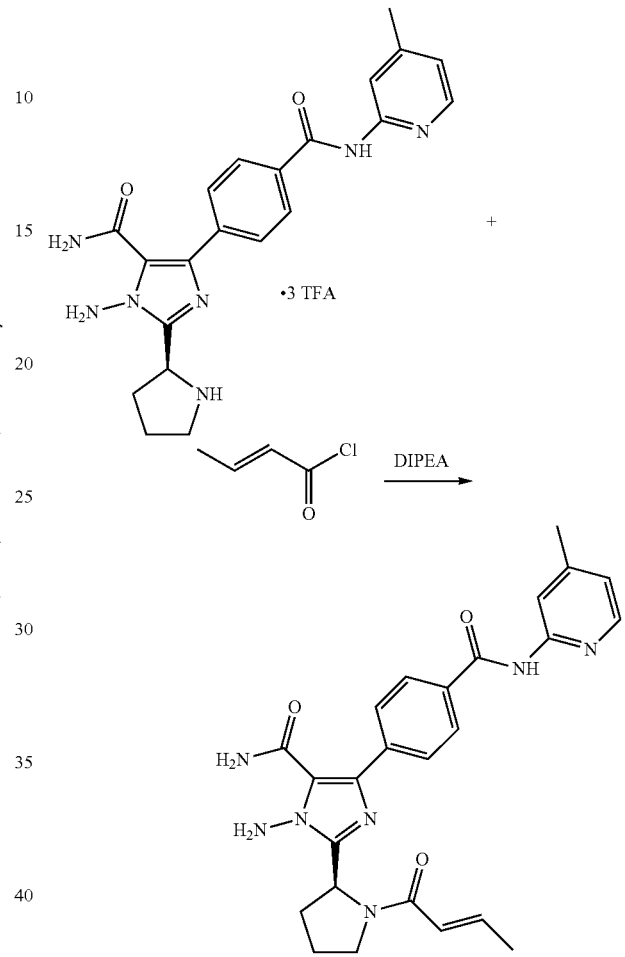

To the solution of 180 mg (0.44 mmol) of the product of Step E of example 10 in dry dichloromethane (5 mL) was added diisopropylethylamine (344 mg, 2.67 mmol). After 5 min, (E)-but-2-enoyl chloride (41.8 mg, 0.40 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S,E)-1-amino-2-(1-(but-2-enoyl)pyrrolidin-2-yl)-4-(4-((4-methylpyridin-2-yl)carbamoyl)phenyl)-1H-imidazole-5-carboxamide as an off-white solid (120 mg, 57%). $^1$H NMR (CDCl$_3$, 600 MHz) δ: 9.26 (s, 1H), 8.20 (s, 1H), 8.09 (d, J=5.0 Hz, 1H), 7.88 (d, J=8.3 Hz, 2H), 7.71 (d, J=8.3 Hz, 2H), 6.97 (s, 1H), 6.88-6.82 (m, 2H), 6.76 (s, 2H), 6.43 (s, 1H), 6.10 (dd, J$_1$=15.0 Hz, J$_2$=1.6 Hz, 1H), 5.25 (dd, J$_1$=8.0 Hz, J$_2$=4.7 Hz, 1H), 3.80-3.76 (m, 1H), 3.66-3.62 (m, 1H), 2.60-2.53 (m, 1H), 2.44-2.39 (m, 1H), 2.36 (s, 3H), 2.23-2.17 (m, 1H), 2.05-1.97 (m, 1H), 1.84 (dd, J$_1$=6.9 Hz, J$_2$=1.4 Hz, 3H); $^{13}$C NMR (CDCl$_3$, 150 MHz) δ:

165.9, 165.4, 162.9, 151.8, 150.2, 148.6, 147.2, 142.4, 141.6, 138.4, 133.7, 129.7, 127.5, 122.8, 121.1, 119.2, 115.1, 51.1, 47.5, 30.7, 25.5, 21.5, 18.3. MS (ESI, m/z): 474.2 [M+H]⁺.

Example 14: (S, E)-1-amino-2-(1-(2-cyano-3-cyclopropylacryloyl)pyrrolidin-2-yl)-4-(4-((4-methylpyridin-2-yl)carbamoyl)phenyl)-1H-imidazole-5-carboxamide

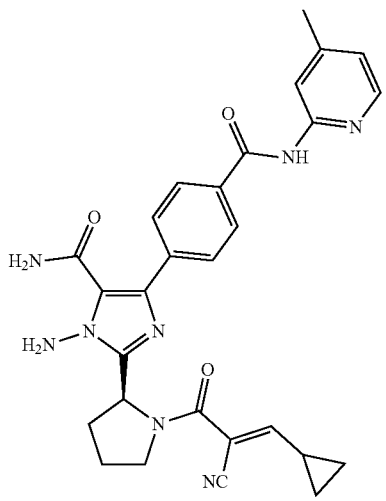 [SMILES: Cc1ccnc(NC(=O)c2ccc(-c3nc([C@@H]4CCCN4C(=O)/C(C#N)=C/C4CC4)n(N)c3C(N)=O)cc2)c1]

Step A: Preparation of (S)-1-amino-2-(1-(2-cyanoacetyl)pyrrolidin-2-yl)-4-(4-((4-methyl-pyridin-2-yl)carbamoyl)phenyl)-1H-imidazole-5-carboxamide

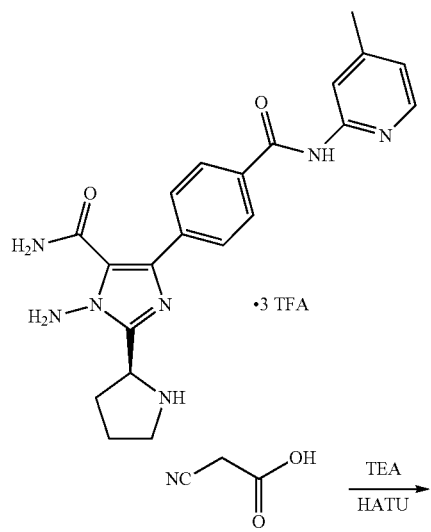

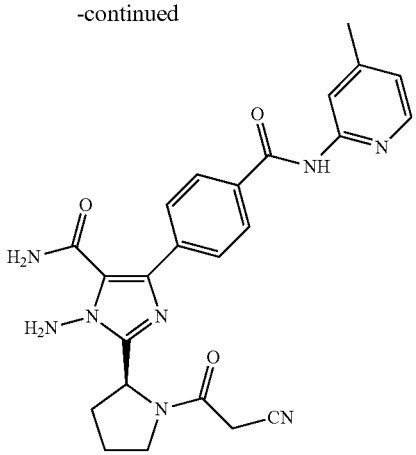

To the solution of 180 mg (0.44 mmol) of the product of Step E of example 10 in dry N,N-Dimethylformamide (5 mL) was added triethylamine (267 mg, 2.64 mmol). After 5 min, 2-cyanoacetic acid (33.6 mg, 0.40 mmol) and HATU (250 mg, 0.66 mmol) was added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na₂SO₄, filtered and concentrated. The residue was purified by chromatography with dichloromethane and methanol (23:1) to give (S)-1-amino-2-(1-(2-cyanoacetyl)pyrrolidin-2-yl)-4-(4-((4-methylpyridin-2-yl)carbamoyl)phenyl)-1H-imidazole-5-carboxamide as an off-white solid (80 mg, 38%). ¹H NMR (CDCl₃, 600 MHz) δ: 9.38 (s, 1H), 8.14 (s, 1H), 8.06 (d, J=4.9 Hz, 1H), 7.81 (d, J=7.5 Hz, 2H), 7.62 (d, J=7.6 Hz, 2H), 6.99 (s, 1H), 6.84 (d, J=5.0 Hz, 1H), 6.74 (s, 1H), 6.29 (s, 2H), 5.24-5.19 (m, 1H), 3.67-3.65 (m, 1H), 3.49-3.41 (m, 3H), 2.44-2.42 (m, 1H), 2.33 (s, 3H), 2.30-2.27 (m, 1H), 2.19-2.17 (m, 1H), 1.99-1.97 (m, 1H); ¹³C NMR (CDCl₃, 150 MHz) δ: 166.0, 162.9, 161.3, 151.8, 150.14, 148.5, 147.3, 141.1, 137.9, 133.7, 129.4, 127.5, 121.2, 120.3, 115.2, 114.2, 52.3, 48.0, 30.9, 26.3, 25.2, 21.5. MS (ESI, m/z): 473.1 [M+H]⁺.

Step B: Preparation of (S, E)-1-amino-2-(1-(2-cyano-3-cyclopropylacryloyl)pyrrolidin-2-yl)-4-(4-((4-methylpyridin-2-yl)carbamoyl)phenyl)-1H-imidazole-5-carboxamide

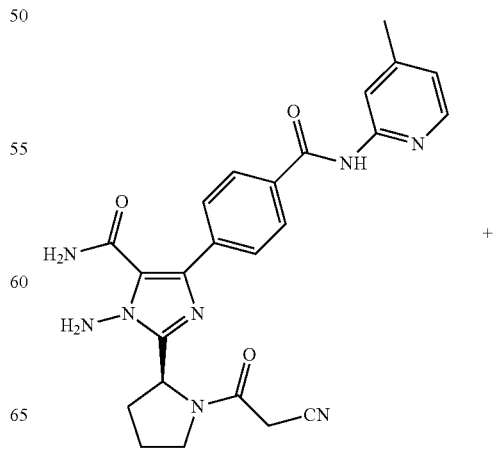

-continued

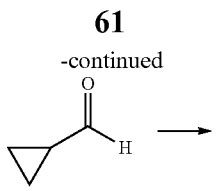

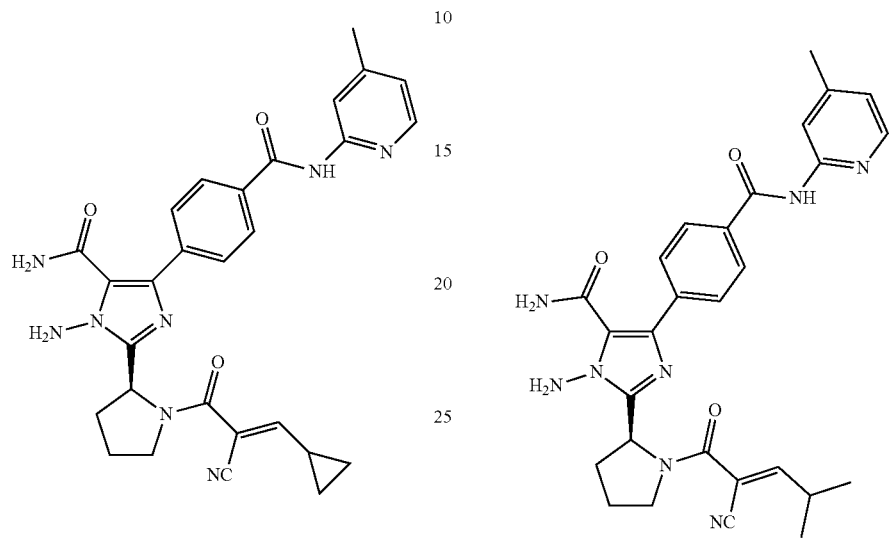

To the solution of cyclopropanecarbaldehyde (7.7 mg, 0.11 mmol) in dry dichloromethane (5 mL) at 0° C. were added pyrrolidine (45 μL, 0.55 mmol) and TMS-Cl (70 μL, 0.55 mmol). The ice bath was removed and the reaction mixture was stirred for 10 min followed by the additions of 50 mg (0.11 mmol) of the product of Step A. The reaction solution was stirred for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (27:1) to afford (S, E)-1-amino-2-(1-(2-cyano-3-cyclopropylacryloyl)pyrrolidin-2-yl)-4-(4-((4-methylpyridin-2-yl)carbamoyl)phenyl)-1H-imidazole-5-carboxamide as a white solid (31 mg, 54%). $^1$H NMR (CDCl$_3$, 600 MHz) δ: 9.01 (s, 1H), 8.22 (s, 1H), 8.12 (d, J=5.0 Hz, 1H), 7.93 (d, J=8.3 Hz, 2H), 7.73 (d, J=8.2 Hz, 2H), 6.89 (d, J=4.9 Hz, 1H), 6.79 (d, J=11.3 Hz, 1H), 6.58 (s, 2H), 6.38 (s, 1H), 6.13 (s, 1H), 5.32-5.30 (m, 1H), 4.06-4.02 (m, 1H), 3.94-3.90 (m, 1H), 2.50-2.44 (m, 2H), 2.39 (s, 3H), 2.32-2.28 (m, 1H), 2.11-2.05 (m, 1H), 2.04-1.99 (m, 1H) 1.26-1.22 (m, 2H), 0.89-0.87 (m, 2H); $^{13}$C NMR (CDCl$_3$, 150 MHz) δ: 167.8, 165.6, 162.9, 161.4, 151.7, 150.2, 147.9, 147.5, 141.5, 138.2, 134.1, 129.8, 127.7, 121.3, 118.9, 115.5, 115.0, 107.4, 53.0, 49.5, 30.7, 26.1, 21.6, 15.8, 11.1, 11.1. MS (ESI, m/z): 525.2 [M+H]$^+$.

Example 15: (S, E)-1-amino-2-(1-(2-cyano-4-methylpent-2-enoyl)pyrrolidin-2-yl)-4-(4-((4-methylpyridin-2-yl)carbamoyl)phenyl)-1H-imidazole-5-carboxamide Preparation of (S,E)-1-amino-2-(1-(2-cyano-4-methylpent-2-enoyl)pyrrolidin-2-yl)-4-(4-((4-methylpyridin-2-yl)carbamoyl)phenyl)-1H-imidazole-5-carboxamide

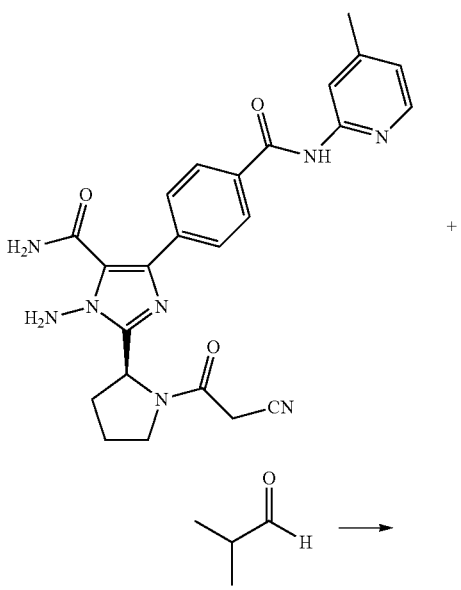

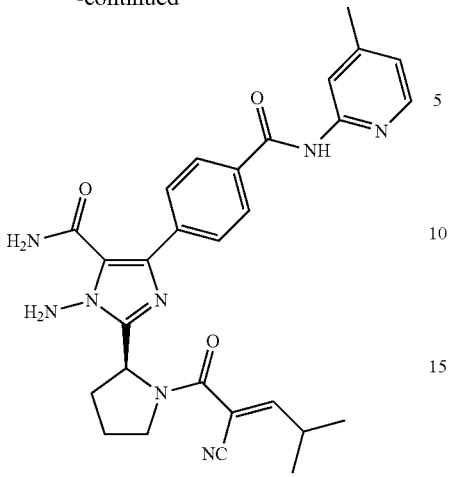

To the solution of isobutyraldehyde (7.9 mg, 0.11 mmol) in dry dichloromethane (5 mL) at 0° C. were added pyrrolidine (45 μL, 0.55 mmol) and TMS-Cl (70 μL, 0.55 mmol). The ice bath was removed and the reaction mixture was stirred for 10 min followed by the additions of 50 mg (0.11 mmol) of the product of Step A of example 14. The reaction solution was stirred for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (27:1) to afford (S, E)-1-amino-2-(1-(2-cyano-4-methylpent-2-enoyl)pyrrolidin-2-yl)-4-(4-((4-methylpyridin-2-yl)carbamoyl)phenyl)-1H-imidazole-5-carboxamide as a white solid (28 mg, 48%). $^1$H NMR (CDCl$_3$, 600 MHz) δ: 9.04 (s, 1H), 8.25 (s, 1H), 8.13 (d, J=4.8 Hz, 1H), 7.96 (d, J=7.9 Hz, 2H), 7.75 (d, J=7.9 Hz, 2H), 7.12 (d, J=10.4 Hz, 1H), 6.91 (d, J=4.6 Hz, 1H), 6.60 (s, 2H), 6.32 (s, 1H), 5.96 (s, 1H), 5.34-5.31 (m, 1H), 4.02-3.98 (m, 1H), 3.87-3.83 (m, 1H), 3.00-2.94 (m, 1H), 2.54-2.43 (m, 2H), 2.41 (s, 3H), 2.35-2.31 (m, 1H), 2.05-1.99 (m, 1H), 1.12 (t, J=7.0 Hz, 6H); $^{13}$C NMR (CDCl$_3$, 150 MHz) δ: 167.2, 165.5, 162.8, 161.4, 151.6, 150.6, 147.7, 147.2, 141.5, 138.2, 134.1, 129.9, 127.8, 121.4, 118.9, 115.1, 114.2, 109.5, 52.9, 49.6, 31.6, 30.8, 26.1, 21.7, 21.6, 21.5. MS (ESI, m/z): 527.2 [M+H]$^+$.

Example 16: (S,E)-1-amino-4-(4-((4-methylpyridin-2-yl)carbamoyl)phenyl)-2-(1-(pent-2-enoyl)pyrrolidin-2-yl)-1H-imidazole-5-carboxamide

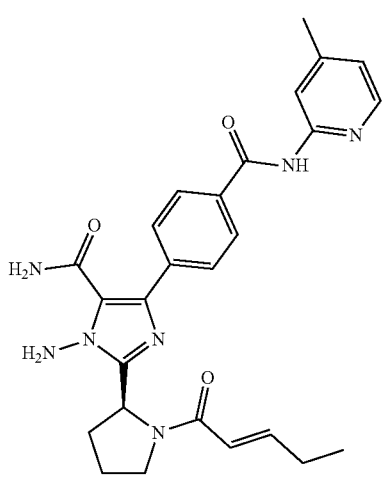 [SMILES: CC/C=C/C(=O)N1CCC[C@H]1c1nc(-c2ccc(C(=O)Nc3cc(C)ccn3)cc2)c(C(N)=O)n1N]

Preparation of (S,E)-1-amino-4-(4-((4-methylpyridin-2-yl)carbamoyl)phenyl)-2-(1-(pent-2-enoyl)pyrrolidin-2-yl)-1H-imidazole-5-carboxamide

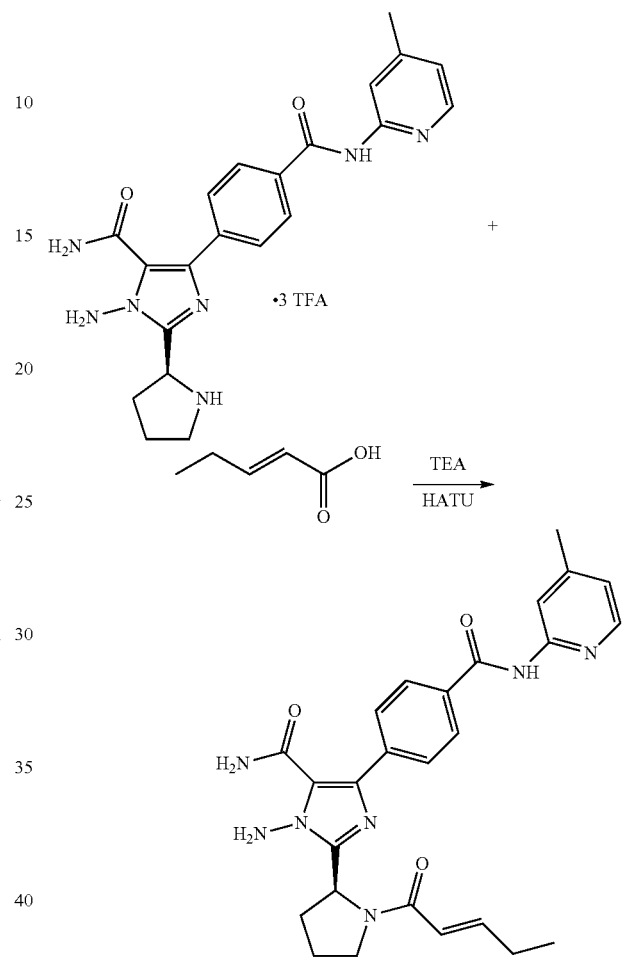

To the solution of 180 mg (0.44 mmol) of the product of Step E of example 10 in dry N,N-Dimethylformamide (5 mL) was added triethylamine (267 mg, 2.64 mmol). After 5 min, (E)-pent-2-enoic acid (40.1 mg, 0.40 mmol) and HATU (250 mg, 0.66 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S,E)-1-amino-4-(4-((4-methylpyridin-2-yl)carbamoyl)phenyl)-2-(1-(pent-2-enoyl)pyrrolidin-2-yl)-1H-imidazole-5-carboxamide as an off-white solid (95 mg, 44%). $^1$H NMR (CDCl$_3$, 600 MHz) δ: 9.24 (s, 1H), 8.17 (s, 1H), 8.08 (d, J=5.0 Hz, 1H), 7.85 (d, J=8.2 Hz, 2H), 7.71 (d, J=8.2 Hz, 2H), 7.07 (s, 1H), 6.91-6.85 (m, 2H), 6.76 (s, 2H), 6.47 (s, 1H), 6.06 (d, J=15.2 Hz, 1H), 5.24 (dd, J$_1$=7.9 Hz, J$_2$=4.8 Hz, 1H), 3.81-3.77 (m, 1H), 3.67-3.63 (m, 1H), 2.60-2.53 (m, 1H), 2.44-2.39 (m, 1H), 2.35 (s, 3H), 2.23-2.16 (m, 3H), 2.05-1.99 (m, 1H) 1.02 (t, J=7.4 Hz, 3H); $^{13}$C NMR (CDCl$_3$, 150 MHz) δ: 165.9, 165.6, 162.9, 151.8, 150.1, 148.7, 148.6, 147.3, 141.7, 138.4, 133.7, 129.7, 127.4, 121.1, 120.4, 119.2, 115.1, 51.2, 47.5, 30.7, 25.6, 25.5, 21.5, 12.6. MS (ESI, m/z): 488.2 [M+H]$^+$.

Example 17: (S)-1-amino-4-(4-((4-methylpyridin-2-yl)carbamoyl)phenyl)-2-(1-propioloylpyrrolidin-2-yl)-1H-imidazole-5-carboxamide

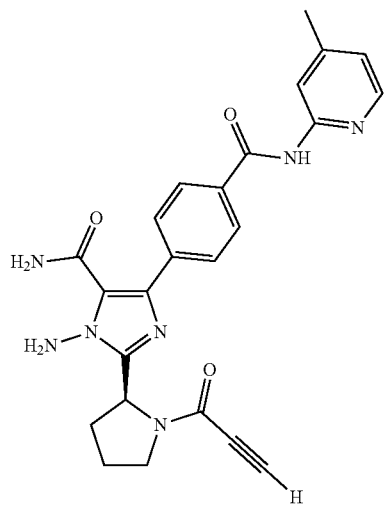 [SMILES: C#CC(=O)N1CCC[C@H]1c1nc(-c2ccc(C(=O)Nc3cc(C)ccn3)cc2)c(C(N)=O)n1N]

Preparation of (S)-1-amino-4-(4-((4-methylpyridin-2-yl)carbamoyl)phenyl)-2-(1-propioloylpyrrolidin-2-yl)-1H-imidazole-5-carboxamide

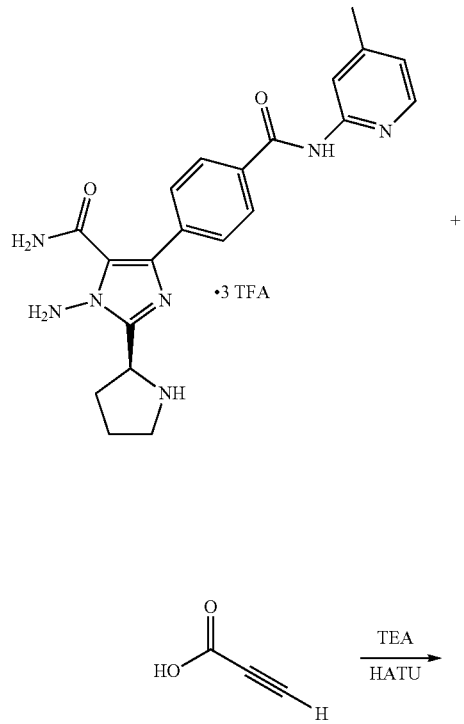

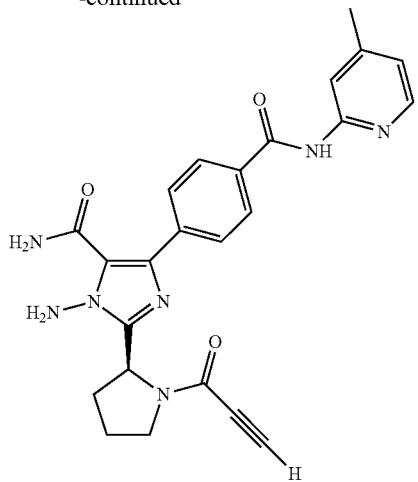

To the solution of 180 mg (0.44 mmol) of the product of Step E of example 10 in dry N,N-Dimethylformamide (5 mL) was added triethylamine (267 mg, 2.64 mmol). After 5 min, propiolic acid (28.2 mg, 0.40 mmol) and HATU (250 mg, 0.66 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (23:1) to give (S)-1-amino-4-(4-((4-methylpyridin-2-yl)carbamoyl)phenyl)-2-(1-propioloylpyrrolidin-2-yl)-1H-imidazole-5-carboxamide as a yellow solid (112 mg, 55%). $^1$H NMR (CDCl$_3$, 600 MHz) δ: 9.30 (s, 1H), 8.18 (s, 1H), 8.09 (d, J=5.0 Hz, 1H), 7.88 (d, J=8.2 Hz, 2H), 7.68 (d, J=8.1 Hz, 2H), 6.86 (d, J=5.0 Hz, 1H), 6.64 (s, 1H), 6.46 (s, 2H), 6.33 (s, 1H), 5.24-5.22 (m, 1H), 3.89-3.83 (m, 2H), 3.07 (s, 1H), 2.47-2.39 (m, 2H), 2.37 (s, 3H), 2.33-2.28 (m, 1H), 2.01-1.96 (m, 1H); $^{13}$C NMR (CDCl$_3$, 150 MHz) δ: 165.8, 163.0, 152.0, 151.8, 150.1, 147.9, 147.4, 141.3, 138.1, 133.9, 129.6, 127.7, 121.2, 119.7, 115.1, 78.8, 76.4, 51.2, 49.3, 31.3, 24.9, 21.6. MS (ESI, m/z): 458.1 [M+H]$^+$.

Example 18: (S)-1-amino-2-(1-(but-2-ynoyl)pyrrolidin-2-yl)-4-(4-((4-methylpyridin-2-yl)carbamoyl)phenyl)-1H-imidazole-5-carboxamide

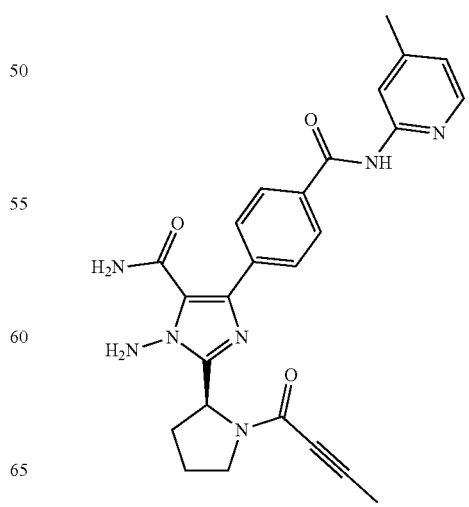

Preparation of (S)-1-amino-2-(1-(but-2-ynoyl)pyrrolidin-2-yl)-4-(4-((4-methylpyridin-2-yl)carbamoyl)phenyl)-1H-imidazole-5-carboxamide

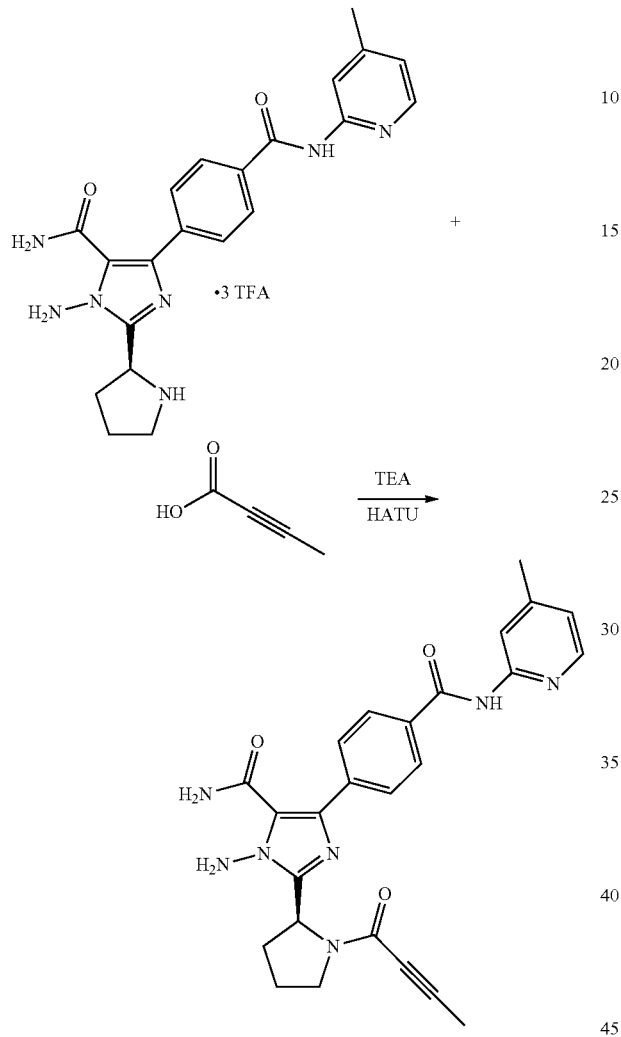

To the solution of 180 mg (0.44 mmol) of the product of Step E of example 10 in dry N,N-Dimethylformamide (5 mL) was added triethylamine (267 mg, 2.64 mmol). After 5 min, but-2-ynoic acid (33.6 mg, 0.40 mmol) and HATU (250 mg, 0.66 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (23:1) to give (S)-1-amino-2-(1-(but-2-ynoyl)pyrrolidin-2-yl)-4-(4-((4-methylpyridin-2-yl)carbamoyl)phenyl)-1H-imidazole-5-carboxamide as an off-white solid (102 mg, 49%). $^1$H NMR (CDCl$_3$, 600 MHz) δ: 8.79 (s, 1H), 8.24 (s, 1H), 8.15 (d, J=3.7 Hz, 1H), 7.95 (d, J=7.6 Hz, 2H), 7.77 (d, J=7.5 Hz, 2H), 6.91 (d, J=4.1 Hz, 1H), 6.66 (s, 2H), 6.48 (s, 1H), 5.70 (s, 1H), 5.27-5.25 (m, 1H), 3.86 (t, J=6.4 Hz, 2H), 2.56-2.46 (m, 2H), 2.40 (s, 3H), 2.34-2.29 (m, 1H), 2.04-1.99 (m, 4H); $^{13}$C NMR (CDCl$_3$, 150 MHz) δ: 165.5, 162.7, 153.5, 151.7, 150.3, 147.8, 147.6, 141.5, 138.4, 134.1, 129.9, 127.6, 121.3, 119.1, 114.9, 89.2, 74.1, 50.7, 49.1, 31.2, 25.0, 21.6, 4.1. MS (ESI, m/z): 472.2 [M+H]$^+$.

Example 19: (S)-2-(1-acryloylpyrrolidin-2-yl)-1-amino-4-(4-((5-methylpyridin-2-yl)carbamoyl)phenyl)-1H-imidazole-5-carboxamide Step A: Preparation of (S)-ethyl 2-(1-(tert-butoxycarbonyl)pyrrolidin-2-yl)-4-(4-((5-methylpyridin-2-yl)carbamoyl)phenyl)-1H-imidazole-5-carboxylate

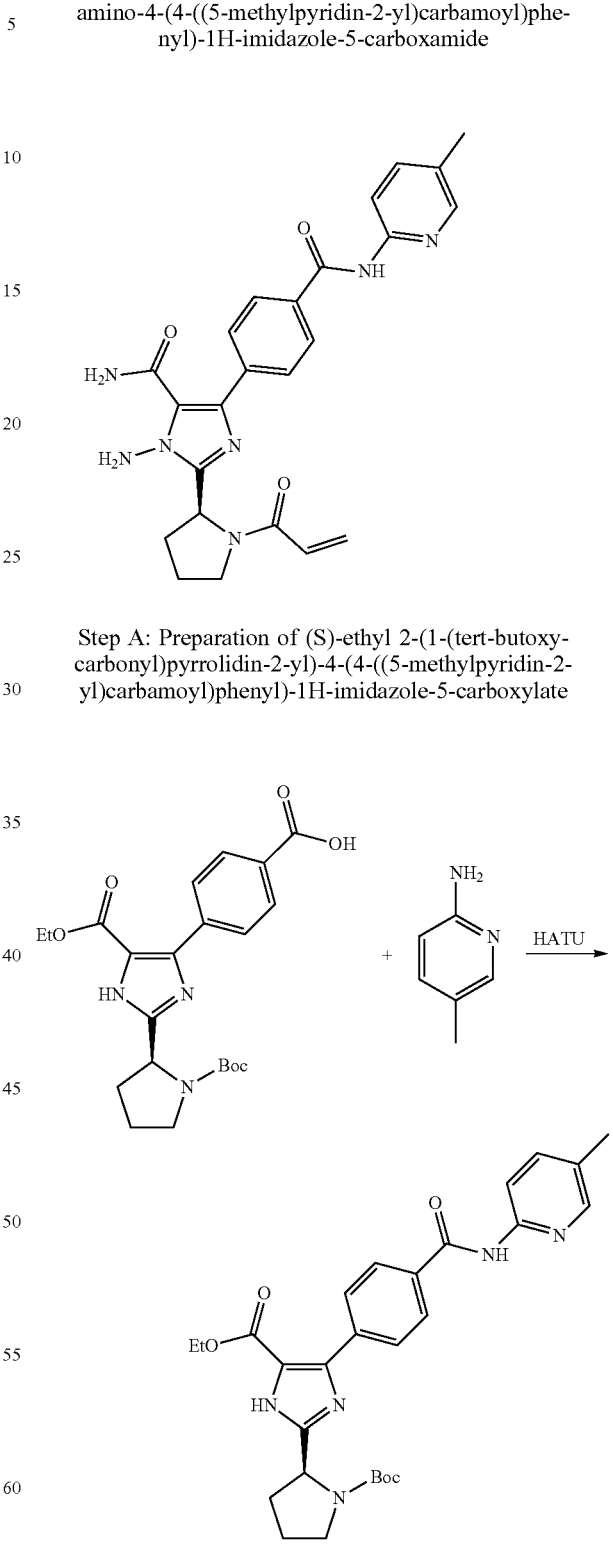

To the solution of 30 g (70 mmol) of the product of Step F of example 1 in dry N, N-Dimethylformamide (250 mL) was stirred and added HATU (32 g, 84 mmol), diisopropylethylamine (60 mL, 350 mmol) and 5-methylpyridin-2-amine (11.3 g, 105 mmol). The reaction mixture was stirred at 80° C. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (2:1) to afford (S)-ethyl 2-(1-(tert-butoxycarbonyl)pyrrolidin-2-yl)-4-(4-((5-methylpyridin-2-yl)carbamoyl)phenyl)-1H-imidazole-5-carboxylate as white solid (28 g, 77%). ¹H NMR (CDCl₃, 400 MHz) δ: 10.98 (m, 1H), 8.80 (s, 1H), 8.28 (d, J=8.5 Hz, 1H), 8.15 (s, 1H), 7.97 (d, J=8.3 Hz, 2H), 7.83 (d, J=8.4 Hz, 2H), 7.59-7.56 (m, 1H), 5.34-5.31 (m, 1H), 4.25 (q, J=7.0 Hz, 2H), 3.54-3.35 (m, 2H), 2.76-2.63 (m, 2H), 2.35 (s, 3H), 2.22-2.18 (m, 1H), 1.99-1.84 (m, 1H), 1.48 (s, 7H), 1.25-1.20 (m, 5H). MS (ESI, m/z): 520.2 [M+H]⁺.

Step B: Preparation of (S)-ethyl 1-amino-2-(1-(tert-butoxycarbonyl)pyrrolidin-2-yl)-4-(4-((5-methylpyridin-2-yl)carbamoyl)phenyl)-1H-imidazole-5-carboxylate quenched with brine and concentrated to dryness in vacuum. The residue was washed three times with ethyl acetate (3×100 mL). The combined organic fractions were dried with Na₂SO₄ and the solvent was removed under reduced pressure to afford the crude residue, which was subjected to column chromatography with petroleum ether and ethyl acetate (2:1) to give the desired product (S)-ethyl 1-amino-2-(1-(tert-butoxycarbonyl)pyrrolidin-2-yl)-4-(4-((5-methylpyridin-2-yl)carbamoyl)phenyl)-1H-imidazole-5-carboxylate (1.7 g, 62%). ¹H NMR (CDCl₃, 400 MHz) δ: 8.74 (s, 1H), 8.29 (d, J=8.5 Hz, 1H), 8.08 (s, 1H), 7.91 (d, J=8.3 Hz, 2H), 7.79 (d, J=8.4 Hz, 2H), 7.57 (dd, J₁=8.5 Hz, J₂=2.0 Hz, 1H), 6.66 (s, 2H), 5.20-5.17 (m, 1H), 4.26 (q, J=7.0 Hz, 2H), 3.60-3.43 (m, 2H), 2.46-2.34 (m, 2H), 2.30 (s, 3H), 2.25-2.17 (m, 1H), 1.95-1.90 (m, 1H), 1.41 (s, 7H), 1.26-1.20 (m, 5H). MS (ESI, m/z): 535.2 [M+H]⁺.

Step C: Preparation of (S)-1-amino-2-(1-(tert-butoxycarbonyl)pyrrolidin-2-yl)-4-(4-((5-methylpyridin-2-yl)carbamoyl)phenyl)-1H-imidazole-5-carboxylic acid

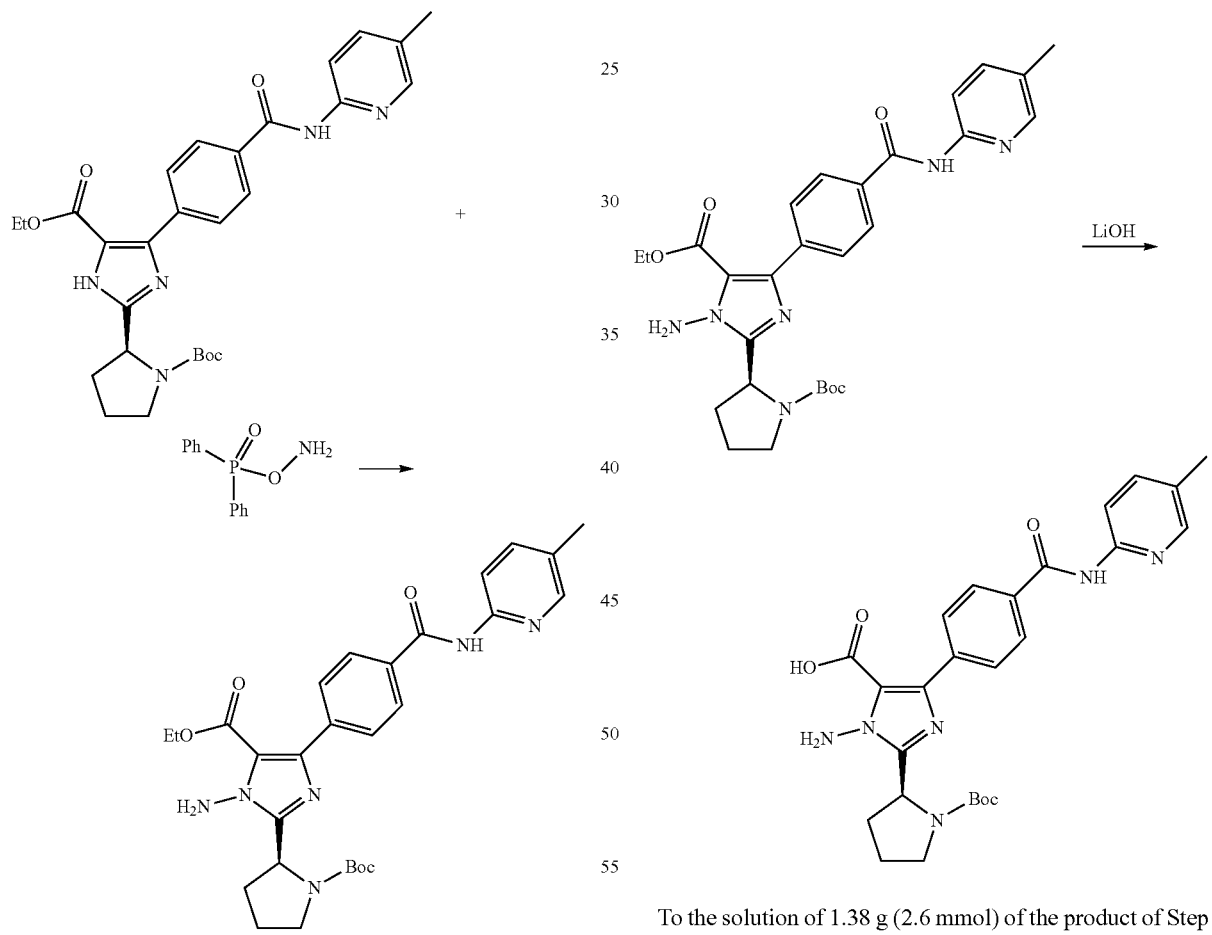

To the solution of 2.6 g (5.1 mmol) of the product of Step A in dry N, N-Dimethylformamide (25 mL) was stirred and slowly added lithium hexamethyldisilazane (6.1 mL, 1 M solution in tetrahydrofuran) at −10° C. After the mixture was stirred for 10 min, O-(diphenylphosphinyl) hydroxylamine (1.2 g, 5.1 mmol) was added at 0° C. and the resulting suspension was stirred 2 h at room temperature (in cases where the reaction mixture became too viscous, additional N, N-dimethylformamide was added). The reaction was To the solution of 1.38 g (2.6 mmol) of the product of Step B in methanol (15 mL) was added aqueous lithium hydroxide (2 mol/L, 14 mL), then stirred at room temperature for 2 h. The reaction mixture was evaporated and diluted with water (100 mL) and acidified with aqueous HCl till pH 3. The mixture was washed with ethyl acetate three times (3×100 mL). The combined organic layers were concentrated under reduced pressure to afford (S)-1-amino-2-(1-(tert-butoxycarbonyl)pyrrolidin-2-yl)-4-(4-((5-methylpyridin-2-yl)carbamoyl)phenyl)-1H-imidazole-5-carboxylic acid as a white solid (1.18 g, 90%).

Step D: Preparation of (S)-tert-butyl 2-(1-amino-5-carbamoyl-4-(4-((5-methylpyridin-2-yl)carbamoyl)phenyl)-1H-imidazol-2-yl)pyrrolidine-1-carboxylate Step E: Preparation of (S)-1-amino-4-(4-((5-methylpyridin-2-yl)carbamoyl)phenyl)-2-(pyrrolidin-2-yl)-1H-imidazole-5-carboxamide

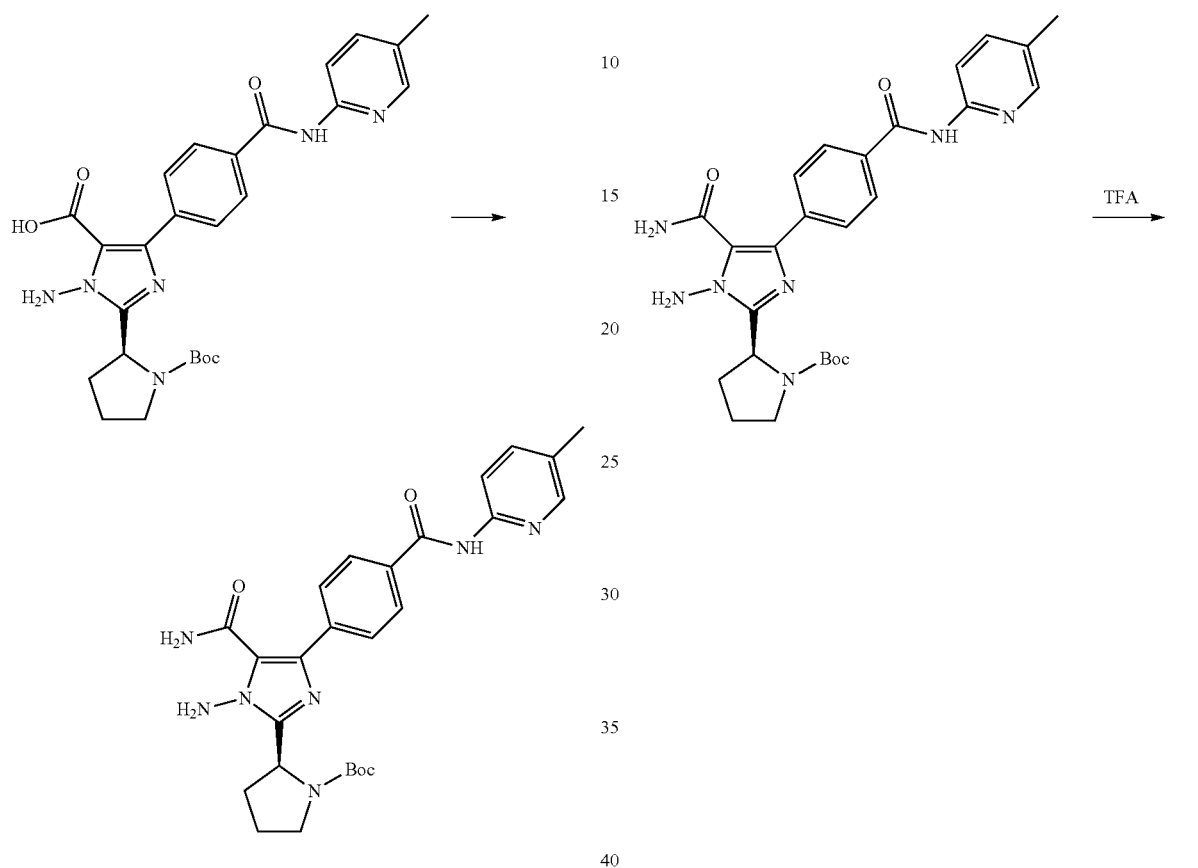

To the solution of 1.01 g (2.0 mmol) of the product of Step C in dry N, N-dimethylformamide (15 mL) was stirred and added HATU (1.1 g, 2.9 mmol), diisopropylethylamine (1 mL, 5.9 mmol) and NH$_4$Cl (1.1 g, 20 mmol). The reaction mixture was stirred at room temperature for 2 h. The reaction mixture was quenched with brine and washed with ethyl acetate three times (3×100 mL). The combined organic layers were concentrated under reduced pressure and purified by flash chromatography with dichloromethane and methanol (30:1) to afford (S)-tert-butyl 2-(1-amino-5-carbamoyl-4-(4-((5-methylpyridin-2-yl)carbamoyl)phenyl)-1H-imidazol-2-yl)pyrrolidine-1-carboxylate as a white solid (0.76 g, 75%). $^1$H NMR (CDCl$_3$, 600 MHz) δ: 8.71 (s, 1H), 8.26-8.25 (m, 1H), 8.13 (s, 1H), 7.97-7.92 (m, 2H), 7.82-7.72 (m, 2H), 7.62-7.60 (m, 1H), 6.85 (s, 1H), 6.65 (s, 2H), 5.52 (s, 1H), 5.17-5.09 (m, 1H), 3.57-3.46 (m, 2H), 2.47-2.41 (m, 2H), 2.33 (s, 3H), 2.26-2.20 (m, 1H), 1.98-1.94 (m, 1H), 1.43 (s, 8H), 1.29 (s, 1H). MS (ESI, m/z): 506.2 [M+H]$^+$.

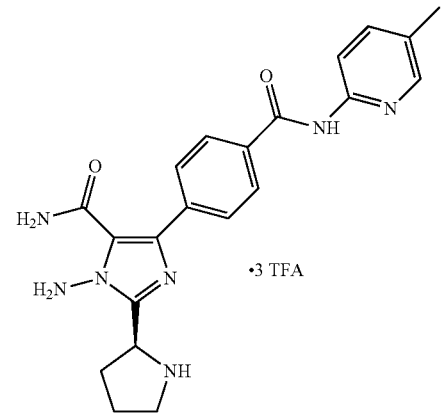

To the solution of 197 mg (0.39 mmol) of the product of Step D in dichloromethane (5 mL) was added trifluoroacetic acid (2.5 mL). The mixture was stirred at room temperature for 1 h and then concentrated to afford (S)-1-amino-4-(4-((5-methylpyridin-2-yl)carbamoyl)phenyl)-2-(pyrrolidin-2-yl)-1H-imidazole-5-carboxamide as a light yellow oil. MS (ESI, m/z): 406.1 [M+H]$^+$.

Step F: Preparation of (S)-2-(1-acryloylpyrrolidin-2-yl)-1-amino-4-(4-((5-methylpyridin-2-yl)carbamoyl)phenyl)-1H-imidazole-5-carboxamide

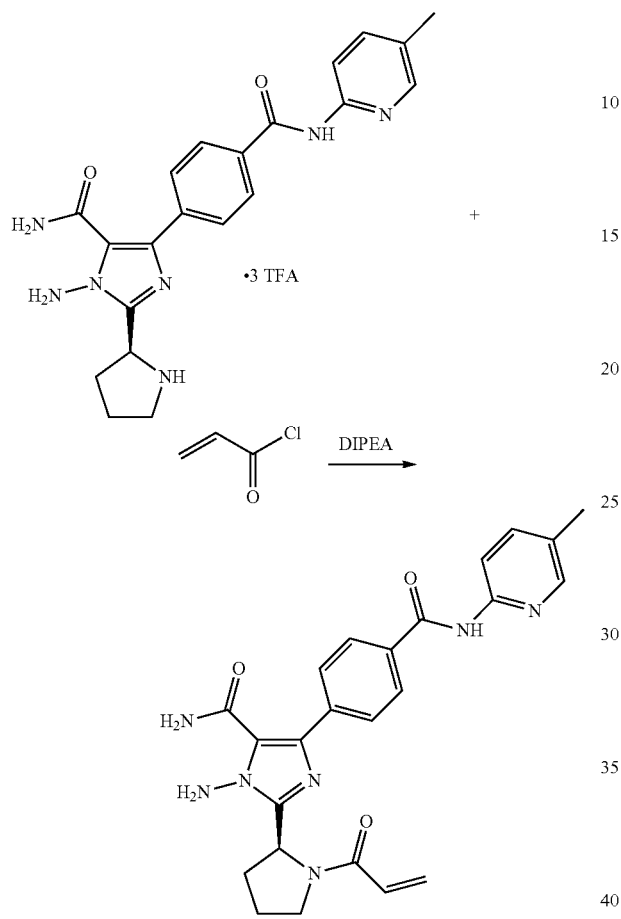

To the solution of 145 mg (0.35 mmol) of the product of Step E in dry dichloromethane (5 mL) was added diisopropylethylamine (275 mg, 2.13 mmol). After 5 min, acryloyl chloride (28.9 mg, 0.32 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-2-(1-acryloyl-pyrrolidin-2-yl)-1-amino-4-(4-((5-methylpyridin-2-yl)carbamoyl)phenyl)-1H-imidazole-5-carboxamide as an off-white solid (70 mg, 44%). $^1$H NMR (CDCl$_3$, 600 MHz) δ: 9.22 (s, 1H), 8.19 (d, J=8.4 Hz, 1H), 8.04 (d, J=1.6 Hz, 1H), 7.82 (d, J=8.3 Hz, 2H), 7.66 (d, J=8.3 Hz, 2H), 7.51 (dd, J$_1$=8.5 Hz, J$_2$=2.0 Hz, 1H), 6.95 (s, 1H), 6.70 (s, 2H), 6.52 (s, 1H), 6.42 (dd, J$_1$=16.7 Hz, J$_2$=10.3 Hz, 1H), 6.29 (dd, J$_1$=16.7 Hz, J$_2$=1.7 Hz, 1H), 5.67 (dd, J$_1$=10.3 Hz, J$_2$=1.7 Hz, 1H), 5.29-5.27 (m, 1H), 3.83-3.79 (m, 1H), 3.68-3.64 (m, 1H), 2.56-2.50 (m, 1H), 2.42-2.37 (m, 1H), 2.25-2.19 (m, 4H), 2.05-1.98 (m, 1H); $^{13}$C NMR (CDCl$_3$, 150 MHz) δ: 165.7, 165.0, 162.9, 149.6, 148.5, 147.7, 141.5, 139.0, 138.1, 133.7, 129.6, 129.3, 128.6, 128.5, 127.4, 119.4, 114.1, 51.4, 47.6, 30.8, 25.5, 17.9. MS (ESI, m/z): 460.2 [M+H]$^+$.

Example 20: (S)-1-amino-2-(1-methacryloylpyrrolidin-2-yl)-4-(4-((5-methylpyridin-2-yl)carbamoyl)phenyl)-1H-imidazole-5-carboxamide

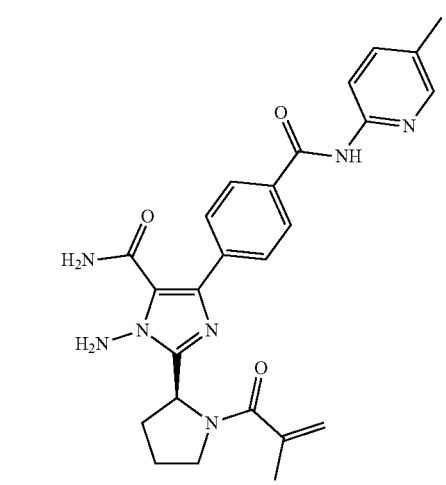 [SMILES: C=C(C)C(=O)N1CCC[C@H]1c1nc(-c2ccc(C(=O)Nc3ccc(C)cn3)cc2)c(C(N)=O)n1N]

Preparation of (S)-1-amino-2-(1-methacryloylpyrrolidin-2-yl)-4-(4-((5-methylpyridin-2-yl)carbamoyl)phenyl)-1H-imidazole-5-carboxamide

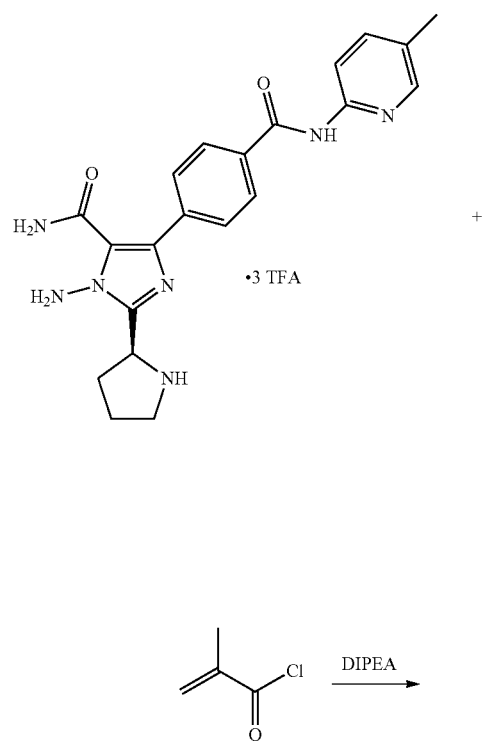

-continued

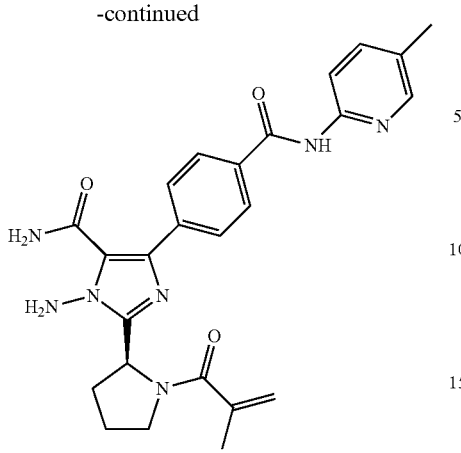

To the solution of 145 mg (0.35 mmol) of the product of Step E of example 19 in dry dichloromethane (5 mL) was added diisopropylethylamine (275 mg, 2.13 mmol). After 5 min, methacryloyl chloride (33.4 mg, 0.32 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-methacryloylpyrrolidin-2-yl)-4-(4-((5-methylpyridin-2-yl)carbamoyl)phenyl)-1H-imidazole-5-carboxamide as an off-white solid (102 mg, 61%). $^1$H NMR (CDCl$_3$, 600 MHz) δ: 9.28 (s, 1H), 8.19 (d, J=8.4 Hz, 1H), 8.03 (s, 1H), 7.83 (d, J=8.2 Hz, 2H), 7.64 (d, J=8.2 Hz, 2H), 7.51 (dd, J$_1$=8.4 Hz, J$_2$=1.9 Hz, 1H), 6.87 (s, 1H), 6.67 (s, 2H), 6.53 (s, 1H), 5.27 (s, 1H), 5.25-5.23 (m, 1H), 5.20 (s, 1H), 3.75-3.67 (m, 2H), 2.52-2.45 (m, 1H), 2.31-2.25 (m, 5H), 1.92-1.85 (m, 4H); $^{13}$C NMR(CDCl$_3$, 150 MHz) δ: 171.1, 165.7, 162.9, 149.6, 148.6, 147.6, 141.5, 140.6, 139.1, 138.1, 133.7, 129.5, 129.3, 127.5, 119.5, 118.0, 114.1, 51.2, 50.0, 30.9, 25.8, 19.7, 17.9. MS (ESI, m/z): 474.2 [M+H]$^+$.

Example 21: (S)-1-amino-2-(1-(3-methylbut-2-enoyl)pyrrolidin-2-yl)-4-(4-((5-methylpyridin-2-yl)carbamoyl)phenyl)-1H-imidazole-5-carboxamide

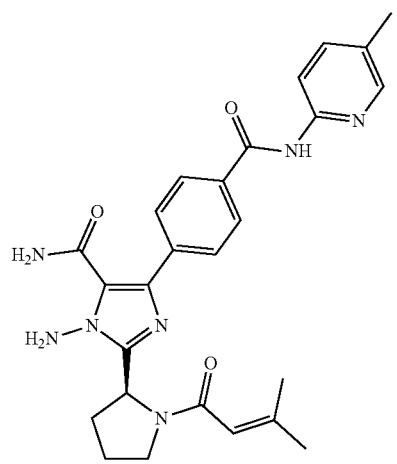 [SMILES: CC(C)=CC(=O)N1CCC[C@H]1c1nc(-c2ccc(C(=O)Nc3ccc(C)cn3)cc2)c(C(N)=O)n1N]

Preparation of (S)-1-amino-2-(1-(3-methylbut-2-enoyl)pyrrolidin-2-yl)-4-(4-((5-methylpyridin-2-yl)carbamoyl)phenyl)-1H-imidazole-5-carboxamide

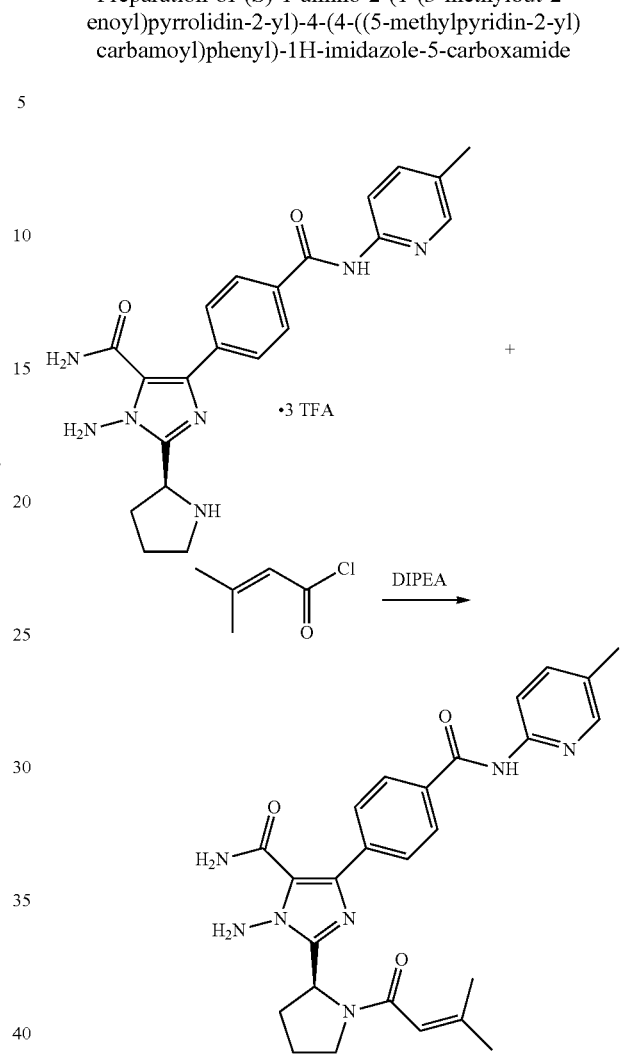

To the solution of 145 mg (0.35 mmol) of the product of Step E of example 19 in dry dichloromethane (5 mL) was added diisopropylethylamine (275 mg, 2.13 mmol). After 5 min, 3-methylbut-2-enoyl chloride (37.9 mg, 0.32 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(3-methylbut-2-enoyl)pyrrolidin-2-yl)-4-(4-((5-methylpyridin-2-yl)carbamoyl)phenyl)-1H-imidazole-5-carboxamide as an off-white solid (98 mg, 57%). $^1$H NMR (CDCl$_3$, 600 MHz) δ: 9.24 (s, 1H), 8.19 (d, J=8.5 Hz, 1H), 8.03 (s, 1H), 7.80 (d, J=8.3 Hz, 2H), 7.65 (d, J=8.3 Hz, 2H), 7.50 (dd, J$_1$=8.6 Hz, J$_2$=2.1 Hz, 1H), 7.11 (s, 1H), 6.73 (s, 2H), 6.51 (s, 1H), 5.75 (s, 1H), 5.22 (dd, J$_1$=8.0 Hz, J$_2$=5.2 Hz, 1H), 3.72-3.68 (m, 1H), 3.58-3.54 (m, 1H), 2.48-2.42 (m, 1H), 2.41-2.35 (m, 1H), 2.24-2.17 (m, 4H), 1.99-1.94 (m, 4H), 1.80 (s, 3H); $^{13}$C NMR (CDCl$_3$, 150 MHz) δ: 166.9, 165.8, 162.9, 150.9, 149.6, 149.0, 147.7, 141.6, 139.0, 138.2, 133.6, 129.6, 129.2, 127.3, 119.4, 117.6, 114.1, 50.8, 47.9, 30.8, 27.1, 25.5, 20.3, 17.9. MS (ESI, m/z): 488.2 [M+H]$^+$.

Example 22: (S,E)-1-amino-2-(1-(but-2-enoyl)pyrrolidin-2-yl)-4-(4-((5-methyl-pyridin-2-yl)carbamoyl)phenyl)-1H-imidazole-5-carboxamide

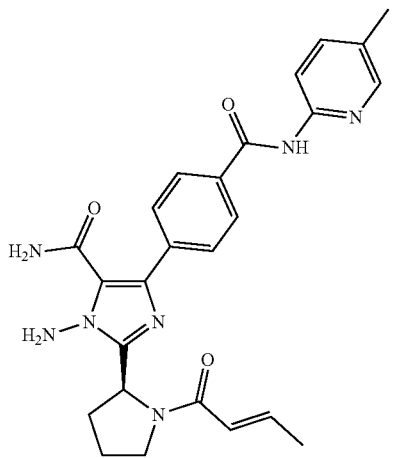 [SMILES: C/C=C/C(=O)N1CCC[C@H]1c1nc(-c2ccc(C(=O)Nc3ccc(C)cn3)cc2)c(C(N)=O)n1N]

Preparation of (S,E)-1-amino-2-(1-(but-2-enoyl)pyrrolidin-2-yl)-4-(4-((5-methylpyridin-2-yl)carbamoyl)phenyl)-1H-imidazole-5-carboxamide

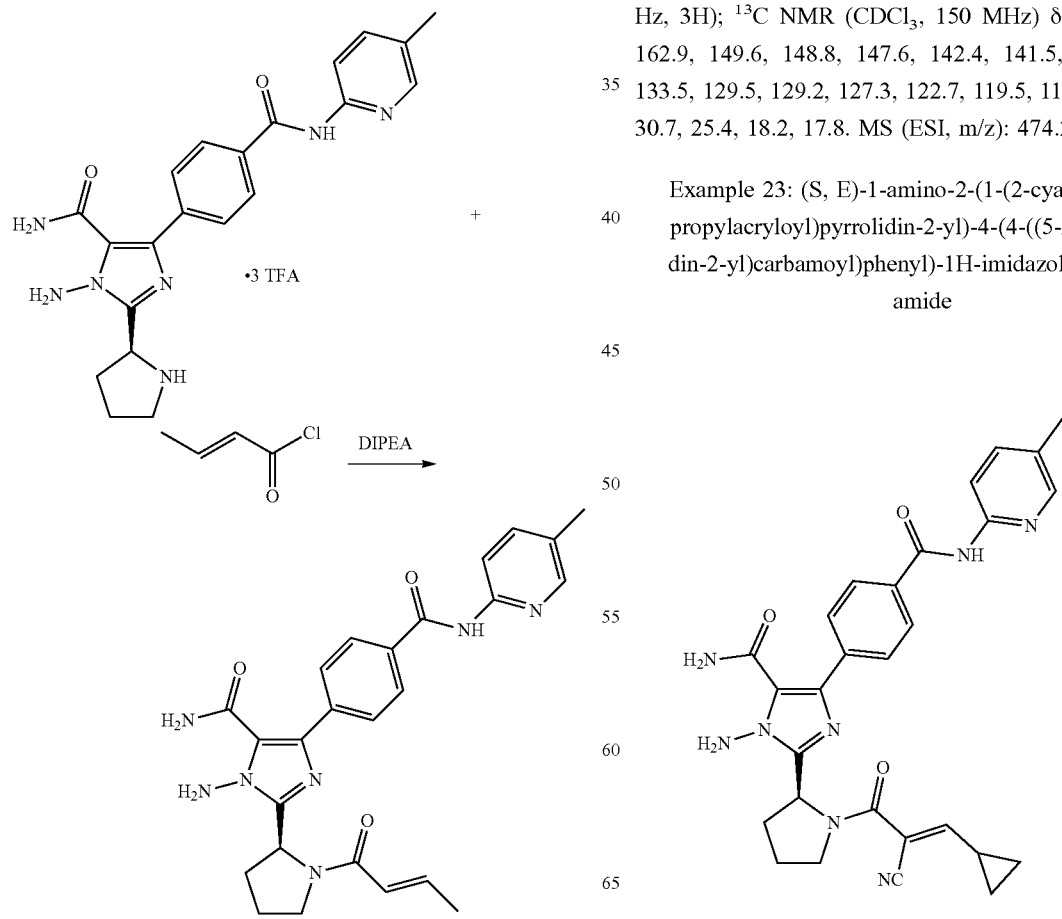

To the solution of 145 mg (0.35 mmol) of the product of Step E of example 19 in drydichloromethane (5 mL) was added diisopropylethylamine (275 mg, 2.13 mmol). After 5 min, (E)-but-2-enoyl chloride (33.4 mg, 0.32 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S,E)-1-amino-2-(1-(but-2-enoyl)pyrrolidin-2-yl)-4-(4-((5-methylpyridin-2-yl)carbamoyl)phenyl)-1H-imidazole-5-carboxamide as an off-white solid (78 mg, 47%). $^1$H NMR (CDCl$_3$, 600 MHz) δ: 9.35 (s, 1H), 8.18 (d, J=8.5 Hz, 1H), 8.01 (d, J=1.9 Hz, 1H), 7.78 (d, J=8.4 Hz, 2H), 7.63 (d, J=8.3 Hz, 2H), 7.48 (dd, J$_1$=8.5 Hz, J$_2$=2.0 Hz, 1H), 7.20 (s, 1H), 6.83-6.77 (m, 1H), 6.74-6.59 (m, 3H), 6.07 (dd, J$_1$=15.1 Hz, J$_2$=1.7 Hz, 1H), 5.20 (dd, J$_1$=8.0 Hz, J$_2$=4.9 Hz, 1H), 3.77-3.73 (m, 1H), 3.62-3.58 (m, 1H), 2.53-2.46 (m, 1H), 2.37-2.32 (m, 1H), 2.22 (s, 3H), 2.19-2.13 (m, 1H), 2.00-1.94 (m, 1H), 1.80 (dd, J$_1$=6.9 Hz, J$_2$=1.5 Hz, 3H); $^{13}$C NMR (CDCl$_3$, 150 MHz) δ: 165.8, 165.4, 162.9, 149.6, 148.8, 147.6, 142.4, 141.5, 138.9, 138.1, 133.5, 129.5, 129.2, 127.3, 122.7, 119.5, 114.1, 51.1, 47.4, 30.7, 25.4, 18.2, 17.8. MS (ESI, m/z): 474.2 [M+H]$^+$.

Example 23: (S, E)-1-amino-2-(1-(2-cyano-3-cyclopropylacryloyl)pyrrolidin-2-yl)-4-(4-((5-methylpyridin-2-yl)carbamoyl)phenyl)-1H-imidazole-5-carboxamide Step A: Preparation of (S)-1-amino-2-(1-(2-cyano-acetyl)pyrrolidin-2-yl)-4-(4-((5-methylpyridin-2-yl)carbamoyl)phenyl)-1H-imidazole-5-carboxamide Step B: Preparation of (S, E)-1-amino-2-(1-(2-cyano-3-cyclopropylacryloyl)pyrrolidin-2-yl)-4-(4-((5-methylpyridin-2-yl)carbamoyl)phenyl)-1H-imidazole-5-carboxamide

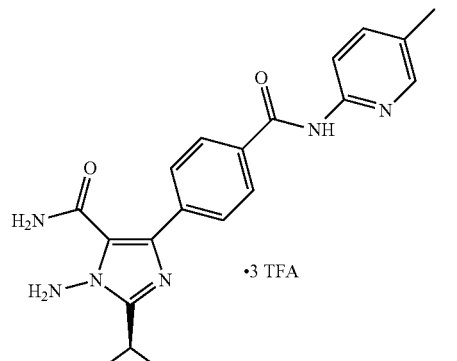

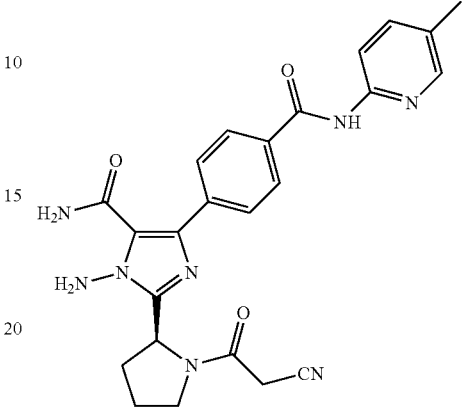

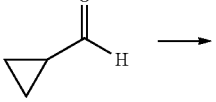

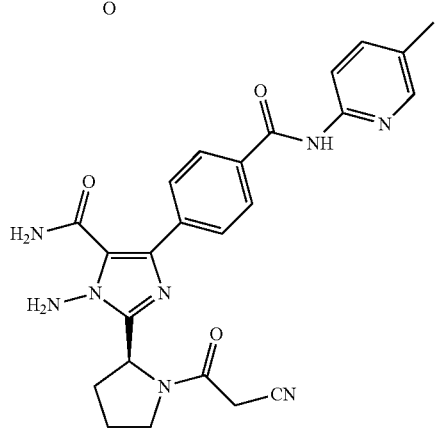

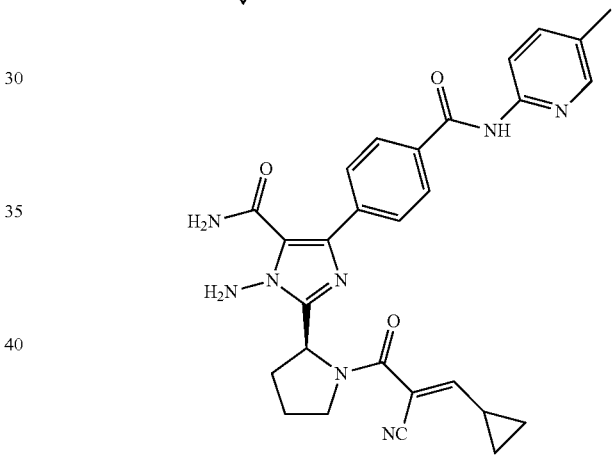

To the solution of 145 mg (0.35 mmol) of the product of Step E of example 19 in dry N, N-Dimethylformamide (5 mL) was added triethylamine (212 mg, 2.10 mmol). After 5 min, 2-cyanoacetic acid (27.2 mg, 0.32 mmol) and HATU (200 mg, 0.52 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (23:1) to give (S)-1-amino-2-(1-(2-cyanoacetyl)pyrrolidin-2-yl)-4-(4-((5-methylpyridin-2-yl)carbamoyl)phenyl)-1H-imidazole-5-carboxamide as an off-white solid (95 mg, 57%). $^1$H NMR (CDCl$_3$, 600 MHz) δ: 9.34 (s, 1H), 8.16 (d, J=8.2 Hz, 1H), 8.02 (s, 1H), 7.78 (d, J=7.7 Hz, 2H), 7.59 (d, J=7.7 Hz, 2H), 7.49 (d, J=8.2 Hz, 1H), 7.02 (s, 1H), 6.74 (s, 1H), 6.27 (s, 2H), 5.24-5.15 (m, 1H), 3.73-3.63 (m, 1H), 3.54-3.45 (m, 3H), 2.69-2.56 (m, 1H), 2.40-2.39 (m, 1H), 2.23 (s, 3H), 2.18-2.16 (m, 1H), 1.97-1.95 (m, 1H); $^{13}$C NMR (CDCl$_3$, 150 MHz) δ: 165.9, 162.9, 161.4, 149.6, 148.6, 147.7, 141.0, 139.1, 137.8, 133.7, 129.4, 129.3, 127.5, 120.4, 114.3, 114.2, 52.4, 48.1, 30.9, 26.3, 25.2, 17.9. MS (ESI, m/z): 473.1 [M+H]$^+$.

To the solution of cyclopropanecarbaldehyde (7.7 mg, 0.11 mmol) in dry dichloromethane (5 mL) at 0° C. was added pyrrolidine (45 μL, 0.55 mmol) and then TMS-Cl (70 μL, 0.55 mmol). The ice bath was removed and the reaction mixture was stirred for 10 min followed by the additions of 50 mg (0.11 mmol) of the product of Step A. The reaction solution was stirred for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (27:1) to afford (S, E)-1-amino-2-(1-(2-cyano-3-cyclopropylacryloyl)pyrrolidin-2-yl)-4-(4-((5-methylpyridin-2-yl)carbamoyl)phenyl)-1H-imidazole-5-carboxamide as a white solid (40 mg, 69%). $^1$H NMR (CDCl$_3$, 600 MHz) δ: 9.09 (s, 1H), 8.25 (d, J=8.4 Hz, 1H), 8.07 (s, 1H), 7.90 (d, J=8.2 Hz, 2H), 7.70 (d, J=8.1 Hz, 2H), 7.55 (d, J=8.5 Hz, 1H), 6.78 (d, J=11.3 Hz, 1H), 6.56 (s, 2H), 6.46 (s, 1H), 6.28 (s, 1H), 5.31-5.29 (m, 1H), 4.05-4.01 (m, 1H), 3.93-3.90 (m, 1H), 2.49-2.43 (m, 2H), 2.31-2.25 (m, 4H), 2.09-2.00 (m, 2H), 1.24-1.23 (m, 2H), 0.88-0.86 (m, 2H); $^{13}$C NMR (CDCl$_3$, 150 MHz) δ: 167.8, 165.6, 162.9, 161.4, 149.6, 148.0, 147.7, 141.5, 139.2, 138.0, 134.1, 129.7, 129.5, 127.7, 119.0, 115.5, 114.1, 107.4, 53.0, 49.5, 30.7, 26.1, 18.0, 15.8, 11.1, 11.0. MS (ESI, m/z): 525.2 [M+H]$^+$.

Example 24: (S, E)-1-amino-2-(1-(2-cyano-4,4-dimethylpent-2-enoyl)pyrrolidin-2-yl)-4-(4-((5-methylpyridin-2-yl)carbamoyl)phenyl)-1H-imidazole-5-carboxamide

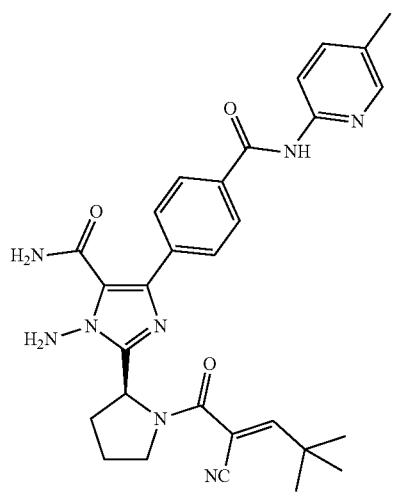 [SMILES: Cc1ccc(NC(=O)c2ccc(-c3nc([C@@H]4CCCN4C(=O)/C(C#N)=C/C(C)(C)C)n(N)c3C(N)=O)cc2)nc1]

Preparation of (S,E)-1-amino-2-(1-(2-cyano-4,4-dimethylpent-2-enoyl)pyrrolidin-2-yl)-4-(4-((5-methylpyridin-2-yl)carbamoyl)phenyl)-1H-imidazole-5-carboxamide

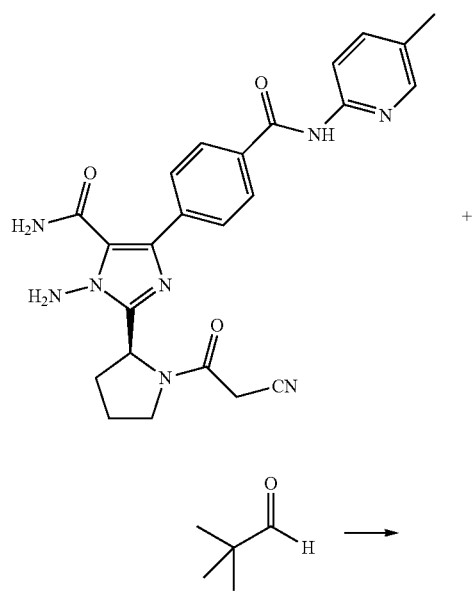

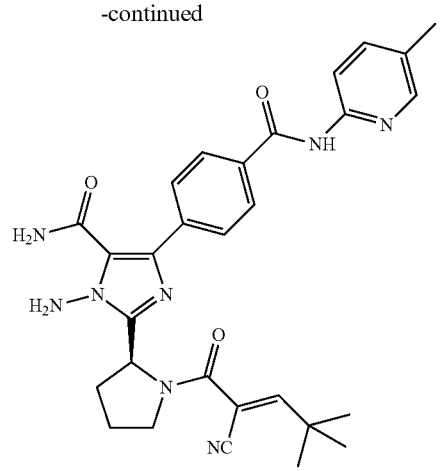

To the solution of pivalaldehyde (9.5 mg, 0.11 mmol) in dry dichloromethane (5 mL) at 0° C. was added pyrrolidine (45 μL, 0.55 mmol) and then TMS-Cl (70 μL, 0.55 mmol). The ice bath was removed and the reaction mixture was stirred for 10 min followed by the additions of 50 mg (0.11 mmol) of the product of Step A of example 23. The reaction solution was stirred for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (27:1) to afford (S, E)-1-amino-2-(1-(2-cyano-4,4-dimethylpent-2-enoyl)pyrrolidin-2-yl)-4-(4-((5-methylpyridin-2-yl)carbamoyl)phenyl)-1H-imidazole-5-carboxamide as a white solid (19 mg, 31%). $^1$H NMR (CDCl$_3$, 400 MHz) δ: 8.75 (s, 1H), 8.29 (d, J=8.5 Hz, 1H), 8.13-8.12 (m, 1H), 7.98 (d, J=8.4 Hz, 2H), 7.77 (d, J=8.4 Hz, 2H), 7.60-7.58 (m, 1H), 7.12 (s, 1H), 6.62 (s, 2H), 6.14 (s, 1H), 5.59 (s, 1H), 5.33 (t, J=7.4 Hz, 1H), 4.00-3.93 (m, 1H), 3.83-3.78 (m, 1H), 2.58-2.36 (m, 3H), 2.33 (s, 3H), 2.06-1.99 (m, 1H), 1.29 (s, 9H); $^{13}$C NMR (CDCl$_3$, 150 MHz) δ: 168.6, 165.2, 162.7, 149.4, 147.8, 147.7, 141.6, 139.3, 138.2, 134.3, 129.9, 129.7, 127.9, 127.8, 118.8, 114.6, 114.0, 108.5, 52.8, 49.9, 35.4, 30.8, 29.1, 26.1, 18.0. MS (ESI, m/z): 541.2 [M+H]$^+$.

Example 25: (S,E)-1-amino-4-(4-((5-methylpyridin-2-yl)carbamoyl)phenyl)-2-(1-(pent-2-enoyl)pyrrolidin-2-yl)-1H-imidazole-5-carboxamide

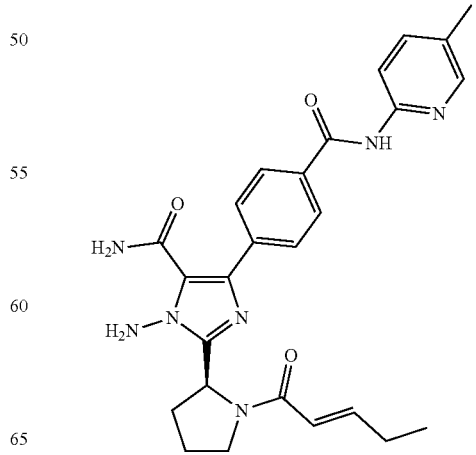

Preparation of (S,E)-1-amino-4-(4-((5-methylpyridin-2-yl)carbamoyl)phenyl)-2-(1-(pent-2-enoyl)pyrrolidin-2-yl)-1H-imidazole-5-carboxamide

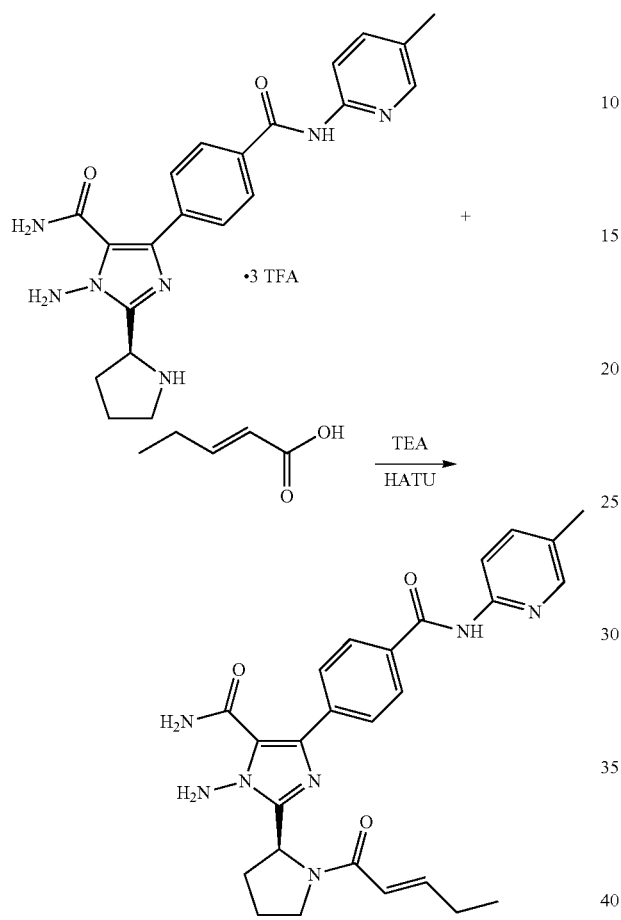

To the solution of 145 mg (0.35 mmol) of the product of Step E of example 19 in dry N,N-Dimethylformamide (5 mL) was added triethylamine (212 mg, 2.10 mmol). After 5 min, (E)-pent-2-enoic acid (32.0 mg, 0.32 mmol) and HATU (200 mg, 0.52 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (23:1) to give (S,E)-1-amino-4-(4-((5-methylpyridin-2-yl)carbamoyl)phenyl)-2-(1-(pent-2-enoyl)pyrrolidin-2-yl)-1H-imidazole-5-carboxamide as an off-white solid (88 mg, 51%). $^1$H NMR (CDCl$_3$, 600 MHz) δ: 9.23 (s, 1H), 8.21 (d, J=8.5 Hz, 1H), 8.04 (s, 1H), 7.84 (d, J=8.3 Hz, 2H), 7.68 (d, J=8.3 Hz, 2H), 7.52 (dd, J$_1$=8.5 Hz, J$_2$=1.9 Hz, 1H), 7.04 (s, 1H), 6.88 (dt, J$_1$=15.1 Hz, J$_2$=6.5 Hz, 1H), 6.75 (s, 2H), 6.46 (s, 1H), 6.06 (dt, J$_1$=15.1 Hz, J$_2$=1.6 Hz, 1H), 5.24 (dd, J$_1$=8.0 Hz, J$_2$=4.9 Hz, 1H), 3.81-3.77 (m, 1H), 3.66-3.62 (m, 1H), 2.58-2.51 (m, 1H), 2.43-2.37 (m, 1H), 2.25 (s, 3H), 2.23-2.16 (m, 3H), 2.05-1.98 (m, 1H), 1.01 (t, J=7.4 Hz, 3H); $^{13}$C NMR (CDCl$_3$, 150 MHz) δ: 165.8, 165.6, 162.9, 149.6, 148.7, 148.6, 147.6, 141.6, 139.1, 138.2, 133.7, 129.6, 129.3, 127.4, 120.4, 119.2, 114.1, 51.2, 47.5, 30.8, 25.6, 25.5, 17.9, 12.6. MS (ESI, m/z): 488.2 [M+H]$^+$.

Example 26: (S)-1-amino-4-(4-((5-methylpyridin-2-yl)carbamoyl)phenyl)-2-(1-propioloylpyrrolidin-2-yl)-1H-imidazole-5-carboxamide

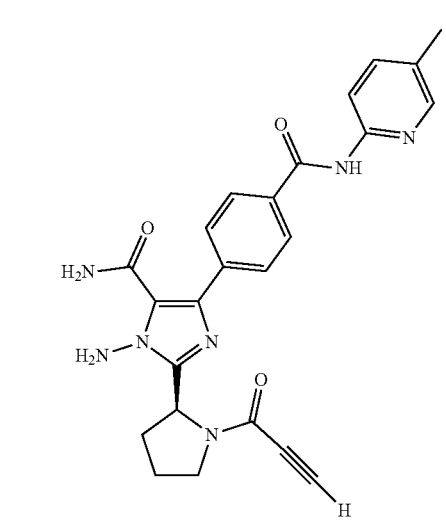 [SMILES: C#CC(=O)N1CCC[C@H]1c1nc(-c2ccc(C(=O)Nc3ccc(C)cn3)cc2)c(C(N)=O)n1N]

Preparation of (S)-1-amino-4-(4-((5-methylpyridin-2-yl)carbamoyl)phenyl)-2-(1-propioloylpyrrolidin-2-yl)-1H-imidazole-5-carboxamide

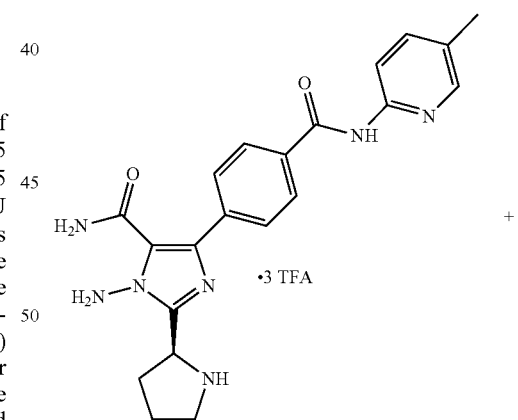

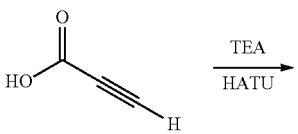

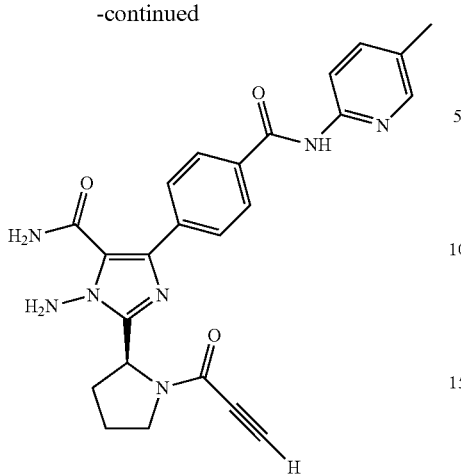

To the solution of 145 mg (0.35 mmol) of the product of Step E of example 19 in dry N,N-Dimethylformamide (5 mL) was added triethylamine (212 mg, 2.10 mmol). After 5 min, propiolic acid (22.4 mg, 0.32 mmol) and HATU (200 mg, 0.52 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (23:1) to give (S)-1-amino-4-(4-((5-methylpyridin-2-yl)carbamoyl)phenyl)-2-(1-propioloylpyrrolidin-2-yl)-1H-imidazole-5-carboxamide as a yellow solid (79 mg, 49%). $^1$H NMR (CDCl$_3$, 600 MHz) δ: 8.55 (s, 1H), 8.28 (d, J=8.5 Hz, 1H), 8.14 (d, J=1.9 Hz, 1H), 7.97 (d, J=8.3 Hz, 2H), 7.78 (d, J=8.3 Hz, 2H), 7.59 (dd, J$_1$=8.4 Hz, J$_2$=2.0 Hz, 1H), 6.65 (s, 2H), 6.21 (s, 1H), 5.46 (s, 1H), 5.32-5.30 (m, 1H), 3.91 (t, J=6.8 Hz, 2H), 3.09 (s, 1H), 2.60-2.54 (m, 1H), 2.53-2.47 (m, 1H), 2.38-2.33 (m, 4H), 2.07-2.02 (m, 1H); $^{13}$C NMR (CDCl$_3$, 150 MHz) δ: 165.1, 162.6, 162.1, 149.4, 148.0, 147.4, 141.5, 139.2, 138.3, 134.3, 130.0, 129.7, 127.6, 118.9, 113.8, 78.6, 76.5, 50.9, 49.3, 31.2, 25.0, 18.0. MS (ESI, m/z): 458.1 [M+H]$^+$.

Example 27: (S)-1-amino-2-(1-(but-2-ynoyl)pyrrolidin-2-yl)-4-(4-((5-methylpyridin-2-yl)carbamoyl)phenyl)-1H-imidazole-5-carboxamide

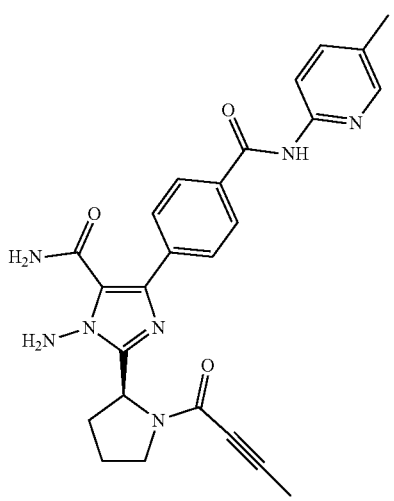 [SMILES: CC#CC(=O)N1CCC[C@H]1c1nc(-c2ccc(C(=O)Nc3ccc(C)cn3)cc2)c(C(N)=O)n1N]

Preparation of (S)-1-amino-2-(1-(but-2-ynoyl)pyrrolidin-2-yl)-4-(4-((5-methylpyridin-2-yl)carbamoyl)phenyl)-1H-imidazole-5-carboxamide

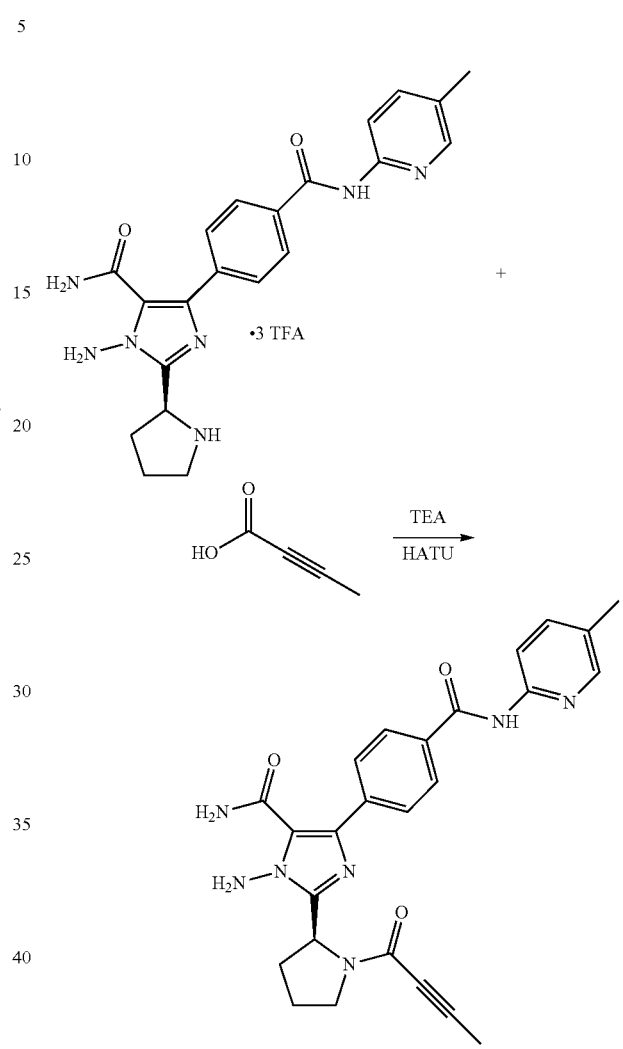

To the solution of 145 mg (0.35 mmol) of the product of Step E of example 19 in dry N,N-Dimethylformamide (5 mL) was added triethylamine (212 mg, 2.10 mmol). After 5 min, but-2-ynoic acid (26.8 mg, 0.32 mmol) and HATU (200 mg, 0.52 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(but-2-ynoyl)pyrrolidin-2-yl)-4-(4-((5-methylpyridin-2-yl)carbamoyl)phenyl)-1H-imidazole-5-carboxamide as an off-white solid (75 mg, 45%). $^1$H NMR (CDCl$_3$, 600 MHz) δ: 8.54 (s, 1H), 8.29 (d, J=8.5 Hz, 1H), 8.14 (s, 1H), 7.96 (d, J=8.5 Hz, 2H), 7.79 (d, J=8.5 Hz, 2H), 7.59 (dd, J$_1$=8.6 Hz, J$_2$=1.9 Hz, 1H), 6.72 (s, 2H), 6.37 (s, 1H), 5.42 (s, 1H), 5.27 (dd, J$_1$=8.0 Hz, J$_2$=5.4 Hz, 1H), 3.88-3.86 (m, 2H), 2.59-2.48 (m, 2H), 2.35-2.31 (m, 4H), 2.04-2.00 (m, 4H); $^{13}$C NMR (DMSO, 150 MHz) δ: 165.5, 162.2, 151.9, 150.1, 148.3, 147.7, 138.5, 138.0, 136.3, 132.2, 128.8, 127.7, 127.2, 124.7, 114.4, 88.7, 74.3, 50.9, 48.5, 31.1, 23.8, 17.4, 3.3. MS (ESI, m/z): 472.2 [M+H]⁺.

Example 28: (S)-2-(1-acryloylpyrrolidin-2-yl)-1-amino-4-(4-((4-methoxypyridin-2-yl)carbamoyl)phenyl)-1H-imidazole-5-carboxamide

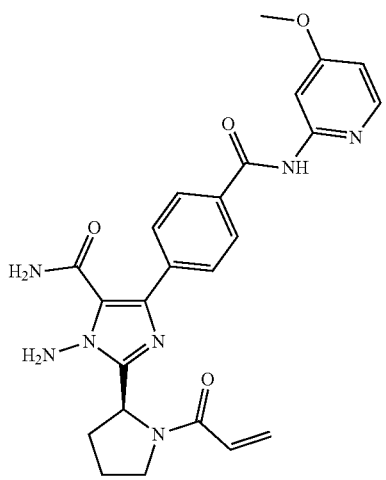 [SMILES: C=CC(=O)N1CCC[C@H]1c1nc(-c2ccc(C(=O)Nc3cc(OC)ccn3)cc2)c(C(N)=O)n1N]

Step A: Preparation of (S)-ethyl 2-(1-(tert-butoxycarbonyl)pyrrolidin-2-yl)-4-(4-((4-methoxypyridin-2-yl)carbamoyl)phenyl)-1H-imidazole-5-carboxylate

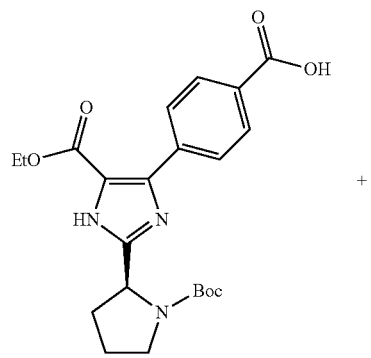

+

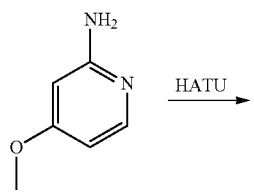 HATU

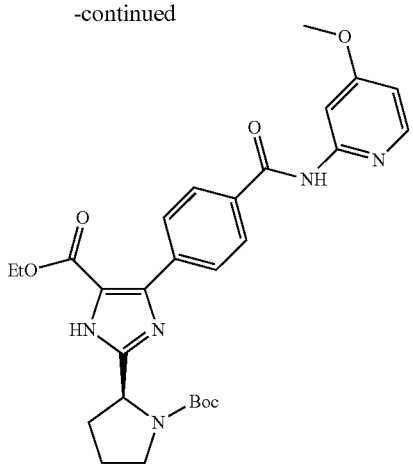

To the solution of 21.0 g (49 mmol) of the product of Step F of example 1 in dry N, N-Dimethylformamide (250 mL) was stirred and added HATU (22.5 g, 59 mmol), diisopropylethylamine (43 mL, 246 mmol) and 4-methoxypyridin-2-amine (9.1 g, 73.5 mmol). The reaction mixture was stirred at 80° C. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (2:1) to afford as a white solid (17 g, 65%). ¹H NMR (CDCl₃, 600 MHz) δ: 11.14 (s, 1H), 8.97 (s, 1H), 8.14-8.13 (m, 2H), 8.05 (d, J=1.6 Hz, 1H), 8.01-8.00 (m, 1H), 7.93 (d, J=7.8 Hz, 2H), 6.58 (dd, $J_1$=5.6 Hz, $J_2$=2.0 Hz, 1H), 4.97-4.93 (m, 1H), 4.33-4.26 (m, 2H), 3.89 (s, 3H), 3.53-3.42 (m, 2H), 2.95-2.89 (m, 1H), 2.34-2.07 (m, 2H), 1.99-1.91 (m, 1H), 1.49 (s, 9H), 1.29 (t, J=6.6 Hz, 3H). MS (ESI, m/z): 536.2 [M+H]⁺.

Step B: Preparation of (S)-ethyl 1-amino-2-(1-(tert-butoxycarbonyl)pyrrolidin-2-yl)-4-(4-((4-methoxypyridin-2-yl)carbamoyl)phenyl)-1H-imidazole-5-carboxylate

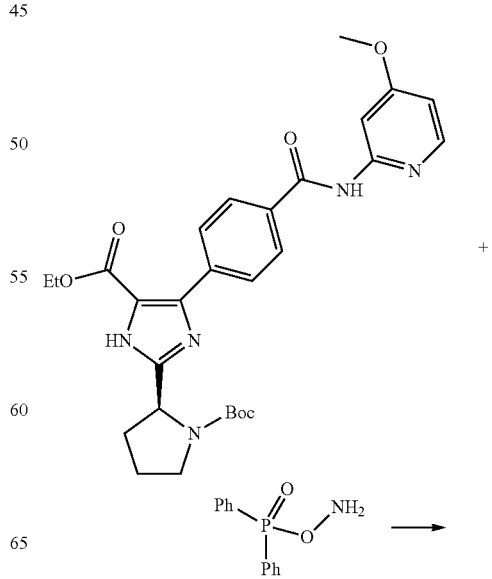

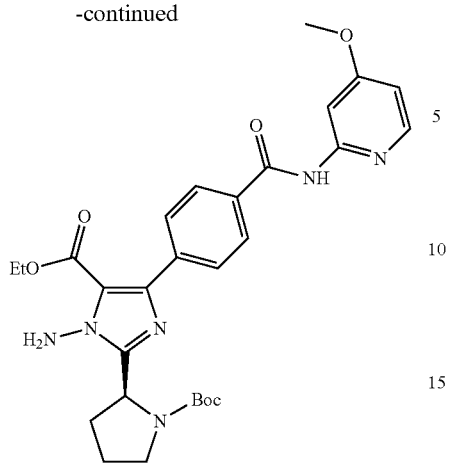

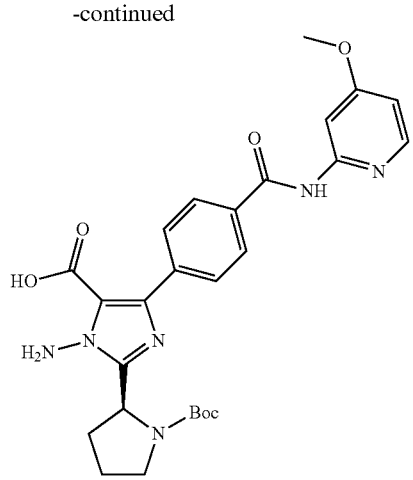

To the solution of 14 g (26 mmol) of the product of Step A in dry N, N-Dimethylformamide (50 mL) was stirred and slowly added lithium hexamethyldisilazane (31 mL, 1 M solution in tetrahydrofuran) at −10° C. After the mixture was stirred for 10 min, O-(diphenylphosphinyl) hydroxylamine (6 g, 26 mmol) was added at 0° C. and the resulting suspension was stirred 2 h at room temperature (in cases where the reaction mixture became too viscous, additional N, N-Dimethylformamide was added). The reaction was quenched with brine and washed three times with ethyl acetate (3×500 mL). The combined organic fractions were dried with anhydrous $Na_2SO_4$ and the solvent was removed under reduced pressure to afford the crude residue, which was subjected to column chromatography with petroleum ether and ethyl acetate (2:1) to give the desired product (S)-ethyl 1-amino-2-(1-(tert-butoxycarbonyl)pyrrolidin-2-yl)-4-(4-((4-methoxy-pyridin-2-yl)carbamoyl)phenyl)-1H-imidazole-5-carboxylate (9 g, 63%). $^1$H NMR (CDCl$_3$, 600 MHz) δ: 8.75 (s, 1H), 8.07-8.06 (m, 2H), 7.91 (d, J=7.8 Hz, 2H), 7.80 (d, J=7.8 Hz, 2H), 6.66 (s, 2H), 6.62 (d, J=5.5 Hz, 1H), 5.19-5.17 (m, 1H), 4.28-4.25 (m, 2H), 3.91 (s, 3H), 3.59-3.55 (m, 1H), 3.49-3.45 (m, 1H), 2.42-2.37 (m, 1H), 2.27-2.22 (m, 1H), 1.95-1.93 (m, 2H), 1.41 (s, 7H), 1.26-1.21 (m, 5H). MS (ESI, m/z): 551.2 [M+H]$^+$.

Step C: Preparation of (S)-1-amino-2-(1-(tert-butoxycarbonyl)pyrrolidin-2-yl)-4-(4-((4-methoxypyridin-2-yl)carbamoyl)phenyl)-1H-imidazole-5-carboxylic acid To the solution of 3.7 g (6.7 mmol) of the product of Step B in methanol (15 mL) was stirred and added aqueous lithium hydroxide (2 mol/L, 34 mL), then stirred at room temperature for 2 h. The reaction mixture was evaporated and diluted with water (100 mL) and acidified with aqueous HCl till pH 3. The mixture was washed with ethyl acetate three times (3×200 mL). The combined organic layers were concentrated under reduced pressure to afford (S)-1-amino-2-(1-(tert-butoxycarbonyl)pyrrolidin-2-yl)-4-(4-((4-methoxypyridin-2-yl)carbamoyl)phenyl)-1H-imidazole-5-carboxylic acid as a white solid (3.2 g, 90%).

Step D: Preparation of (S)-tert-butyl 2-(1-amino-5-carbamoyl-4-(4-((4-methoxypyridin-2-yl)carbamoyl)phenyl)-1H-imidazol-2-yl)pyrrolidine-1-carboxylate

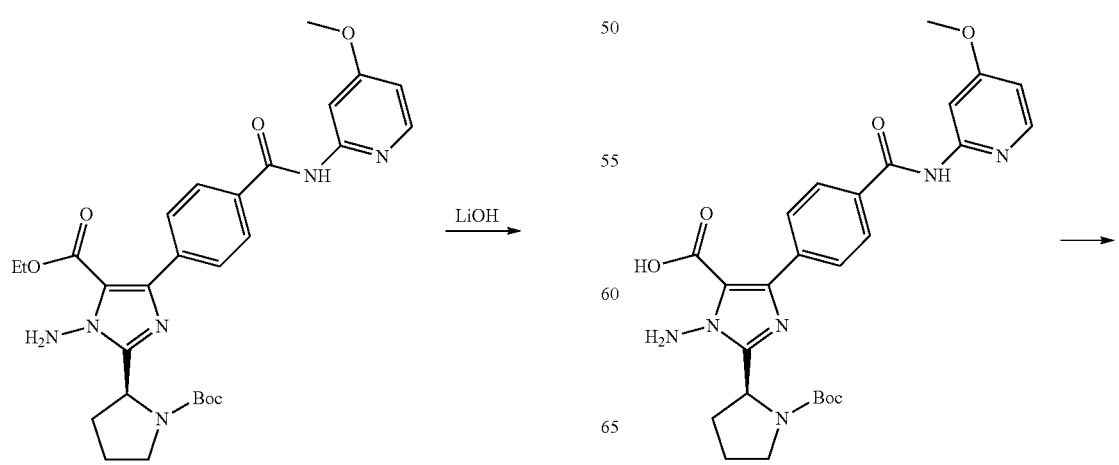

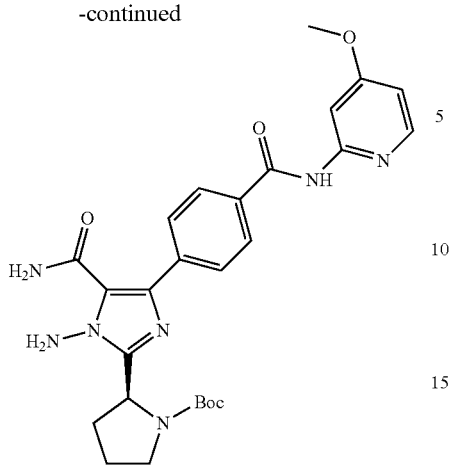

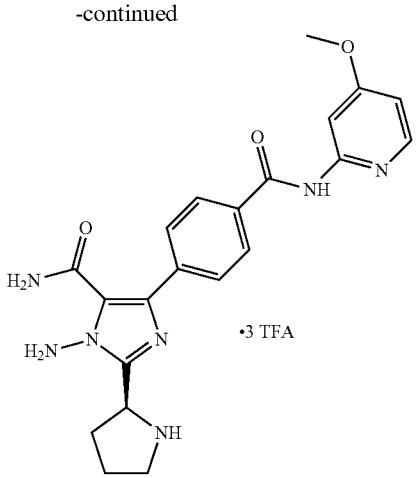

To the solution of 3.1 g (6.0 mmol) of the product of Step C in dry N, N-Dimethylformamide (20 mL) was stirred and added HATU (3.5 g, 9.1 mmol), diisopropylethylamine (3.2 mL, 18.1 mmol) and NH₄Cl (3.3 g, 60 mmol). The reaction mixture was stirred at room temperature for 2 h. The reaction mixture was quenched with brine and washed with ethyl acetate three times (3×200 mL). The combined organic layers were concentrated under reduced pressure and purified by flash chromatography with dichloromethane and methanol (30:1) to afford (S)-tert-butyl 2-(1-amino-5-carbamoyl-4-(4-((4-methoxypyridin-2-yl)carbamoyl)phenyl)-1H-imidazol-2-yl)pyrrolidine-1-carboxylate as a white solid (2.5 g, 80%). ¹H NMR (CDCl₃, 600 MHz) δ: 8.86 (s, 1H), 8.08 (s, 1H), 7.93-7.90 (m, 3H), 7.81-7.73 (m, 2H), 7.07 (s, 1H), 6.65-6.61 (m, 3H), 5.67 (s, 1H), 5.16-5.07 (m, 1H), 3.92 (s, 3H), 3.56-3.53 (m, 1H), 3.47-3.45 (m, 1H), 2.46-2.39 (m, 2H), 2.26-2.20 (m, 1H), 1.97-1.93 (m, 1H), 1.43 (s, 7H), 1.29 (s, 2H). MS (ESI, m/z): 522.2 [M+H]⁺.

Step E: Preparation of (S)-1-amino-4-(4-((4-methoxypyridin-2-yl)carbamoyl)phenyl)-2-(pyrrolidin-2-yl)-1H-imidazole-5-carboxamide

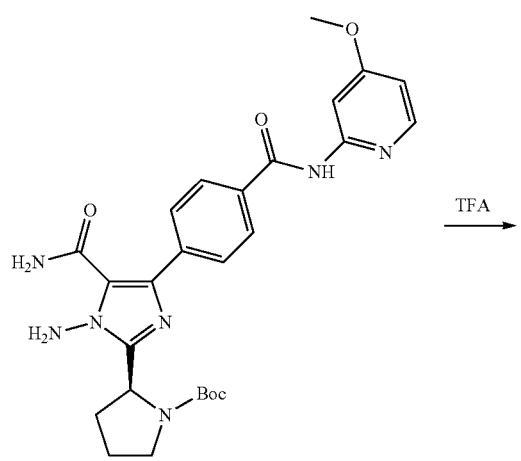

To the solution of 180 mg (0.34 mmol) of the product of Step D in dichloromethane (5 mL) was added trifluoroacetic acid (2.1 mL). The mixture was stirred at room temperature for 1 h and then concentrated to afford (S)-1-amino-4-(4-((4-methoxypyridin-2-yl)carbamoyl)phenyl)-2-(pyrrolidin-2-yl)-1H-imidazole-5-carboxamide as a light yellow oil. MS (ESI, m/z): 422.1 [M+H]⁺.

Step F: Preparation of (S)-2-(1-acryloylpyrrolidin-2-yl)-1-amino-4-(4-((4-methoxypyridin-2-yl)carbamoyl)phenyl)-1H-imidazole-5-carboxamide

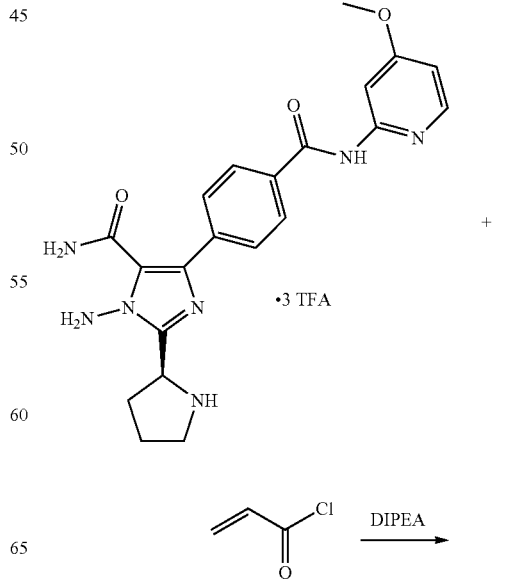

93

-continued

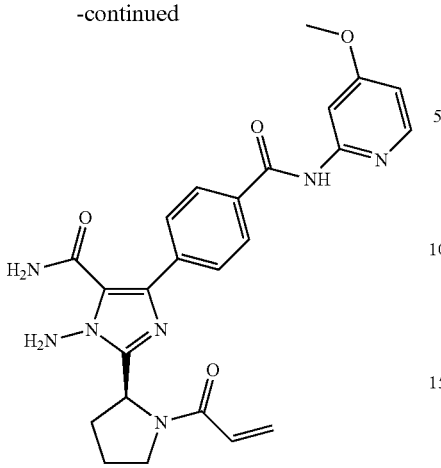

To the solution of 145 mg (0.34 mmol) of the product of Step E of in dry dichloromethane (5 mL) was added diisopropylethylamine (267 mg, 2.07 mmol). After 5 min, acryloyl chloride (27.6 mg, 0.30 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-2-(1-acryloyl-pyrrolidin-2-yl)-1-amino-4-(4-((4-methoxypyridin-2-yl)carba-moyl)phenyl)-1H-imidazole-5-carboxamide as an off-white solid (90 mg, 56%). $^1$H NMR (CDCl$_3$, 600 MHz) δ: 9.09 (s, 1H), 8.06 (d, J=5.7 Hz, 1H), 8.04 (d, J=1.9 Hz, 1H), 7.94 (d, J=8.3 Hz, 2H), 7.78 (d, J=8.3 Hz, 2H), 6.78 (s, 2H), 6.69 (s, 1H), 6.62 (dd, $J_1$=5.8 Hz, $J_2$=2.3 Hz, 1H), 6.46 (dd, $J_1$=16.8 Hz, $J_2$=10.3 Hz, 1H), 6.32 (dd, $J_1$=16.8 Hz, $J_2$=1.7 Hz, 1H), 5.97 (s, 1H), 5.71 (dd, $J_1$=10.3 Hz, $J_2$=1.7 Hz, 1H), 5.32 (dd, $J_1$=8.0 Hz, $J_2$=5.0 Hz, 1H), 3.91 (s, 3H), 3.87-3.83 (m, 1H), 3.72-3.68 (m, 1H), 2.64-2.57 (m, 1H), 2.50-2.45 (m, 1H), 2.30-2.24 (m, 1H), 2.09-2.05 (m, 1H); $^{13}$C NMR (CDCl$_3$, 150 MHz) δ: 167.8, 165.8, 165.1, 162.7, 153.4, 148.3, 148.3, 141.6, 138.6, 133.8, 129.9, 128.7, 128.6, 127.6, 119.0, 108.2, 99.1, 55.6, 51.3, 47.7, 30.8, 25.6. MS (ESI, m/z): 476.2 [M+H]$^+$.

Example 29: (S)-1-amino-2-(1-methacryloylpyrrolidin-2-yl)-4-(4-((4-methoxy-pyridin-2-yl)carbamoyl)phenyl)-1H-imidazole-5-carboxamide

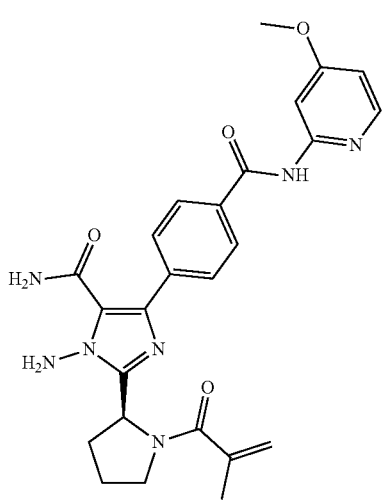 [SMILES: C=C(C)C(=O)N1CCC[C@H]1c1nc(-c2ccc(C(=O)Nc3cc(OC)ccn3)cc2)c(C(N)=O)n1N]

94

Preparation of (S)-1-amino-2-(1-methacryloylpyrrolidin-2-yl)-4-(4-((4-methoxypyridin-2-yl)carbamoyl)phenyl)-1H-imidazole-5-carboxamide

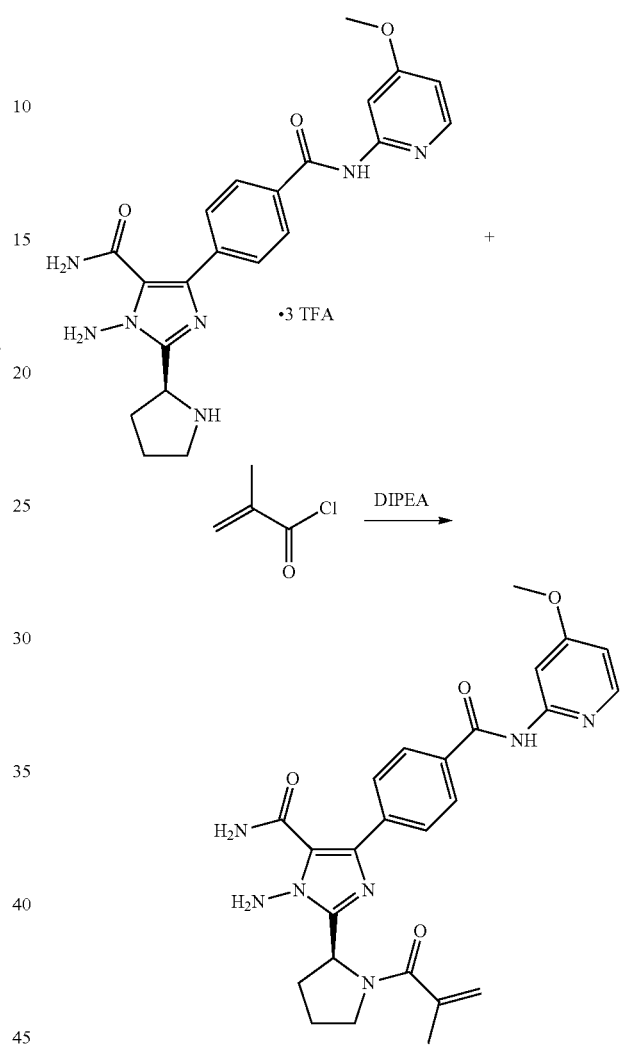

To the solution of 145 mg (0.34 mmol) of the product of Step E of example 28 in dry dichloromethane (5 mL) was added diisopropylethylamine (267 mg, 2.07 mmol). After 5 min, methacryloyl chloride (31.3 mg, 0.30 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-methacryloylpyrrolidin-2-yl)-4-(4-((4-methoxypyridin-2-yl)carbamoyl)phenyl)-1H-imidazole-5-carboxamide as an off-white solid (88 mg, 53%). $^1$H NMR (CDCl$_3$, 600 MHz) δ: 9.48 (s, 1H), 8.02-8.01 (m, 2H), 7.90 (d, J=8.2 Hz, 2H), 7.70 (d, J=8.2 Hz, 2H), 6.79 (s, 1H), 6.70 (s, 2H), 6.59 (dd, $J_1$=5.9 Hz, $J_2$=2.2 Hz, 1H), 6.40 (s, 1H), 5.28 (s, 1H), 5.26-5.23 (m, 1H), 5.20 (s, 1H), 3.88 (s, 3H), 3.75-3.69 (m, 2H), 2.55-2.49 (m, 1H), 2.33-2.26 (m, 2H), 1.91-1.86 (m, 4H); $^{13}$C NMR (CDCl$_3$, 150 MHz) δ: 171.2, 167.9, 166.0, 162.9, 153.4, 148.5, 147.9, 141.6, 140.7, 138.5, 133.6, 129.7, 127.6, 119.3, 118.0, 108.0, 99.2, 55.6, 51.2, 50.0, 30.9, 25.8, 19.8. MS (ESI, m/z): 490.2 [M+H]$^+$.

Example 30: (S)-1-amino-4-(4-((4-methoxypyridin-2-yl)carbamoyl)phenyl)-2-(1-(3-methylbut-2-enoyl)pyrrolidin-2-yl)-1H-imidazole-5-carboxamide

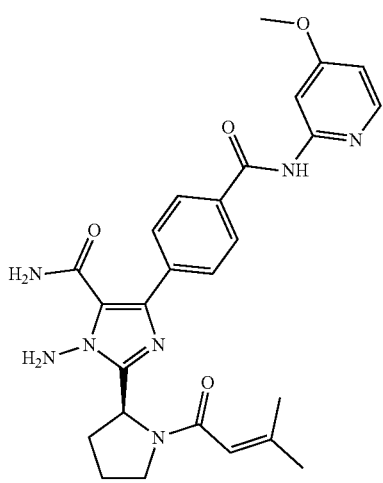

Preparation of (S)-1-amino-4-(4-((4-methoxypyridin-2-yl)carbamoyl)phenyl)-2-(1-(3-methylbut-2-enoyl)pyrrolidin-2-yl)-1H-imidazole-5-carboxamide

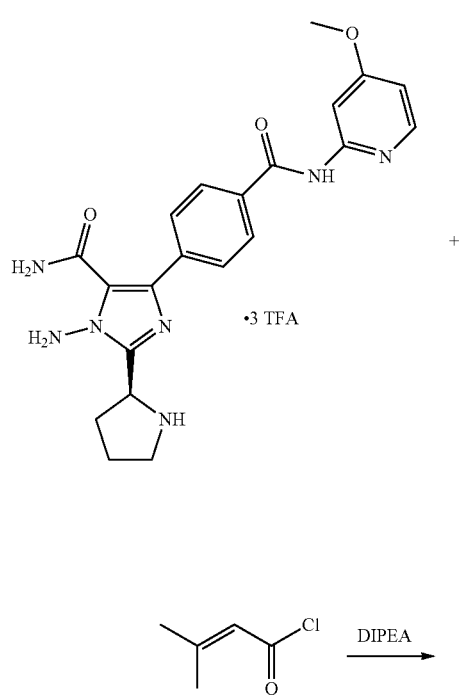

-continued

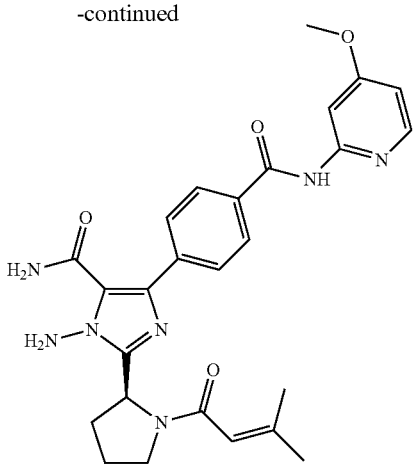

To the solution of 145 mg (0.34 mmol) of the product of Step E of example 28 in dry dichloromethane (5 mL) was added diisopropylethylamine (267 mg, 2.07 mmol). After 5 min, 3-methylbut-2-enoyl chloride (35.5 mg, 0.30 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-1-amino-4-(4-((4-methoxypyridin-2-yl)carbamoyl)phenyl)-2-(1-(3-methylbut-2-enoyl)pyrrolidin-2-yl)-1H-imidazole-5-carboxamide as an off-white solid (78 mg, 46%). $^1$H NMR (CDCl$_3$, 600 MHz) δ: 9.34 (s, 1H), 8.05-8.03 (m, 2H), 7.91 (d, J=8.2 Hz, 2H), 7.75 (d, J=8.2 Hz, 2H), 6.96 (s, 1H), 6.79 (s, 2H), 6.61 (dd, J$_1$=5.8 Hz, J$_2$=2.2 Hz, 1H), 6.12 (s, 1H), 5.77 (s, 1H), 5.25 (dd, J$_1$=7.9 Hz, J$_2$=5.2 Hz, 1H), 3.90 (s, 3H), 3.74-3.70 (m, 1H), 3.61-3.57 (m, 1H), 2.53-2.48 (m, 1H), 2.47-2.42 (m, 1H), 2.26-2.21 (m, 1H), 2.03-1.98 (m, 4H), 1.84 (s, 3H); $^{13}$C NMR (CDCl$_3$, 150 MHz) δ: 167.9, 167.0, 166.0, 162.8, 153.3, 151.0, 148.9, 147.9, 141.7, 138.6, 133.5, 129.8, 127.5, 119.2, 117.6, 108.1, 99.1, 55.6, 50.8, 48.0, 30.8, 27.2, 25.6, 20.4. MS (ESI, m/z): 504.2 [M+H]$^+$.

Example 31: (S,E)-1-amino-2-(1-(but-2-enoyl)pyrrolidin-2-yl)-4-(4-((4-methoxy-pyridin-2-yl)carbamoyl)phenyl)-1H-imidazole-5-carboxamide

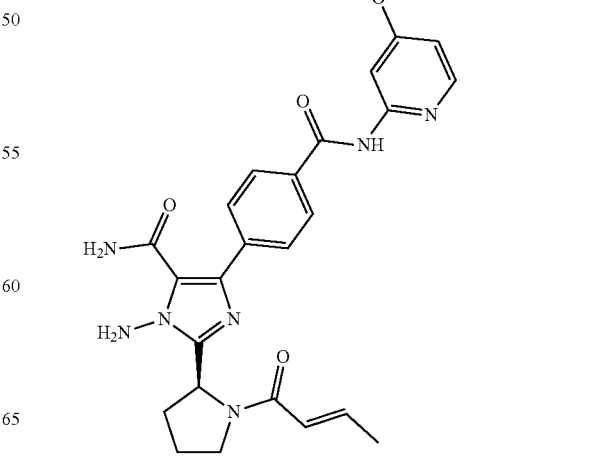

Preparation of (S,E)-1-amino-2-(1-(but-2-enoyl)pyrrolidin-2-yl)-4-(4-((4-methoxypyridin-2-yl)carbamoyl)phenyl)-1H-imidazole-5-carboxamide

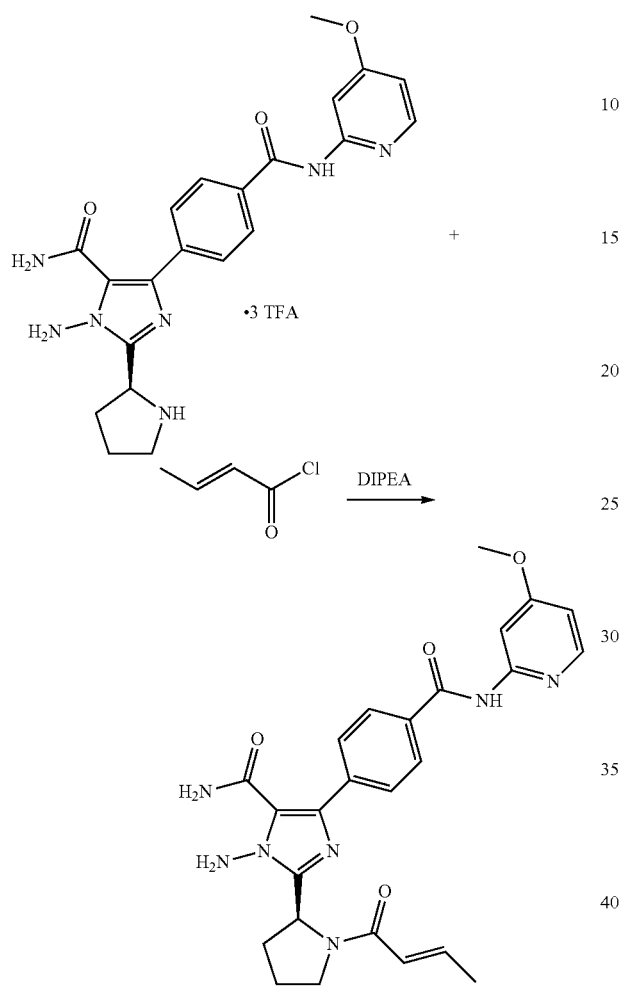

To the solution of 145 mg (0.34 mmol) of the product of Step E of example 28 in dry dichloromethane (5 mL) was added diisopropylethylamine (267 mg, 2.07 mmol). After 5 min, (E)-but-2-enoyl chloride (31.3 mg, 0.30 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S,E)-1-amino-2-(1-(but-2-enoyl)pyrrolidin-2-yl)-4-(4-((4-methoxypyridin-2-yl)carbamoyl)phenyl)-1H-imidazole-5-carboxamide as an off-white solid (102 mg, 61%). $^1$H NMR ($CDCl_3$, 600 MHz) δ: 9.33 (s, 1H), 8.01 (d, J=5.8 Hz, 1H), 7.99 (d, J=2.2 Hz, 1H), 7.87 (d, J=8.3 Hz, 2H), 7.71 (d, J=8.3 Hz, 2H), 6.99 (s, 1H), 6.88-6.82 (m, 1H), 6.74 (s, 2H), 6.58 (dd, $J_1$=5.8 Hz, $J_2$=2.3 Hz, 1H), 6.44 (s, 1H), 6.10 (dd, $J_1$=15.1 Hz, $J_2$=1.7 Hz, 1H), 5.25-5.23 (m, 1H), 3.87 (s, 3H), 3.81-3.77 (m, 1H), 3.66-3.62 (m, 1H), 2.58-2.53 (m, 1H), 2.43-2.38 (m, 1H), 2.23-2.17 (m, 1H), 2.05-2.00 (m, 1H), 1.84 (dd, $J_1$=6.9 Hz, $J_2$=1.5 Hz, 3H); $^{13}$C NMR ($CDCl_3$, 150 MHz) δ: 167.6, 166.0, 165.5, 162.9, 153.6, 148.6, 148.4, 142.5, 141.6, 138.4, 133.6, 129.7, 127.5, 122.8, 119.3, 107.9, 99.2, 55.5, 51.2, 47.5, 30.7, 25.5, 18.3. MS (ESI, m/z): 490.2 $[M+H]^+$.

Example 32: (S,E)-1-amino-4-(4-((4-methoxypyridin-2-yl)carbamoyl)phenyl)-2-(1-(pent-2-enoyl)pyrrolidin-2-yl)-1H-imidazole-5-carboxamide

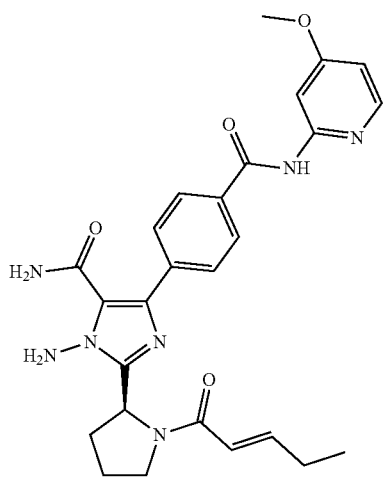 [SMILES: CC/C=C/C(=O)N1CCC[C@H]1c1nc(-c2ccc(C(=O)Nc3cc(OC)ccn3)cc2)c(C(N)=O)n1N]

Preparation of (S,E)-1-amino-4-(4-((4-methoxypyridin-2-yl)carbamoyl)phenyl)-2-(1-(pent-2-enoyl)pyrrolidin-2-yl)-1H-imidazole-5-carboxamide

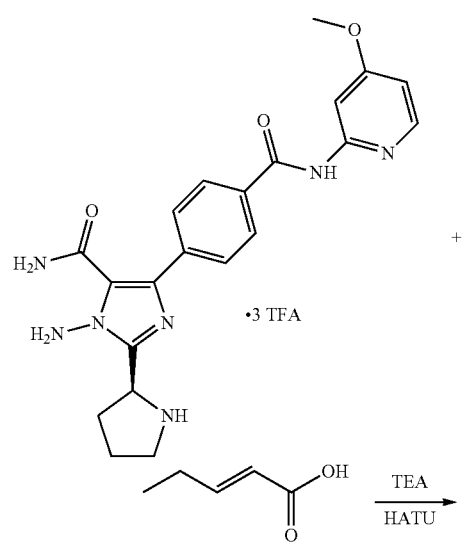

-continued

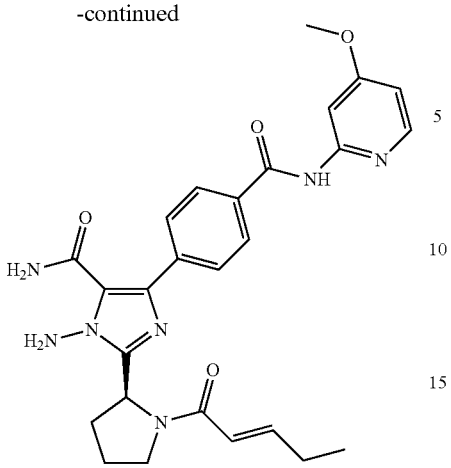

To the solution of 145 mg (0.34 mmol) of the product of Step E of example 28 in dry N, N-Dimethylformamide (5 mL) was added triethylamine (210 mg, 2.07 mmol). After 5 min, (E)-pent-2-enoic acid (31.0 mg, 0.30 mmol) and HATU (194 mg, 0.51 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S,E)-1-amino-4-(4-((4-methoxypyridin-2-yl)carbamoyl)phenyl)-2-(1-(pent-2-enoyl)pyrrolidin-2-yl)-1H-imidazole-5-carboxamide as an off-white solid (110 mg, 64%). $^1$H NMR (CDCl$_3$, 600 MHz) δ: 9.37 (s, 1H), 8.02 (d, J=5.8 Hz, 1H), 7.98 (s, 1H), 7.88 (d, J=7.9 Hz, 2H), 7.73 (d, J=7.9 Hz, 2H), 7.07 (s, 1H), 6.92-6.88 (m, 1H), 6.76 (s, 2H), 6.60 (dd, J$_1$=5.8 Hz, J$_2$=2.3 Hz, 1H), 6.29 (s, 1H), 6.08 (d, J=15.1 Hz, 1H), 5.26-5.24 (m, 1H), 3.88 (s, 3H), 3.82-3.79 (m, 1H), 3.69-3.65 (m, 1H), 2.61-2.54 (m, 1H), 2.46-2.41 (m, 1H), 2.26-2.18 (m, 3H), 2.07-2.01 (m, 1H), 1.03 (t, J=7.4 Hz, 3H); $^{13}$C NMR (CDCl$_3$, 150 MHz) δ: 167.8, 166.1, 165.7, 162.9, 153.4, 148.8, 148.7, 148.0, 141.8, 138.6, 133.5, 129.8, 127.5, 120.4, 119.2, 108.0, 99.2, 55.6, 51.2, 47.6, 30.8, 25.7, 25.5, 12.6. MS (ESI, m/z): 504.2 [M+H]$^+$.

Example 33: (S)-1-amino-4-(4-((4-methoxypyridin-2-yl)carbamoyl)phenyl)-2-(1-propioloylpyrrolidin-2-yl)-1H-imidazole-5-carboxamide Preparation of (S)-1-amino-4-(4-((4-methoxypyridin-2-yl)carbamoyl)phenyl)-2-(1-propioloylpyrrolidin-2-yl)-1H-imidazole-5-carboxamide

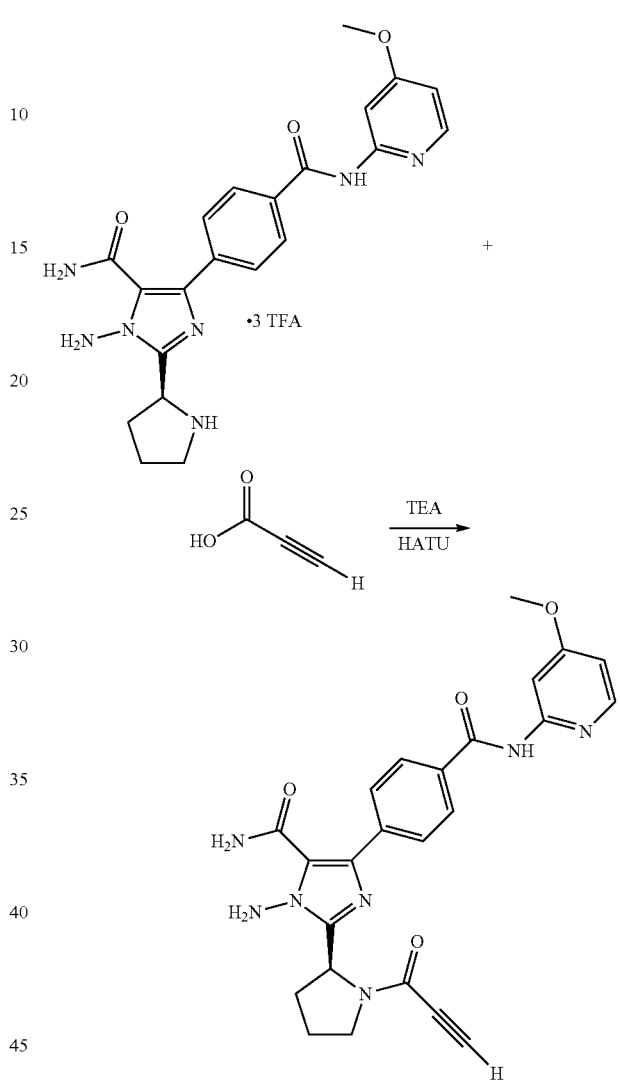

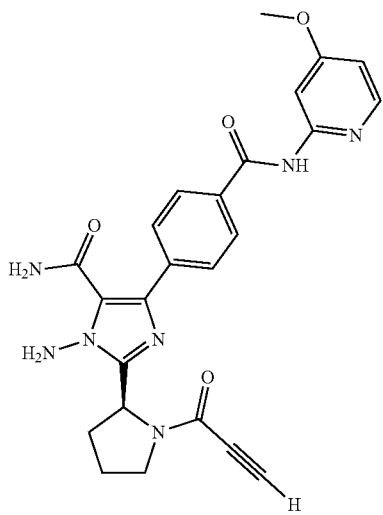 [SMILES: C#CC(=O)N1CCC[C@H]1c1nc(-c2ccc(C(=O)Nc3cc(OC)ccn3)cc2)c(C(N)=O)n1N]

To the solution of 145 mg (0.34 mmol) of the product of Step E of example 28 in dry N, N-Dimethylformamide (5 mL) was added triethylamine (210 mg, 2.07 mmol). After 5 min, propiolic acid (21.0 mg, 0.30 mmol) and HATU (194 mg, 0.51 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (23:1) to give (S)-1-amino-4-(4-((4-methoxypyridin-2-yl)carbamoyl)phenyl)-2-(1-propioloylpyrrolidin-2-yl)-1H-imidazole-5-carboxamide as a yellow solid (80 mg, 50%). $^1$H NMR (CDCl$_3$, 600 MHz) δ: 8.84 (s, 1H), 8.10 (d, J=5.5 Hz, 1H), 8.06-8.03 (m, 1H), 7.98 (d, J=8.3 Hz, 2H), 7.79 (d, J=8.3 Hz, 2H), 6.65-6.63 (m, 3H), 6.29 (s, 1H), 5.59 (s, 1H), 5.31-5.29 (m, 1H), 3.92-3.90 (m, 5H), 3.10 (s, 1H), 2.59-2.48 (m, 2H), 2.38-2.32 (m, 1H), 2.07-2.02 (m, 1H); $^{13}$C NMR (CDCl$_3$, 150 MHz) δ: 167.9, 165.5, 162.6, 153.3, 152.2, 148.4, 147.5, 141.5, 138.4, 134.0, 130.0, 127.7, 119.0, 108.2, 99.0, 78.6, 76.4, 55.6, 50.9, 49.3, 31.2, 25.0. MS (ESI, m/z): 474.1 [M+H]$^+$.

Example 34: (S)-1-amino-2-(1-(but-2-ynoyl)pyrrolidin-2-yl)-4-(4-((4-methoxy-pyridin-2-yl)carbamoyl)phenyl)-1H-imidazole-5-carboxamide

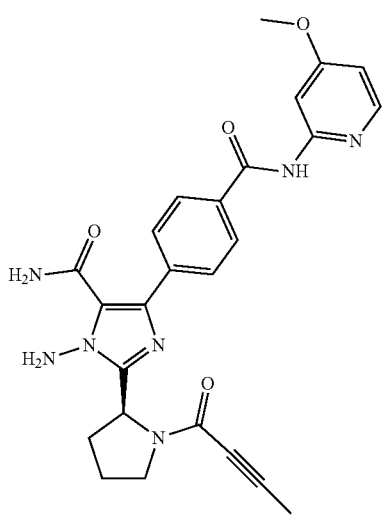 [SMILES: CC#CC(=O)N1CCC[C@H]1c1nc(-c2ccc(C(=O)Nc3cc(OC)ccn3)cc2)c(C(N)=O)n1N]

Preparation of (S)-1-amino-2-(1-(but-2-ynoyl)pyrrolidin-2-yl)-4-(4-((4-methoxypyridin-2-yl)carbamoyl)phenyl)-1H-imidazole-5-carboxamide

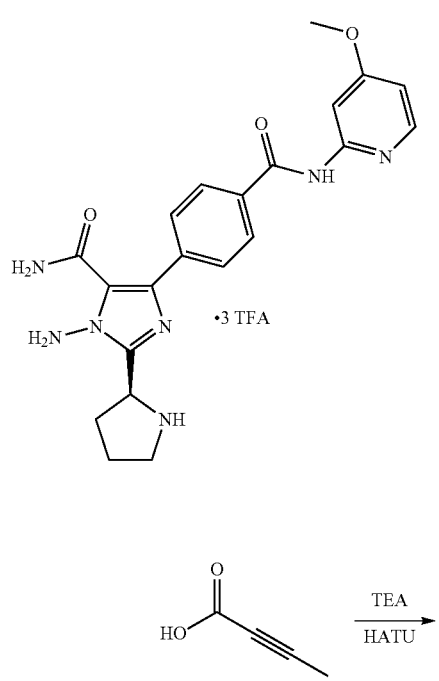

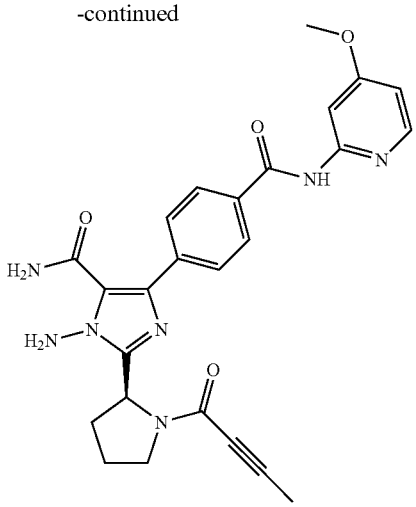

To the solution of 145 mg (0.34 mmol) of the product of Step E of example 28 in dry N, N-Dimethylformamide (5 mL) was added triethylamine (210 mg, 2.07 mmol). After 5 min, but-2-ynoic acid (26.0 mg, 0.30 mmol) and HATU (194 mg, 0.51 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-1-amino-2-(1-(but-2-ynoyl)pyrrolidin-2-yl)-4-(4-((4-methoxypyridin-2-yl)carbamoyl)phenyl)-1H-imidazole-5-carboxamide as an off-white solid (100 mg, 60%). $^1$H NMR (CDCl$_3$, 600 MHz) δ: 8.70 (s, 1H), 8.10 (d, J=5.8 Hz, 1H), 8.04 (d, J=2.1 Hz, 1H), 7.96 (d, J=8.3 Hz, 2H), 7.80 (d, J=8.3 Hz, 2H), 6.70 (s, 2H), 6.64 (dd, J$_1$=5.8 Hz, J$_2$=2.3 Hz, 1H), 6.47 (s, 1H), 5.53 (s, 1H), 5.27-5.25 (m, 1H), 3.92 (s, 3H), 3.88-3.85 (m, 2H), 2.59-2.54 (m, 1H), 2.52-2.47 (m, 1H), 2.35-2.30 (m, 1H), 2.04-1.99 (m, 4H); $^{13}$C NMR (CDCl$_3$, 150 MHz) δ: 167.8, 165.5, 162.5, 153.5, 153.3, 148.6, 147.7, 141.6, 138.6, 133.9, 130.0, 127.6, 119.0, 108.2, 98.9, 89.2, 74.1, 55.6, 50.6, 49.1, 31.2, 25.0, 4.1. MS (ESI, m/z): 488.2 [M+H]$^+$.

Example 35: (S)-2-(1-acryloylpyrrolidin-2-yl)-1-amino-4-(4-((4-ethylpyridin-2-yl) carbamoyl)phenyl)-1H-imidazole-5-carboxamide

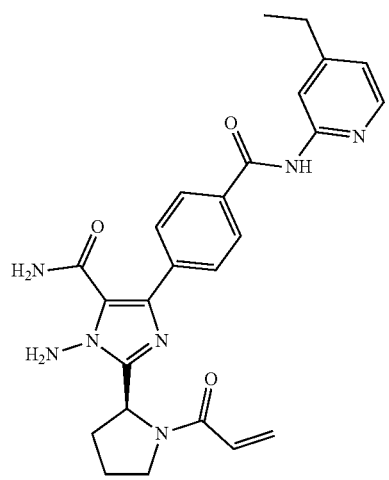 [SMILES: C=CC(=O)N1CCC[C@H]1c1nc(-c2ccc(C(=O)Nc3cc(CC)ccn3)cc2)c(C(N)=O)n1N]

Step A: Preparation of (S)-ethyl 2-(1-(tert-butoxycarbonyl)pyrrolidin-2-yl)-4-(4-((4-ethylpyridin-2-yl)carbamoyl)phenyl)-1H-imidazole-5-carboxylate

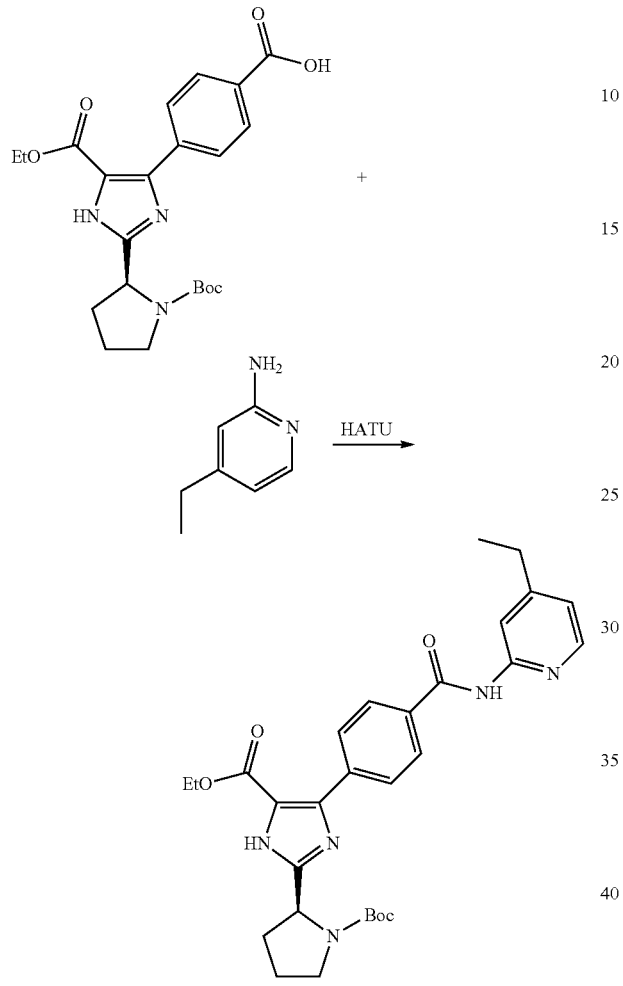

Step B: Preparation of (S)-ethyl 1-amino-2-(1-(tert-butoxycarbonyl)pyrrolidin-2-yl)-4-(4-((4-ethylpyridin-2-yl)carbamoyl)phenyl)-1H-imidazole-5-carboxylate

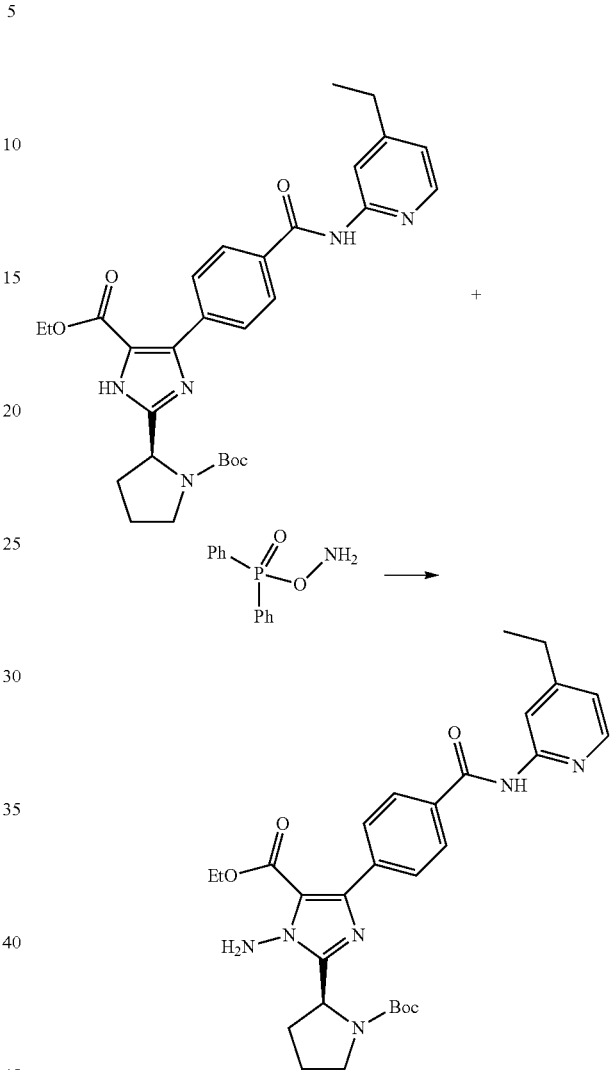

To the solution of 28 g (65 mmol) of the product of Step F of example 1 in dry N, N-Dimethylformamide (250 mL) was stirred and added HATU (30 g, 78 mmol), diisopropylethylamine (60 mL, 327 mmol) and 4-ethylpyridin-2-amine (12 g, 100 mmol). The reaction mixture was stirred at 80° C. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (3:1) to afford (S)-ethyl 2-(1-(tert-butoxycarbonyl)pyrrolidin-2-yl)-4-(4-((4-ethylpyridin-2-yl)carbamoyl)phenyl)-1H-imidazole-5-carboxylate as a white solid (29 g, 84%). $^1$H NMR (CDCl$_3$, 400 MHz) δ: 11.22-11.10 (m, 1H), 8.71 (s, 1H), 8.29 (s, 1H), 8.17-8.14 (m, 3H), 7.96-7.94 (m, 2H), 6.92 (d, J=5.0 Hz, 1H), 5.02-4.91 (m, 1H), 4.37-4.29 (m, 2H), 3.53-3.42 (m, 2H), 2.70 (q, J=7.6 Hz, 2H), 2.27-2.09 (m, 2H), 2.00-1.93 (m, 2H), 1.51-1.48 (m, 9H), 1.34-1.26 (m, 6H). MS (ESI, m/z): 534.2 [M+H]$^+$.

To the solution of 12 g (22 mmol) of the product of Step A in dry N, N-Dimethylformamide (50 mL) was stirred and slowly added lithium hexamethyldisilazane (26 mL, 1 M solution in tetrahydrofuran) at −10° C. After the mixture was stirred for 10 min, O-(diphenylphosphinyl) hydroxylamine (5.2 g, 22 mmol) was added at 0° C. and the resulting suspension was stirred 2 h at room temperature (in cases where the reaction mixture became too viscous, additional N, N-Dimethylformamide was added). The reaction was quenched with brine and concentrated to dryness in vacuum. The residue was washed three times with ethyl acetate (3×50 mL). The combined organic fractions were dried with anhydrous Na$_2$SO$_4$ and the solvent was removed under reduced pressure to afford the crude residue, which was subjected to column chromatography with petroleum ether and ethyl acetate (3:1) to give the desired product (S)-ethyl 1-amino-2-(1-(tert-butoxycarbonyl)pyrrolidin-2-yl)-4-(4-((4-ethylpyridin-2-yl)carbamoyl)phenyl)-1H-imidazole-5-carboxylate (8.4 g, 70%). $^1$H NMR (CDCl$_3$, 400 MHz) δ: 8.60 (s, 1H), 8.29 (s, 1H), 8.19 (d, J=5.1 Hz, 1H), 7.92 (d, J=8.3 Hz, 2H), 7.81 (d, J=8.5 Hz, 2H), 6.93 (dd, J$_1$=5.1 Hz, J$_2$=1.3

Hz, 1H), 6.67 (s, 2H), 5.20-5.18 (m, 1H), 4.28 (q, J=7.2 Hz, 2H), 3.61-3.44 (m, 2H), 2.71 (q, J=7.6 Hz, 2H), 2.45-2.35 (m, 2H), 2.29-2.20 (m, 1H), 1.98-1.91 (m, 1H), 1.42 (s, 7H), 1.31-1.27 (m, 5H), 1.25-1.21 (m, 3H). MS (ESI, m/z): 549.2 [M+H]+.

Step C: Preparation of (S)-1-amino-2-(1-(tert-butoxycarbonyl)pyrrolidin-2-yl)-4-(4-((4-ethylpyridin-2-yl)carbamoyl)phenyl)-1H-imidazole-5-carboxylic acid

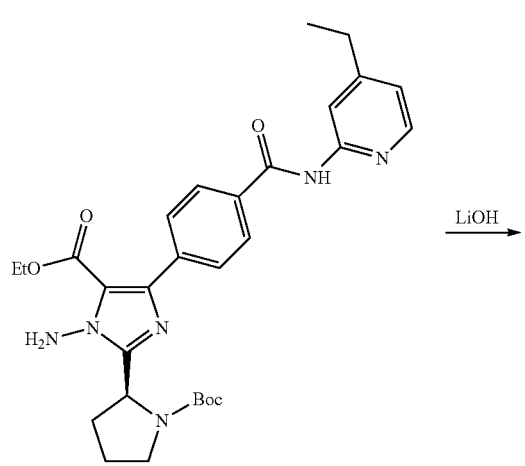

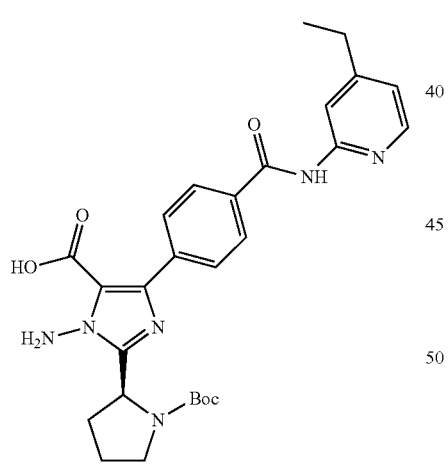

To the solution of 2.0 g (3.6 mmol) of the product of Step B in methanol (15 mL) was stirred and added aqueous lithium hydroxide (2 mol/L, 18 mL), then stirred at room temperature for 2 h. The reaction mixture was evaporated and diluted with water (100 mL) and acidified with aqueous HCl till pH 3. The mixture was washed with ethyl acetate three times (3×100 mL). The combined organic layers were concentrated under reduced pressure to afford (S)-1-amino-2-(1-(tert-butoxycarbonyl)pyrrolidin-2-yl)-4-(4-((4-ethylpyridin-2-yl)carbamoyl)phenyl)-1H-imidazole-5-carboxylic acid as a white solid (1.8 g, 95%).

Step D: Preparation of (S)-tert-butyl 2-(1-amino-5-carbamoyl-4-(4-((4-ethylpyridin-2-yl)carbamoyl)phenyl)-1H-imidazol-2-yl)pyrrolidine-1-carboxylate

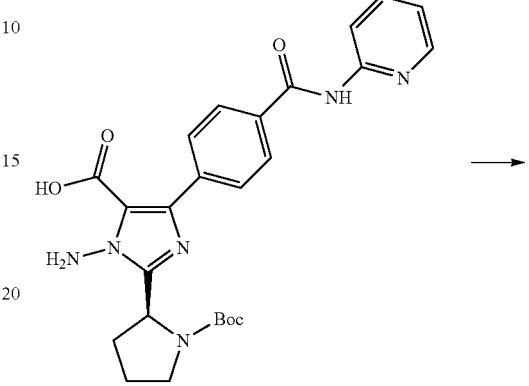

To the solution of 3.1 g (6.0 mmol) of the product of Step C in dry N, N-Dimethylformamide (20 mL) was stirred and added HATU (3.5 g, 9.1 mmol), diisopropylethylamine (3.2 mL, 18.1 mmol) and NH4Cl (3.3 g, 60 mmol). The reaction mixture was stirred at room temperature for 2 h. The reaction mixture was quenched with brine and washed with ethyl acetate three times (3×50 mL). The combined organic layers were concentrated under reduced pressure and purified by flash chromatography with dichloromethane and methanol (30:1) to afford (S)-tert-butyl 2-(1-amino-5-carbamoyl-4-((4-ethylpyridin-2-yl)carbamoyl)phenyl)-1H-imidazol-2-yl)pyrrolidine-1-carboxylate as a white solid (2.4 g, 78%). 1H NMR (CDCl3, 400 MHz) δ: 8.96 (s, 1H), 8.23 (s, 1H), 8.15 (d, J=5.1 Hz, 1H), 7.90 (d, J=8.0 Hz, 2H), 7.78-7.66 (m, 2H), 6.98 (s, 1H), 6.91-6.90 (m, 1H), 6.61 (s, 2H), 6.08 (s, 1H), 5.09-5.07 (m, 1H), 3.57-3.43 (m, 2H), 2.68 (q, J=7.6 Hz, 2H), 2.46-2.38 (m, 2H), 2.26-2.17 (m, 1H), 1.96-1.93 (m, 1H), 1.42 (s, 7H), 1.29-1.25 (m, 5H). MS (ESI, m/z): 520.2 [M+H]+.

Step E: Preparation of (S)-1-amino-4-(4-((4-eth-ylpyridin-2-yl)carbamoyl)phenyl)-2-(pyrrolidin-2-yl)-1H-imidazole-5-carboxamide Step F: Preparation of (S)-2-(1-acryloylpyrrolidin-2-yl)-1-amino-4-(4-((4-ethylpyridin-2-yl)carbamoyl)phenyl)-1H-imidazole-5-carboxamide

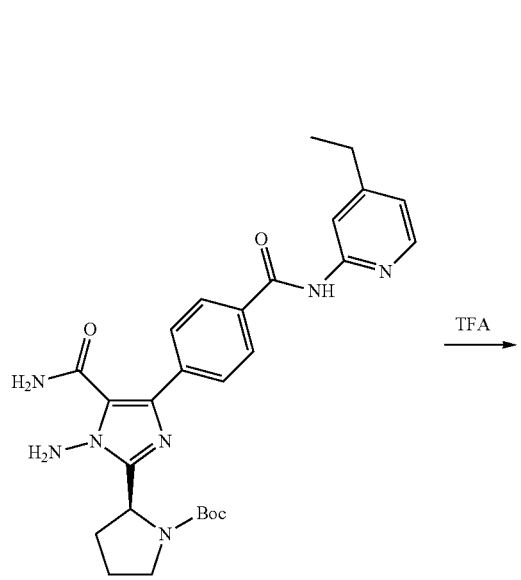

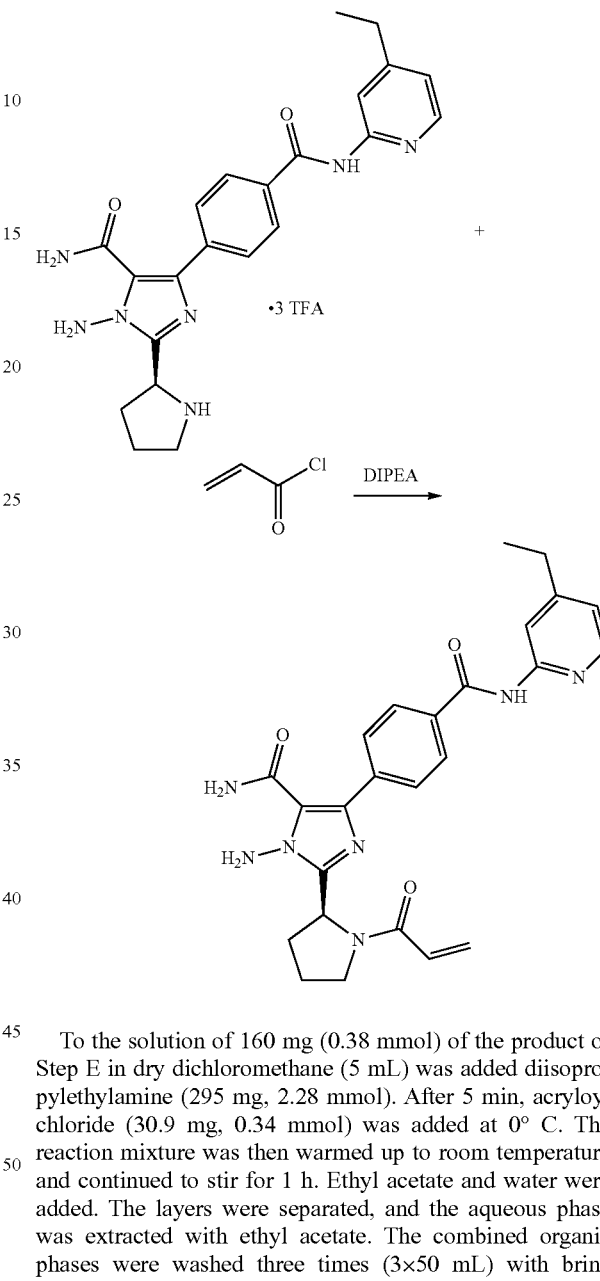

To the solution of 200 mg (0.38 mmol) of the product of Step D in dichloromethane (5 mL) was added trifluoroacetic acid (2.3 mL). The mixture was stirred at room temperature for 1 h and then concentrated to afford (S)-1-amino-4-(4-((4-ethylpyridin-2-yl)carbamoyl)phenyl)-2-(pyrrolidin-2-yl)-1H-imidazole-5-carboxamide as a light yellow oil. MS (ESI, m/z): 420.2 [M+H]$^+$.

To the solution of 160 mg (0.38 mmol) of the product of Step E in dry dichloromethane (5 mL) was added diisopropylethylamine (295 mg, 2.28 mmol). After 5 min, acryloyl chloride (30.9 mg, 0.34 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-2-(1-acryloyl pyrrolidin-2-yl)-1-amino-4-(4-((4-ethylpyridin-2-yl)carbamoyl)phenyl)-1H-imidazole-5-carboxamide as an off-white solid (108 mg, 60%). $^1$H NMR (CDCl$_3$, 400 MHz) δ: 8.81 (s, 1H), 8.26 (s, 1H), 8.17 (d, J=5.0 Hz, 1H), 7.94 (d, J=8.4 Hz, 2H), 7.78 (d, J=8.4 Hz, 2H), 6.92 (d, J=5.0 Hz, 1H), 6.80 (s, 2H), 6.62 (s, 1H), 6.46 (dd, J$_1$=16.8 Hz, J$_2$=10.2 Hz, 1H), 6.32 (dd, J$_1$=16.8 Hz, J$_2$=2.0 Hz, 1H), 5.84 (s, 1H), 5.71 (dd, J$_1$=10.2 Hz, J$_2$=2.0 Hz, 1H), 5.33 (dd, J$_1$=8.0 Hz, J$_2$=5.0 Hz, 1H), 3.88-3.82 (m, 1H), 3.73-3.67 (m, 1H), 2.70 (q, J=7.6 Hz, 2H), 2.64-2.56

(m, 1H), 2.53-2.45 (m, 1H), 2.32-2.23 (m, 1H), 2.12-2.02 (m, 1H), 1.28 (t, J=7.6 Hz, 3H); $^{13}$C NMR (CDCl$_3$, 150 MHz) δ: 165.5, 165.1, 162.7, 156.2, 151.8, 148.3, 147.7, 141.7, 138.5, 134.0, 129.9, 128.6, 128.6, 127.5, 120.1, 118.9, 113.8, 51.3, 47.7, 30.8, 28.8, 25.6, 14.6. MS (ESI, m/z): 474.2 [M+H]$^+$.

Example 36: (S)-1-amino-4-(4-((4-ethylpyridin-2-yl)carbamoyl)phenyl)-2-(1-methacryloylpyrrolidin-2-yl)-1H-imidazole-5-carboxamide

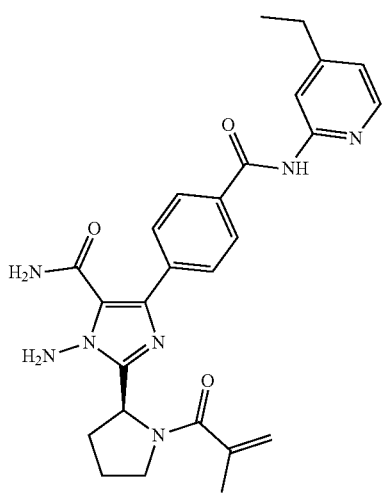

Preparation of (S)-1-amino-4-(4-((4-ethylpyridin-2-yl)carbamoyl)phenyl)-2-(1-methacryloylpyrrolidin-2-yl)-1H-imidazole-5-carboxamide

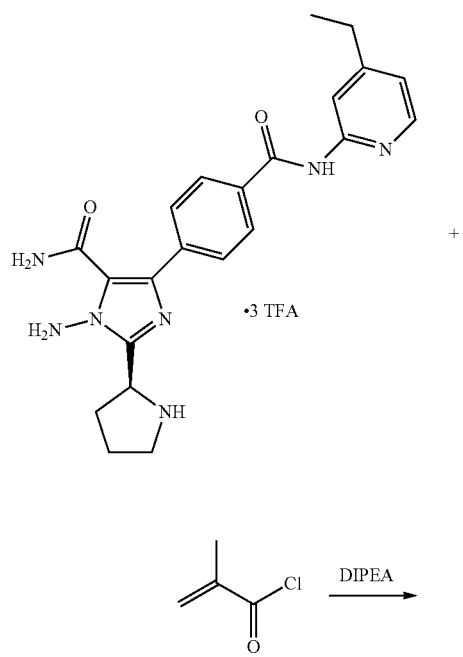

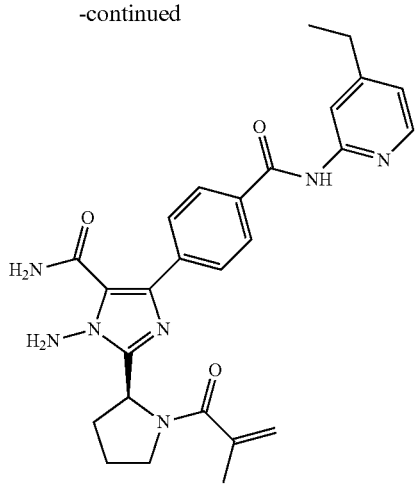

To the solution of 160 mg (0.38 mmol) of the product of Step E of example 35 in dry dichloromethane (5 mL) was added diisopropylethylamine (295 mg, 2.28 mmol). After 5 min, methacryloyl chloride (35.5 mg, 0.34 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-1-amino-4-(4-((4-ethylpyridin-2-yl)carbamoyl)phenyl)-2-(1-methacryloylpyrrolidin-2-yl)-1H-imidazole-5-carboxamide as an off-white solid (120 mg, 65%). $^1$H NMR (CDCl$_3$, 600 MHz) δ: 8.96 (s, 1H), 8.26 (s, 1H), 8.16 (d, J=4.9 Hz, 1H), 7.95 (d, J=8.3 Hz, 2H), 7.75 (d, J=8.2 Hz, 2H), 6.92 (d, J=4.7 Hz, 1H), 6.74 (s, 2H), 6.56 (s, 1H), 5.95 (s, 1H), 5.30 (s, 1H), 5.29-5.27 (m, 1H), 5.22 (s, 1H), 3.78-3.69 (m, 2H), 2.70 (q, J=7.6 Hz, 2H), 2.60-2.53 (m, 1H), 2.36-2.29 (m, 2H), 1.95-1.90 (m, 4H), 1.28 (t, J=7.6 Hz, 3H); $^{13}$C NMR (CDCl$_3$, 150 MHz) δ: 171.2, 165.6, 162.8, 156.3, 151.8, 148.4, 147.6, 141.7, 140.8, 138.5, 134.0, 129.9, 127.6, 120.1, 119.1, 118.0, 113.9, 51.2, 50.0, 30.9, 28.8, 25.9, 19.8, 14.5. MS (ESI, m/z): 488.2 [M+H]$^+$.

Example 37: (S)-1-amino-4-(4-((4-ethylpyridin-2-yl)carbamoyl)phenyl)-2-(1-(3-methylbut-2-enoyl)pyrrolidin-2-yl)-1H-imidazole-5-carboxamide

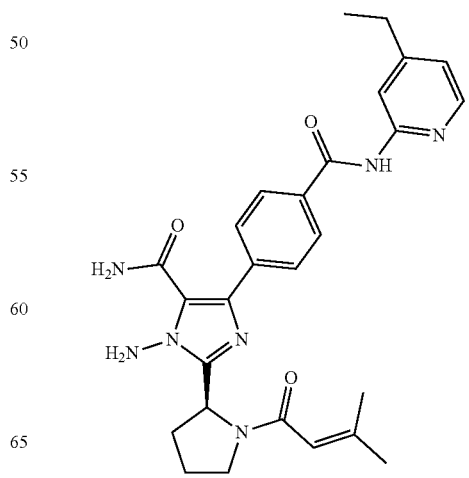

Preparation of (S)-1-amino-4-(4-((4-ethylpyridin-2-yl)carbamoyl)phenyl)-2-(1-(3-methylbut-2-enoyl)pyrrolidin-2-yl)-1H-imidazole-5-carboxamide

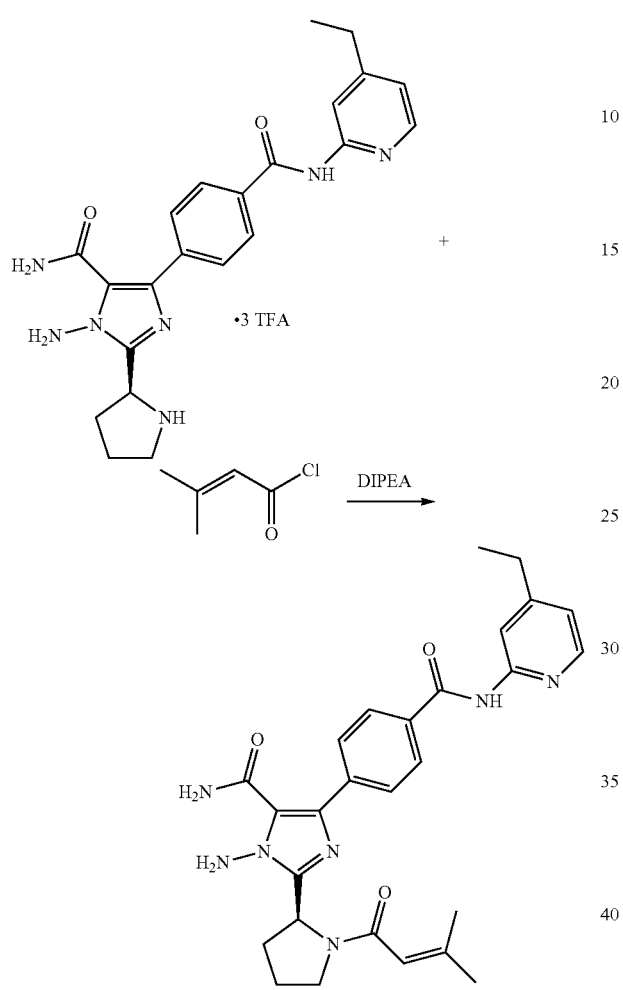

To the solution of 160 mg (0.38 mmol) of the product of Step E of example 35 in dry dichloromethane (5 mL) was added diisopropylethylamine (295 mg, 2.28 mmol). After 5 min, 3-methylbut-2-enoyl chloride (40.3 mg, 0.34 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-1-amino-4-(4-((4-ethylpyridin-2-yl)carbamoyl)phenyl)-2-(1-(3-methylbut-2-enoyl)pyrrolidin-2-yl)-1H-imidazole-5-carboxamide as an off-white solid (110 mg, 58%). $^1$H NMR (CDCl$_3$, 600 MHz) δ: 9.06 (s, 1H), 8.30 (s, 1H), 8.21-8.13 (m, 1H), 7.96 (d, J=8.0 Hz, 2H), 7.79 (d, J=8.0 Hz, 2H), 6.94-6.82 (m, 4H), 5.87 (s, 1H), 5.79 (s, 1H), 5.28-5.26 (m, 1H), 3.75-3.71 (m, 1H), 3.62-3.58 (m, 1H), 2.70 (q, J=7.5 Hz, 2H), 2.56-2.45 (m, 2H), 2.28-2.23 (m, 1H), 2.05-1.99 (m, 4H), 1.85 (s, 3H), 1.28 (t, J=7.6 Hz, 3H); $^{13}$C NMR (CDCl$_3$, 150 MHz) δ: 167.0, 165.6, 162.7, 156.7, 151.7, 150.9, 148.8, 147.0, 141.7, 138.7, 133.7, 130.0, 127.6, 120.0, 119.1, 117.7, 114.0, 50.8, 48.0, 30.9, 28.9, 27.2, 25.6, 20.4, 14.5. MS (ESI, m/z): 502.2 [M+H]$^+$.

Example 38: (S)-1-amino-2-(1-(but-2-ynoyl)pyrrolidin-2-yl)-4-(4-((4-ethylpyridin-2-yl)carbamoyl)phenyl)-1H-imidazole-5-carboxamide

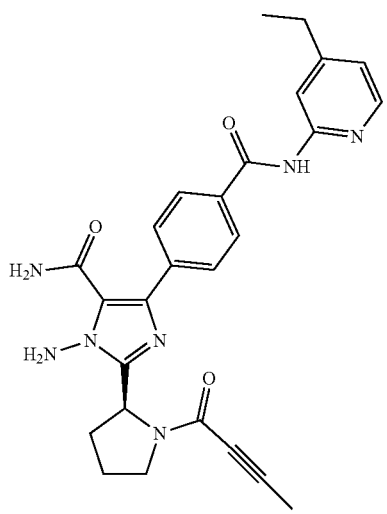 [SMILES: CC#CC(=O)N1CCC[C@H]1c1nc(-c2ccc(C(=O)Nc3cc(CC)ccn3)cc2)c(C(N)=O)n1N]

Preparation of (S)-1-amino-2-(1-(but-2-ynoyl)pyrrolidin-2-yl)-4-(4-((4-ethylpyridin-2-yl)carbamoyl)phenyl)-1H-imidazole-5-carboxamide

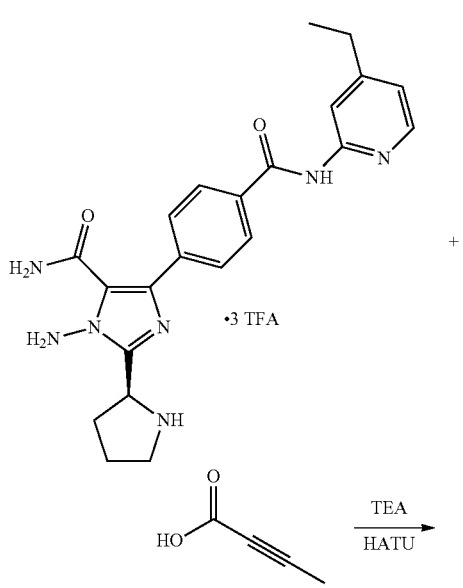

113
-continued

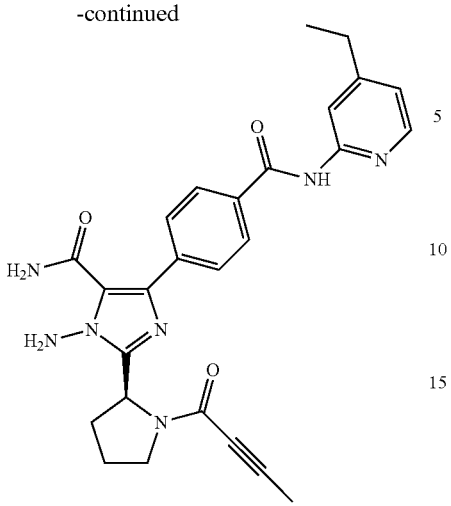

To the solution of 160 mg (0.38 mmol) of the product of Step E of example 35 in dry N, N-Dimethylformamide (5 mL) was added triethylamine (230 mg, 2.28 mmol). After 5 min, but-2-ynoic acid (29.0 mg, 0.34 mmol) and HATU (217 mg, 0.57 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(but-2-ynoyl)pyrrolidin-2-yl)-4-(4-((4-ethylpyridin-2-yl)carbamoyl)phenyl)-1H-imidazole-5-carboxamide as an off-white solid (120 mg, 65%). $^1$H NMR (CDCl$_3$, 400 Mhz) δ: 9.09 (s, 1H), 8.30 (s, 1H), 8.16 (d, J=5.2 Hz, 1H), 7.99 (d, J=8.4 Hz, 2H), 7.79 (d, J=8.4 Hz, 2H), 6.95 (d, J=5.2 Hz, 1H), 6.71 (s, 2H), 6.38 (s, 1H), 5.68 (s, 1H), 5.29-5.25 (m, 1H), 3.88-3.85 (m, 2H), 2.72 (q, J=7.6 Hz, 2H), 2.58-2.46 (m, 2H), 2.37-2.30 (m, 1H), 2.04-1.98 (m, 4H), 1.29 (t, J=7.6 Hz, 3H); $^{13}$C NMR (CDCl$_3$, 150 MHz) δ: 165.5, 162.7, 156.2, 153.5, 151.8, 147.8, 147.7, 141.6, 138.4, 134.1, 129.9, 127.6, 120.1, 119.0, 113.8, 89.2, 74.1, 50.7, 49.1, 31.2, 28.8, 25.0, 14.6, 4.1. MS (ESI, m/z): 486.2 [M+H]$^+$.

Example 39: (S)-1-amino-2-(1-cyanopyrrolidin-2-yl)-4-(4-((4-ethylpyridin-2-yl) carbamoyl)phenyl)-1H-imidazole-5-carboxamide

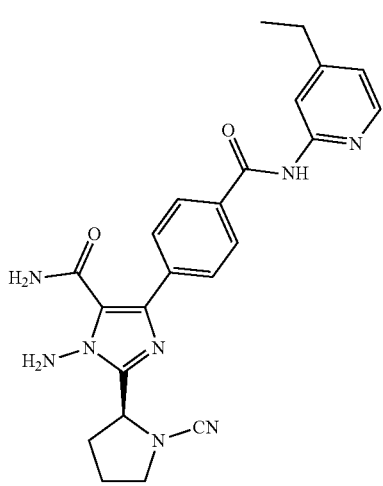 [SMILES: CCc1ccnc(NC(=O)c2ccc(-c3nc([C@@H]4CCCN4C#N)n(N)c3C(N)=O)cc2)c1]

114
Preparation of (S)-1-amino-2-(1-cyanopyrrolidin-2-yl)-4-(4-((4-ethylpyridin-2-yl)carbamoyl)phenyl)-1H-imidazole-5-carboxamide

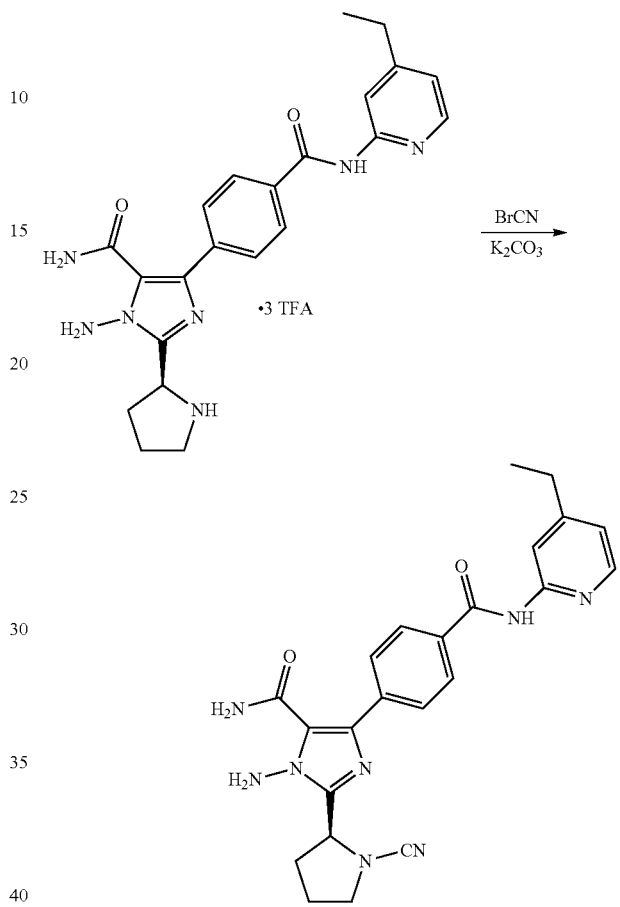

To the solution of 160 mg (0.38 mmol) of the product of Step E of example 35 in dry acetonitrile (5 mL) was added $K_2CO_3$ (158 mg, 1.14 mmol). After 5 min, BrCN (40.2 mg, 0.38 mmol) was added. The reaction mixture was continued to stir at room temperature for 6 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-cyanopyrrolidin-2-yl)-4-(4-((4-ethyl-pyridin-2-yl)carbamoyl)phenyl)-1H-imidazole-5-carboxamide as a yellow solid (85 mg, 50%). $^1$H NMR (CDCl$_3$, 400 MHz) δ: 8.73 (s, 1H), 8.27 (s, 1H), 8.19 (d, J=5.1 Hz, 1H), 8.01 (d, J=8.4 Hz, 2H), 7.77 (d, J=8.4 Hz, 2H), 6.95 (dd, J$_1$=5.1 Hz, J$_2$=1.3 Hz, 1H), 5.72 (s, 2H), 5.67 (s, 2H), 5.24-5.21 (m, 1H), 3.71-3.66 (m, 1H), 3.58-3.53 (m, 1H), 2.72 (q, J=7.6 Hz, 2H), 2.58-2.51 (m, 1H), 2.33-2.26 (m, 2H), 2.08-2.01 (m, 1H), 1.30 (t, J=7.6 Hz, 3H); $^{13}$C NMR (CDCl$_3$, 150 MHz) δ: 165.2, 162.3, 156.3, 151.7, 148.4, 147.8, 141.0, 137.6, 134.7, 129.7, 128.0, 121.2, 120.3, 117.1, 113.8, 56.0, 51.3, 30.5, 28.8, 25.5, 14.6. MS (ESI, m/z): 445.2 [M+H]$^+$.

Example 40: (S)-2-(1-acryloylpyrrolidin-2-yl)-1-amino-4-(4-((4-fluoropyridin-2-yl) carbamoyl)phenyl)-1H-imidazole-5-carboxamide

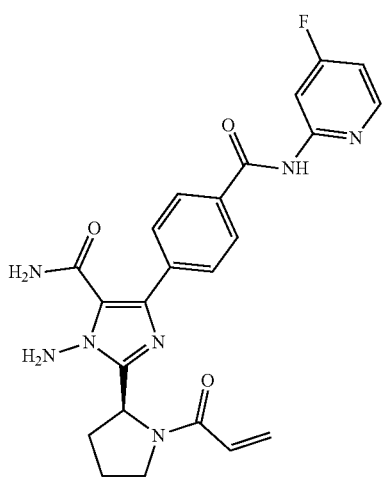

Step A: Preparation of (S)-ethyl 2-(1-(tert-butoxycarbonyl)pyrrolidin-2-yl)-4-(4-((4-fluoropyridin-2-yl)carbamoyl)phenyl)-1H-imidazole-5-carboxylate

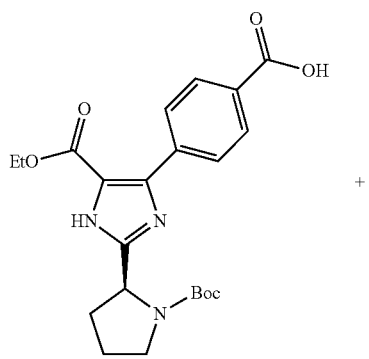

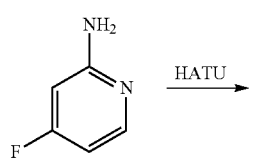

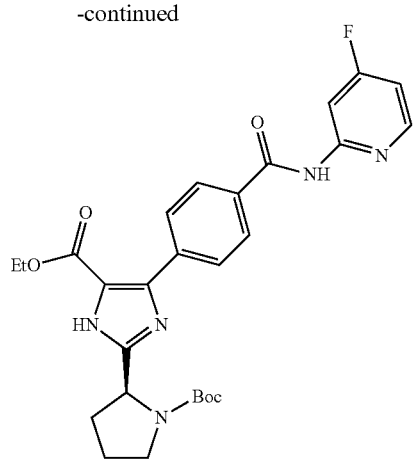

To the solution of 15 g (37 mmol) of the product of Step F of example 1 in dry N, N-Dimethylformamide (150 mL) was stirred and added HATU (17 g, 45 mmol), diisopropylethylamine (33 mL, 186 mmol) and 4-fluoropyridin-2-amine (6.3 g, 56 mmol). The reaction mixture was stirred at 80° C. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (2:1) to afford (S)-ethyl 2-(1-(tert-butoxycarbonyl)pyrrolidin-2-yl)-4-(4-((4-fluoropyridin-2-yl)carbamoyl)phenyl)-1H-imidazole-5-carboxylate as a white solid (10 g, 52%). $^1$H NMR (CDCl$_3$, 400 MHz) δ: 11.12 (s, 1H), 8.92 (s, 1H), 8.24-8.15 (m, 4H), 7.94 (d, J=8.3 Hz, 2H), 6.82-6.78 (m, 1H), 5.02-4.91 (m, 1H), 4.37-4.29 (m, 2H), 3.53-3.43 (m, 2H), 2.22-2.08 (m, 2H), 2.00-1.95 (m, 2H), 1.51 (s, 9H), 1.34-1.29 (m, 3H). MS (ESI, m/z): 524.2 [M+H]$^+$.

Step B: Preparation of (S)-ethyl 1-amino-2-(1-(tert-butoxycarbonyl)pyrrolidin-2-yl)-4-(4-((4-fluoropyridin-2-yl)carbamoyl)phenyl)-1H-imidazole-5-carboxylate

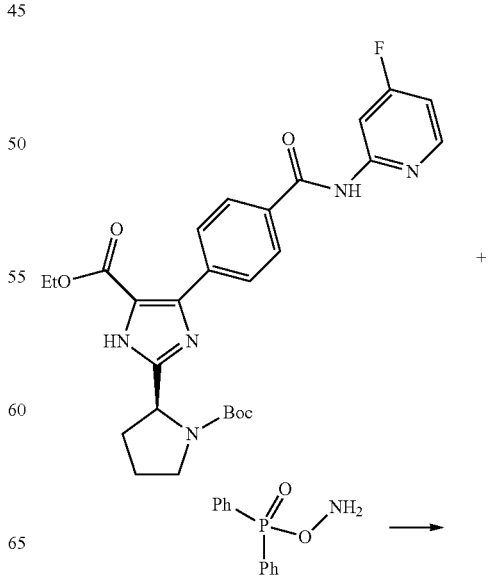

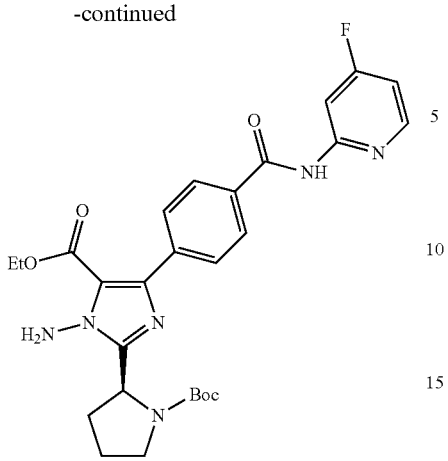
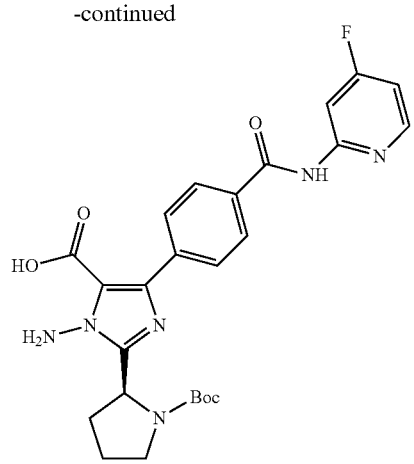

To the solution of 5 g (9.5 mmol) of the product of Step A in dry N, N-Dimethylformamide (30 mL) was stirred and slowly added lithium hexamethyldisilazane (11 mL, 1 M solution in tetrahydrofuran) at −10° C. After the mixture was stirred for 10 min, O-(diphenylphosphinyl) hydroxylamine (2.2 g, 9.5 mmol) was added at 0° C. and the resulting suspension was stirred 2 h at room temperature (in cases where the reaction mixture became too viscous, additional N, N-Dimethylformamide was added). The reaction was quenched with brine and washed three times with ethyl acetate (3×50 mL). The combined organic fractions were dried with anhydrous $Na_2SO_4$ and the solvent was removed under reduced pressure to afford the crude residue, which was subjected to column chromatography with petroleum ether and ethyl acetate (2:1) to give the desired product (S)-ethyl 1-amino-2-(1-(tert-butoxycarbonyl)pyrrolidin-2-yl)-4-(4-((4-fluoropyridin-2-yl)carbamoyl)phenyl)-1H-imidazole-5-carboxylate (3.1 g, 60%). $^1$H NMR ($CDCl_3$, 400 MHz) δ: 8.80 (s, 1H), 8.26-8.20 (m, 2H), 7.92 (d, J=8.3 Hz, 2H), 7.82 (d, J=8.4 Hz, 2H), 6.84-6.80 (m, 1H), 6.66 (s, 2H), 5.20-5.17 (m, 1H), 4.28 (q, J=7.0 Hz, 2H), 3.69-3.44 (m, 2H), 2.44-2.20 (m, 3H), 1.97-1.91 (m, 1H), 1.41 (s, 7H), 1.27-1.21 (m, 5H). MS (ESI, m/z): 539.2 [M+H]$^+$.

Step C: Preparation of (S)-1-amino-2-(1-(tert-butoxycarbonyl)pyrrolidin-2-yl)-4-(4-((4-fluoropyridin-2-yl)carbamoyl)phenyl)-1H-imidazole-5-carboxylic acid To the solution of 2.0 g (3.7 mmol) of the product of Step B in methanol (15 mL) was stirred and added aqueous Lithium hydroxide (2 mol/L, 18 mL), then stirred at room temperature for 2 h. The reaction mixture was evaporated and diluted with water (100 mL) and acidified with aqueous HCl till pH 3. The mixture was washed with ethyl acetate three times (3×50 mL). The combined organic layers were concentrated under reduced pressure to afford (S)-1-amino-2-(1-(tert-butoxycarbonyl)pyrrolidin-2-yl)-4-(4-((4-fluoropyridin-2-yl)carbamoyl)phenyl)-1H-imidazole-5-carboxylic acid as a white solid (1.7 g, 90%).

Step D: Preparation of (S)-tert-butyl 2-(1-amino-5-carbamoyl-4-(4-((4-fluoropyridin-2-yl)carbamoyl) phenyl)-1H-imidazol-2-yl)pyrrolidine-1-carboxylate

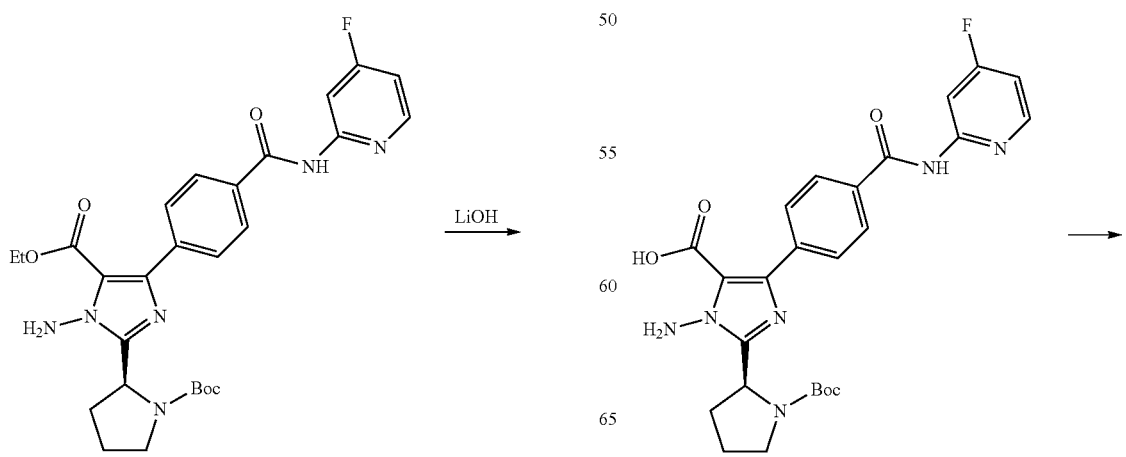

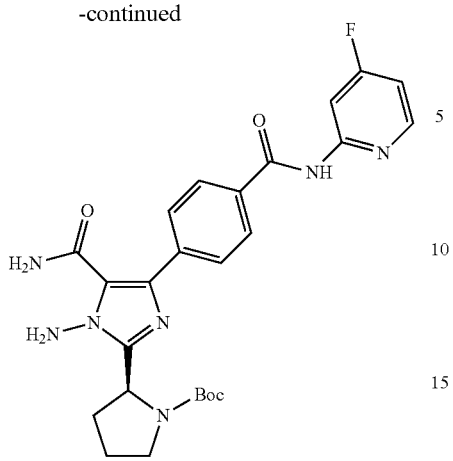

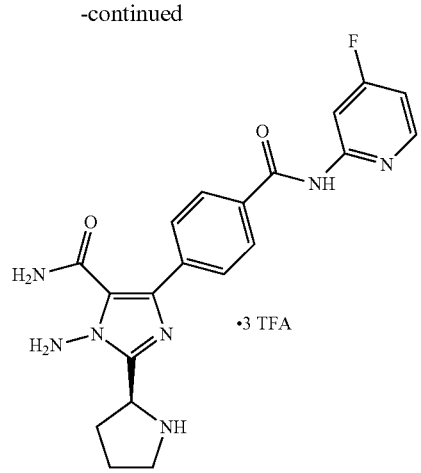

To the solution of 1.7 g (3.4 mmol) of the product of Step C in dry N, N-Dimethylformamide (20 mL) was stirred and added HATU (2.0 g, 5.1 mmol), diisopropylethylamine (1.8 mL, 10.3 mmol) and NH$_4$Cl (1.9 g, 34 mmol). The reaction mixture was stirred at room temperature for 2 h. The reaction mixture was quenched with brine and washed with ethyl acetate three times (3×50 mL). The combined organic layers were concentrated under reduced pressure and purified by flash chromatography with dichloromethane and methanol (28:1) to afford (S)-tert-butyl 2-(1-amino-5-carbamoyl-4-(4-((4-fluoropyridin-2-yl)carbamoyl)phenyl)-1H-imidazol-2-yl)pyrrolidine-1-carboxylate as a white solid (1.4 g, 80%). $^1$H NMR (CDCl$_3$, 400 MHz) δ: 8.98 (s, 1H), 8.25 (dd, J$_1$=8.5 Hz, J$_2$=5.7 Hz, 1H), 8.20 (dd, J$_1$=11.2 Hz, J$_2$=2.2 Hz, 1H), 7.93 (d, J=8.2 Hz, 2H), 7.83 (d, J=8.1 Hz, 2H), 6.97 (s, 1H), 6.84-6.80 (m, 1H), 6.60 (s, 2H), 5.75 (s, 1H), 5.11-5.08 (m, 1H), 3.59-3.45 (m, 2H), 2.48-2.39 (m, 2H), 2.26-2.19 (m, 1H), 2.00-1.92 (m, 1H), 1.43 (s, 7H), 1.28 (s, 2H). MS (ESI, m/z): 510.2 [M+H]$^+$.

Step E: Preparation of (S)-1-amino-4-(4-((4-fluoropyridin-2-yl)carbamoyl)phenyl)-2-(pyrrolidin-2-yl)-1H-imidazole-5-carboxamide To the solution of 193 mg (0.38 mmol) of the product of Step D in dichloromethane (5 mL) was added trifluoroacetic acid (2.3 mL). The mixture was stirred at room temperature for 1 h and then concentrated to afford (S)-1-amino-4-(4-((4-fluoropyridin-2-yl)carbamoyl)phenyl)-2-(pyrrolidin-2-yl)-1H-imidazole-5-carboxamide as a light yellow oil. MS (ESI, m/z): 410.1 [M+H]$^+$.

Step F: Preparation of (S)-2-(1-acryloylpyrrolidin-2-yl)-1-amino-4-(4-((4-fluoropyridin-2-yl)carbamoyl)phenyl)-1H-imidazole-5-carboxamide

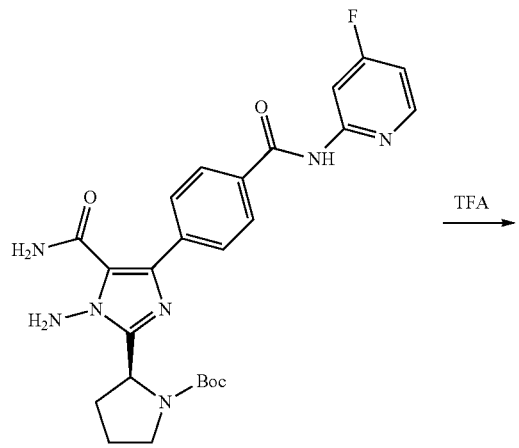

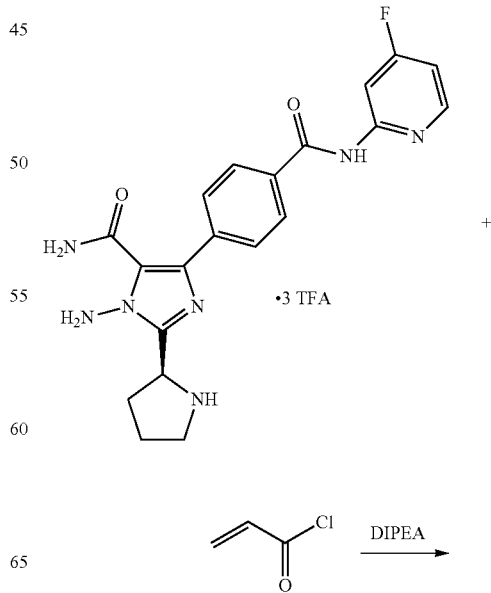

-continued

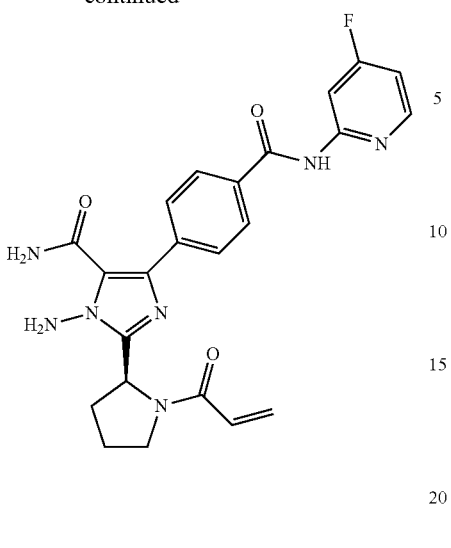

To the solution of 155 mg (0.38 mmol) of the product of Step E in dry dichloromethane (5 mL) was added diisopropylethylamine (295 mg, 2.28 mmol). After 5 min, acryloyl chloride (30.9 mg, 0.34 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-2-(1-acryloyl-pyrrolidin-2-yl)-1-amino-4-(4-((4-fluoropyridin-2-yl)carbamoyl)phenyl)-1H-imidazole-5-carboxamide as an off-white solid (123 mg, 70%). $^1$H NMR (CDCl$_3$, 400 MHz) δ: 9.02 (s, 1H), 8.24 (dd, $J_1$=8.4 Hz, $J_2$=5.8 Hz, 1H), 8.19 (dd, $J_1$=11.2 Hz, $J_2$=2.2 Hz, 1H), 7.92 (d, J=8.4 Hz, 2H), 7.79 (d, J=8.3 Hz, 2H), 6.84-6.76 (m, 4H), 6.46 (dd, $J_1$=16.8 Hz, $J_2$=10.2 Hz, 1H), 6.33 (dd, $J_1$=16.8 Hz, $J_2$=1.9 Hz, 1H), 5.88 (s, 1H), 5.71 (dd, $J_1$=10.2 Hz, $J_2$=1.9 Hz, 1H), 5.31 (dd, $J_1$=8.0 Hz, $J_2$=4.9 Hz, 1H), 3.88-3.82 (m, 1H), 3.73-3.68 (m, 1H), 2.67-2.56 (m, 1H), 2.52-2.45 (m, 1H), 2.32-2.23 (m, 1H), 2.12-2.03 (m, 1H); $^{13}$C NMR (CDCl$_3$, 150 MHz) δ: 170.1 (d, J=258.2 Hz), 165.7, 165.2, 162.6, 154.0 (d, J=12.0 Hz), 150.0 (d, J=9.0 Hz), 148.5, 141.7, 138.8, 133.4, 130.0, 128.7, 128.6, 127.5, 119.2, 108.3 (d, J=18.1 Hz), 102.3 (d, J=24.0 Hz), 51.3, 47.7, 30.8, 25.6. MS (ESI, m/z): 464.1 [M+H]$^+$.

Example 41: (S)-1-amino-2-(1-(but-2-ynoyl)pyrrolidin-2-yl)-4-(4-((4-fluoropyridin-2-yl)carbamoyl)phenyl)-1H-imidazole-5-carboxamide

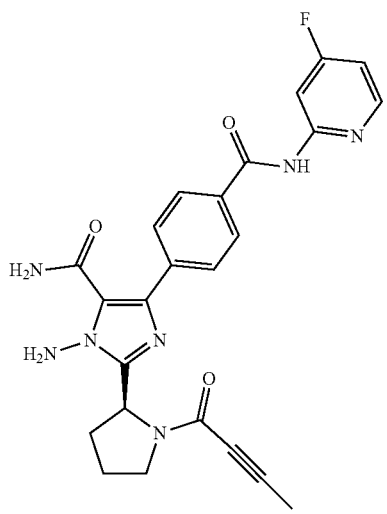 [SMILES: CC#CC(=O)N1CCC[C@H]1c1nc(-c2ccc(C(=O)Nc3cc(F)ccn3)cc2)c(C(N)=O)n1N]

Preparation of (S)-1-amino-2-(1-(but-2-ynoyl)pyrrolidin-2-yl)-4-(4-((4-fluoropyridin-2-yl)carbamoyl)phenyl)-1H-imidazole-5-carboxamide

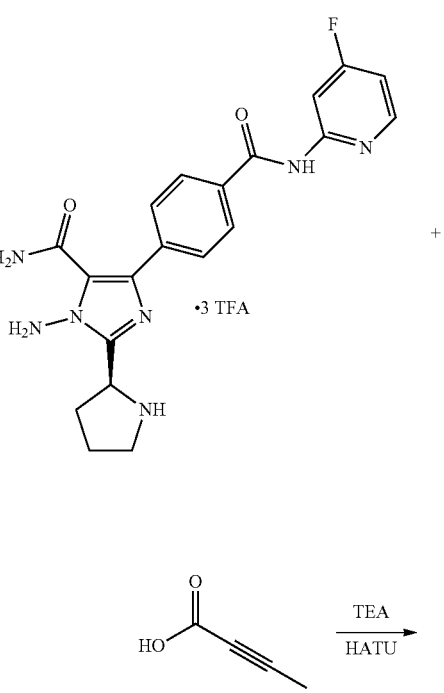

-continued

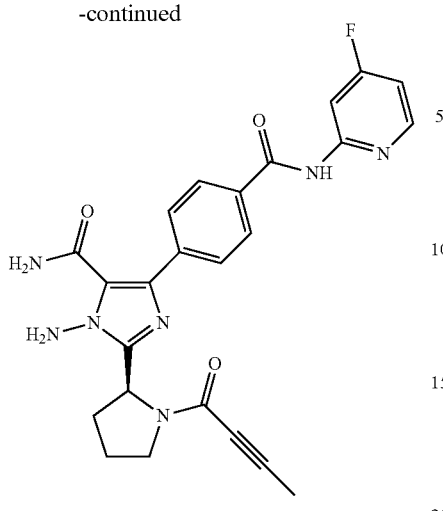

To the solution of 155 mg (0.38 mmol) of the product of Step E of example 40 in dry N, N-Dimethylformamide (5 mL) was added triethylamine (230 mg, 2.28 mmol). After 5 min, but-2-ynoic acid (29.0 mg, 0.34 mmol) and HATU (217 mg, 0.57 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(but-2-ynoyl)pyrrolidin-2-yl)-4-(4-((4-fluoropyridin-2-yl)carbamoyl)phenyl)-1H-imidazole-5-carboxamide as an off-white solid (108 mg, 60%). $^1$H NMR (DMSO-d6, 400 MHz) δ: 11.06 (s, 1H), 8.43 (dd, $J_1$=9.3 Hz, $J_2$=5.7 Hz, 1H), 8.13 (s, 1H), 8.09-8.01 (m, 3H), 7.83 (d, J=8.5 Hz, 2H), 7.71 (s, 1H), 7.14-7.09 (m, 1H), 6.21 (s, 1.4H), 6.05 (s, 0.6H), 5.50-5.47 (m, 0.3H), 5.25-5.22 (m, 0.7H), 3.80-3.77 (m, 2H), 2.31-2.24 (m, 2H), 2.19-2.13 (m, 1H), 2.02 (s, 2H), 2.00-1.95 (m, 1H), 1.88 (s, 1H); $^{13}$C NMR (DMSO-d6, 150 MHz) δ: 168.9 (d, J=254.5 Hz), 166.1, 162.2, 154.6, 151.9, 150.6, 148.3, 138.3, 136.2, 131.6, 127.8, 127.2, 124.7, 107.8, 101.8, 88.6, 74.3, 50.9, 48.5, 31.0, 23.8, 3.3. MS (ESI, m/z): 476.1 [M+H]$^+$.

Example 42: (S)-2-(1-acryloylpyrrolidin-2-yl)-1-amino-4-(4-((4-(trifluoromethyl)pyridin-2-yl)carbamoyl)phenyl)-1H-imidazole-5-carboxamide

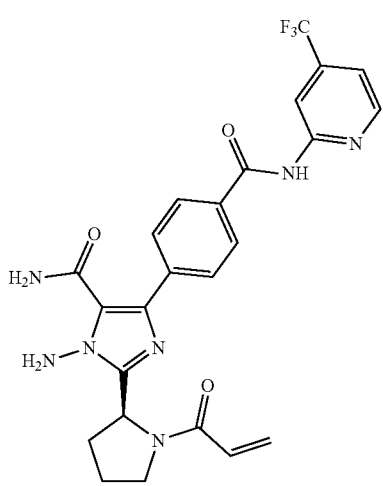

Step A: Preparation of (S)-ethyl 2-(1-(tert-butoxycarbonyl)pyrrolidin-2-yl)-4-(4-((4-(trifluoromethyl)pyridin-2-yl)carbamoyl)phenyl)-1H-imidazole-5-carboxylate

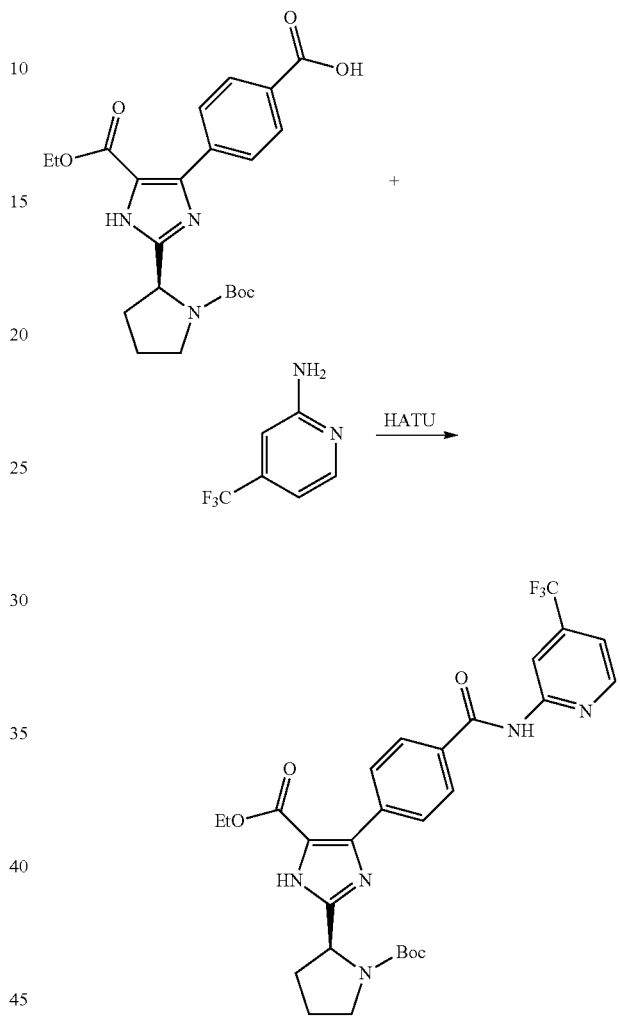

To the solution of 15 g (35 mmol) of the product of Step F of example 1 in dry N,N-Dimethylformamide (150 mL) was stirred and added HATU (16 g, 42 mmol), diisopropylethylamine (30 mL, 175 mmol) and 4-(trifluoromethyl)pyridin-2-amine (8.5 g, 52 mmol). The reaction mixture was stirred at 80° C. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (2:1) to afford (S)-ethyl 2-(1-(tert-butoxycarbonyl)pyrrolidin-2-yl)-4-(4-((4-(trifluoromethyl)pyridin-2-yl)carbamoyl)phenyl)-1H-imidazole-5-carboxylate as a white solid (10 g, 50%). $^1$H NMR (CDCl$_3$, 400 MHz) δ: 11.10 (s, 1H), 8.83 (s, 1H), 8.73 (s, 1H), 8.46 (d, J=5.1 Hz, 1H), 8.19 (d, J=7.8 Hz, 2H), 7.96 (d, J=8.4 Hz, 2H), 7.29 (d, J=5.0 Hz, 1H), 4.99-4.98 (m, 1H), 4.39-4.31 (m, 2H), 3.53-3.43 (m, 2H), 2.32-1.96 (m, 4H), 1.51 (s, 9H), 1.35-1.32 (m, 3H). MS (ESI, m/z): 574.2 [M+H]$^+$.

Step B: Preparation of (S)-ethyl 1-amino-2-(1-(tert-butoxycarbonyl)pyrrolidin-2-yl)-4-(4-((4-(trifluoromethyl)pyridin-2-yl)carbamoyl)phenyl)-1H-imidazole-5-carboxylate

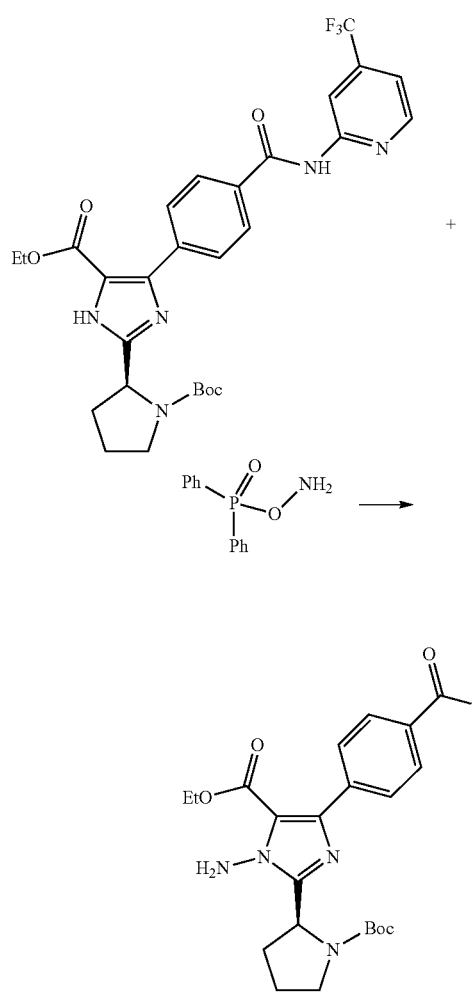

To the solution of 7.5 g (13 mmol) of the product of Step A in dry N, N-Dimethylformamide (50 mL) was stirred and slowly added lithium hexamethyldisilazane (16 mL, 1 M solution in tetrahydrofuran) at −10° C. After the mixture was stirred for 10 min, O-(diphenylphosphinyl) hydroxylamine (3.1 g, 13 mmol) was added at 0° C. and the resulting suspension was stirred 2 h at room temperature (in cases where the reaction mixture became too viscous, additional N, N-Dimethylformamide was added). The reaction was quenched with brine and washed three times with ethyl acetate (3×200 mL). The combined organic fractions were dried with anhydrous $Na_2SO_4$ and the solvent was removed under reduced pressure to afford the crude residue, which was subjected to column chromatography with petroleum ether and ethyl acetate (2:1) to give the desired product (S)-ethyl 1-amino-2-(1-(tert-butoxycarbonyl)pyrrolidin-2-yl)-4-(4-((4-(trifluoro-methyl)pyridin-2-yl)carbamoyl)phenyl)-1H-imidazole-5-carboxylate (4.9 g, 65%). $^1$H NMR (CDCl$_3$, 400 MHz) δ: 8.76 (s, 1H), 8.73 (s, 1H), 8.48 (d, J=5.2 Hz, 1H), 7.93 (d, J=8.4 Hz, 2H), 7.86-7.83 (m, 2H), 7.30 (dd, J$_1$=5.2 Hz, J$_2$=0.9 Hz, 1H), 6.67 (s, 2H), 5.21-5.18 (m, 1H), 4.31-4.26 (m, 2H), 3.61-3.45 (m, 2H), 2.45-2.35 (m, 2H), 2.30-2.20 (m, 1H), 1.98-1.92 (m, 1H), 1.42 (s, 9H), 1.26-1.22 (m, 3H). MS (ESI, m/z): 589.2 [M+H]$^+$.

Step C: Preparation of (S)-1-amino-2-(1-(tert-butoxycarbonyl)pyrrolidin-2-yl)-4-(4-((4-(trifluoromethyl)pyridin-2-yl)carbamoyl)phenyl)-1H-imidazole-5-carboxylic acid

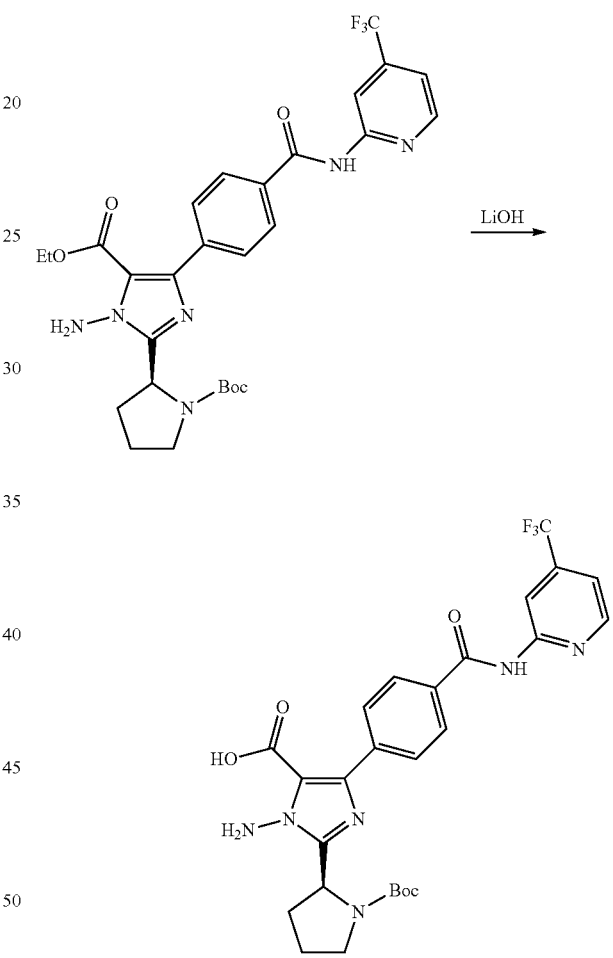

To the solution of 3.8 g (6.4 mmol) of the product of Step B in methanol (20 mL) was stirred and added aqueous lithium hydroxide (2 mol/L, 32 mL), then stirred at room temperature for 2 h. The reaction mixture was evaporated and diluted with water (100 mL) and acidified with aqueous HCl till pH 3. The mixture was washed with ethyl acetate three times (3×50 mL). The combined organic layers were concentrated under reduced pressure to afford (S)-1-amino-2-(1-(tert-butoxycarbonyl)pyrrolidin-2-yl)-4-(4-((4-(trifluoromethyl)pyridin-2-yl)carbamoyl)phenyl)-1H-imidazole-5-carboxylic acid as a white solid (3.4 g, 95%).

Step D: Preparation of (S)-tert-butyl 2-(1-amino-5-carbamoyl-4-(4-((4-(trifluoromethyl)pyridin-2-yl)carbamoyl)phenyl)-1H-imidazol-2-yl)pyrrolidine-1-carboxylate

Step E: Preparation of (S)-1-amino-2-(pyrrolidin-2-yl)-4-(4-((4-(trifluoromethyl)pyridin-2-yl)carbamoyl)phenyl)-1H-imidazole-5-carboxamide

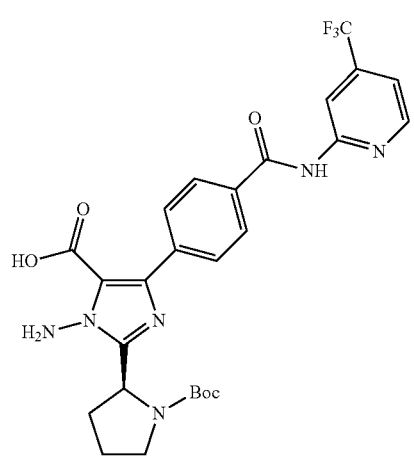
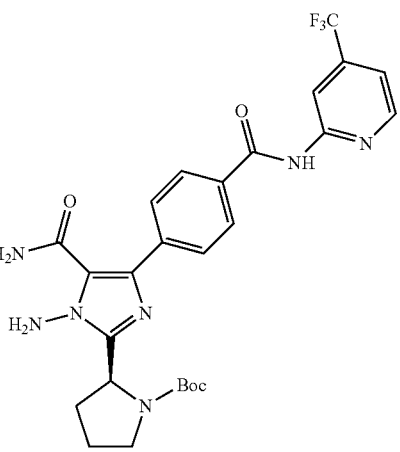

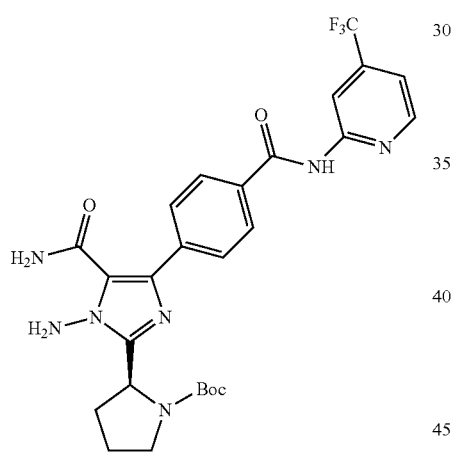

To the solution of 1.9 g (3.4 mmol) of the product of Step C in dry N,N-Dimethylformamide (20 mL) was stirred and added HATU (2.0 g, 5.1 mmol), diisopropylethylamine (1.8 mL, 10.3 mmol) and NH$_4$Cl (1.9 g, 34 mmol). The reaction mixture was stirred at room temperature for 2 h. The reaction mixture was quenched with brine and washed with ethyl acetate three times (3×50 mL). The combined organic layers were concentrated under reduced pressure and purified by flash chromatography with dichloromethane and methanol (30:1) to afford (S)-tert-butyl 2-(1-amino-5-carbamoyl-4-(4-((4-(trifluoromethyl)pyridin-2-yl)carbamoyl)phenyl)-1H-imidazol-2-yl)pyrrolidine-1-carboxylate as a white solid (1.6 g, 83%). $^1$H NMR (CDCl$_3$, 400 MHz) δ: 9.03 (s, 1H), 8.68 (s, 1H), 8.47 (d, J=5.1 Hz, 1H), 7.91 (d, J=8.2 Hz, 2H), 7.82 (d, J=8.2 Hz, 2H), 7.28 (d, J=5.1 Hz, 1H), 7.13 (s, 1H), 6.60 (s, 2H), 5.78 (s, 1H), 5.09-5.06 (m, 1H), 3.58-3.45 (m, 2H), 2.49-2.39 (m, 2H), 2.28-2.19 (m, 1H), 2.01-1.93 (m, 1H), 1.43 (s, 8H), 1.28 (s, 1H). MS (ESI, m/z): 560.2 [M+H]$^+$.

To the solution of 200 mg (0.36 mmol) of the product of Step D in dichloromethane (5 mL) was added trifluoroacetic acid (2.1 mL). The mixture was stirred at room temperature for 1 h and then concentrated to afford (S)-1-amino-2-(pyrrolidin-2-yl)-4-(4-((4-(trifluoromethyl)pyridin-2-yl)carbamoyl)phenyl)-1H-imidazole-5-carboxamide as a light yellow oil. MS (ESI, m/z): 460.1 [M+H]$^+$.

Step F: Preparation of (S)-2-(1-acryloylpyrrolidin-2-yl)-1-amino-4-(4-((4-(trifluoromethyl)pyridin-2-yl)carbamoyl)phenyl)-1H-imidazole-5-carboxamide

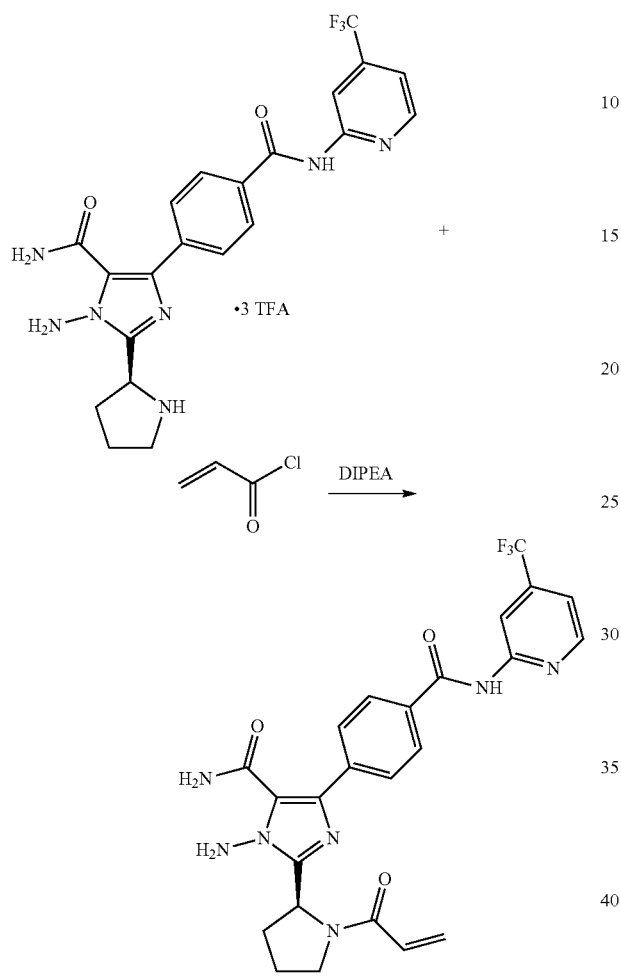

To the solution of 165 mg (0.36 mmol) of the product of Step E in dry dichloromethane (5 mL) was added diisopropylethylamine (280 mg, 2.2 mmol). After 5 min, acryloyl chloride (30.9 mg, 0.34 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-2-(1-acryloyl-pyrrolidin-2-yl)-1-amino-4-(4-((4-(trifluoromethyl)pyridin-2-yl)carbamoyl)phenyl)-1H-imidazole-5-carboxamide as an off-white solid (124 mg, 67%). $^1$H NMR (CDCl$_3$, 400 MHz) δ: 9.37 (s, 1H), 8.65 (s, 1H), 8.43 (d, J=5.1 Hz, 1H), 7.85 (d, J=8.4 Hz, 2H), 7.72 (d, J=8.4 Hz, 2H), 7.25 (d, J=5.1 Hz, 1H), 7.12 (s, 1H), 6.70 (s, 2H), 6.44 (dd, $J_1$=16.8 Hz, $J_2$=10.2 Hz, 1H), 6.32-6.25 (m, 2H), 5.69 (dd, $J_1$=10.2 Hz, $J_2$=1.9 Hz, 1H), 5.28 (dd, $J_1$=8.0 Hz, $J_2$=4.8 Hz, 1H), 3.86-3.80 (m, 1H), 3.72-3.66 (m, 1H), 2.64-2.53 (m, 1H), 2.49-2.41 (m, 1H), 2.30-2.21 (m, 1H), 2.11-2.03 (m, 1H); $^{13}$C NMR (CDCl$_3$, 100 MHz) δ: 166.0, 165.2, 162.7, 152.8, 149.0, 148.7, 141.7, 140.6 (q, J=33.7 Hz), 138.7, 133.1, 129.8, 128.8, 128.5, 127.5, 122.8 (q, J=271.7 Hz), 119.6, 115.5, 110.6, 51.4, 47.7, 30.8, 25.6. MS (ESI, m/z): 514.1 [M+H]$^+$.

Example 43: (S)-1-amino-2-(1-(but-2-ynoyl)pyrrolidin-2-yl)-4-(4-((4-(trifluoro-methyl)pyridin-2-yl)carbamoyl)phenyl)-1H-imidazole-5-carboxamide

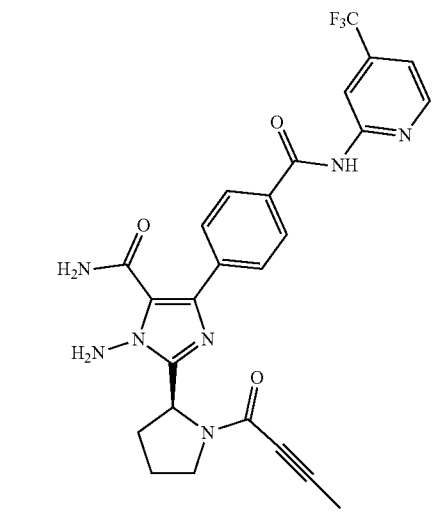 [SMILES: CC#CC(=O)N1CCC[C@H]1c1nc(-c2ccc(C(=O)Nc3cc(C(F)(F)F)ccn3)cc2)c(C(N)=O)n1N]

Preparation of (S)-1-amino-2-(1-(but-2-ynoyl)pyrrolidin-2-yl)-4-(4-((4-(trifluoromethyl)pyridin-2-yl)carbamoyl)phenyl)-1H-imidazole-5-carboxamide

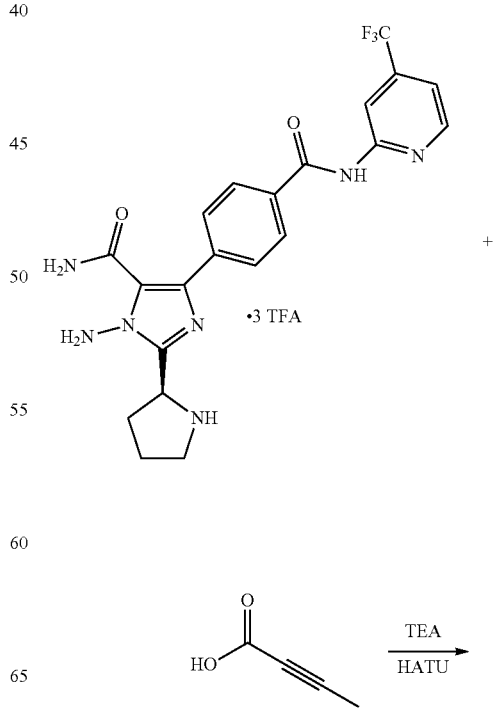

-continued

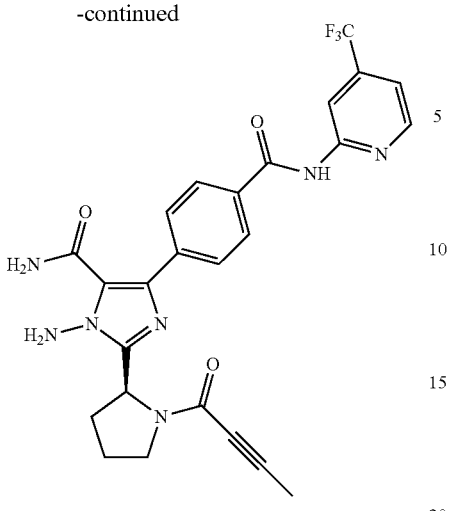

To the solution of 165 mg (0.36 mmol) of the product of Step E of example 42 in dry N,N-Dimethylformamide (5 mL) was added triethylamine (218 mg, 2.16 mmol). After 5 min, but-2-ynoic acid (27.2 mg, 0.32 mmol) and HATU (205 mg, 0.54 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with carbamoyldichloromethane and methanol (25:1) to give (S)-1-amino-2-(1-(but-2-ynoyl)pyrrolidin-2-yl)-4-(4-((4-(trifluoromethyl)pyridin-2-yl)carbamoyl)phenyl)-1H-imidazole-5-carboxamide as an off-white solid (123 mg, 65%). $^1$H NMR (CDCl$_3$, 600 MHz) δ: 8.79 (s, 1H), 8.71 (s, 1H), 8.51-8.47 (m, 1H), 7.97 (d, J=7.9 Hz, 2H), 7.84 (d, J=7.5 Hz, 2H), 7.31-7.30 (m, 1H), 6.66-6.61 (m, 3H), 5.49 (s, 1H), 5.26-5.24 (m, 1H), 3.88-3.86 (m, 2H), 2.59-2.49 (m, 2H), 2.36-2.31 (m, 1H), 2.06-2.00 (m, 4H); $^{13}$C NMR (DMSO-d$_6$, 100 MHz) δ: 166.4, 162.1, 153.4, 151.9, 149.9, 148.3, 138.4, 138.1, 136.1, 131.5, 127.9, 127.1, 124.8, 124.3, 115.1, 109.8, 88.6, 74.3, 50.9, 48.4, 31.0, 23.7, 3.3. MS (ESI, m/z): 526.1 [M+H]$^+$.

Example 44: (S)-2-(1-acryloylpyrrolidin-2-yl)-1-amino-4-(4-((4-isopropylpyridin-2-yl)carbamoyl)phenyl)-1H-imidazole-5-carboxamide

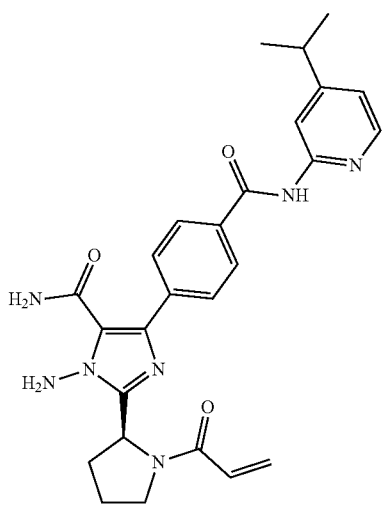 [SMILES: C=CC(=O)N1CCC[C@H]1c1nc(-c2ccc(C(=O)Nc3cc(C(C)C)ccn3)cc2)c(C(N)=O)n1N]

Step A: Preparation of (S)-ethyl 2-(1-(tert-butoxycarbonyl)pyrrolidin-2-yl)-4-(4-((4-isopropylpyridin-2-yl)carbamoyl)phenyl)-1H-imidazole-5-carboxylate

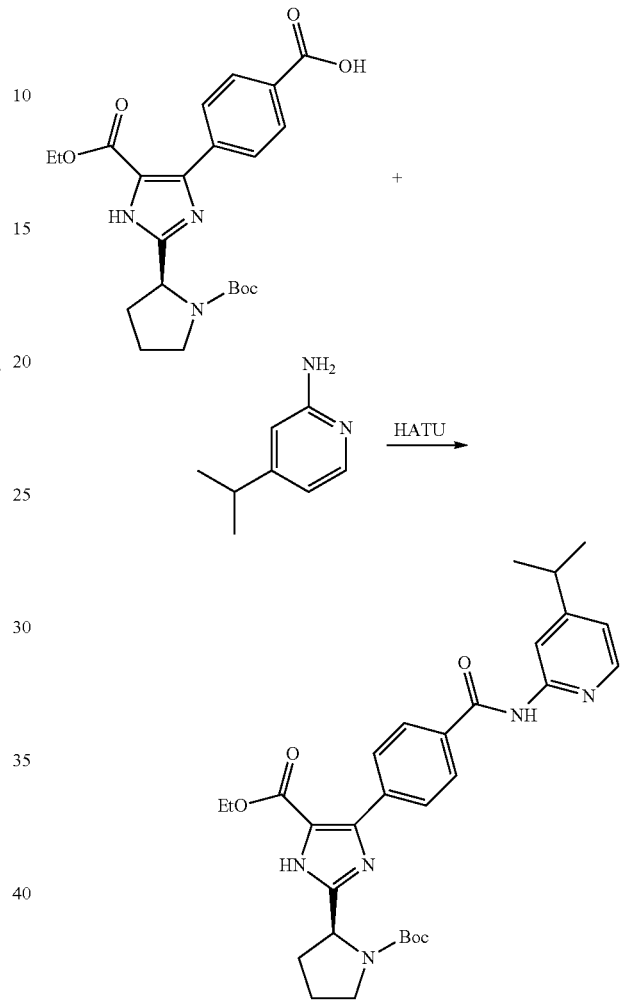

To the solution of 27 g (63 mmol) of the product of Step F of example 1 in dry N,N-Dimethylformamide (200 mL) was stirred and added HATU (30 g, 78 mmol), diisopropylethylamine (55 mL, 315 mmol) and 4-isopropylpyridin-2-amine (13 g, 94 mmol). The reaction mixture was stirred at 80° C. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (2:1) to afford (S)-ethyl 2-(1-(tert-butoxycarbonyl)pyrrolidin-2-yl)-4-(4-((4-isopropylpyridin-2-yl)carbamoyl)phenyl)-1H-imidazole-5-carboxylate as a white solid (24 g, 70%). $^1$H NMR (CDCl$_3$, 600 MHz) δ: 11.10 (s, 1H), 8.76 (s, 1H), 8.32 (s, 1H), 8.17-8.14 (m, 3H), 7.97-7.96 (m, 2H), 6.95-6.94 (m, 1H), 4.98-4.97 (m, 1H), 4.36-4.29 (m, 2H), 3.53-3.43 (m, 2H), 2.98-2.92 (m, 1H), 2.29-2.09 (m, 2H), 1.99-1.92 (m, 2H), 1.51 (s, 9H), 1.33-1.29 (m, 9H). MS (ESI, m/z): 548.2 [M+H]$^+$.

Step B: Preparation of (S)-ethyl 1-amino-2-(1-(tert-butoxycarbonyl)pyrrolidin-2-yl)-4-(4-((4-isopropylpyridin-2-yl)carbamoyl)phenyl)-1H-imidazole-5-carboxylate

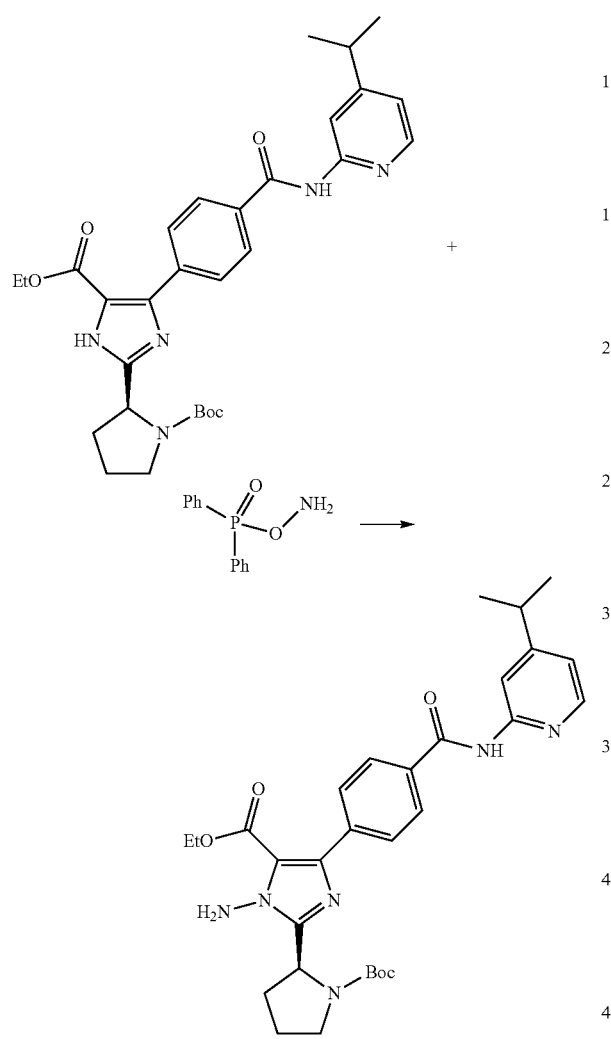

To the solution of 5.0 g (9.1 mmol) of the product of Step A in dry N,N-Dimethylformamide (30 mL) was stirred and slowly added lithium hexamethyldisilazane (11 mL, 1 M solution in tetrahydrofuran) at −10° C. After the mixture was stirred for 10 min, O-(diphenylphosphinyl) hydroxylamine (2.1 g, 9.1 mmol) was added at 0° C. and the resulting suspension was stirred 2 h at room temperature (in cases where the reaction mixture became too viscous, additional N,N-Dimethylformamide was added). The reaction was quenched with brine and washed three times with ethyl acetate (3×200 mL). The combined organic fractions were dried with anhydrous $Na_2SO_4$ and the solvent was removed under reduced pressure to afford the crude residue, which was subjected to column chromatography with petroleum ether and ethyl acetate (2:1) to give the desired product (S)-ethyl 1-amino-2-(1-(tert-butoxycarbonyl)pyrrolidin-2-yl)-4-(4-((4-isopropyl-pyridin-2-yl)carbamoyl)phenyl)-1H-imidazole-5-carboxylate (3.7 g, 72%). $^1$H NMR (CDCl$_3$, 400 MHz) δ: 8.89 (s, 1H), 8.32 (s, 1H), 8.13 (d, J=5.2 Hz, 1H), 7.93 (d, J=8.3 Hz, 2H), 7.79 (d, J=8.5 Hz, 2H), 6.92 (dd, J$_1$=5.2 Hz, J$_2$=1.4 Hz, 1H), 6.64 (s, 2H), 5.20-5.17 (m, 1H), 4.28-4.22 (m, 2H), 3.59-3.43 (m, 2H), 2.97-2.91 (m, 1H), 2.43-2.33 (m, 2H), 2.24-2.20 (m, 1H), 1.97-1.89 (m, 1H), 1.40 (s, 7H), 1.29-1.25 (m, 8H), 1.20 (t, J=7.1 Hz, 3H). MS (ESI, m/z): 563.2 [M+H]$^+$.

Step C: Preparation of (S)-1-amino-2-(1-(tert-butoxycarbonyl)pyrrolidin-2-yl)-4-(4-((4-isopropylpyridin-2-yl)carbamoyl)phenyl)-1H-imidazole-5-carboxylic acid

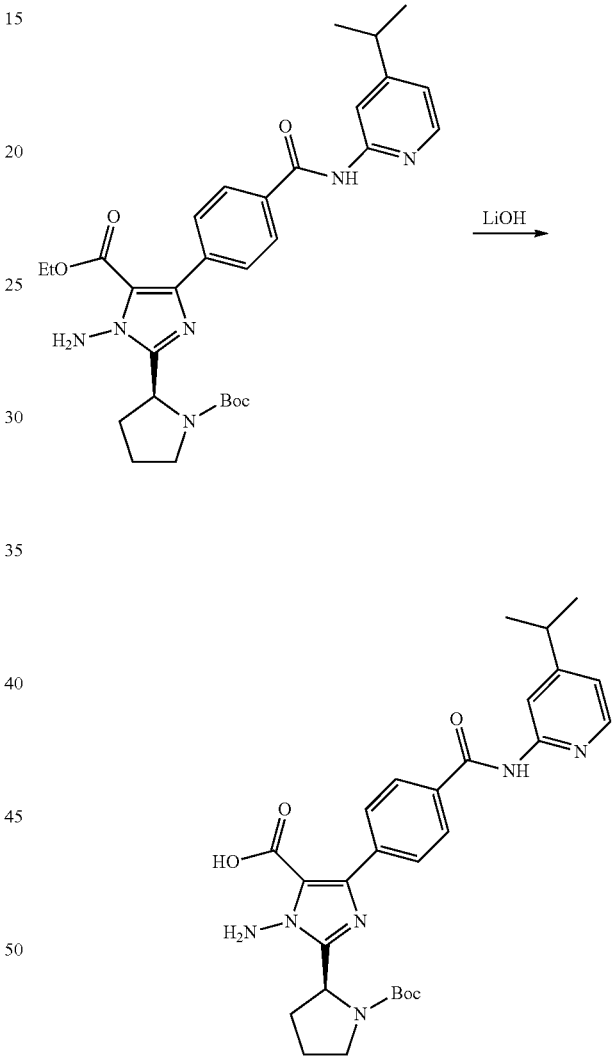

To the solution of 1.3 g (2.3 mmol) of the product of Step B in methanol (10 mL) was stirred and added aqueous lithium hydroxide (2 mol/L, 12 mL), then stirred at room temperature for 2 h. The reaction mixture was evaporated and diluted with water (100 mL) and acidified with aqueous HCl till pH 3. The mixture was washed with ethyl acetate three times (3×50 mL). The combined organic layers were concentrated under reduced pressure to afford (S)-1-amino-2-(1-(tert-butoxycarbonyl)pyrrolidin-2-yl)-4-(4-((4-isopropylpyridin-2-yl)carbamoyl)phenyl)-1H-imidazole-5-carboxylic acid as a white solid (1.14 g, 93%).

Step D: Preparation of (S)-tert-butyl 2-(1-amino-5-carbamoyl-4-(4-((4-isopropylpyridin-2-yl)carbamoyl)phenyl)-1H-imidazol-2-yl)pyrrolidine-1-carboxylate

Step E: Preparation of (S)-1-amino-4-(4-((4-isopropylpyridin-2-yl)carbamoyl)phenyl)-2-(pyrrolidin-2-yl)-1H-imidazole-5-carboxamide

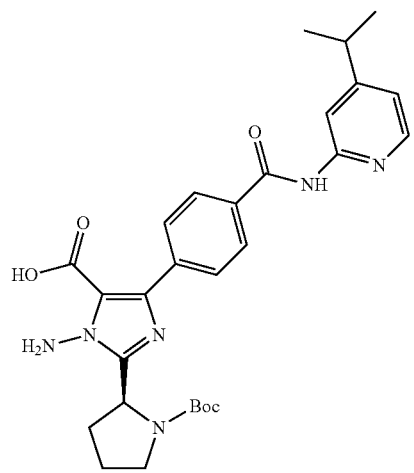

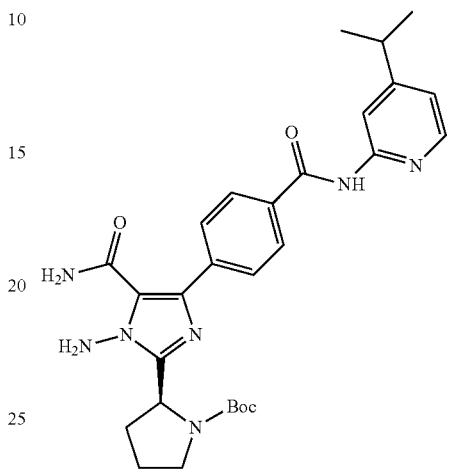

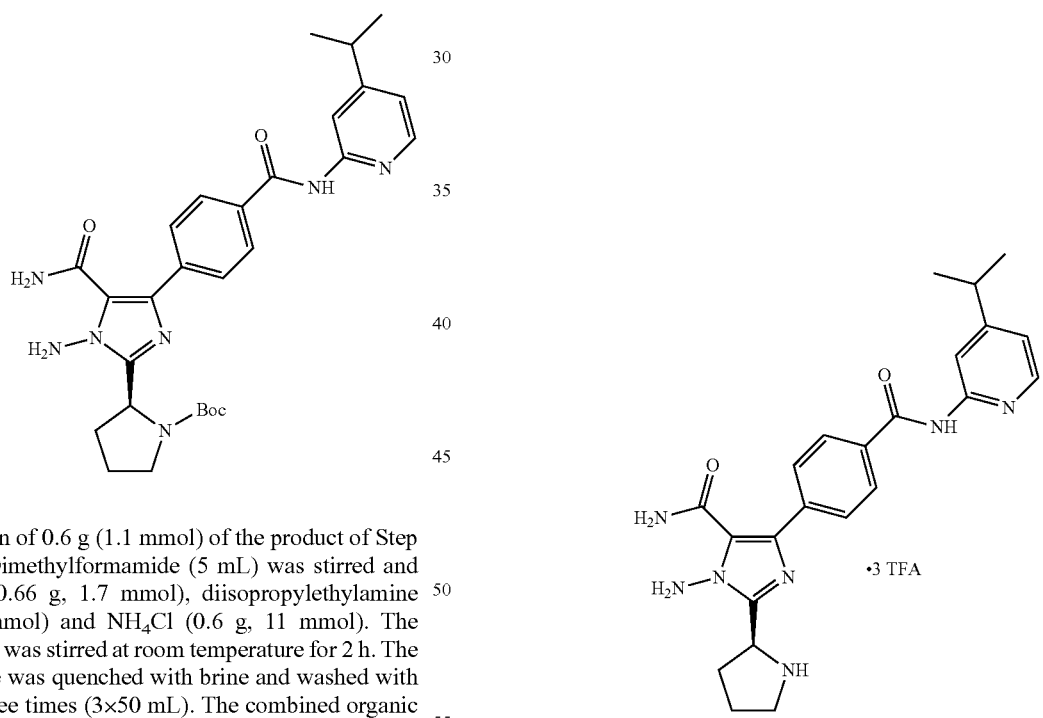

To the solution of 0.6 g (1.1 mmol) of the product of Step C in dry N,N-Dimethylformamide (5 mL) was stirred and added HATU (0.66 g, 1.7 mmol), diisopropylethylamine (0.6 mL, 3.4 mmol) and NH$_4$Cl (0.6 g, 11 mmol). The reaction mixture was stirred at room temperature for 2 h. The reaction mixture was quenched with brine and washed with ethyl acetate three times (3×50 mL). The combined organic layers were concentrated under reduced pressure and purified by flash chromatography with dichloromethane and methanol (30:1) to afford (S)-tert-butyl 2-(1-amino-5-carbamoyl-4-(4-((4-isopropylpyridin-2-yl)carbamoyl)phenyl)-1H-imidazol-2-yl)pyrrolidine-1-carboxylate as a white solid (0.5 g, 85%). $^1$H NMR (CDCl$_3$, 400 MHz) δ: 9.00 (s, 1H), 8.29 (s, 1H), 8.16 (d, J=5.2 Hz, 1H), 7.93 (d, J=8.2 Hz, 2H), 7.79 (d, J=8.1 Hz, 2H), 6.94-6.88 (m, 2H), 6.60 (s, 2H), 6.04 (s, 1H), 5.11-5.08 (m, 1H), 3.58-3.43 (m, 2H), 2.98-2.91 (m, 1H), 2.47-2.38 (m, 2H), 2.24-2.19 (m, 1H), 1.96-1.93 (m, 1H), 1.42 (s, 7H), 1.29-1.25 (m, 8H). MS (ESI, m/z): 534.2 [M+H]$^+$.

To the solution of 145 mg (0.27 mmol) of the product of Step D in dichloromethane (5 mL) was added trifluoroacetic acid (1.6 mL). The mixture was stirred at room temperature for 1 h and then concentrated to afford (S)-1-amino-4-(4-((4-isopropylpyridin-2-yl)carbamoyl)phenyl)-2-(pyrrolidin-2-yl)-1H-imidazole-5-carboxamide as a light yellow oil. MS (ESI, m/z): 434.2 [M+H]$^+$.

Step F: Preparation of (S)-2-(1-acryloylpyrrolidin-2-yl)-1-amino-4-(4-((4-isopropyl-pyridin-2-yl)carbamoyl)phenyl)-1H-imidazole-5-carboxamide

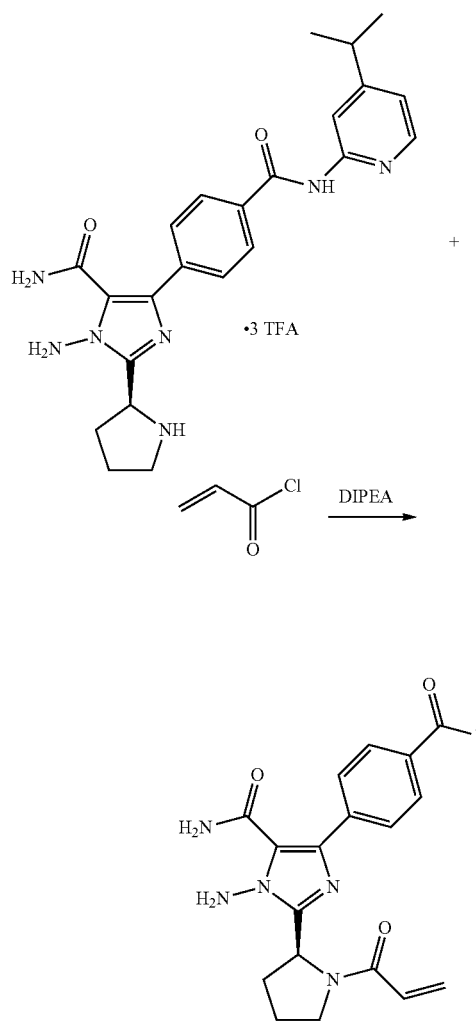

To the solution of 117 mg (0.27 mmol) of the product of Step E in dry dichloromethane (5 mL) was added diisopropylethylamine (210 mg, 1.63 mmol). After 5 min, acryloyl chloride (22 mg, 0.24 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-2-(1-acryloyl-pyrrolidin-2-yl)-1-amino-4-(4-((4-isopropylpyridin-2-yl)carbamoyl)phenyl)-1H-imidazole-5-carboxamide as an off-white solid (83 mg, 63%). $^1$H NMR (CDCl$_3$, 600 MHz) δ: 9.13 (s, 1H), 8.28 (s, 1H), 8.14 (d, J=4.9 Hz, 1H), 7.92 (d, J=7.6 Hz, 2H), 7.74 (d, J=7.6 Hz, 2H), 6.92 (d, J=5.0 Hz, 1H), 6.79-6.68 (m, 3H), 6.44 (dd, $J_1$=16.7 Hz, $J_2$=10.4 Hz, 1H), 6.31-6.26 (m, 2H), 5.69 (d, J=10.3 Hz, 1H), 5.31-5.29 (m, 1H), 3.85-3.81 (m, 1H), 3.70-3.66 (m, 1H), 2.95-2.91 (m, 1H), 2.61-2.54 (m, 1H), 2.47-2.42 (m, 1H), 2.27-2.22 (m, 1H), 2.07-2.01 (m, 1H), 1.27 (d, J=6.8 Hz, 6H); $^{13}$C NMR (CDCl$_3$, 150 MHz) δ: 165.7, 165.1, 162.9, 160.8, 152.0, 148.4, 147.6, 141.6, 138.4, 133.9, 129.8, 128.6, 128.6, 127.6, 119.1, 118.5, 112.7, 51.3, 47.6, 34.1, 30.8, 25.5, 23.2. MS (ESI, m/z): 488.2 [M+H]$^+$.

Example 45: (S)-2-(1-acryloylpyrrolidin-2-yl)-1-(methylamino)-4-(4-((4-methyl-pyridin-2-yl)carbamoyl)phenyl)-1H-imidazole-5-carboxamide

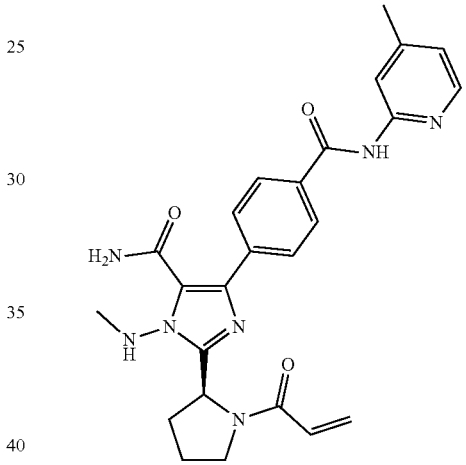

Step A: Preparation of (S)-ethyl 2-(1-(tert-butoxycarbonyl)pyrrolidin-2-yl)-4-(4-((4-methylpyridin-2-yl)carbamoyl)phenyl)-1-(2,2,2-trifluoroacetamido)-1H-imidazole-5-carboxylate

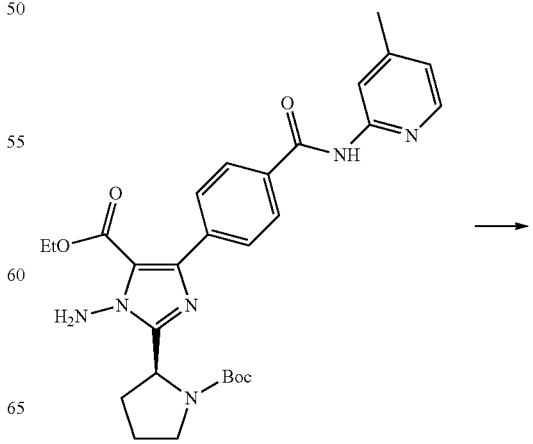

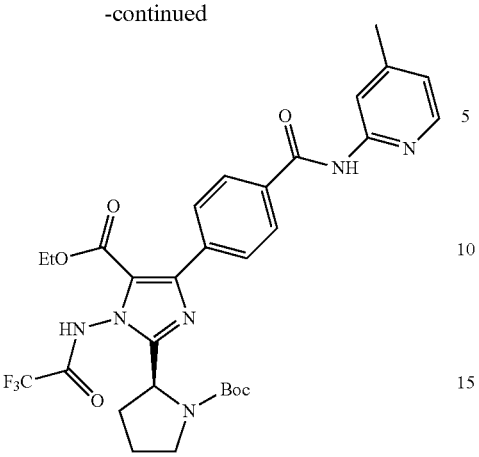
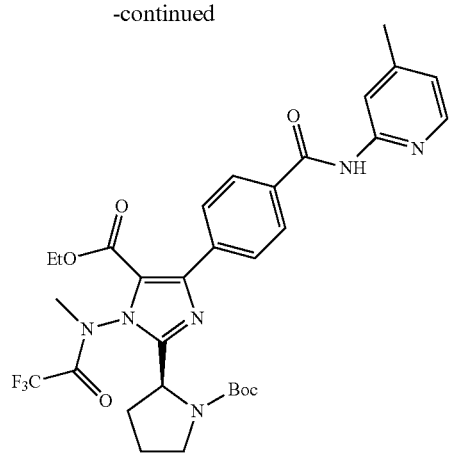

To the solution of 500 mg (0.94 mmol) of the product of Step B of example 10 in dichloromethane (5 mL), the triethylamine (400 μL, 2.82 mmol) was added at 0-10° C. and stirred for 30 min. Then the solution of trifluoroacetic anhydride (330 μL, 2.35 mmol) was added dropwise to the reaction mixture and stirred at room temperature for 10 h. After completion of reaction, the mixture was diluted with water (50 mL) and it was washed with saturated NaHCO$_3$ (15 mL). The aqueous layer was washed with dichloromethane (2×100 mL) and the organic layers were combined, dried with anhydrous Na$_2$SO$_4$, filtered and concentrated. The residue was purified by chromatography with petroleum ether and ethyl acetate (3:1) to afford (S)-ethyl 2-(1-(tert-butoxycarbonyl)pyrrolidin-2-yl)-4-(4-((4-methylpyridin-2-yl)carbamoyl)phenyl)-1-(2,2,2-trifluoroacetamido)-1H-imidazole-5-carboxylate as a yellow oil (300 mg, 51%). $^1$H NMR (CDCl$_3$, 600 MHz) δ: 8.80 (s, 1H), 8.22-8.10 (m, 2H), 7.86-7.65 (m, 4H), 6.88 (d, J=4.4 Hz, 1H), 4.75-4.68 (m, 1H), 4.13-3.99 (m, 2H), 3.70-3.61 (m, 1H), 3.45-3.42 (m, 1H), 2.38 (s, 3H), 2.23-2.16 (m, 3H), 1.88-1.84 (m, 1H), 1.40 (s, 9H), 1.13-1.11 (m, 3H). MS (ESI, m/z): 631.2 [M+H]$^+$.

Step B: Preparation of (S)-ethyl 2-(1-(tert-butoxycarbonyl)pyrrolidin-2-yl)-4-(4-((4-methylpyridin-2-yl)carbamoyl)phenyl)-1-(2,2,2-trifluoro-N-methylacetamido)-1H-imidazole-5-carboxylate To the solution of 400 mg (0.63 mmol) of the product of Step A in acetonitrile (10 mL), the potassium carbonate (265 mg, 1.91 mmol) was added at 0° C. and stirred for 30 min. Then the solution of iodomethane (120 μL, 1.91 mmol) was added dropwise to the reaction mixture and at which point the temperature was increased to 80° C. and the mixture was stirred for an additional 6 h. After completion of reaction, the mixture was diluted with water (20 mL) and partitioned between water and ethylacetate (3×50 mL). The combined organic layers were dried over anhydrous Na$_2$SO$_4$ and evaporated under vacuum. The residue was purified by chromatography with petroleum ether and ethyl acetate (5:1) to afford (S)-ethyl 2-(1-(tert-butoxycarbonyl)pyrrolidin-2-yl)-4-(4-((4-methylpyridin-2-yl)carbamoyl)phenyl)-1-(2,2,2-trifluoro-N-methylacetamido)-1H-imidazole-5-carboxylate as a yellow oil (215 mg, 53%). $^1$H NMR (CDCl$_3$, 400 MHz) δ: 8.88 (s, 1H), 8.29 (s, 1H), 8.14-8.12 (m, 1H), 8.00-7.94 (m, 3H), 7.91-7.89 (m, 1H), 6.92-6.91 (m, 1H), 5.62-5.56 (m, 1H), 4.31-4.22 (m, 2H), 3.92-3.78 (m, 2H), 3.68-3.67 (m, 2H), 3.50 (s, 1H), 2.38 (s, 3H), 2.29-2.15 (m, 1H), 1.91-1.82 (m, 1H), 1.77-1.71 (m, 1H), 1.66-1.60 (m, 1H), 1.41 (s, 9H), 1.15-1.13 (m, 3H). MS (ESI, m/z): 645.2 [M+H]$^+$.

Step C: Preparation of (S)-ethyl 2-(1-(tert-butoxycarbonyl)pyrrolidin-2-yl)-1-(methylamino)-4-(4-((4-methylpyridin-2-yl)carbamoyl)phenyl)-1H-imidazole-5-carboxylate

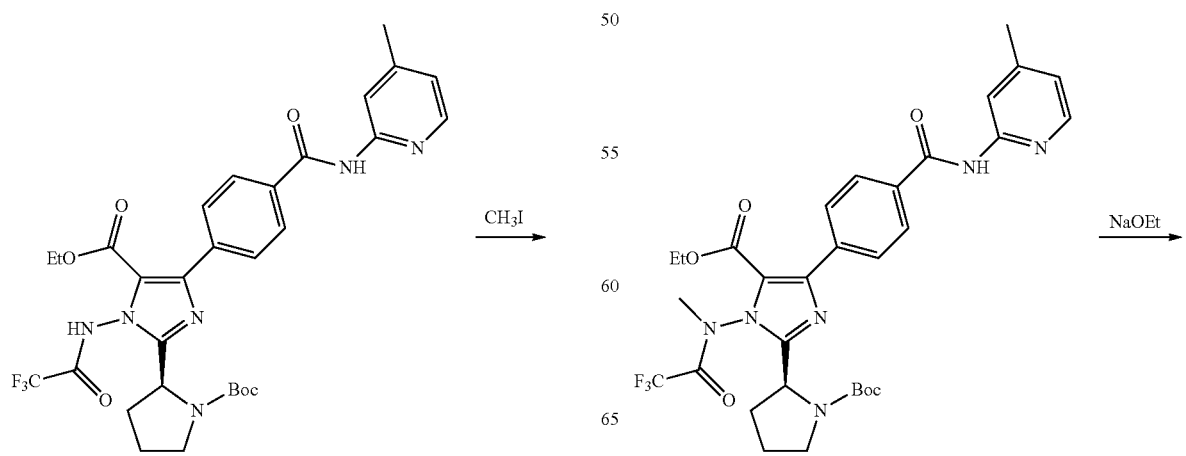


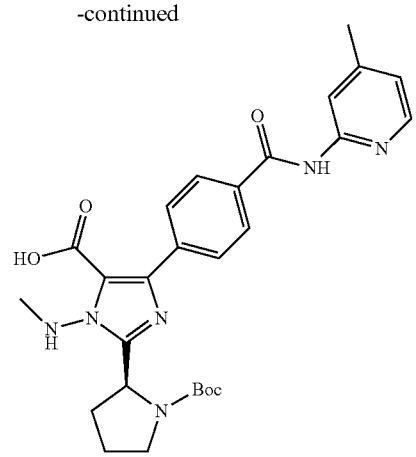

To the solution of 215 mg (0.34 mmol) of the product of Step B in ethanol (5 mL), the sodium ethoxide (35 mg, 0.51 mmol) was added at 10-20° C. and stirred for 6 h. After completion of reaction, the mixture was diluted with water (100 mL) and concentrated under vacuum. Then it was partitioned between water and ethyl acetate (3×50 mL). The combined organic layers were dried over anhydrous Na$_2$SO$_4$ and evaporated under vacuum. The residue was purified by chromatography with petroleum ether and ethyl acetate (2:1) to afford (S)-ethyl 2-(1-(tert-butoxycarbonyl)pyrrolidin-2-yl)-1-(methylamino)-4-(4-((4-methylpyridin-2-yl)carbamoyl)phenyl)-1H-imidazole-5-carboxylate as a white solid (180 mg, 97%). MS (ESI, m/z): 549.2 [M+H]$^+$.

To the solution of 180 mg (0.33 mmol) of the product of Step C in methanol (4 mL) was stirred and added aqueous lithium hydroxide (2 mol/L, 1.7 mL), then stirred at room temperature for 2 h. The reaction mixture was evaporated and diluted with water (10 mL) and acidified with aqueous HCl till pH 3. The mixture was washed with ethyl acetate three times (3×50 mL). The combined organic layers were concentrated under reduced pressure to afford (S)-2-(1-(tert-butoxycarbonyl)pyrrolidin-2-yl)-1-(methylamino)-4-(4-((4-methylpyridin-2-yl)carbamoyl)phenyl)-1H-imidazole-5-carboxylic acid (168 mg, 98%).

Step D: Preparation of (S)-2-(1-(tert-butoxycarbonyl)pyrrolidin-2-yl)-1-(methylamino)-4-(4-((4-methylpyridin-2-yl)carbamoyl)phenyl)-1H-imidazole-5-carboxylic acid Step E: Preparation of (S)-tert-butyl 2-(5-carbamoyl-1-(methylamino)-4-(4-((4-methylpyridin-2-yl)carbamoyl)phenyl)-1H-imidazol-2-yl)pyrrolidine-1-carboxylate

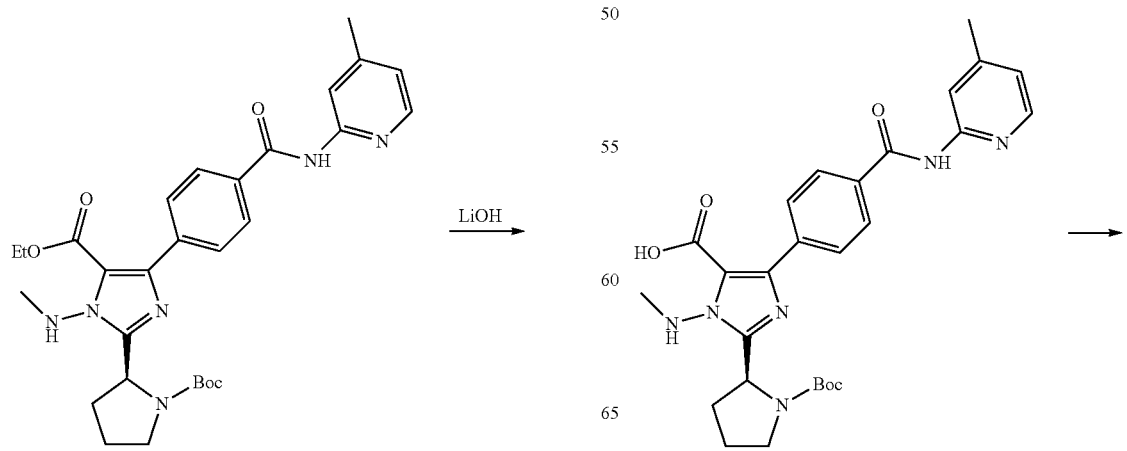

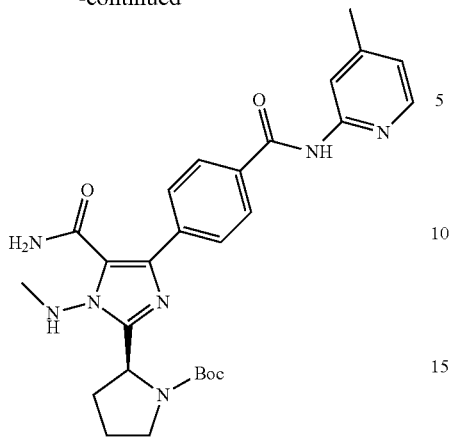

To the solution of 175 mg (0.35 mmol) of the product of Step D in dry N,N-Dimethylformamide (5 mL) was stirred and added HATU (200 mg, 0.52 mmol), diisopropylethylamine (190 μL, 1.05 mmol) and NH$_4$Cl (190 mg, 3.5 mmol). The reaction mixture was stirred at room temperature for 2 h. The reaction mixture was quenched with brine and washed with ethyl acetate three times (3×50 mL). The combined organic layers were concentrated under reduced pressure and purified by flash chromatography with dichloromethane and methanol (30:1) to afford (S)-tert-butyl 2-(5-carbamoyl-1-(methylamino)-4-(4-((4-methylpyridin-2-yl)carbamoyl)phenyl)-1H-imidazol-2-yl)pyrrolidine-1-carboxylate as a white solid (128 mg, 71%). $^1$H NMR (CDCl$_3$, 400 MHz) δ: 8.79 (s, 1H), 8.25 (s, 1H), 8.14 (d, J=5.1 Hz, 1H), 7.99-7.91 (m, 3H), 7.75-7.69 (m, 1H), 7.40-7.33 (m, 1H), 6.90-6.89 (m, 1H), 5.80-5.72 (m, 1H), 5.10-4.99 (m, 1H), 3.60-3.44 (m, 2H), 2.89 (d, J=5.7 Hz, 2H), 2.75 (d, J=5.4 Hz, 1H), 2.57-2.44 (m, 1H), 2.40-2.36 (m, 4H), 2.33-2.21 (m, 1H), 2.02-1.93 (m, 1H), 1.45 (s, 6H), 1.28 (s, 3H). MS (ESI, m/z): 520.2 [M+H]$^+$.

Step F: Preparation of (S)-1-(methylamino)-4-(4-((4-methylpyridin-2-yl)carbamoyl)phenyl)-2-(pyrrolidin-2-yl)-1H-imidazole-5-carboxamide

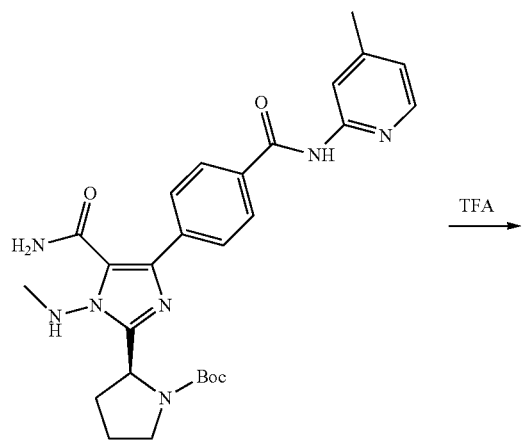

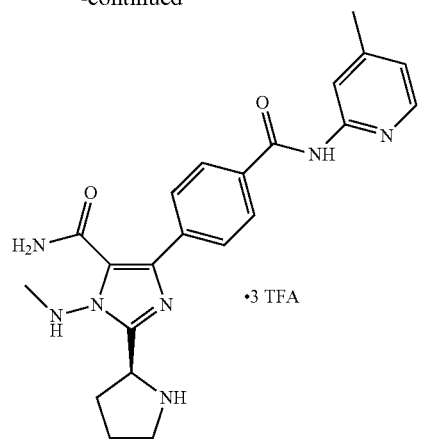

To the solution of 128 mg (0.25 mmol) of the product of Step E in dichloromethane (5 mL) was added trifluoroacetic acid (1.5 mL). The mixture was stirred at room temperature for 1 h and then concentrated to afford (S)-1-(methylamino)-4-(4-((4-methylpyridin-2-yl)carbamoyl)phenyl)-2-(pyrrolidin-2-yl)-1H-imidazole-5-carboxamide as a light yellow oil. MS (ESI, m/z): 420.2 [M+H]$^+$.

Step G: Preparation of (S)-2-(1-acryloylpyrrolidin-2-yl)-1-(methyl-amino)-4-(4-((4-methylpyridin-2-yl)carbamoyl)phenyl)-1H-imidazole-5-carboxamide

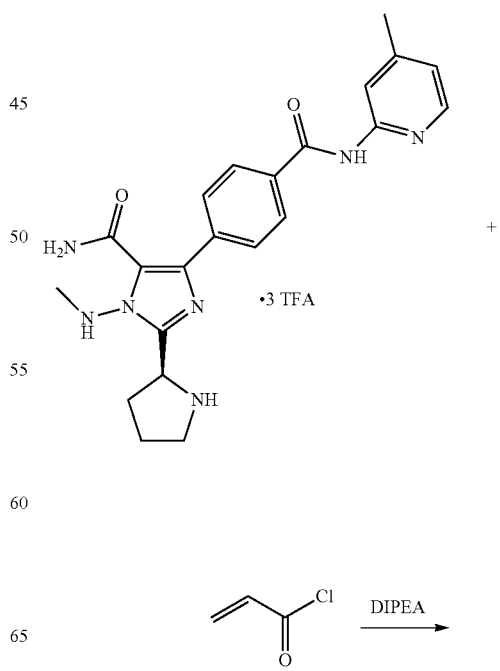

-continued

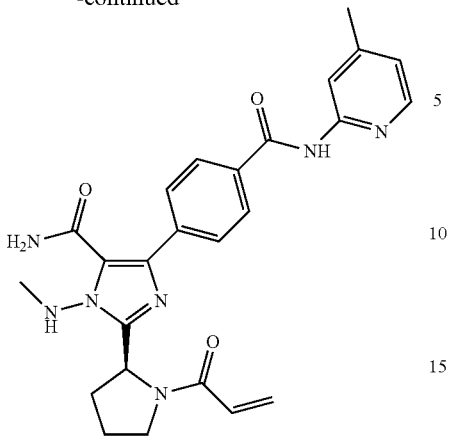

To the solution of 105 mg (0.25 mmol) of the product of Step F in dry dichloromethane (5 mL) was added diisopropylethylamine (192 mg, 1.48 mmol). After 5 min, acryloyl chloride (20.4 mg, 0.23 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-2-(1-acryloylpyrrolidin-2-yl)-1-(methylamino)-4-(4-((4-methylpyridin-2-yl)carbamoyl)phenyl)-1H-imidazole-5-carboxamide as an off-white solid (71 mg, 60%). $^1$H NMR (CDCl$_3$, 400 MHz) δ: 9.15 (s, 1H), 8.23 (s, 1H), 8.11 (d, J=5.1 Hz, 1H), 7.94 (d, J=8.6 Hz, 2H), 7.88 (d, J=8.6 Hz, 2H), 7.80 (s, 1H), 7.47-7.43 (m, 1H), 6.87 (d, J=5.1 Hz, 1H), 6.46 (dd, $J_1$=16.8 Hz, $J_2$=10.1 Hz, 1H), 6.36-6.32 (m, 2H), 5.71 (dd, $J_1$=10.1 Hz, $J_2$=2.0 Hz, 1H), 5.23 (dd, $J_1$=8.1 Hz, $J_2$=3.7 Hz, 1H), 3.89-3.83 (m, 1H), 3.71-3.65 (m, 1H), 2.91 (d, J=5.7 Hz, 3H), 2.73-2.64 (m, 1H), 2.45-2.38 (m, 4H), 2.31-2.24 (m, 1H), 2.13-2.05 (m, 1H); $^{13}$C NMR (CDCl$_3$, 100 MHz) δ: 165.9, 165.2, 162.0, 151.9, 150.1, 149.0, 147.3, 142.6, 138.4, 133.5, 129.9, 128.9, 128.3, 127.2, 121.1, 119.5, 115.1, 51.7, 47.4, 41.0, 30.9, 25.4, 21.5. MS (ESI, m/z): 474.2 [M+H]$^+$.

Example 46

(S)-2-(1-acryloylpiperidin-2-yl)-1-amino-4-(4-(pyridin-2-ylcarbamoyl)phenyl)-1H-imidazole-5-carboxamide

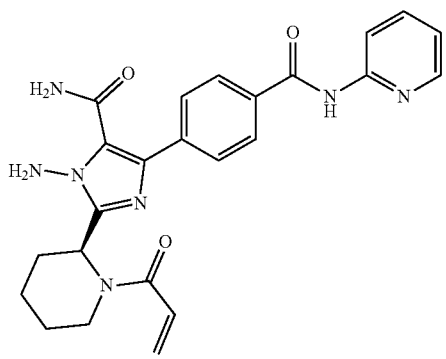 [SMILES: C=CC(=O)N1CCCC[C@H]1c1nc(-c2ccc(C(=O)Nc3ccccn3)cc2)c(C(N)=O)n1N]

Step A: Preparation of 1-(tert-butyl)-2-(1-ethoxy-3-(4-(ethoxycarbonyl)phenyl)-1,3-dioxopropan-2-yl) (2S)-piperidine-1,2-dicarboxylate

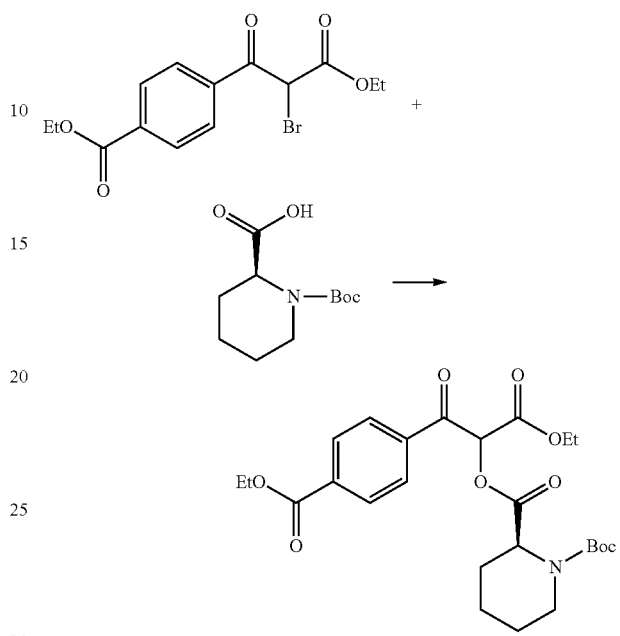

To the solution of 256 g (746 mmol) of the product of Step C of example 1 in acetonitrile (2 L), the diisopropylethylamine (141 mL, 821 mmol) and (S)-1-(tert-butoxycarbonyl) piperidine-2-carboxylic acid (179 g, 781 mmol) were added and stirred at room temperature for 3 h before all volatile were evaporated. The residue was diluted with water (1000 mL) and extracted with ethyl acetate (3000 mL). The organic phase was separated, dried over anhydrous $Na_2SO_4$ and concentrated. The residue was purified by flash column chromatography with petroleum ether and ethyl acetate (8:1) to give 1-(tert-butyl)-2-(1-ethoxy-3-(4-(ethoxycarbonyl) phenyl)-1,3-dioxopropan-2-yl)(2S)-piperidine-1,2-dicarboxylate as a light yellow oil (260 g, 71%). $^1$H NMR (CDCl$_3$, 600 MHz) δ: 8.13 (d, J=7.3 Hz, 2H), 8.01 (d, J=7.5 Hz, 2H), 6.29 (d, J=19.2 Hz, 1H), 5.05-4.86 (m, 1H), 4.39 (q, J=7.1 Hz, 2H), 4.23 (q, J=6.9 Hz, 2H), 4.04-3.88 (m, 1H), 3.10-2.88 (m, 1H), 2.34-2.19 (m, 1H), 1.70-1.67 (m, 3H), 1.44-1.32 (m, 14H), 1.20 (t, J=7.1 Hz, 3H). MS (ESI, m/z): 492.2 [M+H]$^+$.

Step B: Preparation of tert-butyl (S)-2-(5-(ethoxycarbonyl)-4-(4-(ethoxycarbonyl)phenyl)-1H-imidazol-2-yl)piperidine-1-carboxylate

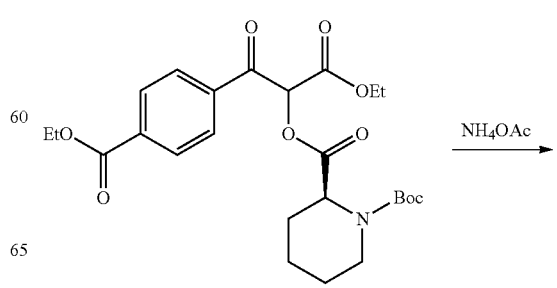

-continued

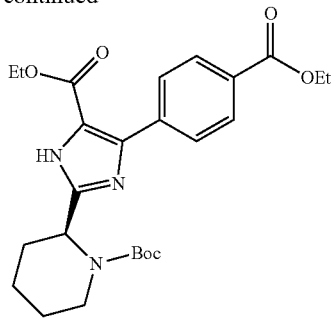

To the solution of 260 g (530 mmol) of the product of Step A in xylene (1250 mL) in a 1 L pressure bottle was added NH₄OAc (490 g, 6357 mmol). The reaction was heated at 140° C. for 2.5 h. After being cooled, the residue was diluted with water (1000 mL) and extracted with ethyl acetate (3000 mL). The organic phase was separated, dried over anhydrous Na₂SO₄ and concentrated. The residue was purified by flash column chromatography with petroleum ether and ethyl acetate (5:1) to give tert-butyl (S)-2-(5-(ethoxycarbonyl)-4-(4-(ethoxycarbonyl)phenyl)-1H-imidazol-2-yl)piperidine-1-carboxylate as a light yellow oil (75 g, 30%). ¹H NMR (CDCl₃, 600 MHz) δ: 10.08 (s, 1H), 8.10-8.06 (m, 4H), 5.44-5.36 (m, 1H), 4.38 (q, J=7.1 Hz, 2H), 4.30 (q, J=7.1 Hz, 2H), 4.07-3.93 (m, 1H), 2.77 (t, J=12.8 Hz, 1H), 2.53 (d, J=12.6 Hz, 1H), 1.91-1.61 (m, 4H), 1.51-1.47 (m, 10H), 1.40 (t, J=7.1 Hz, 3H), 1.30 (t, J=7.1 Hz, 3H). MS (ESI, m/z): 472.2 [M+H]⁺.

Step C: Preparation of (S)-4-(2-(1-(tert-butoxycarbonyl)piperidin-2-yl)-5-(ethoxycarbonyl)-1H-imidazol-4-yl)benzoic acid

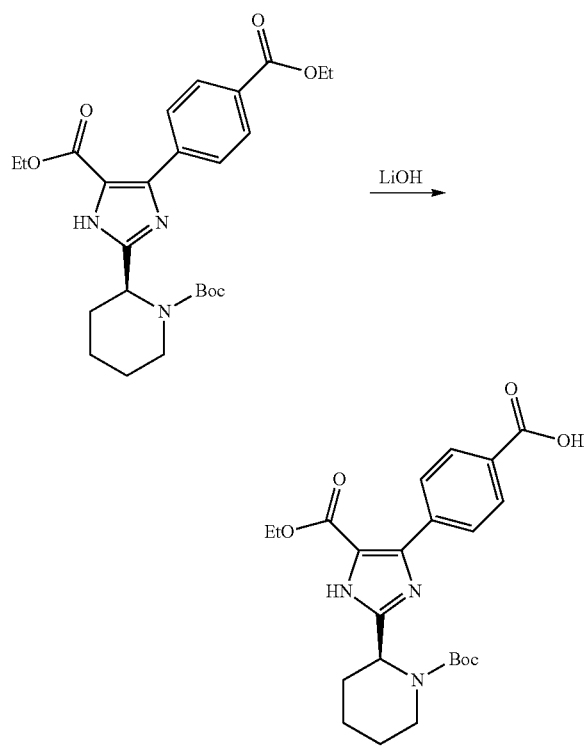

To the solution of 4.57 g (10 mmol) of the product of Step B in 1,4-dioxane (50 mL) was added aqueous lithium hydroxide (2 mol/L, 50 mL) and stirred at room temperature for 2 h. The reaction mixture was evaporated, diluted with water (100 mL) and acidified with aqueous HCl till pH 3. The white precipitate was isolated by filtration and dried to afford (S)-4-(2-(1-(tert-butoxycarbonyl)piperidin-2-yl)-5-(ethoxycarbonyl)-1H-imidazol-4-yl)benzoic acid as a white solid (3.99 g, 90%).

Step D: Preparation of tert-butyl (S)-2-(5-(ethoxycarbonyl)-4-(4-(pyridin-2-ylcarbamoyl)phenyl)-1H-imidazol-2-yl)piperidine-1-carboxylate

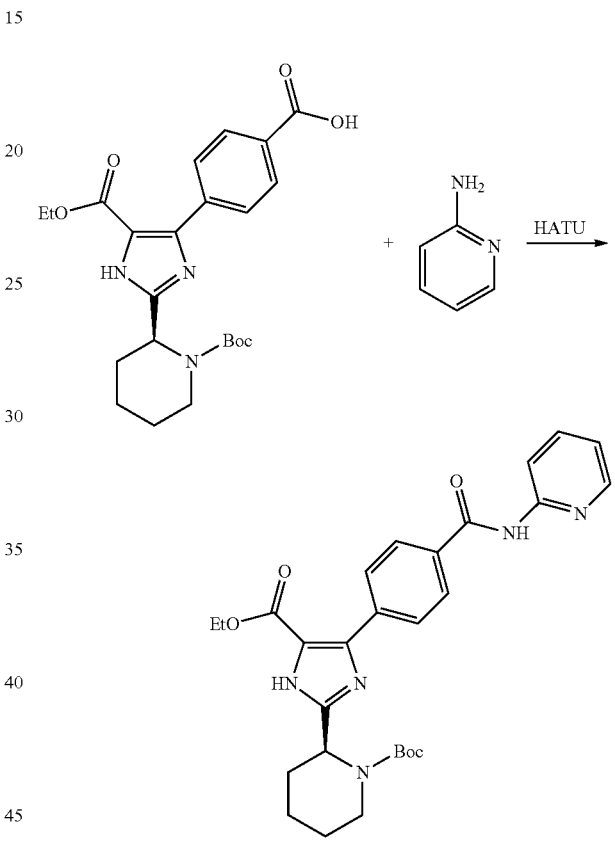

To the solution of 30.0 g (67 mmol) of the product of Step C in dry N,N-Dimethylformamide (250 mL), HATU (30.6 g, 80 mmol), diisopropylethylamine (57.7 mL, 335 mmol) and pyridin-2-amine (9.5 g, 101 mmol) were added and stirred at 80° C. for 3 h. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (3:1) to afford tert-butyl (S)-2-(5-(ethoxycarbonyl)-4-(4-(pyridin-2-ylcarbamoyl)phenyl)-1H-imidazol-2-yl)piperidine-1-carboxylate as a white solid (29.5 g, 85%). ¹H NMR (CDCl₃, 400 MHz) δ: 10.49 (s, 1H), 9.18 (s, 1H), 8.37 (d, J=8.4 Hz, 1H), 8.17-8.16 (m, 1H), 8.11 (d, J=8.4 Hz, 2H), 7.93 (d, J=8.2 Hz, 2H), 7.71-7.67 (m, 1H), 6.98 (dd, J₁=7.3 Hz, J₂=5.8 Hz, 1H), 5.44-5.39 (m, 1H), 4.23 (q, J=7.1 Hz, 2H), 3.97 (d, J=11.9 Hz, 1H), 2.44 (d, J=12.0 Hz, 1H), 1.81-1.61 (m, 4H), 1.50-1.39 (m, 11H), 1.23 (t, J=7.1 Hz, 3H). MS (ESI, m/z): 520.2 [M+H]⁺.

Step E: Preparation of tert-butyl (S)-2-(1-amino-5-(ethoxycarbonyl)-4-(4-(pyridin-2-ylcarbamoyl)phenyl)-1H-imidazol-2-yl)piperidine-1-carboxylate

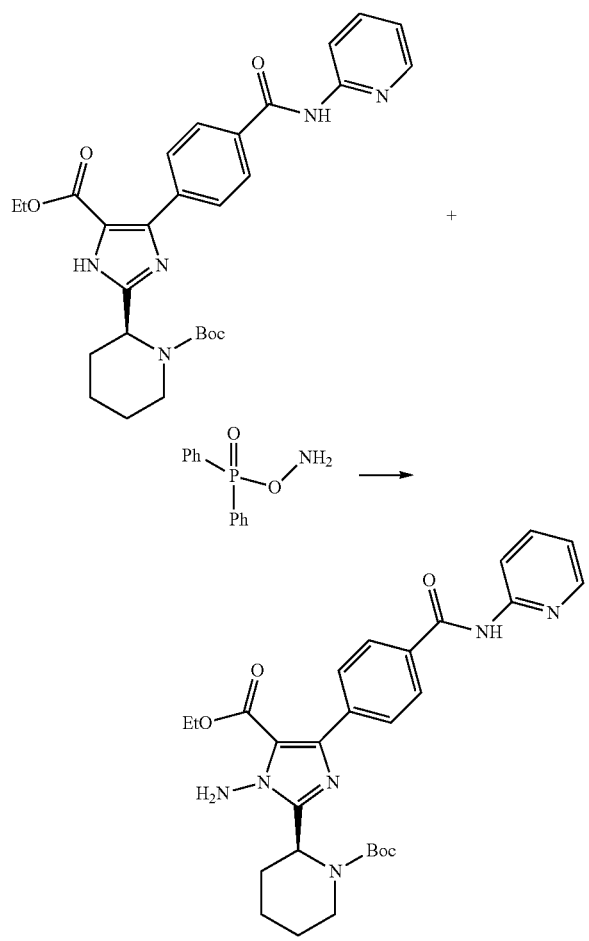

To the solution of 2.6 g (5.0 mmol) of the product of Step D in anhydrous N,N-Dimethylformamide (25 mL) was slowly added lithium hexamethyldisilazane (6.0 mL, 1 M solution in tetrahydrofuran) at −10° C. After the mixture was stirred for 20 min, O-(diphenylphosphinyl) hydroxylamine (1.2 g, 5.0 mmol) was added at 0° C. and the resulting suspension was stirred at room temperature for 2 h (in cases where the reaction mixture become too viscous, additional N,N-Dimethylformamide was added). The mixture was quenched with brine and extracted with ethyl acetate three times (3×100 mL). The combined organic fractions were dried with anhydrous Na$_2$SO$_4$ and the solvent was removed under reduced pressure to afford the crude residue, which was subjected to column chromatography with petroleum ether and ethyl acetate (3:1) to give the product tert-butyl (S)-2-(1-amino-5-(ethoxycarbonyl)-4-(4-(pyridin-2-ylcarbamoyl)phenyl)-1H-imidazol-2-yl)piperidine-1-carboxylate as a white solid (1.9 g, 71%). $^1$H NMR (CDCl$_3$, 400 MHz) δ: 8.80 (s, 1H), 8.40 (d, J=8.4 Hz, 1H), 8.28-8.26 (m, 1H), 7.93 (d, J=8.6 Hz, 2H), 7.84 (d, J=8.6 Hz, 2H), 7.77-7.73 (m, 1H), 7.06 (dd, J$_1$=7.3 Hz, J$_2$=5.9 Hz, 1H), 5.92 (s, 2H), 5.67 (d, J=4.6 Hz, 1H), 4.32-4.24 (m, 2H), 3.95 (d, J=12.8 Hz, 1H), 3.42 (td, J$_1$=13.0 Hz, J$_2$=3.1 Hz, 1H), 2.12-2.04 (m, 2H), 1.92-1.86 (m, 1H), 1.76-1.72 (m, 1H), 1.65-1.61 (m, 1H), 1.53-1.48 (m, 1H), 1.43 (s, 9H), 1.24 (t, J=7.1 Hz, 3H). MS (ESI, m/z): 535.2 [M+H]$^+$.

Step F: Preparation of (S)-1-amino-2-(1-(tert-butoxycarbonyl)piperidin-2-yl)-4-(4-(pyridin-2-ylcarbamoyl)phenyl)-1H-imidazole-5-carboxylic acid

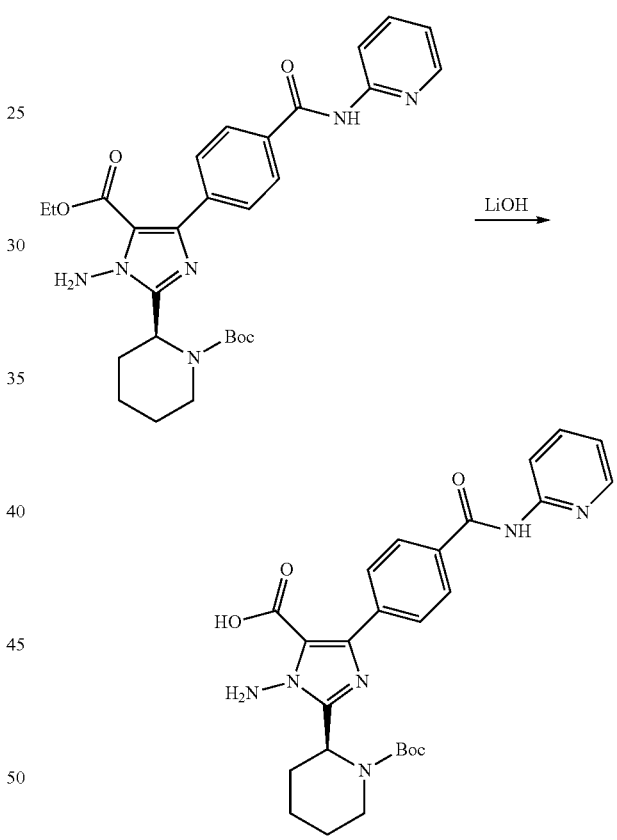

To the solution of 1.49 g (2.8 mmol) of the product of Step E in methanol (15 mL) was added 2 mol/L aqueous lithium hydroxide (14 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl)piperidin-2-yl)-4-(4-(pyridin-2-ylcarbamoyl)phenyl)-1H-imidazole-5-carboxylic acid as a white solid (1.28 g, 90%).

Step G: Preparation of tert-butyl (S)-2-(1-amino-5-carbamoyl-4-(4-(pyridin-2-ylcarbamoyl)phenyl)-1H-imidazol-2-yl)piperidine-1-carboxylate

Step H: Preparation of (S)-1-amino-2-(piperidin-2-yl)-4-(4-(pyridin-2-ylcarbamoyl)phenyl)-1H-imidazole-5-carboxamide

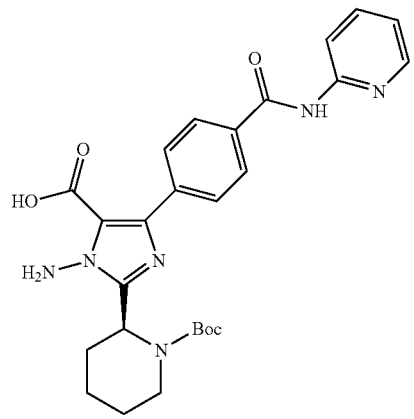

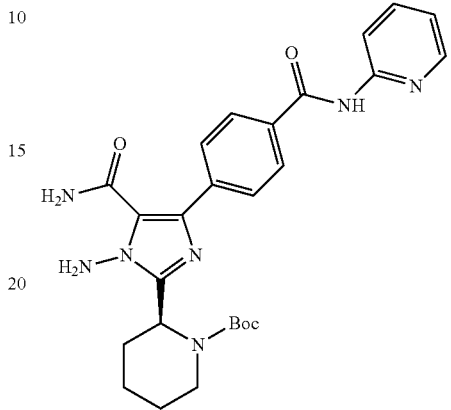

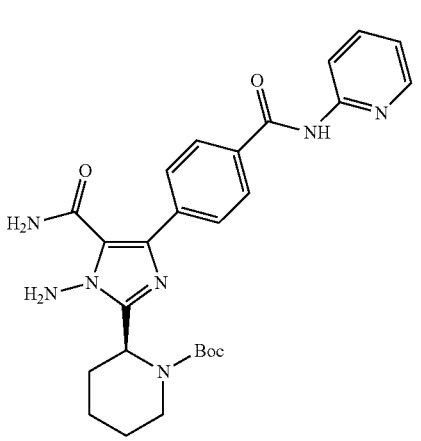

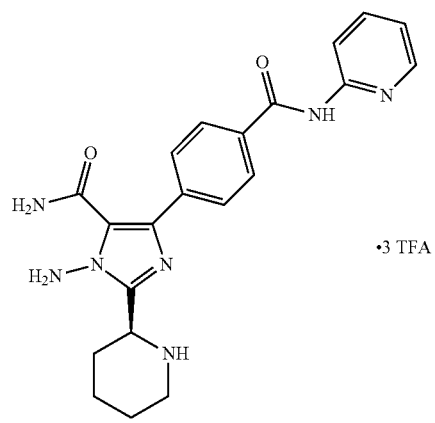

To the solution of 1.0 g (2.0 mmol) of the product of Step F in dry N,N-Dimethylformamide (15 mL), HATU (1.1 g, 2.9 mmol), diisopropylethylamine (1 mL, 5.9 mmol) and NH$_4$Cl (1.1 g, 20 mmol) were added and stirred at room temperature for 2 h. The reaction mixture was quenched with brine and washed with ethyl acetate three times (3×100 mL). The combined organic layers were concentrated under reduced pressure and purified by flash chromatography with dichloromethane and methanol (30:1) to give the product tert-butyl (S)-2-(1-amino-5-carbamoyl-4-(4-(pyridin-2-ylcarbamoyl)phenyl)-1H-imidazol-2-yl)piperidine-1-carboxylate as a white solid (0.84 g, 83%). $^1$H NMR (CDCl$_3$, 600 MHz) δ: 9.15 (s, 1H), 8.37 (d, J=8.1 Hz, 1H), 8.30-8.24 (m, 1H), 7.90 (d, J=6.8 Hz, 2H), 7.77-7.72 (m, 3H), 7.05-7.03 (m, 1H), 6.77 (s, 1H), 6.34 (s, 1H), 6.04 (s, 2H), 5.61-5.58 (m, 1H), 3.93 (d, J=12.5 Hz, 1H), 3.32 (t, J=12.9 Hz, 1H), 2.20-2.12 (m, 2H), 1.90-1.86 (m, 1H), 1.75-1.64 (m, 2H), 1.54-1.50 (m, 1H), 1.45 (s, 9H). MS (ESI, m/z): 506.2 [M+H]$^+$.

To the solution of 190 mg (0.39 mmol) of the product of Step G in dichloromethane (5 mL) was added trifluoroacetic acid (2.5 mL). The mixture was stirred at room temperature for 1 h and then concentrated to afford (S)-1-amino-2-(piperidin-2-yl)-4-(4-(pyridin-2-ylcarbamoyl)phenyl)-1H-imidazole-5-carboxamide as a light yellow oil. MS (ESI, m/z): 406.1 [M+H]$^+$.

Step I: Preparation of (S)-2-(1-acryloylpiperidin-2-yl)-1-amino-4-(4-(pyridin-2-ylcarbamoyl)phenyl)-1H-imidazole-5-carboxamide

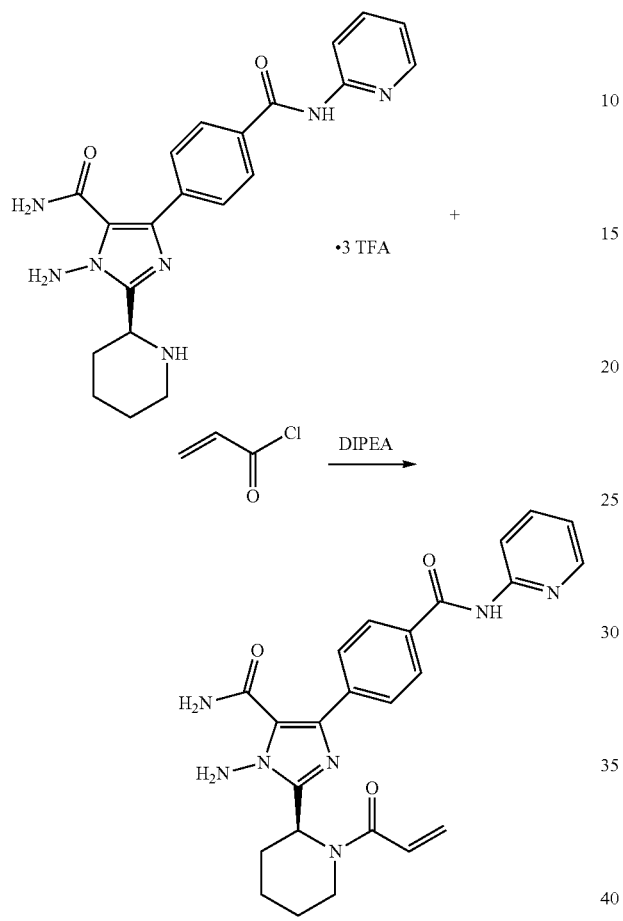

To the solution of 166 mg (0.41 mmol) of the product of Step H in dry dichloromethane (5 mL) was added diisopropylethylamine (318 mg, 2.46 mmol). After 5 min, acryloyl chloride (32.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (28:1) to give (S)-2-(1-acryloylpiperidin-2-yl)-1-amino-4-(4-(pyridin-2-ylcarbamoyl)phenyl)-1H-imidazole-5-carboxamide as an off-white solid (117 mg, 62%). $^1$H NMR (CDCl$_3$, 400 MHz) δ: 9.31 (s, 1H), 8.33 (d, J=8.4 Hz, 1H), 8.24 (d, J=4.0 Hz, 1H), 7.85 (d, J=8.4 Hz, 2H), 7.75-7.69 (m, 3H), 7.32 (s, 1H), 7.03 (dd, J$_1$=6.8 Hz, J$_2$=5.3 Hz, 1H), 6.69 (s, 1H), 6.57 (dd, J$_1$=16.5 Hz, J$_2$=10.7 Hz, 1H), 6.29-6.24 (m, 3H), 6.02-5.97 (m, 1H), 5.69 (d, J=10.5 Hz, 1H), 3.81 (d, J=11.8 Hz, 1H), 3.68 (t, J=11.8 Hz, 1H), 2.39-2.37 (m, 1H), 2.19-2.15 (m, 1H), 1.89-1.83 (m, 2H), 1.70-1.66 (m, 1H), 1.59-1.57 (m, 1H); $^{13}$C NMR (CDCl$_3$, 100 MHz) δ: 167.2, 166.0, 162.8, 151.9, 148.3, 147.9, 141.2, 138.6, 138.3, 133.5, 129.5, 128.6, 127.8, 127.3, 120.2, 120.0, 114.6, 44.4, 43.0, 28.0, 25.8, 19.7. MS (ESI, m/z): 460.2 [M+H]$^+$.

Example 47

(S)-1-amino-2-(1-methacryloylpiperidin-2-yl)-4-(4-(pyridin-2-ylcarbamoyl)phenyl)-1H-imidazole-5-carboxamide

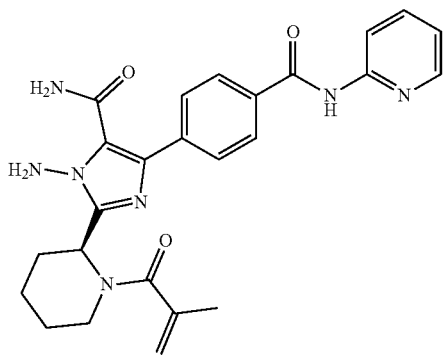 [SMILES: C=C(C)C(=O)N1CCCC[C@H]1c1nc(-c2ccc(C(=O)Nc3ccccn3)cc2)c(C(N)=O)n1N]

Preparation of (S)-1-amino-2-(1-methacryloylpiperidin-2-yl)-4-(4-(pyridin-2-ylcarbamoyl)phenyl)-1H-imidazole-5-carboxamide

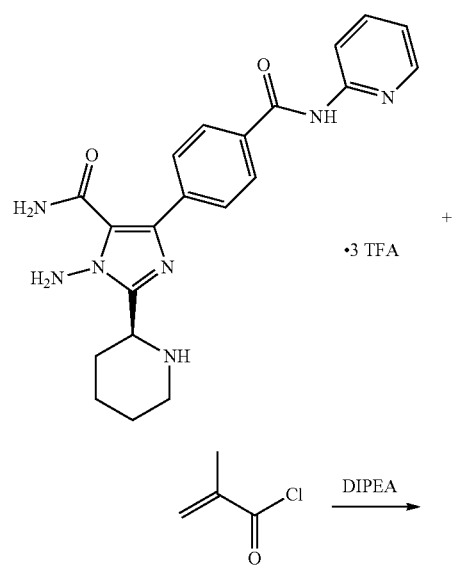

-continued

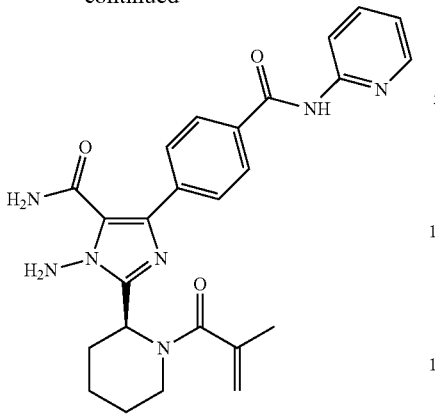

To the solution of 166 mg (0.41 mmol) of the product of Step H of example 46 in dry dichloromethane (5 mL) was added diisopropylethylamine (318 mg, 2.46 mmol). After 5 min, methacryloyl chloride (37.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (28:1) to give (S)-1-amino-2-(1-methacryloylpiperidin-2-yl)-4-(4-(pyridin-2-ylcarbamoyl)phenyl)-1H-imidazole-5-carboxamide as an off-white solid (116 mg, 60%). $^1$H NMR (CDCl$_3$, 600 MHz) δ: 9.23 (s, 1H), 8.38 (d, J=8.3 Hz, 1H), 8.31-8.25 (m, 1H), 7.92 (d, J=8.2 Hz, 2H), 7.80-7.75 (m, 3H), 7.08 (dd, J$_1$=6.7 Hz, J$_2$=5.3 Hz, 1H), 7.03 (s, 1H), 6.77-5.99 (m, 3H), 5.90 (s, 1H), 5.20 (s, 1H), 5.12-5.05 (m, 1H), 3.92-3.78 (m, 1H), 3.64-3.60 (m, 1H), 2.34-2.31 (m, 1H), 2.22-2.20 (m, 1H), 1.95 (s, 3H), 1.93-1.88 (m, 1H), 1.82-1.80 (m, 1H), 1.73-1.70 (m, 1H), 1.58-1.51 (m, 1H); $^{13}$C NMR (CDCl$_3$, 150 MHz) δ: 173.1, 165.9, 162.8, 151.8, 148.2, 147.6, 141.2, 140.5, 138.8, 138.3, 133.6, 129.9, 129.6, 127.5, 120.1, 115.9, 114.7, 44.3, 28.0, 26.0, 20.6, 19.9, 14.3. MS (ESI, m/z): 474.2 [M+H]$^+$.

Example 48

(S,E)-1-amino-2-(1-(but-2-enoyl)piperidin-2-yl)-4-(4-(pyridin-2-ylcarbamoyl)phenyl)-1H-imidazole-5-carboxamide

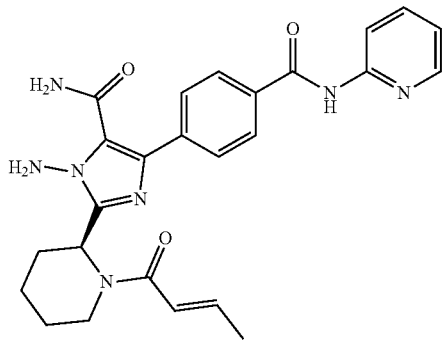 [SMILES: C/C=C/C(=O)N1CCCC[C@H]1c1nc(-c2ccc(C(=O)Nc3ccccn3)cc2)c(C(N)=O)n1N]

Preparation of (S,E)-1-amino-2-(1-(but-2-enoyl)piperidin-2-yl)-4-(4-(pyridin-2-ylcarbamoyl)phenyl)-1H-imidazole-5-carboxamide

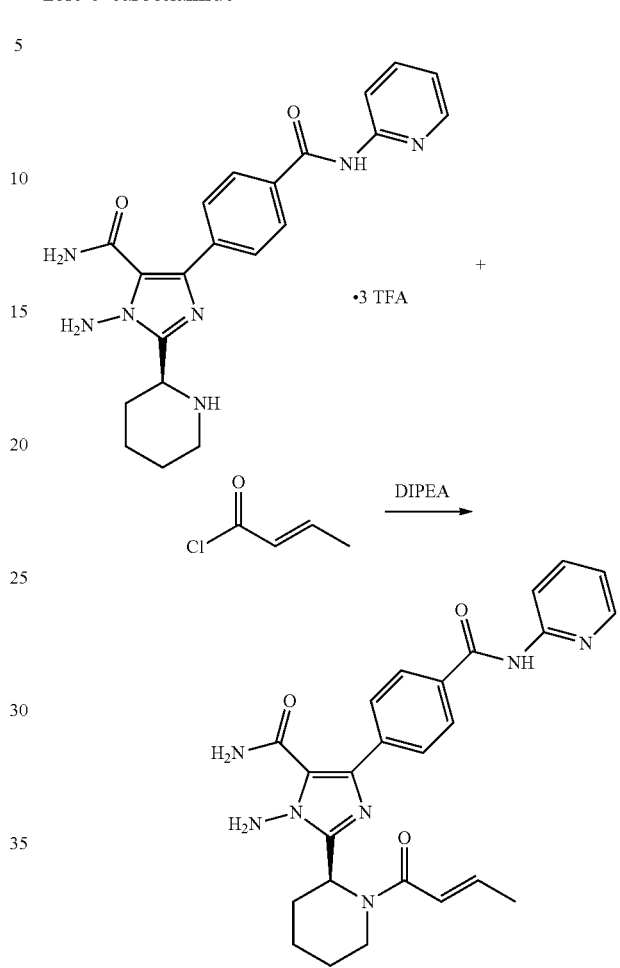

To the solution of 166 mg (0.41 mmol) of the product of Step H of example 46 in dry dichloromethane (5 mL) was added diisopropylethylamine (318 mg, 2.46 mmol). After 5 min, (E)-but-2-enoyl chloride (37.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (28:1) to give (S,E)-1-amino-2-(1-(but-2-enoyl)piperidin-2-yl)-4-(4-(pyridin-2-ylcarbamoyl)phenyl)-1H-imidazole-5-carboxamide as an off-white solid (116 mg, 60%). $^1$H NMR (CDCl$_3$, 600 MHz) δ: 9.18 (s, 1H), 8.37-8.35 (m, 1H), 8.27-8.24 (m, 1H), 7.89-7.87 (m, 2H), 7.78-7.71 (m, 3H), 7.30 (s, 1H), 7.06-7.04 (m, 1H), 6.90-6.84 (m, 1H), 6.65-6.34 (m, 3H), 6.29-6.26 (m, 1H), 5.95-5.91 (m, 1H), 3.82 (d, J=11.6 Hz, 1H), 3.65-3.60 (m, 1H), 2.42-2.41 (m, 1H), 2.18-2.15 (m, 1H), 2.03-2.01 (m, 1H), 1.94-1.79 (m, 4H), 1.70-1.68 (m, 1H), 1.60-1.58 (m, 1H); $^{13}$C NMR (CDCl$_3$, 150 MHz) δ: 167.4, 166.0, 165.9, 162.7, 151.9, 148.3, 147.9, 142.8, 141.3, 138.6, 138.4, 133.5, 129.7, 127.3, 121.7, 120.0, 114.6, 44.3, 42.8, 28.0, 25.8, 19.8, 18.5. MS (ESI, m/z): 474.2 [M+H]$^+$.

Example 49

(S)-1-amino-2-(1-(3-methylbut-2-enoyl)piperidin-2-yl)-4-(4-(pyridin-2-ylcarbamoyl)phenyl)-1H-imidazole-5-carboxamide

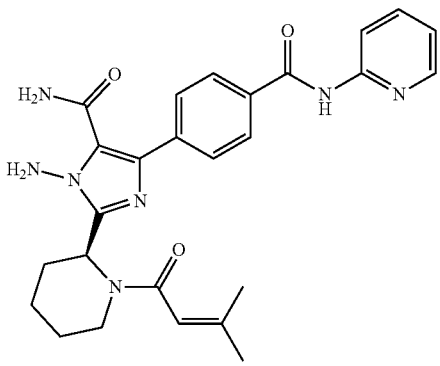 [SMILES: CC(C)=CC(=O)N1CCCC[C@H]1c1nc(-c2ccc(C(=O)Nc3ccccn3)cc2)c(C(N)=O)n1N]

Preparation of (S)-1-amino-2-(1-(3-methylbut-2-enoyl) piperidin-2-yl)-4-(4-(pyridin-2-ylcarbamoyl) phenyl)-1H-imidazole-5-carboxamide

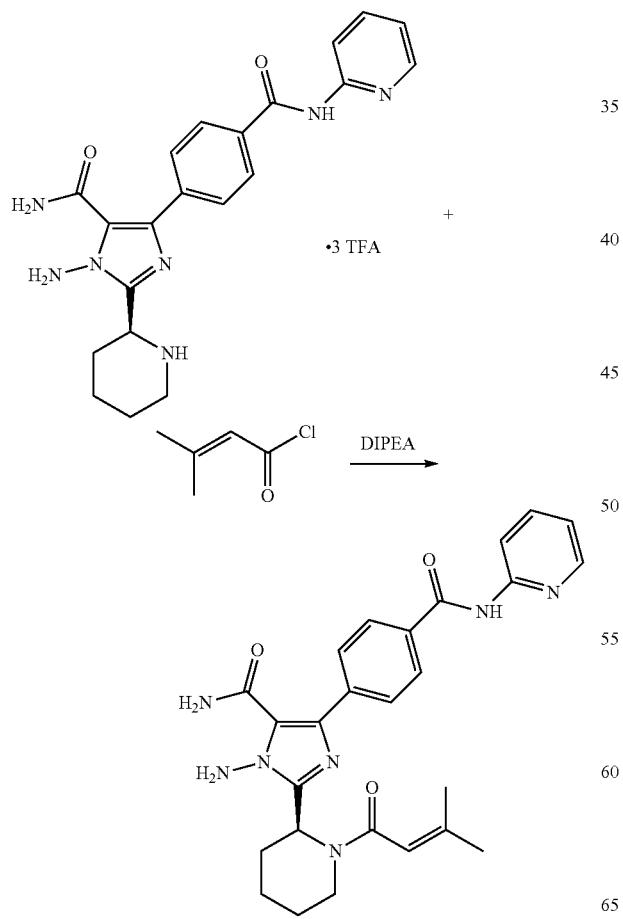

To the solution of 166 mg (0.41 mmol) of the product of Step H of example 46 in dry dichloromethane (5 mL) was added diisopropylethylamine (318 mg, 2.46 mmol). After 5 min, 3-methylbut-2-enoyl chloride (42.7 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (28:1) to give (S)-1-amino-2-(1-(3-methylbut-2-enoyl)piperidin-2-yl)-4-(4-(pyridin-2-ylcarbamoyl)phenyl)-1H-imidazole-5-carboxamide as an off-white solid (130 mg, 65%). $^1$H NMR (CDCl$_3$, 600 MHz) δ: 9.25-9.18 (m, 1H), 8.36-8.35 (m, 1H), 8.30-8.27 (m, 1H), 7.90-7.87 (m, 2H), 7.79-7.73 (m, 3H), 7.24 (s, 1H), 7.05-7.04 (m, 1H), 6.53 (s, 1H), 6.30 (s, 2H), 5.96 (d, J=4.3 Hz, 1H), 5.79 (s, 1H), 3.80 (d, J=12.5 Hz, 1H), 3.58 (t, J=12.4 Hz, 1H), 2.37-2.35 (m, 1H), 2.20-2.17 (m, 1H), 1.92-1.80 (m, 8H), 1.70-1.68 (m, 1H), 1.56-1.54 (m, 1H); $^{13}$C NMR (CDCl$_3$, 150 MHz) δ: 169.0, 165.9, 162.7, 151.9, 148.5, 147.9, 147.0, 141.3, 138.6, 138.4, 133.5, 129.7, 127.3, 120.1, 120.0, 118.0, 114.6, 43.7, 43.5, 27.9, 26.3, 25.8, 20.5, 19.8. MS (ESI, m/z): 488.2 [M+H]$^+$.

Example 50

(S)-1-amino-2-(1-(but-2-ynoyl)piperidin-2-yl)-4-(4-(pyridin-2-ylcarbamoyl)phenyl)-1H-imidazole-5-carboxamide

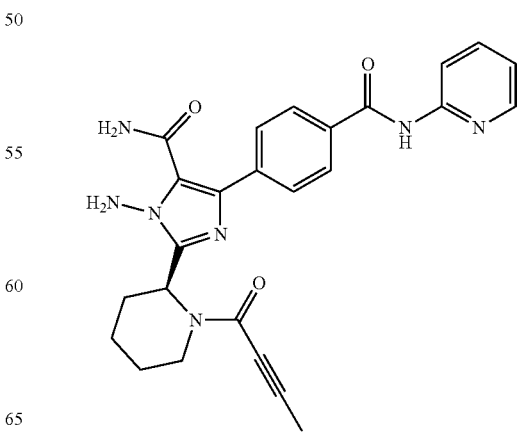

Preparation of (S)-1-amino-2-(1-(but-2-ynoyl)piperidin-2-yl)-4-(4-(pyridin-2-ylcarbamoyl)phenyl)-1H-imidazole-5-carboxamide

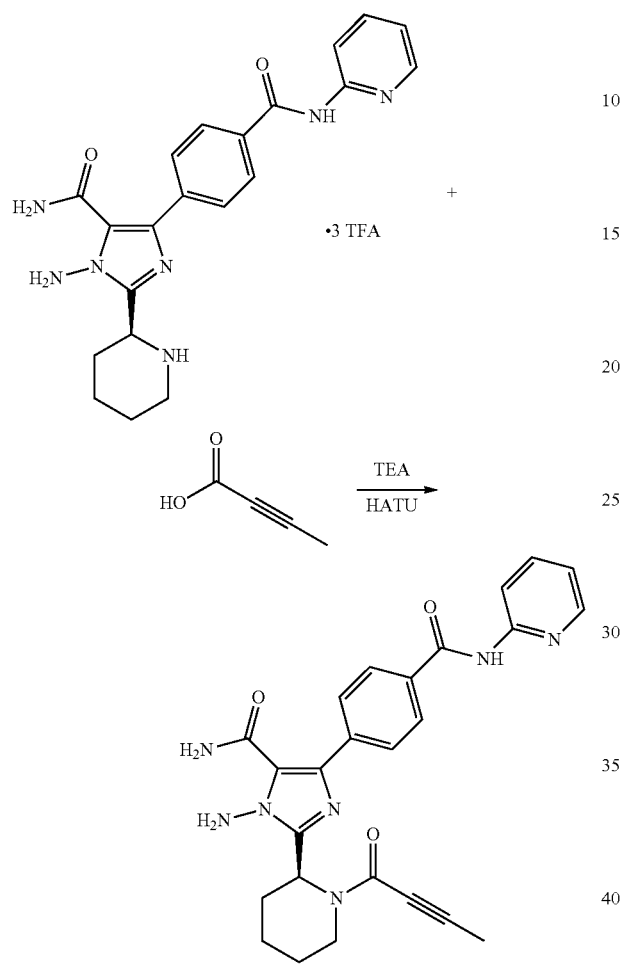

To the solution of 166 mg (0.41 mmol) the product of Step H of example 46 in dry N,N-Dimethylformamide (5 mL) was added triethylamine (248 mg, 2.46 mmol). After 5 min, but-2-ynoic acid (30.3 mg, 0.36 mmol) and HATU (234 mg, 0.61 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-1-amino-2-(1-(but-2-ynoyl)piperidin-2-yl)-4-(4-(pyridin-2-ylcarbamoyl)phenyl)-1H-imidazole-5-carboxamide as an off-white solid (97 mg, 50%). $^1$H NMR (CDCl$_3$, 400 MHz) δ: 9.42 (s, 1H), 8.33-8.20 (m, 2H), 7.81 (d, J=8.2 Hz, 2H), 7.69-7.58 (m, 3H), 7.23 (s, 1H), 7.03-6.98 (m, 1H), 6.85 (s, 1H), 6.11 (s, 2H), 5.93-5.89 (m, 1H), 4.24 (d, J=12.4 Hz, 1H), 3.69-3.63 (m, 1H), 2.31-2.22 (m, 1H), 2.14-2.11 (m, 1H), 1.96 (s, 3H), 1.84-1.81 (m, 2H), 1.68-1.65 (m, 1H), 1.57-1.54 (m, 1H); $^{13}$C NMR (CDCl$_3$, 100 MHz) δ: 166.1, 162.8, 154.8, 151.9, 148.1, 147.8, 140.9, 138.5, 138.1, 133.4, 129.4, 127.3, 120.4, 119.9, 114.6, 90.9, 72.9, 44.5, 43.8, 27.8, 25.7, 19.7, 4.2. MS (ESI, m/z): 472.2 [M+H]$^+$.

Example 51

(S,E)-1-amino-2-(1-(pent-2-enoyl)piperidin-2-yl)-4-(4-(pyridin-2-ylcarbamoyl)phenyl)-1H-imidazole-5-carboxamide

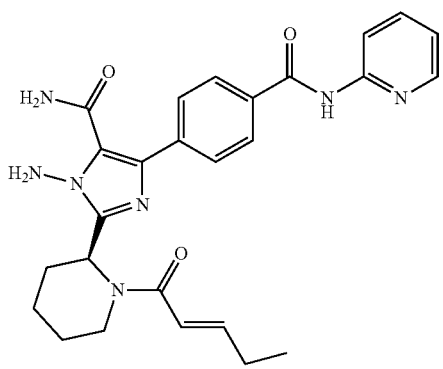 [SMILES: CC/C=C/C(=O)N1CCCC[C@H]1c1nc(-c2ccc(C(=O)Nc3ccccn3)cc2)c(C(N)=O)n1N]

Preparation of (S,E)-1-amino-2-(1-(pent-2-enoyl)piperidin-2-yl)-4-(4-(pyridin-2-ylcarbamoyl)phenyl)-1H-imidazole-5-carboxamide

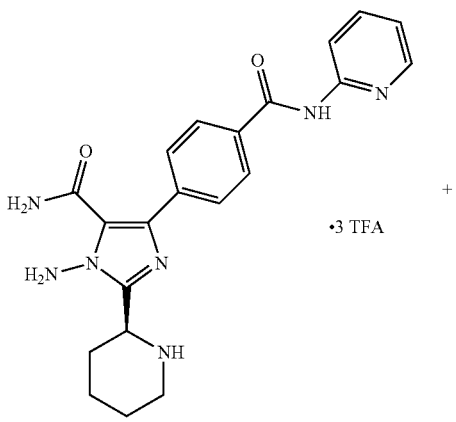

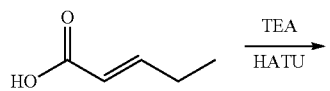

-continued

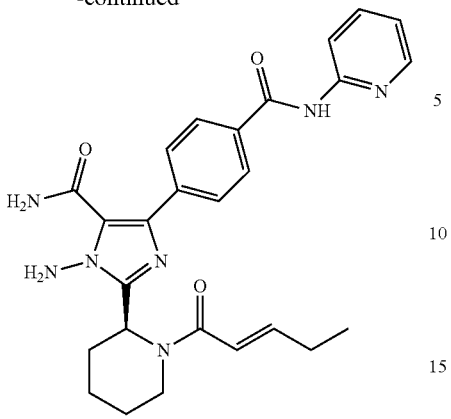

To the solution of (166 mg, 0.41 mmol) the product of Step H of example 46 in dry N,N-Dimethylformamide (5 mL) was added triethylamine (248 mg, 2.46 mmol). After 5 min, (E)-pent-2-enoic acid (36.0 mg, 0.36 mmol) and HATU (234 mg, 0.61 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S,E)-1-amino-2-(1-(pent-2-enoyl)piperidin-2-yl)-4-(4-(pyridin-2-ylcarbamoyl)phenyl)-1H-imidazole-5-carboxamide as an off-white solid (104 mg, 52%). $^1$H NMR (CDCl$_3$, 600 MHz) δ: 9.39 (s, 1H), 8.37-8.31 (m, 1H), 8.28-8.21 (m, 1H), 7.84-7.82 (m, 2H), 7.73-7.71 (m, 3H), 7.45 (s, 1H), 7.07-7.00 (m, 1H), 6.92-6.87 (m, 1H), 6.72 (s, 1H), 6.42-6.33 (s, 1H), 6.28-6.17 (m, 2H), 5.99-5.89 (m, 1H), 3.82 (d, J=11.6 Hz, 1H), 3.62 (t, J=12.1 Hz, 1H), 2.42-2.41 (m, 1H), 2.21-2.14 (m, 3H), 1.88-1.83 (m, 2H), 1.69-1.67 (m, 1H), 1.61-1.58 (m, 1H), 1.05-1.02 (m, 3H); $^{13}$C NMR (CDCl$_3$, 150 MHz) δ: 167.5, 166.1, 162.8, 151.8, 149.1, 148.4, 147.7, 141.3, 138.7, 138.4, 133.3, 129.6, 127.3, 120.1, 120.0, 119.2, 114.7, 44.3, 42.8, 27.9, 25.8, 19.7, 12.6, 8.6. MS (ESI, m/z): 488.2 [M+H]$^+$.

Example 52

(S,E)-1-amino-2-(1-(2-cyano-3-cyclopropylacryloyl)piperidin-2-yl)-4-(4-(pyridin-2-ylcarbamoyl)phenyl)-1H-imidazole-5-carboxamide

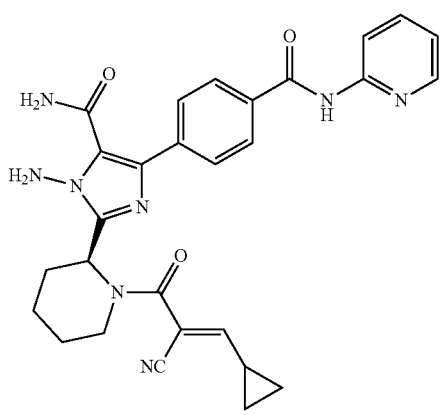 [SMILES: N#C/C(=C\C1CC1)C(=O)N1CCCC[C@H]1c1nc(-c2ccc(C(=O)Nc3ccccn3)cc2)c(C(N)=O)n1N]

Step A: Preparation of (S)-1-amino-2-(1-(2-cyanoacetyl)piperidin-2-yl)-4-(4-(pyridin-2-ylcarbamoyl)phenyl)-1H-imidazole-5-carboxamide

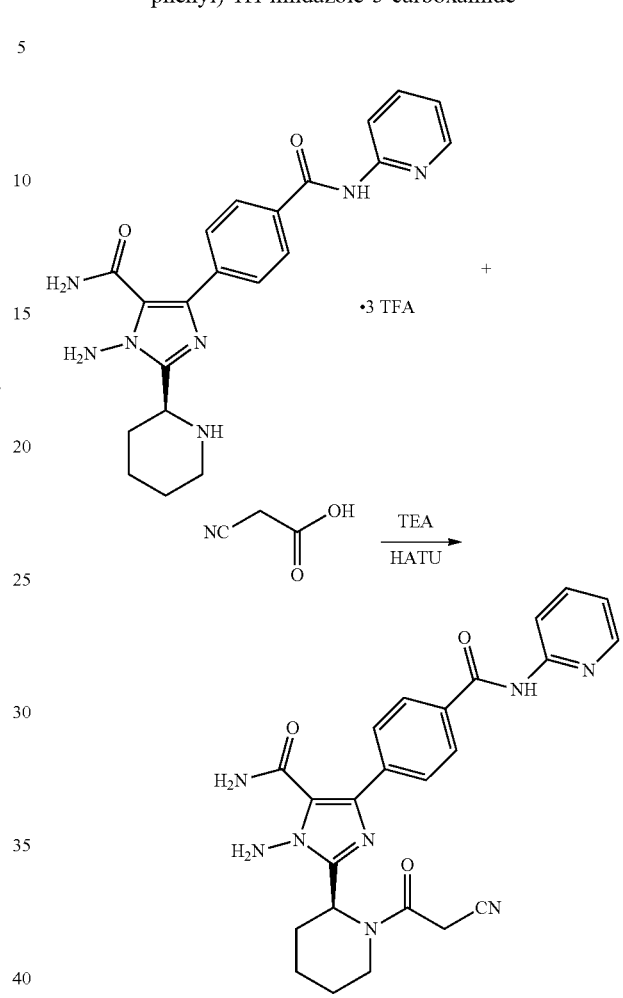

To the solution of (166 mg, 0.41 mmol) the product of Step H of example 46 in dry N,N-Dimethylformamide (5 mL) was added triethylamine (248 mg, 2.46 mmol). After 5 min, 2-cyanoacetic acid (30.6 mg, 0.36 mmol) and HATU (234 mg, 0.61 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(2-cyanoacetyl)piperidin-2-yl)-4-(4-(pyridin-2-ylcarbamoyl)phenyl)-1H-imidazole-5-carboxamide as an off-white solid (97 mg, 50%). $^1$H NMR (CDCl$_3$, 600 MHz) δ: 9.32-9.23 (m, 1H), 8.34 (d, J=4.5 Hz, 1H), 8.26-8.25 (m, 1H), 7.89-7.85 (m, 2H), 7.75-7.69 (m, 3H), 7.08-7.05 (m, 1H), 6.87 (s, 1H), 6.51 (s, 1H), 5.97 (s, 2H), 5.93 (d, J=5.1 Hz, 1H), 3.96-3.82 (m, 1H), 3.58 (s, 2H), 3.50 (d, J=12.8 Hz, 1H), 2.24-2.13 (m, 2H), 1.89-1.87 (m, 2H), 1.75-1.59 (m, 2H); $^{13}$C NMR (CDCl$_3$, 150 MHz) δ: 165.9, 162.8, 162.5, 151.8, 148.3, 147.9, 140.8, 138.7, 138.0, 133.7, 129.5, 127.5, 120.5, 120.2, 114.6, 114.2, 45.3, 44.1, 27.8, 25.7, 25.4, 19.2. MS (ESI, m/z): 473.2 [M+H]$^+$.

Step B: Preparation of (S,E)-1-amino-2-(1-(2-cyano-3-cyclopropyl-acryloyl)piperidin-2-yl)-4-(4-(pyridin-2-ylcarbamoyl)phenyl)-1H-imidazole-5-carboxamide

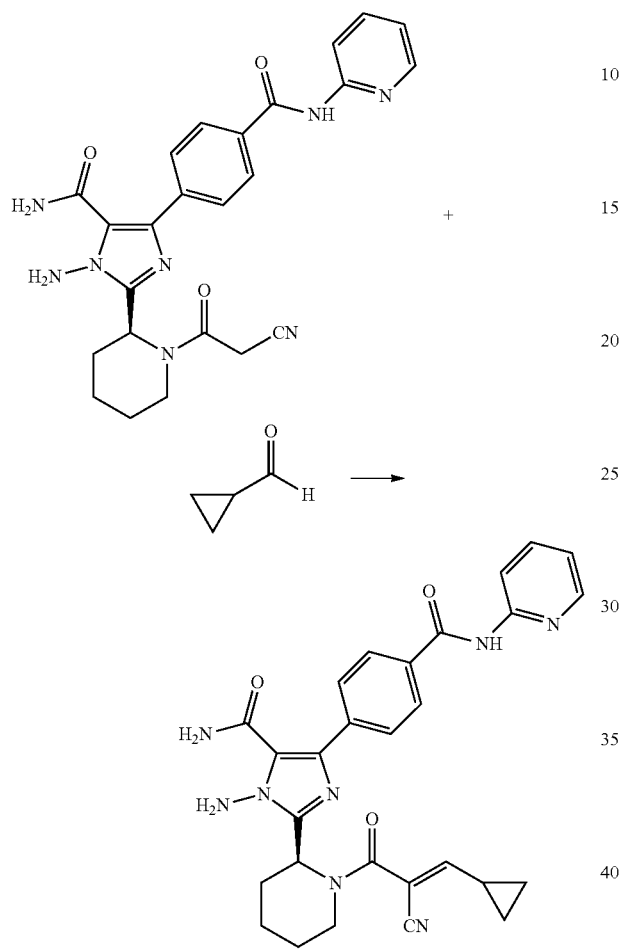

To the solution of cyclopropanecarbaldehyde (8.4 mg, 0.12 mmol) in dry dichloromethane (5 mL) at 0° C., pyrrolidine (42.7 mg, 0.60 mmol) and TMS-Cl (65.2 mg, 0.60 mmol) were added. The ice bath was removed and the reaction mixture was stirred for 10 min followed by the additions of 56.6 mg (0.12 mmol) of the product of Step A. The reaction solution was stirred for 1 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (23:1) to afford (S,E)-1-amino-2-(1-(2-cyano-3-cyclopropylacryloyl)piperidin-2-yl)-4-(4-(pyridin-2-ylcarbamoyl)phenyl)-1H-imidazole-5-carboxamide as a white solid (31.4 mg, 50%). $^1$H NMR (CDCl$_3$, 600 MHz) δ: 9.25 (s, 1H), 8.36 (d, J=8.3 Hz, 1H), 8.28-8.27 (m, 1H), 7.88 (d, J=8.0 Hz, 2H), 7.76-7.73 (m, 2.5H), 7.66-7.65 (m, 0.5H), 7.08-7.06 (m, 1H), 6.94 (s, 1H), 6.58 (d, J=11.2 Hz, 1H), 6.50-6.47 (m, 1H), 6.22 (s, 1H), 6.04-6.00 (m, 1H), 5.77 (d, J=4.0 Hz, 1H), 3.98-3.94 (m, 1H), 3.87-3.81 (m, 1H), 2.33-2.28 (m, 1H), 2.21-2.16 (m, 1H), 2.09-2.03 (m, 1H), 2.00-1.94 (m, 1H), 1.88-1.86 (m, 1H), 1.77-1.70 (m, 2H), 1.24-1.20 (m, 2H), 0.88-0.85 (m, 2H); $^{13}$C NMR (CDCl$_3$, 150 MHz) δ: 166.3, 165.9, 163.1, 162.8, 151.8, 147.8, 138.8, 138.7, 138.1, 133.7, 129.5, 129.2, 127.6, 127.5, 120.1, 115.4, 114.6, 107.6, 45.7, 45.0, 28.3, 25.2, 19.8, 15.8, 10.9, 10.8. MS (ESI, m/z): 525.2 [M+H]$^+$.

Example 53

(S)-2-(1-acryloylpiperidin-2-yl)-1-amino-4-(4-((4-methylpyridin-2-yl)carbamoyl)phenyl)-1H-imidazole-5-carboxamide

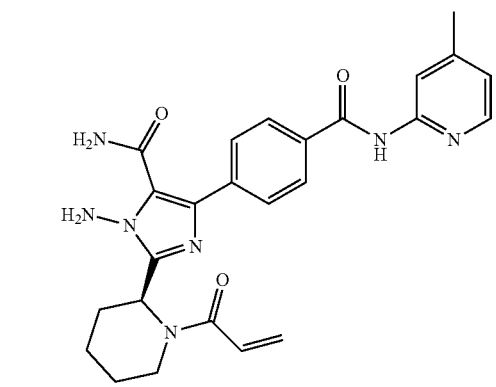 [SMILES: C=CC(=O)N1CCCC[C@H]1c1nc(-c2ccc(C(=O)Nc3cc(C)ccn3)cc2)c(C(N)=O)n1N]

Step A: Preparation of tert-butyl (S)-2-(5-(ethoxycarbonyl)-4-(4-((4-methylpyridin-2-yl)carbamoyl)phenyl)-1H-imidazol-2-yl)piperidine-1-carboxylate

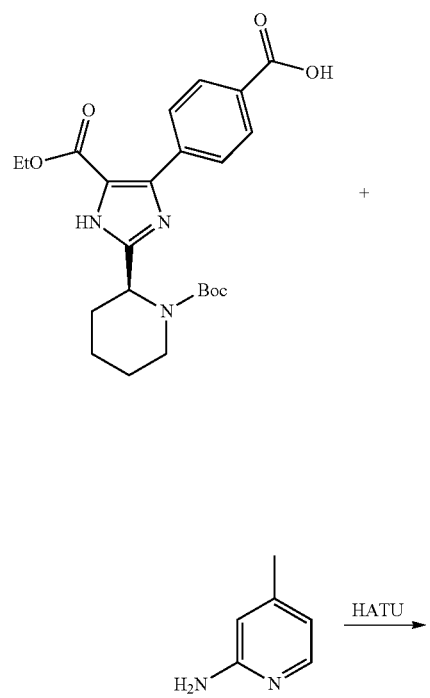

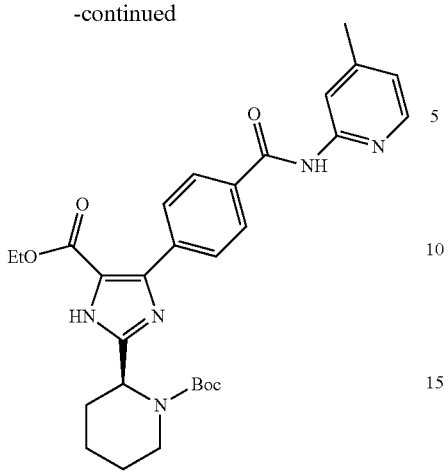

To the solution of 25.2 g (57 mmol) the product of Step C of example 46 in dry N,N-Dimethylformamide (230 mL), HATU (26.0 g, 68 mmol), diisopropylethylamine (49.1 mL, 285 mmol) and 4-methylpyridin-2-amine (9.2 g, 86 mmol) were added and stirred at 80° C. for 3 h. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (3:1) to afford tert-butyl (S)-2-(5-(ethoxycarbonyl)-4-(4-((4-methylpyridin-2-yl)carbamoyl)phenyl)-1H-imidazol-2-yl)piperidine-1-carboxylate as white solid (25.8 g, 85%). $^1$H NMR (CDCl$_3$, 600 MHz) δ: 10.21 (s, 1H), 8.90 (s, 1H), 8.25 (s, 1H), 8.13 (d, J=8.3 Hz, 2H), 8.09 (d, J=5.0 Hz, 1H), 7.95 (d, J=8.3 Hz, 2H), 6.87 (d, J=5.0 Hz, 1H), 5.42-5.40 (m, 1H), 4.31-4.27 (m, 2H), 4.06-3.94 (s, 1H), 2.80-2.76 (m, 1H), 2.51 (d, J=12.8 Hz, 1H), 2.38 (s, 3H), 1.91-1.90 (m, 1H), 1.83-1.79 (m, 1H), 1.73-1.71 (m, 1H), 1.66-1.64 (m, 1H), 1.52-1.48 (m, 10H), 1.29 (t, J=7.1 Hz, 3H). MS (ESI, m/z): 534.2 [M+H]$^+$.

Step B: Preparation of tert-butyl (S)-2-(1-amino-5-(ethoxycarbonyl)-4-(4-((4-methylpyridin-2-yl)carbamoyl)phenyl)-1H-imidazol-2-yl)piperidine-1-carboxylate

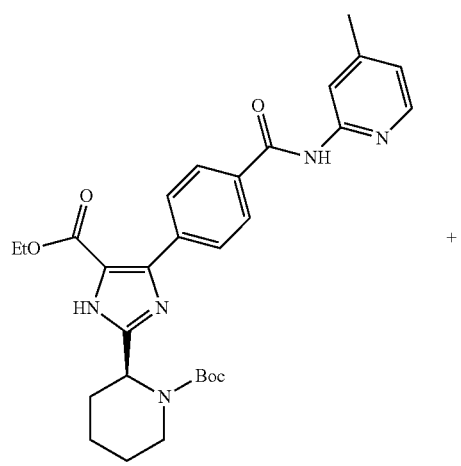

+

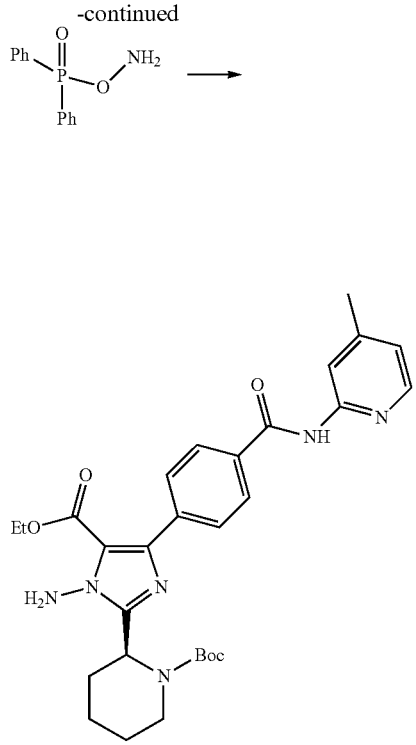

To the solution of 2.9 g (5.5 mmol) of the product of Step A in anhydrous N,N-Dimethylformamide (26 mL), lithium hexamethyldisilazane (6.6 mL, 1 M solution in tetrahydrofuran) was slowly added at −10° C. After the mixture was stirred for 20 min, O-(diphenylphosphinyl) hydroxylamine (1.3 g, 5.5 mmol) was added at 0° C. and the resulting suspension was stirred at room temperature for 2 h (in cases where the reaction mixture became too viscous, additional N,N-Dimethylformamide was added). The mixture was quenched with brine and washed with ethyl acetate three times (3×100 mL). The combined organic fractions were dried with anhydrous Na$_2$SO$_4$ and the solvent was removed under reduced pressure to afford the crude residue, which was subjected to column chromatography with petroleum ether and ethyl acetate (3:1) to afford tert-butyl (S)-2-(1-amino-5-(ethoxycarbonyl)-4-(4-((4-methylpyridin-2-yl)carbamoyl)phenyl)-1H-imidazol-2-yl)piperidine-1-carboxylate as a white solid (2.2 g, 72%). $^1$H NMR (CDCl$_3$, 400 MHz) δ: 8.73 (s, 1H), 8.26 (s, 1H), 8.14-8.12 (m, 1H), 7.93 (d, J=8.6 Hz, 2H), 7.84 (d, J=8.5 Hz, 2H), 6.90 (d, J=5.1 Hz, 1H), 5.92 (s, 2H), 5.68 (d, J=4.8 Hz, 1H), 4.33-4.24 (m, 2H), 3.95 (d, J=12.6 Hz, 1H), 3.45-3.38 (m, 1H), 2.40 (s, 3H), 2.12-2.05 (m, 2H), 1.92-1.87 (m, 1H), 1.76-1.73 (m, 3H), 1.66-1.62 (m, 1H), 1.54-1.49 (m, 1H), 1.44 (s, 9H), 1.24 (t, J=7.2 Hz, 3H). MS (ESI, m/z): 549.2 [M+H]$^+$.

Step C: Preparation of (S)-1-amino-2-(1-(tert-butoxycarbonyl)piperidin-2-yl)-4-(4-((4-methylpyridin-2-yl)carbamoyl)phenyl)-1H-imidazole-5-carboxylic acid

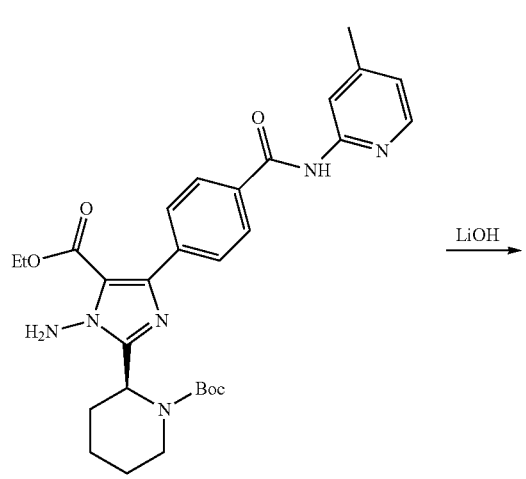

Step D: Preparation of tert-butyl (S)-2-(1-amino-5-carbamoyl-4-(4-((4-methylpyridin-2-yl)carbamoyl)phenyl)-1H-imidazol-2-yl)piperidine-1-carboxylate

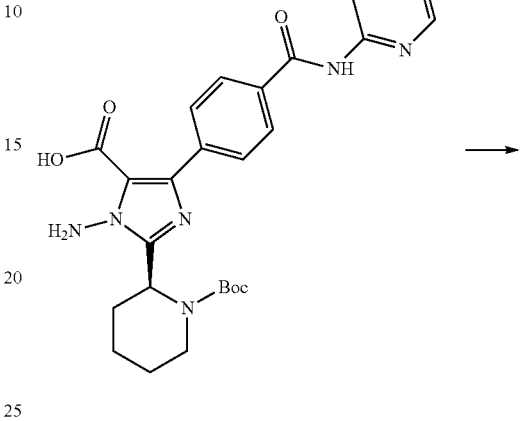

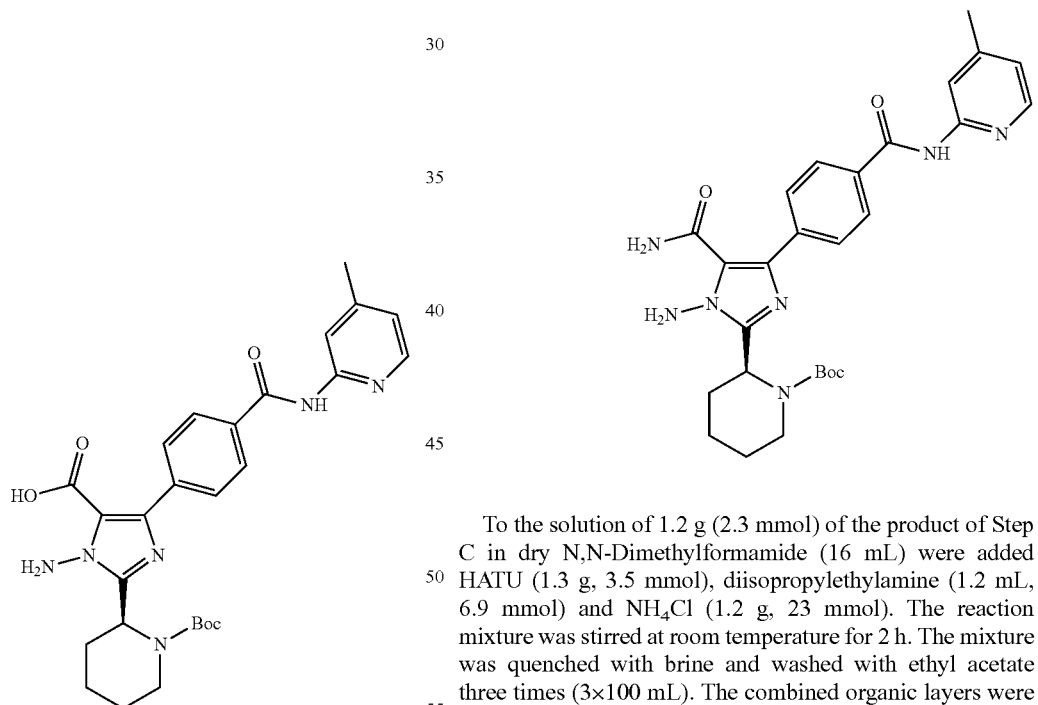

To the solution of 1.53 g (2.8 mmol) of the product of Step B in methanol (15 mL) was added 2 mol/L aqueous lithium hydroxide (14 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl)piperidin-2-yl)-4-(4-((4-methylpyridin-2-yl)carbamoyl)phenyl)-1H-imidazole-5-carboxylic acid (1.38 g, 95%).

To the solution of 1.2 g (2.3 mmol) of the product of Step C in dry N,N-Dimethylformamide (16 mL) were added HATU (1.3 g, 3.5 mmol), diisopropylethylamine (1.2 mL, 6.9 mmol) and NH$_4$Cl (1.2 g, 23 mmol). The reaction mixture was stirred at room temperature for 2 h. The mixture was quenched with brine and washed with ethyl acetate three times (3×100 mL). The combined organic layers were concentrated under reduced pressure and purified by flash chromatography with dichloromethane and methanol (32:1) to afford tert-butyl (S)-2-(1-amino-5-carbamoyl-4-(4-((4-methylpyridin-2-yl)carbamoyl)phenyl)-1H-imidazol-2-yl)piperidine-1-carboxylate as a white solid (1.03 g, 86%). $^1$H NMR (CDCl$_3$, 600 MHz) δ: 9.34 (s, 1H), 8.20 (s, 1H), 8.08 (d, J=4.9 Hz, 1H), 7.85 (d, J=8.0 Hz, 2H), 7.70 (d, J=7.9 Hz, 2H), 6.99 (s, 1H), 6.85 (d, J=4.8 Hz, 1H), 6.68 (s, 1H), 6.04 (s, 2H), 5.61 (d, J=5.4 Hz, 1H), 3.93 (d, J=12.3 Hz, 1H), 3.33 (t, J=11.9 Hz, 1H), 2.36 (s, 3H), 2.18-2.11 (m, 2H), 1.89-1.84 (m, 1H), 1.73-1.71 (m, 1H), 1.64-1.62 (m, 1H), 1.53-1.49 (m, 1H), 1.44 (s, 9H). MS (ESI, m/z): 520.2 [M+H]$^+$.

Step E: Preparation of (S)-1-amino-4-(4-((4-methylpyridin-2-yl)carbamoyl)phenyl)-2-(piperidin-2-yl)-1H-imidazole-5-carboxamide

Step F: Preparation of (S)-2-(1-acryloylpiperidin-2-yl)-1-amino-4-(4-((4-methylpyridin-2-yl)carbamoyl)phenyl)-1H-imidazole-5-carboxamide

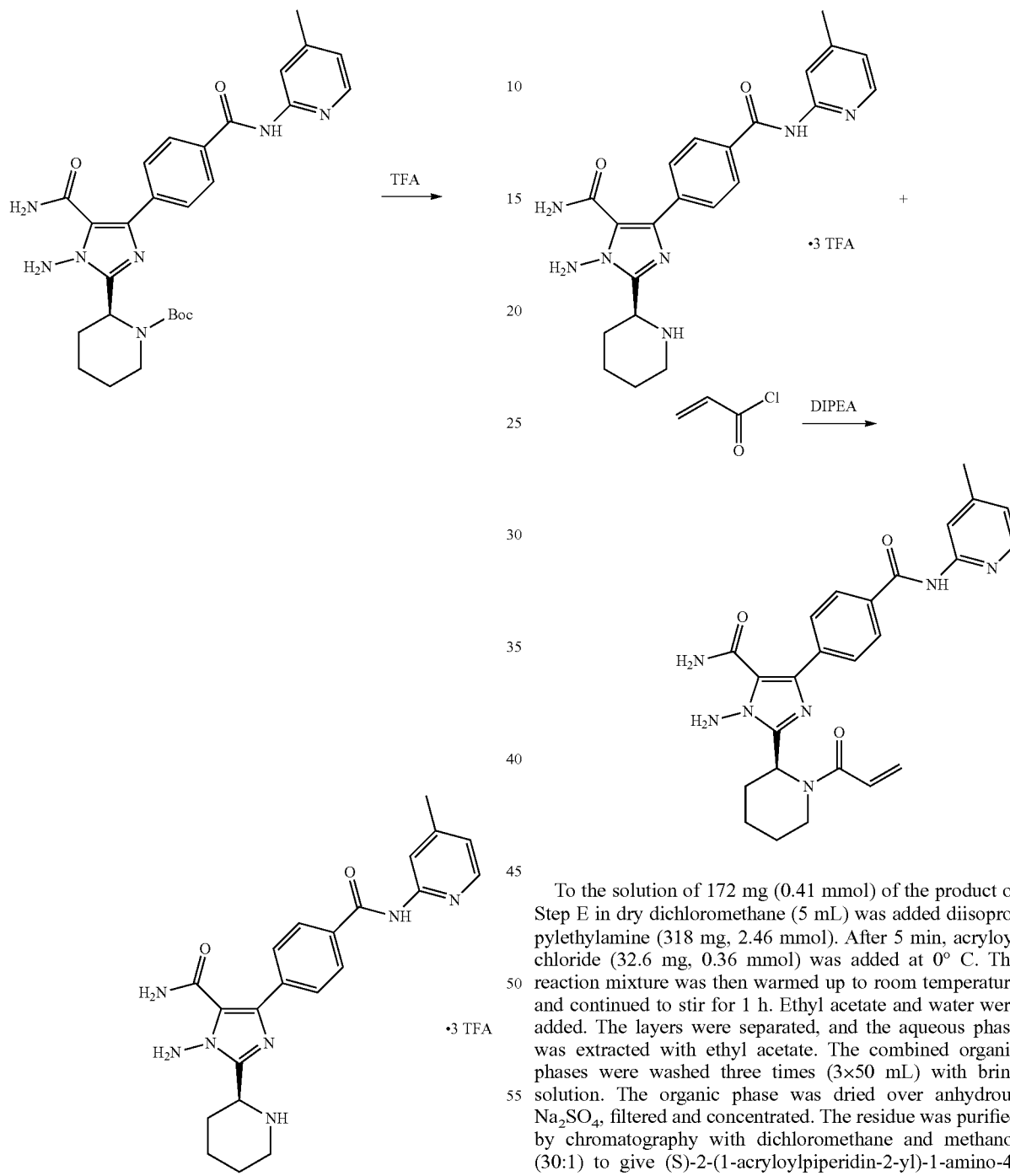

To the solution of 202 mg (0.39 mmol) of the product of Step D in dichloromethane (5 mL) was added trifluoroacetic acid (2.5 mL). The mixture was stirred at room temperature for 1 h and then concentrated to afford (S)-1-amino-4-(4-((4-methylpyridin-2-yl)carbamoyl)phenyl)-2-(piperidin-2-yl)-1H-imidazole-5-carboxamide as a light yellow oil. MS (ESI, m/z): 420.2 [M+H]$^+$.

To the solution of 172 mg (0.41 mmol) of the product of Step E in dry dichloromethane (5 mL) was added diisopropylethylamine (318 mg, 2.46 mmol). After 5 min, acryloyl chloride (32.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (30:1) to give (S)-2-(1-acryloylpiperidin-2-yl)-1-amino-4-(4-((4-methylpyridin-2-yl)carbamoyl)p-henyl)-1H-imidazole-5-carboxamide as an off-white solid (120 mg, 62%). $^1$H NMR (CDCl$_3$, 400 MHz) δ: 9.11 (s, 1H), 8.22 (s, 1H), 8.11 (d, J=5.1 Hz, 1H), 7.89 (d, J=8.4 Hz, 2H), 7.79 (d, J=7.6 Hz, 2H), 7.12 (s, 1H), 6.88 (d, J=4.8 Hz, 1H), 6.61-6.55 (m, 1H), 6.47 (s, 1H), 6.31-6.25 (m, 3H), 5.98-5.97 (m, 1H), 5.70 (d, J=10.5 Hz, 1H), 3.82 (d, J=12.1 Hz, 1H), 3.69 (t, J=12.4 Hz, 1H), 2.38 (s, 3H), 2.20-2.16 (m, 1H), 1.94-1.58 (m, 5H); $^{13}$C NMR (CDCl$_3$, 150 MHz) δ: 167.2, 165.9, 162.8, 151.9, 150.1, 148.2, 147.5, 141.2, 138.3, 133.7, 129.6, 128.7, 127.8, 127.4, 121.2, 120.0, 115.1, 44.4, 43.0, 28.0, 25.8, 21.6, 19.7. MS (ESI, m/z): 474.2 [M+H]$^+$.

Example 54

(S)-1-amino-2-(1-methacryloylpiperidin-2-yl)-4-(4-((4-methylpyridin-2-yl)carbamoyl)phenyl)-1H-imidazole-5-carboxamide

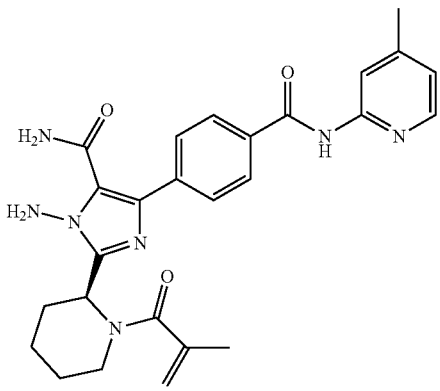 [SMILES: C=C(C)C(=O)N1CCCC[C@H]1c1nc(-c2ccc(C(=O)Nc3cc(C)ccn3)cc2)c(C(N)=O)n1N]

Preparation of (S)-1-amino-2-(1-methacryloylpiperidin-2-yl)-4-(4-((4-methylpyridin-2-yl)carbamoyl)phenyl)-1H-imidazole-5-carboxamide

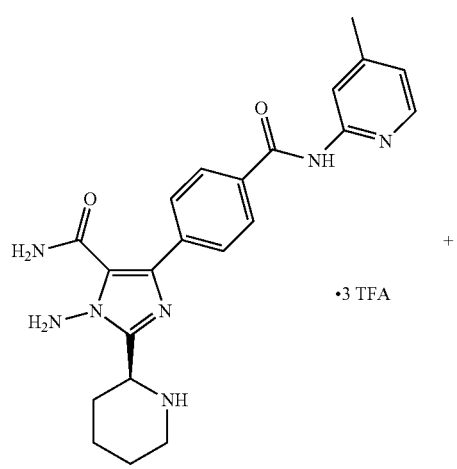

·3 TFA

+

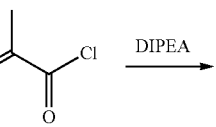

DIPEA ⟶

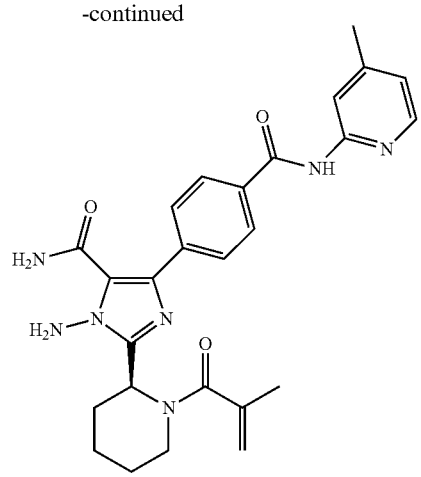

To the solution of 172 mg (0.41 mmol) of the product of Step E of example 53 in dry dichloromethane (5 mL) was added diisopropylethylamine (318 mg, 2.46 mmol). After 5 min, methacryloyl chloride (37.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (30:1) to give (S)-1-amino-2-(1-methacryloylpiperidin-2-yl)-4-(4-((4-methylpyridin-2-yl)carbamoyl)phenyl)-1H-imidazole-5-carboxamide as an off-white solid (120 mg, 60%). $^1$H NMR (CDCl$_3$, 600 MHz) δ: 9.27 (s, 1H), 8.21 (s, 1H), 8.10 (d, J=5.0 Hz, 1H), 7.87 (d, J=8.3 Hz, 2H), 7.74-7.73 (m, 2H), 7.08 (s, 1H), 6.87 (d, J=4.9 Hz, 1H), 6.66 (s, 1H), 6.24 (s, 2H), 5.96-5.85 (m, 1H), 5.18-5.14 (m, 1H), 5.08-5.03 (m, 1H), 3.90-3.79 (m, 1H), 3.65-3.61 (m, 1H), 2.37 (s, 3H), 2.35-2.32 (m, 1H), 2.22-2.19 (m, 1H), 1.94 (s, 3H), 1.92-1.87 (m, 1H), 1.81-1.79 (m, 1H), 1.71-1.68 (m, 1H), 1.57-1.49 (m, 1H); $^{13}$C NMR (CDCl$_3$, 150 MHz) δ: 173.0, 165.9, 162.9, 151.9, 150.2, 148.2, 147.4, 141.1, 140.5, 138.2, 133.7, 129.5, 127.4, 121.2, 120.2, 115.8, 115.1, 44.2, 44.1, 28.0, 26.0, 21.6, 20.5, 19.9. MS (ESI, m/z): 488.2 [M+H]$^+$.

Example 55

(S,E)-1-amino-2-(1-(but-2-enoyl)piperidin-2-yl)-4-(4-((4-methylpyridin-2-yl)carbamoyl)phenyl)-1H-imidazole-5-carboxamide

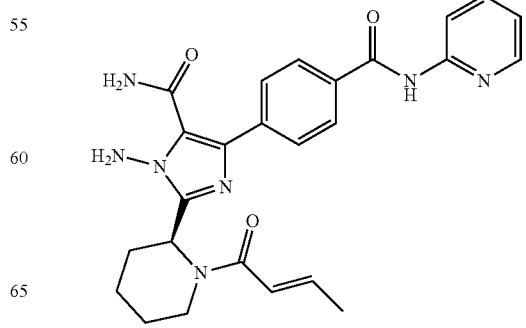

Preparation of (S,E)-1-amino-2-(1-(but-2-enoyl)piperidin-2-yl)-4-(4-((4-methylpyridin-2-yl)carbamoyl)phenyl)-1H-imidazole-5-carboxamide

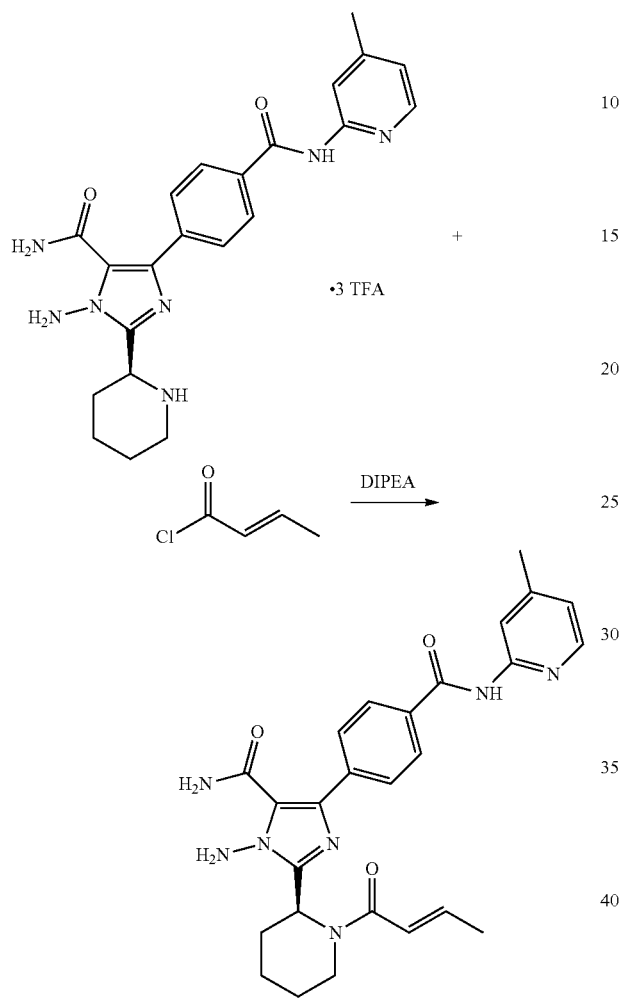

To the solution of 172 mg (0.41 mmol) of the product of Step E of example 53 in dry dichloromethane (5 mL) was added diisopropylethylamine (318 mg, 2.46 mmol). After 5 min, (E)-but-2-enoyl chloride (37.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (28:1) to give (S,E)-1-amino-2-(1-(but-2-enoyl)piperidin-2-yl)-4-(4-((4-methylpyridin-2-yl)carbamoyl)phenyl)-1H-imidazole-5-carboxamide as an off-white solid (120 mg, 60%). $^1$H NMR ($CDCl_3$, 600 MHz) δ: 9.43 (s, 1H), 8.18 (s, 1H), 8.06-8.05 (m, 1H), 7.82 (d, J=7.7 Hz, 2H), 7.77-7.65 (m, 2H), 7.39 (s, 1H), 6.87-6.80 (m, 3H), 6.31-6.24 (m, 3H), 5.98-5.87 (m, 1H), 3.80-3.79 (m, 1H), 3.67-3.55 (m, 1H), 2.43-2.34 (m, 4H), 2.15-2.13 (m, 1H), 1.87-1.83 (m, 5H), 1.66-1.64 (m, 1H), 1.56-1.54 (m, 1H); $^{13}$C NMR ($CDCl_3$, 150 MHz) δ: 167.2, 166.1, 162.8, 151.9, 150.1, 148.3, 147.2, 142.6, 141.1, 138.3, 133.4, 129.4, 127.2, 121.7, 121.0, 120.2, 115.1, 44.2, 42.7, 27.9, 25.8, 21.5, 19.7, 18.4. MS (ESI, m/z): 488.2 $[M+H]^+$.

Example 56

(S)-1-amino-2-(1-(3-methylbut-2-enoyl)piperidin-2-yl)-4-(4-((4-methylpyridin-2-yl)carbamoyl)phenyl)-1H-imidazole-5-carboxamide

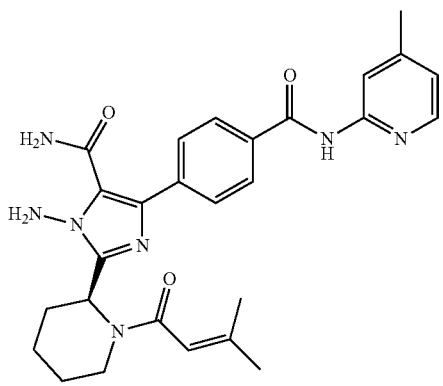 [SMILES: CC(C)=CC(=O)N1CCCC[C@H]1c1nc(-c2ccc(C(=O)Nc3cc(C)ccn3)cc2)c(C(N)=O)n1N]

Preparation of (S)-1-amino-2-(1-(3-methylbut-2-enoyl)piperidin-2-yl)-4-(4-((4-methylpyridin-2-yl)carbamoyl)phenyl)-1H-imidazole-5-carboxamide

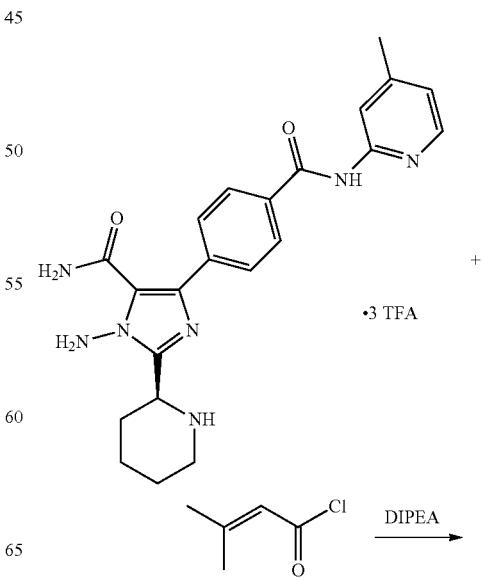

-continued

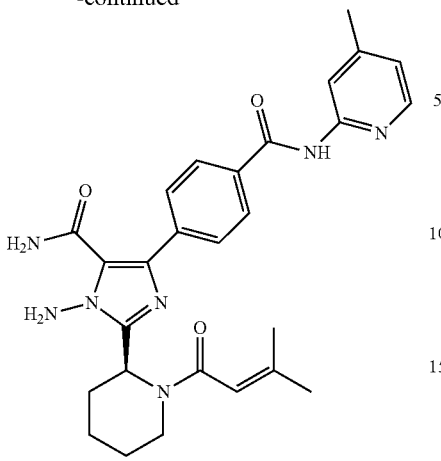

To the solution of 172 mg (0.41 mmol) of the product of Step E of example 53 in dry dichloromethane (5 mL) was added diisopropylethylamine (318 mg, 2.46 mmol). After 5 min, 3-methylbut-2-enoyl chloride (42.7 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (28:1) to give the product (S)-1-amino-2-(1-(3-methylbut-2-enoyl)piperidin-2-yl)-4-(4-((4-methylpyridin-2-yl)carbamoyl)phenyl)-1H-imidazole-5-carboxamide as an off-white solid (134 mg, 65%). $^1$H NMR (CDCl$_3$, 600 MHz) δ: 9.28 (s, 1H), 8.25 (s, 1H), 8.12 (d, J=4.7 Hz, 1H), 7.93 (d, J=8.2 Hz, 2H), 7.82-7.81 (m, 2H), 7.16 (s, 1H), 6.90 (d, J=4.6 Hz, 1H), 6.38-6.30 (m, 3H), 5.97-5.96 (m, 1H), 5.78 (s, 1H), 3.79 (d, J=12.4 Hz, 1H), 3.58 (t, J=12.4 Hz, 1H), 2.40 (s, 3H), 2.36-2.32 (m, 1H), 2.20-2.18 (m, 1H), 1.87-1.80 (m, 8H), 1.70-1.67 (m, 1H), 1.58-1.52 (m, 1H); $^{13}$C NMR (CDCl$_3$, 150 MHz) δ: 169.0, 165.9, 162.7, 151.7, 150.7, 148.5, 147.0, 146.9, 141.2, 138.5, 133.5, 129.7, 127.4, 121.2, 120.0, 118.0, 115.2, 43.7, 43.5, 28.0, 26.3, 25.8, 21.7, 20.5, 19.8. MS (ESI, m/z): 502.2 [M+H]$^+$.

Example 57

(S, E)-1-amino-2-(1-cinnamoylpiperidin-2-yl)-4-(4-((4-methylpyridin-2-yl)carbamoyl)phenyl)-1H-imidazole-5-carboxamide

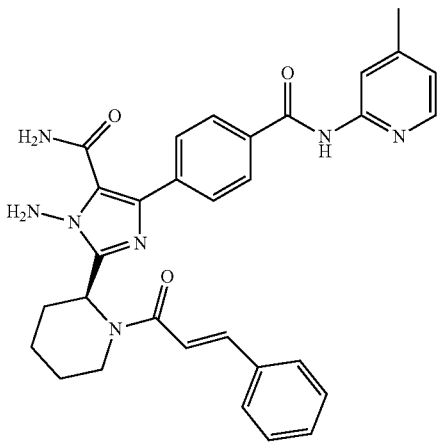 [SMILES: Cc1ccnc(NC(=O)c2ccc(-c3nc([C@@H]4CCCCN4C(=O)/C=C/c4ccccc4)n(N)c3C(N)=O)cc2)c1]

Preparation of (S,E)-1-amino-2-(1-cinnamoylpiperidin-2-yl)-4-(4-((4-methylpyridin-2-yl)carbamoyl)phenyl)-1H-imidazole-5-carboxamide

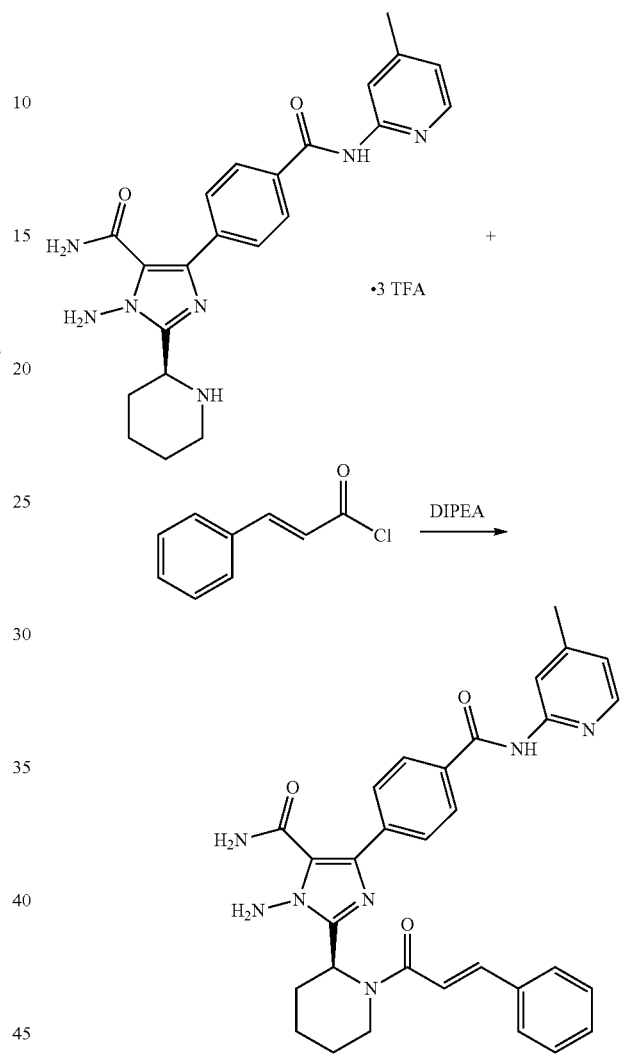

To the solution of 172 mg (0.41 mmol) of the product of Step E of example 53 in dry dichloromethane (5 mL) was added diisopropylethylamine (318 mg, 2.46 mmol). After 5 min, cinnamoyl chloride (60.0 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (28:1) to give (S, E)-1-amino-2-(1-cinnamoylpiperidin-2-yl)-4-(4-((4-methylpyridin-2-yl)carbamoyl)phenyl)-1H-imidazole-5-carboxamide as an off-white solid (113 mg, 50%). $^1$H NMR (CDCl$_3$, 600 MHz) δ: 9.03 (s, 1H), 8.23 (s, 1H), 8.13 (d, J=5.0 Hz, 1H), 7.92 (d, J=8.3 Hz, 2H), 7.87-7.77 (m, 2H), 7.66 (d, J=15.4 Hz, 1H), 7.52-7.51 (m, 2H), 7.36-7.35 (m, 3H), 7.12 (s, 1H), 6.90-6.88 (m, 2H), 6.38 (s, 2H), 6.31-6.21 (m, 1H), 6.08-5.99 (m, 1H), 4.01-

3.88 (m, 1H), 3.81-3.67 (m, 1H), 2.49-2.44 (m, 1H), 2.39 (s, 3H), 2.22-2.20 (m, 1H), 1.97-1.89 (m, 2H), 1.73-1.65 (m, 2H); $^{13}$C NMR (CDCl$_3$, 150 MHz) δ: 167.4, 165.8, 162.7, 151.8, 150.2, 148.3, 147.5, 143.7, 141.3, 138.4, 135.2, 133.8, 130.0, 129.7, 129.0, 128.0, 127.4, 121.3, 119.9, 117.3, 115.1, 44.6, 43.0, 28.1, 25.9, 21.6, 19.8. MS (ESI, m/z): 550.2 [M+H]$^+$.

Example 58

(S)-1-amino-2-(1-(but-2-ynoyl)piperidin-2-yl)-4-(4-((4-methylpyridin-2-yl)carbamoyl)phenyl)-1H-imidazole-5-carboxamide

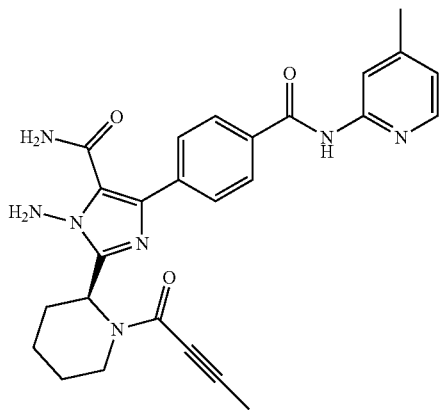 [SMILES: CC#CC(=O)N1CCCC[C@H]1c1nc(-c2ccc(C(=O)Nc3cc(C)ccn3)cc2)c(C(N)=O)n1N]

Preparation of (S)-1-amino-2-(1-(but-2-ynoyl)piperidin-2-yl)-4-(4-((4-methylpyridin-2-yl)carbamoyl)phenyl)-1H-imidazole-5-carboxamide

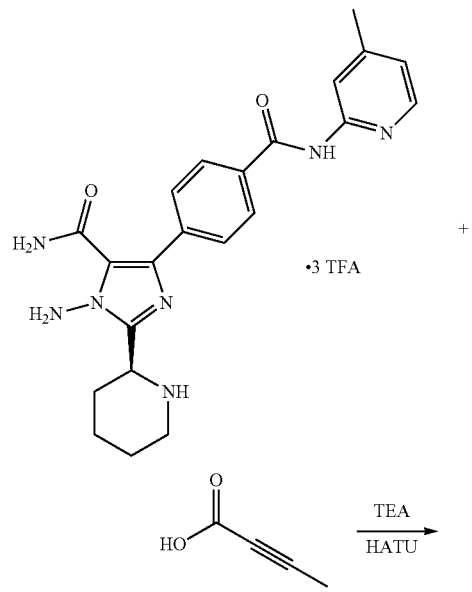

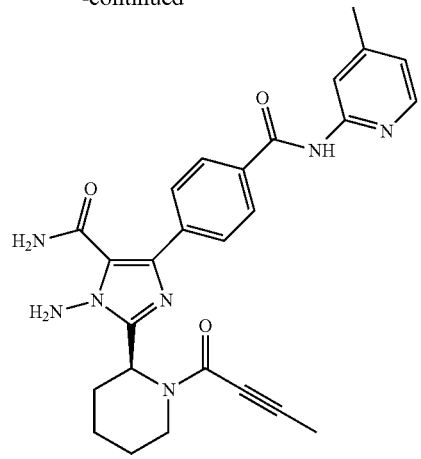

To the solution of 172 mg (0.41 mmol) the product of Step E of example 53 in dry N,N-Dimethylformamide (5 mL) was added triethylamine (248 mg, 2.46 mmol). After 5 min, but-2-ynoic acid (30.3 mg, 0.36 mmol) and HATU (234 mg, 0.61 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-1-amino-2-(1-(but-2-ynoyl)piperidin-2-yl)-4-(4-((4-methylpyridin-2-yl)carbamoyl)phenyl)-1H-imidazole-5-carboxamide as an off-white solid (99.5 mg, 50%). $^1$H NMR (CDCl$_3$, 400 MHz) δ: 8.87 (s, 1H), 8.24 (s, 1H), 8.15 (d, J=5.1 Hz, 1H), 7.95 (d, J=8.4 Hz, 2H), 7.83 (d, J=8.4 Hz, 1.7H), 7.75 (d, J=8.3 Hz, 0.3H), 6.91 (d, J=4.4 Hz, 1H), 6.80 (s, 1H), 6.15 (s, 2H), 6.02 (s, 0.5H), 5.97-5.96 (m, 1H), 5.92 (s, 0.3H), 5.67 (s, 0.2H), 4.28 (d, J=12.5 Hz, 1H), 3.67 (td, J$_1$=13.2 Hz, J$_2$=3.1 Hz, 1H), 2.41 (s, 3H), 2.37-2.33 (m, 1H), 2.20-2.16 (m, 1H), 2.02 (s, 3H), 1.92-1.83 (m, 2H), 1.74-1.58 (m, 2H); $^{13}$C NMR (CDCl$_3$, 150 MHz) δ: 165.6, 162.6, 155.0, 151.8, 150.2, 147.9, 147.6, 141.2, 138.3, 133.9, 129.8, 127.5, 121.3, 119.9, 115.0, 90.9, 73.0, 44.5, 43.8, 27.8, 25.8, 21.6, 19.9, 4.3. MS (ESI, m/z): 486.2 [M+H]$^+$.

Example 59

(S)-1-amino-2-(1-(2-fluoroacryloyl)piperidin-2-yl)-4-(4-((4-methylpyridin-2-yl)carbamoyl)phenyl)-1H-imidazole-5-carboxamide

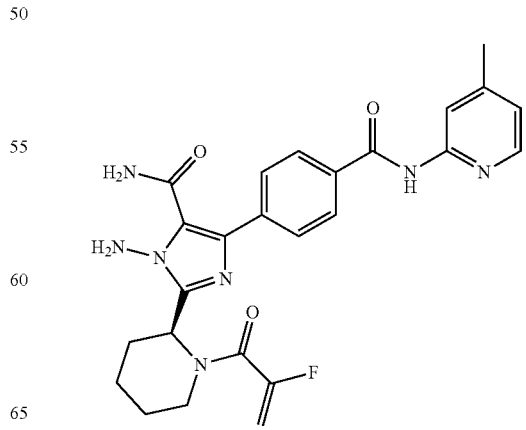

Preparation of (S)-1-amino-2-(1-(2-fluoroacryloyl)piperidin-2-yl)-4-(4-((4-methylpyridin-2-yl)carbamoyl)phenyl)-1H-imidazole-5-carboxamide

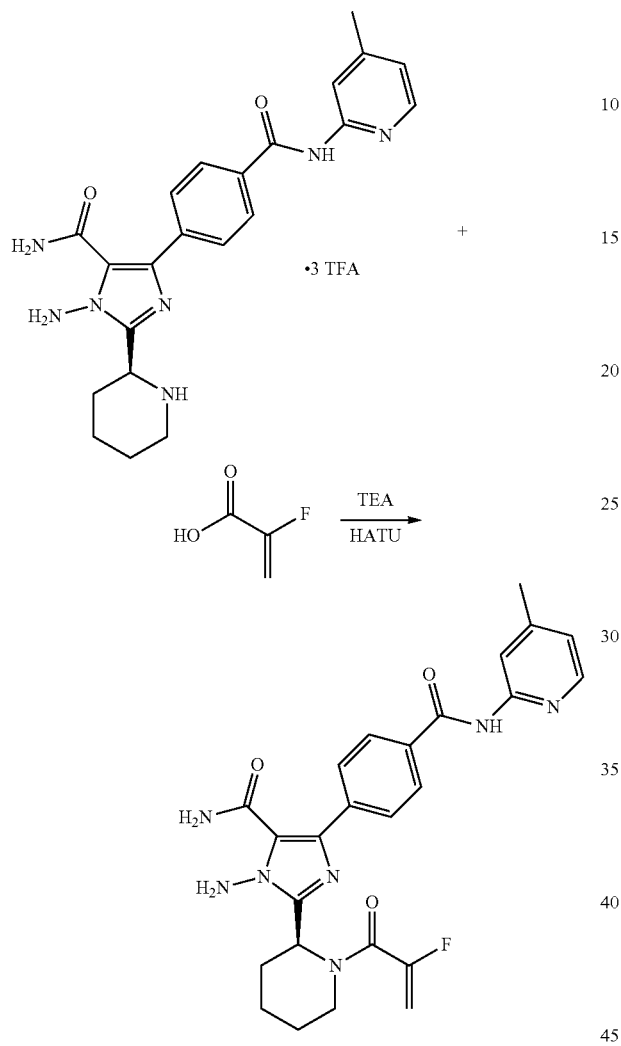

To the solution of 172 mg (0.41 mmol) the product of Step E of example 53 in dry N,N-Dimethylformamide (5 mL) was added triethylamine (248 mg, 2.46 mmol). After 5 min, 2-fluoroacrylic acid (32.4 mg, 0.36 mmol) and HATU (234 mg, 0.61 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(2-fluoroacryloyl)piperidin-2-yl)-4-(4-((4-methylpyridin-2-yl)carbamoyl)phenyl)-1H-imidazole-5-carboxamide as an off-white solid (101 mg, 50%). $^1$H NMR ($CDCl_3$, 400 MHz) δ: 9.42 (s, 1H), 8.17 (s, 1H), 8.06 (d, J=5.1 Hz, 1H), 7.81 (d, J=8.3 Hz, 2H), 7.66 (d, J=8.1 Hz, 2H), 7.13 (s, 1H), 6.95 (s, 1H), 6.84 (d, J=4.9 Hz, 1H), 6.19 (s, 2H), 5.88-5.76 (m, 1H), 5.26 (d, J=3.3 Hz, 0.5H), 5.15-5.12 (m, 1H), 5.09 (d, J=3.4 Hz, 0.5H), 3.83-3.74 (m, 2H), 2.35 (s, 3H), 2.31-2.16 (m, 2H), 1.95-1.80 (m, 2H), 1.70-1.59 (m, 2H); $^{13}$C NMR ($CDCl_3$, 150 MHz) δ: 166.0, 163.0, 158.2, 156.4, 151.9, 150.1, 147.9, 147.4, 140.9, 137.9, 133.6, 129.3, 127.3, 121.1, 120.5, 115.1, 99.8, 45.3, 44.0, 28.1, 25.8, 21.5, 19.7. MS (ESI, m/z): 492.2 $[M+H]^+$.

Example 60

(S,E)-1-amino-4-(4-((4-methylpyridin-2-yl)carbamoyl)phenyl)-2-(1-(4,4,4-trifluorobut-2-enoyl)piperidin-2-yl)-1H-imidazole-5-carboxamide

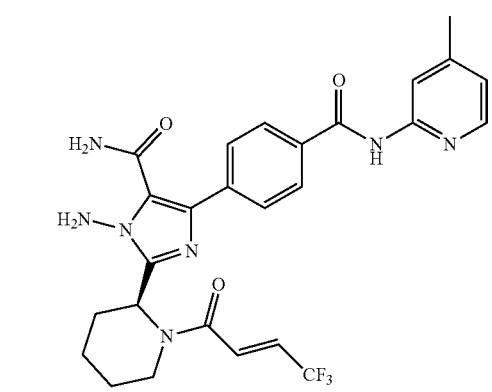 [SMILES: Cc1ccnc(NC(=O)c2ccc(-c3nc([C@@H]4CCCCN4C(=O)/C=C/C(F)(F)F)n(N)c3C(N)=O)cc2)c1]

Preparation of (S,E)-1-amino-4-(4-((4-methylpyridin-2-yl)carbamoyl)phenyl)-2-(1-(4,4,4-trifluorobut-2-enoyl)piperidin-2-yl)-1H-imidazole-5-carboxamide

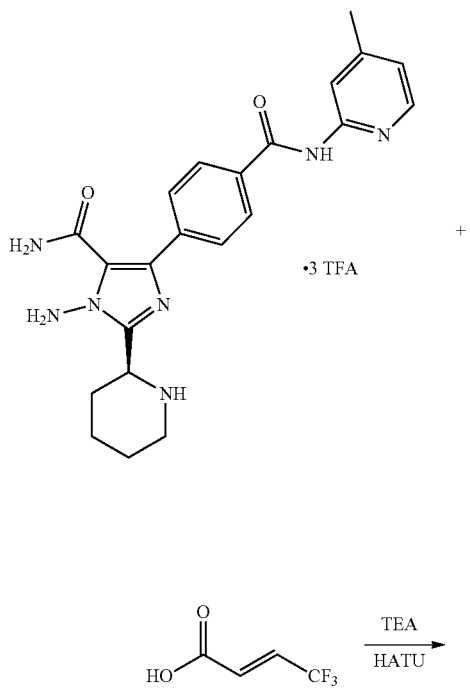

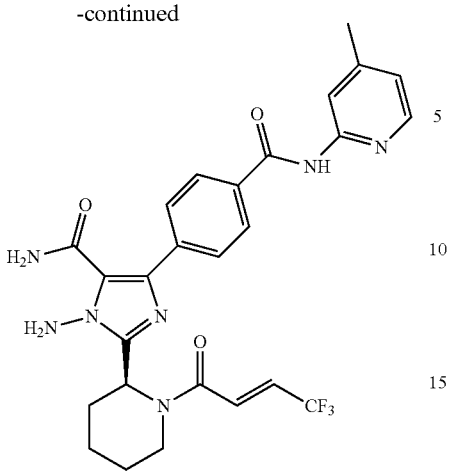

To the solution of 172 mg (0.41 mmol) the product of Step E of example 53, in dry N,N-Dimethylformamide (5 mL) was added triethylamine (248 mg, 2.46 mmol). After 5 min, (E)-4,4,4-trifluorobut-2-enoic acid (50.4 mg, 0.36 mmol) and HATU (234 mg, 0.61 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S,E)-1-amino-4-(4-((4-methylpyridin-2-yl)carbamoyl)phenyl)-2-(1-(4,4,4-trifluorobut-2-enoyl)-piperidin-2-yl)-1H-imidazole-5-carboxamide as an off-white solid (122 mg, 55%). $^1$H NMR (CDCl$_3$, 400 MHz) δ: 9.23 (s, 1H), 8.19 (s, 1H), 8.09 (d, J=5.0 Hz, 1H), 7.83 (d, J=8.3 Hz, 2H), 7.69 (d, J=8.1 Hz, 2H), 7.04 (s, 1H), 7.01-6.96 (m, 1H), 6.87 (d, J=4.8 Hz, 1H), 6.78 (s, 1H), 6.74-6.65 (m, 1H), 6.15 (s, 1.6H), 6.01-6.00 (m, 1H), 5.89 (s, 0.3H), 5.60 (s, 0.1H), 3.87-3.73 (m, 2H), 2.37 (s, 3H), 2.34-2.19 (m, 2H), 1.95-1.88 (m, 2H), 1.73-1.56 (m, 2H); $^{13}$C NMR (CDCl$_3$, 150 MHz) δ: 165.9, 164.1, 162.8, 151.8, 150.2, 148.2, 147.4, 141.2, 138.1, 133.7, 129.5, 128.4, 127.3, 123.5, 121.7, 121.3, 120.2, 115.1, 44.9, 43.5, 28.0, 25.8, 21.5, 19.4. MS (ESI, m/z): 542.2 [M+H]$^+$.

Example 61

(S)-2-(1-acryloylpiperidin-2-yl)-1-amino-4-(4-((5-methylpyridin-2-yl)carbamoyl)phenyl)-1H-imidazole-5-carboxamide

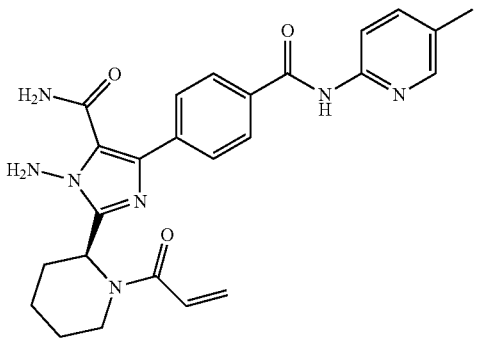 [SMILES: C=CC(=O)N1CCCC[C@H]1c1nc(-c2ccc(C(=O)Nc3ccc(C)cn3)cc2)c(C(N)=O)n1N]

Step A: Preparation of tert-butyl (S)-2-(5-(ethoxycarbonyl)-4-(4-((5-methylpyridin-2-yl)carbamoyl)phenyl)-1H-imidazol-2-yl)piperidine-1-carboxylate

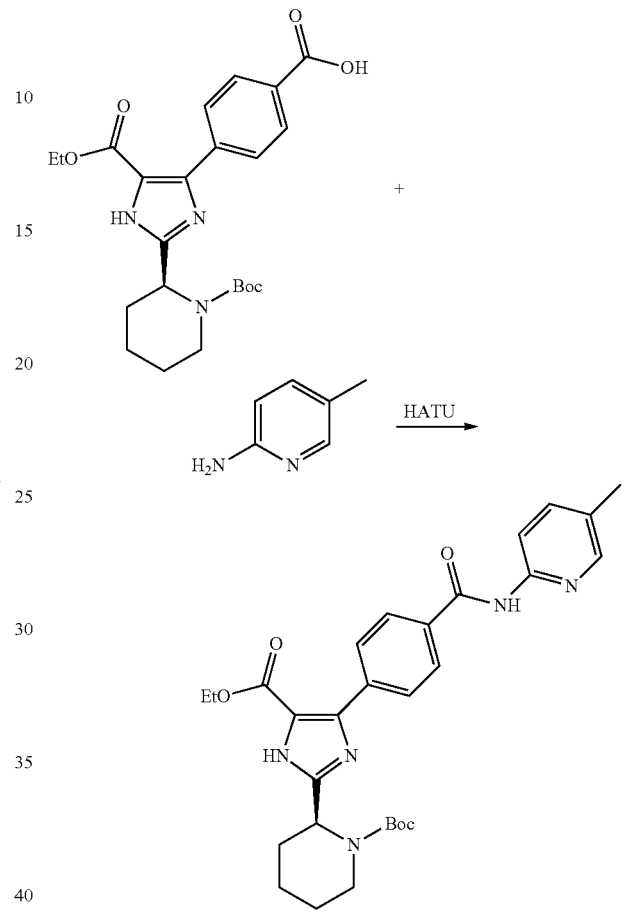

To the solution of 30.0 g (67 mmol) the product of Step C of example 46 in dry N,N-Dimethylformamide (250 mL) were added HATU (30.6 g, 80 mmol), diisopropylethylamine (57.7 mL, 335 mmol) and 5-methylpyridin-2-amine (10.9 g, 101 mmol). The reaction mixture was stirred at 80° C. for 3 h. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (3:1) to give the product tert-butyl (S)-2-(5-(ethoxycarbonyl)-4-(4-((5-methylpyridin-2-yl)carbamoyl)phenyl)-1H-imidazol-2-yl)piperidine-1-carboxylate as white solid (30.4 g, 85%). $^1$H NMR (CDCl$_3$, 600 MHz) δ: 10.08 (s, 1H), 8.76 (s, 1H), 8.31 (d, J=8.5 Hz, 1H), 8.15 (d, J=8.2 Hz, 2H), 8.10 (s, 1H), 7.96 (d, J=8.3 Hz, 2H), 7.58 (dd, J$_1$=8.5 Hz, J$_2$=1.9 Hz, 1H), 5.40 (d, J=4.1 Hz, 1H), 4.34-4.30 (m, 2H), 4.06-3.96 (m, 1H), 2.76 (t, J=12.9 Hz, 1H), 2.54 (d, J=12.6 Hz, 1H), 2.31 (s, 3H), 1.95-1.89 (m, 1H), 1.84-1.79 (m, 1H), 1.75-1.73 (m, 1H), 1.67-1.65 (m, 1H), 1.52-1.44 (m, 10H), 1.32 (t, J=7.1 Hz, 3H). MS (ESI, m/z): 534.2 [M+H]$^+$.

Step B: Preparation of tert-butyl (S)-2-(1-amino-5-(ethoxycarbonyl)-4-(4-((5-methylpyridin-2-yl)carbamoyl)phenyl)-1H-imidazol-2-yl)piperidine-1-carboxylate

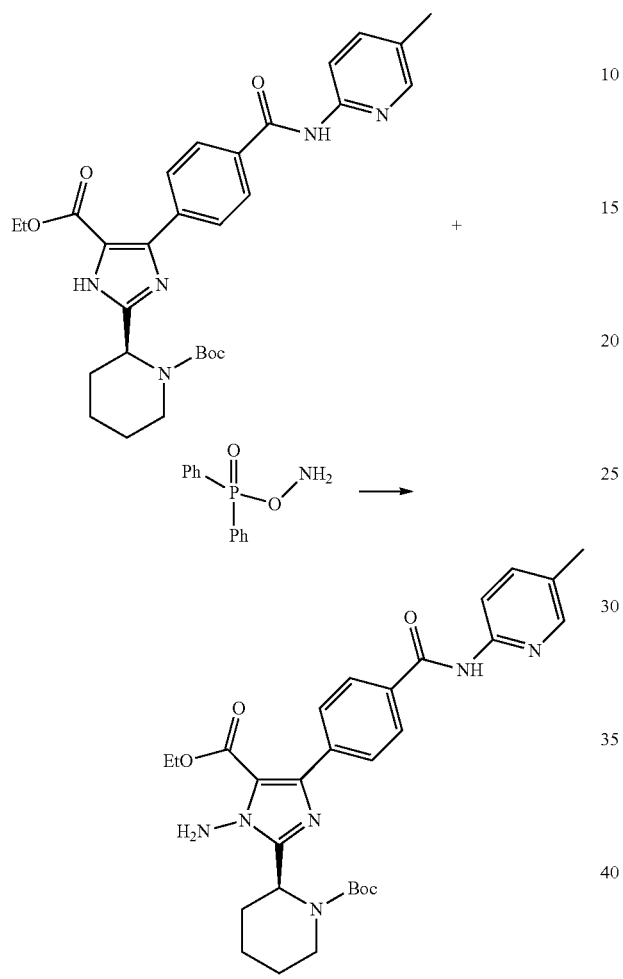

To the solution of 2.7 g (5.0 mmol) of the product of Step A in anhydrous N,N-Dimethylformamide (25 mL) was slowly added lithium hexamethyldisilazane (6.0 mL, 1 M solution in tetrahydrofuran) at −10° C. and stirred for 20 min, O-(diphenylphosphinyl) hydroxylamine (1.2 g, 5.0 mmol) was added at 0° C. Then the resulting suspension was stirred at room temperature for 2 h (in cases where the reaction mixture became too viscous, additional N,N-Dimethylformamide was added). The reaction was quenched with brine and washed three times (3×100 mL) with ethyl acetate. The combined organic fractions were dried with anhydrous $Na_2SO_4$ and the solvent was removed under reduced pressure to afford the crude residue, which was subjected to column chromatography with petroleum ether and ethyl acetate (3:1) to give the product tert-butyl (S)-2-(1-amino-5-(ethoxycarbonyl)-4-(4-((5-methylpyridin-2-yl)carbamoyl)phenyl)-1H-imidazol-2-yl)piperidine-1-carboxylate as a white solid (1.9 g, 70%). $^1$H NMR ($CDCl_3$, 600 MHz) δ: 8.60 (s, 1H), 8.30 (d, J=8.4 Hz, 1H), 8.13 (s, 1H), 7.93 (d, J=8.3 Hz, 2H), 7.84 (d, J=8.3 Hz, 2H), 7.58 (dd, $J_1$=8.4 Hz, $J_2$=1.6 Hz, 1H), 5.93 (s, 2H), 5.68 (d, J=5.2 Hz, 1H), 4.32-4.26 (m, 2H), 3.95 (d, J=13.1 Hz, 1H), 3.42 (td, $J_1$=13.0 Hz, $J_2$=2.9 Hz, 1H), 2.32 (s, 3H), 2.12-2.05 (m, 2H), 1.92-1.86 (m, 1H), 1.76-1.74 (m, 1H), 1.60-1.49 (m, 2H), 1.44 (s, 9H), 1.25 (t, J=7.1 Hz, 3H). MS (ESI, m/z): 549.2 $[M+H]^+$.

Step C: Preparation of (S)-1-amino-2-(1-(tert-butoxycarbonyl) piperidin-2-yl)-4-(4-((5-methylpyridin-2-yl)carbamoyl)phenyl)-1H-imidazole-5-carboxylic acid

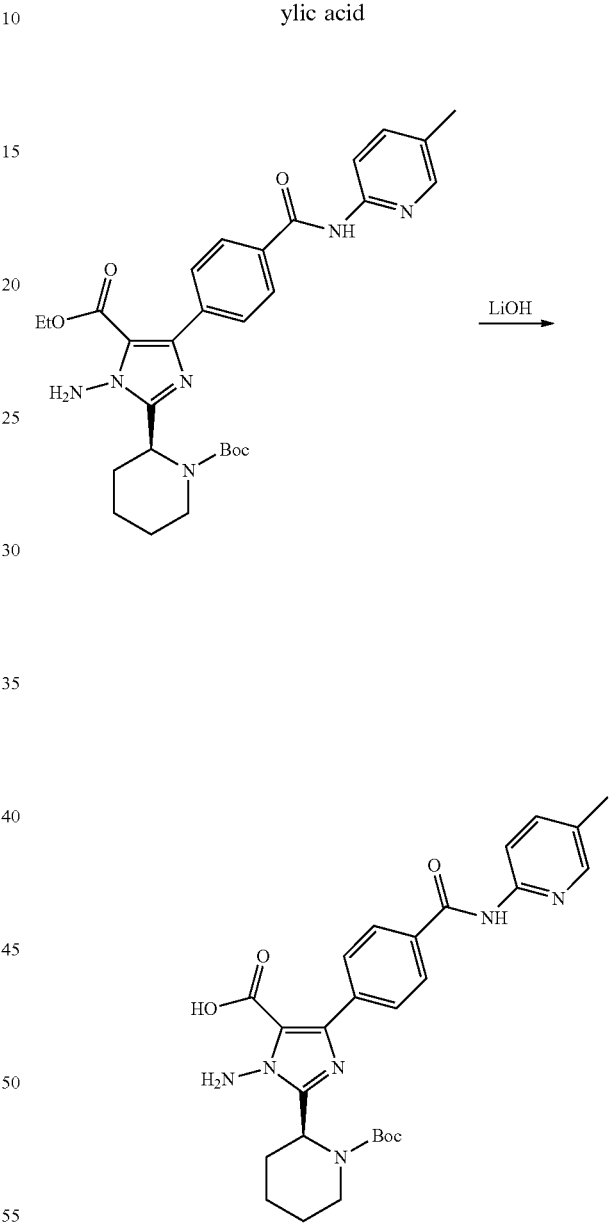

To the solution of 1.53 g (2.8 mmol) of the product of Step B in methanol (15 mL) was added 2 mol/L aqueous lithium hydroxide (14 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl)piperidin-2-yl)-4-(4-((5-methylpyridin-2-yl)carbamoyl)phenyl)-1H-imidazole-5-carboxylic acid (1.38 g, 95%).

Step D: Preparation of tert-butyl (S)-2-(1-amino-5-carbamoyl-4-(4-((5-methylpyridin-2-yl)carbamoyl)phenyl)-1H-imidazol-2-yl)piperidine-1-carboxylate

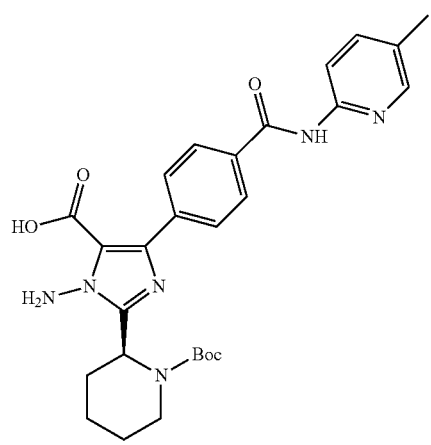

To the solution of 1.04 g (2.0 mmol) of the product of Step C in dry N,N-Dimethylformamide (15 mL) were added HATU (1.1 g, 2.9 mmol), diisopropylethylamine (1.0 mL, 5.9 mmol) and NH₄Cl (1.1 g, 20 mmol). The reaction mixture was stirred at room temperature for 2 h. Ethyl acetate and water were added. The layers were separated, and the aqueous phase was extracted with ethyl acetate. The combined organic phases were washed three times (3×100 mL) with brine solution. The organic phase was dried over anhydrous Na₂SO₄, filtered and concentrated. The residue was purified by chromatography with dichloromethane and methanol (32:1) to give tert-butyl (S)-2-(1-amino-5-carbamoyl-4-(4-((5-methylpyridin-2-yl)carbamoyl)phenyl)-1H-imidazol-2-yl)piperidine-1-carboxylate as a white solid (0.88 g, 85%). ¹H NMR (CDCl₃, 400 MHz) δ: 9.15 (s, 1H), 8.22 (d, J=8.3 Hz, 1H), 8.05 (s, 1H), 7.85 (t, J=6.8 Hz, 2H), 7.72 (t, J=6.8 Hz, 2H), 7.53 (d, J=8.5 Hz, 1H), 6.84 (s, 1H), 6.46 (s, 1H), 6.03 (s, 2H), 5.60 (d, J=4.6 Hz, 1H), 3.92 (d, J=12.5 Hz, 1H), 3.31 (td, J₁=13.0 Hz, J₂=2.7 Hz, 1H), 2.28 (s, 3H), 2.20-2.17 (m, 1H), 2.14-2.10 (m, 1H), 1.90-1.82 (m, 1H), 1.74-1.71 (m, 1H), 1.65-1.60 (m, 1H), 1.55-1.48 (m, 1H), 1.44 (s, 9H). MS (ESI, m/z): 520.2 [M+H]⁺.

Step E: Preparation of (S)-1-amino-4-(4-((5-methylpyridin-2-yl)carbamoyl)phenyl)-2-(piperidin-2-yl)-1H-imidazole-5-carboxamide

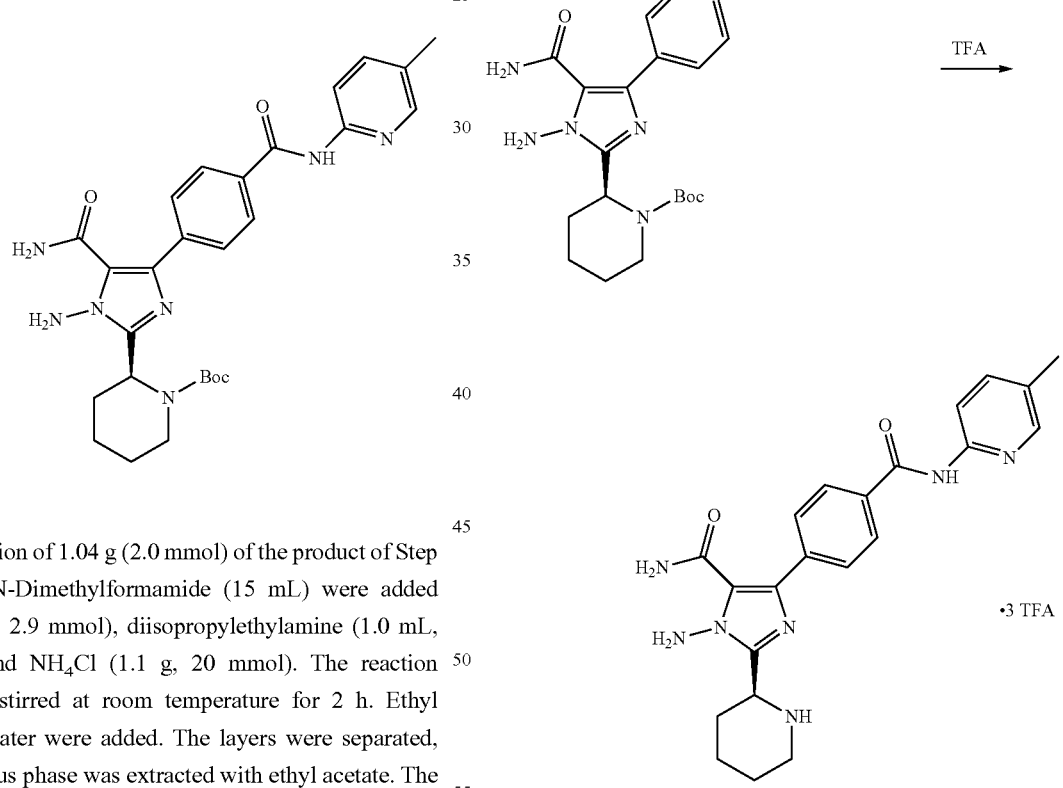

To the solution of 202 mg (0.39 mmol) of the product of Step D in dichloromethane (5 mL) was added trifluoroacetic acid (2.5 mL). The mixture was stirred at room temperature for 1 h and then concentrated to afford (S)-1-amino-4-(4-((5-methylpyridin-2-yl)carbamoyl)phenyl)-2-(piperidin-2-yl)-1H-imidazole-5-carboxamide as a light yellow oil. MS (ESI, m/z): 420.2 [M+H]⁺.

Step F: Preparation of (S)-2-(1-acryloylpiperidin-2-yl)-1-amino-4-(4-((4-methylpyridin-2-yl)carbamoyl)phenyl)-1H-imidazole-5-carboxamide

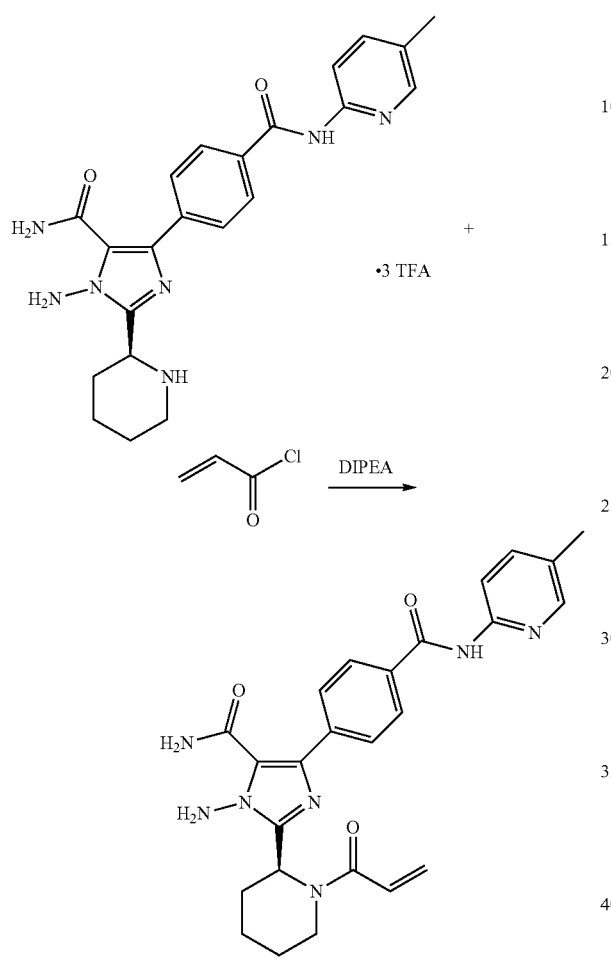

To the solution of 189 mg (0.45 mmol) of the product of Step E in dry dichloromethane (6 mL) was added diisopropylethylamine (349 mg, 2.70 mmol). After 5 min, acryloyl chloride (28.5 mg, 0.32 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (28:1) to give (S)-2-(1-acryloylpiperidin-2-yl)-1-amino-4-(4-((5-methylpyridin-2-yl)carbamoyl)phenyl)-1H-imidazole-5-carboxamide as an off-white solid (132 mg, 62%). $^1$H NMR (CDCl$_3$, 400 MHz) δ: 9.34 (s, 1H), 8.25 (d, J=8.5 Hz, 1H), 8.05 (s, 1H), 7.86 (d, J=8.2 Hz, 2H), 7.75-7.74 (m, 2H), 7.55 (dd, J$_1$=8.5 Hz, J$_2$=1.6 Hz, 1H), 7.21 (s, 1H), 6.64-6.54 (m, 2H), 6.39-6.24 (m, 3H), 6.02-5.93 (m, 1H), 5.69 (d, J=10.5 Hz, 1H), 3.81 (d, J=11.8 Hz, 1H), 3.68 (t, J=12.1 Hz, 1H), 2.44-2.32 (m, 1H), 2.28 (s, 3H), 2.17 (d, J=13.2 Hz, 1H), 1.93-1.83 (m, 2H), 1.70-1.57 (m, 2H); $^{13}$C NMR (CDCl$_3$, 150 MHz) δ: 167.2, 165.9, 162.8, 149.6, 148.3, 147.3, 141.2, 139.4, 138.3, 133.5, 129.5, 129.4, 128.6, 127.8, 127.4, 120.1, 114.2, 44.4, 43.0, 28.0, 25.8, 19.7, 17.9. MS (ESI, m/z): 474.2 [M+H]$^+$.

Example 62

(S)-1-amino-2-(1-methacryloylpiperidin-2-yl)-4-(4-((5-methylpyridin-2-yl)carbamoyl)phenyl)-1H-imidazole-5-carboxamide

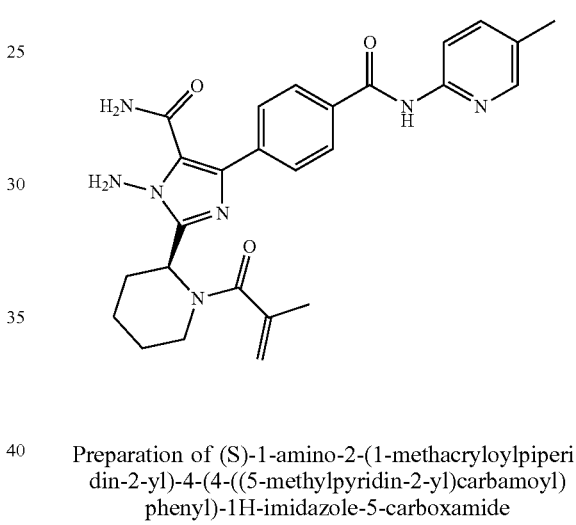

Preparation of (S)-1-amino-2-(1-methacryloylpiperidin-2-yl)-4-(4-((5-methylpyridin-2-yl)carbamoyl)phenyl)-1H-imidazole-5-carboxamide

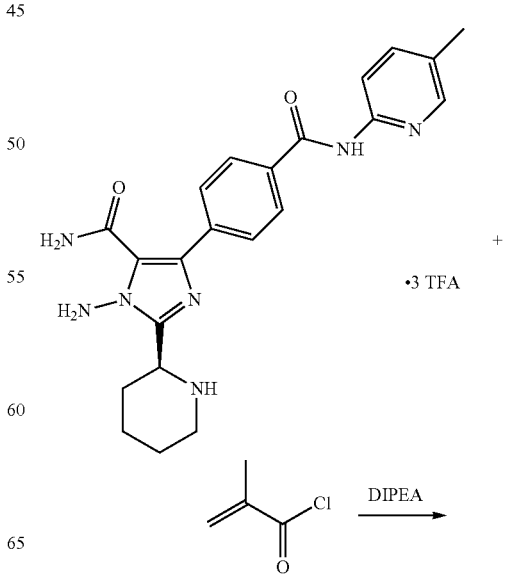

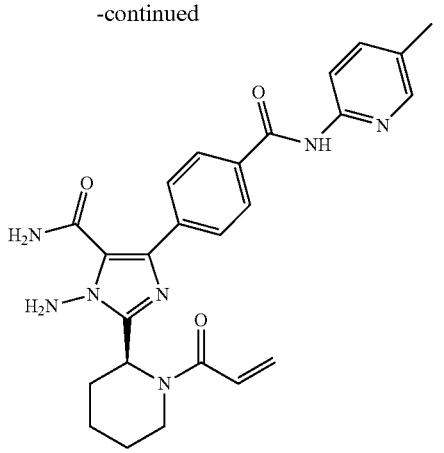

To the solution of 172 mg (0.41 mmol) of the product of Step E of example 61 in dry dichloromethane (5 mL) was added diisopropylethylamine (318 mg, 2.46 mmol). After 5 min, methacryloyl chloride (37.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to give (S)-1-amino-2-(1-methacryloylpiperidin-2-yl)-4-(4-((5-methylpyridin-2-yl)carbamoyl)phenyl)-1H-imidazole-5-carboxamide as an off-white solid (120 mg, 60%). $^1$H NMR (CDCl$_3$, 600 MHz) δ: 8.85 (s, 1H), 8.29 (d, J=8.4 Hz, 1H), 8.12 (s, 1H), 7.95 (d, J=8.2 Hz, 2H), 7.83 (d, J=7.9 Hz, 2H), 7.58 (dd, J$_1$=8.4 Hz, J$_2$=1.9 Hz, 1H), 6.84 (s, 1H), 6.27 (s, 2H), 5.95 (s, 1H), 5.90 (s, 1H), 5.20 (s, 1H), 5.12-5.06 (m, 1H), 3.92-3.79 (m, 1H), 3.61 (t, J=12.1 Hz, 1H), 2.42-2.34 (m, 1H), 2.32 (s, 3H), 2.22 (d, J=13.8 Hz, 1H), 1.95 (s, 3H), 1.93-1.89 (m, 1H), 1.82 (d, J=13.1 Hz, 1H), 1.74-1.71 (m, 1H), 1.59-1.51 (m, 1H); $^{13}$C NMR (CDCl$_3$, 150 MHz) δ: 173.1, 165.7, 162.8, 149.6, 148.2, 147.6, 141.1, 140.5, 139.3, 138.2, 133.8, 129.6, 129.5, 127.5, 120.0, 115.9, 114.2, 44.2, 29.8, 28.0, 26.0, 20.5, 19.9, 18.0. MS (ESI, m/z): 488.2 [M+H]$^+$.

Example 63

(S)-1-amino-2-(1-(3-methylbut-2-enoyl)piperidin-2-yl)-4-(4-((5-methylpyridin-2-yl)carbamoyl)phenyl)-1H-imidazole-5-carboxamide

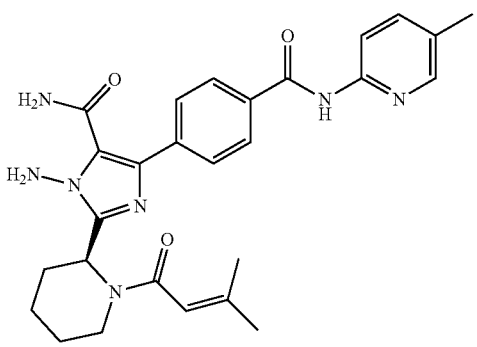 [SMILES: CC(C)=CC(=O)N1CCCC[C@H]1c1nc(-c2ccc(C(=O)Nc3ccc(C)cn3)cc2)c(C(N)=O)n1N]

Preparation of (S)-1-amino-2-(1-(3-methylbut-2-enoyl)piperidin-2-yl)-4-(4-((5-methylpyridin-2-yl)carbamoyl)phenyl)-1H-imidazole-5-carboxamide

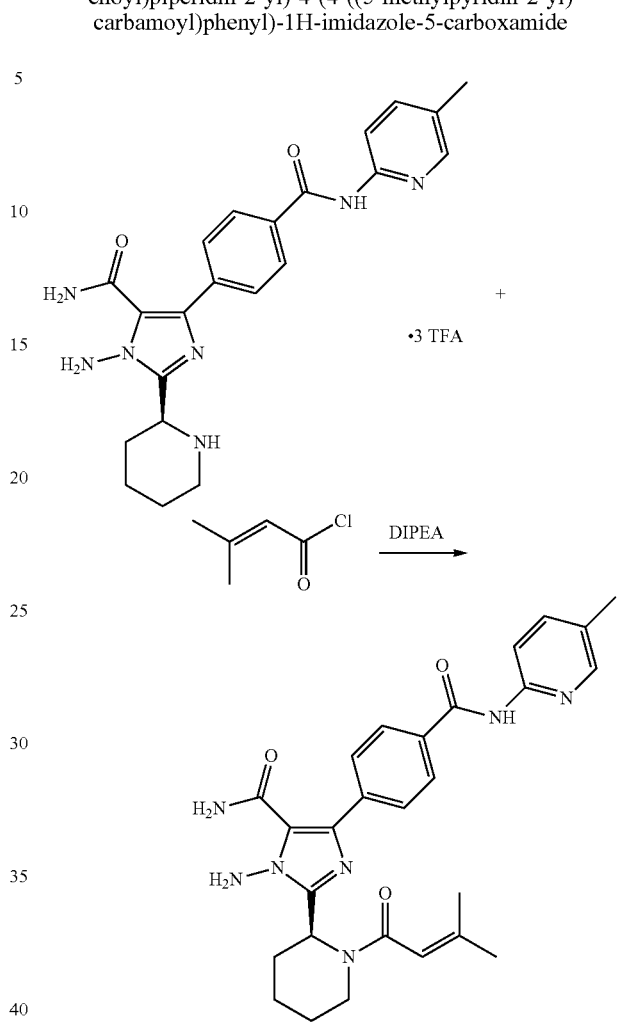

To the solution of 172 mg (0.41 mmol) of the product of Step E of example 61 in dry dichloromethane (5 mL) was added diisopropylethylamine (318 mg, 2.46 mmol). After 5 min, 3-methylbut-2-enoyl chloride (42.7 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to give the product (S)-1-amino-2-(1-(3-methylbut-2-enoyl)piperidin-2-yl)-4-(4-((5-methylpyridin-2-yl)carbamoyl)phenyl)-1H-imidazole-5-carboxamide as an off-white solid (134 mg, 65%). $^1$H NMR (CDCl$_3$, 600 MHz) δ: 9.10 (s, 1H), 8.25 (d, J=8.4 Hz, 1H), 8.07 (s, 1H), 7.88 (d, J=8.2 Hz, 2H), 7.79 (d, J=7.4 Hz, 2H), 7.55 (d, J=8.3 Hz, 1H), 7.15 (s, 1H), 6.44 (s, 1H), 6.31 (s, 2H), 6.00-5.93 (m, 1H), 5.78 (s, 1H), 3.79 (d, J=11.9 Hz, 1H), 3.59 (t, J=12.5 Hz, 1H), 2.41-2.33 (m, 1H), 2.29 (s, 3H), 2.19 (d, J=13.0 Hz, 1H), 1.97-1.93 (m, 1H), 1.87 (s, 3H), 1.83 (s, 3H), 1.80-1.77 (m, 1H), 1.70-1.67 (m, 1H), 1.56-1.54 (m, 1H); $^{13}$C NMR (CDCl$_3$, 150 MHz) δ: 169.0, 165.8, 162.7, 149.7, 148.5, 147.8, 146.9, 141.3, 139.1, 138.3, 133.7, 129.6, 129.4, 127.3, 120.0, 118.0, 114.1, 43.7, 43.5, 28.0, 26.3, 25.8, 20.5, 19.9, 18.0. MS (ESI, m/z): 502.2 [M+H]$^+$.

Example 64

(S)-1-amino-2-(1-(but-2-ynoyl)piperidin-2-yl)-4-(4-((5-methylpyridin-2-yl)carbamoyl)phenyl)-1H-imidazole-5-carboxamide

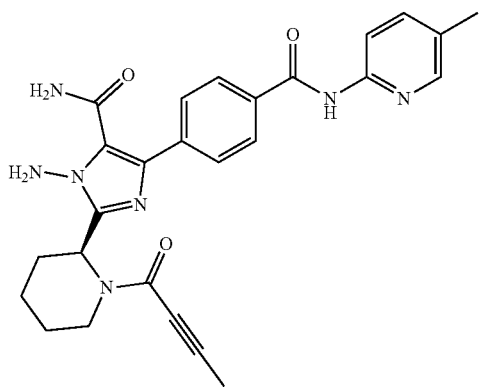 [SMILES: CC#CC(=O)N1CCCC[C@H]1c1nc(-c2ccc(C(=O)Nc3ccc(C)cn3)cc2)c(C(N)=O)n1N]

Preparation of (S)-1-amino-2-(1-(but-2-ynoyl)piperidin-2-yl)-4-(4-((5-methylpyridin-2-yl)carbamoyl)phenyl)-1H-imidazole-5-carboxamide

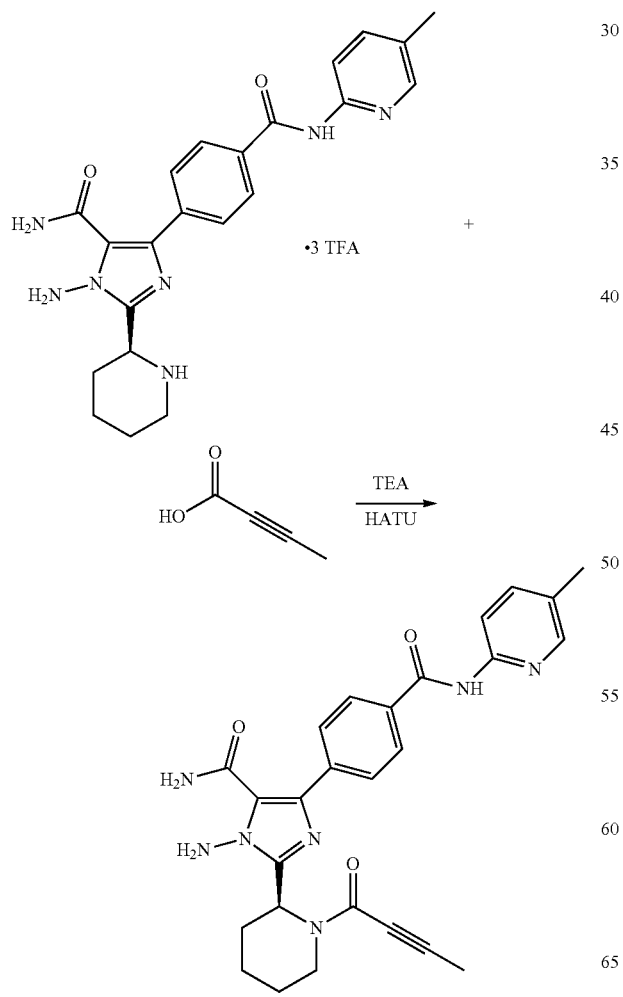

To the solution of 172 mg (0.41 mmol) of the product of Step E of example 61 in dry N,N-dimethylformamide (5 mL) was added triethylamine (248 mg, 2.46 mmol). After 5 min, but-2-ynoic acid (30.3 mg, 0.36 mmol) and HATU (234 mg, 0.61 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to give (S)-1-amino-2-(1-(but-2-ynoyl)piperidin-2-yl)-4-(4-((5-methylpyridin-2-yl)carbamoyl)phenyl)-1H-imidazole-5-carboxamide as an off-white solid (99.5 mg, 50%). $^1$H NMR (CDCl$_3$, 600 MHz) δ: 9.15-9.12 (m, 1H), 8.25 (d, J=8.3 Hz, 1H), 8.08-8.06 (m, 1H), 7.89 (d, J=7.7 Hz, 2H), 7.77 (d, J=7.6 Hz, 1.4H), 7.67-7.62 (m, 0.4H), 7.54 (d, J=8.1 Hz, 1H), 7.33 (d, J=7.6 Hz, 0.2H), 6.98 (s, 1H), 6.42 (s, 1H), 6.20 (s, 0.3H), 6.13 (s, 1.7H), 5.98-5.94 (m, 1H), 4.26 (d, J=12.8 Hz, 1H), 3.66 (td, $J_1$=13.4 Hz, $J_2$=3.1 Hz, 1H), 2.41-2.33 (m, 1H), 2.29 (s, 3H), 2.17-2.14 (m, 1H), 2.00 (s, 3H), 1.86-1.85 (m, 2H), 1.70-1.68 (m, 1H), 1.61-1.55 (m, 1H); $^{13}$C NMR (CDCl$_3$, 150 MHz) δ: 165.7, 162.7, 154.9, 149.6, 148.0, 147.7, 141.2, 139.2, 138.2, 133.7, 129.6, 129.5, 127.4, 120.0, 114.2, 90.9, 73.0, 44.5, 43.8, 27.8, 25.8, 19.8, 18.0, 4.3. MS (ESI, m/z): 486.2 [M+H]$^+$.

Example 65

(S)-2-(1-acryloylpiperidin-2-yl)-1-amino-4-(4-((4-phenylpyridin-2-yl)carbamoyl)phenyl)-1H-imidazole-5-carboxamide

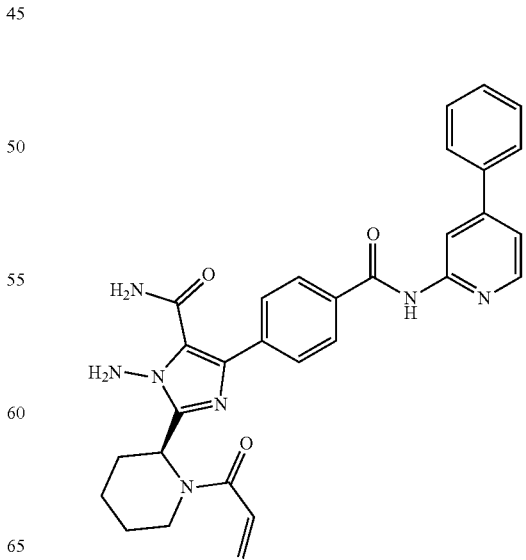

Step A: Preparation of tert-butyl (S)-2-(5-(ethoxy-carbonyl)-4-(4-((4-phenylpyridin-2-yl)carbamoyl)phenyl)-1H-imidazol-2-yl)piperidine-1-carboxylate

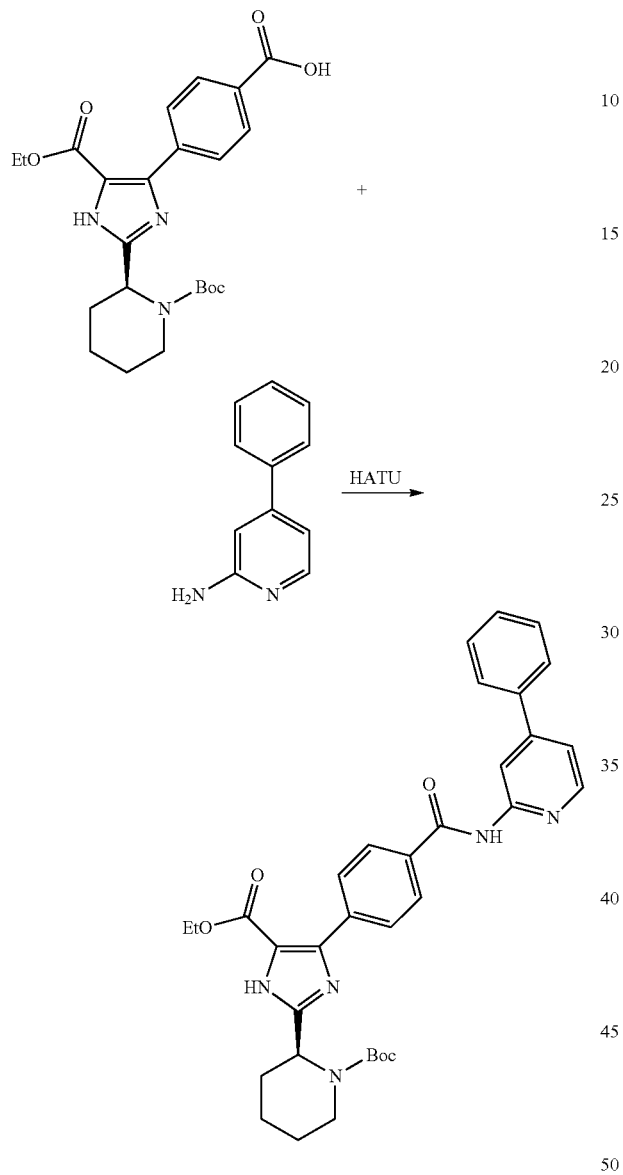

To the solution of 31.0 g (70 mmol) of the product of Step C of example 46 in dry N,N-dimethylformamide (250 mL) were added HATU (31.9 g, 84 mmol), diisopropylethylamine (60.3 mL, 350 mmol) and 4-phenylpyridin-2-amine (17.9 g, 105 mmol). The reaction mixture was stirred at 80° C. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (3:1) to afford tert-butyl (S)-2-(5-(ethoxycarbonyl)-4-(4-((4-phenylpyridin-2-yl)carbamoyl)phenyl)-1H-imidazol-2-yl)piperidine-1-carboxylate as white solid (35.4 g, 85%). $^1$H NMR (CDCl$_3$, 400 MHz) δ: 10.34 (s, 1H), 9.24 (s, 1H), 8.72-8.66 (m, 1H), 8.22-8.15 (m, 3H), 8.00-7.90 (m, 2H), 7.69-7.64 (m, 2H), 7.44-7.43 (m, 3H), 5.42-5.30 (m, 1H), 4.28-4.27 (m, 2H), 4.10-4.08 (m, 1H), 4.01-3.99 (m, 1H), 2.85-2.79 (m, 1H), 2.51-2.48 (m, 1H), 1.96-1.81 (m, 2H), 1.71-1.63 (m, 2H), 1.49 (s, 9H), 1.28-1.21 (m, 4H). MS (ESI, m/z): 596.2 [M+H]$^+$.

Step B: Preparation of tert-butyl (S)-2-(1-amino-5-(ethoxycarbonyl)-4-(4-((4-phenylpyridin-2-yl)carbamoyl)phenyl)-1H-imidazol-2-yl) piperidine-1-carboxylate

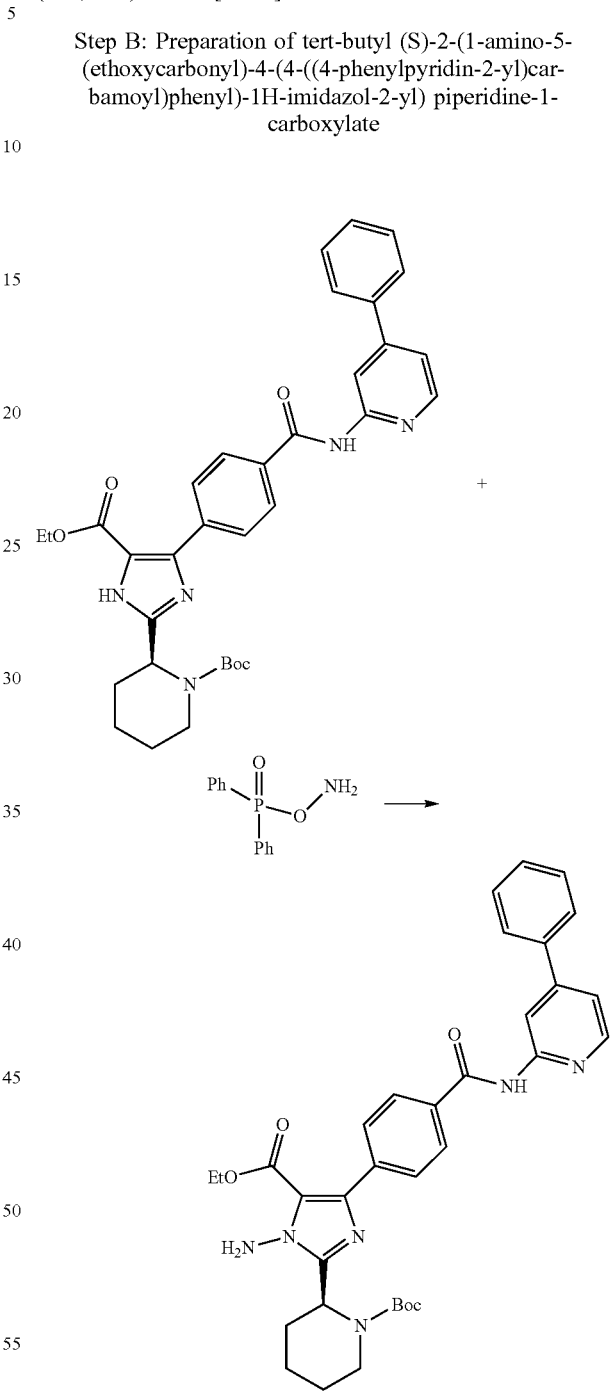

To the solution of 3.6 g (6.0 mmol) of the product of Step A in anhydrous N,N-Dimethylformamide (30 mL) was slowly added lithium hexamethyldisilazane (7.2 mL, 1 M solution in tetrahydrofuran) at −10° C. After the mixture was stirred for 20 min, O-(diphenylphosphinyl) hydroxylamine (1.7 g, 7.2 mmol) was added at 0° C. and the resulting suspension was stirred at room temperature for 2 h (in cases where the reaction mixture became too viscous, additional N,N-Dimethylformamide was added). The mixture was quenched with brine and extracted with ethyl acetate three times (3×100 mL). The combined organic fractions were dried with anhydrous Na₂SO₄ and the solvent was removed under reduced pressure to afford the crude residue, which was subjected to column chromatography with petroleum ether and ethyl acetate (3:1) to give tert-butyl (S)-2-(1-amino-5-(ethoxycarbonyl)-4-(4-((4-phenylpyridin-2-yl)carbamoyl)phenyl)-1H-imidazol-2-yl)piperidine-1-carboxylate as a white solid (2.6 g, 70%). ¹H NMR (CDCl₃, 400 MHz) δ: 8.93 (s, 1H), 8.73-8.72 (m, 1H), 8.30 (d, J=5.2 Hz, 1H), 7.97 (d, J=8.5 Hz, 2H), 7.86 (d, J=8.5 Hz, 2H), 7.74-7.72 (m, 2H), 7.50-7.42 (m, 3H), 7.30 (dd, J₁=5.2 Hz, J₂=1.6 Hz, 1H), 5.93 (s, 2H), 5.68 (d, J=4.8 Hz, 1H), 4.33-4.25 (m, 2H), 3.95 (d, J=12.6 Hz, 1H), 3.43 (td, J₁=13.0 Hz, J₂=3.0 Hz, 1H), 2.12-2.05 (m, 2H), 1.93-1.87 (m, 1H), 1.74 (d, J=13.0 Hz, 1H), 1.66-1.63 (m, 1H), 1.57-1.49 (m, 1H), 1.44 (s, 9H), 1.25 (t, J=7.1 Hz, 3H). MS (ESI, m/z): 611.2 [M+H]⁺.

Step C: Preparation of (S)-1-amino-2-(1-(tert-butoxycarbonyl)piperidin-2-yl)-4-(4-((4-phenylpyridin-2-yl)carbamoyl)phenyl)-1H-imidazole-5-carboxylic acid To the solution of 1.83 g (3.0 mmol) of the product of Step B in methanol (17 mL) was added 2 mol/L aqueous lithium hydroxide (15 mL) and stirred at room temperature for 2 h. The reaction mixture was evaporated and diluted with water (100 mL) and acidified with aqueous HCl till pH 3. The mixture was washed with ethyl acetate three times (3×90 mL). The white precipitate was isolated by filtration and dried to afford (S)-1-amino-2-(1-(tert-butoxycarbonyl)piperidin-2-yl)-4-(4-((4-phenylpyridin-2-yl)carbamoyl)phenyl)-1H-imidazole-5-carboxylic acid (1.68 g, 96%).

Step D: Preparation of tert-butyl (S)-2-(1-amino-5-carbamoyl-4-(4-((4-phenylpyridin-2-yl)carbamoyl)phenyl)-1H-imidazol-2-yl)piperidine-1-carboxylate

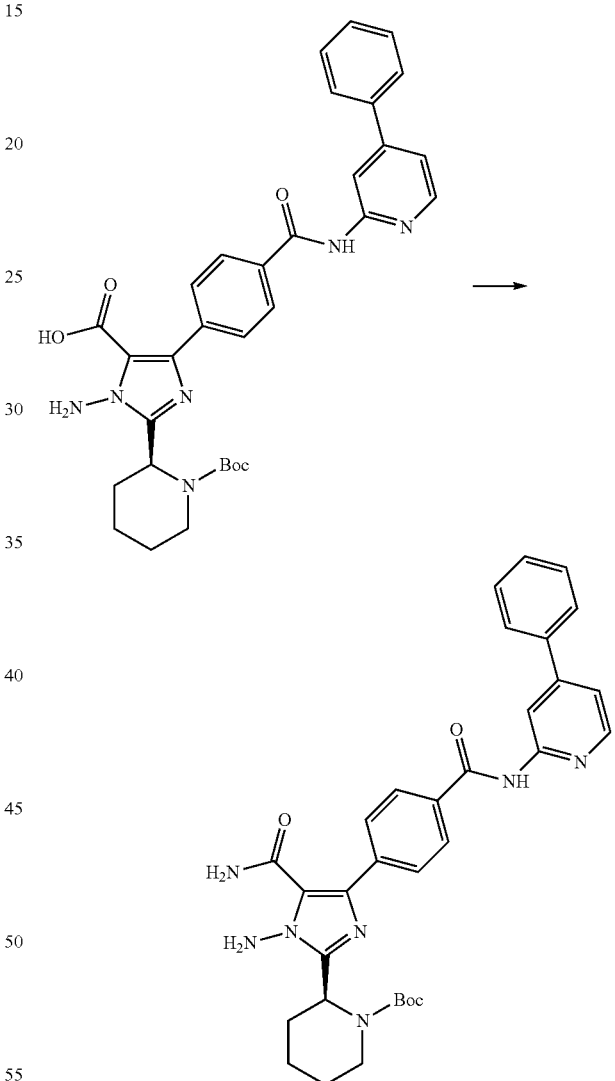

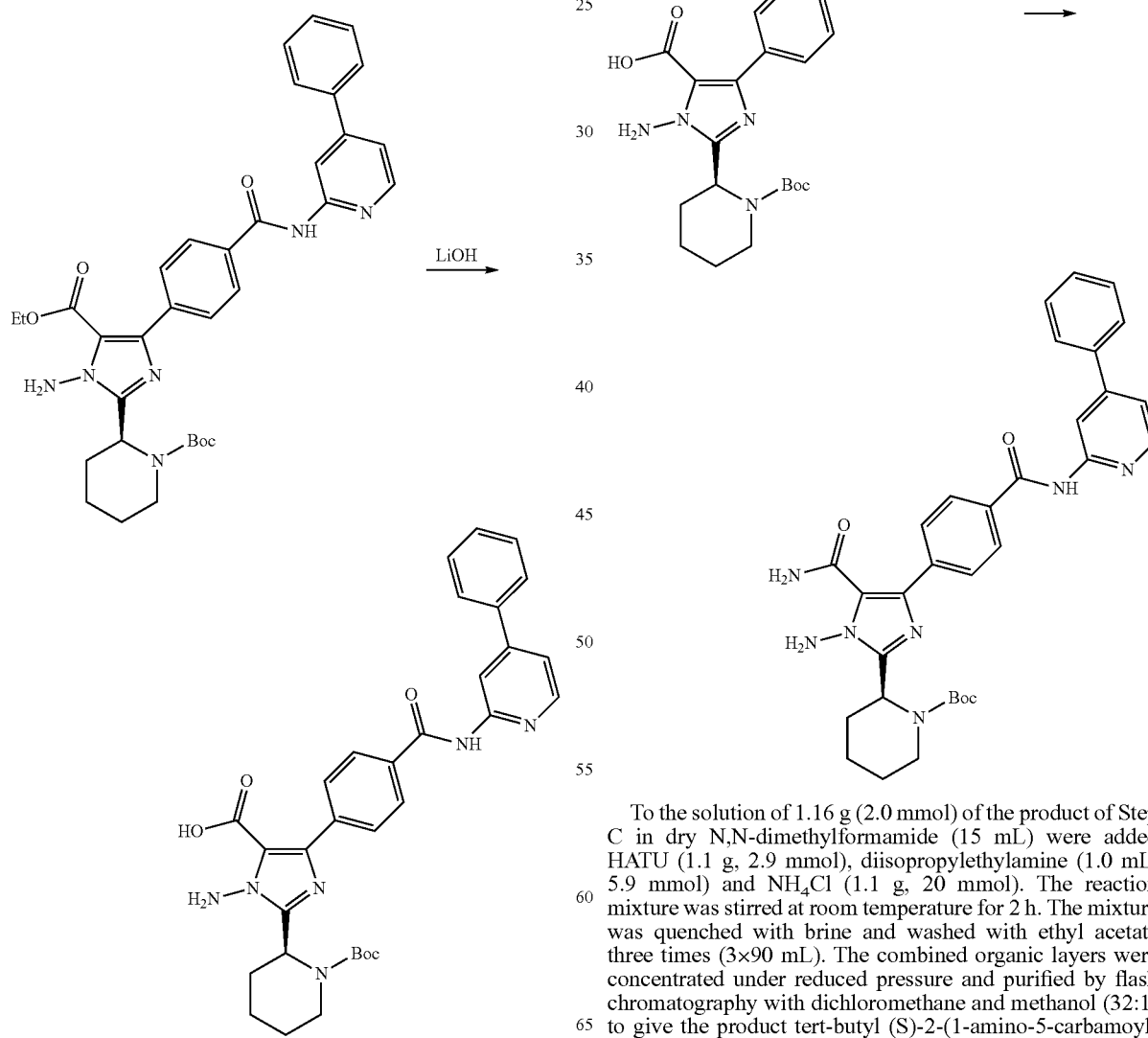

To the solution of 1.16 g (2.0 mmol) of the product of Step C in dry N,N-dimethylformamide (15 mL) were added HATU (1.1 g, 2.9 mmol), diisopropylethylamine (1.0 mL, 5.9 mmol) and NH₄Cl (1.1 g, 20 mmol). The reaction mixture was stirred at room temperature for 2 h. The mixture was quenched with brine and washed with ethyl acetate three times (3×90 mL). The combined organic layers were concentrated under reduced pressure and purified by flash chromatography with dichloromethane and methanol (32:1) to give the product tert-butyl (S)-2-(1-amino-5-carbamoyl-4-(4-((4-phenylpyridin-2-yl)carbamoyl)phenyl)-1H-imidazol-2-yl)piperidine-1-carboxylate as a white solid (0.93 g, 80%). ¹H NMR (CDCl₃, 600 MHz) δ: 9.21 (s, 1H), 8.67 (s, 1H), 8.30 (d, J=5.0 Hz, 1H), 7.93 (d, J=7.7 Hz, 2H), 7.79 (d, J=7.6 Hz, 2H), 7.71 (d, J=7.3 Hz, 2H), 7.49-7.42 (m, 3H), 7.28-7.27 (m, 1H), 6.87 (s, 1H), 6.32 (s, 1H), 6.03 (s, 2H), 5.61 (d, J=5.6 Hz, 1H), 3.94 (d, J=12.5 Hz, 1H), 3.31 (t, J=13.0 Hz, 1H), 2.21-2.12 (m, 2H), 1.90-1.86 (m, 1H), 1.73 (d, J=12.6 Hz, 1H), 1.65 (d, J=12.5 Hz, 1H), 1.56-1.48 (m, 1H), 1.45 (s, 9H). MS (ESI, m/z): 582.2 [M+H]⁺.

Step E: Preparation of (S)-1-amino-4-(4-((4-phenylpyridin-2-yl)carbamoyl)phenyl)-2-(piperidin-2-yl)-1H-imidazole-5-carboxamide

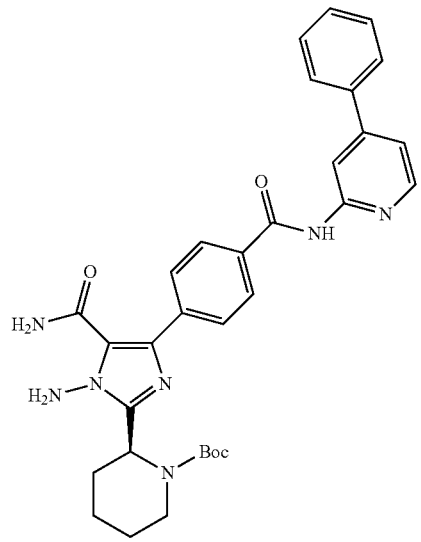

Step F: Preparation of (S)-2-(1-acryloylpiperidin-2-yl)-1-amino-4-(4-((4-phenylpyridin-2-yl)carbamoyl)phenyl)-1H-imidazole-5-carboxamide

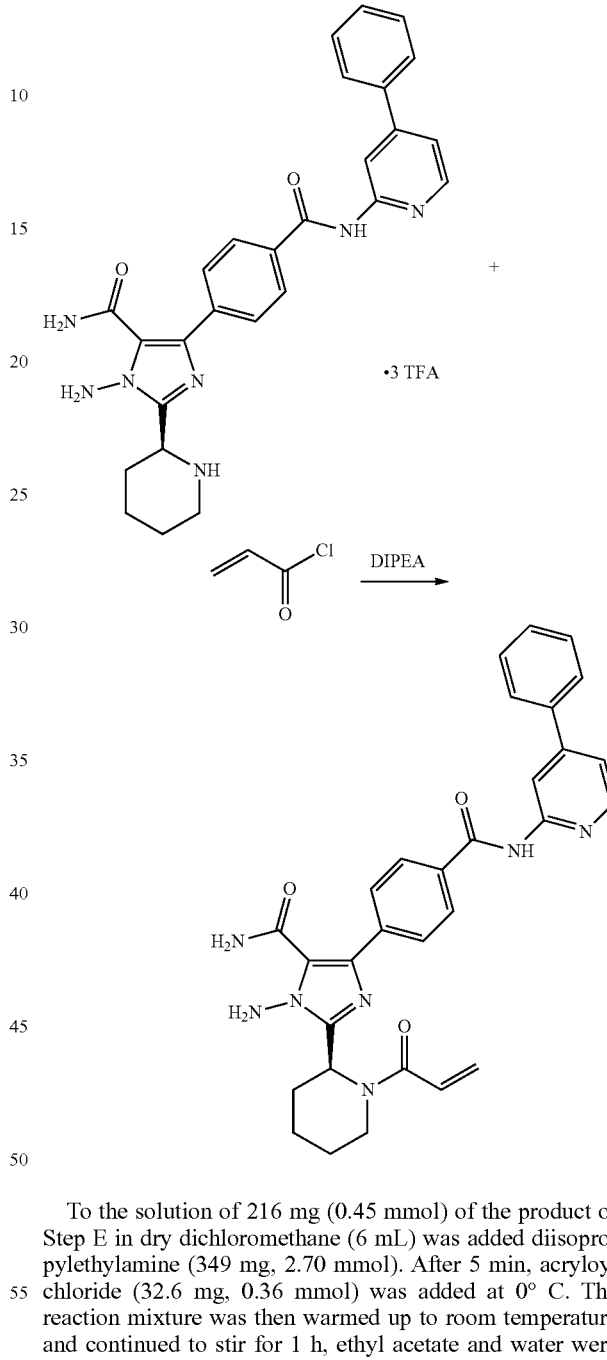

To the solution of 232 mg (0.40 mmol) of the product of Step D in dichloromethane (6 mL) was added trifluoroacetic acid (2.6 mL). The mixture was stirred at room temperature for 1 h and then concentrated to afford (S)-1-amino-4-(4-((4-phenylpyridin-2-yl)carbamoyl)phenyl)-2-(piperidin-2-yl)-1H-imidazole-5-carboxamide as a light yellow oil. MS (ESI, m/z): 482.2 [M+H]⁺.

To the solution of 216 mg (0.45 mmol) of the product of Step E in dry dichloromethane (6 mL) was added diisopropylethylamine (349 mg, 2.70 mmol). After 5 min, acryloyl chloride (32.6 mg, 0.36 mmol) was added at 0° C. The reaction mixture was then warmed up to room temperature and continued to stir for 1 h, ethyl acetate and water were added. The layers were separated, and the aqueous phase was extracted with ethyl acetate. The combined organic phases were washed three times (3×50 mL) with brine solution. The organic phase was dried over anhydrous Na₂SO₄, filtered and concentrated. The residue was purified by chromatography with dichloromethane and methanol (30:1) to give (S)-2-(1-acryloylpiperidin-2-yl)-1-amino-4-(4-((4-phenylpyridin-2-yl)carbamoyl)phenyl)-1H-imidazole-5-carboxamide as an off-white solid (144 mg, 60%). ¹H NMR (CDCl₃, 400 MHz) δ: 9.15 (s, 1H), 8.68 (s, 1H), 8.31

(d, J=5.2 Hz, 1H), 7.95 (d, J=8.3 Hz, 2H), 7.84 (d, J=7.5 Hz, 2H), 7.72 (d, J=6.8 Hz, 2H), 7.50-7.41 (m, 3H), 7.29 (dd, $J_1$=5.2 Hz, $J_2$=1.5 Hz, 1H), 7.12 (s, 1H), 6.62-6.56 (m, 1H), 6.41-6.27 (m, 4H), 5.99-5.98 (m, 1H), 5.72 (d, J=10.5 Hz, 1H), 3.83 (d, J=11.9 Hz, 1H), 3.69 (t, J=11.4 Hz, 1H), 2.44-2.42 (m, 1H), 2.19 (d, J=13.3 Hz, 1H), 1.92-1.86 (m, 2H), 1.72-1.69 (m, 1H), 1.62-1.59 (m, 1H); $^{13}$C NMR (CDCl$_3$, 150 MHz) δ: 167.2, 166.0, 165.9, 162.7, 152.5, 151.1, 148.2, 141.2, 138.4, 138.2, 133.6, 129.7, 129.3, 129.1, 128.7, 127.8, 127.4, 127.4, 118.2, 112.3, 44.4, 43.0, 28.0, 25.8, 19.7. MS (ESI, m/z): 536.2 [M+H]$^+$.

Example 66

(S)-1-amino-2-(1-(but-2-ynoyl)piperidin-2-yl)-4-(4-((4-phenylpyridin-2-yl)carbamoyl)phenyl)-1H-imidazole-5-carboxamide

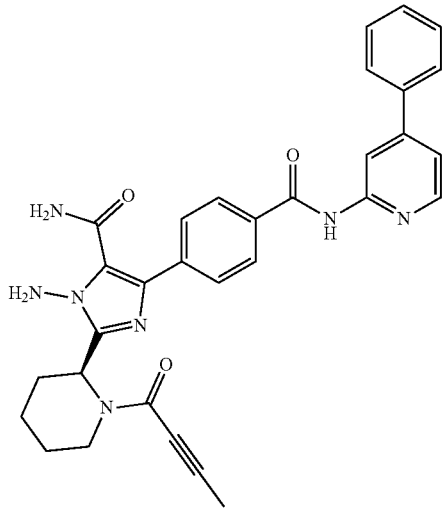 [SMILES: CC#CC(=O)N1CCCC[C@H]1c1nc(-c2ccc(C(=O)Nc3cc(-c4ccccc4)ccn3)cc2)c(C(N)=O)n1N]

Preparation of (S)-1-amino-2-(1-(but-2-ynoyl)piperidin-2-yl)-4-(4-((4-phenylpyridin-2-yl)carbamoyl)phenyl)-1H-imidazole-5-carboxamide

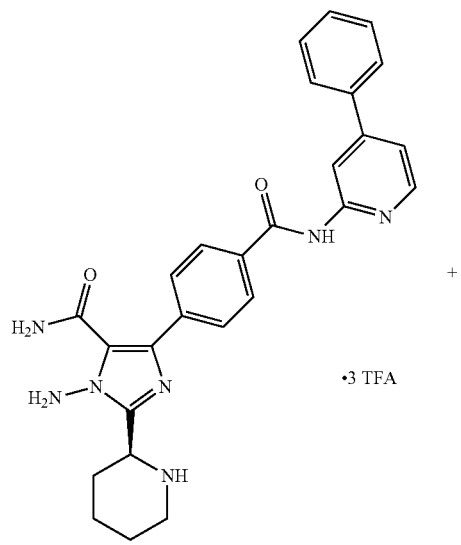

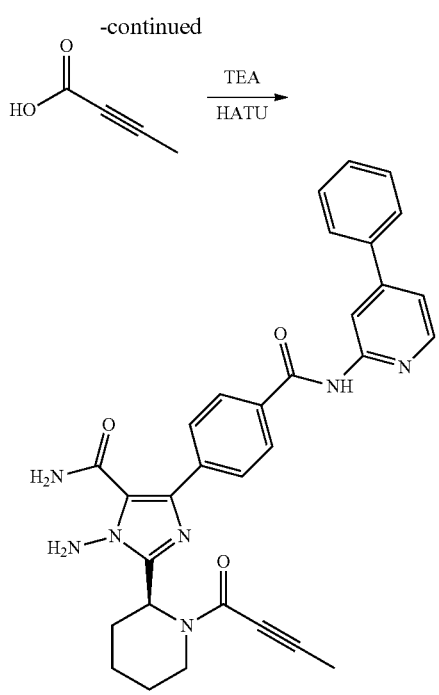

To the solution of 197 mg (0.41 mmol) of the product of Step E of example 65 in dry N,N-dimethylformamide (5 mL) was added triethylamine (248 mg, 2.46 mmol). After 5 min, but-2-ynoic acid (30.3 mg, 0.36 mmol) and HATU (234 mg, 0.61 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (26:1) to give the product (S)-1-amino-2-(1-(but-2-ynoyl)piperidin-2-yl)-4-(4-((4-phenylpyridin-2-yl)carbamoyl)phenyl)-1H-imidazole-5-carboxamide as an off-white solid (114.4 mg, 51%). $^1$H NMR (CDCl$_3$, 400 MHz) δ: 9.25 (s, 1H), 8.66 (s, 1H), 8.29 (d, J=5.2 Hz, 1H), 7.93 (d, J=8.3 Hz, 2H), 7.80 (d, J=8.4 Hz, 2H), 7.70 (d, J=6.8 Hz, 2H), 7.49-7.40 (m, 3H), 7.28 (dd, $J_1$=5.2 Hz, $J_2$=1.5 Hz, 1H), 7.02 (s, 1H), 6.46 (s, 1H), 6.13 (s, 2H), 5.95 (d, J=4.7 Hz, 1H), 4.27 (d, J=12.8 Hz, 1H), 3.67 (td, $J_1$=13.2 Hz, $J_2$=2.8 Hz, 1H), 2.38-2.33 (m, 1H), 2.16 (d, J=13.5 Hz, 1H), 2.00 (s, 3H), 1.87-1.84 (m, 2H), 1.77-1.68 (m, 1H), 1.63-1.56 (m, 1H); $^{13}$C NMR (CDCl$_3$, 150 MHz) δ: 165.9, 162.7, 154.9, 152.5, 151.1, 148.2, 148.0, 141.1, 138.3, 138.2, 133.7, 129.6, 129.3, 129.1, 127.5, 127.3, 120.2, 118.2, 112.3, 90.9, 73.0, 44.5, 43.8, 27.8, 25.8, 19.8, 4.2. MS (ESI, m/z): 548.2 [M+H]$^+$.

Example 67

(S)-2-(1-acryloylpiperidin-2-yl)-1-amino-4-(4-((4-methoxypyridin-2-yl)carbamoyl)phenyl)-1H-imidazole-5-carboxamide

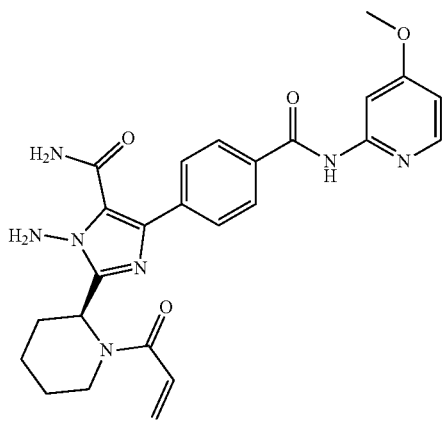 [SMILES: C=CC(=O)N1CCCC[C@H]1c1nc(-c2ccc(C(=O)Nc3cc(OC)ccn3)cc2)c(C(N)=O)n1N]

Step A: Preparation of tert-butyl (S)-2-(5-(ethoxycarbonyl)-4-(4-((4-methoxypyridin-2-yl)carbamoyl)phenyl)-1H-imidazol-2-yl)piperidine-1-carboxylate

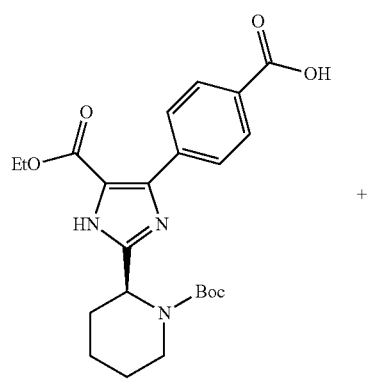

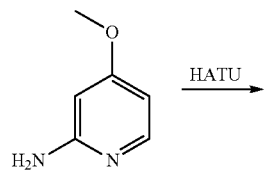

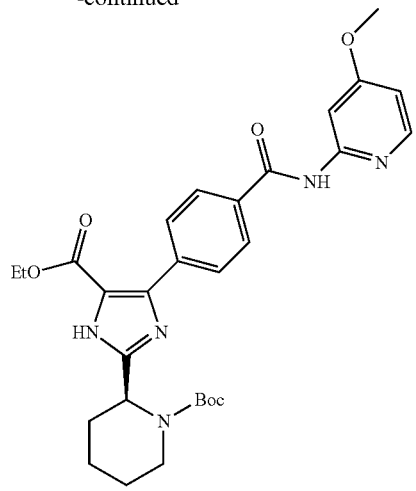

To the solution of 26.6 g (60 mmol) the product of Step C of example 46 in dry N,N-dimethylformamide (240 mL) were added HATU (27.4 g, 72 mmol), diisopropylethylamine (51.7 mL, 300 mmol) and 4-methoxypyridin-2-amine (11.2 g, 90 mmol). The reaction mixture was stirred at 80° C. for 3 h. After the completion of the reaction (monitored by TLC), the mixture was quenched with brine and washed with ethyl acetate three times (3×180 mL). The combined organic layers were dried with anhydrous $Na_2SO_4$ and concentrated under reduced pressure and purified by flash chromatography with petroleum ether and ethyl acetate (3.5:1) to afford tert-butyl (S)-2-(5-(ethoxycarbonyl)-4-(4-((4-methoxypyridin-2-yl)carbamoyl)phenyl)-1H-imidazol-2-yl)piperidine-1-carboxylate as white solid (28.3 g, 86%). $^1$H NMR (CDCl$_3$, 400 MHz) δ: 10.08 (s, 1H), 8.89 (s, 1H), 8.16 (d, J=8.5 Hz, 2H), 8.07-8.05 (m, 2H), 7.96 (d, J=8.6 Hz, 2H), 6.62 (dd, J$_1$=5.8 Hz, J$_2$=2.4 Hz, 1H), 5.41 (d, J=3.9 Hz, 1H), 4.35-4.29 (m, 2H), 4.03-4.00 (s, 1H), 3.91 (s, 3H), 2.76 (td, J$_1$=13.0 Hz, J$_2$=2.8 Hz, 1H), 2.54 (d, J=12.8 Hz, 1H), 1.95-1.92 (m, 1H), 1.86-1.81 (m, 1H), 1.78-1.73 (m, 1H), 1.68-1.65 (m, 1H), 1.55-1.50 (m, 10H), 1.32 (t, J=7.1 Hz, 3H). MS (ESI, m/z): 550.2 [M+H]$^+$.

Step B: Preparation of tert-butyl (S)-2-(1-amino-5-(ethoxycarbonyl)-4-(4-((4-methoxypyridin-2-yl)carbamoyl)phenyl)-1H-imidazol-2-yl)piperidine-1-carboxylate

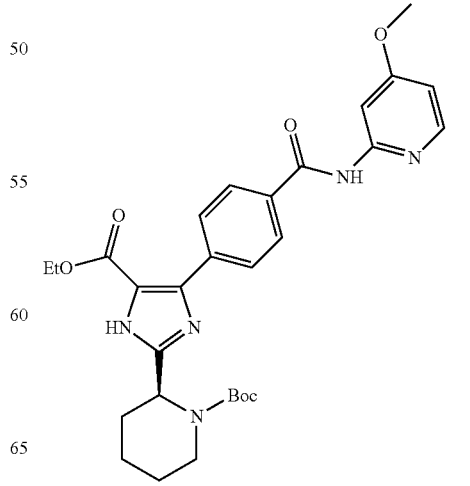

-continued

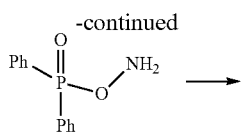

Step C: Preparation of (S)-1-amino-2-(1-(tert-butoxycarbonyl) piperidin-2-yl)-4-(4-((4-methoxypyridin-2-yl)carbamoyl)phenyl)-1H-imidazole-5-carboxylic acid

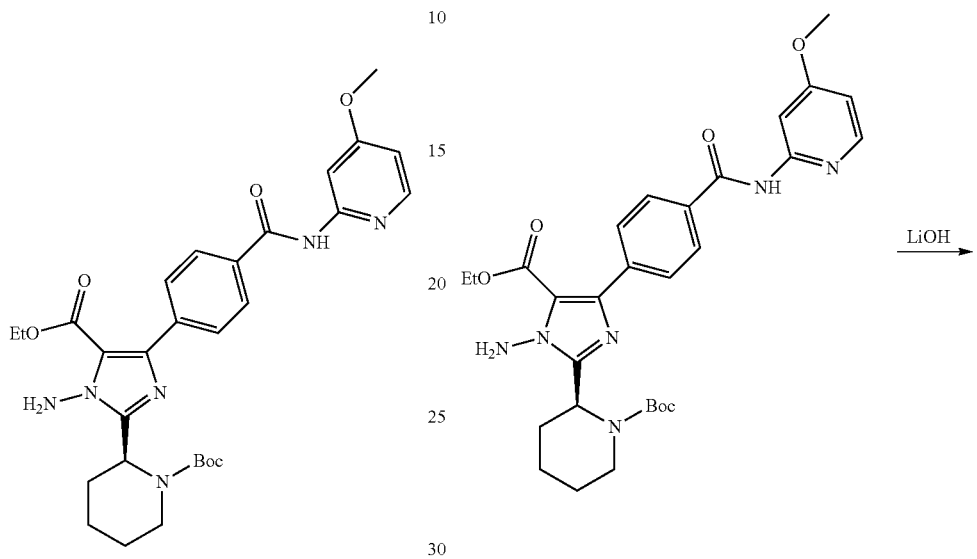

To the solution of 3.4 g (6.2 mmol) of the product of Step A in anhydrous N,N-Dimethylformamide (32 mL) was slowly added lithium hexamethyldisilazane (7.4 mL, 1 M solution in tetrahydrofuran) at −10° C. After the mixture was stirred for 20 min, O-(diphenylphosphinyl) hydroxylamine (1.4 g, 6.2 mmol) was added at 0° C. and the resulting suspension was stirred at room temperature for 2 h (in cases where the reaction mixture became too viscous, additional N,N-Dimethylformamide was added). The mixture was quenched with brine and extracted with ethyl acetate three times (3×150 mL). The combined organic fractions were dried with anhydrous $Na_2SO_4$ and the solvent was removed under reduced pressure to afford the crude residue, which was subjected to column chromatography with petroleum ether and ethyl acetate (4:1) to give tert-butyl (S)-2-(1-amino-5-(ethoxycarbonyl)-4-(4-((4-methoxypyridin-2-yl)carbamoyl)phenyl)-1H-imidazol-2-yl)piperidine-1-carboxylate as a white solid (2.6 g, 75%). $^1$H NMR (CDCl$_3$, 400 MHz) δ: 8.87 (s, 1H), 8.06 (d, J=2.3 Hz, 1H), 8.04 (d, J=5.8 Hz, 1H), 7.93 (d, J=8.6 Hz, 2H), 7.84 (d, J=8.6 Hz, 2H), 6.61 (dd, $J_1$=5.8 Hz, $J_2$=2.4 Hz, 1H), 5.92 (s, 2H), 5.67 (d, J=4.8 Hz, 1H), 4.34-4.22 (m, 2H), 3.94 (d, J=13.1 Hz, 1H), 3.91 (s, 3H), 3.41 (td, $J_1$=13.0 Hz, $J_2$=3.0 Hz, 1H), 2.11-2.03 (m, 2H), 1.92-1.49 (m, 4H), 1.43 (s, 9H), 1.24 (t, J=7.1 Hz, 3H). MS (ESI, m/z): 565.2 [M+H]$^+$.

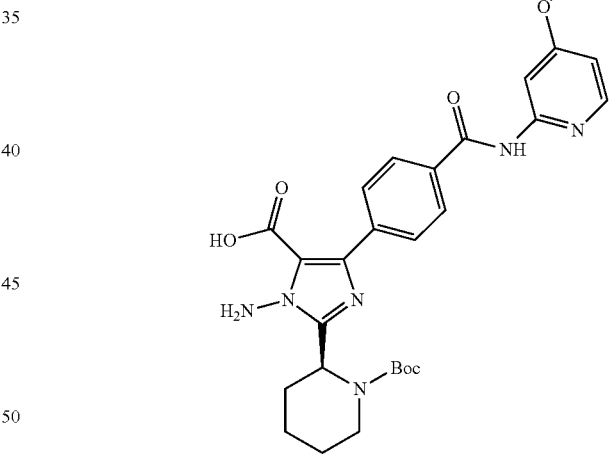

To the solution of 2.82 g (5.0 mmol) of the product of Step B in methanol (20 mL) was added 2 mol/L aqueous lithium hydroxide (25 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl)piperidin-2-yl)-4-(4-((4-methoxypyridin-2-yl)carbamoyl)phenyl)-1H-imidazole-5-carboxylic acid (2.63, 98%).

Step D: Preparation of tert-butyl (S)-2-(1-amino-5-carbamoyl-4-(4-((4-methoxypyridin-2-yl)carbamoyl)phenyl)-1H-imidazol-2-yl)piperidine-1-carboxylate

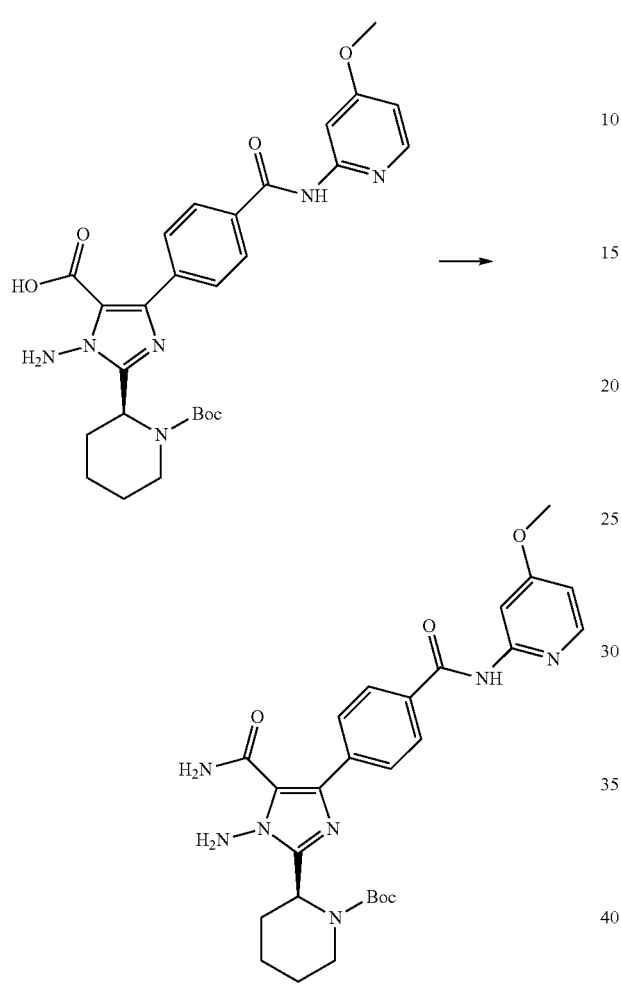

To the solution of 1.18 g (2.2 mmol) of the product of Step C in dry N,N-Dimethylformamide (16 mL) were added HATU (1.3 g, 3.3 mmol), diisopropylethylamine (1.2 mL, 6.6 mmol) and NH$_4$Cl (1.2 g, 22 mmol). The reaction mixture was stirred at room temperature for 2 h. The reaction mixture was quenched with brine and washed with ethyl acetate three times (3×90 mL). The combined organic layers were concentrated under reduced pressure and purified by flash chromatography with dichloromethane and methanol (32:1) to give the product tert-butyl (S)-2-(1-amino-5-carbamoyl-4-(4-((4-methoxypyridin-2-yl)carbamoyl)phenyl)-1H-imidazol-2-yl)piperidine-1-carboxylate as a white solid (0.93 g, 79%). $^1$H NMR (CDCl$_3$, 400 MHz) δ: 8.80 (s, 1H), 8.09 (d, J=5.8 Hz, 1H), 8.04 (d, J=2.3 Hz, 1H), 7.96 (d, J=8.5 Hz, 2H), 7.85 (d, J=8.4 Hz, 2H), 6.84 (s, 1H), 6.63 (dd, J$_1$=5.8 Hz, J$_2$=2.4 Hz, 1H), 6.01 (s, 2H), 5.74 (s, 1H), 5.60 (d, J=4.5 Hz, 1H), 3.98-3.95 (m, 1H), 3.92 (s, 3H), 3.29 (td, J$_1$=13.0 Hz, J$_2$=3.0 Hz, 1H), 2.23-2.12 (m, 2H), 1.93-1.84 (m, 1H), 1.75 (d, J=12.8 Hz, 1H), 1.65-1.49 (m, 2H), 1.46 (s, 9H). MS (ESI, m/z): 536.2 [M+H]$^+$.

Step E: Preparation of (S)-1-amino-4-(4-((4-methoxypyridin-2-yl)carbamoyl)phenyl)-2-(piperidin-2-yl)-1H-imidazole-5-carboxamide

To the solution of 214 mg (0.40 mmol) of the product of Step D in dichloromethane (6 mL) was added trifluoroacetic acid (2.5 mL). The mixture was stirred at room temperature for 1 h and then concentrated to afford (S)-1-amino-4-(4-((4-methoxypyridin-2-yl)carbamoyl)phenyl)-2-(piperidin-2-yl)-1H-imidazole-5-carboxamide as a light yellow oil. MS (ESI, m/z): 436.2 [M+H]$^+$.

Step F: Preparation of (S)-2-(1-acryloylpiperidin-2-yl)-1-amino-4-(4-((4-methoxypyridin-2-yl)carbamoyl)phenyl)-1H-imidazole-5-carboxamide

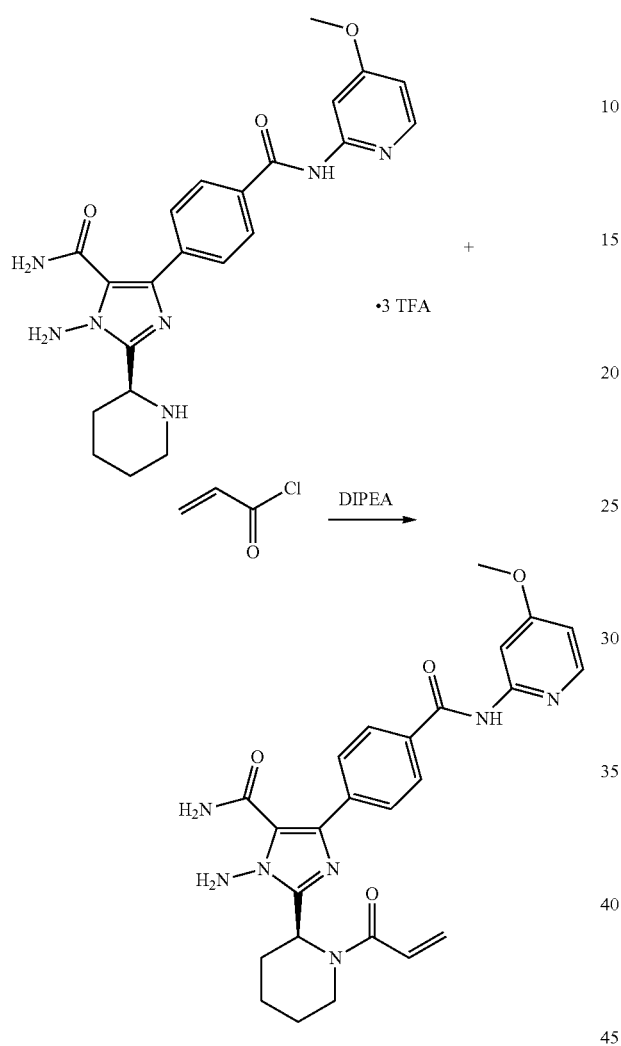

To the solution of 222 mg (0.51 mmol) of the product of Step E in dry dichloromethane (7 mL) was added diisopropylethylamine (395.5 mg, 3.06 mmol). After 5 min, acryloyl chloride (41.5 mg, 0.50 mmol) was added at 0° C. The reaction mixture was then warmed up to room temperature and continued to stir for 1 h, ethyl acetate and water were added. The layers were separated, and the aqueous phase was extracted with ethyl acetate. The combined organic phases were washed three times (3×50 mL) with brine solution. The organic phase was dried over anhydrous Na₂SO₄, filtered and concentrated. The residue was purified by chromatography with dichloromethane and methanol (28:1) to give (S)-2-(1-acryloylpiperidin-2-yl)-1-amino-4-(4-((4-methoxypyridin-2-yl)carbamoyl)phenyl)-1H-imidazole-5-carboxamide as an off-white solid (155 mg, 62%). $^1$H NMR (CDCl$_3$, 400 MHz) δ: 9.15 (s, 1H), 8.05 (d, J=5.8 Hz, 1H), 8.02 (d, J=2.3 Hz, 1H), 7.92 (d, J=8.5 Hz, 2H), 7.82 (d, J=7.7 Hz, 2H), 7.10 (s, 1H), 6.61 (dd, J$_1$=5.8 Hz, J$_2$=2.4 Hz, 1H), 6.58-6.55 (m, 1H), 6.36 (s, 1H), 6.30-6.26 (m, 3H), 5.98-5.97 (m, 1H), 5.71 (d, J=10.7 Hz, 1H), 3.90 (s, 3H), 3.84-3.81 (m, 1H), 3.72-3.65 (m, 1H), 2.43-2.40 (m, 1H), 2.18 (d, J=13.0 Hz, 1H), 1.94-1.88 (m, 2H), 1.73-1.58 (m, 2H); $^{13}$C NMR (CDCl$_3$, 150 MHz) δ: 167.7, 167.2, 166.0, 162.7, 153.5, 148.5, 148.2, 141.2, 138.4, 133.7, 129.7, 128.7, 127.8, 127.4, 120.0, 108.1, 99.1, 55.6, 44.4, 43.0, 28.0, 25.8, 19.7. MS (ESI, m/z): 490.2 [M+H]$^+$.

Example 68

(S)-1-amino-2-(1-(but-2-ynoyl)piperidin-2-yl)-4-(4-((4-methoxy-pyridin-2-yl)carbamoyl)phenyl)-1H-imidazole-5-carboxamide

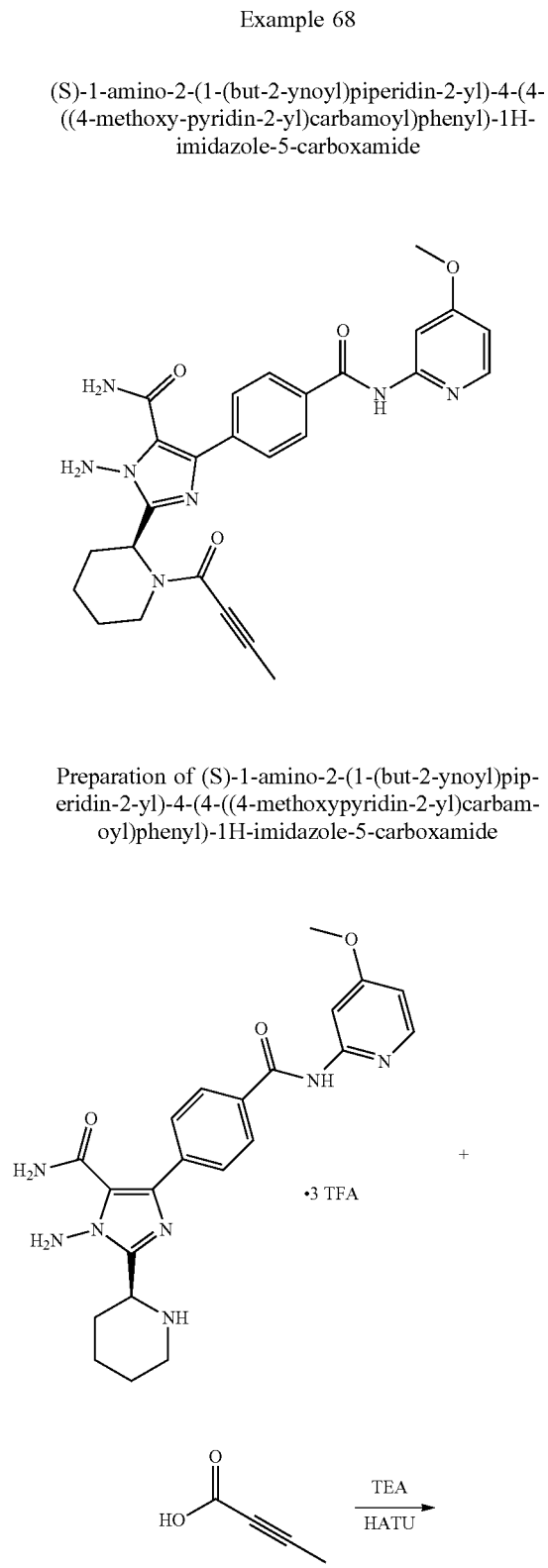

Preparation of (S)-1-amino-2-(1-(but-2-ynoyl)piperidin-2-yl)-4-(4-((4-methoxypyridin-2-yl)carbamoyl)phenyl)-1H-imidazole-5-carboxamide

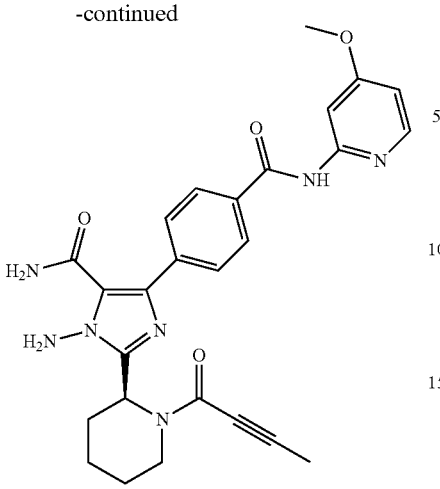

To the solution of 222 mg (0.51 mmol) of the product of Step E of example 67 in dry N,N-Dimethylformamide (7 mL) was added triethylamine (308 mg, 3.06 mmol). After 5 min, but-2-ynoic acid (37.6 mg, 0.45 mmol) and HATU (289 mg, 0.76 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (26:1) to give (S)-1-amino-2-(1-(but-2-ynoyl)piperidin-2-yl)-4-(4-((4-methoxypyridin-2-yl)carbamoyl)phenyl)-1H-imidazole-5-carboxamide as an off-white solid (127.9 mg, 50%). $^1$H NMR (CDCl$_3$, 400 MHz) δ: 9.47-9.44 (m, 1H), 8.00-7.97 (m, 2H), 7.86-7.83 (m, 2H), 7.74-7.71 (m, 1.7H), 7.64-7.61 (m, 0.3H), 7.13 (s, 1H), 6.79 (s, 1H), 6.58-6.55 (m, 1H), 6.10 (s, 2H), 5.92 (d, J=5.6 Hz, 1H), 4.25 (d, J=12.6 Hz, 1H), 3.86 (s, 3H), 3.65 (td, J$_1$=13.0 Hz, J$_2$=2.4 Hz, 1H), 2.35-2.26 (m, 1H), 2.12 (d, J=13.4 Hz, 1H), 1.98 (s, 3H), 1.85-1.82 (m, 2H), 1.68-1.65 (m, 1H), 1.57-1.54 (m, 1H); $^{13}$C NMR (CDCl$_3$, 100 MHz) δ: 167.6, 166.1, 162.8, 154.8, 153.6, 148.4, 148.0, 140.9, 138.2, 133.5, 129.4, 127.4, 120.4, 107.8, 99.2, 90.9, 72.9, 55.5, 44.5, 43.8, 27.8, 25.7, 19.8, 4.2. MS (ESI, m/z): 502.2 [M+H]$^+$.

Example 69

(S,E)-1-amino-4-(4-((4-methoxypyridin-2-yl)carbamoyl)phenyl)-2-(1-(4,4,4-trifluorobut-2-enoyl)piperidin-2-yl)-1H-imidazole-5-carboxamide

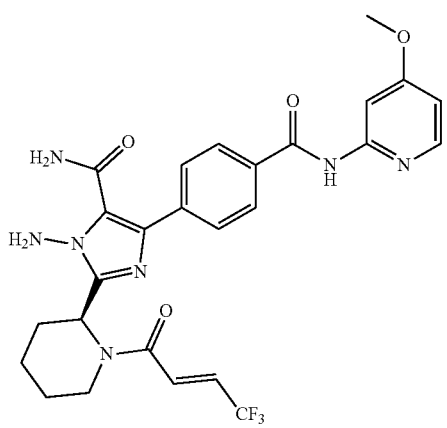 [SMILES: COc1ccnc(NC(=O)c2ccc(-c3nc([C@@H]4CCCCN4C(=O)/C=C/C(F)(F)F)n(N)c3C(N)=O)cc2)c1]

Preparation of (S,E)-1-amino-4-(4-((4-methoxypyridin-2-yl)carbamoyl)phenyl)-2-(1-(4,4,4-trifluorobut-2-enoyl)piperidin-2-yl)-1H-imidazole-5-carboxamide

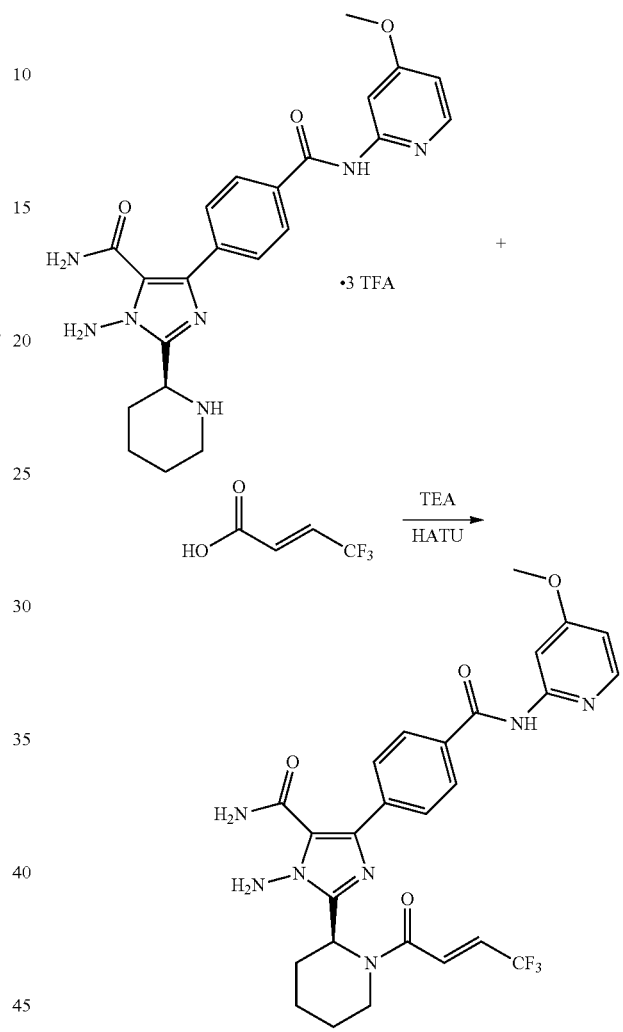

To the solution of 222 mg (0.51 mmol) of the product of Step E of example 67 in dry N,N-Dimethylformamide (7 mL) was added triethylamine (308 mg, 3.06 mmol). After 5 min, (E)-4,4,4-trifluorobut-2-enoic acid (63.0 mg, 0.45 mmol) and HATU (289 mg, 0.76 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (32:1) to give (S,E)-1-amino-4-(4-((4-methoxypyridin-2-yl)carbamoyl)phenyl)-2-(1-(4,4,4-trifluorobut-2-enoyl) piperidin-2-yl)-1H-imidazole-5-carboxamide as an off-white solid (142.2 mg, 50%). $^1$H NMR (CDCl$_3$, 600 MHz) δ: 9.24 (s, 1H), 8.04-8.01 (m, 2H), 7.89 (d, J=8.0 Hz, 2H), 7.74 (d, J=8.0 Hz, 2H), 6.99 (d, J=15.3 Hz, 1H), 6.83 (s, 1H), 6.73-6.68 (m, 1H), 6.61-6.60 (m, 1H), 6.55 (m, 1H), 6.15 (s, 1.6H), 6.02 (d, J=4.3 Hz, 1H), 5.75 (s, 0.3H), 5.56 (s, 0.1H), 3.90 (s, 3H), 3.87-3.83 (m, 1H), 3.77-3.75 (m, 1H), 2.35-2.29 (m, 1H), 2.20 (d, J=13.0 Hz, 1H), 1.95-1.90 (m, 2H), 1.73-1.70 (m, 1H), 1.65-1.59 (m, 1H); $^{13}$C NMR (CDCl$_3$, 150 MHz) δ: 167.7, 165.9, 164.1, 162.8, 153.5, 148.5, 148.1, 141.1, 138.2, 133.8, 129.9, 129.6, 128.3, 127.5, 123.5, 120.0, 108.0, 99.2, 55.6, 44.9, 43.6, 28.0, 25.8, 19.5. MS (ESI, m/z): 558.1 [M+H]$^+$.

Example 70

(S)-1-amino-2-(1-(2-fluoroacryloyl)piperidin-2-yl)-4-(4-((4-methoxy-pyridin-2-yl)carbamoyl)phenyl)-1H-imidazole-5-carboxamide

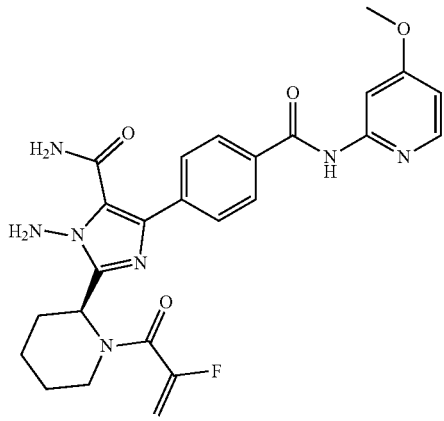 [SMILES: C=C(F)C(=O)N1CCCC[C@H]1c1nc(-c2ccc(C(=O)Nc3cc(OC)ccn3)cc2)c(C(N)=O)n1N]

Preparation of (S)-1-amino-2-(1-(2-fluoroacryloyl)piperidin-2-yl)-4-(4-((4-methoxypyridin-2-yl)carbamoyl)phenyl)-1H-imidazole-5-carboxamide

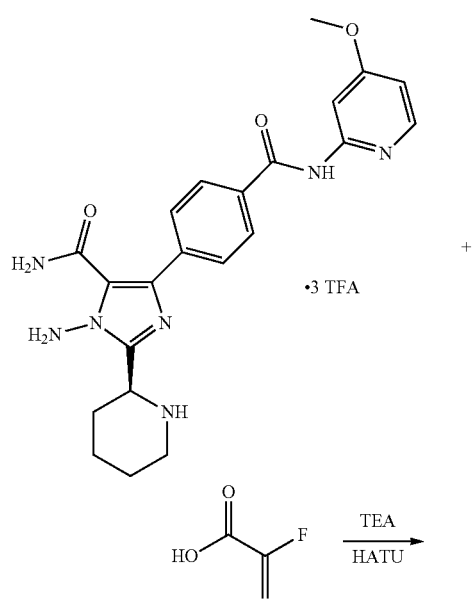

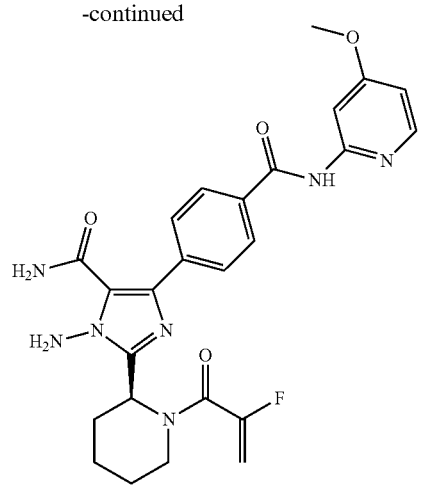

To the solution of 222 mg (0.51 mmol) of the product of Step E of example 67 in dry N,N-Dimethylformamide (7 mL) was added triethylamine (308 mg, 3.06 mmol). After 5 min, 2-fluoroacrylic acid (40.5 mg, 0.45 mmol) and HATU (289 mg, 0.76 mmol) were added. The reaction mixture was continued to stir at room temperature for 2 h, ethyl acetate and water were added. The layers were separated, and the aqueous phase was extracted with ethyl acetate. The combined organic phases were washed three times (3×60 mL) with brine solution. The organic phase was dried over anhydrous Na$_2$SO$_4$, filtered and concentrated. The residue was purified by chromatography with dichloromethane and methanol (32:1) to give (S)-1-amino-2-(1-(2-fluoroacryloyl)piperidin-2-yl)-4-(4-((4-methoxypyridin-2-yl)carbamoyl)phenyl)-1H-imidazole-5-carboxamide as an off-white solid (129.4 mg, 50%). $^1$H NMR (CDCl$_3$, 400 MHz) δ: 9.46 (s, 1H), 8.00-7.98 (m, 2H), 7.84 (d, J=8.3 Hz, 2H), 7.70 (d, J=8.1 Hz, 2H), 7.01 (s, 1H), 6.86 (s, 1H), 6.57 (dd, J$_1$=5.8 Hz, J$_2$=2.4 Hz, 1H), 6.19 (s, 2H), 5.88-5.81 (m, 1H), 5.26 (d, J=3.3 Hz, 0.5H), 5.14-5.13 (m, 1H), 5.09 (d, J=3.5 Hz, 0.5H), 3.87 (s, 3H), 3.83-3.73 (m, 2H), 2.34-2.16 (m, 2H), 1.95-1.81 (m, 2H), 1.71-1.60 (m, 2H); $^{13}$C NMR (CDCl$_3$, 150 MHz) δ: 167.6, 166.1, 163.0, 158.2, 156.4, 153.6, 148.4, 147.8, 140.9, 138.0, 133.7, 129.3, 127.4, 120.4, 107.8, 99.9, 99.3, 55.5, 45.3, 44.0, 28.1, 25.8, 19.8. MS (ESI, m/z): 508.2 [M+H]$^+$.

Example 71

(S)-2-(1-acryloylpiperidin-2-yl)-1-amino-4-(4-((4-isopropylpyridin-2-yl)carbamoyl)phenyl)-1H-imidazole-5-carboxamide

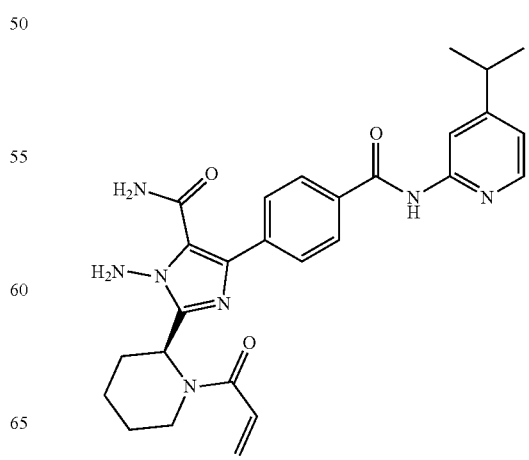

Step A: Preparation of tert-butyl (S)-2-(5-(ethoxycarbonyl)-4-(4-((4-isopropylpyridin-2-yl)carbamoyl)phenyl)-1H-imidazol-2-yl)piperidine-1-carboxylate

Step B: Preparation of tert-butyl (S)-2-(1-amino-5-(ethoxycarbonyl)-4-(4-((4-isopropylpyridin-2-yl)carbamoyl)phenyl)-1H-imidazol-2-yl) piperidine-1-carboxylate

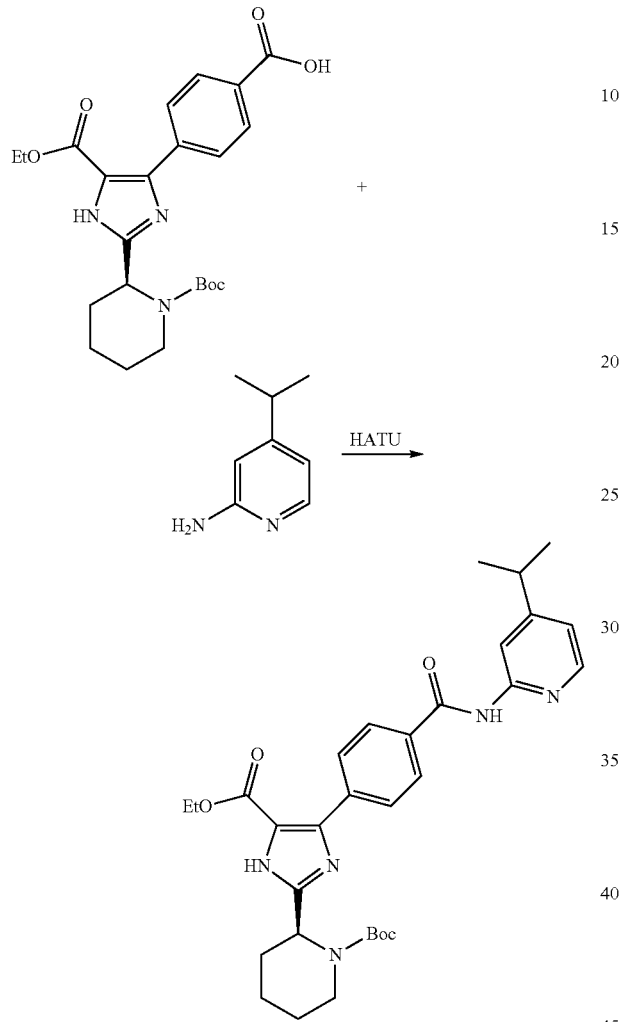

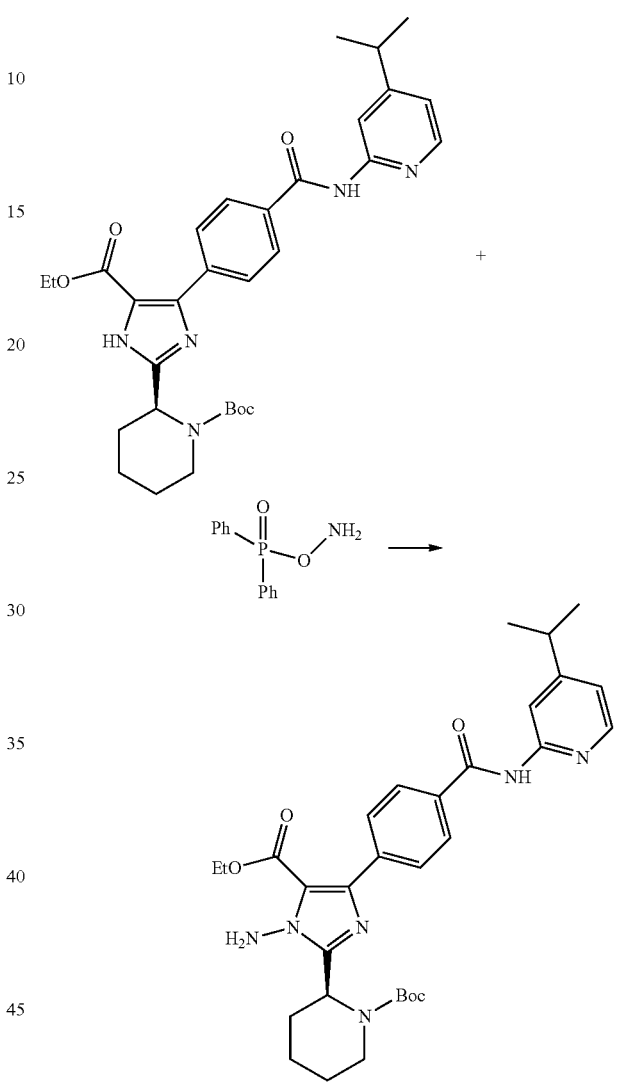

To the solution of 23.5 g (53 mmol) the product of Step C of example 46 in dry N,N-Dimethylformamide (230 mL) were added HATU (24.2 g, 63.6 mmol), diisopropylethylamine (45.7 mL, 365 mmol) and 4-isopropylpyridin-2-amine (10.8 g, 80 mmol). The reaction mixture was stirred at 80° C. After the completion of the reaction (monitored by TLC), the mixture was quenched with brine and washed with ethyl acetate three times (3×180 mL). The combined organic layers were concentrated under reduced pressure and purified by flash chromatography with petroleum ether and ethyl acetate (3:1) to afford tert-butyl (S)-2-(5-(ethoxycarbonyl)-4-(4-((4-isopropylpyridin-2-yl)carbamoyl)phenyl)-1H-imidazol-2-yl)piperidine-1-carboxylate as white solid (25.3 g, 85%). $^1$H NMR (CDCl$_3$, 400 MHz) δ: 10.17 (s, 1H), 8.82 (s, 1H), 8.33-8.32 (m, 1H), 8.17-8.13 (m, 3H), 7.97 (d, J=8.6 Hz, 2H), 6.94 (dd, J$_1$=5.2 Hz, J$_2$=1.5 Hz, 1H), 5.41 (d, J=3.9 Hz, 1H), 4.31 (q, J=7.1 Hz, 2H), 4.02-4.00 (m, 1H), 2.98-2.91 (m, 1H), 2.77 (td, J$_1$=13.1 Hz, J$_2$=2.8 Hz, 1H), 2.53 (d, J=12.6 Hz, 1H), 1.94-1.92 (m, 1H), 1.85-1.81 (m, 1H), 1.75-1.72 (m, 1H), 1.68-1.64 (m, 1H), 1.51-1.49 (m, 10H), 1.31-1.28 (m, 9H). MS (ESI, m/z): 562.2 [M+H]$^+$.

To the solution of 3.4 g (6.0 mmol) of the product of Step A in anhydrous N,N-dimethylformamide (30 mL) was slowly added lithium hexamethyldisilazane (7.2 mL, 1 M solution in tetrahydrofuran) at −10° C. After the mixture was stirred for 20 min, O-(diphenylphosphinyl) hydroxylamine (1.4 g, 6.0 mmol) was added at 0° C. and the resulting suspension was stirred at room temperature for 2 h (in cases where the reaction mixture became too viscous, additional N,N-Dimethylformamide was added). The reaction was quenched with brine and concentrated to dryness in vacuum. The residue was washed three times (3×140 mL) with ethyl acetate. The combined organic fractions were dried with anhydrous Na$_2$SO$_4$ and the solvent was removed under reduced pressure to afford the crude residue, which was subjected to column chromatography with petroleum ether and ethyl acetate (3:1) to give the product tert-butyl (S)-2-(1-amino-5-(ethoxycarbonyl)-4-(4-((4-isopropylpyridin-2-yl)carbamoyl)phenyl)-1H-imidazol-2-yl)piperidine-1-carboxylate as a white solid (2.6 g, 76%). ¹H NMR (CDCl₃, 400 MHz) δ: 8.67 (s, 1H), 8.34-8.30 (m, 1H), 8.15-8.11 (m, 3H), 7.96 (d, J=8.6 Hz, 2H), 6.93 (dd, J₁=5.2 Hz, J₂=1.5 Hz, 1H), 5.92 (s, 2H), 5.56 (d, J=3.9 Hz, 1H), 4.29 (q, J=7.1 Hz, 2H), 4.00-3.98 (m, 1H), 3.20 (td, J₁=13.0 Hz, J₂=2.7 Hz, 1H), 2.98-2.91 (m, 1H), 2.47 (d, J=12.8 Hz, 1H), 1.99-1.94 (m, 1H), 1.86-1.79 (m, 1H), 1.75-1.71 (m, 1H), 1.67-1.62 (m, 1H), 1.50-1.48 (m, 10H), 1.31-1.28 (m, 9H). MS (ESI, m/z): 577.3 [M+H]⁺.

Step C: Preparation of (S)-1-amino-2-(1-(tert-butoxycarbonyl)piperidin-2-yl)-4-(4-((4-isopropylpyridin-2-yl)carbamoyl)phenyl)-1H-imidazole-5-carboxylic acid Step D: Preparation of tert-butyl (S)-2-(1-amino-5-carbamoyl-4-(4-((4-isopropylpyridin-2-1)carbamoyl)phenyl)-1H-imidazol-2-yl)piperidine-1-carboxylate

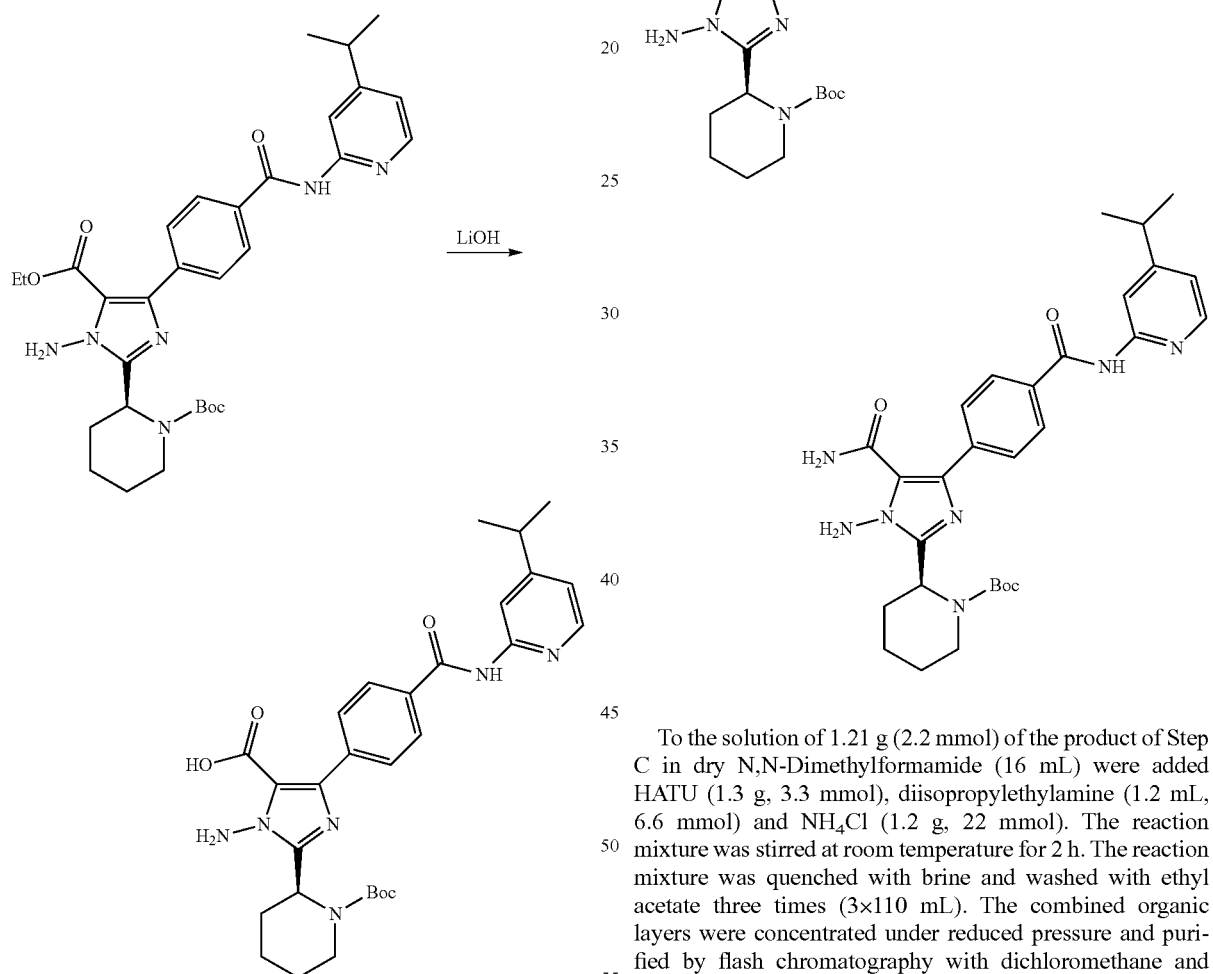

To the solution of 2.88 g (5.0 mmol) of the product of Step B in methanol (20 mL) was added 2 mol/L aqueous lithium hydroxide (25 mL) and stirred at room temperature for 2 h. The reaction mixture was evaporated and diluted with water (100 mL) and acidified with aqueous HCl till pH 3. The mixture was washed with ethyl acetate three times (3×130 mL). The white precipitate was isolated by filtration and dried to afford (S)-1-amino-2-(1-(tert-butoxycarbonyl)piperidin-2-yl)-4-(4-((4-isopropyl-pyridin-2-yl)carbamoyl)phenyl)-1H-imidazole-5-carboxylic acid (2.69 g, 98%).

To the solution of 1.21 g (2.2 mmol) of the product of Step C in dry N,N-Dimethylformamide (16 mL) were added HATU (1.3 g, 3.3 mmol), diisopropylethylamine (1.2 mL, 6.6 mmol) and NH₄Cl (1.2 g, 22 mmol). The reaction mixture was stirred at room temperature for 2 h. The reaction mixture was quenched with brine and washed with ethyl acetate three times (3×110 mL). The combined organic layers were concentrated under reduced pressure and purified by flash chromatography with dichloromethane and methanol (32:1) to give the product tert-butyl (S)-2-(1-amino-5-carbamoyl-4-(4-((4-isopropylpyridin-2-yl)carbamoyl)phenyl)-1H-imidazol-2-yl)piperidine-1-carboxylate as a white solid (0.96 g, 80%). ¹H NMR (CDCl₃, 400 MHz) δ: 9.05 (s, 1H), 8.35 (s, 1H), 8.16 (d, J=5.1 Hz, 1H), 7.98 (d, J=8.4 Hz, 2H), 7.94 (d, J=8.6 Hz, 2H), 7.05 (s, 1H), 6.93 (dd, J₁=5.0 Hz, J₂=1.5 Hz, 1H), 6.28 (s, 1H), 5.93 (s, 2H), 5.56 (d, J=4.0 Hz, 1H), 3.38 (d, J=13.1 Hz, 1H), 3.20 (td, J₁=13.0 Hz, J₂=2.7 Hz, 1H), 2.98-2.90 (m, 1H), 2.45 (d, J=12.8 Hz, 1H), 1.96-1.81 (m, 2H), 1.69-1.66 (m, 1H), 1.64-1.60 (m, 1H), 1.53-1.46 (m, 10H), 1.31 (s, 3H), 1.28 (s, 3H). MS (ESI, m/z): 548.2 [M+H]⁺.

Step E: Preparation of (S)-1-amino-4-(4-((4-isopropylpyridin-2-yl)carbamoyl)phenyl)-2-(piperidin-2-yl)-1H-imidazole-5-carboxamide Step F: Preparation of (S)-2-(1-acryloylpiperidin-2-yl)-1-amino-4-(4-((4-isopropylpyridin-2-yl)carbamoyl)phenyl)-1H-imidazole-5-carboxamide

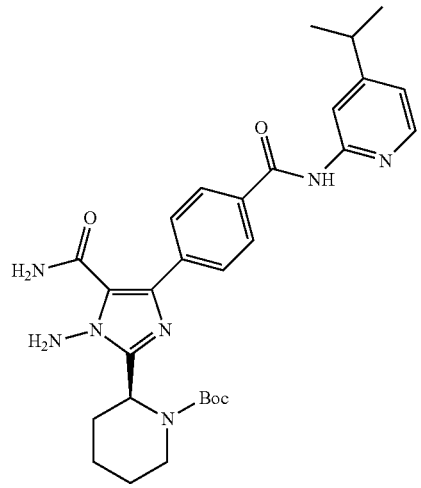

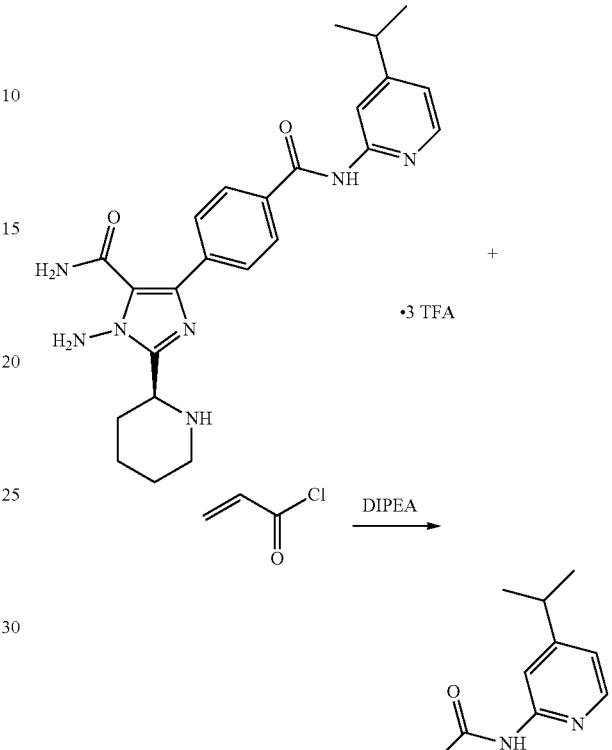

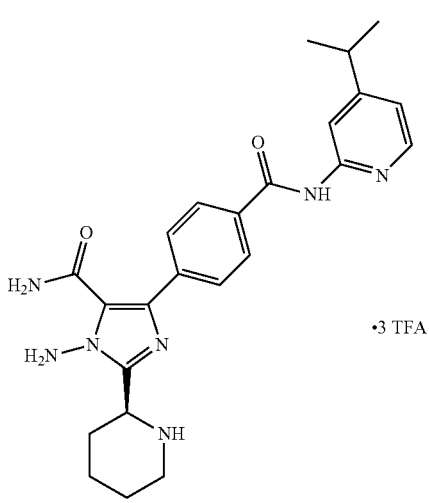

To the solution of 274 mg (0.50 mmol) of the product of Step D in dichloromethane (6 mL) was added trifluoroacetic acid (3.0 mL). The mixture was stirred at room temperature for 1 h and then concentrated to afford (S)-1-amino-4-(4-((4-isopropylpyridin-2-yl)carbamoyl)phenyl)-2-(piperidin-2-yl)-1H-imidazole-5-carboxamide as a light yellow oil. MS (ESI, m/z): 448.2 [M+H]$^+$.

To the solution of 228 mg (0.51 mmol) of the product of Step E in dry dichloromethane (7 mL) was added diisopropylethylamine (395.5 mg, 3.06 mmol). After 5 min, acryloyl chloride (41.5 mg, 0.50 mmol) was added at 0° C. The reaction mixture was then warmed up to room temperature and continued to stir for 1 h, ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (28:1) to give (S)-2-(1-acryloylpiperidin-2-yl)-1-amino-4-(4-((4-isopropylpyridin-2-yl)carbamoyl)phenyl)-1H-imidazole-5-carboxamide as an off-white solid (166.3 mg, 65%). $^1$H NMR (CDCl$_3$, 400 MHz) δ: 9.13 (s, 1H), 8.30 (s, 1H), 8.16 (d, J=5.1 Hz, 1H), 7.94 (d, J=8.4 Hz, 2H), 7.82 (d, J=7.7 Hz, 2H), 7.04 (s, 1H), 6.95-6.94 (m, 1H), 6.62-6.55 (m, 1H), 6.31-6.25 (m, 4H), 5.98-5.97 (m, 1H), 5.71 (d, J=10.7 Hz, 1H), 3.84-3.63 (m, 2H), 2.98-2.91 (m, 1H), 2.42-2.39 (m, 1H), 2.22-2.17 (m, 1H), 1.94-1.85 (m, 2H), 1.72-1.67 (m, 1H), 1.61-1.58 (m, 1H), 1.30 (s, 3H), 1.28 (s, 3H); $^{13}$C NMR (CDCl$_3$, 100 MHz) δ: 167.2, 165.8, 162.7, 160.9, 152.0, 148.2, 147.5, 141.2, 138.4, 133.8, 129.7, 128.7, 127.8, 127.4, 119.9, 118.6, 112.8, 44.4, 43.0, 34.2, 28.0, 27.3, 25.8, 23.2, 19.7. MS (ESI, m/z): 502.2 [M+H]$^+$.

Example 72

(S)-2-(1-acryloylpiperidin-2-yl)-1-amino-4-(4-((4-chloropyridin-2-yl)carbamoyl)phenyl)-1H-imidazole-5-carboxamide

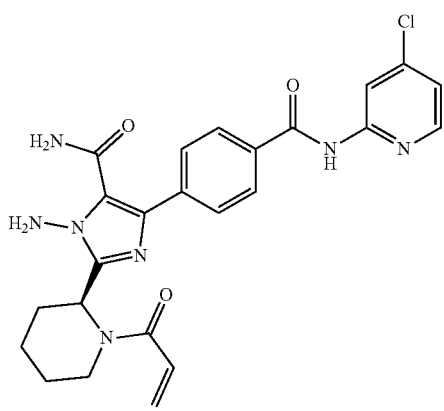 [SMILES: C=CC(=O)N1CCCC[C@H]1c1nc(-c2ccc(C(=O)Nc3cc(Cl)ccn3)cc2)c(C(N)=O)n1N]

Step A: Preparation of tert-butyl (S)-2-(4-(4-((4-chloropyridin-2-yl)carbamoyl)phenyl)-5-(ethoxycarbonyl)-1H-imidazol-2-yl)piperidine-1-carboxylate

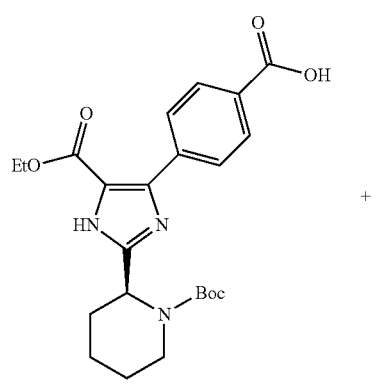

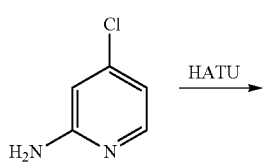

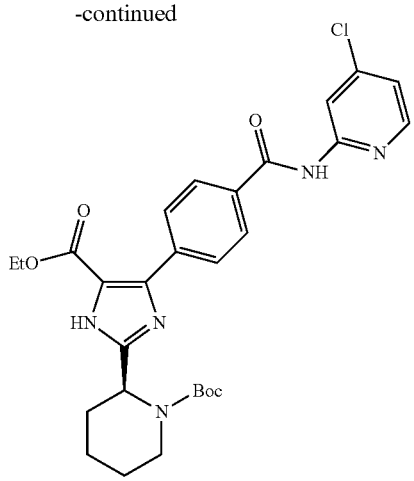

To the solution of 23.0 g (52 mmol) the product of Step C of example 46 in dry N,N-Dimethylformamide (230 mL) were added HATU (23.7 g, 62.4 mmol), diisopropylethylamine (44.8 mL, 260 mmol) and 4-chloropyridin-2-amine (10.0 g, 78 mmol). The reaction mixture was stirred at 80° C. After the completion of the reaction (monitored by TLC), the mixture was quenched with brine and washed with ethyl acetate three times (3×180 mL). The combined organic layers were concentrated under reduced pressure and purified by flash chromatography with petroleum ether and ethyl acetate (2.5:1) to afford tert-butyl (S)-2-(4-(4-((4-chloropyridin-2-yl)carbamoyl)phenyl)-5-(ethoxycarbonyl)-1H-imidazol-2-yl)piperidine-1-carboxylate as white solid (20.1 g, 70%). $^1$H NMR (CDCl$_3$, 600 MHz) δ: 9.70 (s, 1H), 9.60 (s, 1H), 8.58 (d, J=1.7 Hz, 1H), 8.16 (d, J=5.5 Hz, 1H), 8.02 (d, J=8.4 Hz, 2H), 7.96 (d, J=8.4 Hz, 2H), 7.10 (dd, J$_1$=5.5 Hz, J$_2$=1.9 Hz, 1H), 5.46-5.42 (m, 1H), 4.32-4.26 (m, 2H), 4.01-4.00 (m, 1H), 2.84-2.81 (m, 1H), 1.83-1.79 (m, 2H), 1.72-1.71 (m, 2H), 1.68-1.61 (m, 2H), 1.50 (s, 9H), 1.30-1.27 (m, 3H). MS (ESI, m/z): 554.2 [M+H]$^+$.

Step B: Preparation of tert-butyl (S)-2-(1-amino-4-(4-((4-chloropyridin-2-yl)carbamoyl)phenyl)-5-(ethoxycarbonyl)-1H-imidazol-2-ylpiperidine-1-carboxylate

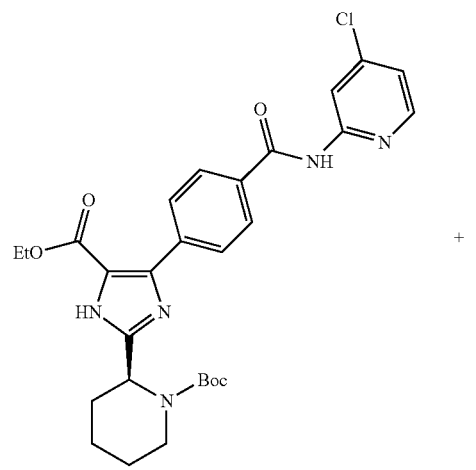

223
-continued

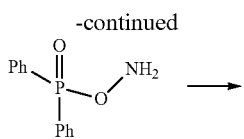

Step C: Preparation of (S)-1-amino-2-(1-(tert-butoxycarbonyl)piperidin-2-yl)-4-(4-((4-chloropyridin-2-yl)carbamoyl)phenyl)-1H-imidazole-5-carboxylic acid

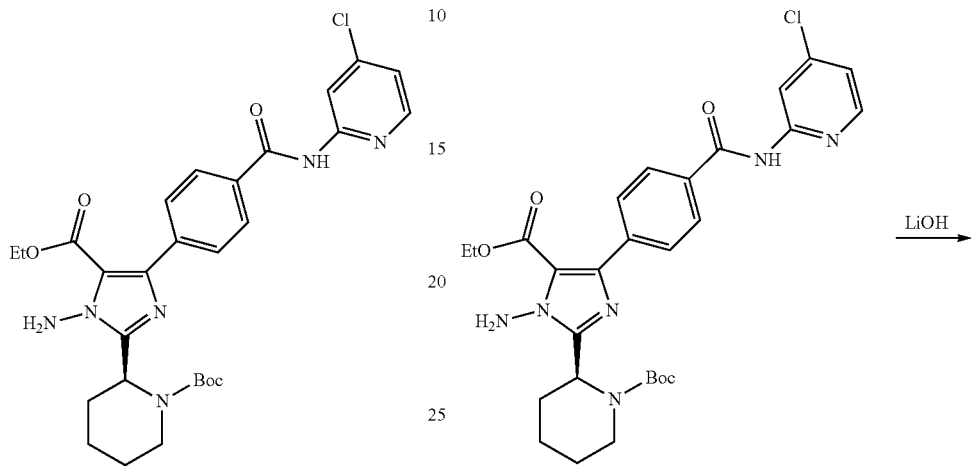

To the solution of 3.9 g (7.0 mmol) of the product of Step A in anhydrous N,N-Dimethylformamide (30 mL) was slowly added lithium hexamethyldisilazane (8.4 mL, 1 M solution in tetrahydrofuran) at −10° C. After the mixture was stirred for 20 min, O-(diphenylphosphinyl) hydroxylamine (1.6 g, 7.0 mmol) was added at 0° C. and the resulting suspension was stirred at room temperature for 2 h (in cases where the reaction mixture became too viscous, additional N,N-Dimethylformamide was added). The reaction was quenched with brine and concentrated to dryness in vacuum. The residue was washed three times (3×120 mL) with ethyl acetate. The combined organic fractions were dried with anhydrous $Na_2SO_4$ and the solvent was removed under reduced pressure to afford the crude residue, which was subjected to column chromatography with petroleum ether and ethyl acetate (3:1) to give tert-butyl (S)-2-(1-amino-4-(4-((4-chloropyridin-2-yl)carbamoyl)phenyl)-5-(ethoxycarbonyl)-1H-imidazol-2-yl)piperidine-1-carboxylate as a white solid (2.8 g, 71%). $^1$H NMR (CDCl$_3$, 600 MHz) δ: 9.78 (s, 1H), 8.47 (s, 1H), 8.15-8.12 (m, 1H), 7.99 (d, J=8.4 Hz, 2H), 7.86 (d, J=8.4 Hz, 2H), 7.11 (dd, J$_1$=5.5 Hz, J$_2$=1.9 Hz, 1H), 5.95 (s, 2H), 5.43-5.39 (m, 1H), 4.27-4.23 (m, 2H), 3.65 (d, J=12.7 Hz, 1H), 3.34 (t, J=13.0 Hz, 1H), 2.96 (d, J=13.1 Hz, 1H), 1.92-1.81 (m, 1H), 1.75-1.71 (m, 2H), 1.65-1.58 (m, 2H), 1.38 (s, 9H), 1.25-1.23 (m, 3H). MS (ESI, m/z): 569.2 [M+H]$^+$.

To the solution of 2.84 g (5.0 mmol) of the product of Step B in methanol (20 mL) was added 2 mol/L aqueous lithium hydroxide (25 mL) and stirred at room temperature for 2 h. The reaction mixture was evaporated and diluted with water (100 mL) and acidified with aqueous HCl till pH 3. The mixture was washed with ethyl acetate three times (3×110 mL). The white precipitate was isolated by filtration and dried to afford (S)-1-amino-2-(1-(tert-butoxycarbonyl)piperidin-2-yl)-4-(4-((4-chloropyridin-2-yl)carbamoyl)phenyl)-1H-imidazole-5-carboxylic acid (2.57 g, 95%).

Step D: Preparation of tert-butyl (S)-2-(1-amino-5-carbamoyl-4-(4-((4-chloropyridin-2-yl)carbamoyl)phenyl)-1H-imidazol-2-yl)piperidine-1-carboxylate Step E: Preparation of (S)-1-amino-4-(4-((4-chloropyridin-2-yl)carbamoyl)phenyl)-2-(piperidin-2-yl)-1H-imidazole-5-carboxamide

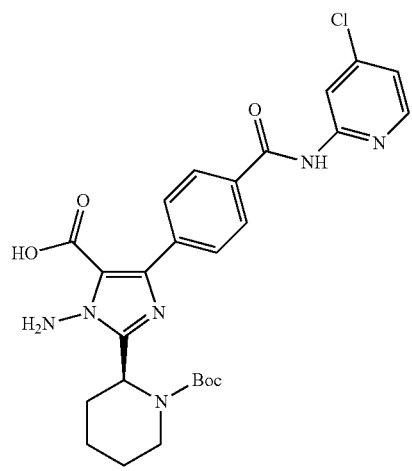

To the solution of 1.24 g (2.3 mmol) of the product of Step C in dry N,N-Dimethylformamide (12 mL) were added HATU (1.3 g, 3.5 mmol), diisopropylethylamine (1.2 mL, 6.9 mmol) and NH₄Cl (1.2 g, 23 mmol). The reaction mixture was stirred at room temperature for 2 h. The mixture was quenched with brine and washed with ethyl acetate three times (3×100 mL). The combined organic layers were concentrated under reduced pressure and purified by flash chromatography with dichloromethane and methanol (30:1) to give the product tert-butyl (S)-2-(1-amino-5-carbamoyl-4-(4-((4-chloropyridin-2-yl)carbamoyl)phenyl)-1H-imidazol-2-yl)piperidine-1-carboxylate as white solid (0.76 g, 70%). $^1$H NMR (CDCl$_3$, 600 MHz) δ: 9.85 (s, 1H), 8.56 (s, 1H), 8.15-8.12 (m, 1H), 7.89 (d, J=8.0 Hz, 2H), 7.76 (d, J=8.1 Hz, 2H), 7.20 (s, 1H), 7.06 (dd, J$_1$=5.5 Hz, J$_2$=1.9 Hz, 1H), 6.41 (s, 1H), 5.96 (s, 2H), 5.44-5.38 (m, 1H), 3.68 (d, J=12.2 Hz, 1H), 3.59 (t, J=12.9 Hz, 1H), 2.97 (d, J=13.0 Hz, 1H), 2.00-1.87 (m, 1H), 1.84-1.79 (m, 2H), 1.65-1.56 (m, 2H), 1.36 (s, 9H). MS (ESI, m/z): 540.2 [M+H]$^+$.

To the solution of 323 mg (0.60 mmol) of the product of Step D in dichloromethane (6 mL) was added trifluoroacetic acid (3.6 mL). The mixture was stirred at room temperature for 1 h and then concentrated to afford (S)-1-amino-4-(4-((4-chloropyridin-2-yl)carbamoyl)phenyl)-2-(piperidin-2-yl)-1H-imidazole-5-carboxamide as a light yellow oil. MS (ESI, m/z): 440.1 [M+H]$^+$.

Step F: Preparation of (S)-2-(1-acryloylpiperidin-2-yl)-1-amino-4-(4-((4-chloropyridin-2-yl)carbamoyl)phenyl)-1H-imidazole-5-carboxamide

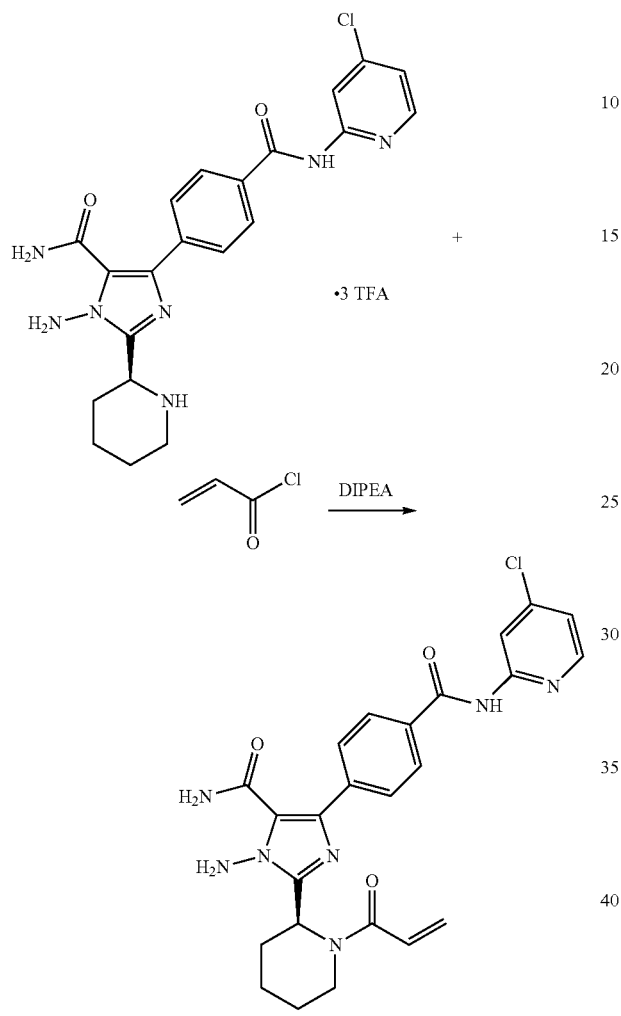

To the solution of 198 mg (0.45 mmol) of the product of Step E in dry dichloromethane (6 mL) was added diisopropylethylamine (348.9 mg, 2.7 mmol). After 5 min, acryloyl chloride (29.0 mg, 0.32 mmol) was added at 0° C. The reaction mixture was then warmed up to room temperature and continued to stir for 1 h, ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (26:1) to give (S)-2-(1-acryloylpiperidin-2-yl)-1-amino-4-(4-((4-chloropyridin-2-yl)carbamoyl)phenyl)-1H-imidazole-5-carboxamide as an off-white solid (133.4 mg, 60%). $^1$H NMR (CDCl$_3$, 400 MHz) δ: 9.22 (s, 1H), 8.48 (s, 1H), 8.18-8.17 (m, 1H), 7.89 (d, J=8.0 Hz, 2H), 7.81-7.79 (m, 2H), 7.24 (s, 1H), 7.08-7.07 (m, 1H), 6.62-6.55 (m, 1H), 6.41 (s, 1H), 6.31-6.22 (m, 3H), 5.97-5.96 (m, 1H), 5.72 (d, J=10.6 Hz, 1H), 3.83 (d, J=12.6 Hz, 1H), 3.68 (t, J=11.9 Hz, 1H), 2.43-2.40 (m, 1H), 2.19 (d, J=13.3 Hz, 1H), 1.93-1.88 (m, 2H), 1.73-1.69 (m, 1H), 1.63-1.60 (m, 1H); $^{13}$C NMR (CDCl$_3$, 150 MHz) δ: 167.3, 165.9, 162.7, 152.8, 148.5, 148.3, 146.2, 141.3, 138.6, 133.1, 129.7, 128.8, 127.8, 127.4, 120.4, 120.1, 114.7, 44.4, 43.0, 28.0, 25.8, 19.7. MS (ESI, m/z): 494.1 [M+H]$^+$.

Example 73

(S)-2-(1-acryloylpiperidin-2-yl)-1-amino-4-(4-((4-ethylpyridin-2-yl)carbamoyl)phenyl)-1H-imidazole-5-carboxamide

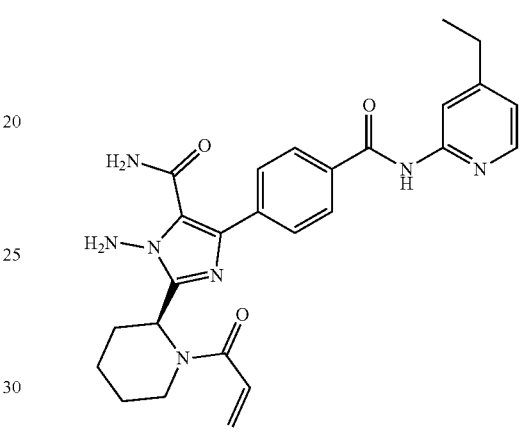

Step A: Preparation of tert-butyl (S)-2-(5-(ethoxycarbonyl)-4-(4-((4-ethylpyridin-2-yl)carbamoyl)phenyl)-1H-imidazol-2-yl)piperidine-1-carboxylate

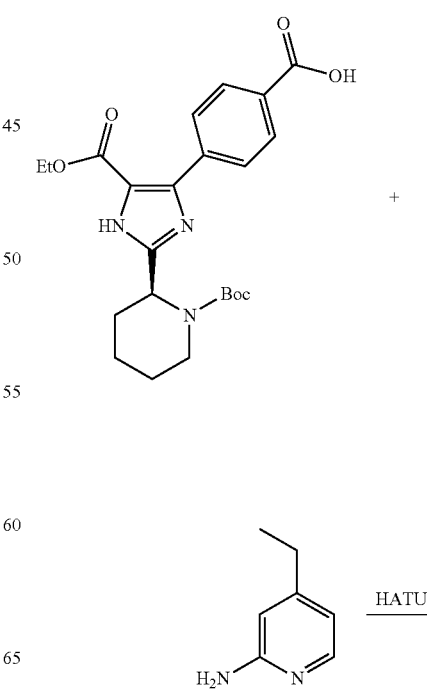

-continued

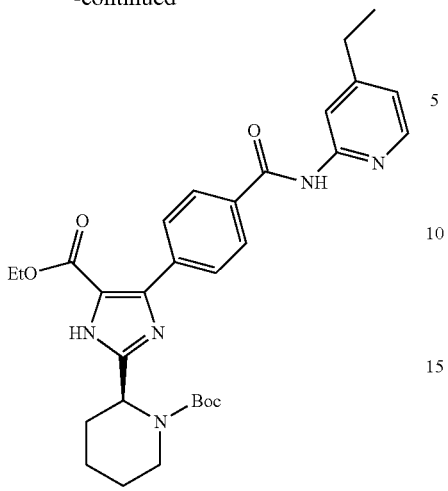

To the solution of 31.0 g (70 mmol) the product of Step C of example 46 in dry N,N-Dimethylformamide (250 mL) were added HATU (31.9 g, 84.0 mmol), diisopropylethylamine (60.3 mL, 350 mmol) and 4-ethylpyridin-2-amine (12.8 g, 105 mmol). The reaction mixture was stirred at 80° C. After the completion of the reaction (monitored by TLC), the mixture was quenched with brine and washed with ethyl acetate three times (3×180 mL). The combined organic layers were concentrated under reduced pressure and purified by flash chromatography with petroleum ether and ethyl acetate (3:1) to afford tert-butyl (S)-2-(5-(ethoxycarbonyl)-4-(4-((4-ethylpyridin-2-yl)carbamoyl)phenyl)-1H-imidazol-2-yl)piperidine-1-carboxylate as white solid (32.5 g, 85%). $^1$H NMR (CDCl$_3$, 600 MHz) δ: 10.13 (s, 1H), 8.88 (s, 1H), 8.29 (s, 1H), 8.15 (d, J=8.5 Hz, 2H), 8.12 (d, J=5.1 Hz, 1H), 7.96 (d, J=8.5 Hz, 2H), 6.90 (dd, J$_1$=5.1 Hz, J$_2$=1.4 Hz, 1H), 5.41-5.40 (m, 1H), 4.32-4.28 (m, 2H), 4.01-4.00 (m, 1H), 2.75-2.73 (m, 1H), 2.69 (q, J=7.6 Hz, 2H), 2.52 (d, J=13.0 Hz, 1H), 1.91-1.89 (m, 1H), 1.84-1.78 (m, 1H), 1.74-1.72 (m, 1H), 1.65 (d, J=13.0 Hz, 1H), 1.50 (s, 9H), 1.48-1.47 (m, 1H), 1.31-1.27 (m, 6H). MS (ESI, m/z): 548.2 [M+H]$^+$.

Step B: Preparation of tert-butyl (S)-2-(1-amino-5-(ethoxycarbonyl)-4-(4-((4-ethylpyridin-2-yl)carbamoyl)phenyl)-1H-imidazol-2-yl)piperidine-1-carboxylate

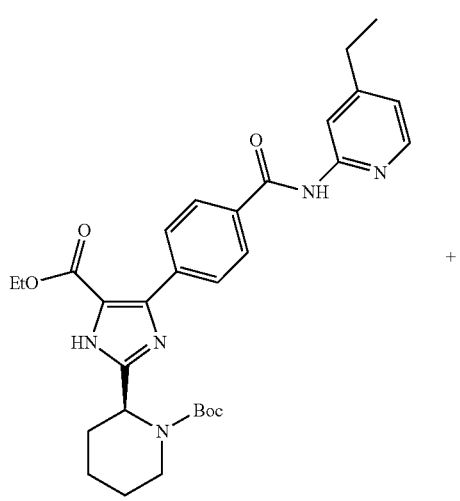

+

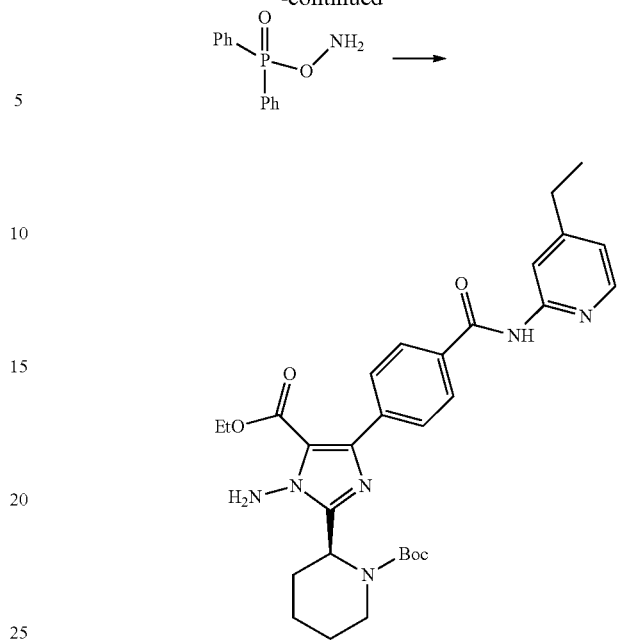

To the solution of 4.4 g (8.0 mmol) of the product of Step A in anhydrous N,N-Dimethylformamide (30 mL) was slowly added lithium hexamethyldisilazane (9.6 mL, 1 M solution in tetrahydrofuran) at −10° C. After the mixture was stirred for 20 min, O-(diphenylphosphinyl) hydroxylamine (1.9 g, 8.0 mmol) was added at 0° C. and the resulting suspension was stirred at room temperature for 2 h (in cases where the reaction mixture became too viscous, additional N,N-Dimethylformamide was added). The reaction was quenched with brine and concentrated to dryness in vacuum. The residue was washed three times (3×130 mL) with ethyl acetate. The combined organic fractions were dried with anhydrous Na$_2$SO$_4$ and the solvent was removed under reduced pressure to afford the crude residue, which was subjected to column chromatography with petroleum ether and ethyl acetate (3:1) to give the product tert-butyl (S)-2-(1-amino-5-(ethoxycarbonyl)-4-(4-((4-ethylpyridin-2-yl)carbamoyl)phenyl)-1H-imidazol-2-yl)piperidine-1-carboxylate as a white solid (3.4 g, 75%). $^1$H NMR (CDCl$_3$, 600 MHz) δ: 8.67 (s, 1H), 8.29 (s, 1H), 8.17 (d, J=5.1 Hz, 1H), 7.93 (d, J=8.5 Hz, 2H), 7.85 (d, J=8.5 Hz, 2H), 6.93 (dd, J$_1$=5.1 Hz, J$_2$=1.4 Hz, 1H), 5.93 (s, 2H), 5.68 (d, J=5.0 Hz, 1H), 4.32-4.26 (m, 2H), 3.95 (d, J=12.5 Hz, 1H), 3.42 (td, J$_1$=13.1 Hz, J$_2$=3.1 Hz, 1H), 2.71 (q, J=7.6 Hz, 2H), 2.11 (d, J=13.3 Hz, 1H), 1.92-1.87 (m, 1H), 1.75 (d, J=13.1 Hz, 1H), 1.66-1.64 (m, 1H), 1.55-1.49 (m, 1H), 1.44-1.42 (m, 10H), 1.29 (t, J=7.6 Hz, 3H), 1.25 (t, J=7.1 Hz, 3H). MS (ESI, m/z): 563.2 [M+H]$^+$.

Step C: Preparation of (S)-1-amino-2-(1-(tert-butoxycarbonyl) piperidin-2-yl)-4-(4-((4-ethylpyridin-2-yl)carbamoylphenyl)-1H-imidazole-5-carboxylic acid

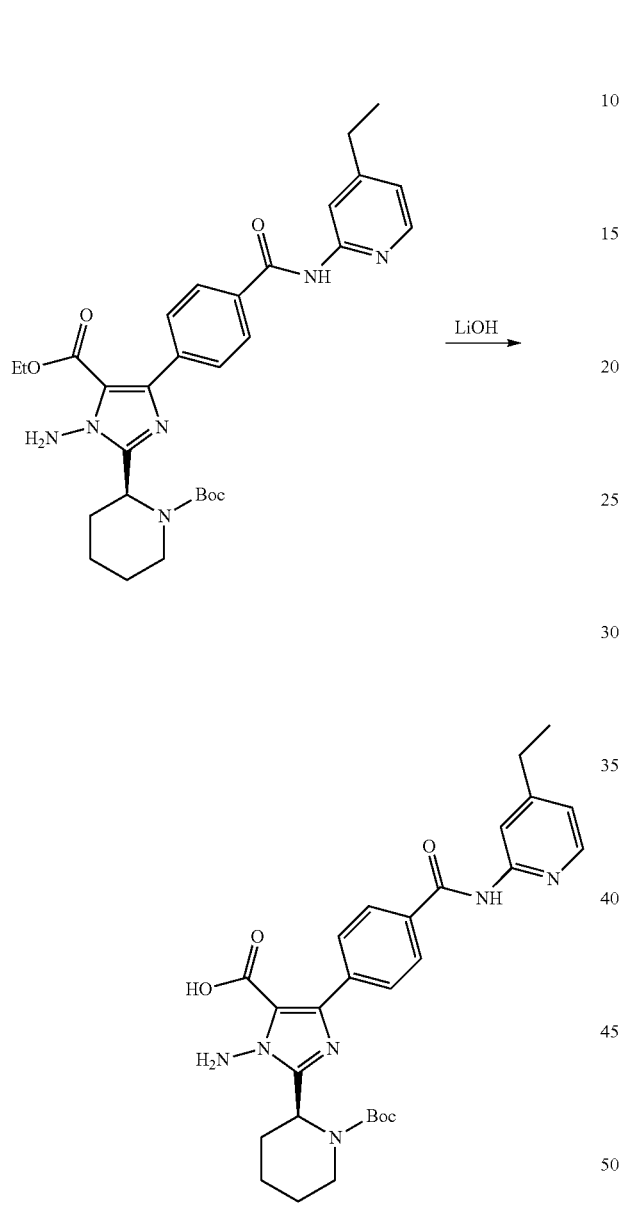

To the solution of 3.90 g (7.0 mmol) of the product of Step B in methanol (25 mL) was added 2 mol/L aqueous lithium hydroxide (35 mL) and stirred at room temperature for 2 h. The reaction mixture was evaporated and diluted with water (100 mL) and acidified with aqueous HCl till pH 3. The mixture was washed with ethyl acetate three times (3×130 mL). The white precipitate was isolated by filtration and dried to afford (S)-1-amino-2-(1-(tert-butoxycarbonyl)piperidin-2-yl)-4-(4-((4-ethylpyridin-2-yl)carbamoyl)phenyl)-1H-imidazole-5-carboxylic acid (3.60 g, 97%).

Step D: Preparation of tert-butyl (S)-2-(1-amino-5-carbamoyl-4-(4-((4-ethylpyridin-2-yl)carbamoyl)phenyl)-1H-imidazol-2-yl)piperidine-1-carboxylate

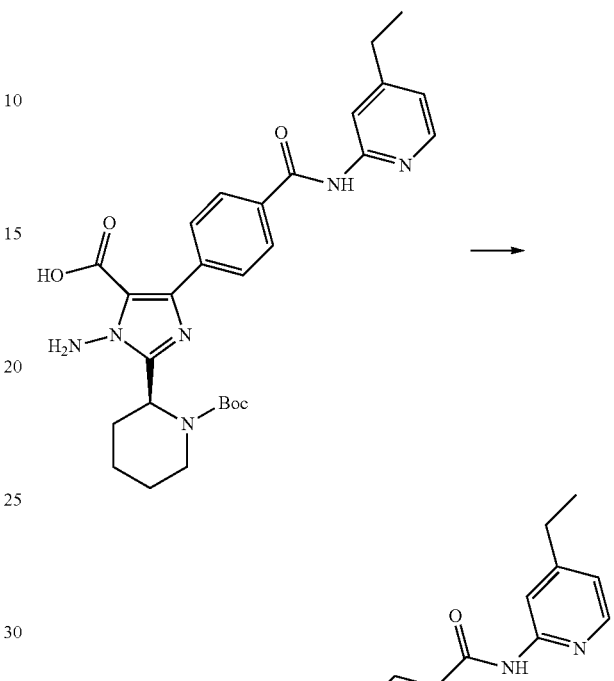

To the solution of 1.60 g (3.0 mmol) of the product of Step C in dry N,N-Dimethylformamide (17 mL) were added HATU (1.7 g, 4.5 mmol), diisopropylethylamine (1.6 mL, 9.0 mmol) and NH$_4$Cl (1.6 g, 30 mmol). The reaction mixture was stirred at room temperature for 2 h. The reaction mixture was quenched with brine and washed with ethyl acetate three times (3×90 mL). The combined organic layers were concentrated under reduced pressure and purified by flash chromatography with dichloromethane and methanol (30:1) to give the product tert-butyl (S)-2-(1-amino-5-carbamoyl-4-(4-((4-ethylpyridin-2-yl)carbamoyl)phenyl)-1H-imidazol-2-yl)piperidine-1-carboxylate as white solid (1.20 g, 75%). $^1$H NMR (CDCl$_3$, 400 MHz) δ: 8.74 (s, 1H), 8.27 (s, 1H), 8.18 (d, J=5.1 Hz, 1H), 7.96 (d, J=8.5 Hz, 2H), 7.85 (d, J=8.4 Hz, 2H), 6.94 (dd, J$_1$=5.2 Hz, J$_2$=1.4 Hz, 1H), 6.67 (s, 1H), 6.01 (s, 2H), 5.73 (s, 1H), 5.61-5.60 (m, 1H), 3.93 (d, J=13.0 Hz, 1H), 3.29 (td, J$_1$=13.0 Hz, J$_2$=2.9 Hz, 1H), 2.71 (q, J=7.6 Hz, 2H), 2.23-2.13 (m, 2H), 1.94-1.84 (m, 1H), 1.68-1.61 (m, 2H), 1.57-1.50 (m, 1H), 1.46 (s, 9H), 1.29 (t, J=7.6 Hz, 3H). MS (ESI, m/z): 534.2 [M+H]$^+$.

233
Step E: Preparation of (S)-1-amino-4-(4-((4-ethylpyridin-2-yl)carbamoyl)phenyl)-2-(piperidin-2-yl)-1H-imidazole-5-carboxamide

234
Step F: Preparation of (S)-2-(1-acryloylpiperidin-2-yl)-1-amino-4-(4-((4-ethylpyridin-2-yl)carbamoyl)phenyl)-1H-imidazole-5-carboxamide

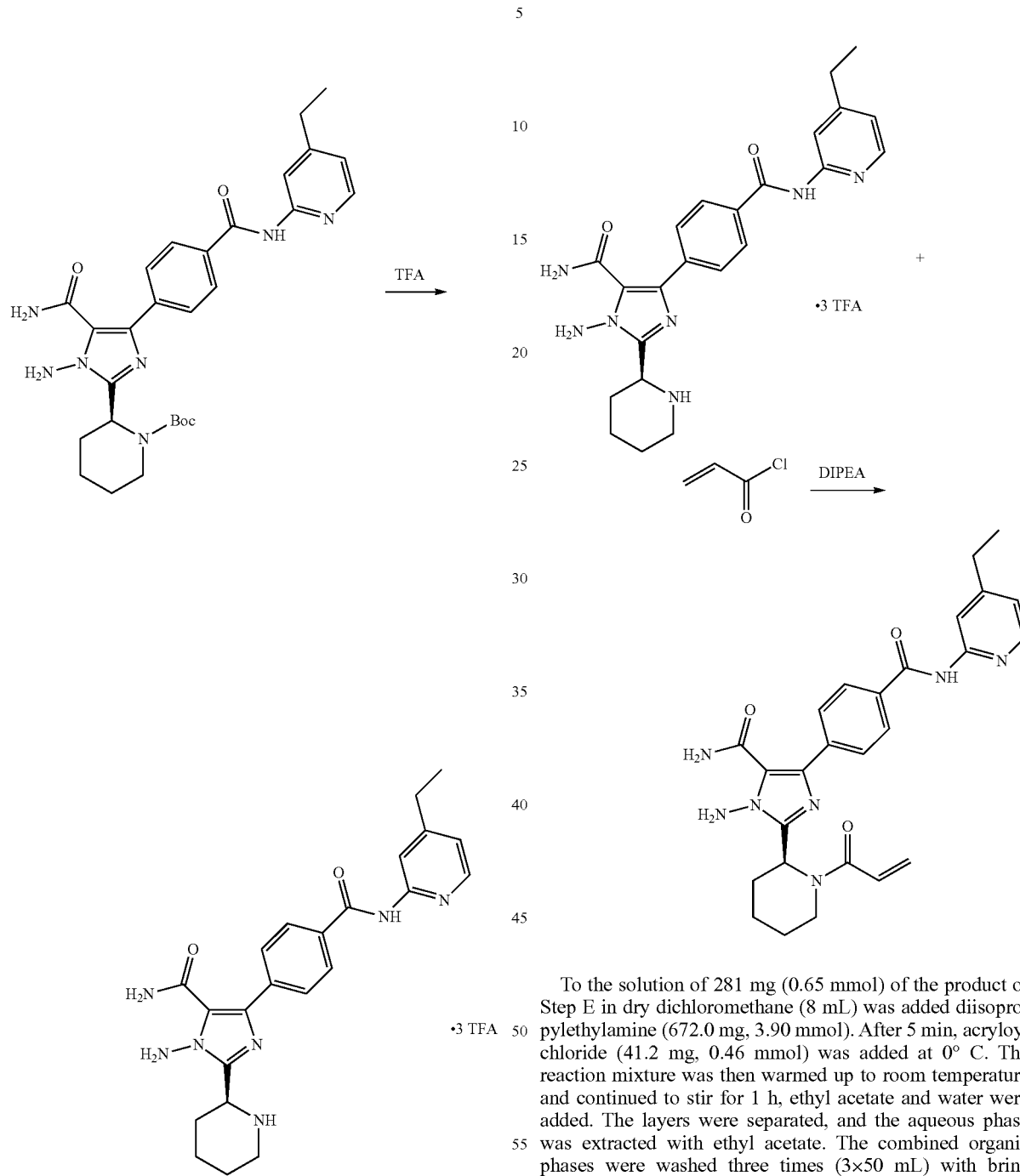

To the solution of 426 mg (0.80 mmol) of the product of Step D in dichloromethane (6 mL) was added trifluoroacetic acid (4.8 mL). The mixture was stirred at room temperature for 1 h and then concentrated to afford (S)-1-amino-4-(4-((4-ethylpyridin-2-yl)carbamoyl)phenyl)-2-(piperidin-2-yl)-1H-imidazole-5-carboxamide as a light yellow oil. MS (ESI, m/z): 434.2 [M+H]$^+$.

To the solution of 281 mg (0.65 mmol) of the product of Step E in dry dichloromethane (8 mL) was added diisopropylethylamine (672.0 mg, 3.90 mmol). After 5 min, acryloyl chloride (41.2 mg, 0.46 mmol) was added at 0° C. The reaction mixture was then warmed up to room temperature and continued to stir for 1 h, ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (26:1) to give the product (S)-2-(1-acryloylpiperidin-2-yl)-1-amino-4-(4-((4-ethylpyridin-2-yl)carbamoyl)phenyl)-1H-imidazole-5-carboxamide as an off-white solid (237.7 mg, 75%). $^1$H NMR (CDCl$_3$, 600 MHz) δ: 8.96 (s, 1H), 8.26 (s, 1H), 8.16 (d, J=5.0 Hz, 1H), 7.93 (d, J=7.9 Hz, 2H), 7.83 (d, J=6.8 Hz, 2H), 7.03 (s, 1H), 6.92 (d, J=4.9 Hz, 1H), 6.61-6.56 (m, 1H), 6.32-6.27 (m, 3H), 6.14 (s, 1H), 6.01-5.98 (m, 1H), 5.71 (d, J=10.3 Hz, 1H), 3.83 (d, J=11.5 Hz, 1H), 3.69 (t, J=12.3 Hz, 1H), 2.70 (q, J=7.6 Hz, 2H), 2.43-2.40 (m, 1H), 2.19 (d, J=13.0 Hz, 1H), 1.92-1.88 (m, 2H), 1.72-1.69 (m, 1H), 1.62-1.60 (m, 1H), 1.28 (t, J=7.6 Hz, 3H); $^{13}$C NMR(CDCl$_3$, 150 MHz) δ: 167.3, 165.7, 162.6, 156.2, 151.9, 148.2, 147.6, 141.3, 138.4, 133.8, 129.8, 128.7, 127.8, 127.4, 120.1, 119.8, 113.9, 44.4, 43.0, 28.8, 28.0, 25.8, 19.7, 14.6. MS (ESI, m/z): 488.2 [M+H]$^+$.

Example 74

(S)-1-amino-4-(4-(4-ethylpyridin-2-yl)carbamoyl)phenyl)-2-(1-methacryloylpiperidin-2-yl)-1H-imidazole-5-carboxamide

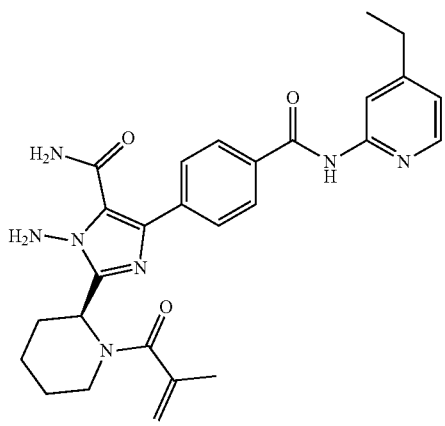 [SMILES: C=C(C)C(=O)N1CCCC[C@H]1c1nc(-c2ccc(C(=O)Nc3cc(CC)ccn3)cc2)c(C(N)=O)n1N]

Preparation of (S)-1-amino-4-(4-((4-ethylpyridin-2-yl)carbamoyl)phenyl)-2-(1-methacryloylpiperidin-2-yl)-1H-imidazole-5-carboxamide

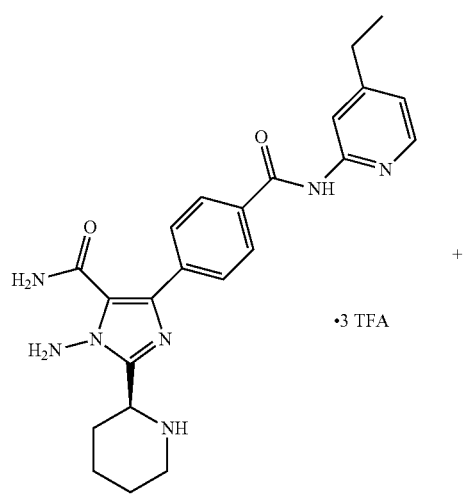

·3 TFA

+

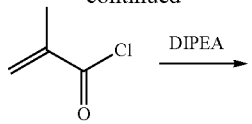

-continued

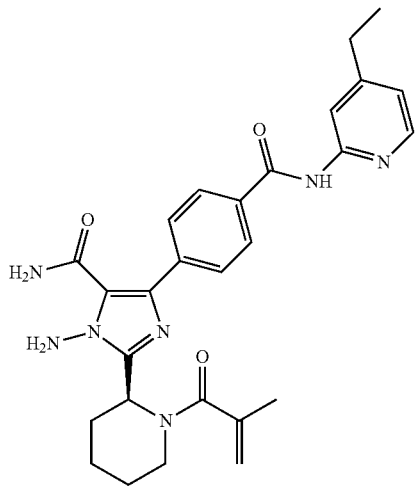

To the solution of 281 mg (0.65 mmol) of the product of Step E of example 73 in dry dichloromethane (8 mL) was added diisopropylethylamine (672.0 mg, 3.90 mmol). After 5 min, methacryloyl chloride (48.1 mg, 0.46 mmol) was added at 0° C. The reaction mixture was then warmed up to room temperature and continued to stir for 1 h, ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (26:1) to give (S)-1-amino-4-(4-((4-ethylpyridin-2-yl)carbamoyl)phenyl)-2-(1-methacryloylpiperidin-2-yl)-1H-imidazole-5-carboxamide as an off-white solid (245 mg, 75%). $^1$H NMR (CDCl$_3$, 600 MHz) δ: 9.22 (s, 1H), 8.25 (s, 1H), 8.14 (d, J=4.9 Hz, 1H), 7.91 (d, J=7.7 Hz, 2H), 7.77 (d, J=6.7 Hz, 2H), 7.02 (s, 1H), 6.91 (d, J=4.8 Hz, 1H), 6.51 (s, 1H), 6.24 (s, 2H), 5.95-5.90 (m, 1H), 5.18 (s, 1H), 5.08 (s, 1H), 3.85-3.83 (m, 1H), 3.64-3.61 (m, 1H), 2.69 (q, J=7.6 Hz, 2H), 2.34-2.32 (m, 1H), 2.20 (d, J=13.2 Hz, 1H), 1.94 (s, 3H), 1.92-1.87 (m, 1H), 1.80 (d, J=12.9 Hz, 1H), 1.70 (d, J=13.2 Hz, 1H), 1.57-1.50 (m, 1H), 1.27 (t, J=7.6 Hz, 3H); $^{13}$C NMR (CDCl$_3$, 150 MHz) δ: 173.0, 165.9, 162.8, 156.2, 151.9, 148.2, 147.5, 141.1, 140.5, 138.3, 133.8, 129.6, 127.5, 120.1, 120.0, 115.9, 114.0, 44.2, 29.8, 28.8, 28.1, 26.0, 20.5, 19.9, 14.5. MS (ESI, m/z): 502.2 [M+H]$^+$.

Example 75

(S,E)-1-amino-2-(1-(but-2-enoyl)piperidin-2-yl)-4-(4-((4-ethylpyridin-2-yl)carbamoyl)phenyl)-1H-imidazole-5-carboxamide

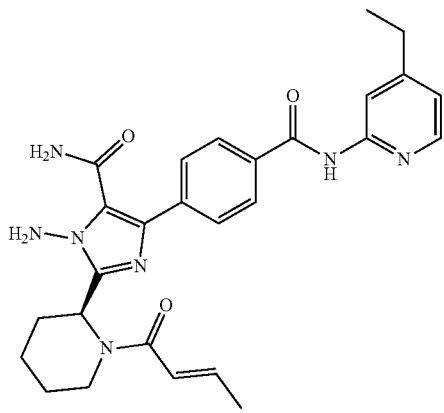 [SMILES: C/C=C/C(=O)N1CCCC[C@H]1c1nc(-c2ccc(C(=O)Nc3cc(CC)ccn3)cc2)c(C(N)=O)n1N]

Preparation of (S,E)-1-amino-2-(1-(but-2-enoyl)piperidin-2-yl)-4-(4-((4-ethylpyridin-2-yl)carbamoyl)phenyl)-1H-imidazole-5-carboxamide

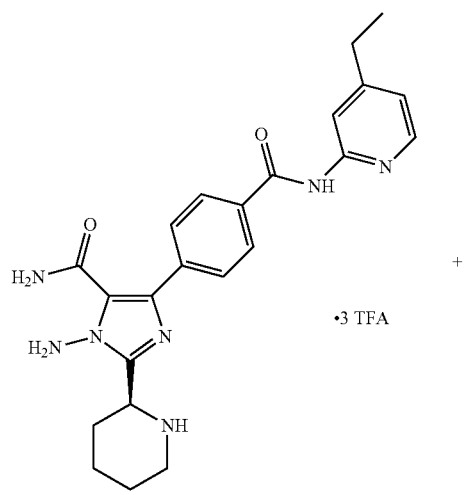

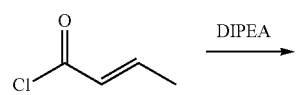

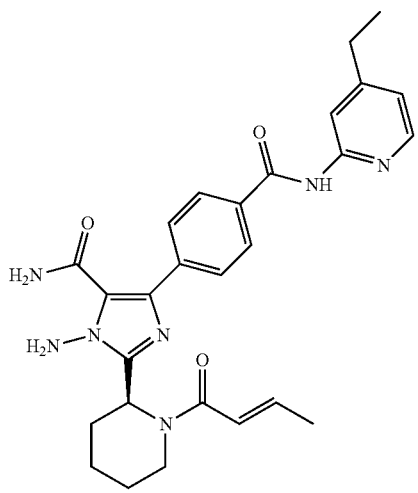

To the solution of 281 mg (0.65 mmol) of the product of Step E of example 73 in dry dichloromethane (8 mL) was added diisopropylethylamine (672.0 mg, 3.90 mmol). After 5 min, (E)-but-2-enoyl chloride (48.1 mg, 0.46 mmol) was added at 0° C. The reaction mixture was then warmed up to room temperature and continued to stir for 1 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (26:1) to give (S,E)-1-amino-2-(1-(but-2-enoyl)piperidin-2-yl)-4-(4-((4-ethylpyridin-2-yl)carbamoyl)phenyl)-1H-imidazole-5-carboxamide as an off-white solid (245 mg, 75%). $^1$H NMR ($CDCl_3$, 600 MHz) δ: 9.32 (s, 1H), 8.24 (s, 1H), 8.12-8.11 (m, 1H), 7.87 (d, J=7.3 Hz, 2H), 7.83-7.72 (m, 2H), 7.29 (s, 1H), 6.89 (d, J=4.3 Hz, 1H), 6.87-6.83 (m, 1H), 6.69 (s, 1H), 6.32 (s, 2H), 6.28-6.25 (m, 1H), 6.01-5.87 (m, 1H), 3.81-3.80 (m, 1H), 3.68-3.57 (m, 1H), 2.67 (q, J=7.3 Hz, 2H), 2.40-2.39 (m, 1H), 2.15 (d, J=12.4 Hz, 1H), 1.93-1.76 (m, 5H), 1.68-1.66 (m, 1H), 1.58-1.56 (m, 1H), 1.26 (t, J=7.5 Hz, 3H); $^{13}$C NMR ($CDCl_3$, 150 MHz) δ: 167.3, 166.0, 162.8, 156.1, 152.0, 148.3, 147.5, 142.7, 141.2, 138.3, 133.6, 129.5, 127.3, 121.7, 120.1, 119.9, 114.0, 44.3, 42.8, 28.7, 28.0, 25.8, 19.7, 18.4, 14.5. MS (ESI, m/z): 502.2 [M+H]$^+$.

Example 76

(S)-1-amino-4-(4-((4-ethylpyridin-2-yl)carbamoyl)phenyl)-2-(1-(3-methylbut-2-enoyl)piperidin-2-yl)-1H-imidazole-5-carboxamide

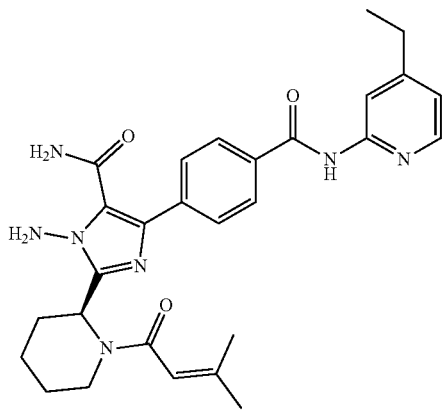 [SMILES: CCc1ccnc(NC(=O)c2ccc(-c3nc([C@@H]4CCCCN4C(=O)C=C(C)C)n(N)c3C(N)=O)cc2)c1]

Preparation of (S)-1-amino-4-(4-((4-ethylpyridin-2-yl)carbamoyl)phenyl)-2-(1-(3-methylbut-2-enoyl)piperidin-2-yl)-1H-imidazole-5-carboxamide

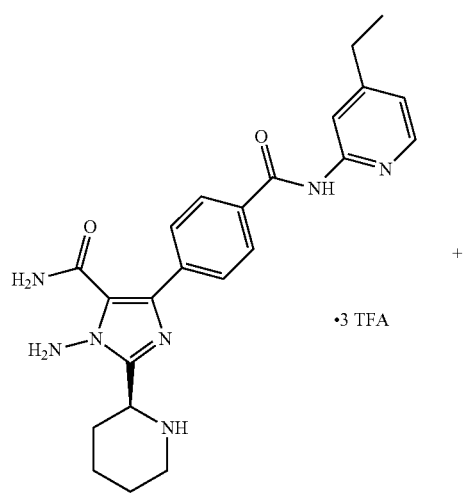
·3 TFA

+

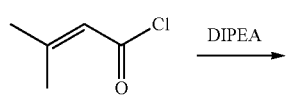
DIPEA

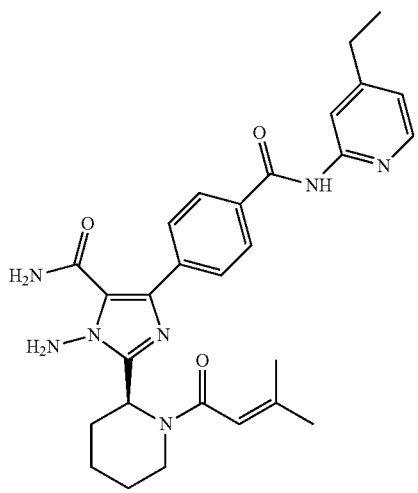

To the solution of 281 mg (0.65 mmol) of the product of Step E of example 73 in dry dichloromethane (8 mL) was added diisopropylethylamine (672.0 mg, 3.90 mmol). After 5 min, 3-methylbut-2-enoyl chloride (54.5 mg, 0.46 mmol) was added at 0° C. The reaction mixture was then warmed up to room temperature and continued to stir for 1 h, then ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (26:1) to give (S)-1-amino-4-(4-((4-ethylpyridin-2-yl)carbamoyl)phenyl)-2-(1-(3-methylbut-2-enoyl)piperidin-2-yl)-1H-imidazole-5-carboxamide as an off-white solid (251 mg, 75%). $^1$H NMR ($CDCl_3$, 400 MHz) δ: 9.46 (s, 1H), 8.29 (s, 1H), 8.13 (d, J=4.9 Hz, 1H), 7.94 (d, J=8.1 Hz, 2H), 7.80 (d, J=7.3 Hz, 2H), 7.20 (s, 1H), 6.92 (d, J=4.8 Hz, 1H), 6.48 (s, 1H), 6.30 (s, 2H), 6.01-5.91 (m, 1H), 5.77 (s, 1H), 3.79 (d, J=12.4 Hz, 1H), 3.61-3.55 (m, 1H), 2.69 (q, J=7.6 Hz, 2H), 2.37-2.31 (m, 1H), 2.18 (d, J=12.9 Hz, 1H), 1.94-1.79 (m, 8H), 1.69-1.52 (m, 2H), 1.27 (t, J=7.6 Hz, 3H); $^{13}$C NMR ($CDCl_3$, 150 MHz) δ: 169.0, 166.0, 162.7, 156.9, 151.7, 148.5, 146.9, 146.6, 141.2, 138.5, 133.4, 129.6, 127.5, 120.1, 119.9, 118.0, 114.2, 43.7, 43.5, 28.8, 27.9, 26.2, 25.8, 20.5, 19.8, 14.5. MS (ESI, m/z): 516.2 [M+H]$^+$.

Example 77

(S)-1-amino-2-(1-(but-2-ynoyl)piperidin-2-yl)-4-(4-((4-ethylpyridin-2-yl)carbamoyl)phenyl)-1H-imidazole-5-carboxamide

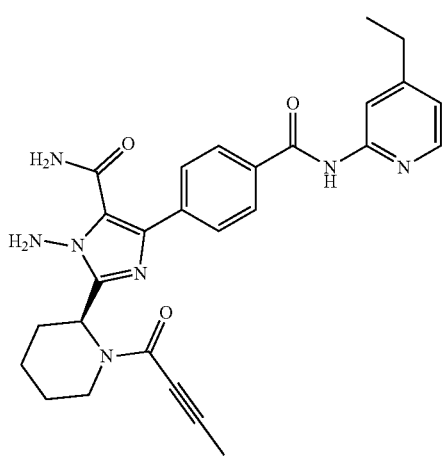 [SMILES: CC#CC(=O)N1CCCC[C@H]1c1nc(-c2ccc(C(=O)Nc3cc(CC)ccn3)cc2)c(C(N)=O)n1N]

Preparation of (S)-1-amino-2-(1-(but-2-ynoyl)piperidin-2-yl)-4-(4-((4-ethylpyridin-2-yl)carbamoyl)phenyl)-1H-imidazole-5-carboxamide

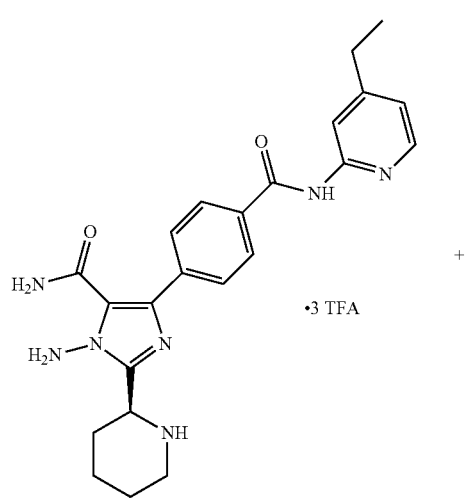

·3 TFA

+

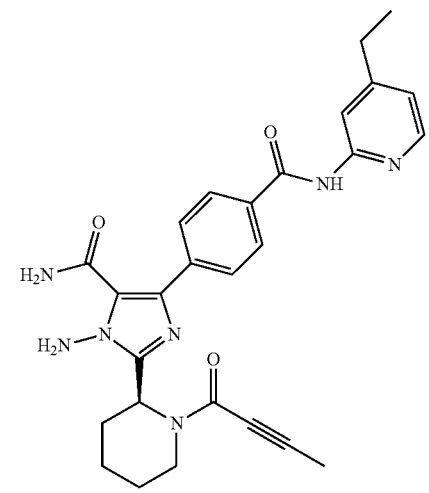

To the solution of 281 mg (0.65 mmol) of the product of Step E of example 73 in dry N,N-Dimethylformamide (5 mL) was added triethylamine (394.6 mg, 3.9 mmol). After 5 min, but-2-ynoic acid (51.9 mg, 0.62 mmol) and HATU (370.7 mg, 0.98 mmol) were added. The reaction mixture was continued to stir at room temperature for 2 h, then ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(but-2-ynoyl)piperidin-2-yl)-4-(4-((4-ethylpyridin-2-yl)carbamoyl)phenyl)-1H-imidazole-5-carboxamide as an off-white solid (194.8 mg, 60%). $^1$H NMR ($CDCl_3$, 400 MHz) δ: 9.04 (s, 1H), 8.25 (s, 1H), 8.15 (d, J=5.1 Hz, 1H), 7.92 (d, J=8.4 Hz, 2H), 7.80 (d, J=8.4 Hz, 1.7H), 7.71 (d, J=8.4 Hz, 0.3H), 6.96 (s, 1H), 6.92-6.90 (m, 1H), 6.30 (s, 1H), 6.13 (s, 2H), 5.95-5.94 (m, 1H), 4.27 (d, J=12.6 Hz, 1H), 3.66 (td, $J_1$=13.2 Hz, $J_2$=3.0 Hz, 1H), 2.69 (q, J=7.6 Hz, 2H), 2.40-2.30 (m, 1H), 2.17-2.14 (m, 1H), 2.00 (s, 3H), 1.90-1.84 (m, 2H), 1.72-1.68 (m, 1H), 1.61-1.56 (m, 1H), 1.27 (t, J=7.6 Hz, 3H); $^{13}$C NMR ($CDCl_3$, 150 MHz) δ: 165.6, 162.5, 156.3, 155.0, 151.8, 147.9, 147.6, 141.2, 138.3, 133.9, 129.8, 127.5, 120.1, 119.8, 113.9, 90.9, 73.0, 44.5, 43.8, 28.8, 27.8, 25.8, 19.9, 14.6, 4.3. MS (ESI, m/z): 500.2 [M+H]$^+$.

Example 78

(S,E)-1-amino-2-(1-(2-cyano-3-cyclopropylacryloyl)piperidin-2-yl)-4-(4-((4-ethylpyridin-2-yl)carbamoyl)phenyl)-1H-imidazole-5-carboxamide

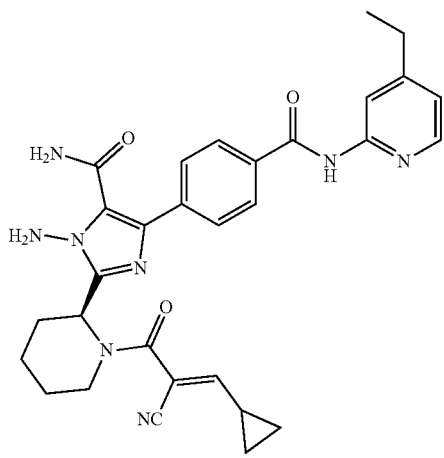 [SMILES: CCc1ccnc(NC(=O)c2ccc(-c3nc([C@@H]4CCCCN4C(=O)/C(C#N)=C/C4CC4)n(N)c3C(N)=O)cc2)c1]

Step A: Preparation of (S)-1-amino-2-(1-(2-cyanoacetyl)piperidin-2-yl)-4-(4-((4-ethylpyridin-2-yl)carbamoyl)phenyl)-1H-imidazole-5-carboxamide

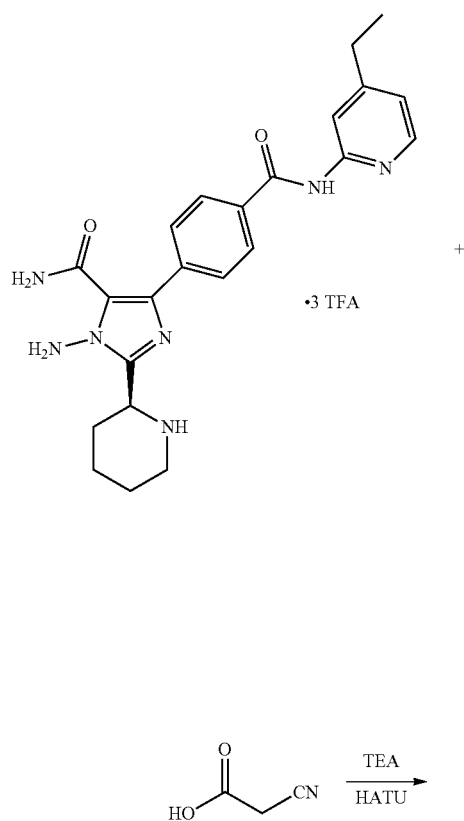

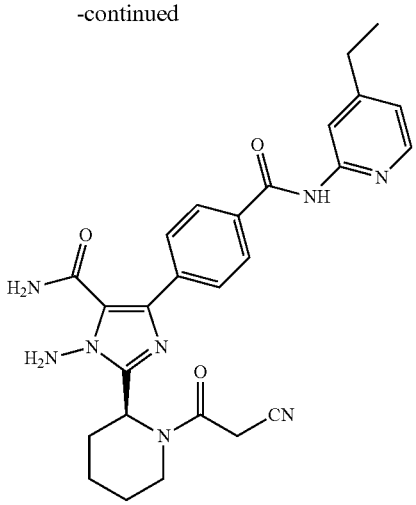

To the solution of 281 mg (0.65 mmol) of the product of Step E of example 73 in dry N,N-Dimethylformamide (5 mL) was added triethylamine (394.6 mg, 3.9 mmol). After 5 min, 2-cyanoacetic acid (52.7 mg, 0.62 mmol) and HATU (370.7 mg, 0.98 mmol) were added. The reaction mixture was continued to stir at room temperature for 2 h. Then, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(2-cyanoacetyl)piperidin-2-yl)-4-(4-((4-ethylpyridin-2-yl)carbamoyl)phenyl)-1H-imidazole-5-carboxamide as an off-white solid (195.2 mg, 60%). $^1$H NMR ($CDCl_3$, 600 MHz) δ: 9.38 (s, 1H), 8.19 (s, 1H), 8.14-8.10 (m, 1H), 7.89-7.83 (m, 2H), 7.70-7.69 (m, 2H), 7.08 (s, 1H), 6.92-6.89 (m, 1H), 6.79 (s, 1H), 6.09-5.82 (m, 3H), 3.87-3.81 (m, 1H), 3.61-3.55 (m, 2H), 3.47-3.45 (m, 1H), 2.72-2.66 (m, 2H), 2.23-2.14 (m, 2H), 1.90-1.83 (m, 2H), 1.65-1.59 (m, 2H), 1.24-1.19 (m, 3H); $^{13}$C NMR ($CDCl_3$, 150 MHz) δ: 166.0, 163.0, 162.6, 156.3, 151.9, 148.2, 147.4, 140.7, 137.9, 133.7, 129.3, 128.7, 127.8, 127.4, 120.0, 114.1, 45.3, 44.0, 28.7, 27.7, 25.6, 25.34, 19.2, 14.5. MS (ESI, m/z): 501.2 [M+H]$^+$.

Step B: Preparation of (S,E)-1-amino-2-(1-(2-cyano-3-cyclopropyl-acryloyl)piperidin-2-yl)-4-(4-((4-ethylpyridin-2-yl)carbamoyl)phenyl)-1H-imidazole-5-carboxamide

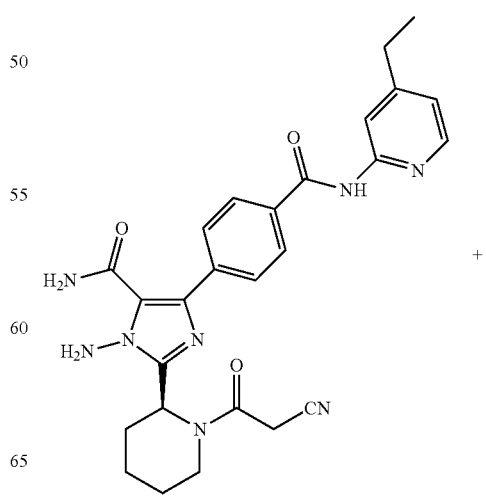

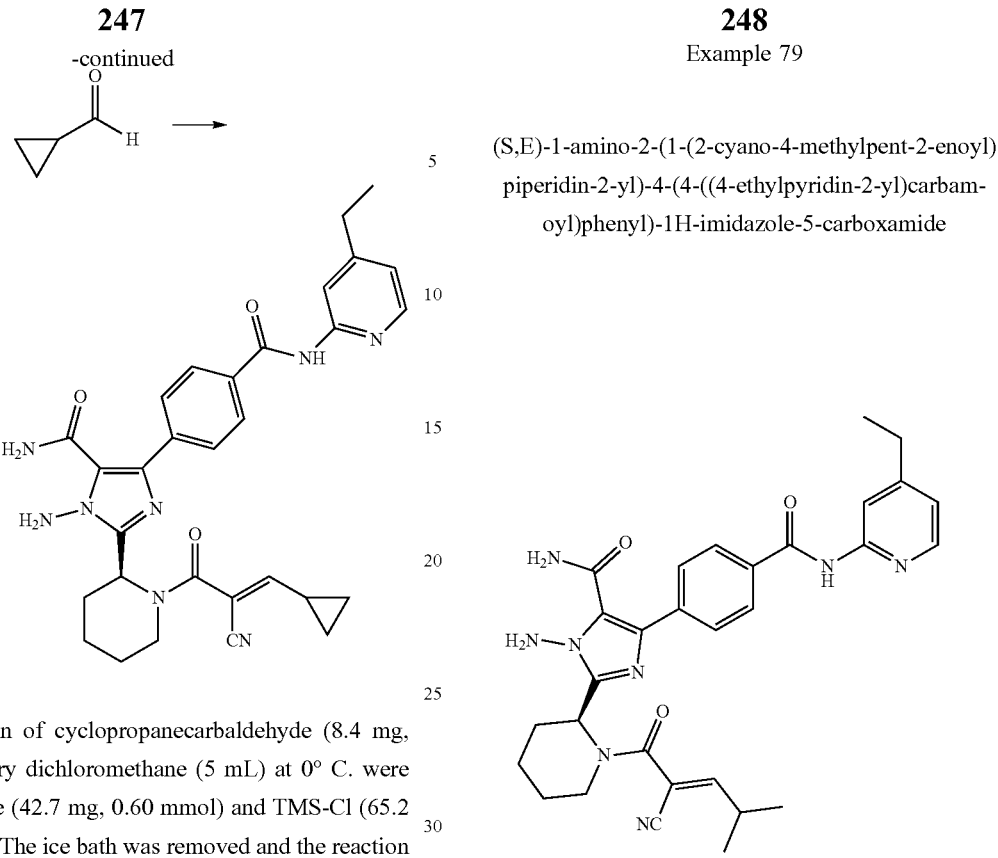

To the solution of cyclopropanecarbaldehyde (8.4 mg, 0.12 mmol) in dry dichloromethane (5 mL) at 0° C. were added pyrrolidine (42.7 mg, 0.60 mmol) and TMS-Cl (65.2 mg, 0.60 mmol). The ice bath was removed and the reaction mixture was stirred for 10 min followed by the additions of 60.1 mg (0.12 mmol) of the product of Step A. The reaction solution was stirred for 1 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to afford (S,E)-1-amino-2-(1-(2-cyano-3-cyclopropylacryloyl)piperidin-2-yl)-4-(4-((4-ethylpyridin-2-yl)carbamoyl)phenyl)-1H-imidazole-5-carboxamide as a white solid (33.2 mg, 50%). $^1$H NMR (CDCl$_3$, 400 MHz) δ: 9.17 (s, 1H), 8.31 (s, 1H), 8.18 (d, J=5.0 Hz, 1H), 7.99 (d, J=8.0 Hz, 2H), 7.83 (d, J=7.9 Hz, 2H), 6.97 (d, J=4.8 Hz, 1H), 6.56 (d, J=11.2 Hz, 1H), 6.45 (s, 1H), 6.20 (s, 2H), 5.88 (s, 1H), 5.77 (d, J=4.1 Hz, 1H), 4.03-3.98 (m, 1H), 3.84-3.78 (m, 1H), 2.73 (q, J=7.6 Hz, 2H), 2.36-2.32 (m, 1H), 2.21-2.17 (m, 1H), 2.11-2.04 (m, 1H), 2.01-1.96 (m, 1H), 1.90-1.87 (m, 1H), 1.78-1.70 (m, 2H), 1.30 (t, J=7.6 Hz, 3H), 1.25-1.23 (m, 2H), 0.93-0.83 (m, 2H); $^{13}$C NMR (CDCl$_3$, 150 MHz) δ: 166.2, 165.9, 165.7, 164.1, 162.9, 156.2, 151.9, 147.5, 138.0, 133.8, 129.5, 129.2, 127.6, 127.5, 120.0, 115.4, 114.0, 107.6, 45.7, 45.0, 28.7, 28.3, 25.2, 19.7, 15.8, 14.6, 10.9, 10.8. MS (ESI, m/z): 553.2 [M+H]$^+$.

Example 79

(S,E)-1-amino-2-(1-(2-cyano-4-methylpent-2-enoyl)piperidin-2-yl)-4-(4-((4-ethylpyridin-2-yl)carbamoyl)phenyl)-1H-imidazole-5-carboxamide

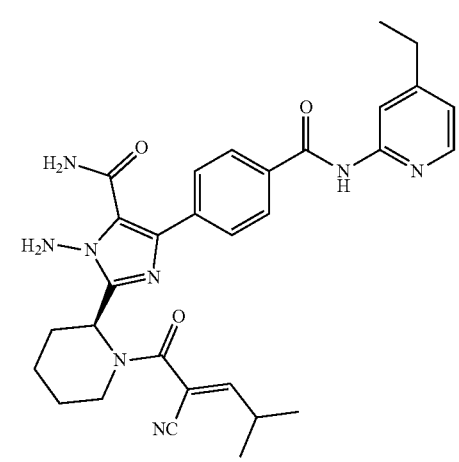 [SMILES: CCc1ccnc(NC(=O)c2ccc(-c3nc([C@@H]4CCCCN4C(=O)/C(C#N)=C/C(C)C)n(N)c3C(N)=O)cc2)c1]

Preparation of (S,E)-1-amino-2-(1-(2-cyano-4-methylpent-2-enoyl)piperidin-2-yl)-4-(4-((4-ethylpyridin-2-yl)carbamoyl)phenyl)-1H-imidazole-5-carboxamide

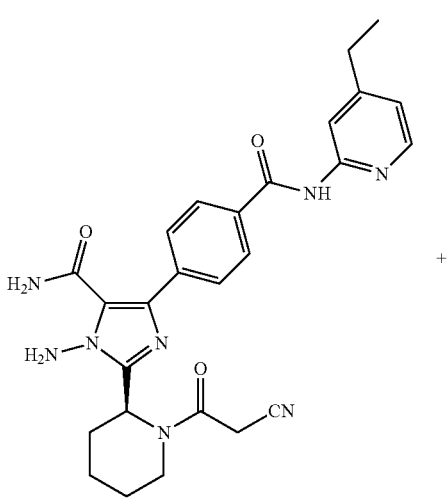

249

-continued

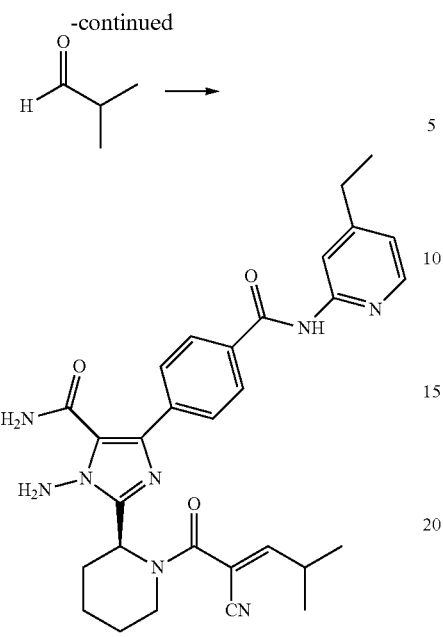

To the solution of isobutyraldehyde (8.6 mg, 0.12 mmol) in dry dichloromethane (5 mL) at 0° C. were added pyrrolidine (42.7 mg, 0.60 mmol) and TMS-Cl (65.2 mg, 0.60 mmol). The ice bath was removed and the reaction mixture was stirred for 10 min followed by the additions of 60.1 mg (0.12 mmol) of the product of Step A of example 78. The reaction solution was stirred for 1 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to afford (S,E)-1-amino-2-(1-(2-cyano-4-methylpent-2-enoyl)piperidin-2-yl)-4-(4-((4-ethylpyridin-2-yl)carbamoyl)phenyl)-1H-imidazole-5-carboxamide as a white solid (33.3 mg, 50%). $^1H$ NMR (CDCl$_3$, 400 MHz) δ: 8.87 (s, 1H), 8.27 (s, 1H), 8.18 (d, J=5.1 Hz, 1H), 7.97 (d, J=8.4 Hz, 2H), 7.82 (d, J=8.4 Hz, 1.5H), 7.77 (d, J=8.4 Hz, 0.5H) 6.94 (dd, $J_1$=5.2 Hz, $J_2$=1.4 Hz, 1H), 6.90 (d, J=10.4 Hz, 1H), 6.56 (s, 1H), 6.22 (s, 2H), 5.98-5.81 (m, 2H), 3.88-3.74 (m, 1H), 3.03-2.90 (m, 1H), 2.71 (q, J=7.5 Hz, 2H), 2.36-2.18 (m, 2H), 2.04-1.94 (m, 1H), 1.89-1.86 (m, 1H), 1.76-1.73 (m, 3H), 1.29 (t, J=7.6 Hz, 3H), 1.17-1.00 (m, 6H); $^{13}C$ NMR (CDCl$_3$, 150 MHz) δ: 165.5, 162.6, 160.6, 156.3, 151.8, 147.6, 140.6, 138.0, 134.1, 129.7, 129.5, 127.7, 127.6, 120.2, 120.1, 114.3, 113.9, 109.5, 45.6, 45.1, 31.8, 30.2, 28.8, 25.2, 21.7, 21.6, 20.0, 14.6. MS (ESI, m/z): 555.2 [M+H]$^+$.

250

Example 80

(S,E)-1-amino-4-(4-((4-ethylpyridin-2-yl)carbamoyl)phenyl)-2-(1-(pent-2-enoyl)piperidin-2-yl)-1H-imidazole-5-carboxamide

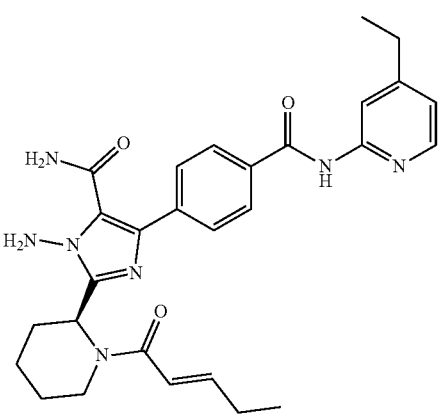 [SMILES: CC/C=C/C(=O)N1CCCC[C@H]1c1nc(-c2ccc(C(=O)Nc3cc(CC)ccn3)cc2)c(C(N)=O)n1N]

Preparation of (S,E)-1-amino-4-(4-((4-ethylpyridin-2-yl)carbamoyl)phenyl)-2-(1-(pent-2-enoyl)piperidin-2-yl)-1H-imidazole-5-carboxamide

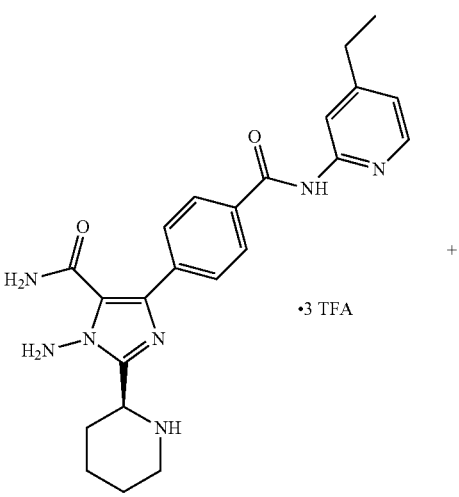

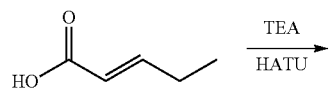

-continued

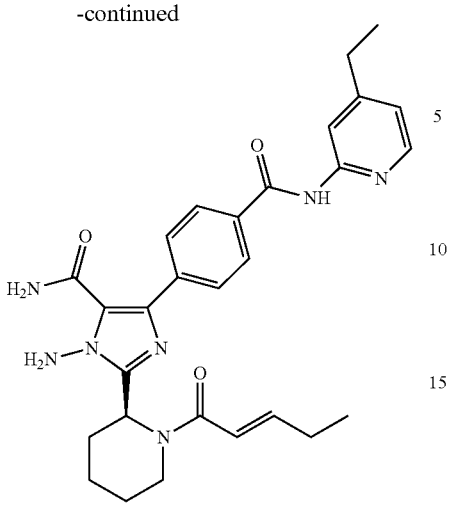

To the solution of 281 mg (0.65 mmol) of the product of Step E of example 73 in dry N,N-Dimethylformamide (5 mL) was added triethylamine (394.6 mg, 3.9 mmol). After 5 min, (E)-pent-2-enoic acid (62.1 mg, 0.62 mmol) and HATU (370.7 mg, 0.98 mmol) were added. The reaction mixture was continued to stir at room temperature for 2 h. Then, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S,E)-1-amino-4-(4-((4-ethylpyridin-2-yl)carbamoyl)phenyl)-2-(1-(pent-2-enoyl)piperidin-2-yl)-1H-imidazole-5-carboxamide as an off-white solid (201.1 mg, 60%). $^1$H NMR (600 MHz, $CDCl_3$) δ: 9.32 (s, 1H), 8.24 (s, 1H), 8.12 (d, J=4.6 Hz, 1H), 7.88 (d, J=7.9 Hz, 2H), 7.83-7.73 (m, 2H), 7.30 (s, 1H), 6.92-6.87 (m, 2H), 6.69 (s, 2H), 6.35 (s, 2H), 6.23 (d, J=14.6 Hz, 1H), 6.00-5.95 (m, 1H), 3.82-3.81 (m, 1H), 3.65-3.63 (m, 1H), 2.67 (q, J=7.6 Hz, 2H), 2.43-2.41 (m, 1H), 2.23-2.14 (m, 3H), 1.90-1.83 (m, 2H), 1.69-1.67 (m, 1H), 1.59-1.57 (m, 1H), 1.26 (t, J=7.6 Hz, 3H), 1.04 (t, J=7.4 Hz, 3H); $^{13}$C NMR (150 MHz, $CDCl_3$) δ: 167.5, 166.0, 162.8, 156.1, 152.0, 149.0, 148.3, 147.4, 141.2, 138.3, 133.5, 129.6, 127.3, 120.0, 119.9, 119.3, 114.0, 44.2, 42.8, 28.7, 28.0, 25.8, 25.8, 19.7, 14.5, 12.6. MS (ESI, m/z): 516.2 [M+H]$^+$.

Example 81

(S)-2-(1-acryloylpiperidin-2-yl)-4-(4-((4-ethylpyridin-2-yl)carbamoyl)phenyl)-1-(methylamino)-1H-imidazole-5-carboxamide

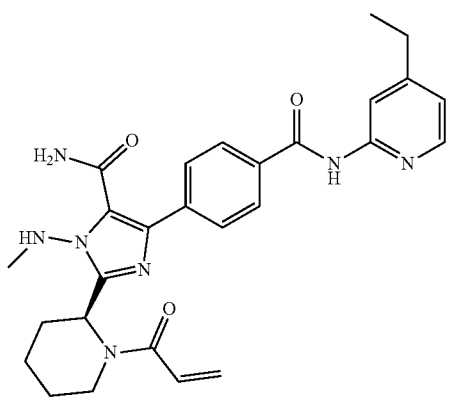 [SMILES: C=CC(=O)N1CCCC[C@H]1c1nc(-c2ccc(C(=O)Nc3cc(CC)ccn3)cc2)c(C(N)=O)n1NC]

Step A: Preparation of (S)-tert-butyl 2-(5-(ethoxycarbonyl)-4-(4-((4-ethylpyridin-2-yl)carbamoyl)phenyl)-1-(2,2,2-trifluoroacetamido)-1H-imidazol-2-yl)piperidine-1-carboxylate

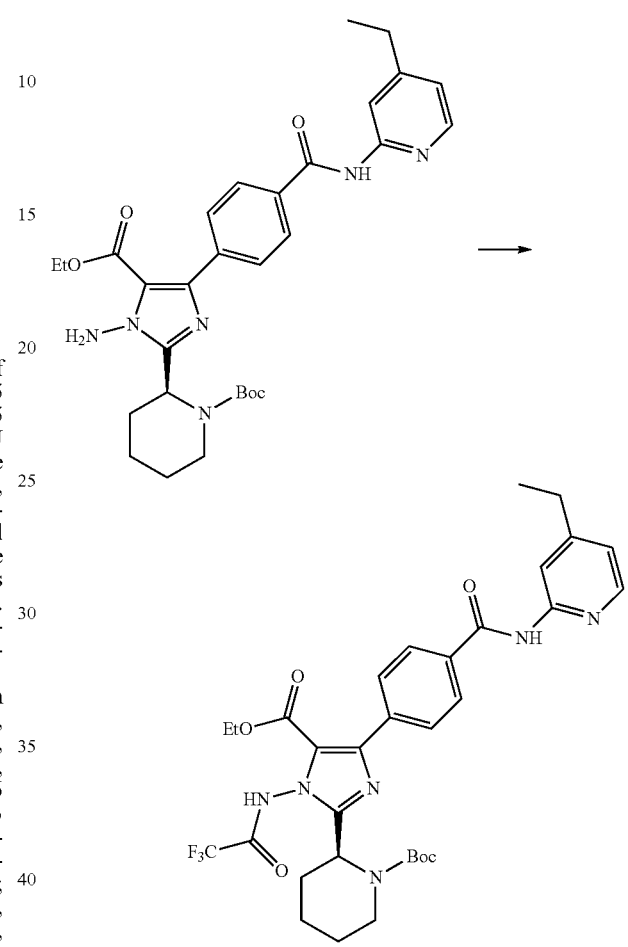

To the solution of 528 mg (0.94 mmol) of the product of Step B of example 73 in dichloromethane (5 mL), the triethylamine (400 μL, 2.82 mmol) was added at 0° C. and stirred for 30 min. Then the solution of trifluoroacetic anhydride (330 μL, 2.35 mmol) was added dropwise to the reaction mixture and stirred at room temperature for 10 h. After completion of reaction, the mixture was diluted with water (50 mL) and it was washed with saturated $NaHCO_3$ (15 mL). The aqueous layer was washed with dichloromethane (2×15 mL) and the organic layers were combined, dried with anhydrous $Na_2SO_4$, filtered and concentrated. The residue was purified by chromatography with petroleum ether and ethyl acetate (2.5:1) to afford (S)-tert-butyl 2-(5-(ethoxycarbonyl)-4-(4-((4-ethylpyridin-2-yl)carbamoyl)phenyl)-1-(2,2,2-trifluoroacetamido)-1H-imidazol-2-yl) piperidine-1-carboxylate as yellow oil (305 g, 49%). $^1$H NMR ($CDCl_3$, 600 MHz) δ: 9.03 (s, 1H), 8.30 (s, 1H), 8.17 (d, J=4.6 Hz, 1H), 7.85-7.82 (m, 4H), 6.95 (d, J=4.6 Hz, 1H), 5.39-5.38 (m, 1H), 4.13-4.12 (m, 2H), 3.93-3.91 (m, 1H), 3.36-3.21 (m, 1H), 2.71 (q, J=7.5 Hz, 2H), 2.22-2.17 (m, 1H), 2.09-2.07 (m, 1H), 1.84-1.80 (m, 1H), 1.73-1.65 (m, 2H), 1.50-1.48 (m, 1H), 1.43 (s, 9H), 1.29 (t, J=7.2 Hz, 3H), 1.14 (t, J=7.0 Hz, 3H). MS (ESI, m/z): 659.2 [M+H]$^+$.

Step B: Preparation of (S)-tert-butyl2-(5-(ethoxy-carbonyl)-4-(4-((4-ethylpyridin-2-yl)carbamoyl)phenyl)-1-(2,2,2-trifluoro-N-methylacetamido)-1H-imidazol-2-yl)piperidine-1-carboxylate

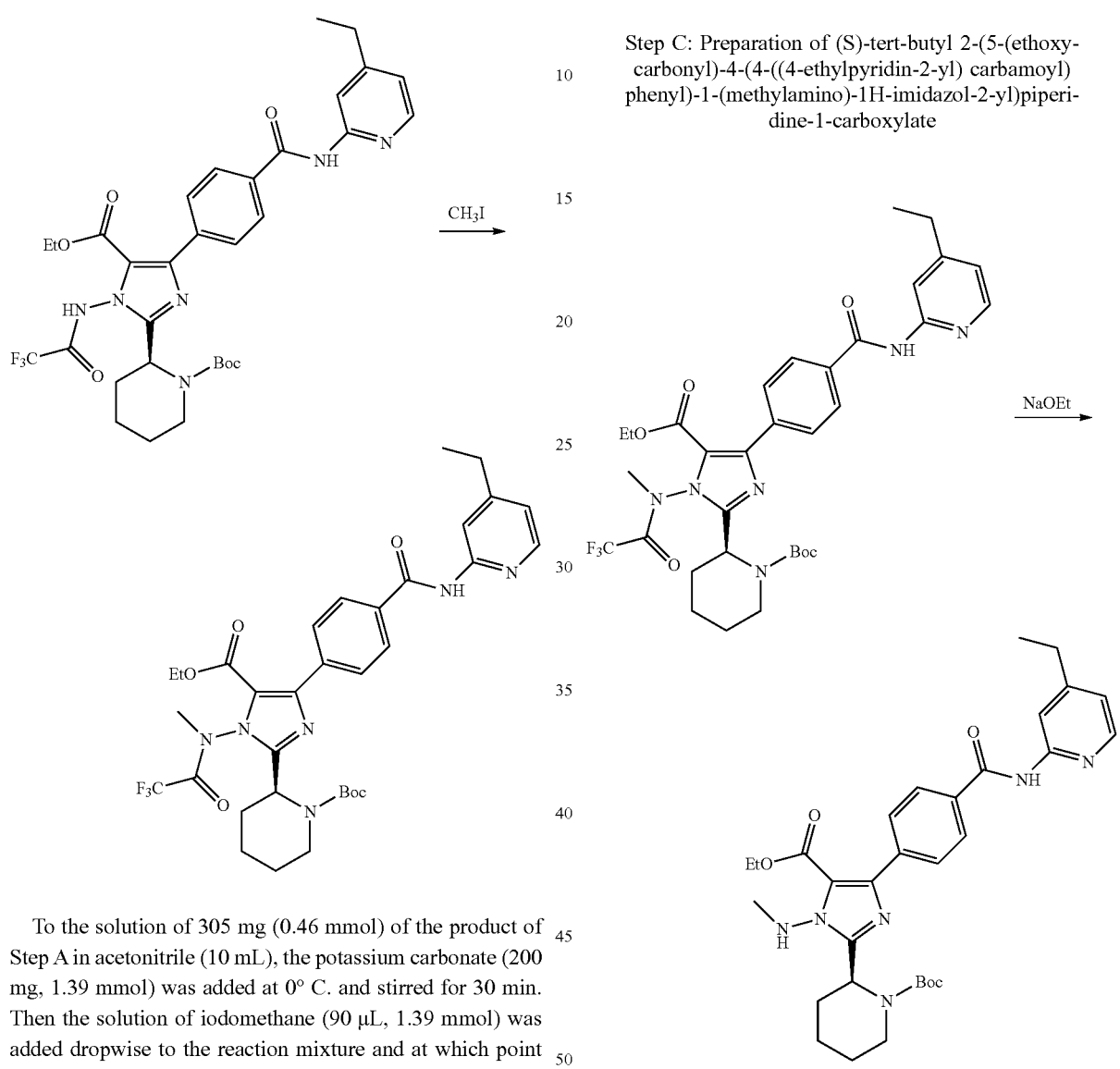

To the solution of 305 mg (0.46 mmol) of the product of Step A in acetonitrile (10 mL), the potassium carbonate (200 mg, 1.39 mmol) was added at 0° C. and stirred for 30 min. Then the solution of iodomethane (90 µL, 1.39 mmol) was added dropwise to the reaction mixture and at which point the temperature was increased to 80° C. and the mixture was stirred for an additional 6 h. After completion of reaction, the mixture was diluted with water (20 mL) and partitioned between water and ethylacetate (3×30 mL). The combined organic layers were dried over anhydrous sodium sulphate and evaporated under vacuum. The residue was purified by chromatography with petroleum ether and ethyl acetate (3:1) to give the product (S)-tert-butyl-2-(5-(ethoxycarbonyl)-4-(4-((4-ethylpyridin-2-yl)carbamoyl)phenyl)-1-(2,2,2-trifluoro-N-methylacetamido)-1H-imidazol-2-yl) piperidine-1-carboxylate as yellow oil (130 mg, 42%). $^1$H NMR (CDCl$_3$, 400 MHz) δ: 8.88 (s, 1H), 8.29 (s, 1H), 8.14-8.12 (m, 1H), 8.00-7.94 (m, 3H), 7.91-7.89 (m, 1H), 6.92-6.91 (m, 1H), 5.62-5.56 (m, 1H), 4.31-4.22 (m, 2H), 3.92-3.80 (m, 1H), 3.68-3.67 (m, 1.8H), 3.50 (s, 1.2H), 2.99-2.81 (m, 1H), 2.70 (q, J=7.6 Hz, 2H), 2.49-2.40 (m, 1H), 2.29-2.15 (m, 1H), 1.91-1.82 (m, 1H), 1.77-1.71 (m, 1H), 1.66-1.60 (m, 1H), 1.44-1.41 (m, 10H), 1.30-1.22 (m, 6H). MS (ESI, m/z): 673.2 [M+H]$^+$.

Step C: Preparation of (S)-tert-butyl 2-(5-(ethoxycarbonyl)-4-(4-((4-ethylpyridin-2-yl) carbamoyl)phenyl)-1-(methylamino)-1H-imidazol-2-yl)piperidine-1-carboxylate

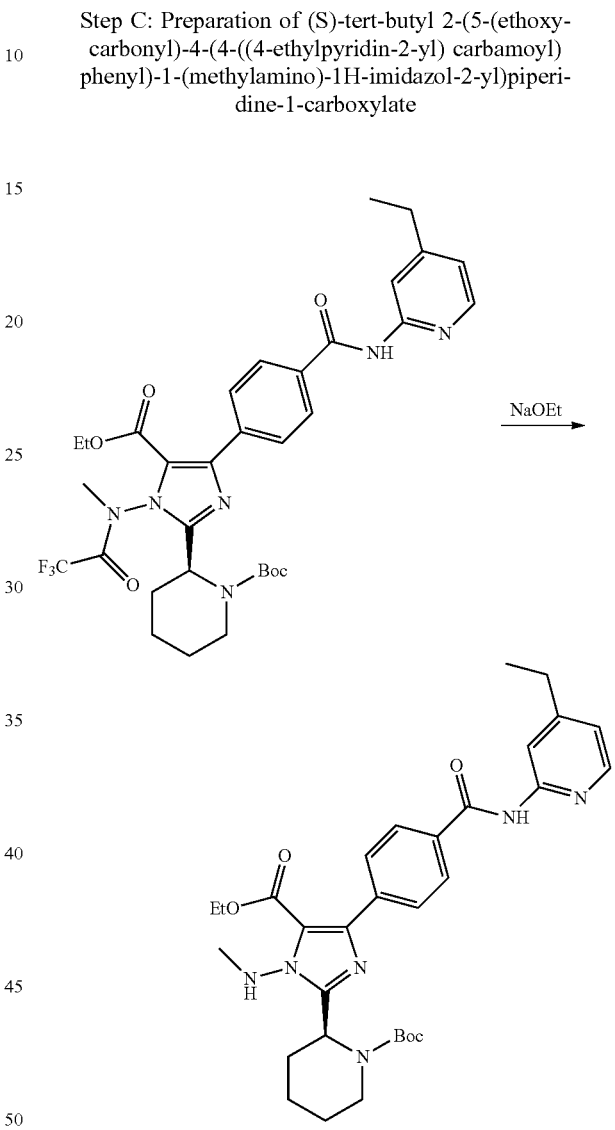

To the solution of 130 mg (0.19 mmol) of the product of Step B in ethanol (5 mL), the sodium ethoxide (20 mg, 0.29 mmol) was added at 10° C.-20° C. and stirred for 6 h. After completion of reaction, the mixture was diluted with water (100 mL) and concentrated under vacuum. Then it was partitioned between water and ethyl acetate (3×50 mL). The combined organic layers were dried over anhydrous sodium sulfate and evaporated under vacuum. The residue was purified by chromatography with petroleum ether and ethyl acetate (4:1) to afford (S)-tert-butyl 2-(5-(ethoxycarbonyl)-4-(4-((4-ethylpyridin-2-yl)carbamoyl)phenyl)-1-(methylamino)-1H-imidazol-2-yl)piperidine-1-carboxylate as a white solid (104 mg, 95%). MS (ESI, m/z): 577.3 [M+H]$^+$.

Step D: Preparation of (S)-2-(1-(tert-butoxycarbonyl) piperidin-2-yl)-4-(4-((4-ethylpyridin-2-yl)carbamoyl)phenyl)-1-(methylamino)-1H-imidazole-5-carboxylic acid

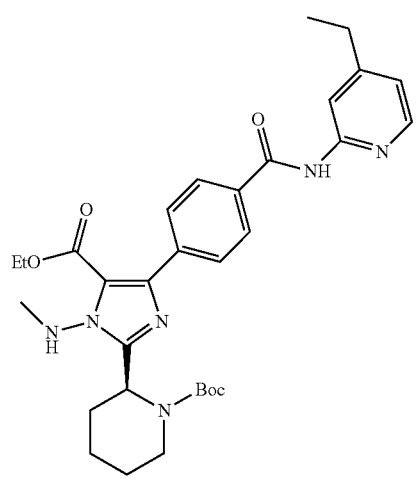

Step E: Preparation of (S)-tert-butyl 2-(5-carbamoyl-4-(4-((4-ethylpyridin-2-yl)carbamoyl)phenyl)-1-(methylamino)-1H-imidazol-2-yl)piperidine-1-carboxylate

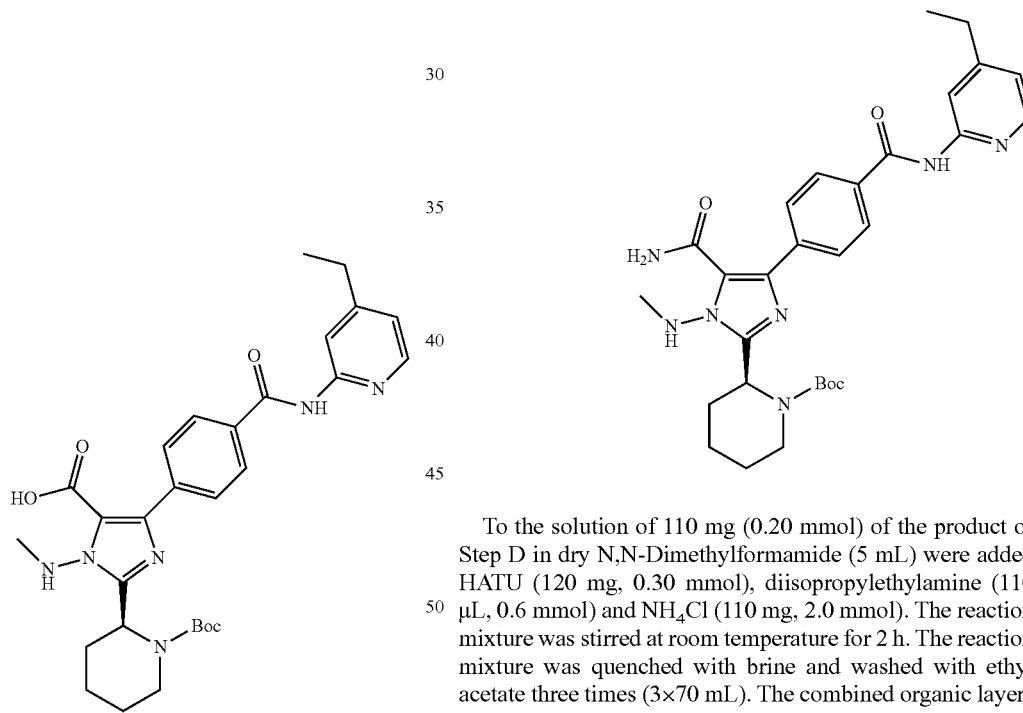

To the solution of 104 mg (0.18 mmol) of the product of Step C in methanol (3 mL) was added 2 mol/L aqueous lithium hydroxide (0.9 mL) and stirred at room temperature for 2 h. The reaction mixture was evaporated and diluted with ethyl acetate (30 mL) and acidified with aqueous HCl till pH 3. The mixture was washed with water three times (3×90 mL). The combined organic layers were concentrated under reduced pressure to afford (S)-2-(1-(tert-butoxycarbonyl)piperidin-2-yl)-4-(4-((4-ethylpyridin-2-yl)carbamoyl)phenyl)-1-(methylamino)-1H-imidazole-5-carboxylic acid (96 mg, 97%).

To the solution of 110 mg (0.20 mmol) of the product of Step D in dry N,N-Dimethylformamide (5 mL) were added HATU (120 mg, 0.30 mmol), diisopropylethylamine (110 μL, 0.6 mmol) and NH$_4$Cl (110 mg, 2.0 mmol). The reaction mixture was stirred at room temperature for 2 h. The reaction mixture was quenched with brine and washed with ethyl acetate three times (3×70 mL). The combined organic layers were concentrated under reduced pressure and purified by flash chromatography with dichloromethane and methanol (30:1) to afford (S)-tert-butyl 2-(5-carbamoyl-4-(4-((4-ethylpyridin-2-yl)carbamoyl)phenyl)-1-(methylamino)-1H-imidazol-2-yl)piperidine-1-carboxylate as white solid (60 mg, 55%). $^1$H NMR (CDCl$_3$, 600 MHz) δ: 9.06 (s, 1H), 8.27 (s, 1H), 8.15 (d, J=5.1 Hz, 1H), 7.98-7.91 (m, 4H), 6.91 (dd, J$_1$=5.2 Hz, J$_2$=1.4 Hz, 1H), 6.73 (s, 1H), 6.21 (s, 1H), 5.52-5.51 (m, 1H), 3.98-3.89 (m, 1H), 3.39-3.29 (m, 1H), 2.80 (d, J=5.3 Hz, 3H), 2.70 (q, J=7.6 Hz, 2H), 2.14-2.12 (m, 1H), 2.00-1.86 (m, 2H), 1.75-1.73 (m, 1H), 1.66-1.63 (m, 1H), 1.53-1.48 (m, 1H), 1.45 (s, 9H), 1.28 (t, J=7.6 Hz, 3H). MS (ESI, m/z): 548.2 [M+H]$^+$.

Step F: Preparation of (S)-4-(4-((4-ethylpyridin-2-yl)carbamoyl)phenyl)-1-(methylamino)-2-(piperidin-2-yl)-1H-imidazole-5-carboxamide Step G: Preparation of (S)-2-(1-acryloylpiperidin-2-yl)-4-(4-((4-ethylpyridin-2-yl)carbamoyl)phenyl)-1-(methylamino)-1H-imidazole-5-carboxamide

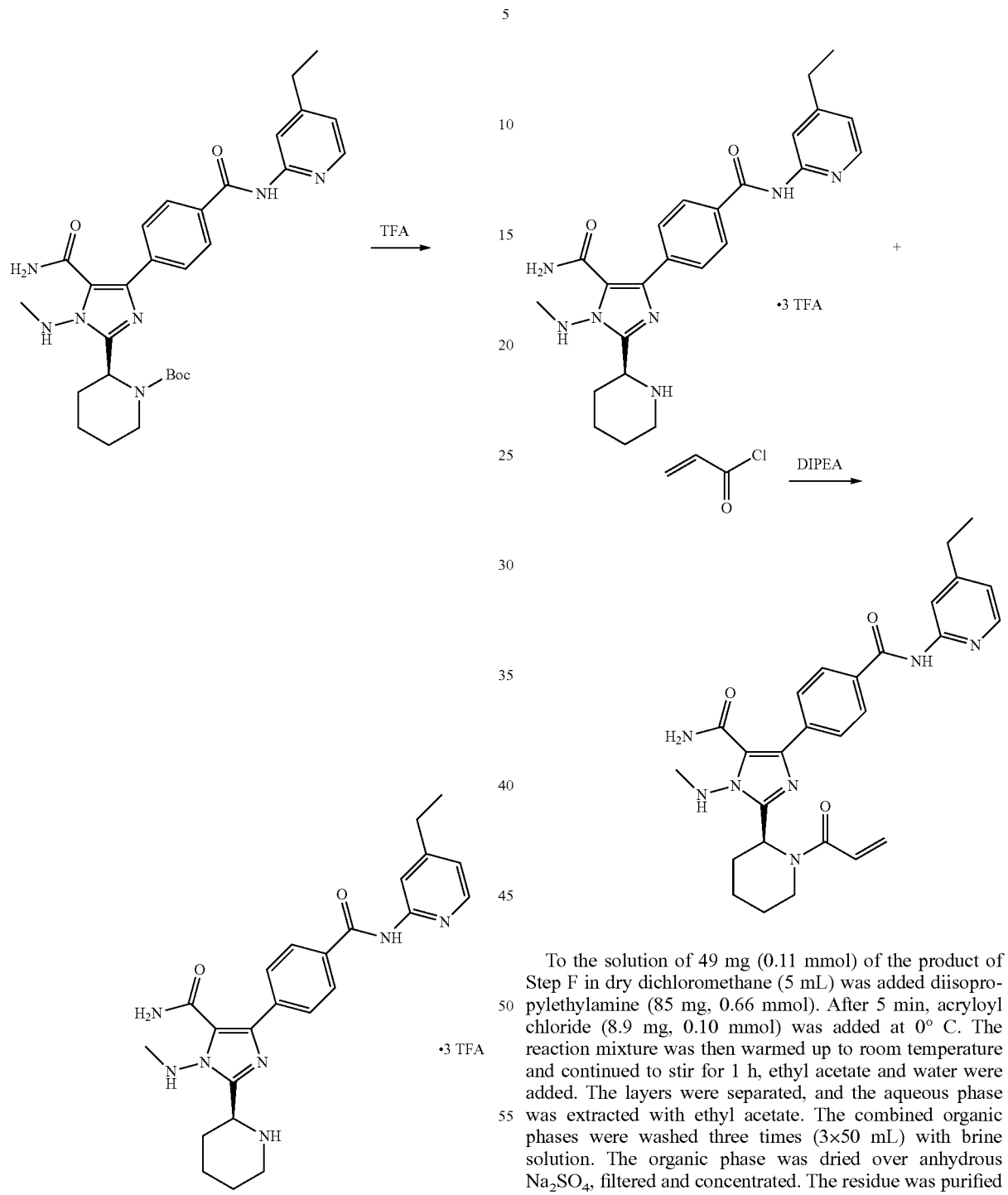

To the solution of 60 mg (0.11 mmol) of the product of Step E in dichloromethane (5 mL) was added trifluoroacetic acid (0.7 mL). The mixture was stirred at room temperature for 1 h and then concentrated to afford (S)-4-(4-((4-ethylpyridin-2-yl)carbamoyl)phenyl)-1-(methylamino)-2-(piperidin-2-yl)-1H-imidazole-5-carboxamide as a light yellow oil. MS (ESI, m/z): 448.2 [M+H]$^+$.

To the solution of 49 mg (0.11 mmol) of the product of Step F in dry dichloromethane (5 mL) was added diisopropylethylamine (85 mg, 0.66 mmol). After 5 min, acryloyl chloride (8.9 mg, 0.10 mmol) was added at 0° C. The reaction mixture was then warmed up to room temperature and continued to stir for 1 h, ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (28:1) to give the product (S)-2-(1-acryloylpiperidin-2-yl)-4-(4-((4-ethylpyridin-2-yl)carbamoyl)phenyl)-1-(methylamino)-1H-imidazole-5-carboxamide (30 mg, 55%). $^1$H NMR (CDCl$_3$, 600 MHz) δ: 9.14 (s, 1H), 8.28 (s, 1H), 8.15 (d, J=5.1 Hz, 1H), 7.98-7.94 (m, 4H), 7.67 (s, 1H), 7.08 (s, 1H), 6.91 (d, J=4.7 Hz, 1H), 6.60 (dd, J$_1$=16.6 Hz, J$_2$=10.6 Hz, 1H), 6.32-6.29 (m, 2H), 5.89 (d, J=4.6 Hz, 1H), 5.73 (d, J=10.6 Hz, 1H), 3.85-3.83 (m, 1H), 3.76-3.72 (m, 1H), 2.86

(d, J=5.4 Hz, 2.6H), 2.71-2.66 (m, 2.4H), 2.45-2.41 (m, 1H), 2.19-2.17 (m, 1H), 2.00-1.93 (m, 1H), 1.89-1.87 (m, 1H), 1.72-1.70 (m, 1H), 1.64-1.57 (m, 1H), 1.28 (t, J=7.6 Hz, 3H); $^{13}$C NMR (CDCl$_3$, 150 MHz) δ: 167.2, 165.9, 162.0, 156.2, 152.0, 148.3, 147.5, 142.2, 138.4, 133.6, 129.8, 128.8, 127.7, 127.2, 119.9, 119.5, 114.0, 44.4, 43.1, 41.1, 28.8, 28.3, 25.8, 19.6, 14.5. MS (ESI, m/z): 502.2 [M+H]$^+$.

Example 82: (S)-1-amino-2-(1-(but-2-ynoyl)piperidin-2-yl)-4-(4-((4-cyanopyridin-2-yl) carbamoyl)phenyl)-1H-imidazole-5-carboxamide

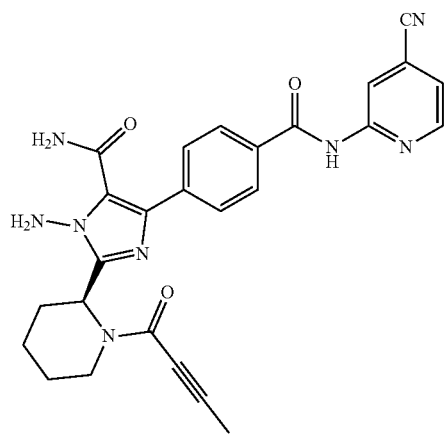 [SMILES: CC#CC(=O)N1CCCC[C@H]1c1nc(-c2ccc(C(=O)Nc3cc(C#N)ccn3)cc2)c(C(N)=O)n1N]

Step A: Preparation of (S)-tert-butyl 2-(4-(4-((4-cyanopyridin-2-yl)carbamoyl)phenyl)-5-(ethoxycarbonyl)-1H-imidazol-2-yl)piperidine-1-carboxylate

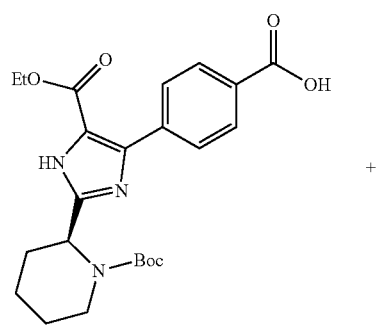

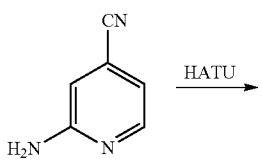

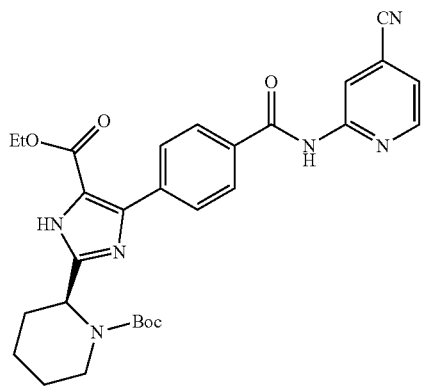

To the solution of 1.3 g (2.8 mmol) the product of Step C of example 46 in dry N,N-Dimethylformamide (10 mL) were added HATU (1.3 g, 3.5 mmol), diisopropylethylamine (2.5 mL, 14 mmol) and 2-aminoisonicotinonitrile (0.5 g, 4.2 mmol). The reaction mixture was stirred at 80° C. After the completion of the reaction (monitored by TLC), the mixture was quenched with brine and washed with ethyl acetate three times (3×100 mL). The combined organic layers were concentrated under reduced pressure and purified by flash chromatography with petroleum ether and ethyl acetate (2.5:1) to afford (S)-tert-butyl 2-(4-(4-((4-cyanopyridin-2-yl)carbamoyl)phenyl)-5-(ethoxycarbonyl)-1H-imidazol-2-yl)piperidine-1-carboxylate as white solid (0.92 g, 60%). $^1$H NMR (CDCl$_3$, 400 MHz) δ: 10.06 (s, 1H), 8.75 (dd, J$_1$=4.5 Hz, J$_2$=1.3 Hz, 1H), 8.47 (dd, J$_1$=8.4 Hz, J$_2$=1.4 Hz, 1H), 8.34-8.29 (m, 4H), 8.11 (s, 1H), 7.47 (dd, J$_1$=8.4 Hz, J$_2$=4.5 Hz, 1H), 5.43-5.42 (m, 1H), 4.39-4.30 (m, 3H), 4.04-4.01 (m, 1H), 2.79-2.74 (m, 1H), 2.58-2.55 (m, 1H), 1.88-1.82 (m, 2H), 1.79-1.76 (m, 1H), 1.71-1.67 (m, 1H), 1.54 (s, 9H), 1.36 (t, J=7.2 Hz, 3H). MS (ESI, m/z): 545.2 [M+H]+.

Step B: Preparation of (S)-tert-butyl 2-(1-amino-4-(4-((4-cyanopyridin-2-yl)carbamoyl)phenyl)-5-(ethoxycarbonyl)-1H-imidazol-2-yl)piperidine-1-carboxylate

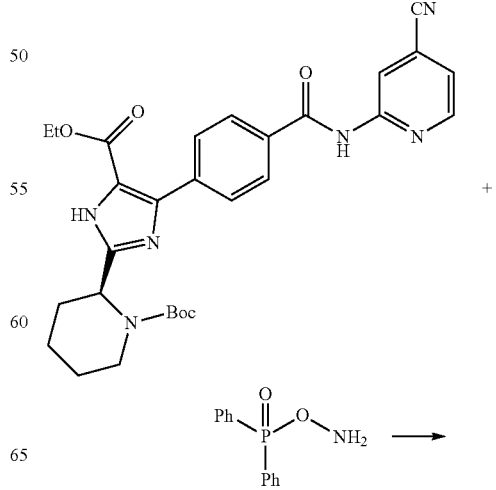

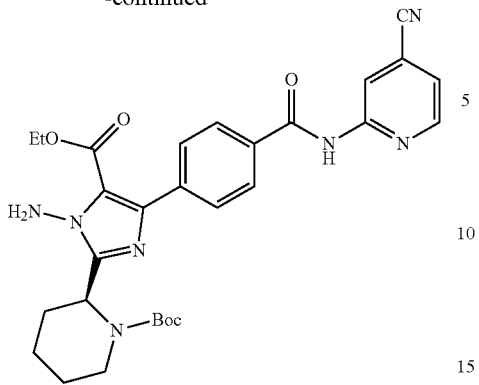

To the solution of 0.92 g (1.7 mmol) of the product of Step A in anhydrous N,N-Dimethylformamide (10 mL) was slowly added lithium hexamethyldisilazane (2.1 mL, 1 M solution in tetrahydrofuran) at −10° C. After the mixture was stirred for 20 min, O-(diphenylphosphinyl) hydroxylamine (0.4 g, 1.7 mmol) was added at 0° C. and the resulting suspension was stirred at room temperature for 2 h (in cases where the reaction mixture became too viscous, additional N,N-Dimethylformamide was added). The reaction was quenched with brine and concentrated to dryness in vacuo. The residue was washed three times (3×100 mL) with ethyl acetate. The combined organic fractions were dried with anhydrous $Na_2SO_4$ and the solvent was removed under reduced pressure to afford the crude residue, which was subjected to column chromatography with petroleum ether and ethyl acetate (3:1) to give (S)-tert-butyl 2-(1-amino-4-(4-((4-cyanopyridin-2-yl)carbamoyl)phenyl)-5-(ethoxycarbonyl)-1H-imidazol-2-yl)piperidine-1-carboxylate as a white solid (0.5 g, 53%). $^1$H NMR ($CDCl_3$, 400 MHz) δ: 8.79 (s, 1H), 8.73 (s, 1H), 8.45 (d, J=5.0 Hz, 1H), 7.92 (d, J=7.8 Hz, 2H), 7.87 (d, J=8.4 Hz, 2H), 7.29-7.27 (m, 1H), 5.91 (s, 2H), 5.68-5.67 (m, 1H), 4.33-4.26 (m, 2H), 3.97-3.93 (m, 1H), 3.45-3.38 (m, 1H), 2.12-2.06 (m, 2H), 1.92-1.87 (m, 1H), 1.76-1.73 (m, 1H), 1.66-1.63 (m, 1H), 1.53-1.50 (m, 1H), 1.44 (s, 9H), 1.28-1.25 (m, 3H). MS (ESI, m/z): 560.2 [M+H]+.

Step C: Preparation of (S)-1-amino-2-(1-(tert-butoxycarbonyl)piperidin-2-yl)-4-(4-((4-cyanopyridin-2-yl)carbamoyl)phenyl)-1H-imidazole-5-carboxylic acid

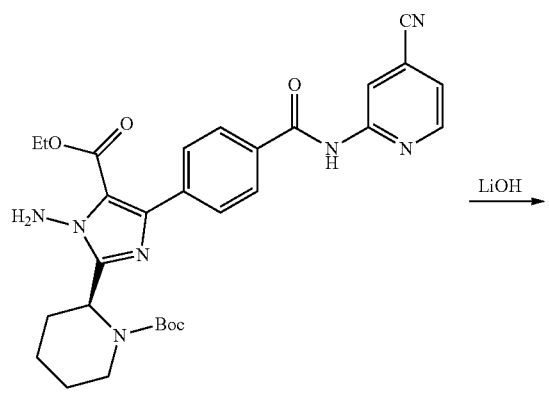

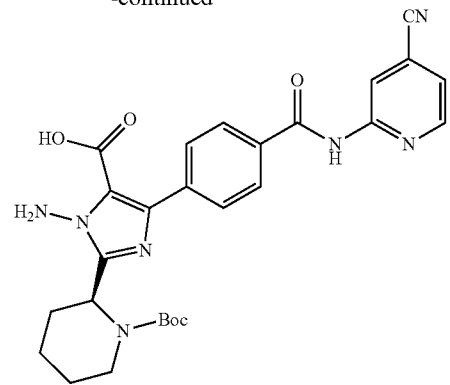

To the solution of 0.5 g (0.9 mmol) of the product of Step B in methanol (5 mL) was added 2 mol/L aqueous lithium hydroxide (4.5 mL) and stirred at room temperature for 2 h. The reaction mixture was evaporated and diluted with water (50 mL) and acidified with aqueous HCl till pH 3. The mixture was washed with ethyl acetate three times (3×50 mL). The white precipitate was isolated by filtration and dried to afford (S)-1-amino-2-(1-(tert-butoxycarbonyl)piperidin-2-yl)-4-(4-((4-cyanopyridin-2-yl)carbamoyl)phenyl)-1H-imidazole-5-carboxylic acid (0.4 g, 80%).

Step D: Preparation of (S)-tert-butyl 2-(1-amino-5-carbamoyl-4-(4-((4-cyanopyridin-2-yl)carbamoyl)phenyl)-1H-imidazol-2-yl)piperidine-1-carboxylate

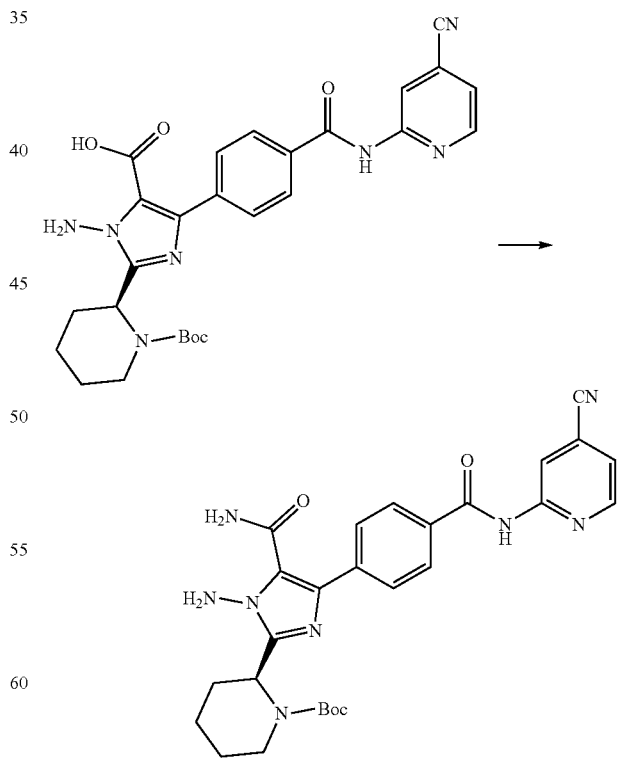

To the solution of 0.4 g (0.7 mmol) of the product of Step C in dry N,N-Dimethylformamide (5 mL) were added HATU (0.4 g, 1.1 mmol), diisopropylethylamine (0.4 mL, 2.2 mmol) and NH₄Cl (0.4 g, 7.3 mmol). The reaction mixture was stirred at room temperature for 2 h. The mixture was quenched with brine and washed with ethyl acetate three times (3×50 mL). The combined organic layers were concentrated under reduced pressure and purified by flash chromatography with dichloromethane and methanol (30:1) to give the product (S)-tert-butyl 2-(1-amino-5-carbamoyl-4-(4-((4-cyanopyridin-2-yl)carbamoyl)phenyl)-1H-imidazol-2-yl)piperidine-1-carboxylate as white solid (0.2 g, 54%). ¹H NMR (CDCl₃, 400 MHz) δ: 8.82 (s, 1H), 8.72 (t, $J$=1.1 Hz, 1H), 8.48 (dd, $J_1$=5.0 Hz, $J_2$=0.8 Hz, 1H), 7.95 (d, $J$=8.6 Hz, 2H), 7.90 (d, $J$=8.5 Hz, 2H), 7.29 (dd, $J_1$=5.0 Hz, $J_2$=1.4 Hz, 1H), 6.88 (s, 1H), 6.00 (s, 2H), 5.62-5.58 (m, 2H), 3.95-3.92 (m, 1H), 3.30-3.23 (m, 1H), 2.31-2.21 (m, 1H), 2.17-2.13 (m, 1H), 1.95-1.86 (m, 1H), 1.77-1.74 (m, 1H), 1.70-1.65 (m, 1H), 1.56-1.51 (m, 1H), 1.46 (s, 9H). MS (ESI, m/z): 531.2 [M+H]+.

Step E: Preparation of (S)-1-amino-4-(4-((4-cyano-pyridin-2-yl)carbamoyl)phenyl)-2-(piperidin-2-yl)-1H-imidazole-5-carboxamide

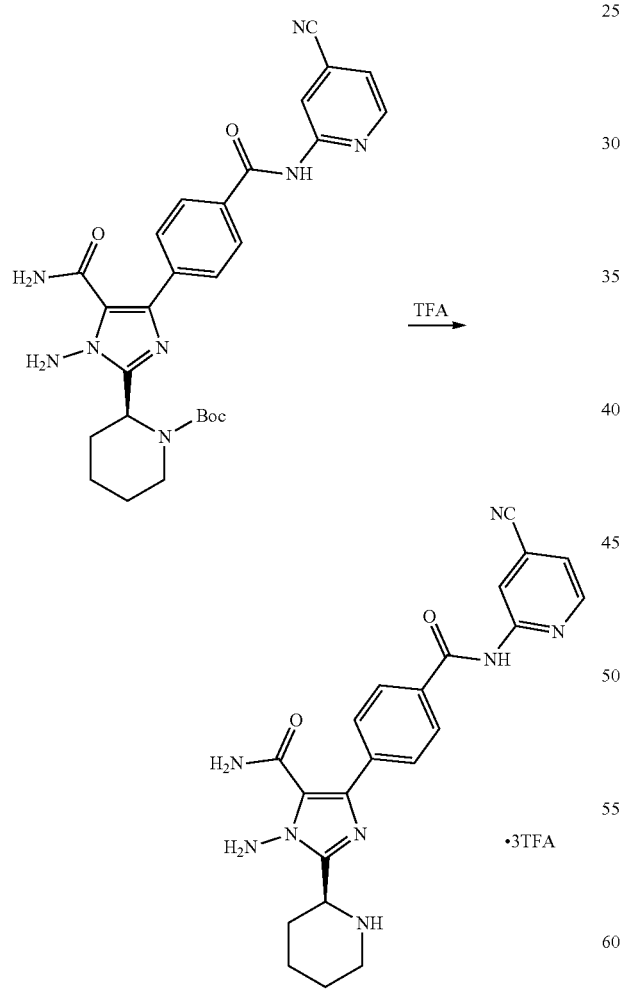

To the solution of 60 mg (0.11 mmol) of the product of Step D in dichloromethane (5 mL) was added trifluoroacetic acid (0.66 mL). The mixture was stirred at room temperature for 1 h and then concentrated to afford (S)-1-amino-4-(4-((4-cyanopyridin-2-yl)carbamoyl)phenyl)-2-(piperidin-2-yl)-1H-imidazole-5-carboxamide as a light yellow oil. MS (ESI, m/z): 431.1 [M+H]+.

Step F: Preparation of (S)-1-amino-2-(1-(but-2-ynoyl)piperidin-2-yl)-4-(4-((4-cyanopyridin-2-yl)carbamoyl)phenyl)-1H-imidazole-5-carboxamide

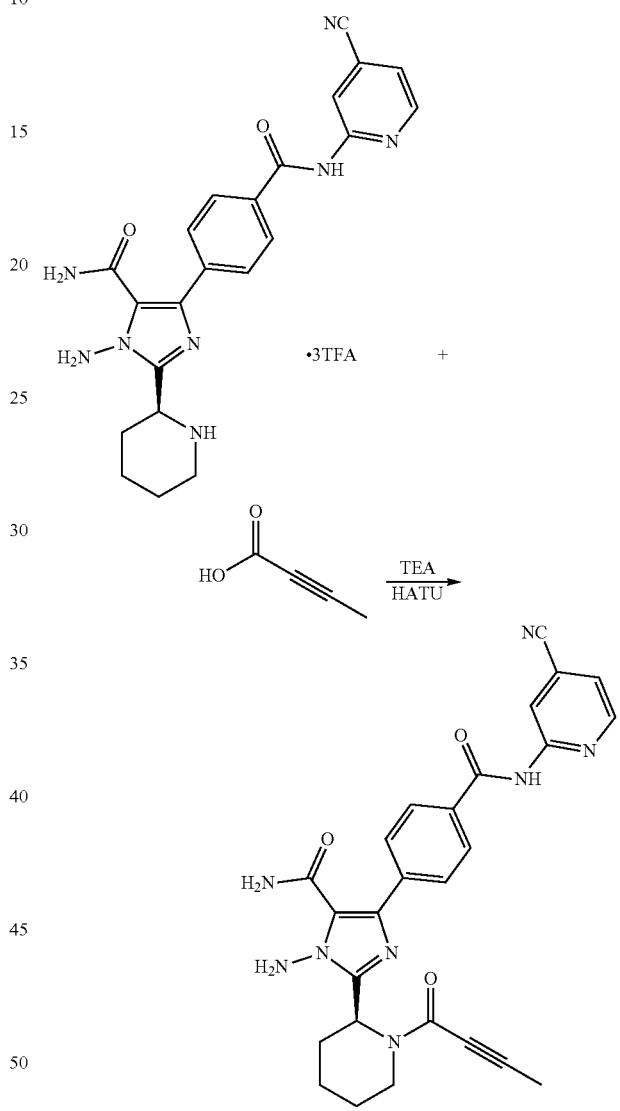

To the solution of 48 mg (0.11 mmol) of the product of Step E in dry N,N-Dimethylformamide (5 mL) was added triethylamine (67 mg, 0.66 mmol). After 5 min, but-2-ynoic acid (8.4 mg, 0.10 mmol) and HATU (63 mg, 0.16 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous Na₂SO₄, filtered and concentrated. The residue was purified by chromatography with dichloromethane and methanol (26:1) to give (S)-1-amino-2-(1-(but-2-ynoyl)piperidin-2-yl)-4-(4-((4-cyanopyridin-2-yl)carbamoyl)phenyl)-1H-imidazole-5-carboxamide as an off-white solid (44 mg, 80%). ¹H NMR (CDCl₃, 400 MHz) δ: 9.45 (s, 1H), 8.66 (s, 1H), 8.43 (d, J=5.0 Hz, 1H), 7.84 (d, J=8.5 Hz, 2H), 7.75 (d, J=8.4 Hz, 2H), 7.33 (s, 1H), 7.26-7.24 (m, 1H), 6.46 (s, 1H), 6.13 (s, 2H), 5.91-5.90 (m, 1H), 4.28-4.25 (m, 1H), 3.66-3.59 (m, 1H), 2.41-2.31 (m, 1H), 2.17-2.14 (m, 1H), 2.00 (s, 3H), 1.88-1.85 (m, 2H), 1.73-1.69 (m, 1H), 1.62-1.57 (m, 1H); ¹³C NMR (CDCl₃, 150 MHz) δ: 166.2, 162.7, 155.0, 152.7, 149.2, 148.2, 141.2, 138.7, 132.7, 129.6, 127.4, 122.5, 121.2, 120.5, 116.7, 116.5, 91.2, 72.9, 44.5, 43.8, 27.8, 25.7, 19.8, 4.3. MS (ESI, m/z): 497.1 [M+H]+.

Example 83: (S)-2-(1-acryloylpiperidin-2-yl)-1-amino-4-(4-((4-cyanopyridin-2-yl)carbamoyl)phenyl)-1H-imidazole-5-carboxamide

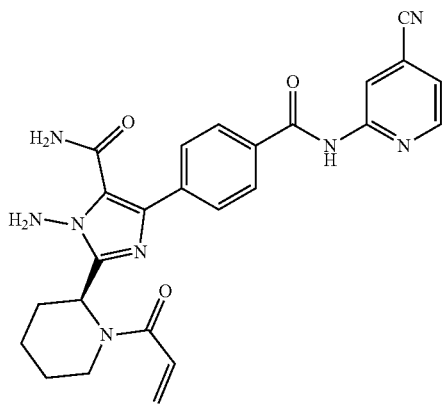

Preparation of (S)-2-(1-acryloylpiperidin-2-yl)-1-amino-4-(4-((4-cyanopyridin-2-yl)carbamoyl)phenyl)-1H-imidazole-5-carboxamide

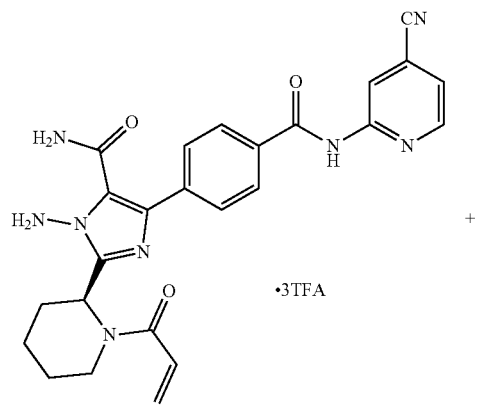

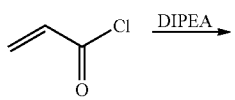

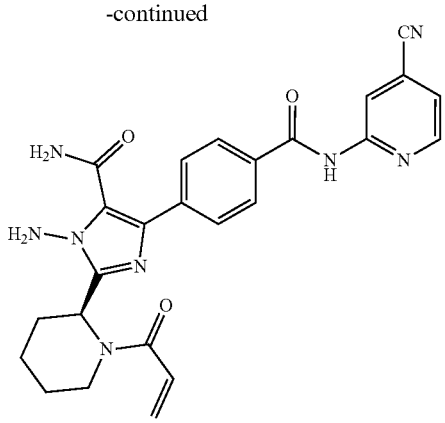

To the solution of 48 mg (0.11 mmol) of the product of Step E of example 82 in dry dichloromethane (3 mL) was added diisopropylethylamine (114 μL, 0.66 mmol). After 5 min, acryloyl chloride (6.2 μL, 0.10 mmol) was added at 0° C. The reaction mixture was then warmed up to room temperature and continued to stir for 1 h, ethyl acetate and water were added. The layers were separated, and the aqueous phase was extracted with ethyl acetate. The combined organic phases were washed three times (3×30 mL) with brine solution. The organic phase was dried over anhydrous Na₂SO₄, filtered and concentrated. The residue was purified by chromatography with dichloromethane and methanol (30:1) to give (S)-2-(1-acryloylpiperidin-2-yl)-1-amino-4-(4-((4-cyanopyridin-2-yl)carbamoyl)phenyl)-1H-imidazole-5-carboxamide as an off-white solid (43 mg, 80%). 1H NMR (CDCl₃, 600 MHz) δ: 9.52 (s, 1H), 8.66 (s, 1H), 8.42 (d, J=4.6 Hz, 1H), 7.85 (d, J=8.2 Hz, 2H), 7.82 (d, J=8.2 Hz, 2H), 7.48 (s, 1H), 7.24 (d, J=5.0 Hz, 1H), 6.60-6.56 (m, 2H), 6.33-6.27 (m, 4H), 5.72-5.70 (m, 1H), 3.83-3.81 (m, 1H), 3.70-3.67 (m, 1H), 2.43-2.41 (m, 1H), 2.19-2.17 (m, 1H), 1.92-1.85 (m, 2H), 1.71-1.60 (m, 2H). MS (ESI, m/z): 485.1 [M+H]+.

Example 84

(S)-2-(1-acryloylpiperidin-2-yl)-1-amino-4-(4-((4-(trifluoromethyl)pyridin-2-yl)carbamoyl)phenyl)-1H-imidazole-5-carboxamide

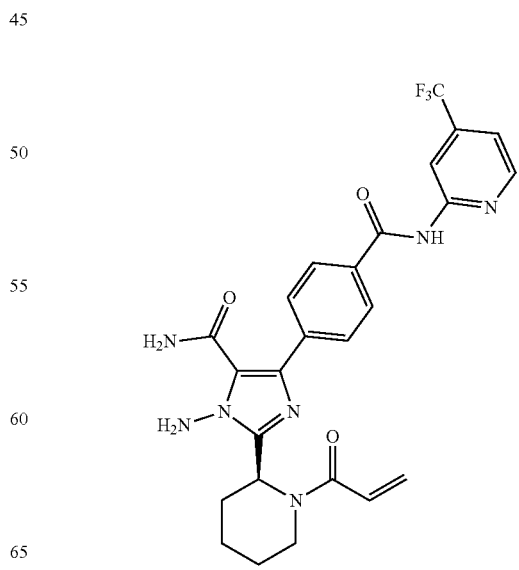

Step A: Preparation of tert-butyl (S)-2-(5-(ethoxycarbonyl)-4-(4-((4-(trifluoromethyl)pyridin-2-yl)carbamoyl)phenyl)-1H-imidazol-2-yl)piperidine-1-carboxylate Step B: Preparation of tert-butyl (S)-2-(1-amino-5-(ethoxycarbonyl)-4-(4-((4-(trifluoromethyl)pyridin-2-yl)carbamoyl)phenyl)-1H-imidazol-2-yl)piperidine-1-carboxylate

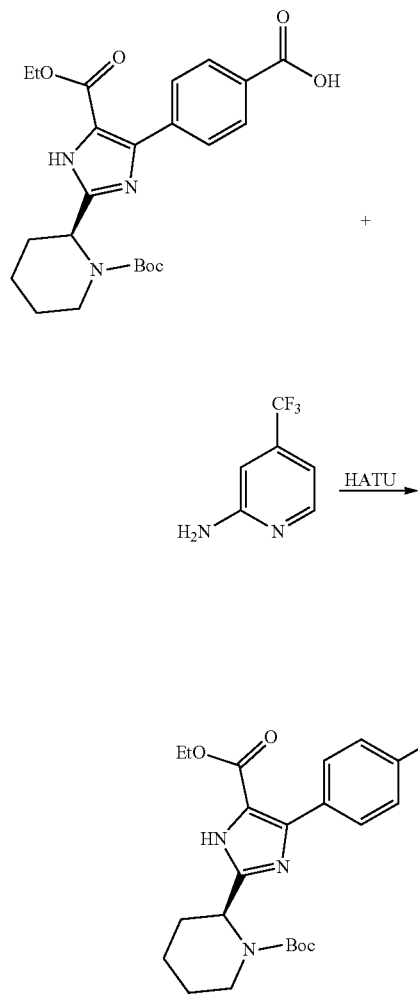

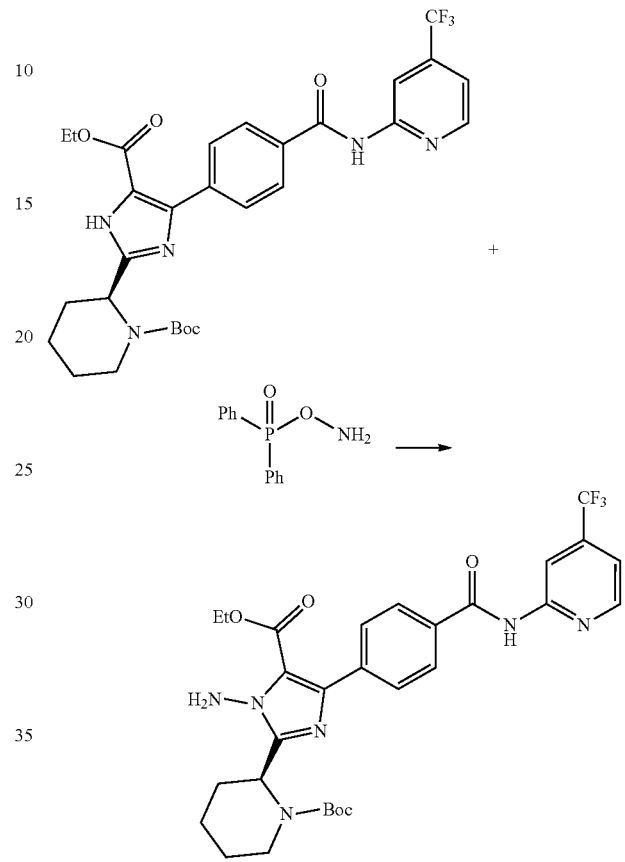

To the solution of 7.0 g (16 mmol) of the product of Step C of example 46 in dry N,N-Dimethylformamide (50 mL), HATU (7.2 g, 19 mmol), diisopropylethylamine (13.6 mL, 79 mmol) and 4-(trifluoromethyl)pyridin-2-amine (3.8 g, 24 mmol) were added and stirred at 80° C. for 3 h. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (2:1) to afford tert-butyl (S)-2-(5-(ethoxycarbonyl)-4-(4-((4-(trifluoromethyl)pyridin-2-yl)carbamoyl)phenyl)-1H-imidazol-2-yl)piperidine-1-carboxylate as white solid (5.4 g, 57%). $^1$H NMR (CDCl$_3$, 400 MHz) δ: 10.21 (s, 1H), 9.13 (s, 1H), 8.72 (s, 1H), 8.45 (d, J=5.2 Hz, 1H), 8.17 (d, J=8.4 Hz, 2H), 7.95 (d, J=8.4 Hz, 2H), 7.28-7.27 (m, 1H), 5.41-5.40 (m, 1H), 4.31 (q, J=7.1 Hz, 2H), 2.83-2.76 (m, 1H), 2.53-2.50 (m, 1H), 1.95-1.90 (m, 1H), 1.86-1.79 (m, 2H), 1.75-1.71 (m, 1H), 1.68-1.64 (m, 1H), 1.50 (s, 9H), 1.48-1.46 (m, 1H), 1.30 (t, J=7.1 Hz, 3H). MS (ESI, m/z): 588.2 [M+H]$^+$.

To the solution of 5.4 g (9.1 mmol) of the product of Step A in anhydrous N,N-Dimethylformamide (30 mL), lithium hexamethyldisilazane (11 mL, 1 M solution in tetrahydrofuran) was slowly added at −10° C. After the mixture was stirred for 20 min, O-(diphenylphosphinyl) hydroxylamine (2.5 g, 10.9 mmol) was added at 0° C. and the resulting suspension was stirred at room temperature for 2 h (in cases where the reaction mixture became too viscous, additional N,N-Dimethylformamide was added). The mixture was quenched with brine and washed with ethyl acetate three times (3×150 mL). The combined organic fractions were dried with anhydrous Na$_2$SO$_4$ and the solvent was removed under reduced pressure to afford the crude residue, which was subjected to column chromatography with petroleum ether and ethyl acetate (2:1) to afford tert-butyl (S)-2-(1-amino-5-(ethoxycarbonyl)-4-(4-((4-(trifluoromethyl)pyridin-2-yl)carbamoyl)phenyl)-1H-imidazol-2-yl)piperidine-1-carboxylate as a white solid (2.7 g, 49%). $^1$H NMR (CDCl$_3$, 400 MHz) δ: 9.45 (s, 1H), 8.71 (s, 1H), 8.37 (d, J=5.2 Hz, 1H), 7.91 (d, J=8.6 Hz, 2H), 7.82 (d, J=8.5 Hz, 2H), 7.23 (dd, J$_1$=5.1 Hz, J$_2$=0.9 Hz, 1H), 5.89 (s, 2H), 5.69-5.68 (m, 1H), 4.28-4.20 (m, 2H), 3.96-3.93 (m, 1H), 3.48-3.41 (m, 1H), 2.09-2.06 (m, 1H), 1.96-1.81 (m, 2H), 1.73-1.69 (m, 1H), 1.62-1.59 (m, 1H), 1.51-1.46 (m, 1H), 1.41 (s, 9H), 1.19 (t, J=7.1 Hz, 3H). MS (ESI, m/z): 603.2 [M+H]$^+$.

Step C: Preparation of (S)-1-amino-2-(1-(tert-butoxycarbonyl)piperidin-2-yl)-4-(4-((4-(trifluoromethyl)pyridin-2-yl)carbamoyl)phenyl)-1H-imidazole-5-carboxylic acid

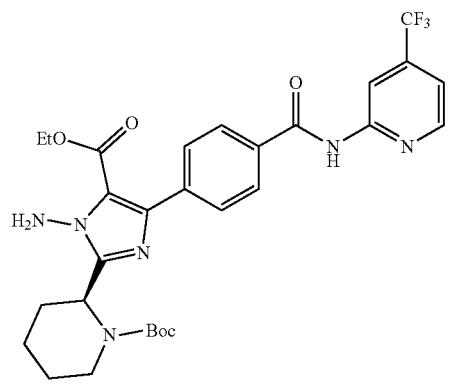

LiOH →

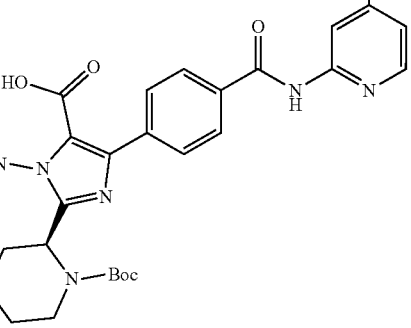

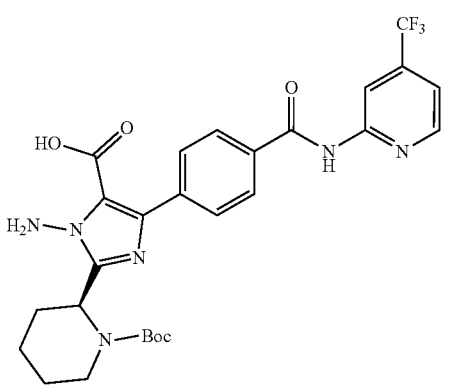

To the solution of 2.7 g (4.5 mmol) of the product of Step B in methanol (20 mL) was added 2 mol/L aqueous lithium hydroxide (23 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl)piperidin-2-yl)-4-(4-((4-(trifluoromethyl)pyridin-2-yl)carbamoyl)phenyl)-1H-imidazole-5-carboxylic acid (2.5 g, 96%).

Step D: Preparation of tert-butyl (S)-2-(1-amino-5-carbamoyl-4-(4-((4-(trifluoromethyl)pyridin-2-yl)carbamoyl)phenyl)-1H-imidazol-2-yl)piperidine-1-carboxylate

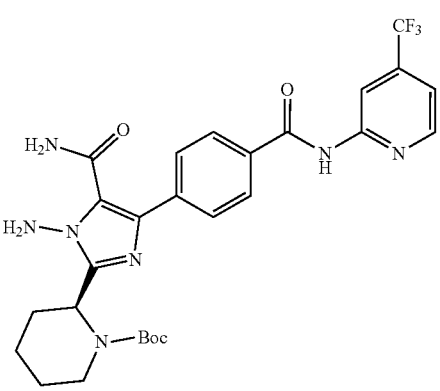

To the solution of 2.5 g (4.3 mmol) of the product of Step C in dry N,N-Dimethylformamide (16 mL) were added HATU (2.5 g, 6.5 mmol), diisopropylethylamine (2.2 mL, 12.9 mmol) and $NH_4Cl$ (2.3 g, 43 mmol). The reaction mixture was stirred at room temperature for 2 h. The mixture was quenched with brine and washed with ethyl acetate three times (3×100 mL). The combined organic layers were concentrated under reduced pressure and purified by flash chromatography with dichloromethane and methanol (30:1) to afford tert-butyl (S)-2-(1-amino-5-carbamoyl-4-(4-((4-(trifluoromethyl)pyridin-2-yl)carbamoyl)phenyl)-1H-imidazol-2-yl)piperidine-1-carboxylate as a white solid (1.5 g, 61%). $^1$H NMR (CDCl$_3$, 400 MHz) δ: 8.80 (s, 1H), 8.71 (s, 1H), 8.49 (d, J=5.1 Hz, 1H), 7.96 (d, J=8.5 Hz, 2H), 7.90 (d, J=8.4 Hz, 2H), 7.30 (dd, J$_1$=5.2 Hz, J$_2$=0.9 Hz, 1H), 6.89 (s, 1H), 6.08 (s, 1H), 6.00 (s, 2H), 5.60-5.59 (m, 1H), 3.95-3.91 (m, 1H), 3.30-3.23 (m, 1H), 2.31-2.22 (m, 1H), 2.17-2.13 (m, 1H), 1.95-1.86 (m, 1H), 1.77-1.74 (m, 1H), 1.70-1.65 (m, 1H), 1.58-1.51 (m, 1H), 1.46 (s, 9H). MS (ESI, m/z): 574.2 [M+H]$^+$.

Step E: Preparation of (S)-1-amino-4-(4-((4-(trifluoromethyl)pyridin-2-yl)carbamoyl)phenyl)-2-(piperidin-2-yl)-1H-imidazole-5-carboxamide

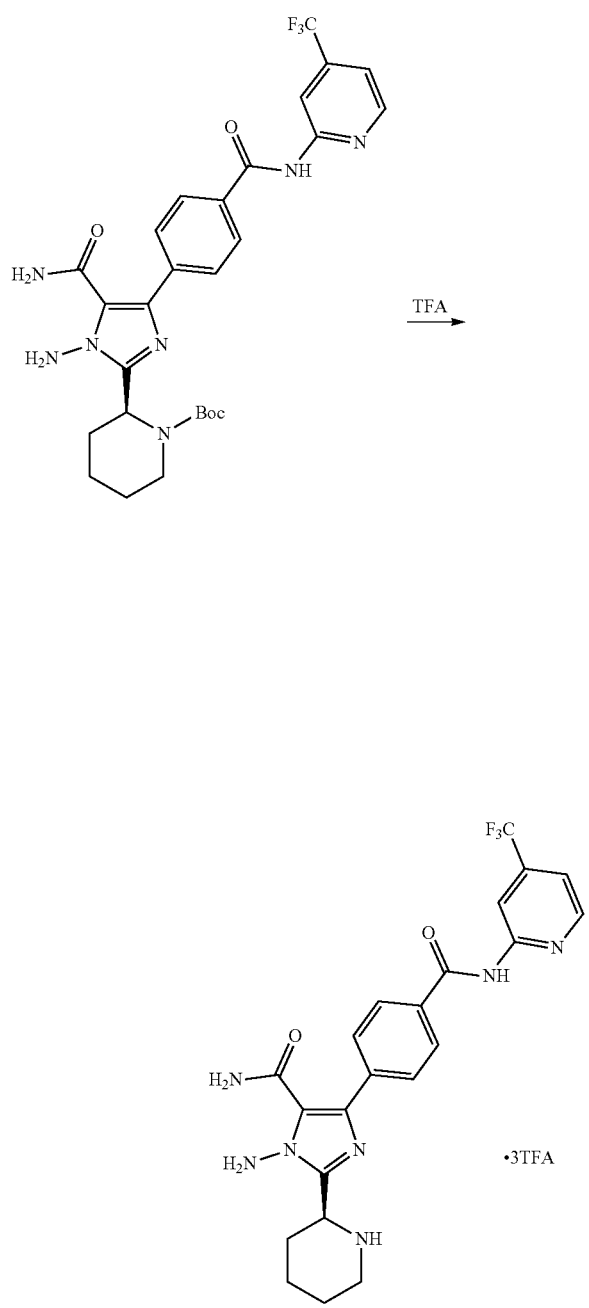

To the solution of 120 mg (0.21 mmol) of the product of Step D in dichloromethane (5 mL) was added trifluoroacetic acid (1.2 mL). The mixture was stirred at room temperature for 1 h and then concentrated to afford (S)-1-amino-4-(4-((4-(trifluoromethyl)pyridin-2-yl)carbamoyl)phenyl)-2-(piperidin-2-yl)-1H-imidazole-5-carboxamide as a light yellow oil. MS (ESI, m/z): 474.1 [M+H]⁺.

Step F: Preparation of (S)-2-(1-acryloylpiperidin-2-yl)-1-amino-4-(4-((4-(trifluoromethyl)pyridin-2-yl)carbamoyl)phenyl)-1H-imidazole-5-carboxamide

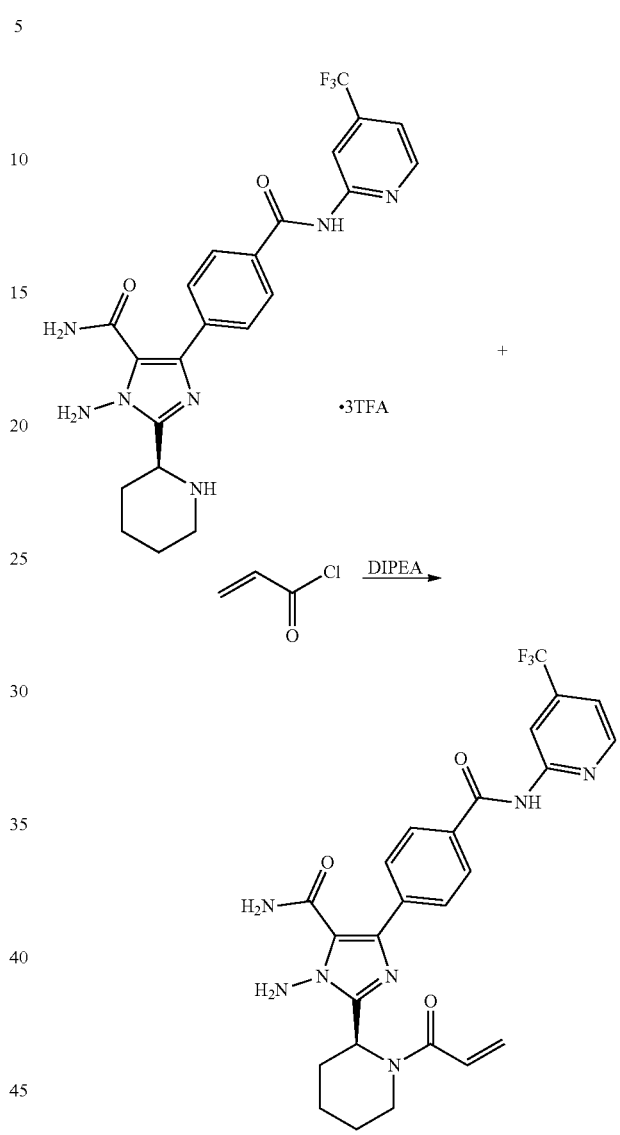

To the solution of 100 mg (0.21 mmol) of the product of Step E in dry dichloromethane (5 mL) was added diisopropylethylamine (155 mg, 1.2 mmol). After 5 min, acryloyl chloride (16.2 mg, 0.18 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na₂SO₄, filtered and concentrated. The residue was purified by chromatography with dichloromethane and methanol (28:1) to give (S)-2-(1-acryloylpiperidin-2-yl)-1-amino-4-(4-((4-(trifluoromethyl)pyridin-2-yl)carbamoyl)p-henyl)-1H-imidazole-5-carboxamide as an off-white solid (65 mg, 58%). ¹H NMR (CDCl₃, 400 MHz) δ: 9.44 (s, 1H), 8.67 (s, 1H), 8.43 (d, J=4.8 Hz, 1H), 7.85 (d, J=8.2 Hz, 2H), 7.78-7.76 (m, 2H), 7.40 (s, 1H), 7.26-7.25 (m, 1H), 6.62-6.52 (m, 2H), 6.31-6.26 (m, 3H), 6.00-5.96 (m, 1H), 5.72 (d, J=10.5 Hz, 1H), 3.85-3.82 (m, 1H), 3.70-3.64 (m, 1H), 2.45-2.42 (m, 1H), 2.21-2.18 (m, 1H), 1.97-1.85 (m, 2H), 1.73-1.70 (m, 1H), 1.63-1.60 (m, 1H). $^{13}$C NMR (CDCl$_3$, 150 MHz) δ: 167.3, 166.1, 162.7, 152.9, 149.0, 148.4, 141.4, 140.6 (q, J=33.0 Hz), 138.7, 132.9, 129.7, 128.8, 127.7, 127.3, 122.8 (q, J=271.5 Hz), 120.2, 115.5, 110.6, 44.4, 43.0, 28.0, 25.8, 19.7. MS (ESI, m/z): 528.1 [M+H]$^+$.

Example 85

(S)-1-amino-2-(1-(but-2-ynoyl)piperidin-2-yl)-4-(4-((4-(trifluoromethyl)pyridin-2-yl)carbamoyl)phenyl)-1H-imidazole-5-carboxamide

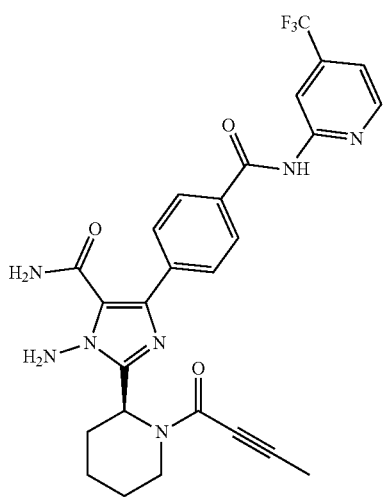 [SMILES: CC#CC(=O)N1CCCC[C@H]1c1nc(-c2ccc(C(=O)Nc3cc(C(F)(F)F)ccn3)cc2)c(C(N)=O)n1N]

Preparation of (S)-1-amino-2-(1-(but-2-ynoyl)piperidin-2-yl)-4-(4-((4-(trifluoromethyl)pyridin-2-yl)carbamoyl)phenyl)-1H-imidazole-5-carboxamide

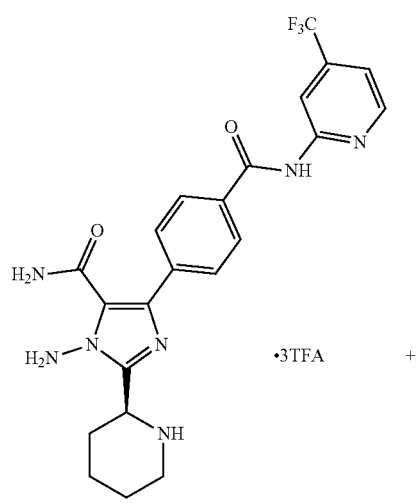

·3TFA +

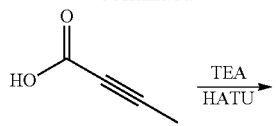

-continued

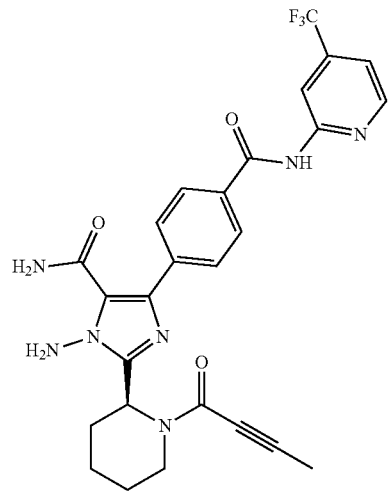

To the solution of 100 mg (0.21 mmol) of the product of Step E of example 84 in dry N,N-Dimethylformamide (5 mL) was added triethylamine (127 mg, 1.26 mmol). After 5 min, but-2-ynoic acid (15.8 mg, 0.19 mmol) and HATU (120 mg, 0.31 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-1-amino-2-(1-(but-2-ynoyl)piperidin-2-yl)-4-(4-((4-(trifluoromethyl)pyridin-2-yl)carbamoyl)phenyl)-1H-imidazole-5-carboxamide as an off-white solid (45 mg, 40%). $^1$H NMR (CDCl$_3$, 400 MHz) δ: 9.26 (s, 1H), 8.68 (s, 1H), 8.46-8.45 (m, 1H), 7.92-7.89 (m, 2H), 7.84-7.80 (m, 2H), 7.27 (d, J=4.8 Hz, 1H), 7.13 (s, 1H), 6.24 (s, 1H), 6.14 (s, 2H), 5.94-5.92 (m, 1H), 4.29-4.26 (m, 1H), 3.67-3.60 (m, 1H), 2.43-2.34 (m, 1H), 2.19-2.15 (m, 1H), 2.01 (s, 3H), 1.93-1.86 (m, 2H), 1.74-1.70 (m, 1H), 1.63-1.58 (m, 1H). $^{13}$C NMR (CDCl$_3$, 150 MHz) δ: 160.0, 162.6, 155.0, 152.8, 149.1, 148.1, 141.3, 140.7 (q, J=33.0 Hz), 138.7, 133.1, 129.8, 127.4, 122.8 (q, J=271.5 Hz), 120.2, 115.6, 110.5, 91.1, 72.9, 44.5, 43.8, 27.8, 25.7, 19.8, 4.3. MS (ESI, m/z): 540.1 [M+H]$^+$.

Example 86

(S)-2-(1-acryloylpiperidin-2-yl)-1-amino-4-(4-((5-chloropyridin-2-yl)carbamoyl)phenyl)-1H-imidazole-5-carboxamide

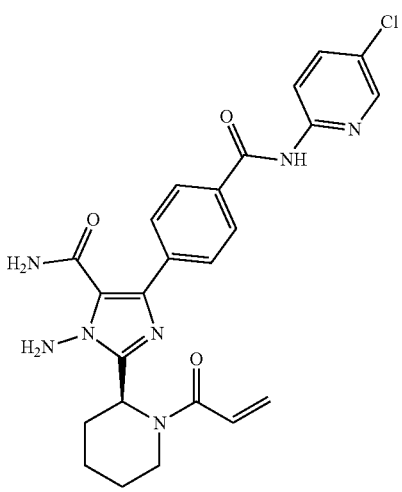 [SMILES: C=CC(=O)N1CCCC[C@H]1c1nc(-c2ccc(C(=O)Nc3ccc(Cl)cn3)cc2)c(C(N)=O)n1N]

Step A: Preparation of tert-butyl (S)-2-(5-(ethoxycarbonyl)-4-(4-((5-chloropyridin-2-yl)carbamoyl)phenyl)-1H-imidazol-2-yl)piperidine-1-carboxylate

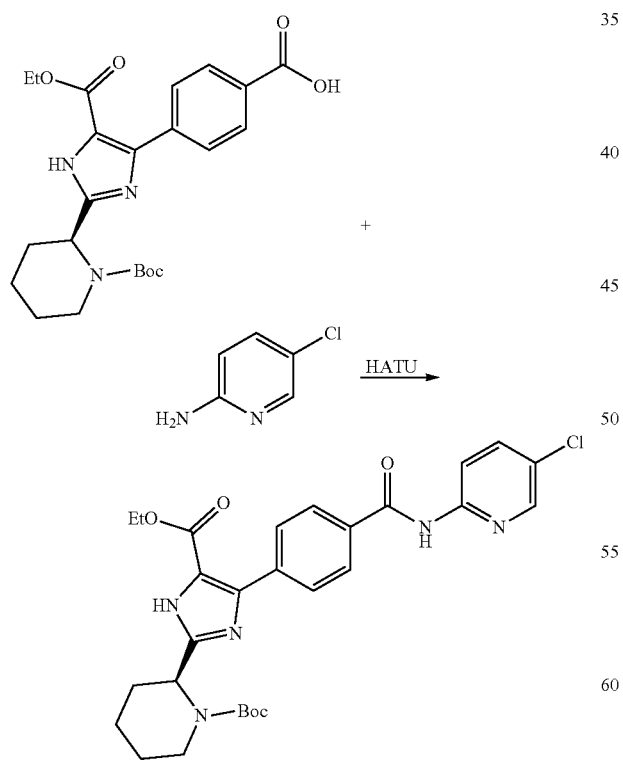

To the solution of 2.0 g (4.5 mmol) of the product of Step C of example 46 in dry N,N-Dimethylformamide (20 mL) were added HATU (2.0 g, 5.4 mmol), diisopropylethylamine (3.9 mL, 22.5 mmol) and 5-chloropyridin-2-amine (0.9 g, 6.7 mmol). The reaction mixture was stirred at 80° C. for 3 h. After the completion of the reaction (monitored by TLC), the mixture was quenched with brine and washed with ethyl acetate three times (3×100 mL). The combined organic layers were concentrated under reduced pressure and purified by flash chromatography with petroleum ether and ethyl acetate (3:1) to give the product tert-butyl (S)-2-(5-(ethoxycarbonyl)-4-(4-((5-chloropyridin-2-yl)carbamoyl)phenyl)-1H-imidazol-2-yl)piperidine-1-carboxylate as white solid (2.3 g, 92%). $^1$H NMR (CDCl$_3$, 600 MHz) δ: 9.94 (s, 1H), 8.58 (s, 1H), 8.41 (d, J=8.9 Hz, 1H), 8.28 (d, J=2.4 Hz, 1H), 8.19 (d, J=8.3 Hz, 2H), 7.95 (d, J=8.4 Hz, 2H), 7.73 (dd, J$_1$=8.9 Hz, J$_2$=2.5 Hz, 1H), 5.41-5.40 (m, 1H), 4.36-4.32 (m, 2H), 2.77-2.72 (m, 1H), 2.57-2.55 (m, 1H), 2.03-1.99 (m, 1H), 1.85-1.81 (m, 1H), 1.77-1.75 (m, 1H), 1.68-1.66 (m, 2H), 1.53 (s, 9H), 1.50-1.48 (m, 1H), 1.34 (t, J=7.1 Hz, 3H). MS (ESI, m/z): 554.2 [M+H]$^+$.

Step B: Preparation of tert-butyl (S)-2-(1-amino-5-(ethoxycarbonyl)-4-(4-((5-chloropyridin-2-yl)carbamoyl)phenyl)-1H-imidazol-2-yl)piperidine-1-carboxylate

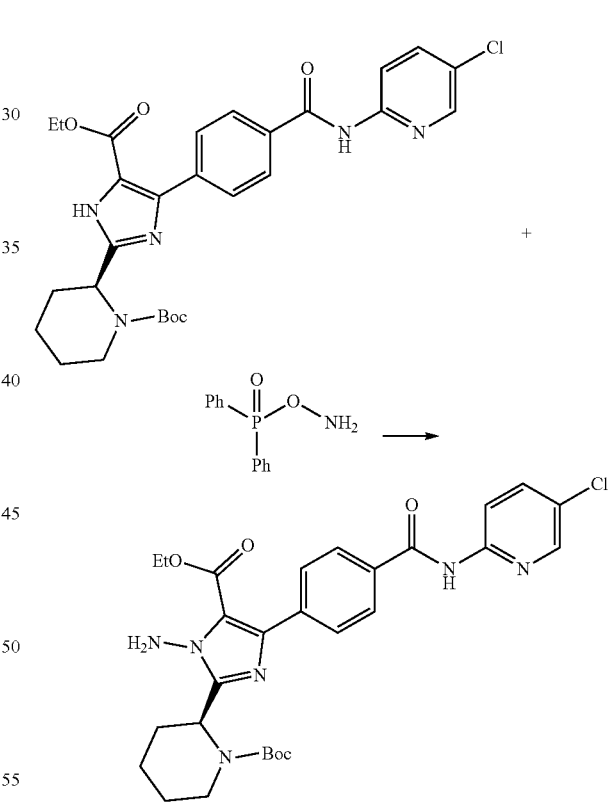

To the solution of 2.3 g (4.1 mmol) of the product of Step A in anhydrous N,N-Dimethylformamide (15 mL) was slowly added lithium hexamethyldisilazane (5.0 mL, 1 M solution in tetrahydrofuran) at −10° C. and stirred for 20 min, O-(diphenylphosphinyl) hydroxylamine (1.1 g, 4.9 mmol) was added at 0° C. Then the resulting suspension was stirred at room temperature for 2 h (in cases where the reaction mixture became too viscous, additional N,N-Dimethylformamide was added). The reaction was quenched with brine and concentrated to dryness in vacuo. The residue was washed three times (3×100 mL) with ethyl acetate. The combined organic fractions were dried with anhydrous Na₂SO₄ and the solvent was removed under reduced pressure to afford the crude residue, which was subjected to column chromatography with petroleum ether and ethyl acetate (3:1) to give the product tert-butyl (S)-2-(1-amino-5-(ethoxycarbonyl)-4-(4-((5-chloropyridin-2-yl)carbamoyl)phenyl)-1H-imidazol-2-yl)piperidine-1-carboxylate as a white solid (0.7 g, 30%). ¹H NMR (CDCl₃, 600 MHz) δ: 8.57 (s, 1H), 8.41 (d, J=8.9 Hz, 1H), 8.28 (d, J=2.4 Hz, 1H), 7.92 (d, J=8.5 Hz, 2H), 7.87 (d, J=8.5 Hz, 2H), 7.74 (dd, J₁=8.9 Hz, J₂=2.5 Hz, 1H), 5.94 (s, 2H), 5.68-5.67 (m, 1H), 4.33-4.27 (m, 2H), 3.97-3.95 (m, 1H), 3.44-3.39 (m, 1H), 2.12-2.10 (m, 1H), 1.83-1.87 (m, 1H), 1.76-1.74 (m, 1H), 1.66-1.64 (m, 1H), 1.55-1.51 (m, 1H), 1.45 (s, 9H), 1.34-1.29 (m, 1H), 1.26 (t, J=7.1 Hz, 3H). MS (ESI, m/z): 569.2 [M+H]⁺.

Step C: Preparation of (S)-1-amino-2-(1-(tert-butoxycarbonyl)piperidin-2-yl)-4-(4-((5-chloropyridin-2-yl)carbamoyl)phenyl)-1H-imidazole-5-carboxylic acid Step D: Preparation of tert-butyl (S)-2-(1-amino-5-carbamoyl-4-(4-((5-chloropyridin-2-yl)carbamoyl)phenyl)-1H-imidazol-2-yl)piperidine-1-carboxylate

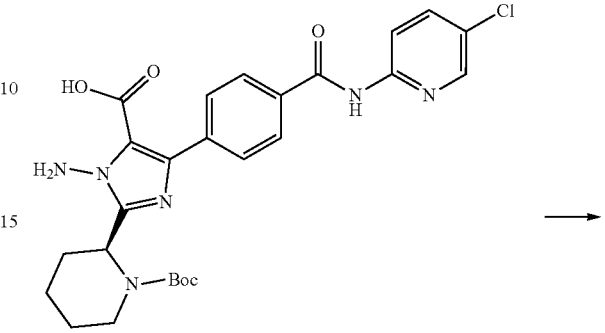

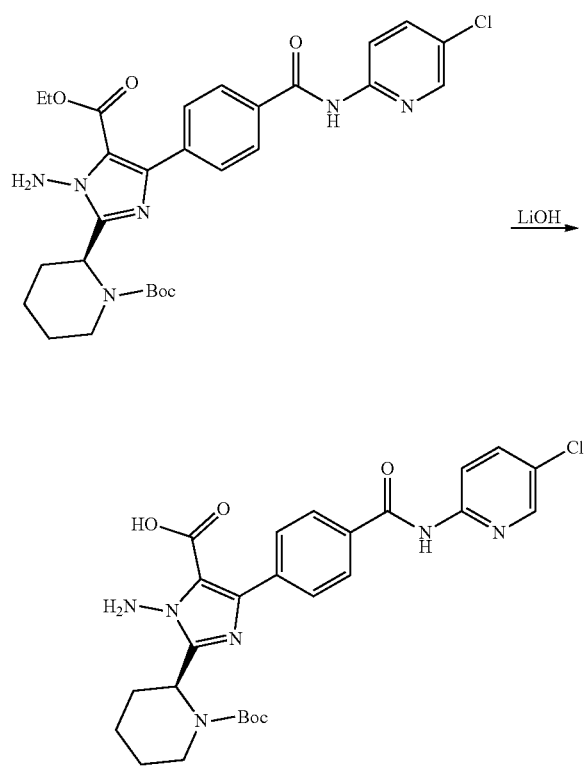

To the solution of 0.7 g (1.2 mmol) of the product of Step B in methanol (7 mL) was added 2 mol/L aqueous lithium hydroxide (6 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford(S)-1-amino-2-(1-(tert-butoxycarbonyl)piperidin-2-yl)-4-(4-((5-chloropyridin-2-yl)carbamoyl)phenyl)-1H-imidazole-5-carboxylic acid (0.6 g, 93%).

To the solution of 0.68 g (1.2 mmol) of the product of Step C in dry N,N-Dimethylformamide (5 mL) were added HATU (7.2 g, 1.9 mmol), diisopropylethylamine (0.6 mL, 3.6 mmol) and NH₄Cl (6.7 g, 12 mmol). The reaction mixture was stirred at room temperature for 2 h. Ethyl acetate and water were added. The layers were separated, and the aqueous phase was extracted with ethyl acetate. The combined organic phases were washed three times (3×100 mL) with brine solution. The organic phase was dried over anhydrous Na₂SO₄, filtered and concentrated. The residue was purified by chromatography with dichloromethane and methanol (30:1) to give tert-butyl (S)-2-(1-amino-5-carbamoyl-4-(4-((5-chloropyridin-2-yl)carbamoyl)phenyl)-1H-imidazol-2-yl)piperidine-1-carboxylate as a white solid (0.45 g, 69%). ¹H NMR (CDCl₃, 600 MHz) δ: 8.61 (s, 1H), 8.39 (d, J=8.9 Hz, 1H), 8.28 (d, J=2.4 Hz, 1H), 7.95 (d, J=8.3 Hz, 2H), 7.87 (d, J=8.2 Hz, 2H), 7.73 (dd, J₁=8.9 Hz, J₂=2.5 Hz, 1H), 6.72 (s, 1H), 6.01 (s, 2H), 5.61-5.60 (m, 1H), 5.50 (s, 1H), 3.95-3.93 (m, 1H), 3.31-3.26 (m, 1H), 2.23-2.20 (m, 1H), 2.16-2.14 (m, 1H), 1.93-1.87 (m, 1H), 1.77-1.74 (m, 1H), 1.68-1.66 (m, 1H), 1.57 (s, 9H), 1.55-1.52 (m, 1H). MS (ESI, m/z): 540.2 [M+H]⁺.

Step E: Preparation of (S)-1-amino-4-(4-((5-chloro-pyridin-2-yl)carbamoyl)phenyl)-2-(piperidin-2-yl)-1H-imidazole-5-carboxamide

Step F: Preparation of (S)-2-(1-acryloylpiperidin-2-yl)-1-amino-4-(4-((4-chloropyridin-2-yl)carbamoyl)phenyl)-1H-imidazole-5-carboxamide

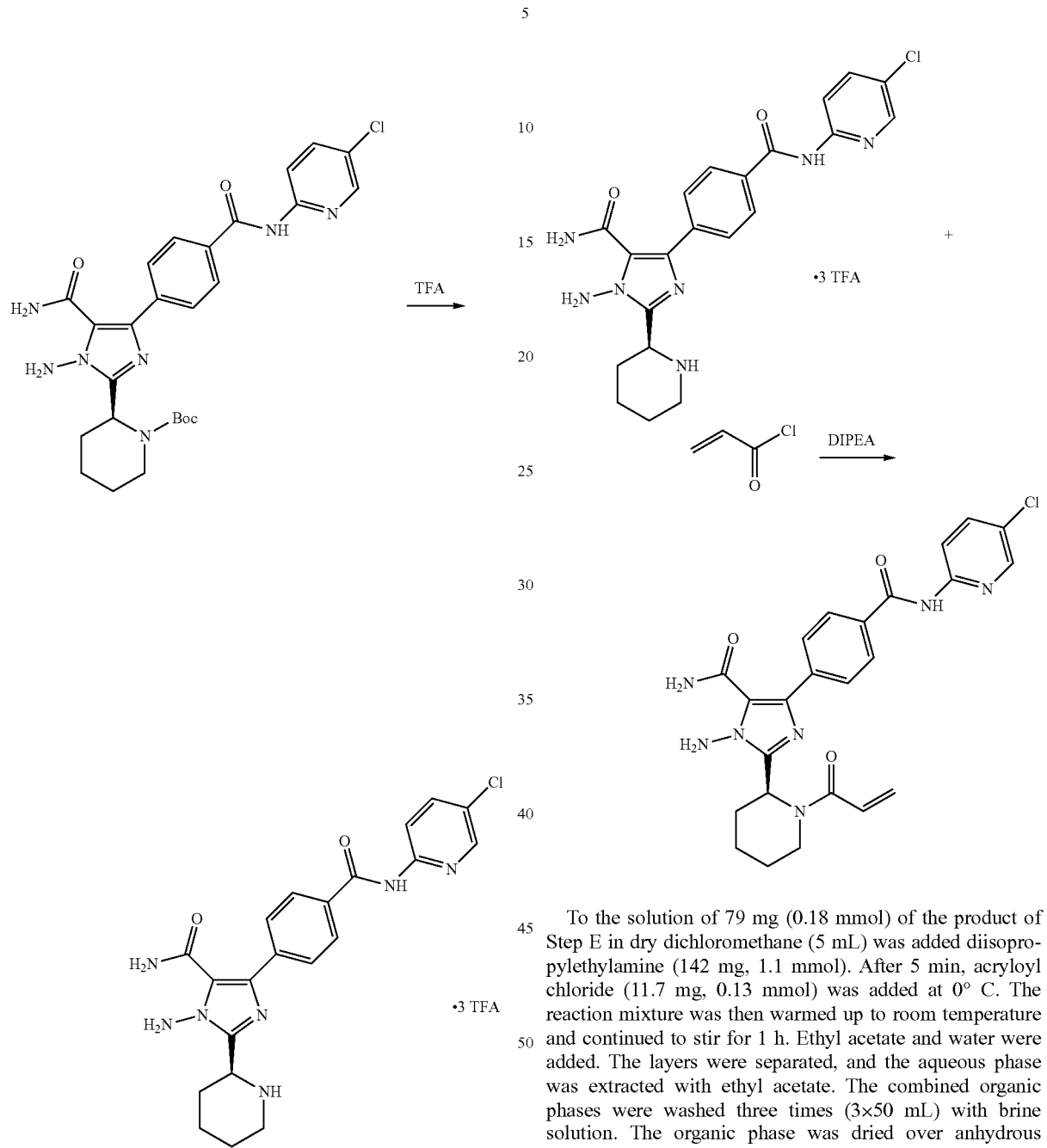

To the solution of 100 mg (0.18 mmol) of the product of Step D in dichloromethane (5 mL) was added trifluoroacetic acid (1.1 mL). The mixture was stirred at room temperature for 1 h and then concentrated to afford (S)-1-amino-4-(4-((5-chloropyridin-2-yl)carbamoyl)phenyl)-2-(piperidin-2-yl)-1H-imidazole-5-carboxamide as a light yellow oil. MS (ESI, m/z): 440.1 [M+H]$^+$.

To the solution of 79 mg (0.18 mmol) of the product of Step E in dry dichloromethane (5 mL) was added diisopropylethylamine (142 mg, 1.1 mmol). After 5 min, acryloyl chloride (11.7 mg, 0.13 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (28:1) to give (S)-2-(1-acryloylpiperidin-2-yl)-1-amino-4-(4-((5-chloropyridin-2-yl)carbamoyl)phenyl)-1H-imidazole-5-carboxamide as an off-white solid (50 mg, 56%). $^1$H NMR (CDCl$_3$, 400 MHz) δ: 9.14 (s, 1H), 8.35 (d, J=8.9 Hz, 1H), 8.23 (d, J=2.1 Hz, 1H), 7.84 (d, J=8.3 Hz, 2H), 7.77-7.75 (m, 2H), 7.70 (dd, J$_1$=8.9 Hz, J$_2$=2.4 Hz, 1H), 7.26 (s, 1H), 6.58 (dd, J$_1$=16.4 Hz, J$_2$=10.7 Hz, 1H), 6.33-6.27 (m, 4H), 5.97-5.96 (m, 1H), 5.72 (d, J=10.7 Hz, 1H), 3.84-3.81 (m, 1H), 3.70-3.64 (m, 1H), 2.45-2.42 (m, 1H), 2.22-2.18 (m, 1H), 1.97-1.92 (m, 1H), 1.89-1.85 (m, 1H), 1.73-1.70 (m, 1H), 1.63-1.60 (m, 1H). $^{13}$C NMR (CDCl$_3$, 150 MHz) δ: 167.3, 165.8, 162.6, 150.2, 148.3, 146.6, 141.3, 138.5, 138.2, 133.2, 129.7, 128.8, 127.7, 127.3, 127.0, 120.1, 115.2, 44.4, 43.0, 28.0, 25.8, 19.7. MS (ESI, m/z): 494.2 [M+H]⁺.

Example 87

(S)-2-(1-acryloylpiperidin-2-yl)-1-amino-4-(4-((4-bromopyridin-2-yl)carbamoyl)phenyl)-1H-imidazole-5-carboxamide

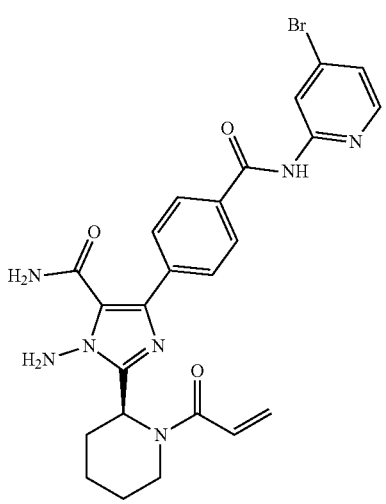

Step A: Preparation of tert-butyl (S)-2-(5-(ethoxycarbonyl)-4-(4-((4-bromopyridin-2-yl)carbamoyl)phenyl)-1H-imidazol-2-yl)piperidine-1-carboxylate

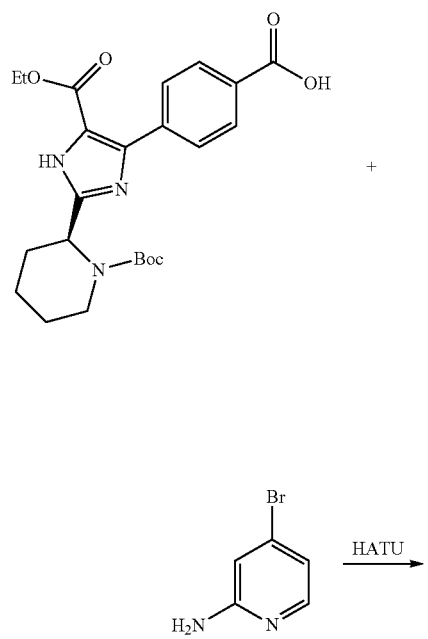

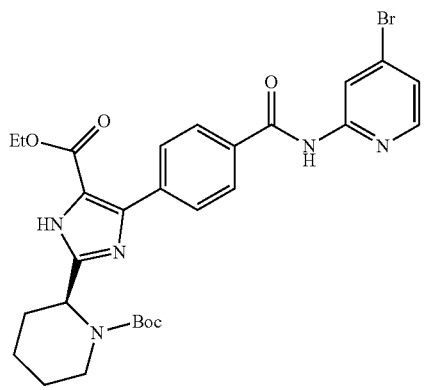

To the solution of 2.0 g (4.5 mmol) of the product of Step C of example 46 in dry N,N-Dimethylformamide (20 mL), HATU (2.0 g, 5.4 mmol), diisopropylethylamine (3.8 mL, 22 mmol) and 4-bromopyridin-2-amine (1.2 g, 6.7 mmol) were added and stirred at 80° C. for 3 h. After the completion of the reaction (monitored by TLC), the mixture was quenched with brine and washed with ethyl acetate three times (3×100 mL). The combined organic layers were concentrated under reduced pressure and purified by flash chromatography with petroleum ether and ethyl acetate (2:1) to afford tert-butyl (S)-2-(5-(ethoxycarbonyl)-4-(4-((4-bromopyridin-2-yl)carbamoyl)phenyl)-1H-imidazol-2-yl)piperidine-1-carboxylate as white solid (1.4 g, 52%). ¹H NMR (CDCl₃, 600 MHz) δ: 9.97 (s, 1H), 8.69 (s, 1H), 8.68 (s, 1H), 8.19 (d, J=8.1 Hz, 2H), 8.12 (d, J=5.3 Hz, 1H), 7.95 (d, J=8.2 Hz, 2H), 7.24 (d, J=5.3 Hz, 1H), 5.40 (d, J=3.8 Hz, 1H), 4.36-4.32 (m, 2H), 2.77-2.73 (m, 1H), 2.56 (d, J=13.0 Hz, 1H), 1.97-1.91 (m, 1H), 1.85-1.80 (m, 1H), 1.77-1.75 (m, 1H), 1.68-1.63 (m, 2H), 1.53 (s, 9H), 1.51-1.49 (m, 1H), 1.34 (t, J=7.1 Hz, 3H). MS (ESI, m/z): 598.2 [M+H]⁺.

Step B: Preparation of tert-butyl (S)-2-(1-amino-5-(ethoxycarbonyl)-4-(4-((4-bromopyridin-2-yl)carbamoyl)phenyl)-1H-imidazol-2-yl)piperidine-1-carboxylate

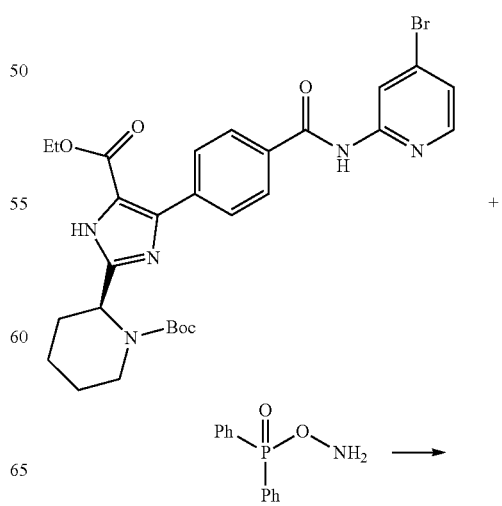

-continued

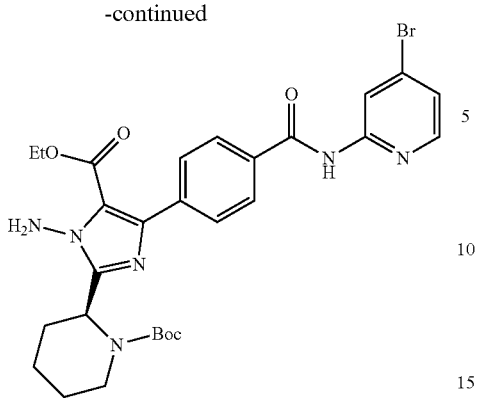

To the solution of 1.4 g (2.3 mmol) of the product of Step A in anhydrous N,N-Dimethylformamide (10 mL), lithium hexamethyldisilazane (2.7 mL, 1 M solution in tetrahydrofuran) was slowly added at −10° C. After the mixture was stirred for 20 min, O-(diphenylphosphinyl) hydroxylamine (0.6 g, 2.7 mmol) was added at 0° C. and the resulting suspension was stirred at room temperature for 2 h (in cases where the reaction mixture became too viscous, additional N,N-Dimethylformamide was added). The mixture was quenched with brine and washed with ethyl acetate three times (3×100 mL). The combined organic fractions were dried with anhydrous $Na_2SO_4$ and the solvent was removed under reduced pressure to afford the crude residue, which was subjected to column chromatography with petroleum ether and ethyl acetate (3:1) to afford tert-butyl (S)-2-(1-amino-5-(ethoxycarbonyl)-4-(4-((4-bromopyridin-2-yl)carbamoyl)phenyl)-1H-imidazol-2-yl)piperidine-1-carboxylate as a white solid (0.7 g, 50%). $^1$H NMR (CDCl$_3$, 600 MHz) δ: 8.71 (s, 1H), 8.69 (d, J=1.5 Hz, 1H), 8.12 (d, J=5.3 Hz, 1H), 7.93 (d, J=8.5 Hz, 2H), 7.87 (d, J=8.5 Hz, 2H), 7.25 (dd, J$_1$=5.3 Hz, J$_2$=1.7 Hz, 1H), 5.93 (s, 2H), 5.68 (d, J=4.9 Hz, 1H), 4.34-4.26 (m, 2H), 3.95 (d, J=12.8 Hz, 1H), 3.42 (td, J$_1$=13.1 Hz, J$_2$=3.1 Hz, 1H), 2.12-2.10 (m, 1H), 1.92-1.86 (m, 1H), 1.75 (d, J=13.1 Hz, 1H), 1.66-1.64 (m, 2H), 1.56-1.49 (m, 1H), 1.44 (s, 9H), 1.26 (t, J=7.1 Hz, 3H). MS (ESI, m/z): 613.1 [M+H]$^+$.

Step C: Preparation of (S)-1-amino-2-(1-(tert-butoxycarbonyl)piperidin-2-yl)-4-(4-((4-bromopyridin-2-yl)carbamoyl)phenyl)-1H-imidazole-5-carboxylic acid

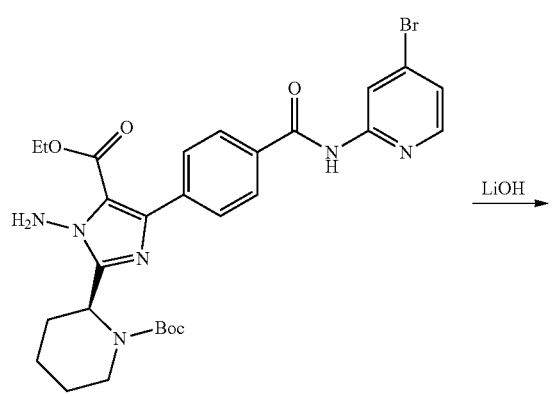

-continued

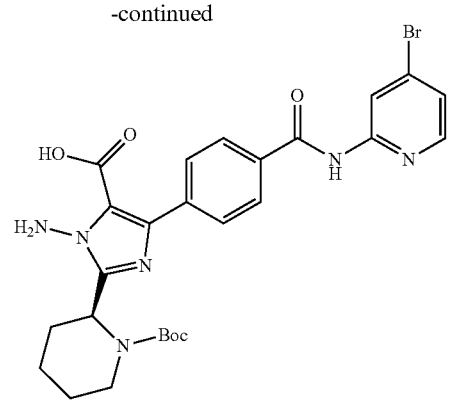

To the solution of 0.72 g (1.2 mmol) of the product of Step B in methanol (10 mL) was added 2 mol/L aqueous lithium hydroxide (6 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl)piperidin-2-yl)-4-(4-((4-bromopyridin-2-yl)carbamoyl)phenyl)-1H-imidazole-5-carboxylic acid (0.70 g, 99%).

Step D: Preparation of tert-butyl (S)-2-(1-amino-5-carbamoyl-4-(4-((4-bromopyridin-2-yl)carbamoyl)phenyl)-1H-imidazol-2-yl)piperidine-1-carboxylate

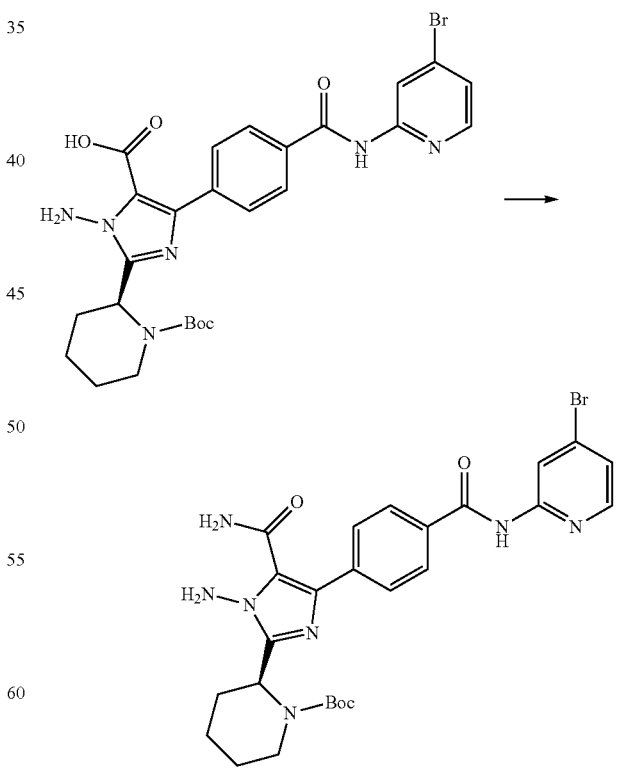

To the solution of 0.7 g (1.2 mmol) of the product of Step C in dry N,N-Dimethylformamide (10 mL) were added HATU (0.7 g, 1.8 mmol), diisopropylethylamine (0.6 mL, 3.6 mmol) and NH₄Cl (0.6 g, 12 mmol). The reaction mixture was stirred at room temperature for 2 h. The mixture was quenched with brine and washed with ethyl acetate three times (3×100 mL). The combined organic layers were concentrated under reduced pressure and purified by flash chromatography with dichloromethane and methanol (30:1) to afford tert-butyl (S)-2-(1-amino-5-carbamoyl-4-(4-((4-bromopyridin-2-yl)carbamoyl)phenyl)-1H-imidazol-2-yl) piperidine-1-carboxylate as a white solid (0.5 g, 71%). $^1$H NMR (CDCl₃, 600 MHz) δ: 9.08 (s, 1H), 8.65 (d, J=1.5 Hz, 1H), 8.10 (d, J=5.3 Hz, 1H), 7.88 (d, J=8.3 Hz, 2H), 7.78 (d, J=8.3 Hz, 2H), 7.23 (dd, J₁=5.3 Hz, J₂=1.7 Hz, 1H), 6.91 (s, 1H), 6.19 (s, 1H), 6.03 (s, 2H), 5.61-5.60 (m, 1H), 3.94 (d, J=12.9 Hz, 1H), 3.30 (td, J₁=13.1 Hz, J₂=2.9 Hz, 1H), 2.23-2.21 (m, 1H), 2.14 (d, J=13.6 Hz, 1H), 1.92-1.86 (m, 1H), 1.74 (d, J=13.2 Hz, 1H), 1.67-1.65 (m, 1H), 1.57-1.51 (m, 1H), 1.46 (s, 9H). MS (ESI, m/z): 584.1 [M+H]⁺.

Step E: Preparation of (S)-1-amino-4-(4-((4-bromopyridin-2-yl)carbamoyl)phenyl)-2-(piperidin-2-yl)-1H-imidazole-5-carboxamide To the solution of 30 mg (0.05 mmol) of the product of Step D in dichloromethane (5 mL) was added trifluoroacetic acid (0.3 mL). The mixture was stirred at room temperature for 1 h and then concentrated to afford (S)-1-amino-4-(4-((4-bromopyridin-2-yl)carbamoyl)phenyl)-2-(piperidin-2-yl)-1H-imidazole-5-carboxamide as a light yellow oil. MS (ESI, m/z): 484.1 [M+H]⁺.

Step F: Preparation of (S)-2-(1-acryloylpiperidin-2-yl)-1-amino-4-(4-((4-bromopyridin-2-yl)carbamoyl) phenyl)-1H-imidazole-5-carboxamide

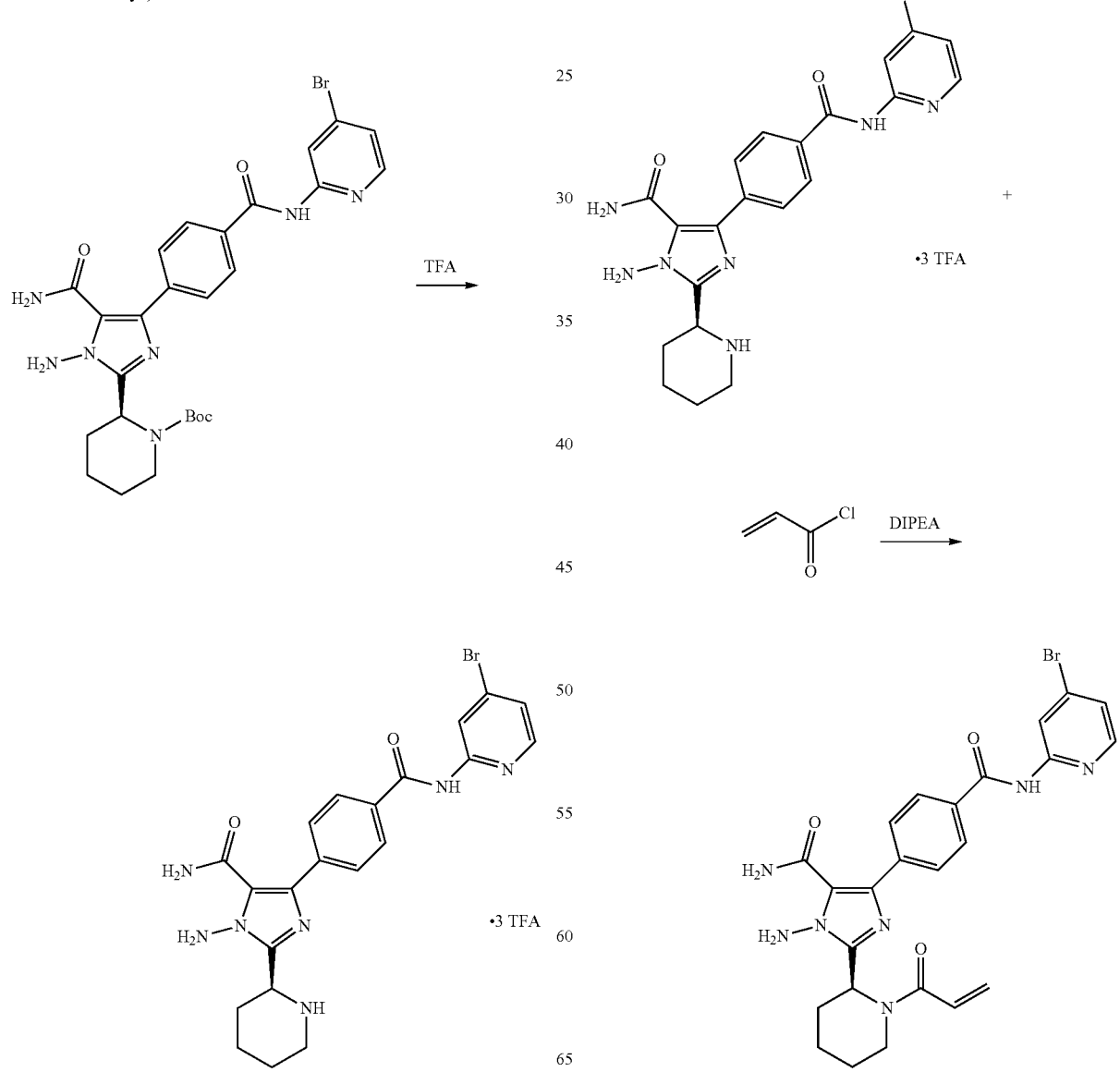

To the solution of 24.2 mg (0.05 mmol) of the product of Step E in dry dichloromethane (5 mL) was added diisopropylethylamine (40 mg, 0.31 mmol). After 5 min, acryloyl chloride (4.1 mg, 0.045 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to give (S)-2-(1-acryloylpiperidin-2-yl)-1-amino-4-(4-((4-bromopyridin-2-yl)carbamoyl)p-henyl)-1H-imidazole-5-carboxamide as an off-white solid (20 mg, 74%). $^1$H NMR (CDCl$_3$, 600 MHz) δ: 8.95 (s, 1H), 8.67 (d, J=1.3 Hz, 1H), 8.12 (d, J=5.3 Hz, 1H), 7.93 (d, J=8.2 Hz, 2H), 7.87 (d, J=7.3 Hz, 2H), 7.24 (dd, J$_1$=5.2 Hz, J$_2$=1.3 Hz, 1H), 7.16 (s, 1H), 6.62-6.57 (m, 1H), 6.32-6.29 (m, 3H), 5.97 (s, 2H), 5.74 (d, J=10.5 Hz, 1H), 3.84 (d, J=13.0 Hz, 1H), 3.68 (t, J=12.4 Hz, 1H), 2.46-2.45 (m, 1H), 2.21-2.19 (m, 1H), 1.94-1.88 (m, 2H), 1.74-1.71 (m, 1H), 1.64-1.62 (m, 1H); $^{13}$C NMR (CDCl$_3$, 150 MHz) δ: 167.3, 165.7, 162.5, 152.5, 148.5, 148.3, 141.4, 138.8, 134.8, 133.2, 129.9, 128.8, 127.8, 127.4, 123.5, 120.0, 117.6, 44.4, 43.0, 28.0, 25.8, 19.7. MS (ESI, m/z): 538.1 [M+H]$^+$.

Example 88

(S)-1-amino-4-(4-((4-bromopyridin-2-yl)carbamoyl)phenyl)-2-(1-(but-2-ynoyl)piperidin-2-yl)-1H-imidazole-5-carboxamide

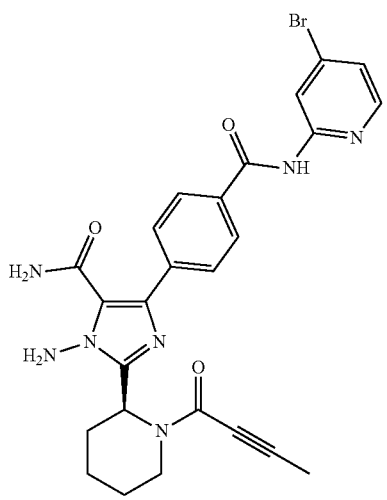 [SMILES: CC#CC(=O)N1CCCC[C@H]1c1nc(-c2ccc(C(=O)Nc3cc(Br)ccn3)cc2)c(C(N)=O)n1N]

Preparation of (S)-1-amino-4-(4-((4-bromopyridin-2-yl)carbamoyl)phenyl)-2-(1-(but-2-ynoyl)piperidin-2-yl)-1H-imidazole-5-carboxamide

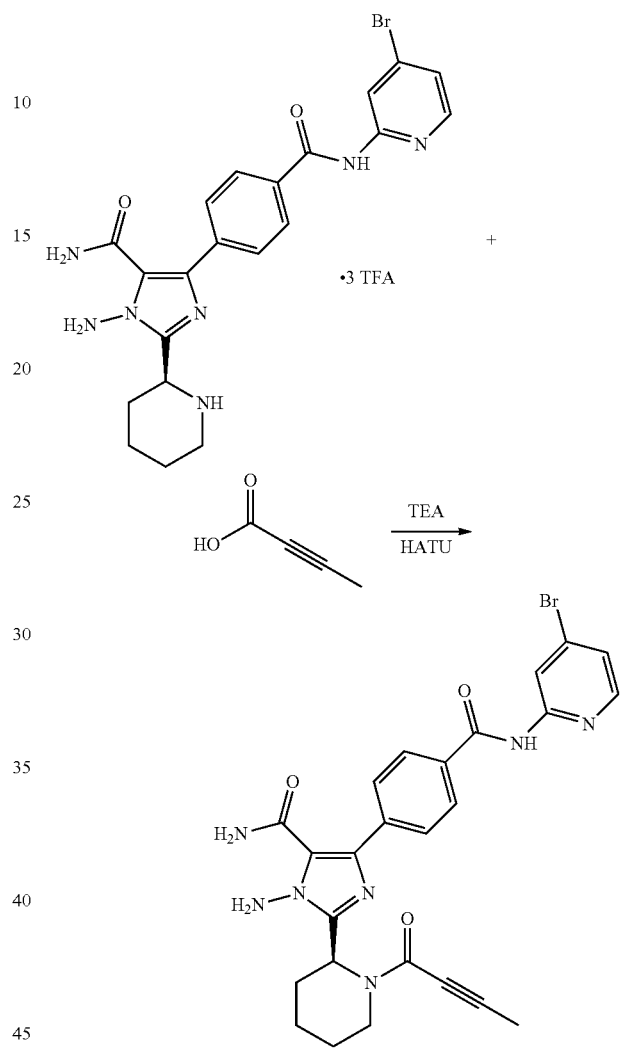

To the solution of 24.2 mg (0.05 mmol) of the product of Step E of example 87 in dry N,N-dimethylformamide (5 mL) was added triethylamine (31 mg, 0.31 mmol). After 5 min, but-2-ynoic acid (3.8 mg, 0.045 mmol) and HATU (28.5 mg, 0.075 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give(S)-1-amino-4-(4-((4-bromopyridin-2-yl)carbamoyl)phenyl)-2-(1-(but-2-ynoyl)piperidin-2-yl)-1H-imidazole-5-carboxamides an off-white solid (17 mg, 62%). $^1$H NMR (CDCl$_3$, 600 MHz) δ: 9.18 (s, 1H), 8.63 (d, J=1.4 Hz, 1H), 8.08 (d, J=5.3 Hz, 1H), 7.87 (d, J=8.3 Hz, 2H), 7.77 (d, J=8.3 Hz, 2H), 7.22 (dd, J$_1$=5.3 Hz, J$_2$=1.6 Hz, 1H), 7.11 (s, 1H), 6.37 (s, 1H), 6.13 (s, 2H), 5.94-5.93 (m, 1H), 4.27 (d, J=12.7 Hz, 1H), 3.64 (td, J$_1$=13.2 Hz, J$_2$=2.9

Hz, 1H), 2.38-2.34 (m, 1H), 2.17-2.15 (m, 1H), 2.00 (s, 3H), 1.90-1.84 (m, 2H), 1.72-1.70 (m, 1H), 1.63-1.58 (m, 1H); $^{13}$C NMR (CDCl$_3$, 150 MHz) δ: 165.9, 162.6, 155.0, 152.6, 148.5, 148.1, 141.2, 138.5, 134.7, 133.2, 129.7, 127.4, 123.4, 120.2, 117.6, 91.0, 73.0, 44.5, 43.8, 27.8, 25.7, 19.8, 4.3. MS (ESI, m/z): 550.1 [M+H]$^+$.

Example 89

(S)-2-(1-acryloylpiperidin-2-yl)-1-amino-4-(4-((4-iodopyridin-2-yl)carbamoyl)phenyl)-1H-imidazole-5-carboxamide

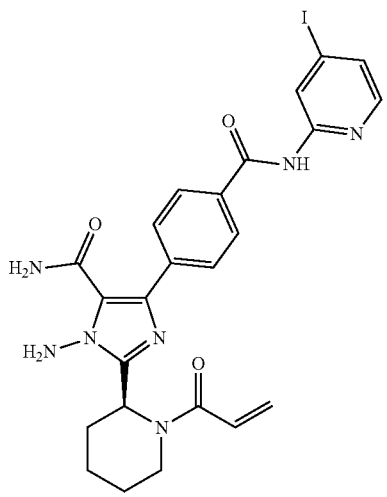

Step A: Preparation of tert-butyl (S)-2-(5-(ethoxycarbonyl)-4-(4-((4-iodopyridin-2-yl)carbamoyl)phenyl)-1H-imidazol-2-yl)piperidine-1-carboxylate

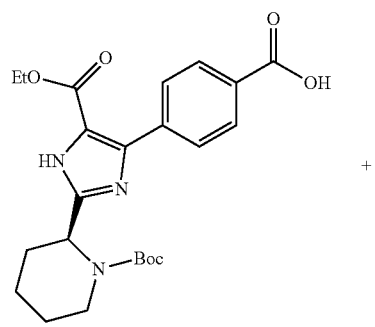

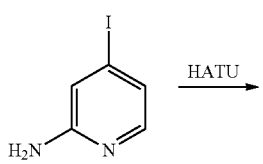

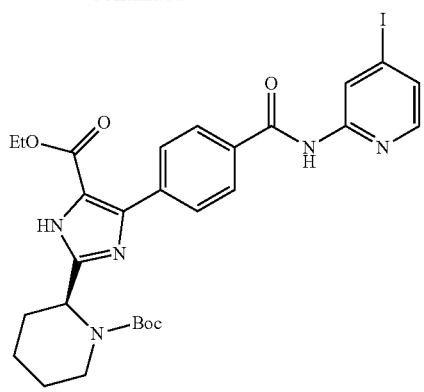

To the solution of 4.5 g (10.1 mmol) of the product of Step C of example 46 in dry N,N-Dimethylformamide (30 mL), HATU (4.6 g, 12.2 mmol), diisopropylethylamine (8.7 mL, 50.5 mmol) and 4-iodopyridin-2-amine (3.3 g, 15.1 mmol) were added and stirred at 80° C. for 3 h. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (2:1) to afford tert-butyl (S)-2-(5-(ethoxycarbonyl)-4-(4-((4-iodopyridin-2-yl)carbamoyl)phenyl)-1H-imidazol-2-yl)piperidine-1-carboxylate as white solid (4.1 g, 63%). $^1$H NMR (CDCl$_3$, 400 MHz) δ: 9.94 (s, 1H), 8.90 (s, 1H), 8.63 (s, 1H), 8.19 (d, J=8.4 Hz, 2H), 7.98-7.95 (m, 3H), 7.46 (dd, J$_1$=5.2 Hz, J$_2$=1.4 Hz, 1H), 5.41 (d, J=4.6 Hz, 1H), 4.37-4.32 (m, 2H), 2.77-2.72 (m, 1H), 2.56 (d, J=11.8 Hz, 1H), 1.86-1.84 (m, 1H), 1.78-1.75 (m, 2H), 1.69-1.66 (m, 2H), 1.53 (s, 9H), 1.52-1.50 (m, 1H), 1.34 (t, J=7.1 Hz, 3H). MS (ESI, m/z): 646.1 [M+H]$^+$.

Step B: Preparation of tert-butyl (S)-2-(1-amino-5-(ethoxycarbonyl)-4-(4-((4-iodopyridin-2-yl)carbamoyl)phenyl)-1H-imidazol-2-yl)piperidine-1-carboxylate

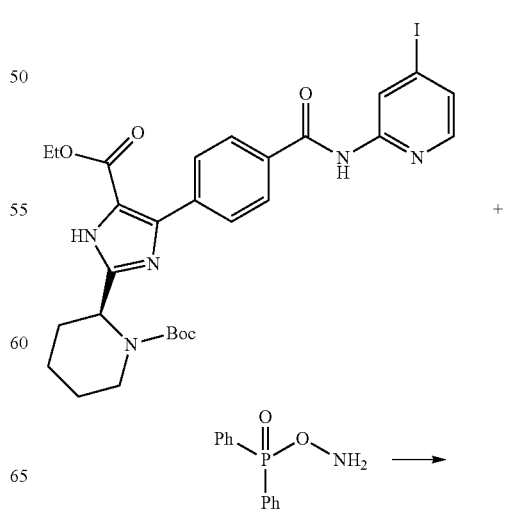

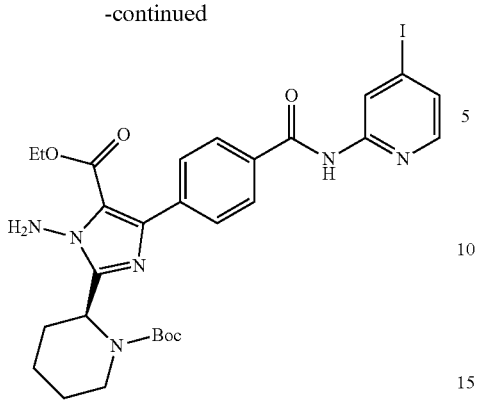

To the solution of 4.1 g (6.4 mmol) of the product of Step A in anhydrous N,N-Dimethylformamide (30 mL), lithium hexamethyldisilazane (7.7 mL, 1 M solution in tetrahydrofuran) was slowly added at −10° C. After the mixture was stirred for 20 min, O-(diphenylphosphinyl) hydroxylamine (1.8 g, 7.7 mmol) was added at 0° C. and the resulting suspension was stirred at room temperature for 2 h (in cases where the reaction mixture became too viscous, additional N,N-Dimethylformamide was added). The mixture was quenched with brine and washed with ethyl acetate three times (3×150 mL). The combined organic fractions were dried with anhydrous $Na_2SO_4$ and the solvent was removed under reduced pressure to afford the crude residue, which was subjected to column chromatography with petroleum ether and ethyl acetate (3:1) to afford tert-butyl (S)-2-(1-amino-5-(ethoxycarbonyl)-4-(4-((4-iodopyridin-2-yl)carbamoyl)phenyl)-1H-imidazol-2-yl)piperidine-1-carboxylate as a white solid (1.6 g, 38%). $^1$H NMR (CDCl$_3$, 400 MHz) δ: 8.89 (d, J=1.2 Hz, 1H), 8.74 (s, 1H), 7.94-7.91 (m, 3H), 7.85 (d, J=8.4 Hz, 2H), 7.44 (d, J=5.2 Hz, 1H), 5.92 (s, 2H), 5.68 (d, J=4.9 Hz, 1H), 4.32-4.26 (m, 2H), 3.95 (d, J=12.8 Hz, 1H), 3.41 (td, J$_1$=13.0 Hz, J$_2$=3.0 Hz, 1H), 2.12-2.08 (m, 1H), 1.93-1.87 (m, 1H), 1.76-1.73 (m, 2H), 1.66-1.63 (m, 1H), 1.54-1.50 (m, 1H), 1.44 (s, 9H), 1.25 (t, J=7.2 Hz, 3H). MS (ESI, m/z): 661.1 [M+H]$^+$.

Step C: Preparation of (S)-1-amino-2-(1-(tert-butoxycarbonyl)piperidin-2-yl)-4-(4-((4-iodopyridin-2-yl)carbamoyl)phenyl)-1H-imidazole-5-carboxylic acid

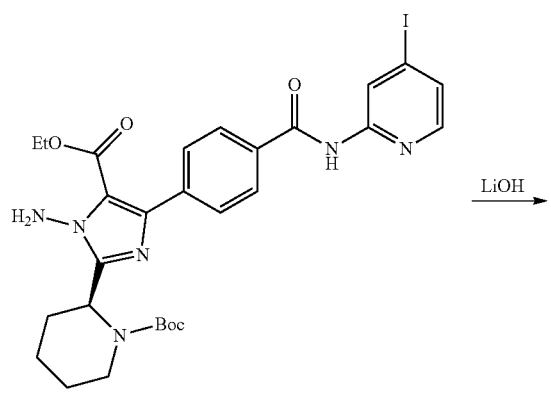

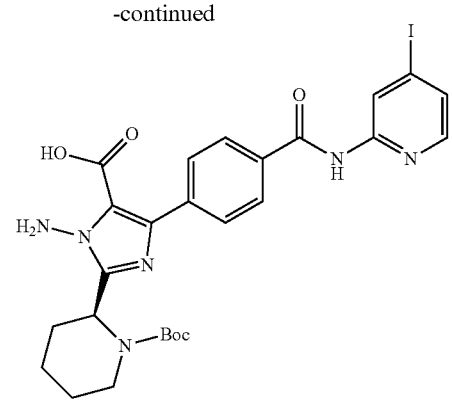

To the solution of 1.6 g (2.5 mmol) of the product of Step B in methanol (15 mL) was added 2 mol/L aqueous lithium hydroxide (12 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl)piperidin-2-yl)-4-(4-((4-iodopyridin-2-yl)carbamoyl)phenyl)-1H-imidazole-5-carboxylic acid (1.5 g, 95%).

Step D: Preparation of tert-butyl (S)-2-(1-amino-5-carbamoyl-4-(4-((4-iodopyridin-2-yl)carbamoyl)phenyl)-1H-imidazol-2-yl)piperidine-1-carboxylate

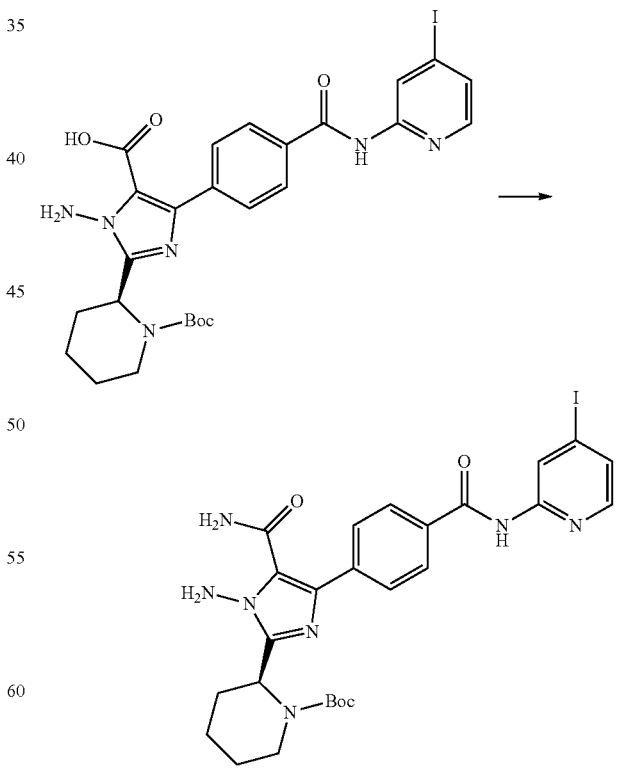

To the solution of 1.5 g (2.3 mmol) of the product of Step C in dry N,N-Dimethylformamide (10 mL) were added HATU (1.3 g, 3.5 mmol), diisopropylethylamine (1.2 mL, 7.1 mmol) and NH$_4$Cl (1.3 g, 23 mmol). The reaction mixture was stirred at room temperature for 2 h. The mixture was quenched with brine and washed with ethyl acetate three times (3×100 mL). The combined organic layers were concentrated under reduced pressure and purified by flash chromatography with dichloromethane and methanol (30:1) to afford tert-butyl (S)-2-(1-amino-5-carbamoyl-4-(4-((4-iodopyridin-2-yl)carbamoyl)phenyl)-1H-imidazol-2-yl)piperidine-1-carboxylate as a white solid (0.9 g, 62%). $^1$H NMR (CDCl$_3$, 400 MHz) δ: 8.87 (d, J=1.0 Hz, 1H), 8.67 (s, 1H), 7.98-7.93 (m, 3H), 7.87 (d, J=8.4 Hz, 2H), 7.46 (dd, J$_1$=5.2 Hz, J$_2$=1.4 Hz, 1H), 6.80 (s, 1H), 6.01 (s, 2H), 5.68 (s, 1H), 5.60 (d, J=4.5 Hz, 1H), 3.93 (d, J=12.4 Hz, 1H), 3.28 (td, J$_1$=13.0 Hz, J$_2$=3.0 Hz, 1H), 2.26-2.13 (m, 2H), 1.94-1.87 (m, 1H), 1.77-1.65 (m, 2H), 1.57-1.52 (m, 1H), 1.46 (s, 9H). MS (ESI, m/z): 632.1 [M+H]$^+$.

To the solution of 185 mg (0.29 mmol) of the product of Step D in dichloromethane (5 mL) was added trifluoroacetic acid (1.7 mL). The mixture was stirred at room temperature for 1 h and then concentrated to afford (S)-1-amino-4-(4-((4-iodopyridin-2-yl)carbamoyl)phenyl)-2-(piperidin-2-yl)-1H-imidazole-5-carboxamide as a light yellow oil. MS (ESI, m/z): 532.0 [M+H]$^+$.

Step F: Preparation of (S)-2-(1-acryloylpiperidin-2-yl)-1-amino-4-(4-((4-iodopyridin-2-yl)carbamoyl)phenyl)-1H-imidazole-5-carboxamide Step E: Preparation of (S)-1-amino-4-(4-((4-iodopyridin-2-yl)carbamoyl)phenyl)-2-(piperidin-2-yl)-1H-imidazole-5-carboxamide

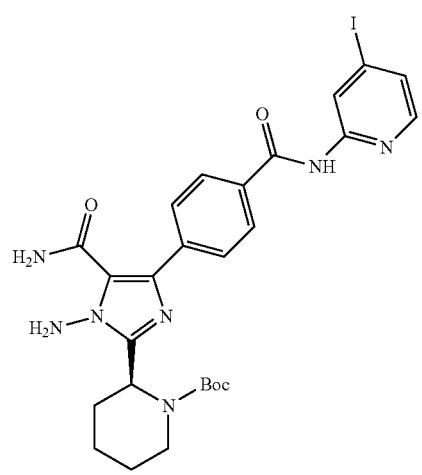

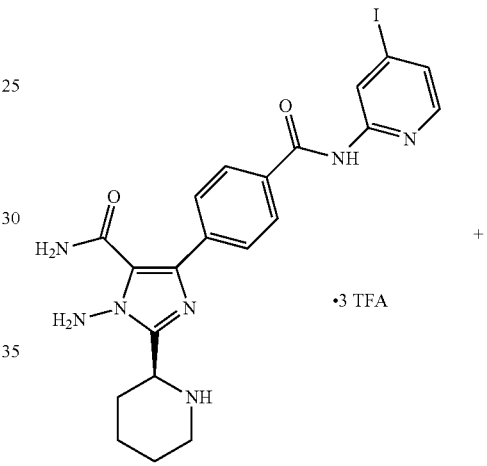

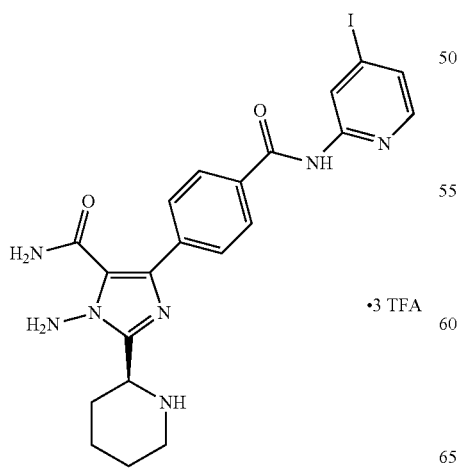

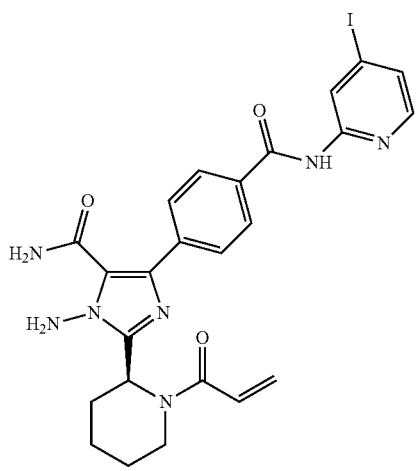

To the solution of 154 mg (0.29 mmol) of the product of Step E in dry dichloromethane (5 mL) was added diisopropylethylamine (224 mg, 1.74 mmol). After 5 min, acryloyl chloride (23.6 mg, 0.26 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to give (S)-2-(1-acryloylpiperidin-2-yl)-1-amino-4-(4-((4-iodopyridin-2-yl)carbamoyl)p-henyl)-1H-imidazole-5-carboxamide as an off-white solid (112 mg, 66%). $^1$H NMR (CDCl$_3$, 400 MHz) δ: 9.29 (s, 1H), 8.82 (d, J=1.1 Hz, 1H), 7.91 (d, J=5.1 Hz, 1H), 7.82 (d, J=8.4 Hz, 2H), 7.73 (d, J=7.8 Hz, 2H), 7.41 (dd, J$_1$=5.2 Hz, J$_2$=1.0 Hz, 1H), 7.36 (s, 1H), 6.58 (dd, J$_1$=16.3 Hz, J$_2$=10.7 Hz, 2H), 6.30-6.26 (m, 3H), 5.97-5.96 (m, 1H), 5.71 (d, J=10.6 Hz, 1H), 3.82 (d, J=12.9 Hz, 1H), 3.67 (t, J=12.4 Hz, 1H), 2.42-2.39 (m, 1H), 2.18 (d, J=12.6 Hz, 1H), 1.95-1.84 (m, 2H), 1.72-1.59 (m, 2H). MS (ESI, m/z): 586.0 [M+H]$^+$.

Example 90

(S)-1-amino-2-(1-(but-2-ynoyl)piperidin-2-yl)-4-(4-((4-iodopyridin-2-yl)carbamoyl)phenyl)-1H-imidazole-5-carboxamide

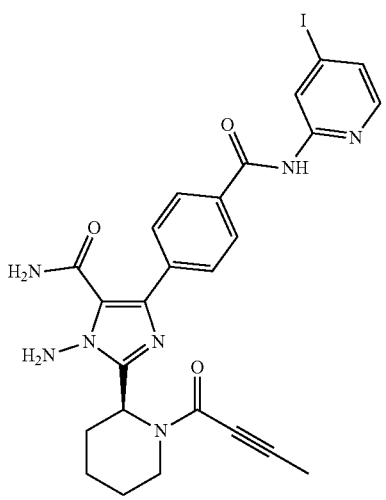 [SMILES: CC#CC(=O)N1CCCC[C@H]1c1nc(-c2ccc(C(=O)Nc3cc(I)ccn3)cc2)c(C(N)=O)n1N]

Preparation of (S)-1-amino-2-(1-(but-2-ynoyl)piperidin-2-yl)-4-(4-((4-iodopyridin-2-yl)carbamoyl)phenyl)-1H-imidazole-5-carboxamide

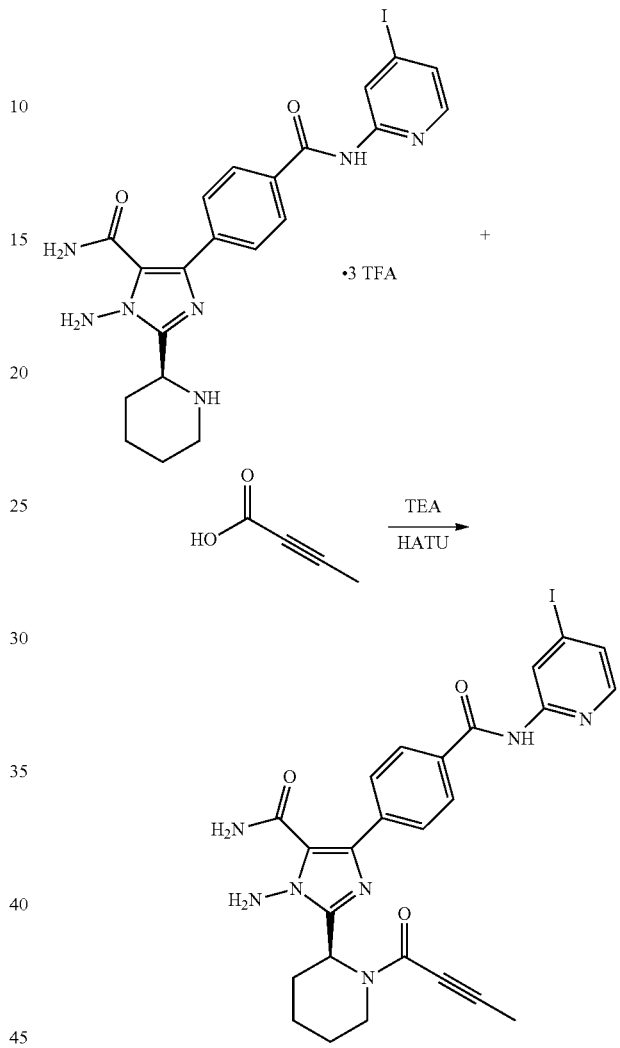

To the solution of 154 mg (0.29 mmol) of the product of Step E of example 89 in dry N,N-Dimethylformamide (5 mL) was added triethylamine (172 mg, 1.7 mmol). After 5 min, but-2-ynoic acid (22 mg, 0.26 mmol) and HATU (167 mg, 0.44 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(but-2-ynoyl)piperidin-2-yl)-4-(4-((4-iodopyridin-2-yl)carbamoyl)phenyl)-1H-imidazole-5-carboxamide as an off-white solid (90 mg, 52%). $^1$H NMR (CDCl$_3$, 400 MHz) δ: 9.26 (s, 1H), 8.81 (s, 1H), 7.90 (d, J=5.2 Hz, 1H), 7.83 (d, J=8.3 Hz, 2H), 7.73 (d, J=8.3 Hz, 2H), 7.40 (dd, J$_1$=5.2 Hz, J$_2$=1.3 Hz, 1H), 7.20 (s, 1H), 6.57 (s, 1H), 6.13 (s, 2H), 5.92 (d, J=4.7 Hz, 1H), 4.26 (d, J=12.7 Hz, 1H), 3.65 (td, J$_1$=13.1 Hz, J$_2$=2.7 Hz, 1H), 2.36-2.33 (m, 1H), 2.17-2.13 (m, 1H), 2.00 (s, 3H), 1.87-1.84 (m, 2H), 1.72-1.69 (m, 1H), 1.61-1.56 (m, 1H). MS (ESI, m/z): 598.1 [M+H]$^+$.

Example 91

(S)-2-(1-acryloylpiperidin-2-yl)-1-amino-4-(4-((4-(4-fluorophenyl)pyridin-2-yl)carbamoyl)phenyl)-1H-imidazole-5-carboxamide

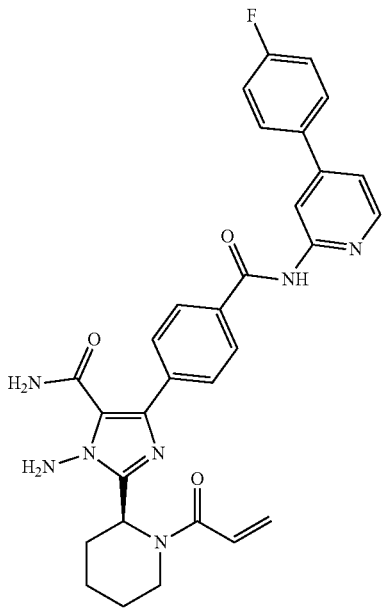

Step A: Preparation of tert-butyl (S)-2-(5-(ethoxycarbonyl)-4-(4-((4-(4-fluorophenyl)pyridin-2-yl)carbamoyl)phenyl)-1H-imidazol-2-yl)piperidine-1-carboxylate

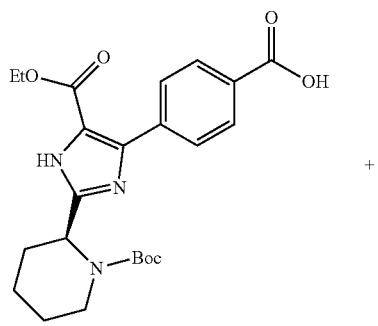

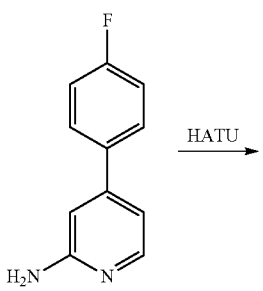

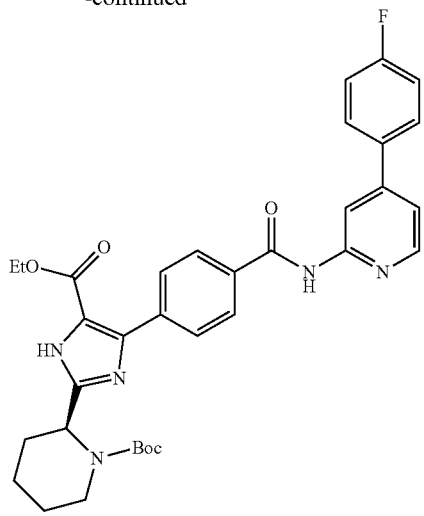

To the solution of 5.0 g (11.2 mmol) of the product of Step C of example 46 in dry N,N-dimethylformamide (30 mL) were added HATU (5.1 g, 13.5 mmol), diisopropylethylamine (9.7 mL, 56.4 mmol) and 4-(4-fluorophenyl)pyridin-2-amine (3.1 g, 16.8 mmol). The reaction mixture was stirred at 80° C. After the completion of the reaction (monitored by TLC), the mixture was quenched with brine and washed with ethyl acetate three times (3×200 mL). The combined organic layers were concentrated under reduced pressure and purified by flash chromatography with petroleum ether and ethyl acetate (2:1) to afford tert-butyl (S)-2-(5-(ethoxycarbonyl)-4-(4-((4-(4-fluorophenyl)pyridin-2-yl)carbamoyl)phenyl)-1H-imidazol-2-yl)piperidine-1-carboxylate as white solid (4.6 g, 67%). $^1$H NMR (CDCl$_3$, 400 MHz) δ: 9.99 (s, 1H), 8.93 (s, 1H), 8.69 (s, 1H), 8.31 (d, J=5.2 Hz, 1H), 8.19 (d, J=8.3 Hz, 2H), 7.99 (d, J=8.4 Hz, 2H), 7.72-7.69 (m, 2H), 7.27-7.25 (m, 1H), 7.19-7.15 (m, 2H), 5.41-5.40 (m, 1H), 4.35-4.30 (m, 2H), 2.79-2.72 (m, 1H), 2.56-2.53 (m, 1H), 1.87-1.73 (m, 3H), 1.68-1.65 (m, 1H), 1.52 (s, 9H), 1.49-1.48 (m, 2H), 1.33 (t, J=7.2 Hz, 3H). MS (ESI, m/z): 614.2 [M+H]$^+$.

Step B: Preparation of tert-butyl (S)-2-(1-amino-5-(ethoxycarbonyl)-4-(4-((4-(4-fluorophenyl)pyridin-2-yl)carbamoyl)phenyl)-1H-imidazol-2-yl) piperidine-1-carboxylate

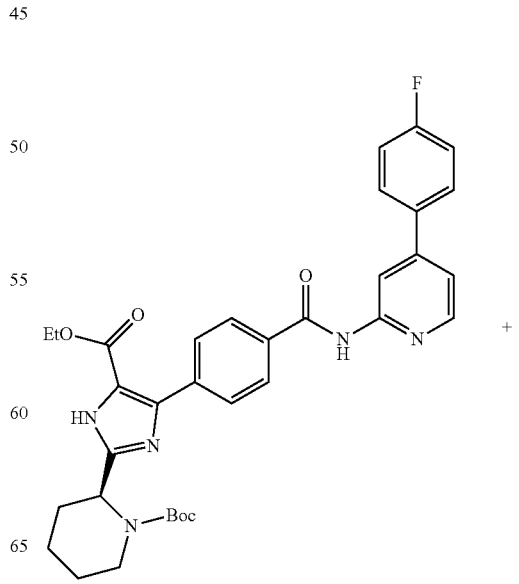

-continued

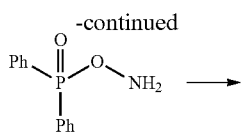

Step C: Preparation of (S)-1-amino-2-(1-(tert-butoxycarbonyl)piperidin-2-yl)-4-(4-((4-(4-fluorophenyl)pyridin-2-yl)carbamoyl)phenyl)-1H-imidazole-5-carboxylic acid

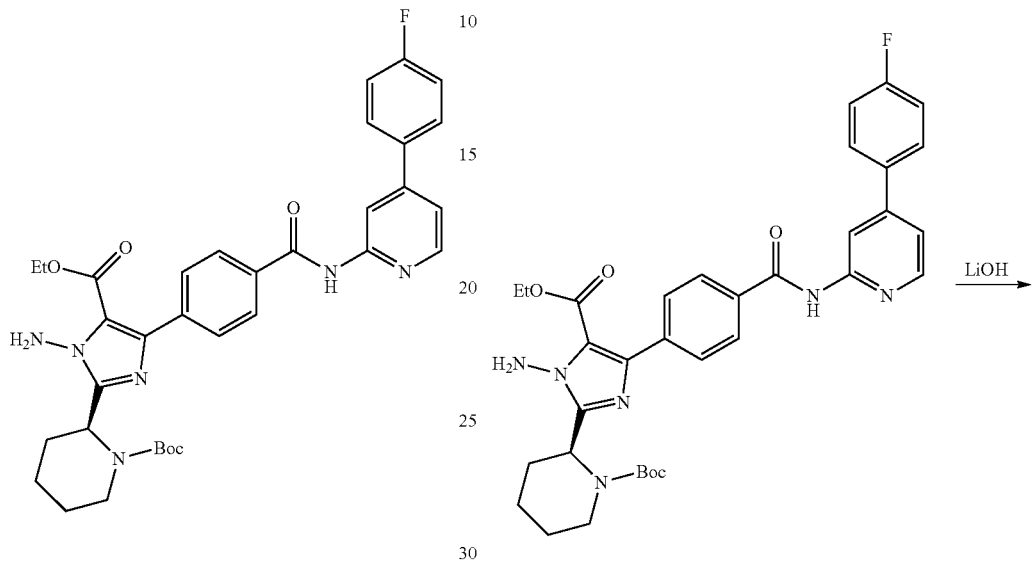

To the solution of 4.6 g (7.6 mmol) of the product of Step A in anhydrous N,N-Dimethylformamide (30 mL) was slowly added lithium hexamethyldisilazane (9.0 mL, 1 M solution in tetrahydrofuran) at −10° C. After the mixture was stirred for 20 min, O-(diphenylphosphinyl) hydroxylamine (2.1 g, 9.1 mmol) was added at 0° C. and the resulting suspension was stirred at room temperature for 2 h (in cases where the reaction mixture became too viscous, additional N,N-Dimethylformamide was added). The mixture was quenched with brine and extracted with ethyl acetate three times (3×150 mL). The combined organic fractions were dried with anhydrous $Na_2SO_4$ and the solvent was removed under reduced pressure to afford the crude residue, which was subjected to column chromatography with petroleum ether and ethyl acetate (2:1) to give tert-butyl (S)-2-(1-amino-5-(ethoxycarbonyl)-4-(4-((4-(4-fluorophenyl)pyridin-2-yl)carbamoyl)phenyl)-1H-imidazol-2-yl)piperidine-1-carboxylate as a white solid (3.0 g, 63%). $^1$H NMR ($CDCl_3$, 400 MHz) δ: 8.70 (s, 1H), 8.68 (s, 1H), 8.35 (d, J=4.7 Hz, 1H), 7.96 (d, J=8.6 Hz, 2H), 7.87 (d, J=8.5 Hz, 2H), 7.74-7.72 (m, 2H), 7.28 (dd, $J_1$=5.3 Hz, $J_2$=1.6 Hz, 1H), 7.20-7.16 (m, 2H), 5.90 (s, 2H), 5.68-5.67 (m, 1H), 4.29-4.25 (m, 2H), 3.97-3.93 (m, 1H), 3.43-3.39 (m, 1H), 2.13-2.09 (m, 1H), 1.90-1.87 (m, 1H), 1.75-1.72 (m, 1H), 1.64-1.65 (m, 2H), 1.51-1.48 (m, 1H), 1.44 (s, 9H), 1.26 (t, J=7.1 Hz, 3H). MS (ESI, m/z): 629.2 [M+H]$^+$.

To the solution of 3.0 g (4.7 mmol) of the product of Step B in methanol (17 mL) was added 2 mol/L aqueous lithium hydroxide (24 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl)piperidin-2-yl)-4-(4-((4-(4-fluorophenyl)pyridin-2-yl)carbamoyl)phenyl)-1H-imidazole-5-carboxylic acid (2.8 g, 99%).

Step D: Preparation of tert-butyl (S)-2-(1-amino-5-carbamoyl-4-(4-((4-(4-fluorophenyl)pyridin-2-yl)carbamoyl)phenyl)-1H-imidazol-2-yl)piperidine-1-carboxylate

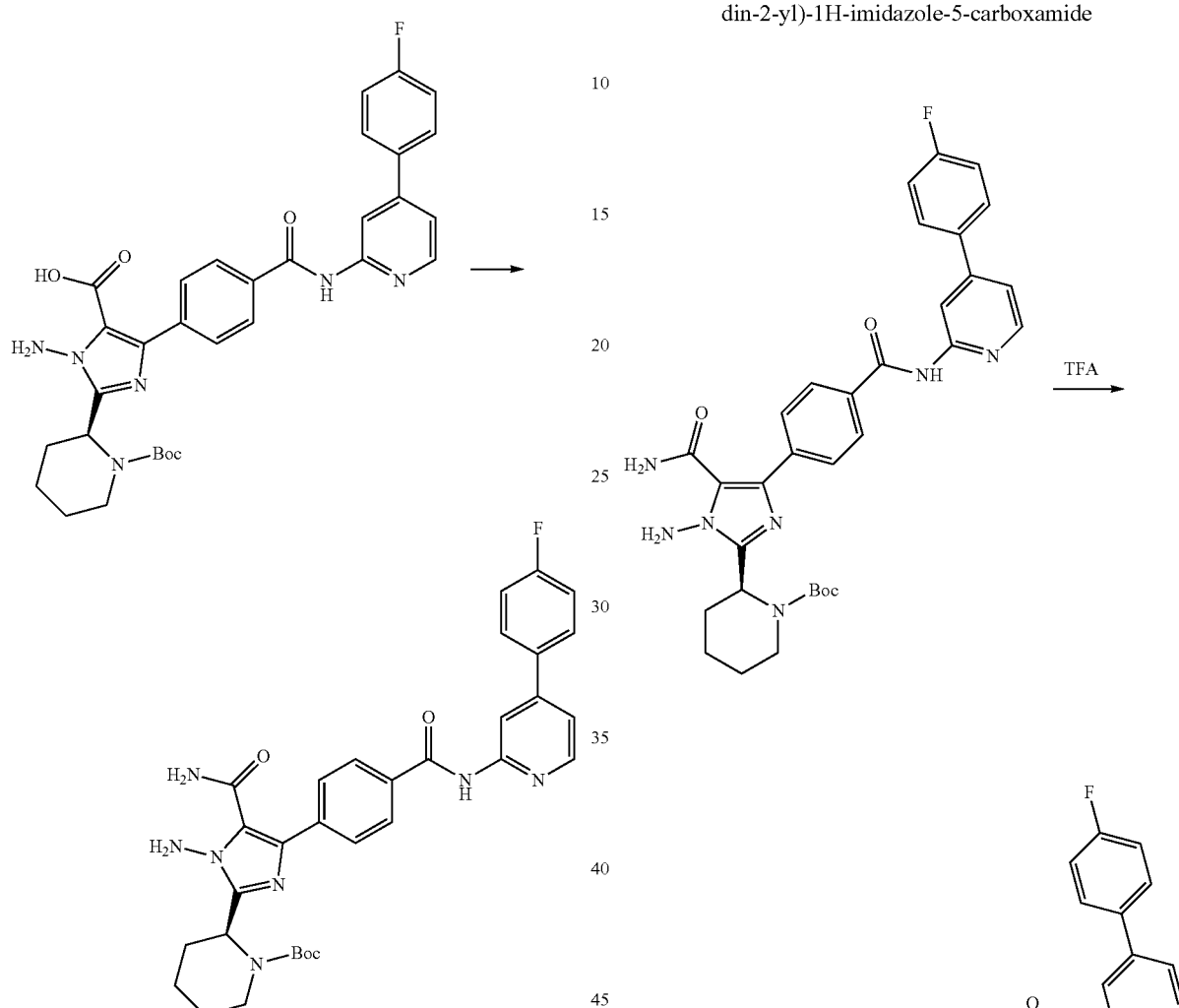

To the solution of 2.8 g (4.7 mmol) of the product of Step C in dry N,N-Dimethylformamide (20 mL) were added HATU (2.7 g, 7.0 mmol), diisopropylethylamine (2.4 mL, 14.1 mmol) and NH$_4$Cl (2.5 g, 47 mmol). The reaction mixture was stirred at room temperature for 2 h. The mixture was quenched with brine and washed with ethyl acetate three times (3×100 mL). The combined organic layers were concentrated under reduced pressure and purified by flash chromatography with dichloromethane and methanol (30:1) to give the product tert-butyl (S)-2-(1-amino-5-carbamoyl-4-(4-((4-(4-fluorophenyl)pyridin-2-yl)carbamoyl)phenyl)-1H-imidazol-2-yl)piperidine-1-carboxylate as a white solid (1.5 g, 53%). $^1$H NMR (CDCl$_3$, 400 MHz) δ: 9.23 (s, 1H), 8.62 (s, 1H), 8.29 (d, J=5.2 Hz, 1H), 7.92 (d, J=8.4 Hz, 2H), 7.79 (d, J=8.3 Hz, 2H), 7.70-7.65 (m, 2H), 7.23 (dd, J$_1$=5.2 Hz, J$_2$=1.6 Hz, 1H), 7.18-7.12 (m, 2H), 7.00 (s, 1H), 6.37 (s, 1H), 6.05 (s, 2H), 5.61-5.60 (m, 1H), 3.95-3.92 (m, 1H), 3.33-3.26 (m, 1H), 2.27-2.21 (m, 1H), 2.15-2.12 (m, 1H), 1.93-1.83 (m, 1H), 1.75-1.72 (m, 1H), 1.67-1.64 (m, 1H), 1.54-1.48 (m, 1H), 1.45 (s, 9H). MS (ESI, m/z): 600.2 [M+H]$^+$.

Step E: Preparation of (S)-1-amino-4-(4-((4-(4-fluorophenyl)pyridin-2-yl)carbamoyl)phenyl)-2-(piperidin-2-yl)-1H-imidazole-5-carboxamide

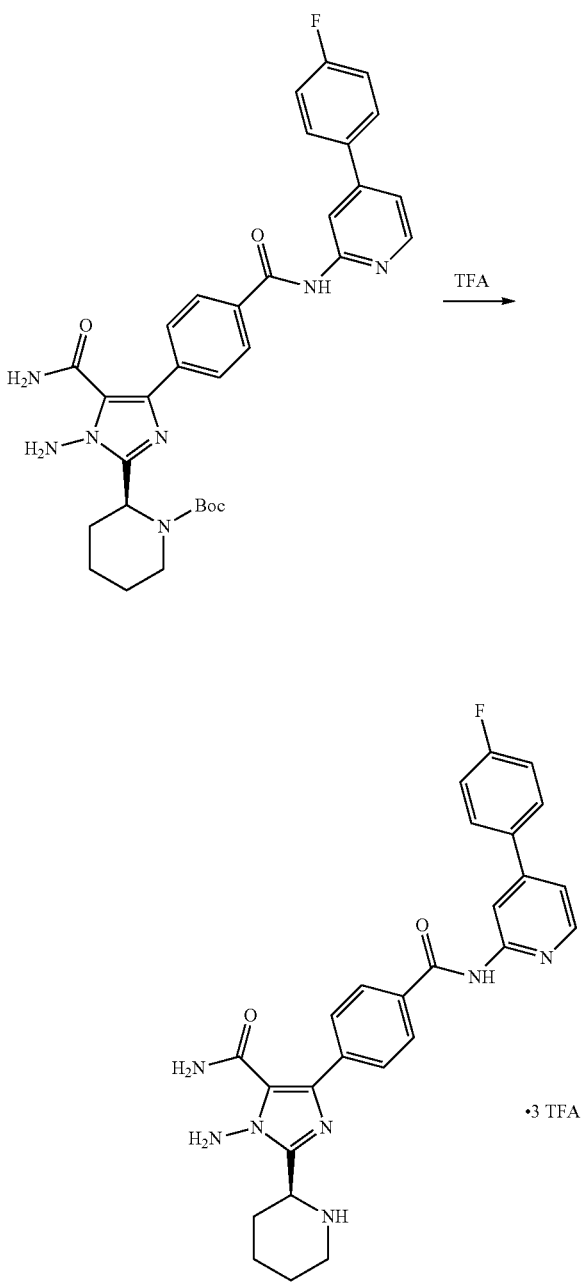

To the solution of 180 mg (0.30 mmol) of the product of Step D in dichloromethane (6 mL) was added trifluoroacetic acid (1.8 mL). The mixture was stirred at room temperature for 1 h and then concentrated to afford (S)-1-amino-4-(4-((4-(4-fluorophenyl)pyridin-2-yl)carbamoyl)phenyl)-2-(piperidin-2-yl)-1H-imidazole-5-carboxamide as a light yellow oil. MS (ESI, m/z): 500.2 [M+H]$^+$.

Step F: Preparation of (S)-2-(1-acryloylpiperidin-2-yl)-1-amino-4-(4-((4-(4-fluorophenyl)pyridin-2-yl)carbamoyl)phenyl)-1H-imidazole-5-carboxamide

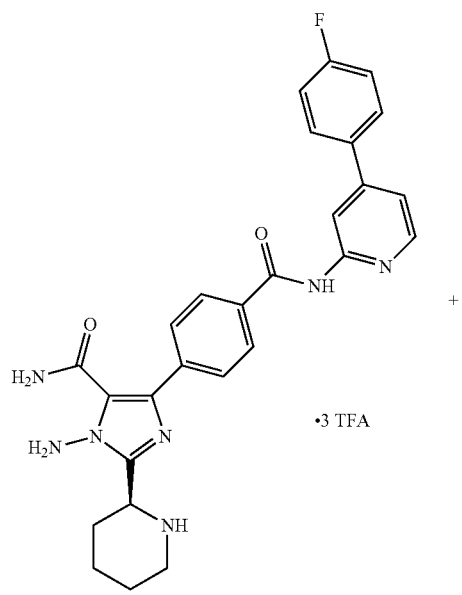

·3 TFA

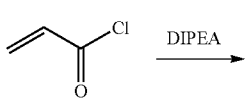

DIPEA

To the solution of 150 mg (0.30 mmol) of the product of Step E in dry dichloromethane (5 mL) was added diisopropylethylamine (232 mg, 1.80 mmol). After 5 min, acryloyl chloride (24.4 mg, 0.27 mmol) was added at 0° C. The reaction mixture was then warmed up to room temperature and continued to stir for 1 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to give (S)-2-(1-acryloylpiperidin-2-yl)-1-amino-4-(4-((4-(4-fluorophenyl)pyridin-2-yl)carbamoyl)phenyl)-1H-imidazole-5-carboxamide as an off-white solid (120 mg, 72%). $^1$H NMR (CDCl$_3$, 400 MHz) δ: 9.24 (s, 1H), 8.62 (s, 1H), 8.29 (d, J=5.2 Hz, 1H), 7.92 (d, J=8.4 Hz, 2H), 7.82 (d, J=7.8 Hz, 2H), 7.70-7.66 (m, 2H), 7.24-7.22 (m, 2H), 7.18-7.13 (m, 2H), 6.59 (dd, J$_1$=16.5 Hz, J$_2$=10.7 Hz, 1H), 6.43 (s, 1H), 6.33-6.26 (m, 3H), 5.98-5.97 (m, 1H), 5.72 (d, J=10.6 Hz, 1H), 3.84-3.81 (m, 1H), 3.70-3.65 (m, 1H), 2.44-2.41 (m, 1H), 2.20-2.17 (m, 1H), 1.92-1.85 (m, 2H), 1.73-1.68 (m, 1H), 1.62-1.59 (m, 1H). MS (ESI, m/z): 554.2 [M+H]$^+$.

Example 92

(S)-1-amino-2-(1-(but-2-ynoyl)piperidin-2-yl)-4-(4-((4-(4-fluorophenyl)pyridin-2-yl)carbamoyl)phenyl)-1H-imidazole-5-carboxamide

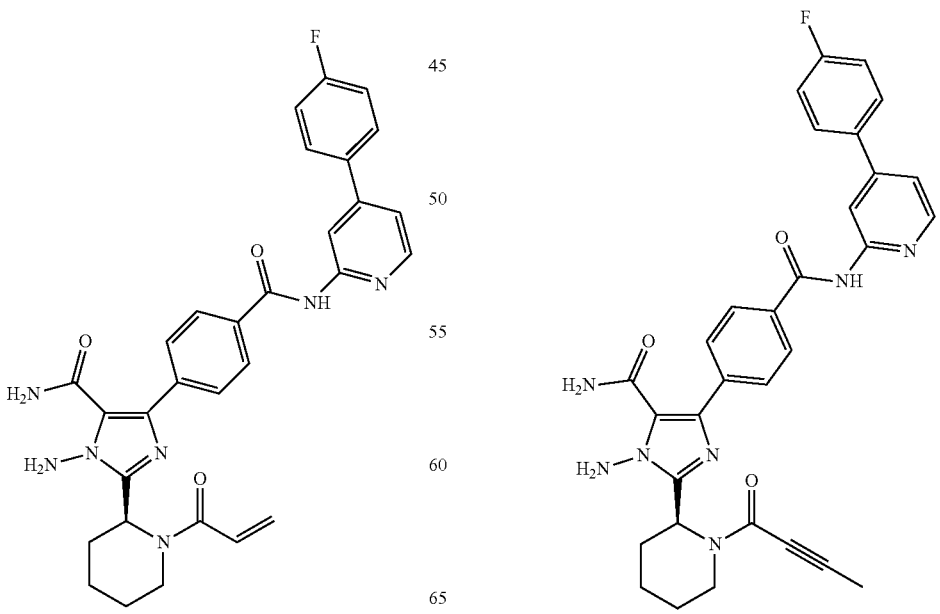

Preparation of (S)-1-amino-2-(1-(but-2-ynoyl)piperidin-2-yl)-4-(4-((4-(4-fluorophenyl)pyridin-2-yl)carbamoyl)phenyl)-1H-imidazole-5-carboxamide

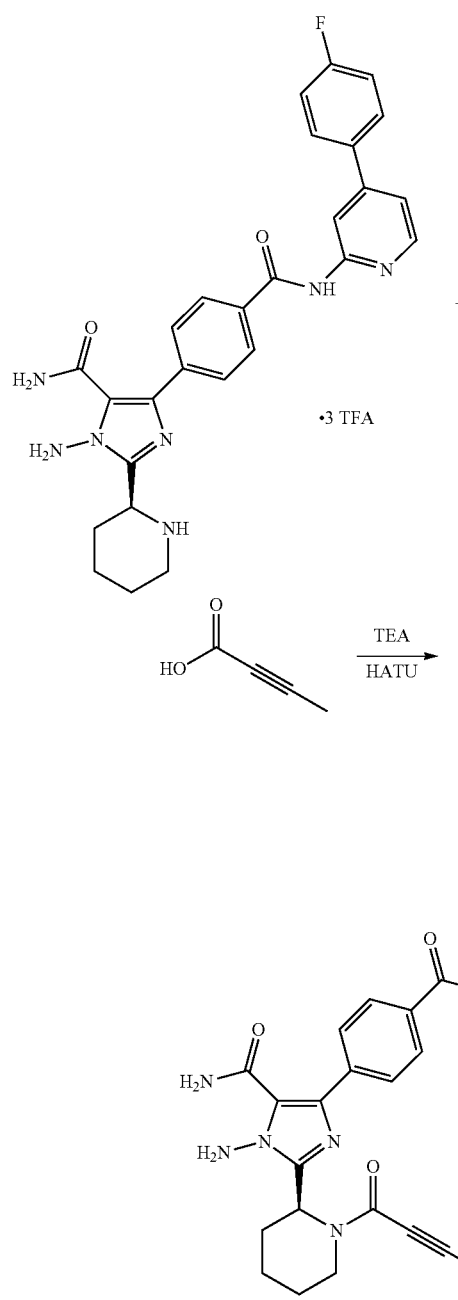

To the solution of 145 mg (0.29 mmol) the product of Step E of example 91 in dry N,N-Dimethylformamide (5 mL) was added triethylamine (172 mg, 1.7 mmol). After 5 min, but-2-ynoic acid (22 mg, 0.26 mmol) and HATU (167 mg, 0.44 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na₂SO₄, filtered and concentrated. The residue was purified by chromatography with dichloromethane and methanol (25:1) to give (S)-1-amino-2-(1-(but-2-ynoyl)piperidin-2-yl)-4-(4-((4-(4-fluorophenyl)pyridin-2-yl)carbamoyl)phenyl)-1H-imidazole-5-carboxamide as an off-white solid (85 mg, 52%). $^1$H NMR (CDCl$_3$, 400 MHz) δ: 9.57 (s, 1H), 8.53 (s, 1H), 8.21-8.19 (m, 1H), 7.84-7.82 (m, 2H), 7.72-7.70 (m, 2H), 7.63-7.60 (m, 2H), 7.40 (s, 1H), 7.16-7.15 (m, 1H), 7.12-7.08 (m, 2H), 6.94 (s, 1H), 6.12 (s, 2H), 5.91 (d, J=5.4 Hz, 1H), 4.25 (d, J=12.2 Hz, 1H), 3.68-3.62 (m, 1H), 2.32-2.26 (m, 1H), 2.14-2.10 (m, 1H), 1.96 (s, 3H), 1.84-1.81 (m, 2H), 1.67-1.54 (m, 2H). MS (ESI, m/z): 566.2 [M+H]$^+$.

Example 93: (R)-2-(1-acryloylpiperidin-3-yl)-1-amino-4-(4-((4-ethylpyridin-2-yl) carbamoyl)phenyl)-1H-imidazole-5-carboxamide

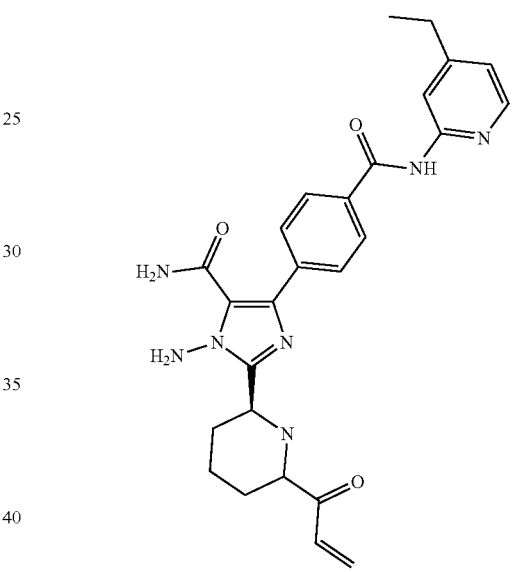

Step A: Preparation of (3R)-1-tert-butyl 3-(1-ethoxy-3-(4-(ethoxy-carbonyl)phenyl)-1,3-dioxopropan-2-yl)piperidine-1,3-dicarboxylate

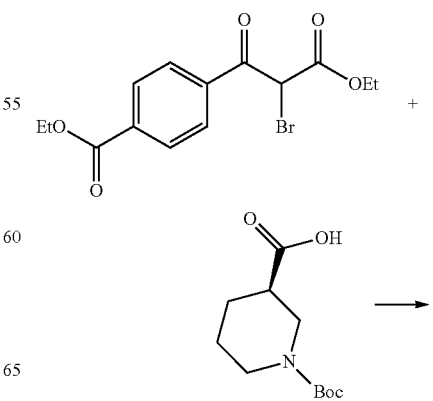

-continued

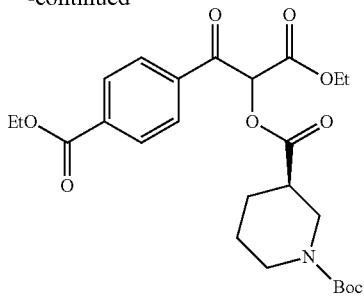

To the solution of 10 g (29 mmol) of the product of Step C of example 1 in acetonitrile (50 mL) were added (R)-1-(tert-butoxycarbonyl)piperidine-3-carboxylic acid (7.1 g, 31 mmol) and diisopropylethylamine (5.6 mL, 32 mmol). The mixture was stirred at room temperature for 3 h before all volatile were evaporated. The residue was diluted with water (100 mL) and extracted with ethyl acetate (300 mL). The organic phase was separated, dried over anhydrous $Na_2SO_4$ and concentrated. The residue was purified by flash column chromatography with petroleum ether and ethyl acetate (7:1) to give the (3R)-1-tert-butyl 3-(1-ethoxy-3-(4-(ethoxycarbonyl)phenyl)-1,3-dioxopropan-2-yl)piperidine-1,3-dicarboxylate as a light yellow oil (12.8 g, 90%). $^1$H NMR (CDCl$_3$, 400 MHz) δ: 8.13 (d, J=7.9 Hz, 2H), 8.02-8.00 (m, 2H), 6.27 (s, 1H), 4.39 (q, J=7.1 Hz, 2H), 4.23 (q, J=7.1 Hz, 2H), 4.16-4.07 (m, 1H), 3.99-3.80 (m, 1H), 3.03-2.98 (m, 1H), 2.80-2.74 (m, 1H), 2.63-2.58 (m, 1H), 2.14-2.06 (m, 1H), 1.74-1.60 (m, 2H), 1.42-1.38 (m, 13H), 1.19 (t, J=7.1 Hz, 3H). MS (ESI, m/z): 492.2 [M+H]$^+$.

Step B: Preparation of (R)-tert-butyl 3-(5-(ethoxycarbonyl)-4-(4-(ethoxycarbonyl)phenyl)-1H-imidazol-2-yl)piperidine-1-carboxylate

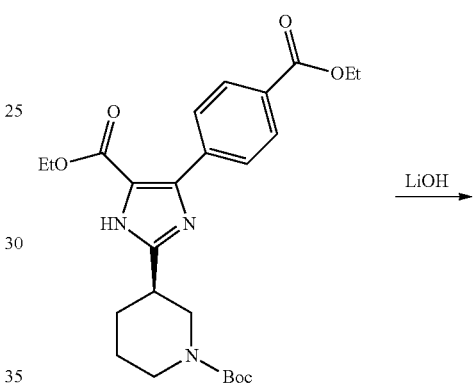

To the solution of 11 g (22 mmol) of the product of Step A in xylene (20 mL) in a 150 mL pressure bottle was added $NH_4OAc$ (21 g, 264 mmol). And the reaction was heated at 140° C. for 3.5 h. After being cooled, the solution was partition between ethyl acetate (500 mL) and water (200 mL). The organic layer was concentrated and the residue was purified by chromatography with petroleum ether and ethyl acetate (5:1) to afford (R)-tert-butyl 3-(5-(ethoxycarbonyl)-4-(4-(ethoxycarbonyl) phenyl)-1H-imidazol-2-yl)piperidine-1-carboxylate as a light yellow oil (2.8 g, 27%). $^1$H NMR (CDCl$_3$, 400 MHz) δ: 11.24 (s, 1H), 8.06-8.00 (m, 4H), 4.40-4.28 (m, 4H), 4.13-3.96 (m, 1H), 3.73-3.49 (m, 2H), 3.36-3.06 (m, 2H), 2.54-2.28 (m, 1H), 2.09-2.01 (m, 2H), 1.51-1.47 (m, 10H), 1.39 (t, J=7.1 Hz, 3H), 1.34-1.31 (m, 3H). MS (ESI, m/z): 472.2 [M+H]$^+$.

Step C: Preparation of (R)-4-(2-(1-(tert-butoxycarbonyl)piperidin-3-yl)-5-(ethoxycarbonyl)-1H-imidazol-4-yl)benzoic acid

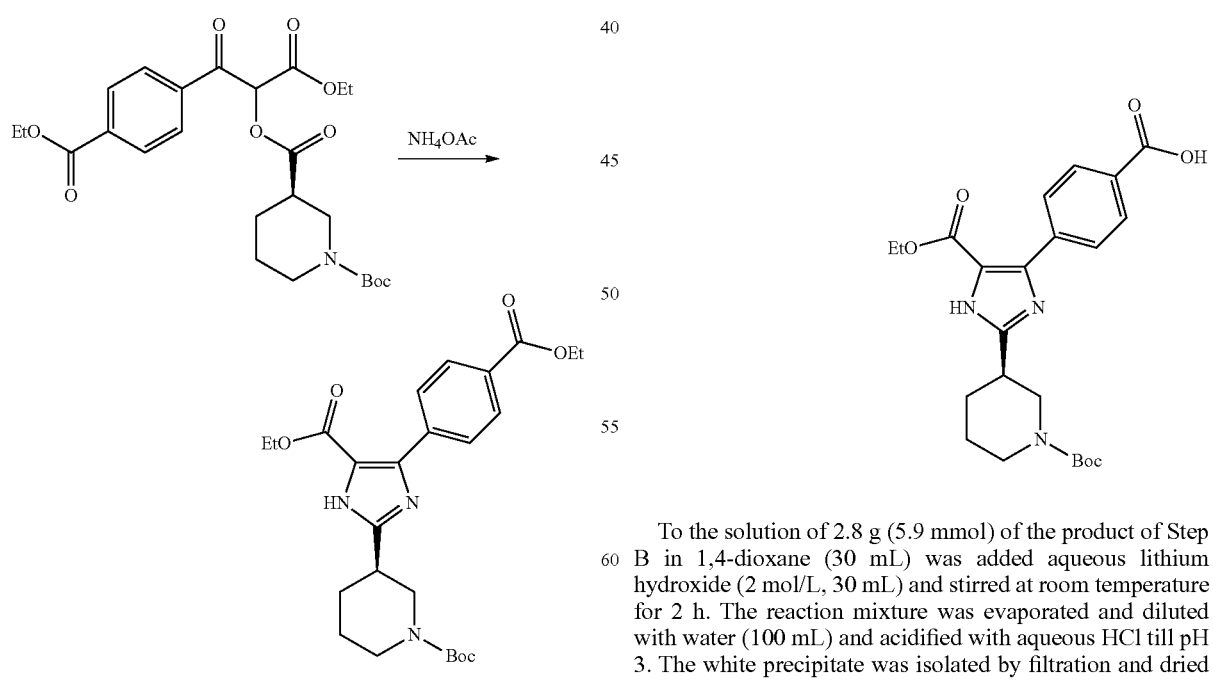

To the solution of 2.8 g (5.9 mmol) of the product of Step B in 1,4-dioxane (30 mL) was added aqueous lithium hydroxide (2 mol/L, 30 mL) and stirred at room temperature for 2 h. The reaction mixture was evaporated and diluted with water (100 mL) and acidified with aqueous HCl till pH 3. The white precipitate was isolated by filtration and dried to afford (R)-4-(2-(1-(tert-butoxycarbonyl)piperidin-3-yl)-5-(ethoxy-carbonyl)-1H-imidazol-4-yl)benzoic acid (2.3 g, 88%).

Step D: Preparation of (R)-tert-butyl 3-(5-(ethoxy-carbonyl)-4-(4-((4-ethylpyridin-2-yl)carbamoyl)phe-nyl)-1H-imidazol-2-yl)piperidine-1-carboxylate

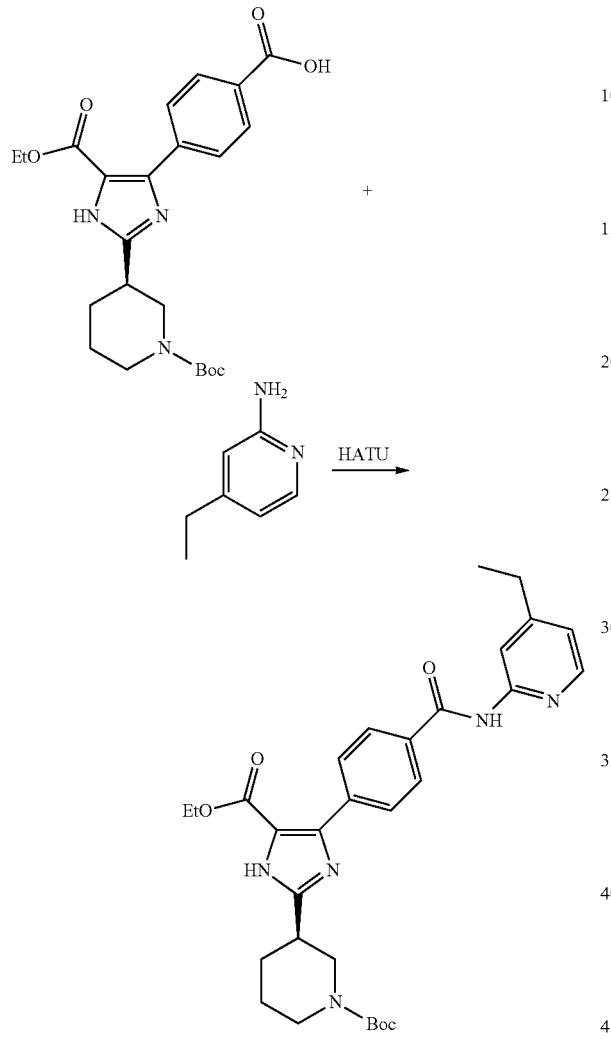

Step E: Preparation of (R)-tert-butyl 3-(1-amino-5-(ethoxycarbonyl)-4-(4-((4-ethylpyridin-2-yl)carbam-oyl)phenyl)-1H-imidazol-2-yl)piperidine-1-carboxy-late

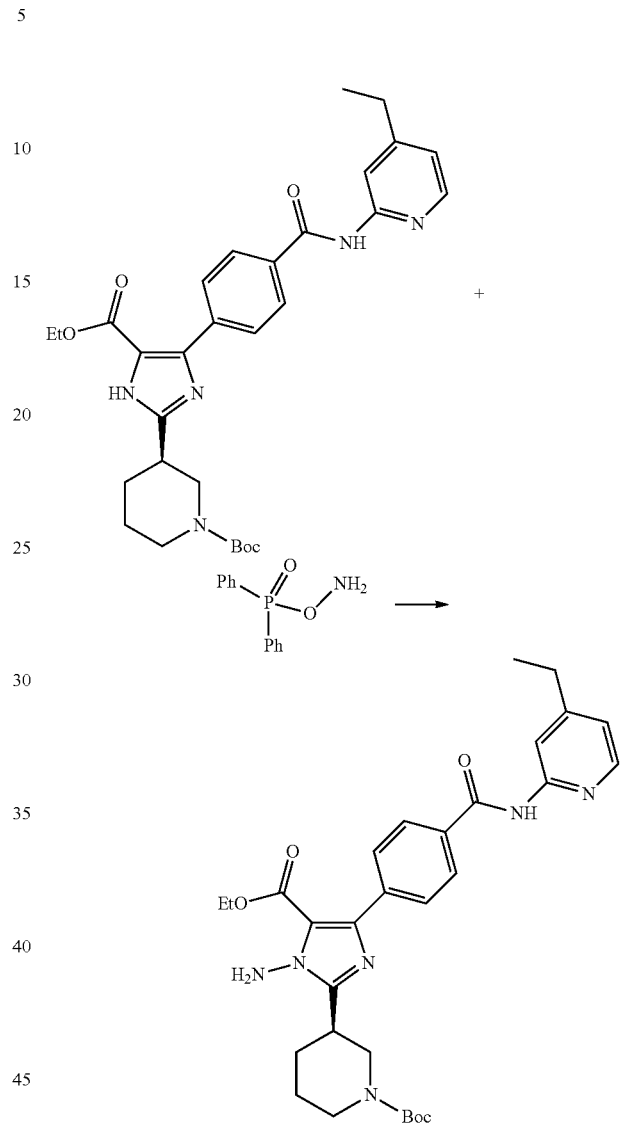

To the solution of 2.3 g (5.2 mmol) of the product of Step C in dry N,N-Dimethylformamide (20 mL) were added HATU (2.4 g, 6.2 mmol), diisopropylethylamine (4.5 mL, 26 mmol) and 4-ethylpyridin-2-amine (1.0 g, 7.8 mmol). The reaction mixture was stirred at 80° C. After the completion of the reaction (monitored by TLC), the mixture was quenched with brine and washed with ethyl acetate three times (3×100 mL). The combined organic layers were concentrated under reduced pressure and purified by flash chromatography with petroleum ether and ethyl acetate (2:1) to afford (R)-tert-butyl 3-(5-(ethoxycarbonyl)-4-(4-((4-ethylpyridin-2-yl)carbamoyl)phenyl)-1H-imidazol-2-yl)piperidine-1-carboxylate as a white solid (2.3 g, 81%). $^1$H NMR (CDCl$_3$, 600 MHz) δ: 8.85 (s, 1H), 8.28 (s, 1H), 8.15 (d, J=5.0 Hz, 1H), 8.08-8.03 (m, 2H), 7.94 (d, J=7.9 Hz, 2H), 6.91 (d, J=5.0 Hz, 1H), 4.34-4.28 (m, 2H), 4.16-3.98 (m, 1H), 3.71-3.46 (m, 2H), 3.26-3.12 (m, 2H), 2.69 (q, J=7.6 Hz, 2H), 2.50-2.33 (m, 1H), 2.05-1.95 (m, 1H), 1.55-1.51 (m, 2H), 1.45 (s, 9H), 1.32 (t, J=7.0 Hz, 3H), 1.27 (t, J=7.6 Hz, 3H). MS (ESI, m/z): 548.2 [M+H]$^+$.

To the solution of 2.3 g (4.2 mmol) of the product of Step D in dry N,N-Dimethylformamide (20 mL) was slowly added lithium hexamethyldisilazane (5.1 mL, 1 M solution in tetrahydrofuran) at −10° C. After the mixture was stirred for 10 min, O-(diphenylphosphinyl) hydroxylamine (1.0 g, 4.2 mmol) was added at 0° C. and the resulting suspension was stirred 2 h at room temperature (in cases where the reaction mixture became too viscous, additional N,N-Dimethylformamide was added). The reaction was quenched with brine and concentrated to dryness in vacuum. The residue was washed three times with ethyl acetate (3×200 mL). The combined organic fractions were dried with anhydrous Na$_2$SO$_4$ and the solvent was removed under reduced pressure to afford the crude residue, which was subjected to column chromatography with petroleum ether and ethyl acetate (2:1) to give the desired product (R)-tert-butyl 3-(1-amino-5-(ethoxycarbonyl)-4-(4-((4-ethylpyridin-2-yl)car-bamoyl)phenyl)-1H-imidazol-2-yl)piperidine-1-carboxylate (1.3 g, 55%). $^1$H NMR (CDCl$_3$, 400 MHz) δ: 8.65 (s, 1H), 8.29 (s, 1H), 8.18 (d, J=5.1 Hz, 1H), 7.94 (d, J=8.4 Hz, 2H), 7.80 (d, J=8.4 Hz, 2H), 6.93 (dd, J$_1$=5.1 Hz, J$_2$=1.1 Hz, 1H), 5.36 (s, 2H), 4.30-4.24 (m, 3H), 4.14-4.04 (m, 1H), 3.30-3.06 (m, 2H), 2.89-2.78 (m, 1H), 2.71 (q, J=7.6 Hz, 2H), 2.09-2.06 (m, 1H), 1.96-1.88 (m, 1H), 1.85-1.81 (m, 1H), 1.63-1.55 (m, 1H), 1.45 (s, 9H), 1.29 (t, J=7.6 Hz, 3H), 1.22 (t, J=7.1 Hz, 3H). MS (ESI, m/z): 563.2 [M+H]$^+$.

Step F: Preparation of (R)-1-amino-2-(1-(tert-butoxycarbonyl)piperidin-3-yl)-4-(4-((4-ethylpyridin-2-yl)carbamoyl)phenyl)-1H-imidazole-5-carboxylic acid

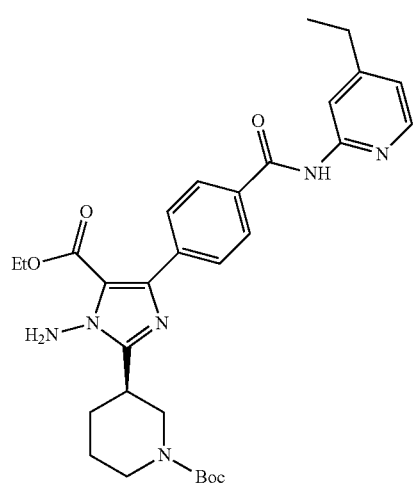

To the solution of 1.3 g (2.3 mmol) of the product of Step E in methanol (10 mL) was added aqueous lithium hydroxide (2 mol/L, 12 mL), then stirred at room temperature for 2 h. The reaction mixture was evaporated and diluted with water (100 mL) and acidified with aqueous HCl till pH 3. The mixture was washed with ethyl acetate three times (3×100 mL). The combined organic layers were concentrated under reduced pressure to afford (R)-1-amino-2-(1-(tert-butoxycarbonyl)piperidin-3-yl)-4-(4-((4-ethylpyridin-2-yl)carbamoyl)phenyl)-1H-imidazole-5-carboxylic acid (1.14 g, 93%).

Step G: Preparation of (R)-tert-butyl 3-(1-amino-5-carbamoyl-4-(4-((4-ethylpyridin-2-yl)carbamoyl)phenyl)-1H-imidazol-2-yl)piperidine-1-carboxylate

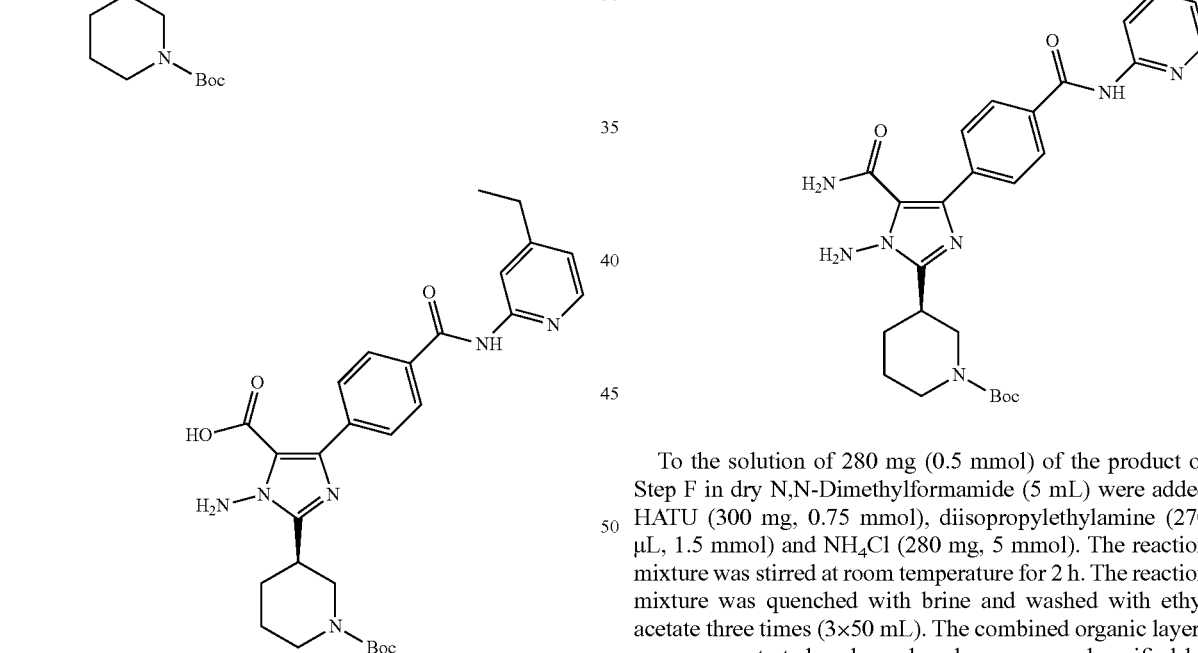

To the solution of 280 mg (0.5 mmol) of the product of Step F in dry N,N-Dimethylformamide (5 mL) were added HATU (300 mg, 0.75 mmol), diisopropylethylamine (270 μL, 1.5 mmol) and NH$_4$Cl (280 mg, 5 mmol). The reaction mixture was stirred at room temperature for 2 h. The reaction mixture was quenched with brine and washed with ethyl acetate three times (3×50 mL). The combined organic layers were concentrated under reduced pressure and purified by flash chromatography with dichloromethane and methanol (30:1) to afford (R)-tert-butyl 3-(1-amino-5-carbamoyl-4-(4-((4-ethylpyridin-2-yl)carbamoyl)phenyl)-1H-imidazol-2-yl)piperidine-1-carboxylate as a white solid (220 mg, 82%). $^1$H NMR (CDCl$_3$, 600 MHz) δ: 8.87 (s, 1H), 8.25 (s, 1H), 8.16 (d, J=4.9 Hz, 1H), 7.97 (d, J=7.7 Hz, 2H), 7.72 (d, J=7.6 Hz, 2H), 6.93 (d, J=4.9 Hz, 1H), 5.92-5.82 (m, 2H), 5.58 (s, 2H), 4.24-4.05 (m, 2H), 3.25-3.21 (m, 1H), 3.15-3.04 (m, 1H), 2.87-2.78 (m, 1H), 2.70 (q, J=7.6 Hz, 2H), 2.09-2.07 (m, 1H), 1.96-1.90 (m, 1H), 1.83-1.80 (m, 1H), 1.59-1.56 (m, 1H), 1.45 (s, 9H), 1.28 (t, J=7.6 Hz, 3H). MS (ESI, m/z): 534.2 [M+H]$^+$.

Step H: Preparation of (R)-1-amino-4-(4-((4-ethylpyridin-2-yl)carbamoyl)phenyl)-2-(piperidin-3-yl)-1H-imidazole-5-carboxamide

Step I: Preparation of (R)-2-(1-acryloylpiperidin-3-yl)-1-amino-4-(4-((4-ethylpyridin-2-yl)carbamoyl)phenyl)-1H-imidazole-5-carboxamide

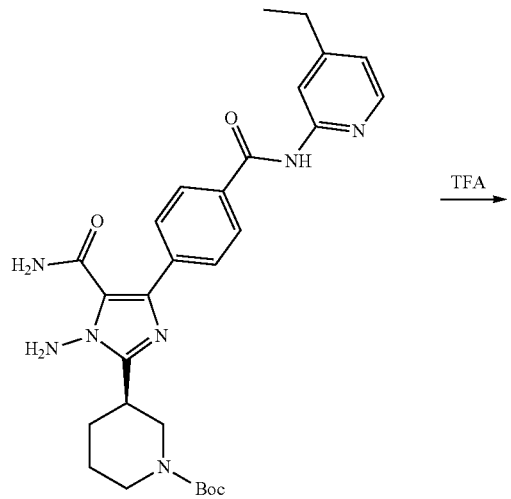

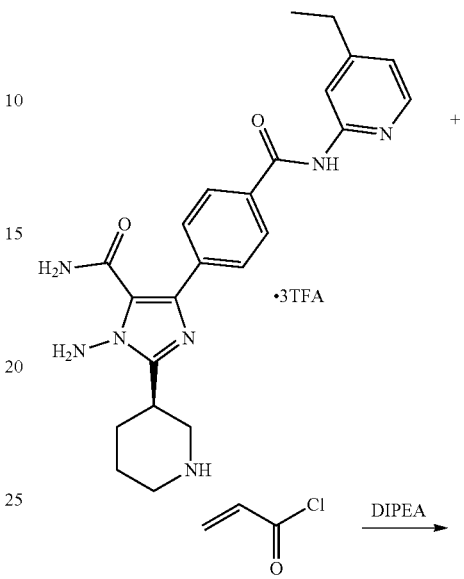

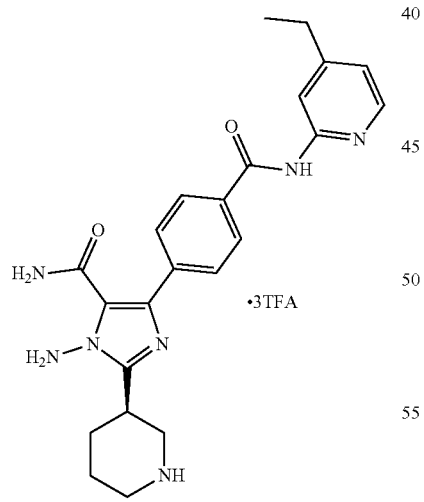

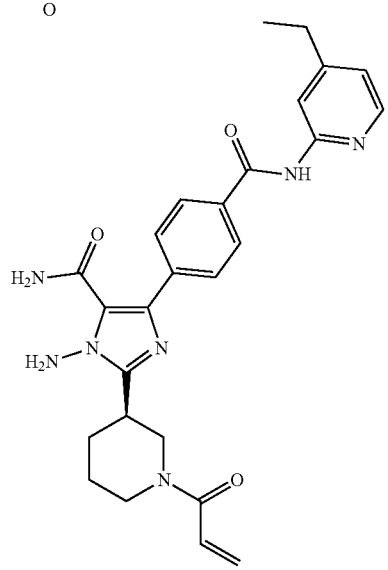

To the solution of 220 mg (0.41 mmol) of the product of Step G in dichloromethane (5 mL) was added trifluoroacetic acid (2.5 mL). The mixture was stirred at room temperature for 1 h and then concentrated to afford (R)-1-amino-4-(4-((4-ethylpyridin-2-yl)carbamoyl)phenyl)-2-(piperidin-3-yl)-1H-imidazole-5-carboxamide as a light yellow oil. MS (ESI, m/z): 434.2 [M+H]$^+$.

To the solution of 178 mg (0.41 mmol) of the product of Step H in dry dichloromethane (5 mL) was added diisopropylethylamine (318 mg, 2.46 mmol). After 5 min, acryloyl chloride (32.6 mg, 0.36 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (R)-2-(1-acryloyl-piperidin-3-yl)-1-amino-4-(4-((4-ethylpyridin-2-yl)carbamoyl)phenyl)-1H-imidazole-5-carboxamide as an off-white solid (112 mg, 56%). $^1$H NMR (CDCl$_3$, 400 MHz) δ: 9.15-9.11 (m, 1H), 8.22 (s, 1H), 8.14-8.12 (m, 1H), 7.95-7.89 (m, 2H), 7.67 (d, J=8.0 Hz, 2H), 6.91-6.90 (m, 1H), 6.66-6.55 (m, 1H), 6.46 (s, 0.6H), 6.26-6.22 (m, 2H), 5.96 (s, 0.4H), 5.70-5.61 (m, 3H), 4.70-4.61 (m, 1H), 4.23-4.20 (m, 0.4H), 3.99-3.96 (m, 0.6H), 3.43-3.37 (m, 0.4H), 3.27-3.13 (m, 1.6H), 3.03-2.97 (m, 0.6H), 2.75-2.65 (m, 2.4H), 2.10-1.84 (m, 3H), 1.66-1.52 (m, 1H), 1.26 (t, J=7.6 Hz, 3H); $^{13}$C NMR (DMSO-d$_6$, 150 MHz) δ: 165.6, 164.3, 162.5, 154.6, 152.4, 149.8, 147.7, 138.0, 135.8, 132.0, 128.6, 127.7, 127.1, 126.9, 125.1, 119.6, 113.9, 49.1, 45.6, 45.3, 42.0, 33.7, 32.8, 29.4, 28.9, 27.9, 25.6, 24.3, 14.4. MS (ESI, m/z): 488.2 [M+H]$^+$.

Example 94

2-(1-acryloylazepan-2-yl)-1-amino-4-(4-((4-ethylpyridin-2-yl)carbamoyl)phenyl)-1H-imidazole-5-carboxamide

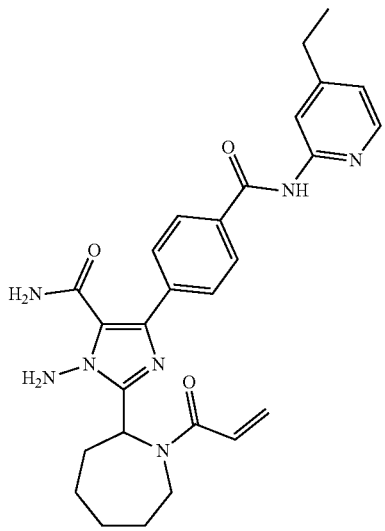 [SMILES: C=CC(=O)N1CCCCCC1c1nc(-c2ccc(C(=O)Nc3cc(CC)ccn3)cc2)c(C(N)=O)n1N]

Step A: Preparation of 1-(tert-butyl) 2-(1-ethoxy-3-(4-(ethoxycarbonyl)phenyl)-1,3-dioxopropan-2-yl) azepane-1,2-dicarboxylate

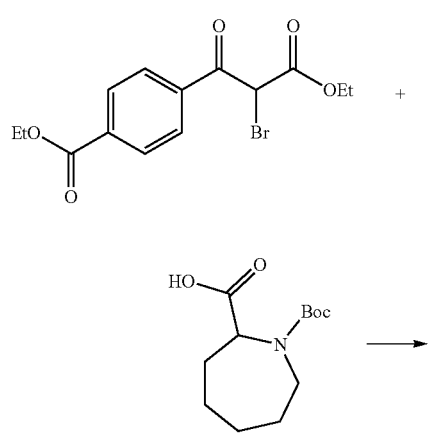

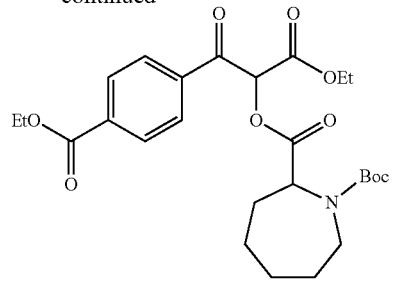

To the solution of 2.4 g (7 mmol) of the product of Step C of example 1 in acetonitrile (20 mL) were added 1-(tert-butoxycarbonyl)azepane-2-carboxylic acid (1.7 g, 7 mmol) and diisopropylethylamine (1.4 mL, 7.7 mmol). The mixture was stirred at room temperature for 3 h before all volatiles were evaporated. The residue was diluted with water (100 mL) and extracted with ethyl acetate (200 mL). The organic phase was separated, dried over anhydrous Na$_2$SO$_4$ and concentrated. The residue was purified by flash column chromatography with petroleum ether and ethyl acetate (8:1) to give the 1-(tert-butyl) 2-(1-ethoxy-3-(4-(ethoxycarbonyl)phenyl)-1,3-dioxopropan-2-yl) azepane-1,2-dicarboxylate as a light yellow oil (3.4 g, 96%). $^1$H NMR (CDCl$_3$, 400 MHz) δ: 8.15-8.12 (m, 2H), 8.05-8.00 (m, 2H), 6.29-6.25 (m, 1H), 4.83-4.54 (m, 1H), 4.44-4.38 (m, 2H), 4.27-4.21 (m, 2H), 3.98-3.77 (m, 1H), 3.03-2.92 (m, 1H), 2.50-2.30 (m, 1H), 1.93-1.87 (m, 1H), 1.81-1.67 (m, 3H), 1.45-1.30 (m, 15H), 1.23-1.19 (m, 3H). MS (ESI, m/z): 506.2 [M+H]$^+$.

Step B: Preparation of tert-butyl 2-(5-(ethoxycarbonyl)-4-(4-(ethoxycarbonyl)phenyl)-1H-imidazol-2-yl)azepane-1-carboxylate

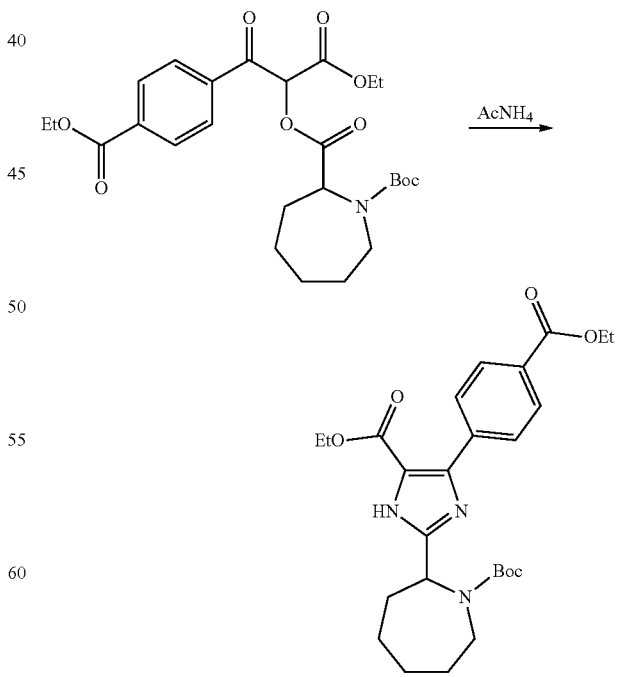

To the solution of 1.6 g (3.1 mmol) of the product of Step A in xylene (5 mL) was added NH$_4$OAc (3 g, 38 mmol) in a 15 mL pressure bottle. And the reaction was heated at 140° C. for 3.5 h. After being cooled, the solution was partition between ethyl acetate (200 mL) and water (100 mL). The organic layer was concentrated and the residue was purified by chromatography with petroleum ether and ethyl acetate (6:1) to afford tert-butyl 2-(5-(ethoxycarbonyl)-4-(4-(ethoxycarbonyl)phenyl)-1H-imidazol-2-yl)azepane-1-carboxylate as a light yellow oil (360 mg, 24%). $^1$H NMR (CDCl$_3$, 400 MHz) δ: 11.49 (s, 1H), 8.09-8.02 (m, 4H), 5.12-4.98 (m, 1H), 4.42-4.25 (m, 4H), 3.64-3.53 (m, 1H), 3.07-2.94 (m, 1H), 2.45-2.32 (m, 2H), 2.01-1.96 (m, 1H), 1.86-1.74 (m, 2H), 1.54-1.47 (m, 10H), 1.41-1.38 (m, 5H), 1.30 (t, J=7.1 Hz, 3H). MS (ESI, m/z): 486.2 [M+H]$^+$.

Step C: Preparation of 4-(2-(1-(tert-butoxycarbonyl)azepan-2-yl)-5-(ethoxycarbonyl)-1H-imidazol-4-yl)benzoic acid

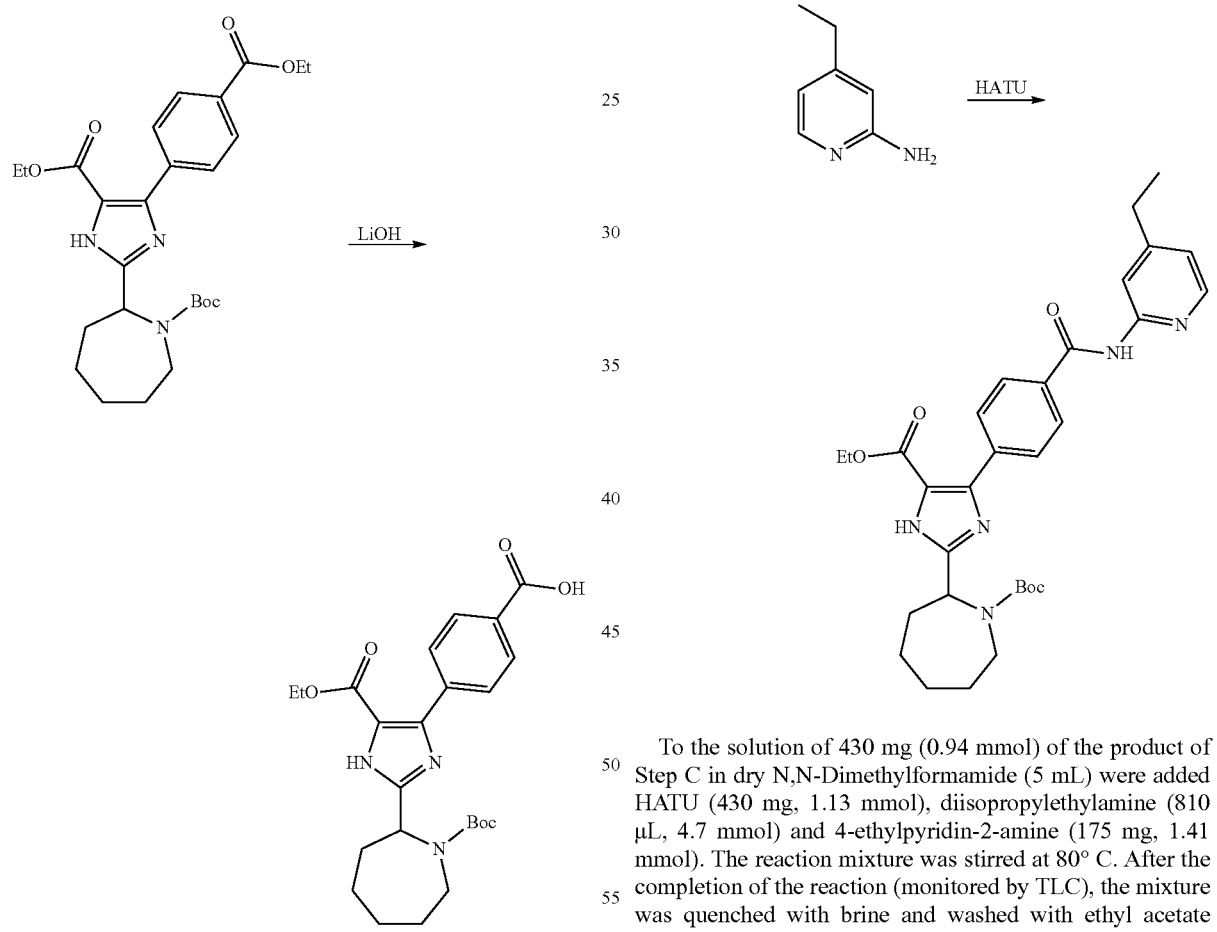

To the solution of 360 mg (0.7 mmol) of the product of Step B in 1,4-dioxane (2 mL) was added aqueous lithium hydroxide (2 mol/L, 2 mL) and stirred at room temperature for 2 h. The reaction mixture was evaporated and diluted with water (100 mL) and acidified with aqueous HCl till pH 3. The white precipitate was isolated by filtration and dried to afford 4-(2-(1-(tert-butoxycarbonyl)azepan-2-yl)-5-(ethoxycarbonyl)-1H-imidazol-4-yl)benzoic acid (300 mg, 93%).

Step D: Preparation of tert-butyl 2-(5-(ethoxycarbonyl)-4-(4-((4-ethylpyridin-2-yl)carbamoyl)phenyl)-1H-imidazol-2-yl)azepane-1-carboxylate

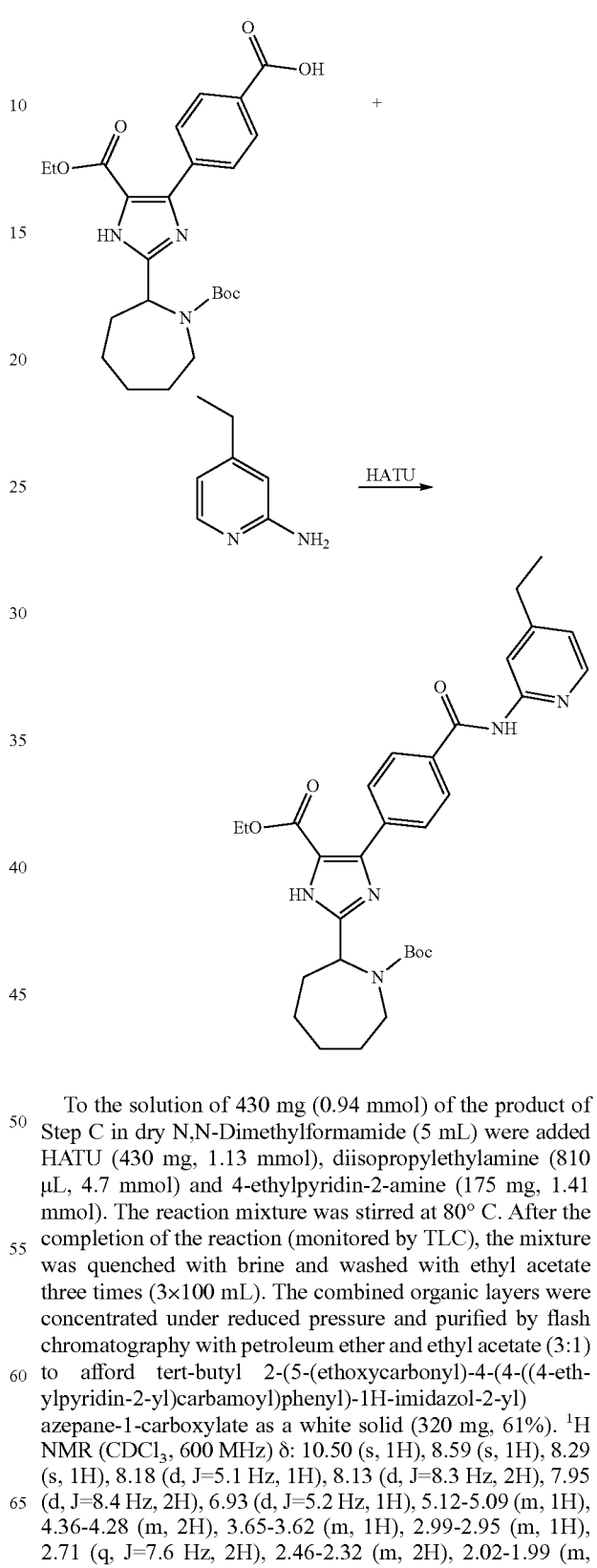

To the solution of 430 mg (0.94 mmol) of the product of Step C in dry N,N-Dimethylformamide (5 mL) were added HATU (430 mg, 1.13 mmol), diisopropylethylamine (810 μL, 4.7 mmol) and 4-ethylpyridin-2-amine (175 mg, 1.41 mmol). The reaction mixture was stirred at 80° C. After the completion of the reaction (monitored by TLC), the mixture was quenched with brine and washed with ethyl acetate three times (3×100 mL). The combined organic layers were concentrated under reduced pressure and purified by flash chromatography with petroleum ether and ethyl acetate (3:1) to afford tert-butyl 2-(5-(ethoxycarbonyl)-4-(4-((4-ethylpyridin-2-yl)carbamoyl)phenyl)-1H-imidazol-2-yl)azepane-1-carboxylate as a white solid (320 mg, 61%). $^1$H NMR (CDCl$_3$, 600 MHz) δ: 10.50 (s, 1H), 8.59 (s, 1H), 8.29 (s, 1H), 8.18 (d, J=5.1 Hz, 1H), 8.13 (d, J=8.3 Hz, 2H), 7.95 (d, J=8.4 Hz, 2H), 6.93 (d, J=5.2 Hz, 1H), 5.12-5.09 (m, 1H), 4.36-4.28 (m, 2H), 3.65-3.62 (m, 1H), 2.99-2.95 (m, 1H), 2.71 (q, J=7.6 Hz, 2H), 2.46-2.32 (m, 2H), 2.02-1.99 (m, 1H), 1.87-1.85 (m, 1H), 1.78-1.75 (m, 1H), 1.55-1.53 (m, 1H), 1.51-1.49 (m, 9H), 1.42-1.39 (m, 2H), 1.33-1.28 (m, 6H). MS (ESI, m/z): 562.2 [M+H]$^+$.

Step E: Preparation of tert-butyl 2-(1-amino-5-(ethoxycarbonyl)-4-(4-((4-ethylpyridin-2-yl)carbamoyl)phenyl)-1H-imidazol-2-yl)azepane-1-carboxylate

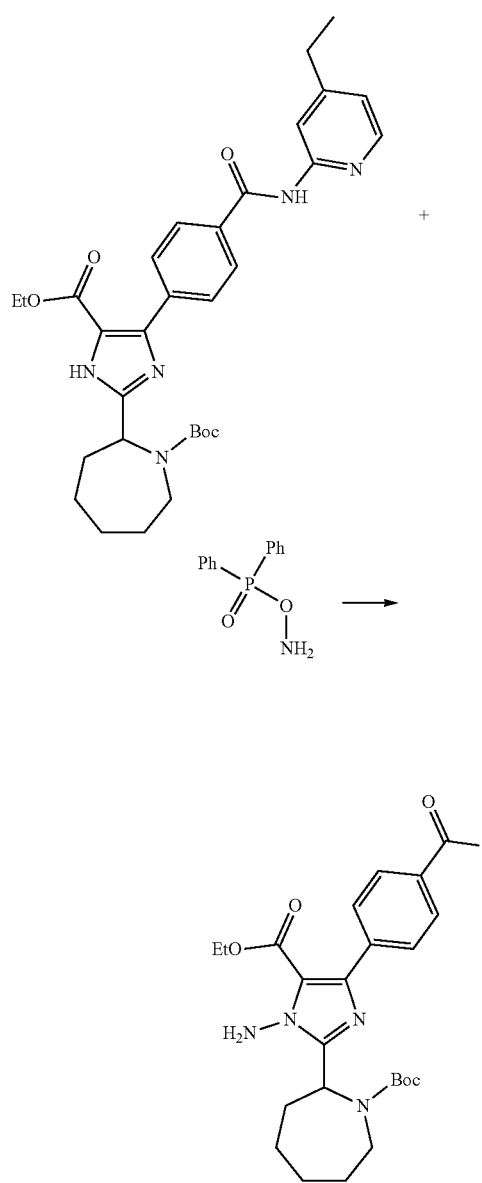

To the solution of 320 mg (0.57 mmol) of the product of Step D in dry N,N-Dimethylformamide (8 mL) was slowly added lithium hexamethyldisilazane (700 μL, 1 M solution in tetrahydrofuran) at −10° C. After the mixture was stirred for 10 min, O-(diphenylphosphinyl) hydroxylamine (133 mg, 0.57 mmol) was added at 0° C. and the resulting suspension was stirred 2 h at room temperature (in cases where the reaction mixture became too viscous, additional N,N-Dimethylformamide was added). The reaction was quenched with brine and concentrated to dryness in vacuum. The residue was washed three times with ethyl acetate (3×50 mL). The combined organic fractions were dried with anhydrous Na$_2$SO$_4$ and the solvent was removed under reduced pressure to afford the crude residue, which was subjected to column chromatography with petroleum ether and ethyl acetate (3:1) to give the desired product tert-butyl 2-(1-amino-5-(ethoxycarbonyl)-4-(4-((4-ethylpyridin-2-yl)carbamoyl)phenyl)-1H-imidazol-2-yl)azepane-1-carboxylate (240 mg, 73%). $^1$H NMR (CDCl$_3$, 600 MHz) δ: 8.60 (s, 1H), 8.29 (s, 1H), 8.19 (d, J=5.1 Hz, 1H), 7.92 (d, J=8.3 Hz, 2H), 7.80 (d, J=8.3 Hz, 2H), 6.93 (d, J=5.0 Hz, 1H), 6.64 (s, 2H), 5.43 (dd, J$_1$=11.8 Hz, J$_2$=6.7 Hz, 1H), 4.31-4.23 (m, 2H), 3.71-3.68 (m, 1H), 3.37-3.33 (m, 1H), 2.71 (q, J=7.6 Hz, 2H), 2.29-2.17 (m, 2H), 1.96-1.93 (m, 1H), 1.89-1.82 (m, 1H), 1.77-1.75 (m, 1H), 1.56-1.50 (m, 1H), 1.46-1.43 (m, 9H), 1.41-1.37 (m, 2H), 1.29 (t, J=7.6 Hz, 3H), 1.22 (t, J=7.1 Hz, 3H). MS (ESI, m/z): 577.3 [M+H]$^+$.

Step F: Preparation of 1-amino-2-(1-(tert-butoxycarbonyl)azepan-2-yl)-4-(4-((4-ethylpyridin-2-yl)carbamoyl)phenyl)-1H-imidazole-5-carboxylic acid

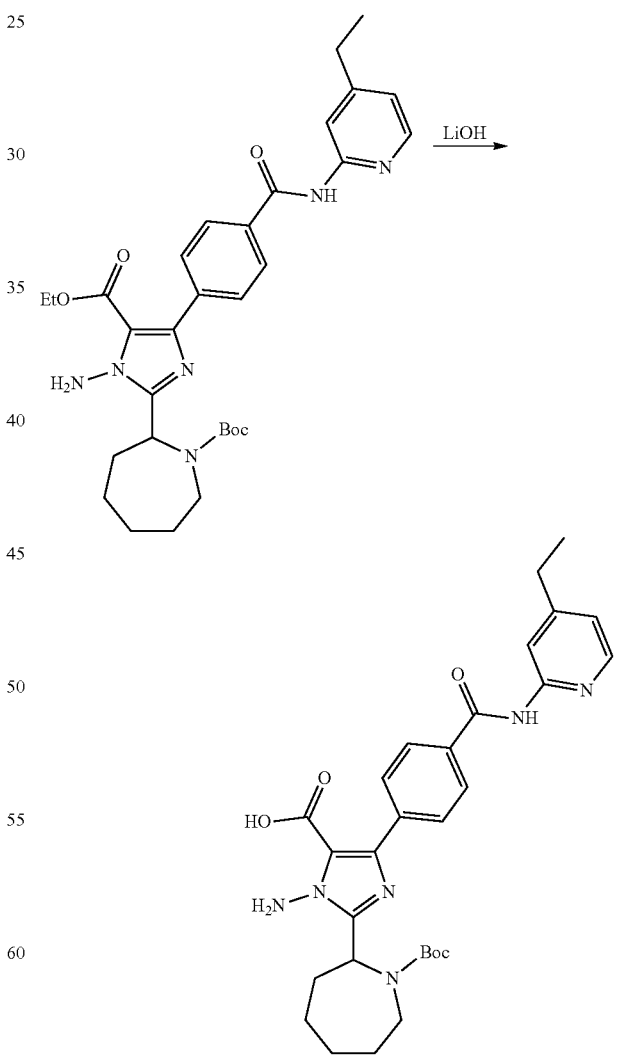

To the solution of 240 mg (0.41 mmol) of the product of Step E in methanol (4 mL) was added aqueous lithium 2hydroxide (2 mol/L, 2 mL), then stirred at room temperature for 2 h. The reaction mixture was evaporated and diluted with water (10 mL) and acidified with aqueous HCl till pH 3. The mixture was washed with ethyl acetate three times (3×50 mL). The combined organic layers were concentrated under reduced pressure to afford 1-amino-2-(1-(tert-butoxycarbonyl)azepan-2-yl)-4-(4-((4-ethylpyridin-2-yl)carbamoyl)phenyl)-1H-imidazole-5-carboxylic acid (220 mg, 98%).

Step G: Preparation of tert-butyl 2-(1-amino-5-carbamoyl-4-(4-((4-ethylpyridin-2-yl)carbamoyl)phenyl)-1H-imidazol-2-yl)azepane-1-carboxylate

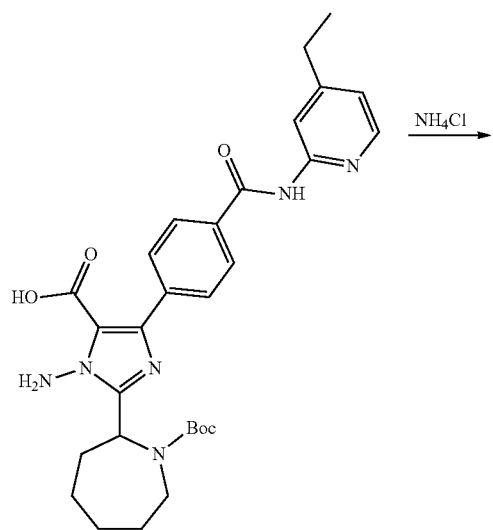

To the solution of 260 mg (0.47 mmol) of the product of Step F in dry N,N-Dimethylformamide (5 mL) were added HATU (270 mg, 0.71 mmol), diisopropylethylamine (250 µL, 1.42 mmol) and NH₄Cl (255 mg, 4.70 mmol). The reaction mixture was stirred at room temperature for 2 h. The reaction mixture was quenched with brine and washed with ethyl acetate three times (3×50 mL). The combined organic layers were concentrated under reduced pressure and purified by flash chromatography with dichloromethane and methanol (30:1) to afford tert-butyl 2-(1-amino-5-carbamoyl-4-(4-((4-ethylpyridin-2-yl)carbamoyl)phenyl)-1H-imidazol-2-yl)azepane-1-carboxylate (170 mg, 66%). $^1$H NMR (CDCl$_3$, 600 MHz) δ: 8.67 (s, 1H), 8.28 (s, 1H), 8.19 (d, J=5.1 Hz, 1H), 7.95 (d, J=8.3 Hz, 2H), 7.85 (d, J=8.3 Hz, 2H), 7.08 (s, 1H), 6.93 (d, J=5.1 Hz, 1H), 6.53 (s, 2H), 5.65 (s, 1H), 5.34 (dd, J$_1$=12.1 Hz, J$_2$=6.4 Hz, 1H), 3.66-3.63 (m, 1H), 3.33-3.29 (m, 1H), 2.71 (q, J=7.6 Hz, 2H), 2.39-2.33 (m, 1H), 2.20-2.15 (m, 1H), 1.98-1.94 (m, 1H), 1.88-1.86 (m, 1H), 1.77-1.75 (m, 1H), 1.57-1.50 (m, 1H), 1.47-1.45 (m, 9H), 1.42-1.35 (m, 2H), 1.29 (t, J=7.6 Hz, 3H). MS (ESI, m/z): 548.2 [M+H]$^+$.

Step H: Preparation of 1-amino-2-(azepan-2-yl)-4-(4-((4-ethylpyridin-2-yl)carbamoyl)phenyl)-1H-imidazole-5-carboxamide

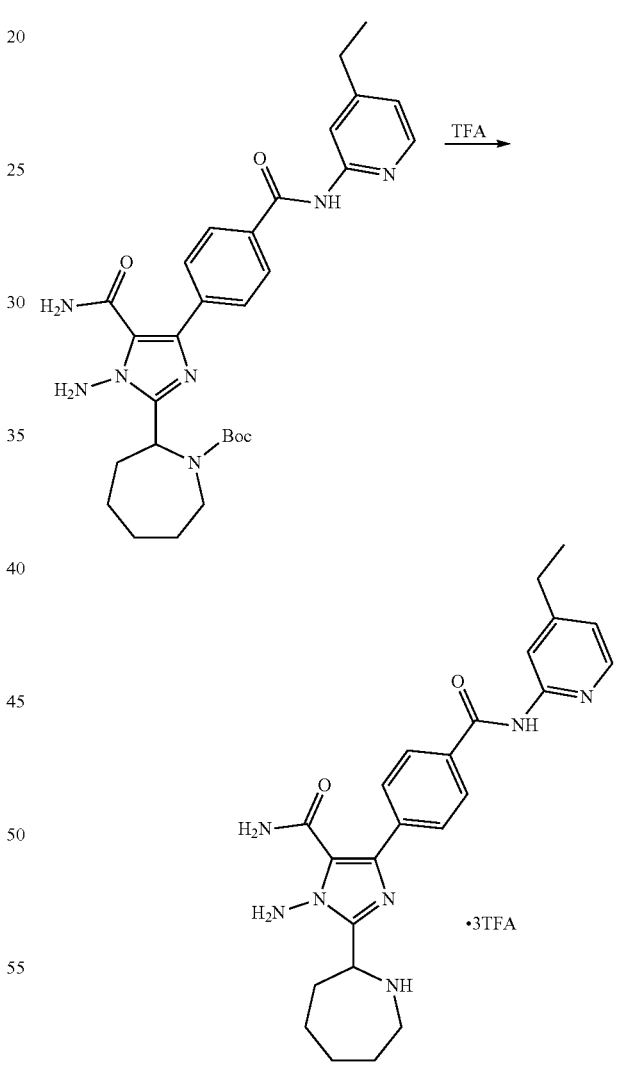

To the solution of 170 mg (0.31 mmol) of the product of Step G in dichloromethane (5 mL) was added trifluoroacetic acid (1.8 mL). The mixture was stirred at room temperature for 1 h and then concentrated to afford 1-amino-2-(azepan-2-yl)-4-(4-((4-ethylpyridin-2-yl)carbamoyl)phenyl)-1H-imidazole-5-carboxamide as a light yellow oil. MS (ESI, m/z): 448.2 [M+H]$^+$.

Step I: Preparation of 2-(1-acryloylazepan-2-yl)-1-amino-4-(4-((4-ethylpyridin-2-yl)carbamoyl)phenyl)-1H-imidazole-5-carboxamide

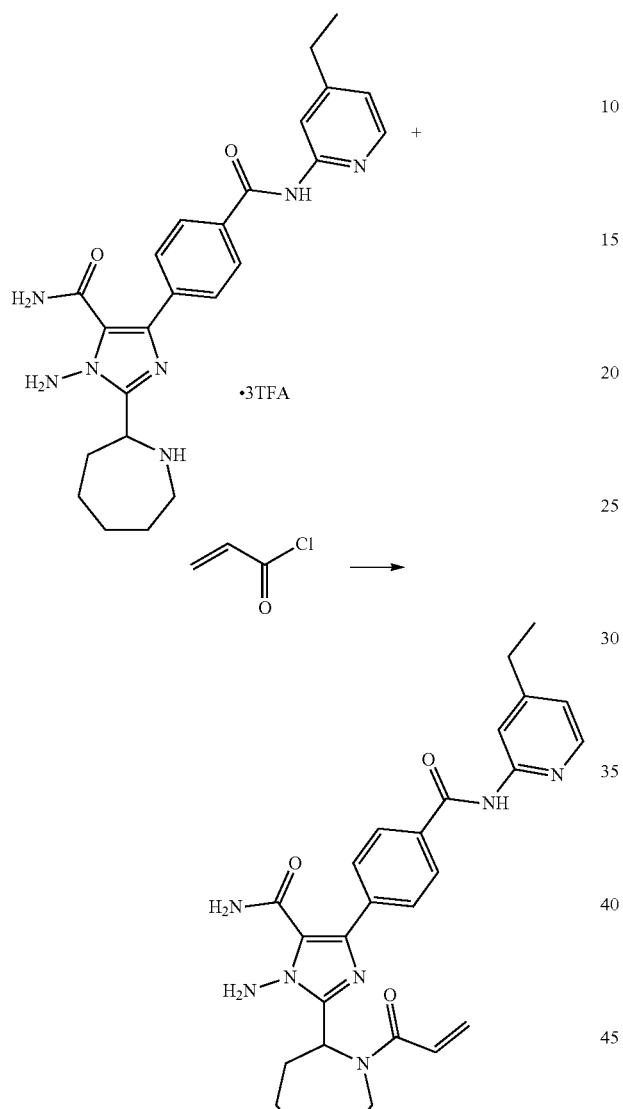

To the solution of 138 mg (0.31 mmol) of the product of Step H in dry dichloromethane (5 mL) was added diisopropylethylamine (240 mg, 1.86 mmol). After 5 min, acryloyl chloride (25.3 mg, 0.28 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give 2-(1-acryloylazepan-2-yl)-1-amino-4-(4-((4-ethylpyridin-2-yl)carbamoyl)phenyl)-1H-imidazole-5-carboxamide as an off-white solid (93 mg, 60%). $^1$H NMR (CDCl$_3$, 600 MHz) δ: 9.19 (s, 1H), 8.23 (s, 1H), 8.13 (d, J=5.2 Hz, 1H), 7.88 (d, J=8.3 Hz, 2H), 7.74 (d, J=8.3 Hz, 2H), 7.25 (s, 1H), 6.89 (d, J=5.0 Hz, 1H), 6.68 (s, 2H), 6.57 (dd, J$_1$=16.6 Hz, J$_2$=10.4 Hz, 1H), 6.48 (s, 1H), 6.37 (dd, J$_1$=16.6 Hz, J$_2$=1.9 Hz, 1H), 5.73 (dd, J$_1$=10.4 Hz, J$_2$=1.9 Hz, 1H), 5.60 (dd, J$_1$=12.2 Hz, J$_2$=6.4 Hz, 1H), 3.77-3.67 (m, 2H), 2.67 (q, J=7.6 Hz, 2H), 2.39-2.33 (m, 1H), 2.22-2.17 (m, 1H), 1.97-1.89 (m, 3H), 1.54-1.41 (m, 2H), 1.37-1.31 (m, 1H), 1.25 (t, J=7.6 Hz, 3H); $^{13}$C NMR (CDCl$_3$, 150 MHz) δ: 167.6, 165.9, 162.6, 156.0, 152.0, 148.8, 147.6, 141.9, 138.4, 133.7, 129.7, 129.5, 127.4, 127.3, 119.9, 119.6, 113.9, 49.1, 43.6, 31.7, 30.4, 29.0, 28.7, 25.4, 14.5. MS (ESI, m/z): 502.2 [M+H]$^+$.

Example 95

2-(2-acryloyl-2-azaspiro[3.3]heptan-6-yl)-1-amino-4-(4-((4-ethylpyridin-2-yl)carbamoyl)phenyl)-1H-imidazole-5-carboxamide

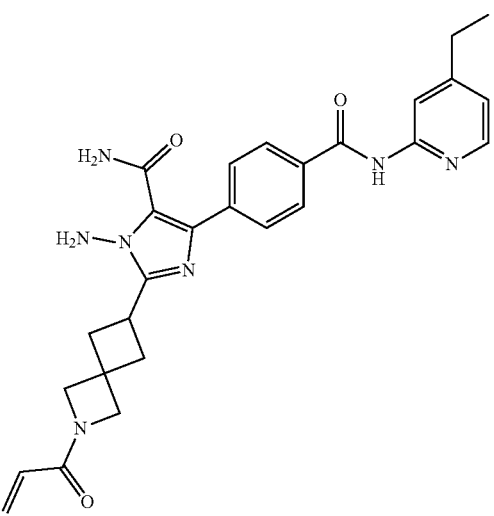 [SMILES: C=CC(=O)N1CC2(CC(c3nc(-c4ccc(C(=O)Nc5cc(CC)ccn5)cc4)c(C(N)=O)n3N)C2)C1]

Step A: Preparation of 2-(tert-butyl) 6-(1-ethoxy-3-(4-(ethoxycarbonyl)phenyl)-1,3-dioxopropan-2-yl) 2-azaspiro[3.3]heptane-2,6-dicarboxylate

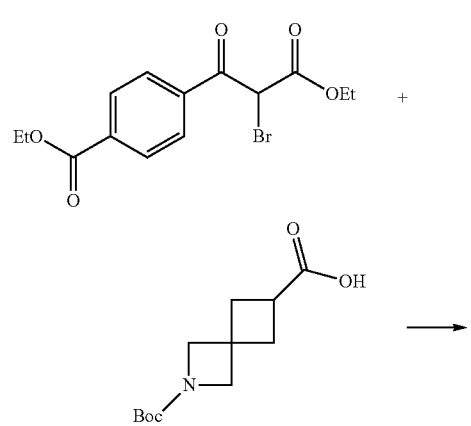

-continued

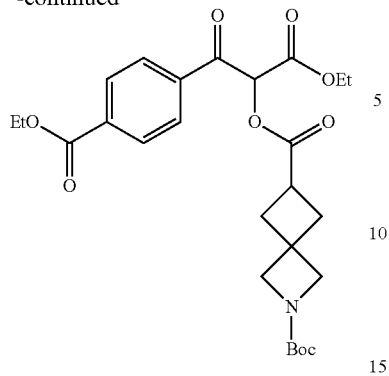

To the solution of 7.1 g (20.7 mmol) of the product of Step C of example 1 in acetonitrile (20 mL) were added 2-(tert-butoxycarbonyl)-2-azaspiro [3.3]heptane-6-carboxylic acid (5 g, 20.7 mmol) and diisopropylethylamine (3.9 mL, 22.8 mmol). The mixture was stirred at room temperature for 3 h before all volatile were evaporated. The residue was diluted with water (200 mL) and extracted with ethyl acetate (200 mL). The organic phase was separated, dried over anhydrous $Na_2SO_4$ and concentrated. The residue was purified by flash column chromatography with petroleum ether and ethyl acetate (2:1) to give the 2-(tert-butyl) 6-(1-ethoxy-3-(4-(ethoxycarbonyl)phenyl)-1,3-dioxopropan-2-yl) 2-azaspiro[3.3]heptane-2,6-dicarboxylate as a light yellow oil (6.8 g, 65%). $^1$H NMR (CDCl$_3$, 400 MHz) δ: 8.15 (d, J=8.1 Hz, 2H), 7.98 (d, J=8.0 Hz, 2H), 5.05-4.86 (m, 1H), 4.43 (q, J=7.1 Hz, 2H), 4.26 (q, J=7.1 Hz, 2H), 3.95 (s, 2H), 3.78 (s, 2H), 3.46-3.35 (m, 1H), 2.60-2.43 (m, 4H), 1.42 (s, 9H), 1.38-1.33 (m, 3H), 1.29 (t, J=7.0 Hz, 3H). MS (ESI, m/z): 504.2 [M+H]$^+$.

Step B: Preparation of tert-butyl 6-(5-(ethoxycarbonyl)-4-(4-(ethoxycarbonyl)phenyl)-1H-imidazol-2-yl)-2-azaspiro[3.3]heptane-2-carboxylate -continued

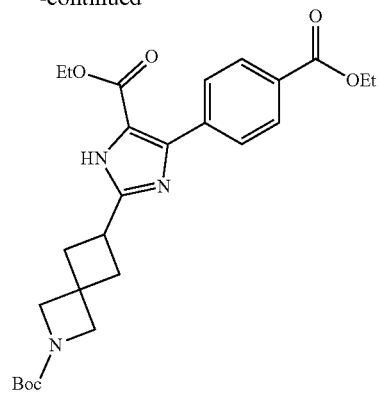

To the solution of 200 mg (0.40 mmol) of the product of Step A in xylene (7 mL) in a 25 mL pressure bottle was added NH$_4$OAc (367.8 mg, 4.77 mmol), and the reaction was heated at 140° C. for 2.5 h. After being cooled, the residue was diluted with water (100 mL) and extracted with ethyl acetate (100 mL). The organic phase was separated, dried over anhydrous $Na_2SO_4$ and concentrated. The residue was purified by flash column chromatography with petroleum ether and ethyl acetate (1:1.5) to give the product tert-butyl 6-(5-(ethoxycarbonyl)-4-(4-(ethoxycarbonyl)phenyl)-1H-imidazol-2-yl)-2-azaspiro[3.3]heptane-2-carboxylate as a light yellow oil (39 mg, 20%). $^1$H NMR (CDCl$_3$, 400 MHz) δ: 10.21-10.09 (m, 1H), 8.05 (d, J=8.1 Hz, 2H), 7.97 (d, J=8.0 Hz, 2H), 4.38 (q, J=7.1 Hz, 2H), 4.29 (q, J=7.1 Hz, 2H), 3.98 (s, 2H), 3.87 (s, 2H), 3.48-3.39 (m, 1H), 2.64-2.45 (m, 4H), 1.42-1.38 (m, 12H), 1.29 (t, J=7.0 Hz, 3H). MS (ESI, m/z): 484.2 [M+H]$^+$.

Step C: Preparation of 4-(2-(2-(tert-butoxycarbonyl)-2-azaspiro[3.3]heptan-6-yl)-5-(ethoxycarbonyl)-1H-imidazol-4-yl)benzoic acid

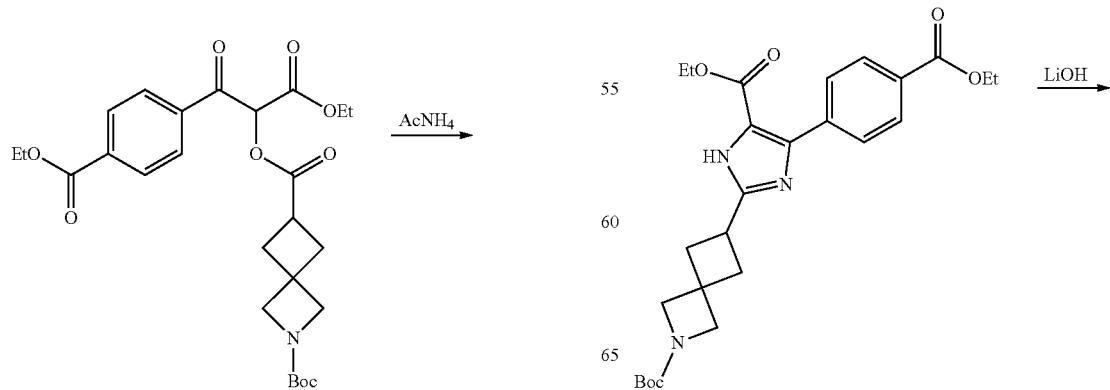

-continued

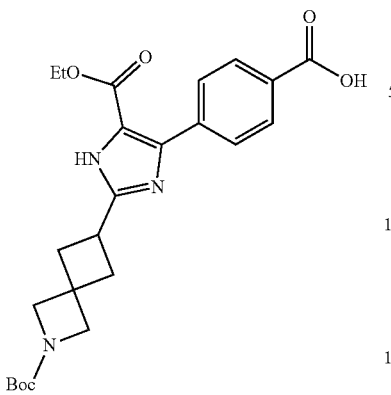

To the solution of 39 mg (0.08 mmol) of the product of Step B in 1,4-dioxane (195 µL) was added aqueous lithium hydroxide (2 mol/L, 195 µL) and stirred at room temperature for 2 h. The reaction mixture was diluted with ethyl acetate (30 mL) and acidified with aqueous HCl till pH 3. The white precipitate was isolated by filtration and dried to afford 4-(2-(2-(tert-butoxycarbonyl)-2-azaspiro[3.3]heptan-6-yl)-5-(ethoxycarbonyl)-1H-imidazol-4-yl)benzoic acid as a white solid (32.8 mg, 90%).

Step D: Preparation of tert-butyl 6-(5-(ethoxycarbonyl)-4-(4-((4-ethylpyridin-2-yl)carbamoyl)phenyl)-1H-imidazol-2-yl)-2-azaspiro[3.3]heptane-2-carboxylate

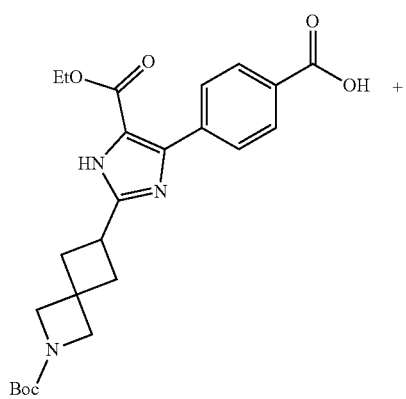

+

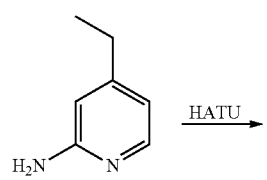

HATU →

-continued

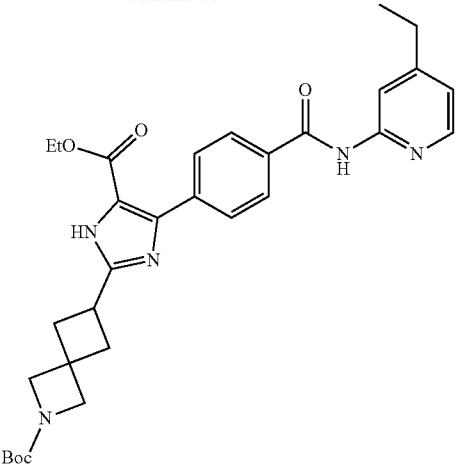

To the solution of 410 mg (0.9 mmol) of the product of Step C in dry N,N-Dimethylformamide (10 mL) were added HATU (411 mg, 1.08 mmol), diisopropylethylamine (776 µL, 4.5 mmol) and 4-ethylpyridin-2-amine (165 mg, 1.35 mmol). The reaction mixture was stirred at 80° C. After the completion of the reaction (monitored by TLC), the mixture was quenched with brine and washed with ethyl acetate three times (3×70 mL). The combined organic layers were concentrated under reduced pressure and purified by flash chromatography with ethyl acetate to afford tert-butyl 6-(5-(ethoxycarbonyl)-4-(4-((4-ethylpyridin-2-yl)carbamoyl)phenyl)-1H-imidazol-2-yl)-2-azaspiro[3.3]heptane-2-carboxylate as white solid (252 mg, 50%). $^1$H NMR (CDCl$_3$, 400 MHz) δ: 8.61 (s, 1H), 8.29 (s, 1H), 8.12 (d, J=5.1 Hz, 1H), 8.05 (d, J=8.4 Hz, 2H), 7.95-7.93 (m, 2H), 6.94 (dd, J$_1$=5.1 Hz, J$_2$=1.1 Hz, 1H), 6.35 (s, 1H), 4.33 (q, J=7.1 Hz, 2H), 4.02 (s, 2H), 3.89 (s, 2H), 3.46 (t, J=8.5 Hz, 1H), 2.71 (q, J=7.6 Hz, 2H), 2.53 (q, J=7.6 Hz, 4H), 1.44 (s, 9H), 1.31-1.29 (m, 3H), 1.20 (t, J=7.6 Hz, 3H). MS (ESI, m/z): 560.2 [M+H]$^+$.

Step E: Preparation of tert-butyl 6-(1-amino-5-(ethoxycarbonyl)-4-(4-((4-ethylpyridin-2-yl)carbamoyl)phenyl)-1H-imidazol-2-yl)-2-azaspiro[3.3]heptane-2-carboxylate

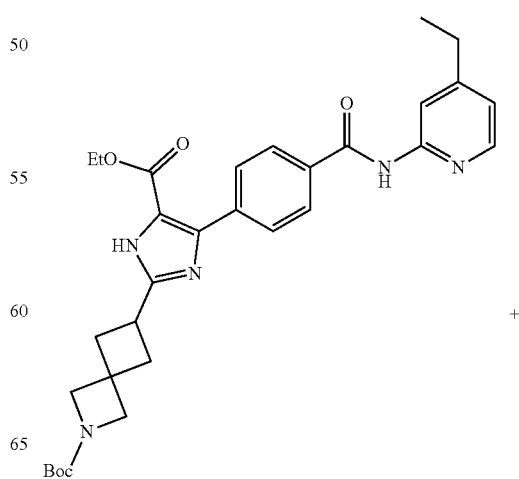

+

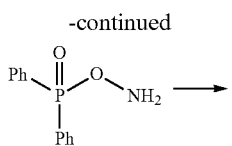

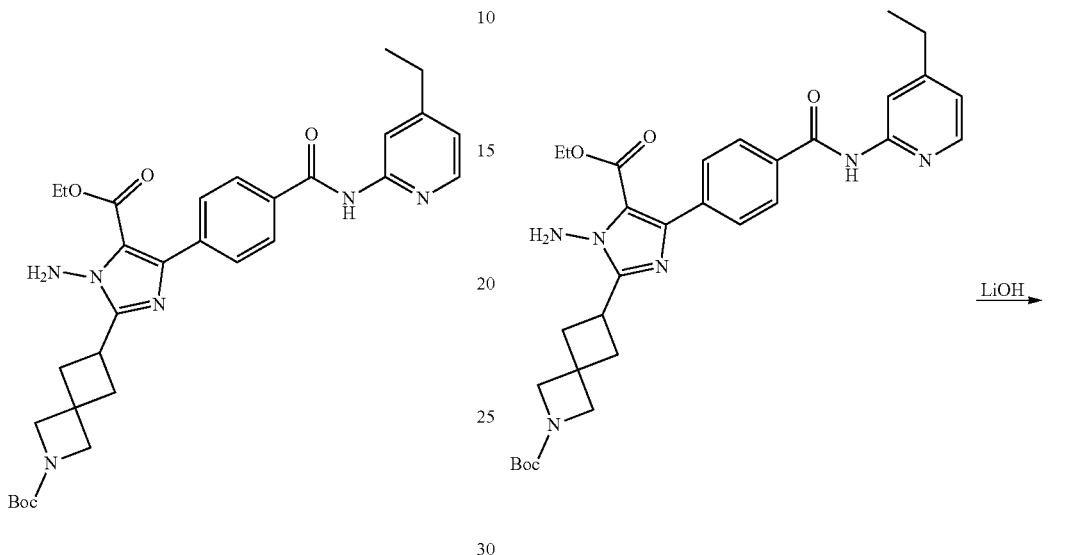

To the solution of 134 mg (0.24 mmol) of the product of Step D in anhydrous N,N-Dimethylformamide (10 mL) was slowly added lithium hexamethyldisilazane (288 µL, 1 M solution in tetrahydrofuran) at −10° C. After the mixture was stirred for 20 min, O-(diphenylphosphinyl) hydroxylamine (67.1 mg, 0.29 mmol) was added at 0° C. and the resulting suspension was stirred at room temperature for 2 h (in cases where the reaction mixture became too viscous, additional N,N-Dimethylformamide was added). The reaction was quenched with brine and concentrated to dryness in vacuum. The residue was washed three times (3×60 mL) with ethyl acetate. The combined organic fractions were dried with anhydrous Na$_2$SO$_4$ and the solvent was removed under reduced pressure to afford the crude residue, which was subjected to column chromatography with ethyl acetate to give the product tert-butyl 6-(1-amino-5-(ethoxycarbonyl)-4-(4-((4-ethylpyridin-2-yl)carbamoyl)phenyl)-1H-imidazol-2-yl)-2-azaspiro[3.3]heptane-2-carboxylate as a white solid (69 mg, 50%). $^1$H NMR (CDCl$_3$, 400 MHz) δ: 8.81 (s, 1H), 8.29 (s, 1H), 8.15 (d, J=5.1 Hz, 1H), 7.94 (d, J=8.4 Hz, 2H), 7.80 (d, J=8.4 Hz, 2H), 6.92 (dd, J$_1$=5.1 Hz, J$_2$=1.3 Hz, 1H), 6.29 (s, 2H), 4.25 (d, J=7.1 Hz, 2H), 4.05 (s, 2H), 3.88 (s, 2H), 3.77 (t, J=8.6 Hz, 1H), 2.73-2.66 (m, 4H), 2.57-2.52 (m, 2H), 1.42 (s, 9H), 1.28 (t, J=7.6 Hz, 3H), 1.21 (t, J=7.1 Hz, 3H). MS (ESI, m/z): 575.2 [M+H]$^+$.

Step F: Preparation of 1-amino-2-(2-(tert-butoxycarbonyl)-2-azaspiro[3.3]heptan-6-yl)-4-(4-((4-ethylpyridin-2-yl)carbamoyl)phenyl)-1H-imidazole-5-carboxylic acid

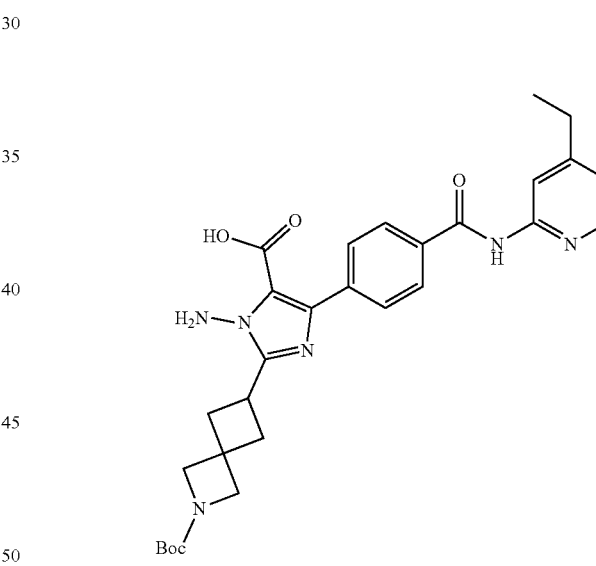

To the solution of 80 mg (0.14 mmol) of the product of Step E in methanol (3 mL) was added 2 mol/L aqueous lithium hydroxide (697 µL) and stirred at room temperature for 2 h. The reaction mixture was evaporated and diluted with ethyl acetate (80 mL) and acidified with aqueous HCl till pH 3. The mixture was washed with water three times (3×50 mL). The white precipitate was isolated by filtration and dried to afford 1-amino-2-(2-(tert-butoxycarbonyl)-2-azaspiro[3.3]heptan-6-yl)-4-(4-((4-ethylpyridin-2-yl)carbamoyl)phenyl)-1H-imidazole-5-carboxylic acid (69 mg, 90%).

Step G: Preparation of tert-butyl 6-(1-amino-5-carbamoyl-4-(4-((4-ethylpyridin-2-yl)carbamoyl)phenyl)-1H-imidazol-2-yl)-2-azaspiro[3.3]heptane-2-carboxylate

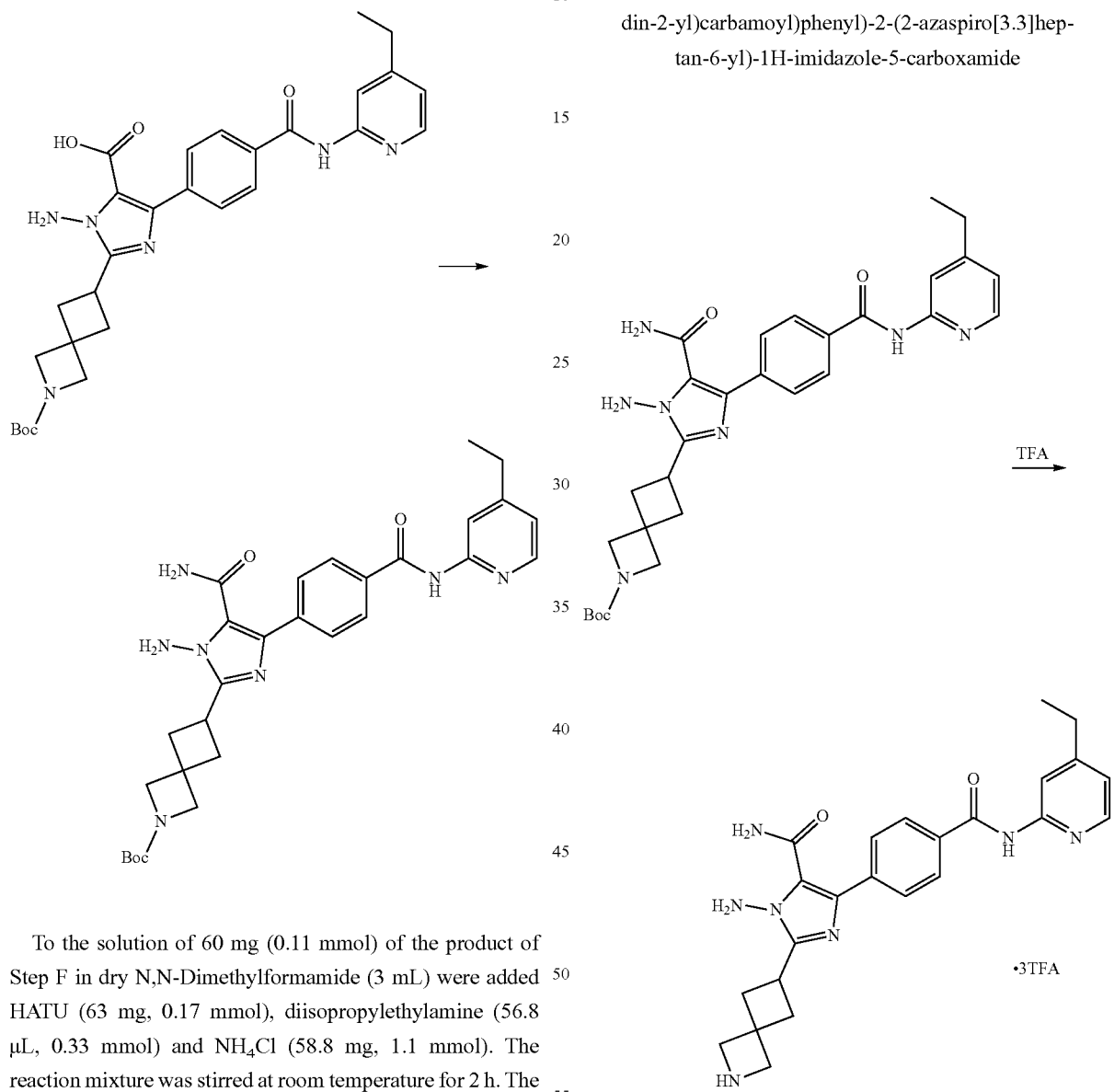

To the solution of 60 mg (0.11 mmol) of the product of Step F in dry N,N-Dimethylformamide (3 mL) were added HATU (63 mg, 0.17 mmol), diisopropylethylamine (56.8 µL, 0.33 mmol) and NH$_4$Cl (58.8 mg, 1.1 mmol). The reaction mixture was stirred at room temperature for 2 h. The reaction mixture was quenched with brine and washed with ethyl acetate three times (3×40 mL). The combined organic layers were concentrated under reduced pressure and purified by flash chromatography with dichloromethane and methanol (10:1) to give the product tert-butyl 6-(1-amino-5-carbamoyl-4-(4-((4-ethylpyridin-2-yl)carbamoyl)phenyl)-1H-imidazol-2-yl)-2-azaspiro[3.3]heptane-2-carboxylate as white solid (24 mg, 40%). $^1$H NMR (CDCl$_3$, 600 MHz) δ: 9.02 (s, 1H), 8.24 (s, 1H), 8.14 (d, J=5.2 Hz, 1H), 7.93 (d, J=8.3 Hz, 2H), 7.69 (d, J=8.3 Hz, 2H), 6.92 (dd, J$_1$=5.0 Hz, J$_2$=1.0 Hz, 1H), 6.05-5.99 (m, 2H), 5.53 (s, 2H), 4.03 (s, 2H), 3.86 (s, 2H), 3.72 (t, J=8.6 Hz, 1H), 2.70 (q, J=7.6 Hz, 2H), 2.65-2.62 (m, 2H), 2.56-2.52 (m, 2H), 1.42 (s, 9H), 1.28 (t, J=7.6 Hz, 3H). MS (ESI, m/z): 546.2 [M+H]$^+$.

Step H: Preparation of 1-amino-4-(4-((4-ethylpyridin-2-yl)carbamoyl)phenyl)-2-(2-azaspiro[3.3]heptan-6-yl)-1H-imidazole-5-carboxamide

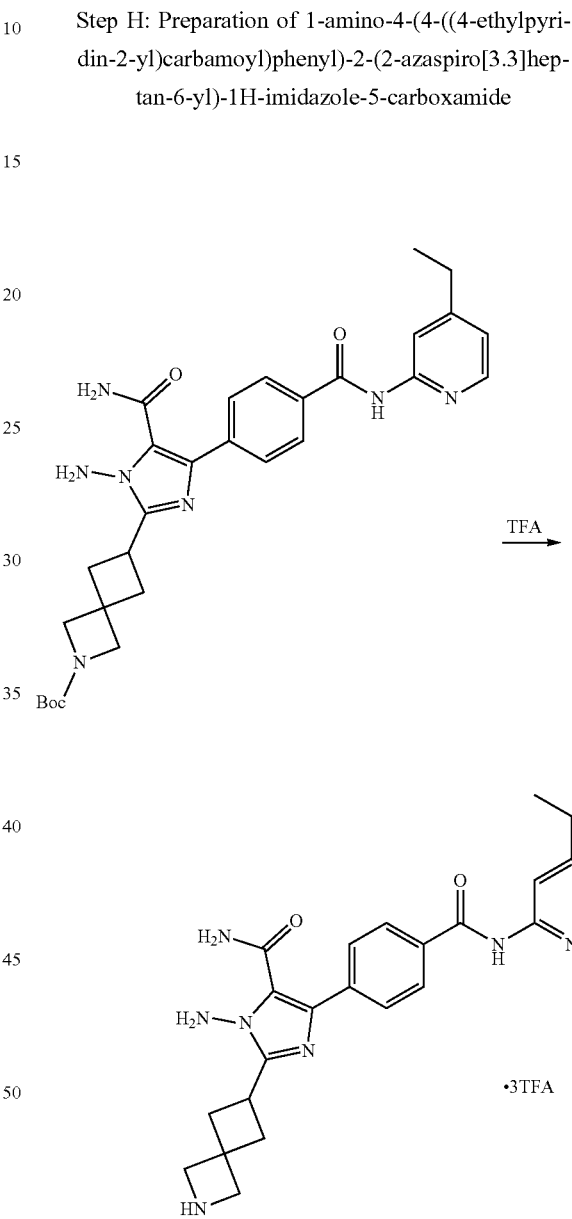

To the solution of 60 mg (0.11 mmol) of the product of Step G in dichloromethane (1.5 mL) was added trifluoroacetic acid (661 µL). The mixture was stirred at room temperature for 1 h and then concentrated to afford 1-amino-4-(4-((4-ethylpyridin-2-yl)carbamoyl)phenyl)-2-(2-azaspiro[3.3]heptan-6-yl)-1H-imidazole-5-carboxamide as a light yellow oil. MS (ESI, m/z): 446.2 [M+H]$^+$.

Step I: Preparation of 2-(2-acryloyl-2-azaspiro[3.3]heptan-6-yl)-1-amino-4-(4-((4-ethylpyridin-2-yl)carbamoyl)phenyl)-1H-imidazole-5-carboxamide

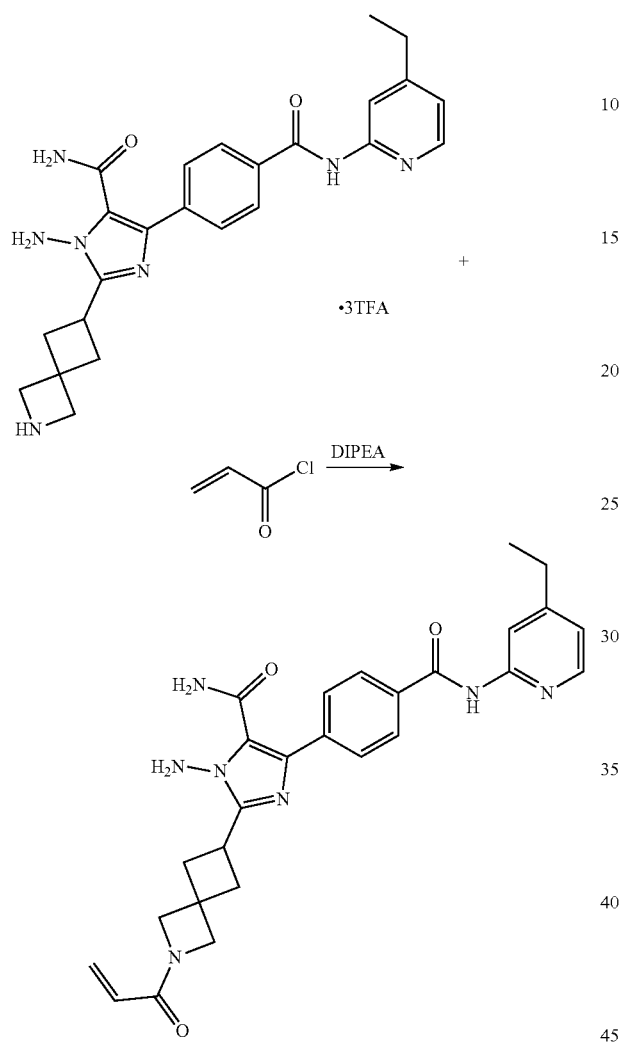

To the solution of 49.0 mg (0.11 mmol) of the product of Step H in dry dichloromethane (2 mL) was added diisopropylethylamine (113.7 μL, 0.66 mmol). After 5 min, acryloyl chloride (6.2 μL, 0.08 mmol) was added at 0° C. The reaction mixture was then warmed up to room temperature and continued to stir for 1 h, ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (10:1) to give 2-(2-acryloyl-2-azaspiro[3.3]heptan-6-yl)-1-amino-4-(4-((4-ethylpyridin-2-yl)carbamoyl)phenyl)-1H-imidazole-5-carboxamides an off-white solid (27 mg, 50%). $^1$H NMR (DMSO-d6, 400 MHz) δ: 11.19 (s, 1H), 8.32 (d, J=5.4 Hz, 1H), 8.19 (s, 1H), 8.13 (d, J=8.4 Hz, 2H), 8.07 (s, 1H), 7.94 (s, 1H), 7.88 (d, J=8.6 Hz, 2H), 7.19 (d, J=5.3 Hz, 1H), 6.35-6.26 (m, 1H), 6.09 (dt, J$_1$=17.0 Hz, J$_2$=2.6 Hz, 1H), 5.69-5.64 (m, 1H), 4.81 (s, 2H), 4.37 (s, 1H), 4.21 (s, 1H), 4.08 (s, 1H), 3.92 (s, 1H), 3.84 (dd, J$_1$=16.4 Hz, J$_2$=8.4 Hz, 1H), 2.75-2.62 (m, 6H), 1.23 (t, J=7.6 Hz, 3H); $^{13}$C NMR (DMSO-d6, 150 MHz) δ: 165.8, 164.4, 158.5, 158.3, 158.1, 151.1, 150.6, 128.1, 127.8, 127.1, 126.3, 126.3, 125.6, 120.0, 116.8, 114.9, 114.3, 62.1, 60.8, 60.0, 58.7, 37.4, 34.3, 28.0, 14.1. MS (ESI, m/z): 500.2 [M+H]$^+$.

Example: 96 (S)-1-amino-4-(4-((4-methylpyridin-2-yl)carbamoyl)phenyl)-2-(1-propioloylpiperidin-2-yl)-1H-imidazole-5-carboxamide

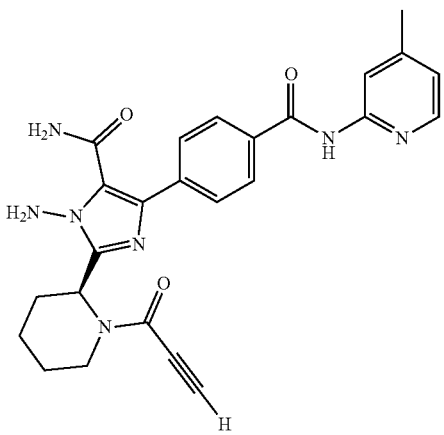 [SMILES: C#CC(=O)N1CCCC[C@H]1c1nc(-c2ccc(C(=O)Nc3cc(C)ccn3)cc2)c(C(N)=O)n1N]

Preparation of (S)-1-amino-4-(4-((4-methylpyridin-2-yl)carbamoyl)phenyl)-2-(1-propioloylpiperidin-2-yl)-1H-imidazole-5-carboxamide

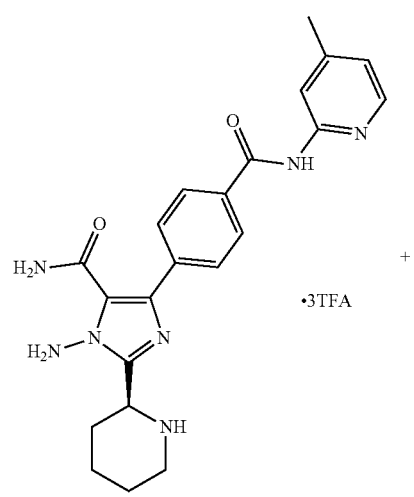

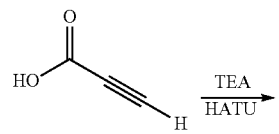

-continued

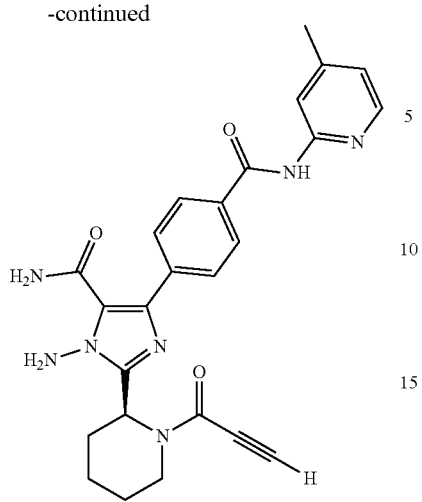

To the solution of 214 mg (0.51 mmol) of the product of Step E of example 53 in dry N,N-Dimethylformamide (7 mL) was added triethylamine (308 mg, 3.06 mmol). After 5 min, propiolic acid (31.5 mg, 0.45 mmol) and HATU (289 mg, 0.76 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (26:1) to give (S)-1-amino-4-(4-((4-methylpyridin-2-yl)carbamoyl)phenyl)-2-(1-propioloylpiperidin-2-yl)-1H-imidazole-5-carboxamide as an off-white solid (120.2 mg, 50%). $^1$H NMR (CDCl$_3$, 400 MHz) δ: 8.84 (s, 1H), 8.25 (s, 1H), 8.15 (d, J=4.8 Hz, 1H), 7.97 (d, J=7.9 Hz, 2H), 7.83 (d, J=8.0 Hz, 1.6H), 7.77 (d, J=7.8 Hz, 0.4H), 6.92 (d, J=4.6 Hz, 1H), 6.50 (s, 1H), 6.09 (s, 2H), 6.00 (d, J=5.1 Hz, 1H), 5.81 (s, 1H), 4.31 (d, J=13.6 Hz, 1H), 3.80-3.72 (m, 1H), 3.18 (s, 1H), 2.41 (s, 3H), 2.36-2.32 (m, 1H), 2.21-2.17 (m, 1H), 1.91-1.88 (m, 2H), 1.74-1.61 (m, 2H); $^{13}$C NMR (CDCl$_3$, 150 MHz) δ: 165.5, 162.5, 153.6, 151.7, 150.3, 147.8, 147.5, 141.1, 138.2, 134.1, 129.8, 127.6, 121.4, 119.8, 115.0, 80.3, 75.5, 44.7, 44.1, 27.9, 25.7, 21.6, 19.8. MS (ESI, m/z): 472.2 [M+H]$^+$.

Example 97: (S)-1-amino-4-(4-((4-methoxypyridin-2-yl)carbamoyl)phenyl)-2-(1-propioloylpiperidin-2-yl)-1H-imidazole-5-carboxamide Preparation of (S)-1-amino-4-(4-((4-methoxypyridin-2-yl)carbamoyl)phenyl)-2-(1-propioloylpiperidin-2-yl)-1H-imidazole-5-carboxamide

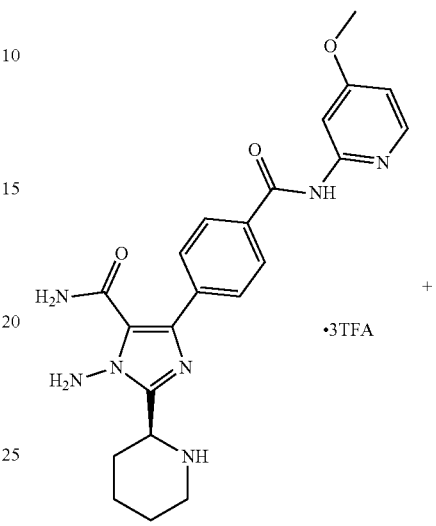

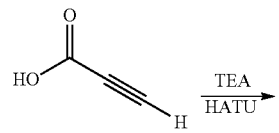

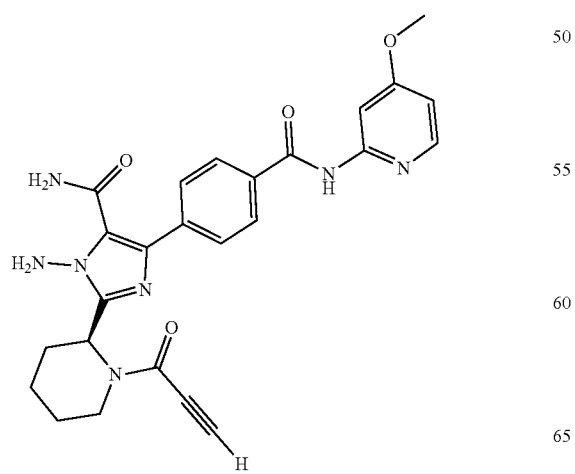

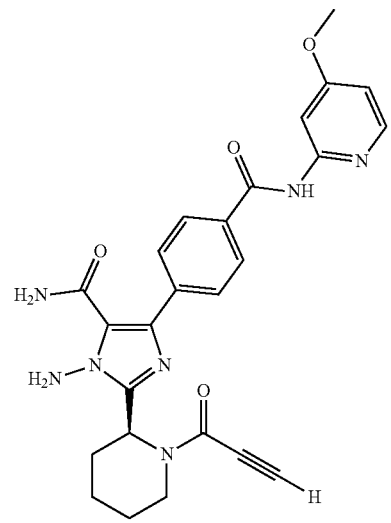

To the solution of 222 mg (0.51 mmol) of the product of Step E of example 67 in dry N,N-Dimethylformamide (7 mL) was added triethylamine (308 mg, 3.06 mmol). After 5 min, propiolic acid (31.5 mg, 0.45 mmol) and HATU (289 mg, 0.76 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (26:1) to give (S)-1-amino-4-(4-((4-methoxypyridin-2-yl)carbamoyl)phenyl)-2-(1-propioloylpiperidin-2-yl)-1H-imidazole-5-carboxamide as an off-white solid (124.2 mg, 50%). $^1$H NMR (CDCl$_3$, 400 MHz) δ: 8.87 (s, 1H), 8.09 (d, J=5.8 Hz, 1H), 8.04 (s, 1H), 7.96 (d, J=8.1 Hz, 2H), 7.85-7.76 (m, 2H), 6.65-6.63 (m, 1H), 6.53 (s, 1H), 6.08 (s, 2H), 5.99 (d, J=5.3 Hz, 1H), 5.82 (s, 1H), 4.31 (d, J=13.1 Hz, 1H), 3.92 (s, 3H), 3.77 (dt, J$_1$=12.9 Hz, J$_2$=2.3 Hz, 1H), 3.18 (s, 1H), 2.36-2.30 (m, 1H), 2.21-2.17 (m, 1H), 1.91-1.88 (m, 2H), 1.75-1.71 (m, 1H), 1.65-1.61 (m, 1H); $^{13}$C NMR (CDCl$_3$, 150 MHz) δ: 167.9, 165.6, 162.5, 153.6, 153.3, 148.5, 147.8, 141.0, 138.3, 134.0, 130.0, 127.6, 119.8, 108.2, 99.1, 80.3, 75.5, 55.6, 44.7, 44.1, 27.9, 25.7, 19.8. MS (ESI, m/z): 488.2 [M+H]$^+$.

Example 98: (S)-1-amino-2-(1-(but-2-ynoyl)piperidin-2-yl)-4-(4-((4-chloropyridin-2-yl)carbamoyl)phenyl)-1H-imidazole-5-carboxamide

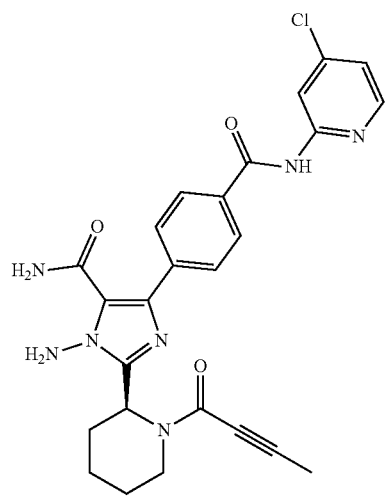

Preparation of (S)-1-amino-2-(1-(but-2-ynoyl)piperidin-2-yl)-4-(4-((4-chloropyridin-2-yl)carbamoyl)phenyl)-1H-imidazole-5-carboxamide

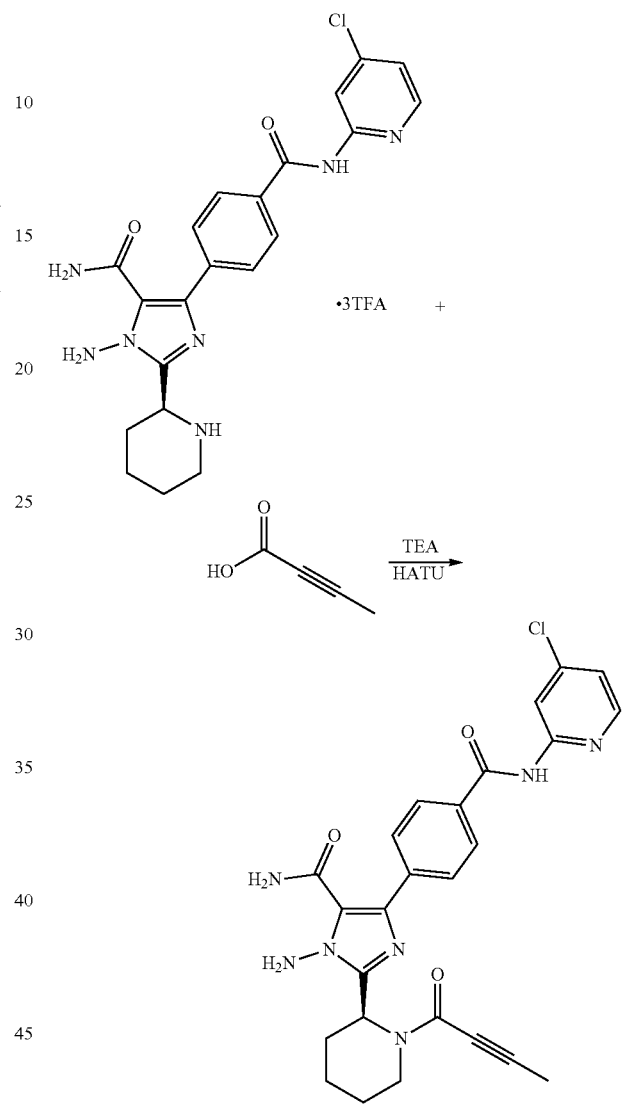

To the solution of 224 mg (0.51 mmol) of the product of Step E of example 72 in dry N,N-Dimethylformamide (7 mL) was added triethylamine (308 mg, 3.06 mmol). After 5 min, but-2-ynoic acid (37.6 mg, 0.45 mmol) and HATU (289 mg, 0.76 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (26:1) to give (S)-1-amino-2-(1-(but-2-ynoyl)piperidin-2-yl)-4-(4-((4-chloropyridin-2-yl)carbamoyl)phenyl)-1H-imidazole-5-carboxamide as an off-white solid (129.0 mg, 50%). $^1$H NMR (CDCl$_3$, 400 MHz) δ: 9.41 (s, 1H), 8.43 (s, 1H), 8.12 (d, J=5.3 Hz, 1H), 7.80 (d, J=8.0 Hz, 2H), 7.70 (d, J=8.0 Hz, 2H), 7.26 (s, 1H), 7.03 (d, J=5.4 Hz, 1H), 6.72 (s, 1H), 6.13 (s, 2H), 5.92 (d, J=5.1 Hz, 1H), 4.26 (d, J=12.7 Hz, 1H), 3.67-3.61 (m, 1H), 2.39-2.30 (m, 1H), 2.17-2.13 (m, 1H), 1.99 (s, 3H), 1.87-1.84 (m, 2H), 1.71-1.68 (m, 1H), 1.63-1.54 (m, 1H); $^{13}$C NMR (CDCl$_3$, 150 MHz) δ: 166.1, 162.7, 154.9, 152.8, 148.6, 148.1, 146.0, 141.1, 138.4, 133.0, 129.5, 127.3, 120.4, 120.3, 114.6, 91.0, 72.9, 44.5, 43.8, 27.8, 25.7, 19.8, 4.2. MS (ESI, m/z): 506.1 [M+H]$^+$.

Example 99: (S)-1-amino-4-(4-((4-chloropyridin-2-yl)carbamoyl)phenyl)-2-(1-propioloylpiperidin-2-yl)-1H-imidazole-5-carboxamide

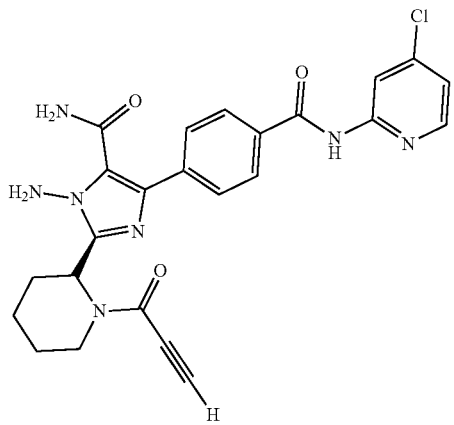

Preparation of (S)-1-amino-4-(4-((4-chloropyridin-2-yl)carbamoyl)phenyl)-2-(1-propioloylpiperidin-2-yl)-1H-imidazole-5-carboxamide

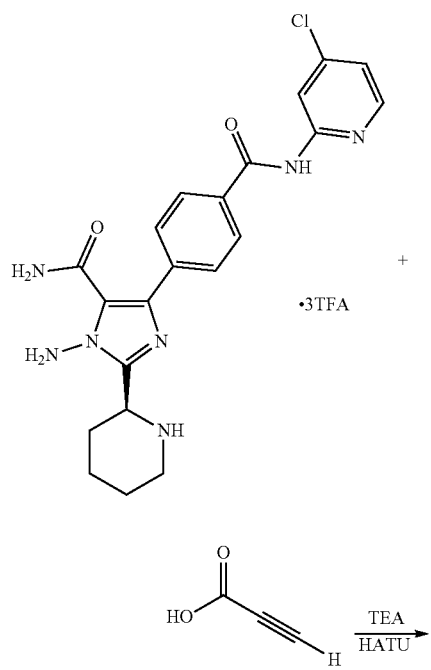

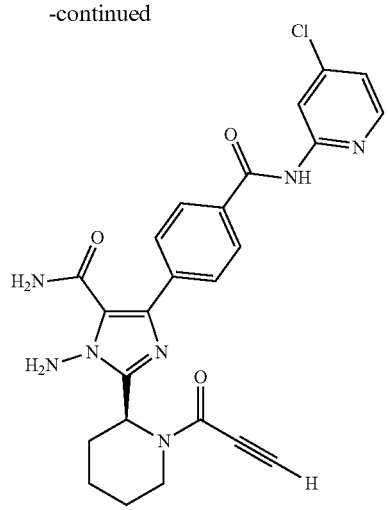

To the solution of 224 mg (0.51 mmol) of the product of Step E of example 72 in dry N,N-Dimethylformamide (7 mL) was added triethylamine (308 mg, 3.06 mmol). After 5 min, propiolic acid (31.5 mg, 0.45 mmol) and HATU (289 mg, 0.76 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (26:1) to give (S)-1-amino-4-(4-((4-chloropyridin-2-yl)carbamoyl)phenyl)-2-(1-propioloylpiperidin-2-yl)-1H-imidazole-5-carboxamide as an off-white solid (125.4 mg, 50%). $^1$H NMR (CDCl$_3$, 400 MHz) δ: 9.02 (s, 1H), 8.48 (s, 1H), 8.18 (d, J=5.2 Hz, 1H), 7.92 (d, J=7.9 Hz, 2H), 7.81 (d, J=8.1 Hz, 2H), 7.08 (d, J=5.3 Hz, 1H), 6.78 (s, 1H), 6.10-6.07 (m, 3H), 5.97 (d, J=5.1 Hz, 1H), 4.32-4.28 (m, 1H), 3.78-3.72 (m, 1H), 3.18 (s, 1H), 2.39-2.29 (m, 1H), 2.20-2.17 (m, 1H), 1.91-1.88 (m, 2H), 1.74-1.71 (m, 1H), 1.64-1.61 (m, 1H); $^{13}$C NMR (CDCl$_3$, 150 MHz) δ: 165.7, 162.6, 153.7, 152.7, 148.6, 147.9, 146.2, 141.0, 138.5, 133.4, 129.7, 127.5, 120.5, 120.1, 114.6, 80.4, 75.5, 44.7, 44.1, 27.9, 25.7, 19.7. MS (ESI, m/z): 492.1 [M+H]$^+$.

Example 100: (S)-1-amino-4-(4-((4-ethylpyridin-2-yl)carbamoyl)phenyl)-2-(1-propioloylpiperidin-2-yl)-1H-imidazole-5-carboxamide

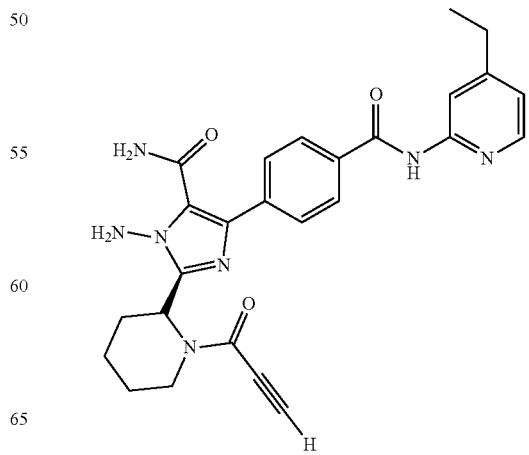

341

Preparation of (S)-1-amino-4-(4-((4-ethylpyridin-2-yl)carbamoyl)phenyl)-2-(1-propioloylpiperidin-2-yl)-1H-imidazole-5-carboxamide

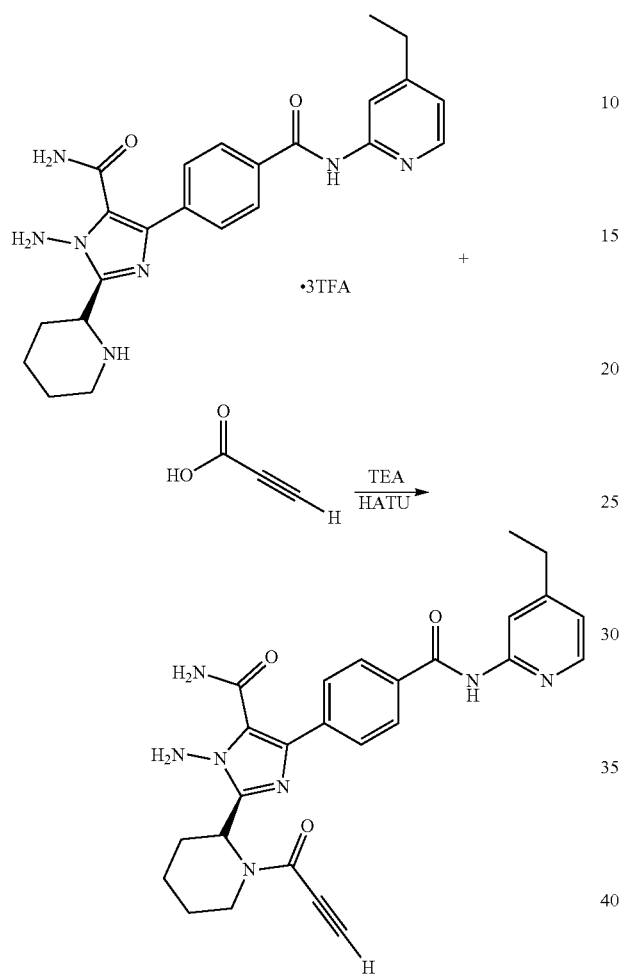

To the solution of 281 mg (0.65 mmol) of the product of Step E of example 73 in dry N,N-Dimethylformamide (5 mL) was added triethylamine (394.6 mg, 3.9 mmol). After 5 min, propiolic acid (43.4 mg, 0.62 mmol) and HATU (370.7 mg, 0.98 mmol) were added. The reaction mixture was continued to stir at room temperature for 2 h. Then, ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (25:1) to give (S)-1-amino-4-(4-((4-ethylpyridin-2-yl)carbamoyl)phenyl)-2-(1-propioloylpiperidin-2-yl)-1H-imidazole-5-carboxamide (189.3 mg, 60%). $^1$H NMR (CDCl$_3$, 400 MHz) δ: 9.13 (s, 1H), 8.32 (s, 1H), 8.19 (d, J=5.1 Hz, 1H), 8.00 (d, J=8.3 Hz, 2H), 7.83 (d, J=8.2 Hz, 2H), 6.97-6.96 (m, 1H), 6.51 (s, 1H), 6.09 (s, 2H), 5.99 (d, J=4.8 Hz, 1H), 5.78 (s, 1H), 4.30 (d, J=13.4 Hz, 1H), 3.77 (td, J$_1$=13.3 Hz, J$_2$=3.0 Hz, 1H), 3.18 (s, 1H), 2.73 (q, J=7.6 Hz, 2H), 2.35-2.32 (m, 1H), 2.21-2.18 (m, 1H), 1.94-1.85 (m, 2H), 1.74-1.71 (m, 1H), 1.65-1.60 (m, 1H), 1.30 (t, J=7.6 Hz, 3H); $^{13}$C NMR (CDCl$_3$, 150 MHz) δ: 165.6, 162.5, 153.6, 151.6, 147.8, 146.8, 141.1, 138.3, 133.9, 129.8, 129.6, 127.7, 120.1, 119.8, 114.1, 80.3, 75.5, 44.7, 44.1, 28.9, 27.9, 25.7, 19.8, 14.5. MS (ESI, m/z): 486.2 [M+H]$^+$.

Example 101: (S)-2-(1-acryloylpiperidin-2-yl)-1-amino-4-(4-(pyridazin-3-ylcarbamoyl)phenyl)-1H-imidazole-5-carboxamide

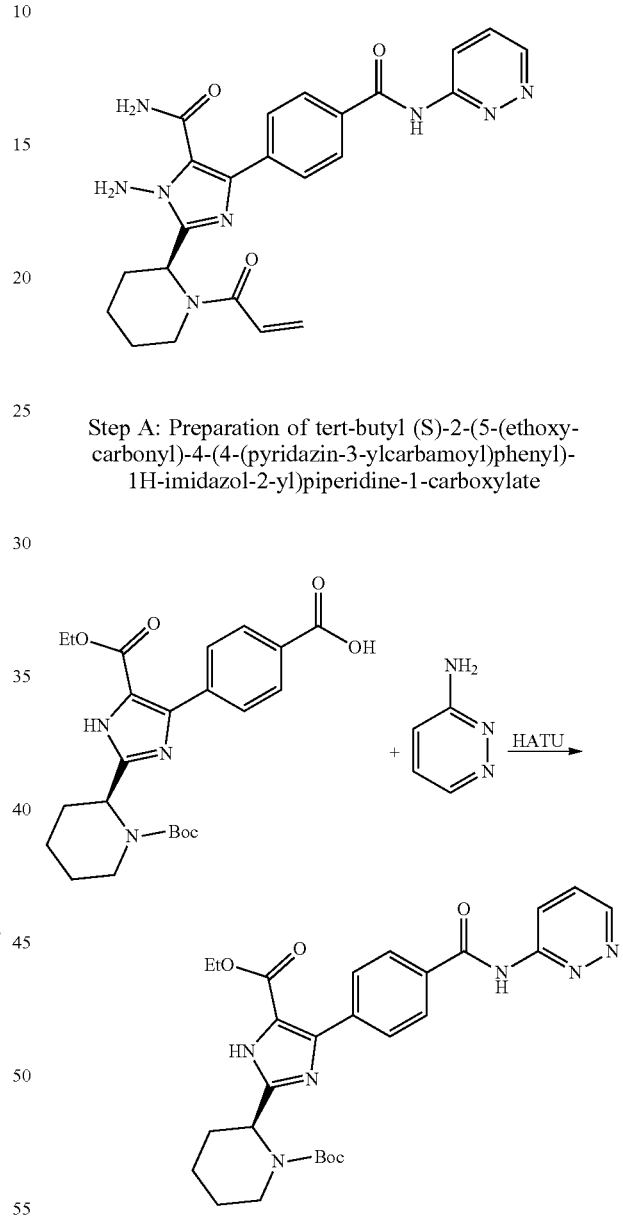

Step A: Preparation of tert-butyl (S)-2-(5-(ethoxycarbonyl)-4-(4-(pyridazin-3-ylcarbamoyl)phenyl)-1H-imidazol-2-yl)piperidine-1-carboxylate To the solution of 4.0 g (9 mmol) of the product of Step C of example 46 in dry N,N-Dimethylformamide (30 mL), HATU (4.2 g, 11 mmol), diisopropylethylamine (7.8 mL, 39.5 mmol) and pyridazin-3-amine (1.8 g, 17.4 mmol) were added and stirred at 80° C. for 3 h. After the completion of the reaction (monitored by TLC), the mixture was quenched with brine and washed with ethyl acetate three times (3×120 mL). The combined organic layers were concentrated under reduced pressure and purified by flash chromatography with petroleum ether and ethyl acetate (3:1) to afford tert-butyl (S)-2-(5-(ethoxycarbonyl)-4-(4-(pyridazin-3-ylcarbamoyl)

phenyl)-1H-imidazol-2-yl)piperidine-1-carboxylate as a white solid (3.3 g, 71%). ¹H NMR (CDCl₃, 400 MHz) δ: 9.97 (s, 1H), 9.07 (s, 1H), 8.98 (dd, J₁=4.7 Hz, J₂=1.4 Hz, 1H), 8.67 (dd, J₁=9.0 Hz, J₂=1.3 Hz, 1H), 8.22 (d, J=8.4 Hz, 2H), 8.00 (d, J=8.4 Hz, 2H), 7.54 (q, J=4.7 Hz, 1H), 5.42 (d, J=4.1 Hz, 1H), 4.37-4.32 (m, 2H), 4.04-4.01 (m, 1H), 2.76-2.72 (m, 1H), 2.56 (d, J=12.9 Hz, 1H), 2.00-1.91 (m, 1H), 1.87-1.69 (m, 3H), 1.56-1.53 (m, 10H), 1.35 (t, J=7.1 Hz, 3H). MS (ESI, m/z): 521.2 [M+H]⁺.

Step B: Preparation of tert-butyl (S)-2-(1-amino-5-(ethoxycarbonyl)-4-(4-(pyridazin-3-ylcarbamoyl)phenyl)-1H-imidazol-2-yl)piperidine-1-carboxylate

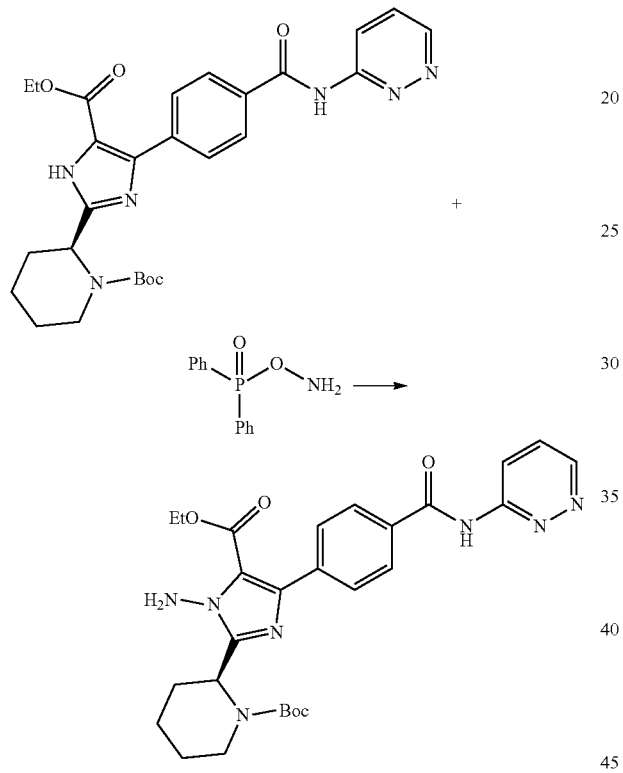

To the solution of 3.3 g (6.3 mmol) of the product of Step A in anhydrous N,N-Dimethylformamide (10 mL) was slowly added lithium hexamethyldisilazane (7.6 mL, 1 M solution in tetrahydrofuran) at −10° C. After the mixture was stirred for 20 min, O-(diphenylphosphinyl) hydroxylamine (1.5 g, 6.3 mmol) was added at 0° C. and the resulting suspension was stirred at room temperature for 2 h (in cases where the reaction mixture become too viscous, additional N,N-Dimethylformamide was added). The mixture was quenched with brine and extracted with ethyl acetate three times (3×100 mL). The combined organic fractions were dried with anhydrous Na₂SO₄ and the solvent was removed under reduced pressure to afford the crude residue, which was subjected to column chromatography with petroleum ether and ethyl acetate (2:1) to give the product tert-butyl (S)-2-(1-amino-5-(ethoxycarbonyl)-4-(4-(pyridazin-3-ylcarbamoyl)phenyl)-1H-imidazol-2-yl)piperidine-1-carboxylate as a white solid (2.0 g, 59%). ¹H NMR (CDCl₃, 400 MHz) δ: 9.97 (s, 1H), 8.93-8.86 (m, 1H), 8.57-8.56 (m, 1H), 8.04-7.97 (m, 2H), 7.80-7.79 (m, 2H), 7.48-7.46 (m, 1H), 5.88 (s, 2H), 5.68-5.63 (m, 1H), 4.29-4.20 (m, 2H), 3.90 (d, J=11.4 Hz, 1H), 3.40 (t, J=12.0 Hz, 1H), 2.10-2.02 (m, 1H), 1.96-1.95 (m, 2H), 1.80-1.65 (m, 2H), 1.57-1.55 (m, 1H), 1.36 (s, 9H), 1.26-1.16 (m, 3H). MS (ESI, m/z): 536.2 [M+H]⁺.

Step C: Preparation of (S)-1-amino-2-(1-(tert-butoxycarbonyl)piperidin-2-yl)-4-(4-(pyridazin-3-ylcarbamoyl)phenyl)-1H-imidazole-5-carboxylic acid

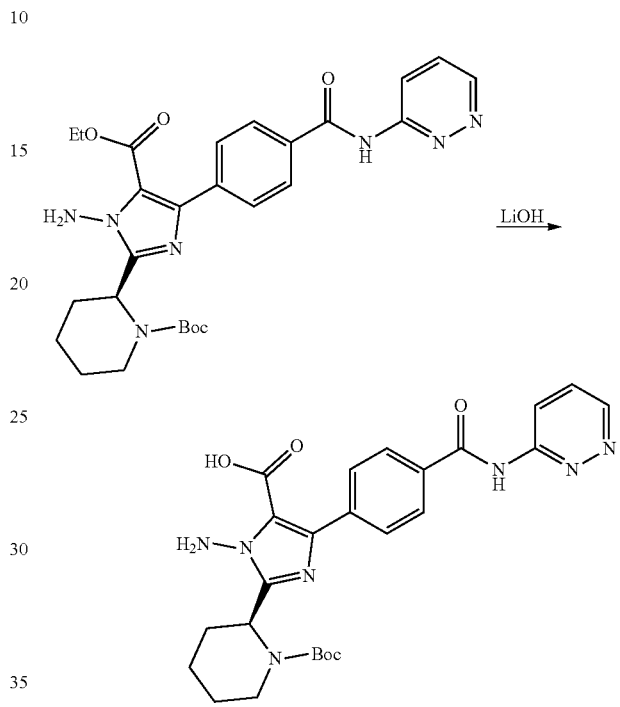

To the solution of 1.9 g (3.6 mmol) of the product of Step B in methanol (19 mL), 2 mol/L aqueous lithium hydroxide (19 mL) was added and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl)piperidin-2-yl)-4-(4-(pyridazin-3-ylcarbamoyl)phenyl)-1H-imidazole-5-carboxylic acid as a white solid (1.7 g, 93%).

Step D: Preparation of tert-butyl (S)-2-(1-amino-5-carbamoyl-4-(4-(pyridazin-3-ylcarbamoyl)phenyl)-1H-imidazol-2-yl)piperidine-1-carboxylate

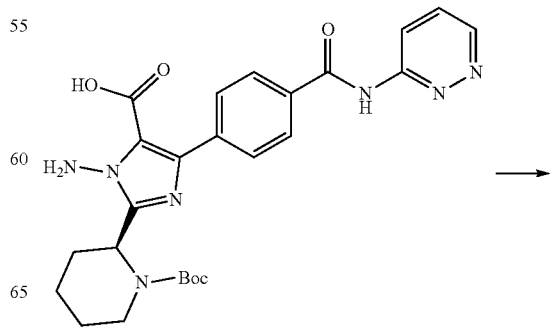

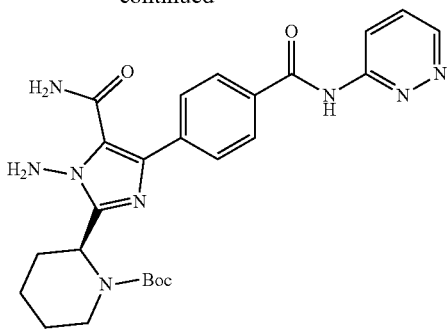

To the solution of 2.2 g (4.4 mmol) of the product of Step C in dry N,N-Dimethylformamide (15 mL), HATU (2.5 g, 6.7 mmol), diisopropylethylamine (2.3 mL, 13.4 mmol) and NH₄Cl (2.4 g, 45 mmol) were added and stirred at room temperature for 2 h. The reaction mixture was quenched with brine and washed with ethyl acetate three times (3×100 mL). The combined organic layers were concentrated under reduced pressure and purified by flash chromatography with dichloromethane and methanol (35:1) to give the product tert-butyl (S)-2-(1-amino-5-carbamoyl-4-(4-(pyridazin-3-ylcarbamoyl)phenyl)-1H-imidazol-2-yl)piperidine-1-carboxylate as a white solid (1.4 g, 77%). $^1$H NMR (CDCl$_3$, 400 MHz) δ: 10.28 (s, 1H), 8.72 (d, J=3.6 Hz, 1H), 8.62 (d, J=8.8 Hz, 1H), 8.03 (s, 1H), 7.86 (d, J=8.2 Hz, 2H), 7.75 (d, J=8.0 Hz, 2H), 7.44 (dd, J$_1$=9.0 Hz, J$_2$=4.7 Hz, 1H), 7.07 (s, 1H), 6.05 (s, 2H), 5.66 (d, J=5.1 Hz, 1H), 3.95 (d, J=12.2 Hz, 1H), 3.37-3.31 (m, 1H), 2.19-2.09 (m, 2H), 1.93-1.86 (m, 2H), 1.76-1.62 (m, 2H), 1.50 (s, 9H). MS (ESI, m/z): 507.2 [M+H]$^+$.

Step E: Preparation of (S)-1-amino-2-(piperidin-2-yl)-4-(4-(pyridazin-3-ylcarbamoyl)phenyl)-1H-imidazole-5-carboxamide

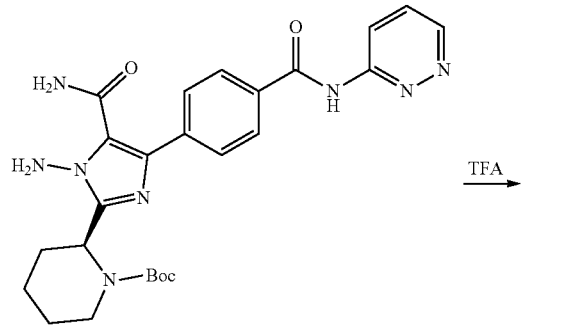

To the solution of 180 mg (0.35 mmol) of the product of Step D in dichloromethane (5 mL), trifluoroacetic acid (1.4 mL) was added. The mixture was stirred at room temperature for 1 h and then concentrated to afford (S)-1-amino-2-(piperidin-2-yl)-4-(4-(pyridazin-3-ylcarbamoyl)phenyl)-1H-imidazole-5-carboxamide as a light yellow oil. MS (ESI, m/z): 407.2 [M+H]$^+$.

Step F: Preparation of (S)-2-(1-acryloylpiperidin-2-yl)-1-amino-4-(4-(pyridazin-3-ylcarbamoyl)phenyl)-1H-imidazole-5-carboxamide

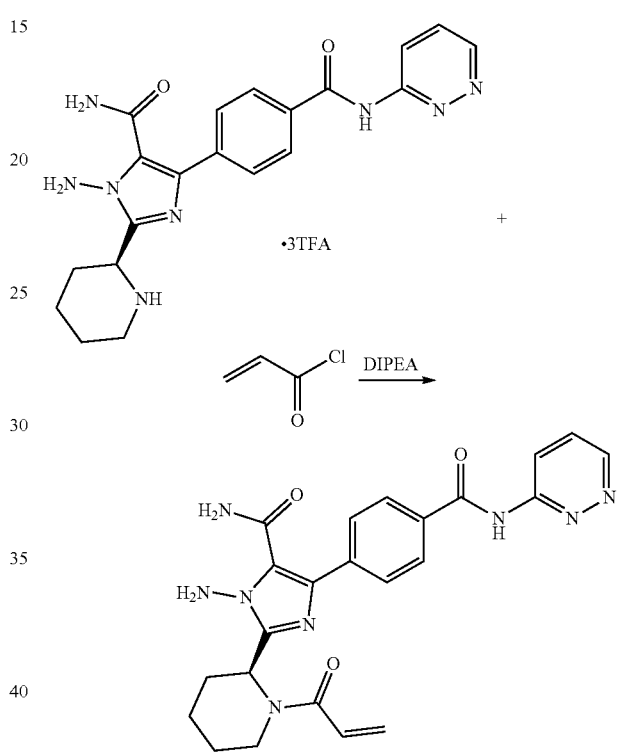

To the solution of 142 mg (0.35 mmol) of the product of Step E in dry dichloromethane (5 mL) was added diisopropylethylamine (271 mg, 2.10 mmol). After 5 min, acryloyl chloride (29.1 mg, 0.32 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na₂SO₄, filtered and concentrated. The residue was purified by chromatography with dichloromethane and methanol (18:1) to give (S)-2-(1-acryloylpiperidin-2-yl)-1-amino-4-(4-(pyridazin-3-ylcarbamoyl)phenyl)-1H-imidazole-5-carboxamide as an off-white solid (98 mg, 61%). $^1$H NMR (CDCl$_3$, 600 MHz) δ: 10.49 (s, 1H), 8.69 (s, 1H), 8.60 (d, J=8.3 Hz, 1H), 8.40 (s, 1H), 7.83 (d, J=7.1 Hz, 2H), 7.73-7.72 (m, 2H), 7.56 (s, 1H), 7.43 (dd, J=8.5 Hz, J$_2$=4.5 Hz, 1H), 6.66-6.62 (m, 1H), 6.41 (d, J=16.3 Hz, 1H), 6.35 (s, 2H), 6.16-6.12 (m, 1H), 5.77 (d, J=10.0 Hz, 1H), 3.86 (d, J=11.3 Hz, 1H), 3.71-3.69 (m, 1H), 2.38-2.36 (m, 1H), 2.14 (d, J=13.1 Hz, 1H), 1.91-1.85 (m, 2H), 1.69-1.59 (m, 2H); $^{13}$C NMR (CDCl$_3$, 150 MHz) δ: 166.9, 166.8, 164.0, 156.2, 148.5, 147.7, 140.2, 138.7, 132.4, 129.0, 128.9, 128.5, 127.9, 127.7, 121.2, 119.5, 50.9, 43.1, 28.1, 26.0, 19.8. MS (ESI, m/z): 461.1 [M+H]$^+$.

Example 102: (S)-1-amino-2-(1-(but-2-ynoyl)piperidin-2-yl)-4-(4-(pyridazin-3-ylcarbamoyl)phenyl)-1H-imidazole-5-carboxamide

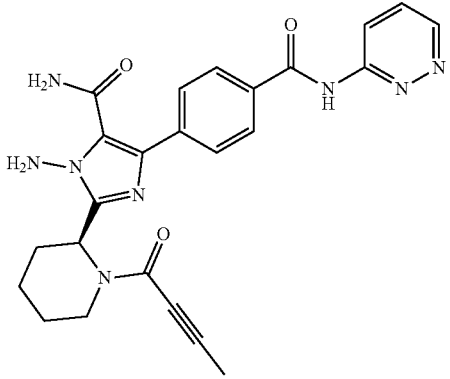 [SMILES: CC#CC(=O)N1CCCC[C@H]1c1nc(-c2ccc(C(=O)Nc3cccnn3)cc2)c(C(N)=O)n1N]

Preparation of (S)-1-amino-2-(1-(but-2-ynoyl)piperidin-2-yl)-4-(4-(pyridazin-3-ylcarbamoyl)phenyl)-1H-imidazole-5-carboxamide

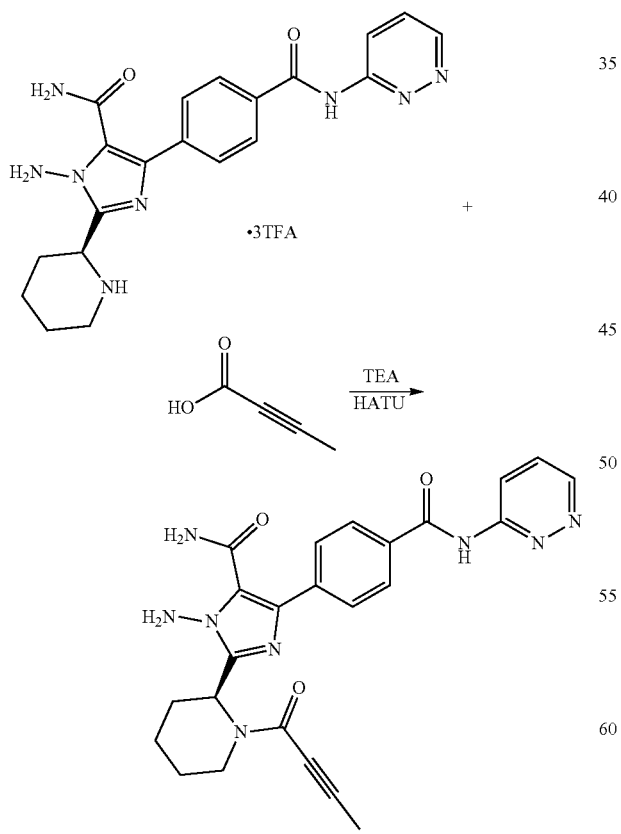

To the solution of 142 mg (0.35 mmol) of the product of Step E of example 101 in dry N,N-Dimethylformamide (5 mL) was added triethylamine (212 mg, 2.1 mmol). After 5 min, but-2-ynoic acid (26.5 mg, 0.32 mmol) and HATU (203 mg, 0.53 mmol) were added. The reaction mixture was continued to stir at room temperature for 2 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (20:1) to give (S)-1-amino-2-(1-(but-2-ynoyl)piperidin-2-yl)-4-(4-(pyridazin-3-ylcarbamoyl)phenyl)-1H-imidazole-5-carboxamide as an off-white solid (87 mg, 53%). $^1$H NMR (CDCl$_3$, 400 MHz) δ: 10.67 (s, 1H), 8.63-8.58 (m, 3H), 7.78 (d, J=8.2 Hz, 2H), 7.68-7.58 (m, 3H) 7.43 (dd, J=9.0 Hz, J$_2$=4.7 Hz, 1H), 6.19-6.09 (m, 3H), 4.31 (d, J=13.0 Hz, 1H), 3.78 (t, J=11.1 Hz, 1H), 4.31 (d, J=13.0 Hz, 1H), 2.23-2.20 (m, 1H), 2.12-2.08 (m, 1H), 2.03 (s, 3H), 1.85-1.83 (m, 2H), 1.66-1.56 (m, 2H); $^{13}$C NMR (CDCl$_3$, 100 MHz) δ: 166.9, 164.3, 156.2, 154.6, 148.7, 147.6, 139.9, 138.5, 132.4, 128.6, 128.1, 127.9, 121.7, 119.5, 90.6, 73.2, 44.7, 44.0, 28.0, 26.0, 19.8, 4.3. MS (ESI, m/z): 473.1 [M+H]$^+$.

Example 103: 2-((1-acryloylpiperidin-4-yl)methyl)-1-amino-4-(4-(pyridin-2-ylcarbamoyl)phenyl)-1H-imidazole-5-carboxamide

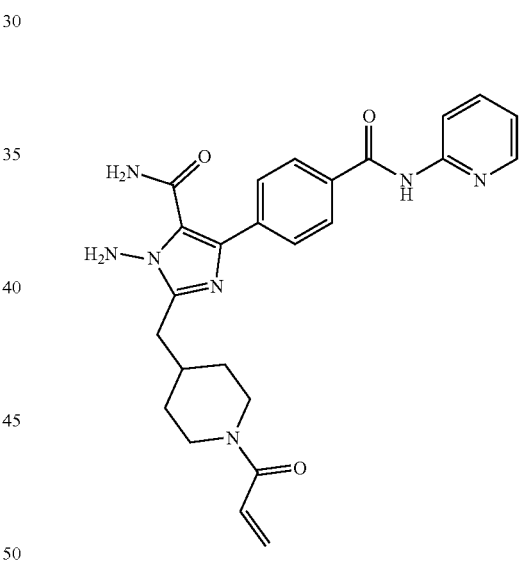

Step A: Preparation of tert-butyl 4-(2-((1-ethoxy-3-(4-(ethoxycarbonyl)phenyl)-1,3-dioxopropan-2-yl)oxy)-2-oxoethyl)piperidine-1-carboxylate

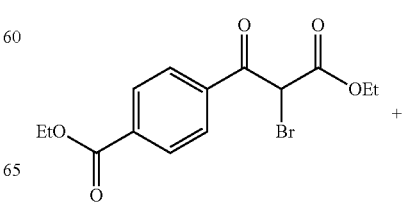

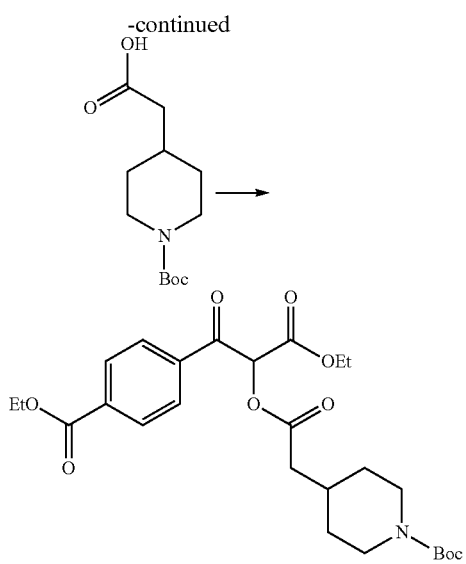

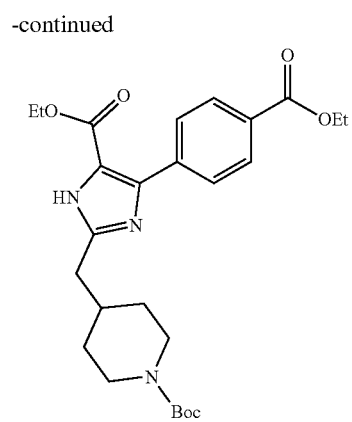

To the solution of 11.5 g (34 mmol) of the product of Step C of example 1 in acetonitrile (35 mL), the diisopropylethylamine (6.4 mL, 37 mmol) and 2-(1-(tert-butoxycarbonyl)piperidin-4-yl)acetic acid (8.7 g, 36 mmol) were added and stirred at room temperature for 3 h before all volatiles were evaporated. The residue was diluted with water (150 mL) and extracted with ethyl acetate (500 mL). The organic phase was separated, dried over anhydrous Na$_2$SO$_4$ and concentrated. The residue was purified by flash column chromatography with petroleum ether and ethyl acetate (8:1) to give tert-butyl 4-(2-((1-ethoxy-3-(4-(ethoxycarbonyl)phenyl)-1,3-dioxopropan-2-yl)oxy)-2-oxoethyl)piperidine-1-carboxylate as a light yellow oil (12.9 g, 76%). $^1$H NMR (CDCl$_3$, 400 MHz) δ: 8.14 (d, J=8.5 Hz, 2H), 8.02 (d, J=8.6 Hz, 2H), 6.29 (s, 1H), 4.40 (q, J=7.1 Hz, 2H), 4.23 (q, J=7.1 Hz, 2H), 4.07-4.05 (m, 2H), 2.78-2.60 (m, 2H), 2.40 (d, J=7.0 Hz, 2H), 1.99-1.93 (m, 1H), 1.71 (d, J=12.6 Hz, 2H), 1.43 (s, 9H), 1.40 (t, J=7.2 Hz, 3H), 1.21-1.11 (m, 5H). MS (ESI, m/z): 506.2 [M+H]$^+$.

Step B: Preparation of tert-butyl 4-((5-(ethoxycarbonyl)-4-(4-(ethoxycarbonyl)phenyl)-1H-imidazol-2-yl)methyl)-piperidine-1-carboxylate

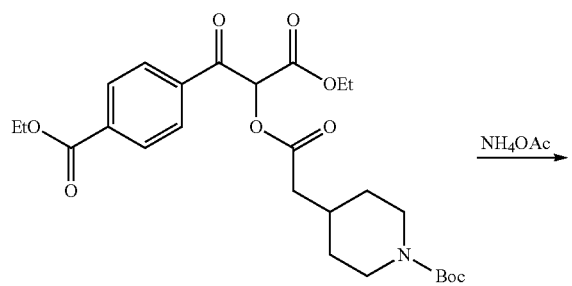

To the solution of 14.1 g (28 mmol) of the product of Step A in xylene (40 mL) in a 150 mL pressure bottle was added NH$_4$OAc (25.8 g, 336 mmol). The reaction was heated at 140° C. for 2.5 h. After being cooled, the residue was diluted with water (100 mL) and extracted with ethyl acetate (300 mL). The organic phase was separated, dried over anhydrous Na$_2$SO$_4$ and concentrated. The residue was purified by flash column chromatography with petroleum ether and ethyl acetate (3:1) to give tert-butyl 4-((5-(ethoxycarbonyl)-4-(4-(ethoxycarbonyl)phenyl)-1H-imidazol-2-yl)methyl) piperidine-1-carboxylate as a light yellow oil (4.5 g, 33%). $^1$H NMR (CDCl$_3$, 400 MHz) δ: 10.25 (s, 1H), 8.06 (d, J=8.6 Hz, 2H), 7.93 (d, J=8.6 Hz, 2H), 4.39 (q, J=7.1 Hz, 2H), 4.31 (q, J=7.1 Hz, 2H), 4.10-4.07 (m, 2H), 2.71-2.69 (m, 4H), 2.04-1.97 (m, 1H), 1.67 (d, J=11.8 Hz, 2H), 1.44 (s, 9H), 1.40 (t, J=7.1 Hz, 3H), 1.31 (t, J=7.1 Hz, 3H), 1.21-1.17 (m, 2H). MS (ESI, m/z): 486.2 [M+H]$^+$.

Step C: Preparation of 4-(2-((1-(tert-butoxycarbonyl)piperidin-4-yl)methyl)-5-(ethoxycarbonyl)-1H-imidazol-4-yl)benzoic acid

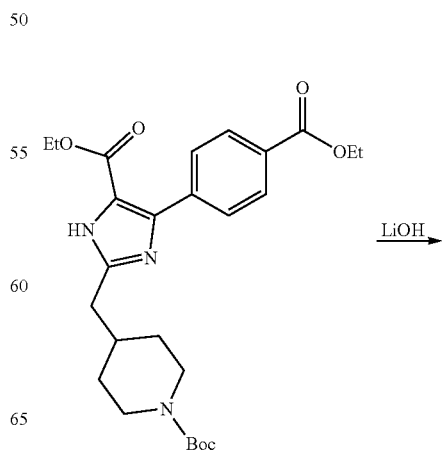

-continued

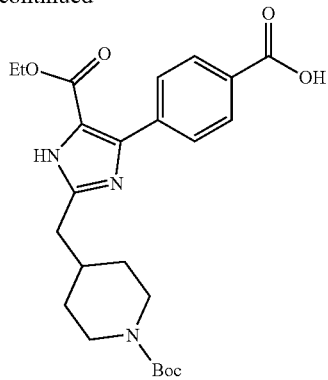

To the solution of 4.46 g (9.2 mmol) of the product of Step B in 1,4-dioxane (22 mL), aqueous Lithium hydroxide (2 mol/L, 22 mL) was added and stirred at room temperature for 2 h. The reaction mixture was evaporated, diluted with water (100 mL) and acidified with aqueous HCl till pH 3. The white precipitate was isolated by filtration and dried to afford 4-(2-((1-(tert-butoxycarbonyl)piperidin-4-yl)methyl)-5-(ethoxycarbonyl)-1H-imidazol-4-yl)-benzoic acid as a white solid (3.78 g, 90%).

Step D: Preparation of tert-butyl 4-((5-(ethoxycarbonyl)-4-(4-(pyridin-2-ylcarbamoyl)phenyl)-1H-imidazol-2-yl)methyl)piperidine-1-carboxylate

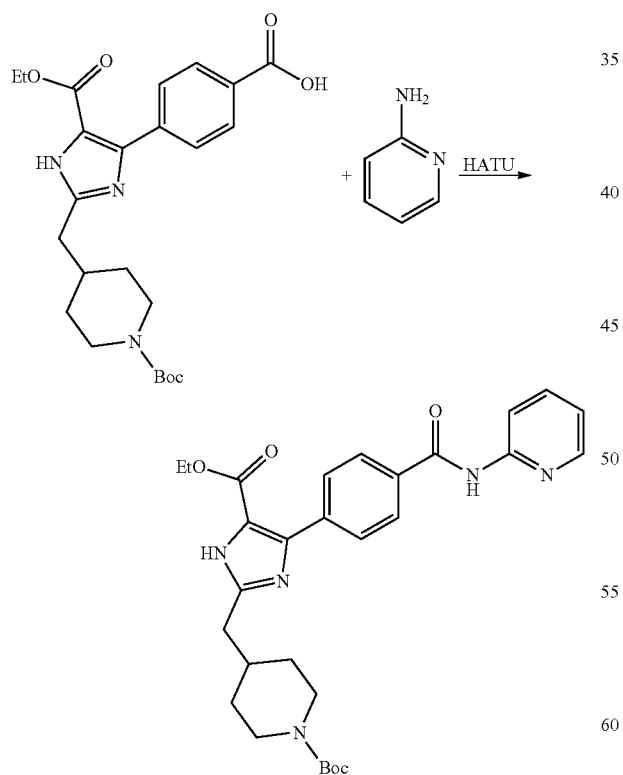

To the solution of 3.66 g (8.0 mmol) of the product of Step C in dry N,N-Dimethylformamide (50 mL), HATU (3.6 g, 9.6 mmol), diisopropylethylamine (6.9 mL, 39.9 mmol) and pyridin-2-amine (1.66 g, 17.7 mmol) were added and stirred at 80° C. for 3 h. After the completion of the reaction (monitored by TLC), the mixture was quenched with brine and washed with ethyl acetate three times (3×100 mL). The combined organic layers were concentrated under reduced pressure and purified by flash chromatography with petroleum ether and ethyl acetate (1:2) to afford tert-butyl 4-((5-(ethoxycarbonyl)-4-(4-(pyridin-2-ylcarbamoyl)phenyl)-1H-imidazol-2-yl)methyl)piperidine-1-carboxylate as a white solid (3.48 g, 81%). $^1$H NMR (CDCl$_3$, 400 MHz) S: 10.25 (s, 1H), 9.69 (s, 1H), 8.33 (d, J=8.5 Hz, 1H), 8.20 (d, J=4.1 Hz, 1H), 8.04 (d, J=8.6 Hz, 2H), 7.85-7.80 (m, 3H), 7.13-7.09 (m, 1H), 4.25 (q, J=7.1 Hz, 2H), 4.09-4.05 (m, 2H), 2.80 (d, J=7.1 Hz, 2H), 2.69-2.66 (m, 2H), 2.07-2.05 (m, 1H), 1.68 (d, J=12.0 Hz, 2H), 1.40 (s, 9H), 1.33-1.24 (m, 2H), 1.23-1.21 (m, 3H). MS (ESI, m/z): 534.2 [M+H]$^+$.

Step E: Preparation of tert-butyl 4-((1-amino-5-(ethoxycarbonyl)-4-(4-(pyridin-2-ylcarbamoyl)phenyl)-1H-imidazol-2-yl)methyl)piperidine-1-carboxylate

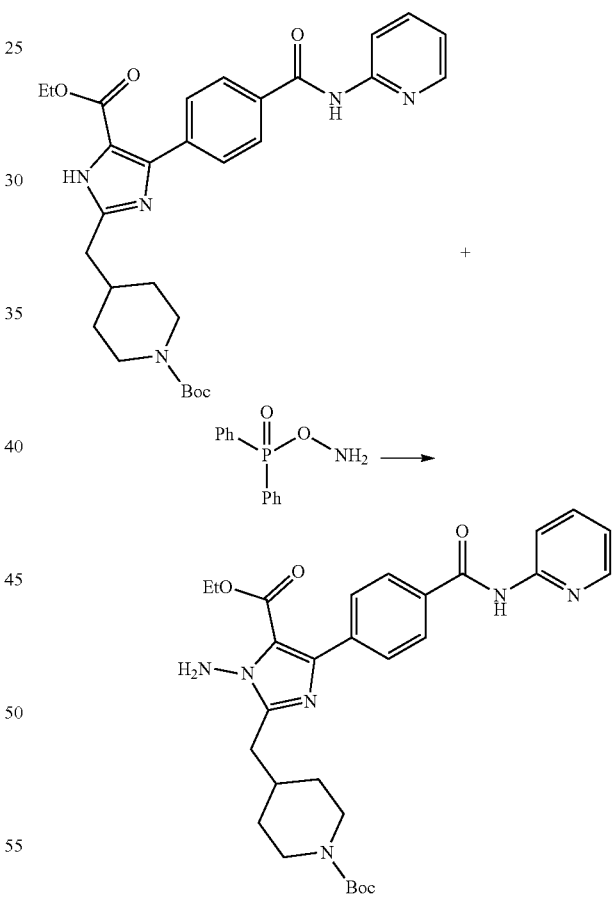

To the solution of 3.48 g (6.5 mmol) of the product of Step D in anhydrous N,N-Dimethylformamide (40 mL), lithium hexamethyldisilazane (7.8 mL, 1 M solution in tetrahydrofuran) was slowly added at −10° C. After the mixture was stirred for 20 min, O-(diphenylphosphinyl)hydroxylamine (1.5 g, 6.5 mmol) was added at 0° C. and the resulting suspension was stirred at room temperature for 2 h (in cases where the reaction mixture become too viscous, additional N,N-Dimethylformamide was added). The mixture was quenched with brine and extracted with ethyl acetate three times (3×100 mL). The combined organic fractions were dried with anhydrous Na₂SO₄ and the solvent was removed under reduced pressure to afford the crude residue, which was subjected to column chromatography with petroleum ether and ethyl acetate (1:1) to give the product tert-butyl 4-((1-amino-5-(ethoxycarbonyl)-4-(4-(pyridin-2-ylcarbamoyl)phenyl)-1H-imidazol-2-yl)methyl)piperidine-1-carboxylate as a white solid (1.8 g, 51%). ¹H NMR (CDCl₃, 400 MHz) δ: 9.71 (s, 1H), 8.46 (d, J=8.4 Hz, 1H), 8.22 (d, J=4.0 Hz, 1H), 8.01 (d, J=8.6 Hz, 2H), 7.82-7.78 (m, 3H), 7.11-7.08 (m, 1H), 5.33 (s, 2H), 4.26 (q, J=7.1 Hz, 2H), 4.11-4.07 (m, 2H), 2.84 (d, J=7.1 Hz, 2H), 2.71-2.66 (m, 2H), 2.03-2.01 (m, 1H), 1.67 (d, J=11.9 Hz, 2H), 1.44 (s, 9H), 1.31-1.27 (m, 2H), 1.24-1.21 (m, 3H). MS (ESI, m/z): 549.2 [M+H]⁺.

Step F: Preparation of 1-amino-2-((1-(tert-butoxycarbonyl)piperidin-4-yl)methyl)-4-(4-(pyridin-2-ylcarbamoyl)phenyl)-1H-imidazole-5-carboxylic acid To the solution of 1.8 g (3.3 mmol) of the product of Step E in methanol (20 mL), 2 mol/L aqueous lithium hydroxide (18 mL) was added and stirred at room temperature for 2 h. The reaction mixture was evaporated and diluted with water (100 mL) and acidified with aqueous HCl till pH 3. The mixture was washed with ethyl acetate three times (3×60 mL). The white precipitate was isolated by filtration and dried to afford 1-amino-2-((1-(tert-butoxycarbonyl)piperidin-4-yl)methyl)-4-(4-(pyridin-2-ylcarbamoyl)phenyl)-1H-imidazole-5-carboxylic acid as a white solid (1.62 g, 95%).

Step G: Preparation of tert-butyl 4-((1-amino-5-carbamoyl-4-(4-(pyridin-2-ylcarbamoyl)phenyl)-1H-imidazol-2-yl)methyl)piperidine-1-carboxylate

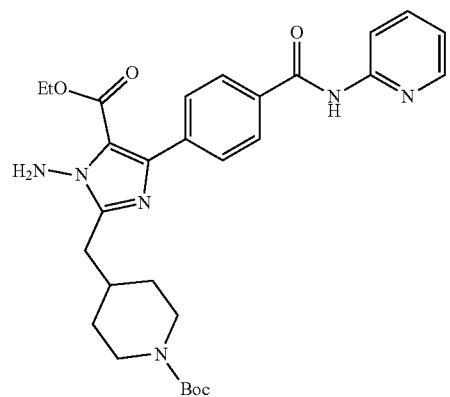

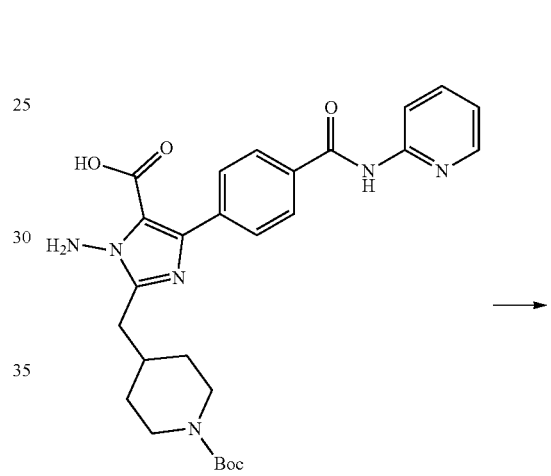

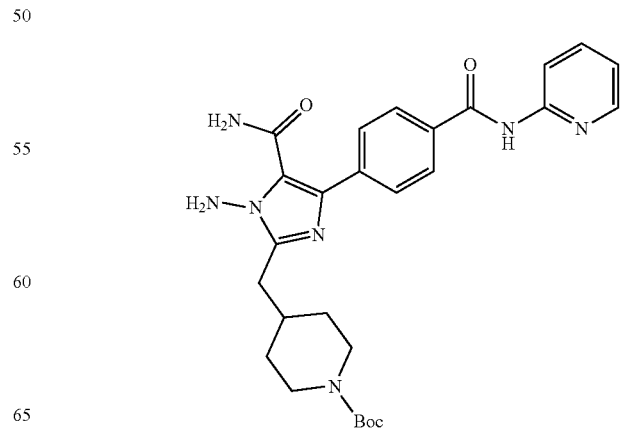

To the solution of 1.62 g (3.1 mmol) of the product of Step F in dry N,N-Dimethylformamide (20 mL), HATU (1.8 g, 4.7 mmol), diisopropylethylamine (1.7 mL, 9.3 mmol) and NH₄Cl (1.6 g, 31 mmol) were added and stirred at room temperature for 2 h. The reaction mixture was quenched with brine and washed with ethyl acetate three times (3×60 mL). The combined organic layers were concentrated under reduced pressure and purified by flash chromatography with dichloromethane and methanol (25:1) to give the product tert-butyl 4-((1-amino-5-carbamoyl-4-(4-(pyridin-2-ylcarbamoyl)phenyl)-1H-imidazol-2-yl)methyl)piperidine-1-carboxylate as a white solid (1.37 g, 85%). ¹H NMR (DMSO-d₆, 400 MHz) δ: 10.74 (s, 1H), 8.39 (dd, $J_1$=4.8 Hz, $J_2$=1.1 Hz, 1H), 8.21 (d, J=8.4 Hz, 1H), 8.03-8.01 (m, 3H), 7.86-7.82 (m, 3H), 7.70 (s, 1H), 7.18-7.15 (m, 1H), 6.01 (s, 2H), 3.92 (d, J=11.0 Hz, 2H), 2.69-2.67 (m, 4H), 2.01-1.97 (m, 1H), 1.68 (d, J=11.1 Hz, 2H), 1.39 (s, 9H), 1.18-1.05 (m, 2H). MS (ESI, m/z): 520.2 [M+H]⁺.

Step H: Preparation of 1-amino-2-(piperidin-4-ylmethyl)-4-(4-(pyridin-2-ylcarbamoyl)phenyl)-1H-imidazole-5-carboxamide

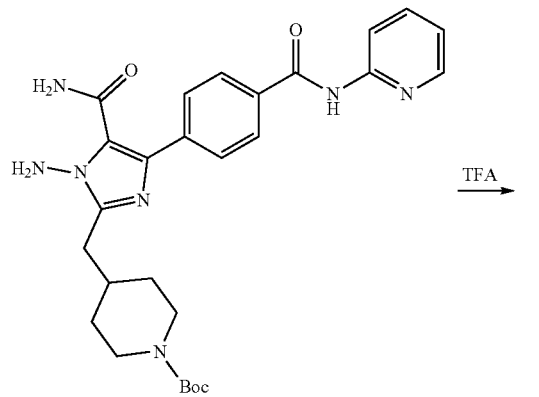

TFA →

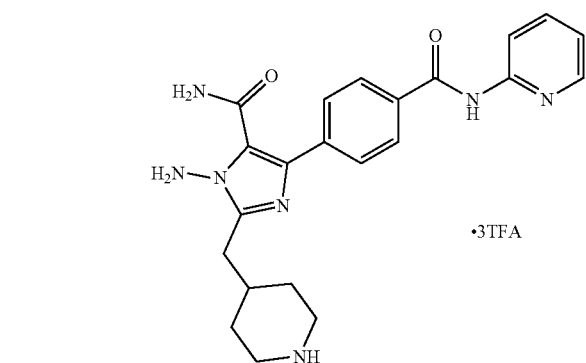

To the solution of 330 mg (0.63 mmol) of the product of Step G in dichloromethane (8 mL), trifluoroacetic acid (2.5 mL) was added. The mixture was stirred at room temperature for 1 h and then concentrated to afford 1-amino-2-(piperidin-4-ylmethyl)-4-(4-(pyridin-2-ylcarbamoyl)phenyl)-1H-imidazole-5-carboxamide as a light yellow oil. MS (ESI, m/z): 420.2 [M+H]⁺.

Step I: Preparation of 2-((1-acryloylpiperidin-4-yl)methyl)-1-amino-4-(4-(pyridin-2-ylcarbamoyl)phenyl)-1H-imidazole-5-carboxamide

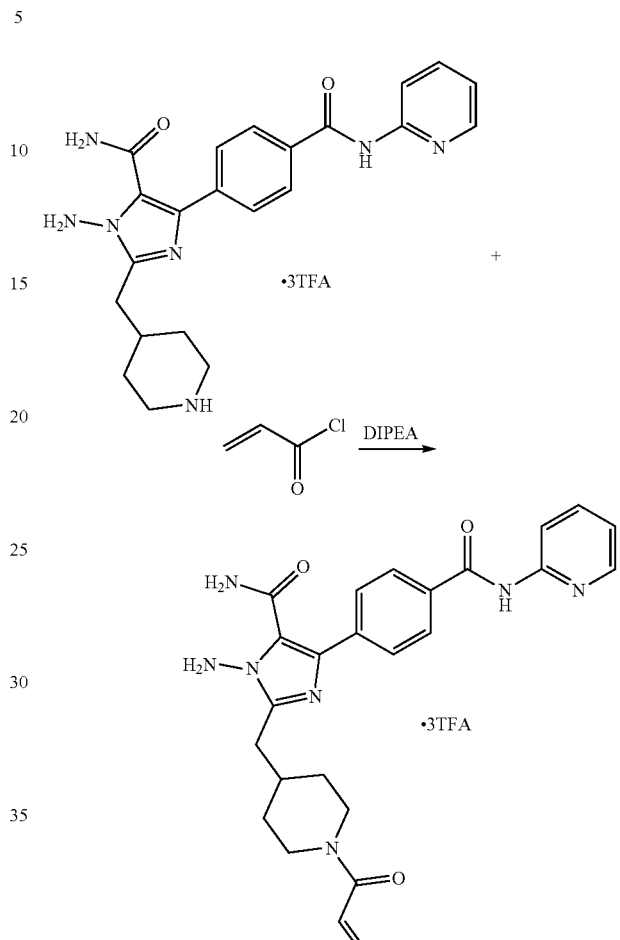

To the solution of 240 mg (0.57 mmol) of the product of Step H in dry dichloromethane (8 mL) was added diisopropylethylamine (442 mg, 3.42 mmol). After 5 min, acryloyl chloride (41.3 mg, 0.46 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na₂SO₄, filtered and concentrated. The residue was purified by chromatography with dichloromethane and methanol (18:1) to give 2-((1-acryloylpiperidin-4-yl)methyl)-1-amino-4-(4-(pyridin-2-ylcarbamoyl)phenyl)-1H-imidazole-5-carboxamide as an off-white solid (175 mg, 65%). ¹H NMR (DMSO-d₆, 400 MHz) δ: 10.71 (s, 1H), 8.39 (d, J=3.8 Hz, 1H), 8.20 (d, J=8.4 Hz, 1H), 8.05-8.01 (m, 3H), 7.87-7.82 (m, 3H), 7.68 (s, 1H), 7.17 (dd, $J_1$=6.9 Hz, $J_2$=5.1 Hz, 1H), 6.83-6.76 (m, 1H), 6.07 (dd, $J_1$=16.3 Hz, $J_2$=2.3 Hz, 1H), 6.03 (s, 2H), 5.64 (dd, $J_1$=10.4 Hz, $J_2$=2.3 Hz, 1H), 4.41 (d, J=12.8 Hz, 1H), 4.03 (d, J=12.8 Hz, 1H), 3.07-3.04 (m, 1H), 2.70-2.61 (m, 3H), 2.16-2.09 (m, 1H), 1.78-1.76 (m, 2H), 1.18-1.11 (m, 2H); ¹³C NMR (DMSO-d₆, 100 MHz) δ: 165.7, 164.1, 162.5, 152.3, 147.9, 147.8, 138.2, 138.1, 136.0, 131.9, 128.6, 127.7, 127.0, 126.9, 124.7, 119.7, 114.7, 45.2, 41.6, 34.4, 32.5, 31.7, 31.5. MS (ESI, m/z): 474.2 [M+H]⁺.

Example 104: 1-amino-2-((1-(but-2-ynoyl)piperidin-4-yl)methyl)-4-(4-(pyridin-2-ylcarbamoyl)phenyl)-1H-imidazole-5-carboxamide

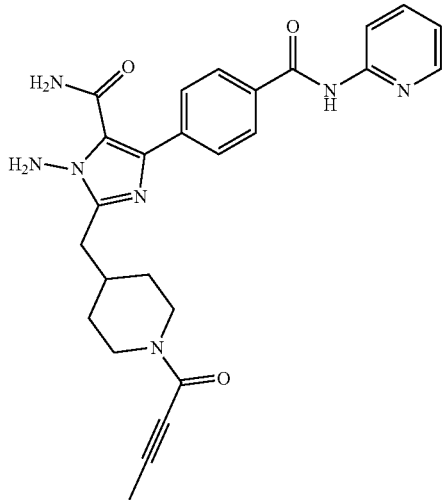 [SMILES: CC#CC(=O)N1CCC(Cc2nc(-c3ccc(C(=O)Nc4ccccn4)cc3)c(C(N)=O)n2N)CC1]

Preparation of 1-amino-2-((1-(but-2-ynoyl)piperidin-4-yl)methyl)-4-(4-(pyridin-2-ylcarbamoyl) phenyl)-1H-imidazole-5-carboxamide

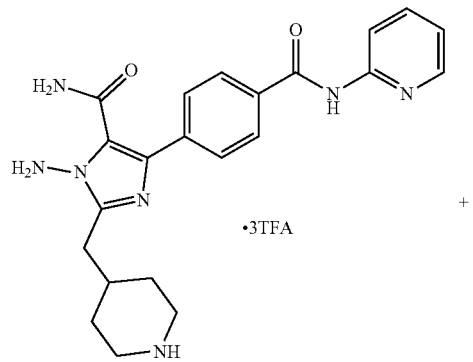

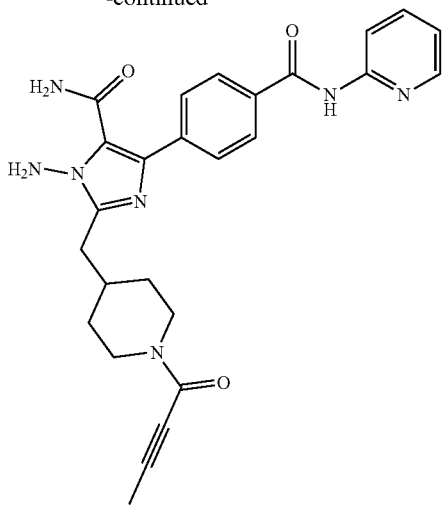

To the solution of 240 mg (0.57 mmol) of the product of Step H of example 103 in dry N,N-Dimethylformamide (8 mL) was added triethylamine (346 mg, 3.42 mmol). After 5 min, but-2-ynoic acid (42.9 mg, 0.51 mmol) and HATU (325 mg, 0.85 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous Na₂SO₄, filtered and concentrated. The residue was purified by chromatography with dichloromethane and methanol (16:1) to give 1-amino-2-((1-(but-2-ynoyl)piperidin-4-yl)methyl)-4-(4-(pyridin-2-ylcarbamoyl)phenyl)-1H-imidazole-5-carboxamide as an off-white solid (160 mg, 58%). $^1$H NMR (CDCl₃, 600 MHz) δ: 8.86 (s, 1H), 8.37 (d, J=8.3 Hz, 1H), 8.29 (d, J=4.2 Hz, 1H), 7.98 (d, J=8.2 Hz, 2H), 7.79-7.76 (m, 1H), 7.74 (d, J=8.2 Hz, 2H), 7.10-7.08 (m, 1H), 5.81 (s, 2H), 5.52 (s, 2H), 4.51 (d, J=13.4 Hz, 1H), 4.36 (d, J=13.5 Hz, 1H), 3.08-3.03 (m, 1H), 2.86-2.79 (m, 2H), 2.66-2.61 (m, 1H), 2.22-2.12 (m, 1H), 1.99 (s, 3H), 1.81 (d, J=12.7 Hz, 1H), 1.76 (d, J=13.1 Hz, 1H), 1.36-1.30 (m, 2H); $^{13}$C NMR (CDCl₃, 150 MHz) δ: 165.3, 162.7, 153.2, 151.6, 150.4, 148.0, 141.0, 138.7, 138.0, 134.4, 129.6, 127.9, 120.3, 119.9, 114.5, 89.4, 73.2, 47.2, 41.4, 35.6, 32.6, 32.3, 31.6, 4.2. MS (ESI, m/z): 486.2 [M+H]⁺.

Example 105

(S)-2-(1-acryloylpiperidin-2-yl)-1-amino-4-(4-(thiazol-2-ylcarbamoyl)phenyl)-1H-imidazole-5-carboxamide

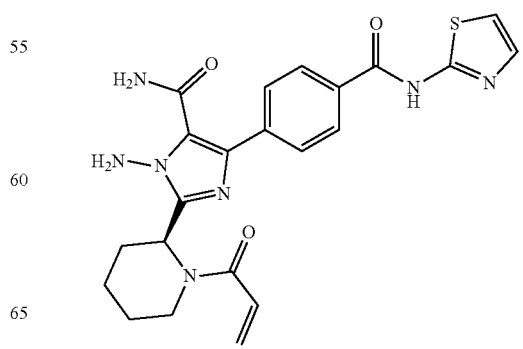

Step A: Preparation of (S)-4-(1-amino-2-(1-(tert-butoxycarbonyl)piperidin-2-yl)-5-carbamoyl-1H-imidazol-4-yl)benzoic acid

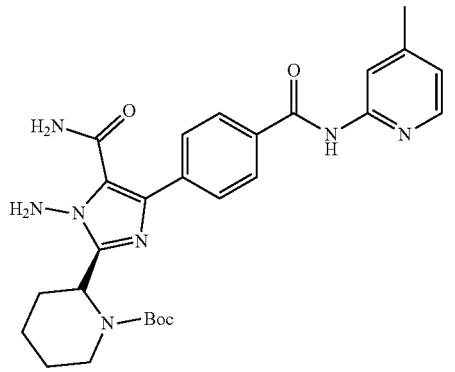

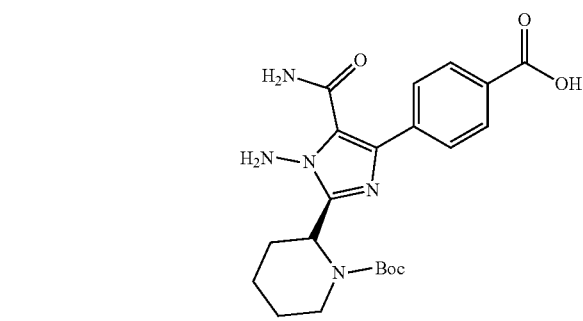

To the solution of 300 mg (0.58 mmol) of the product of Step D of example 58 in ethanol (15 mL) was added aqueous lithium hydroxide (2 mol/L, 3 mL), then stirred at 80° C. for 3 h. The reaction mixture was evaporated and diluted with water (100 mL) and acidified with aqueous HCl till pH 3. The mixture was washed with ethyl acetate three times (3×50 mL). The combined organic layers were concentrated under reduced pressure to afford (S)-4-(1-amino-2-(1-(tert-butoxycarbonyl)piperidin-2-yl)-5-carbamoyl-1H-imidazol-4-yl)benzoic acid as a white solid (224 mg, 90%).

Step B: Preparation of tert-butyl (S)-2-(1-amino-5-carbamoyl-4-(4-(thiazol-2-ylcarbamoyl)phenyl)-1H-imidazol-2-yl)piperidine-1-carboxylate

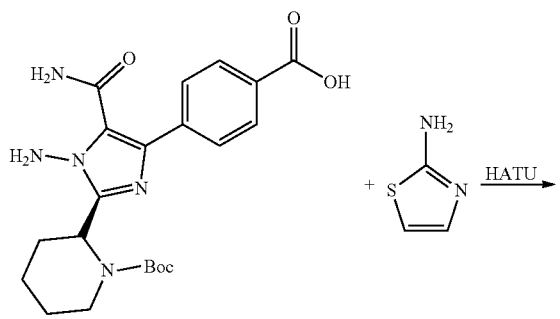

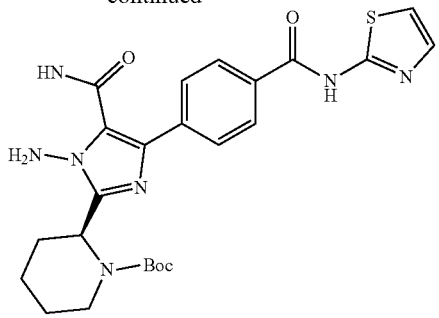

To the solution of 200 mg (0.47 mmol) of the product of Step A in dry N,N-Dimethylformamide (10 mL), HATU (212.7 mg, 0.56 mmol), diisopropylethylamine (402 µL, 2.33 mmol) and thiazol-2-amine (70 mg, 0.70 mmol) were added and stirred at 80° C. for 3 h. After the completion of the reaction (monitored by TLC), the mixture was quenched with brine and washed with ethyl acetate three times (3×200 mL). The combined organic layers were concentrated under reduced pressure and purified by flash chromatography with dichloromethane and methanol (40:1) to afford tert-butyl (S)-2-(1-amino-5-carbamoyl-4-(4-(thiazol-2-ylcarbamoyl)phenyl)-1H-imidazol-2-yl)piperidine-1-carboxylate as white solid (120 mg, 50%). $^1$H NMR (CDCl$_3$, 600 MHz) δ: 11.03 (s, 1H), 8.03 (d, J=8.1 Hz, 2H), 7.88 (d, J=8.2 Hz, 2H), 7.44 (d, J=3.5 Hz, 1H), 7.28 (s, 1H), 7.01 (d, J=3.4 Hz, 1H), 6.40 (s, 1H), 5.97 (s, 2H), 5.57 (d, J=5.2 Hz, 1H), 3.93 (d, J=11.7 Hz, 1H), 3.24 (dt, J$_1$=13.3 Hz, J$_2$=2.7 Hz, 1H), 2.33-2.28 (m, 1H), 2.12 (d, J=13.9 Hz, 1H), 1.90-1.88 (m, 1H), 1.75 (d, J=13.0 Hz, 1H), 1.68-1.65 (m, 1H), 1.54-1.51 (m, 1H), 1.47 (s, 9H). MS (ESI, m/z): 512.2 [M+H]$^+$

Step C: Preparation of (S)-1-amino-2-(piperidin-2-yl)-4-(4-(thiazol-2-ylcarbamoyl)phenyl)-1H-imidazole-5-carboxamide

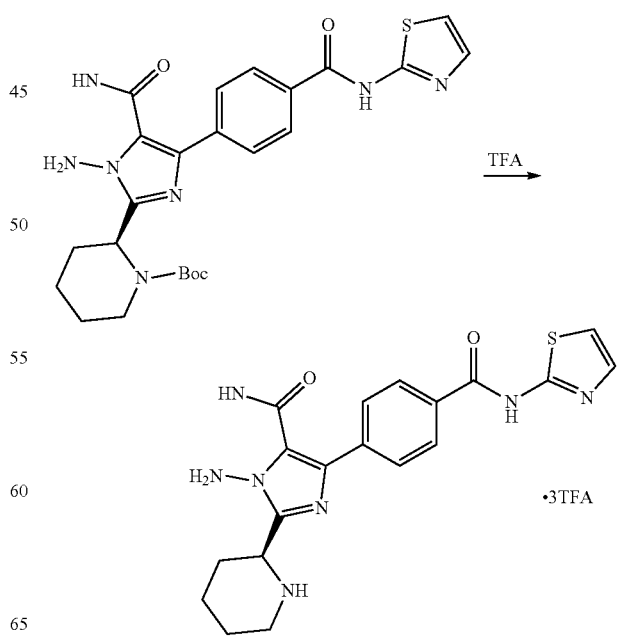

To the solution of 50 mg (0.09 mmol) of the product of Step D in dichloromethane (2 mL) was added trifluoroacetic acid (587 µL). The mixture was stirred at room temperature for 1 h and then concentrated to afford (S)-1-amino-2-(piperidin-2-yl)-4-(4-(thiazol-2-ylcarbamoyl)phenyl)-1H-imidazole-5-carboxamide as a light yellow oil. MS (ESI, m/z): 412.1 [M+H]+.

Step D: Preparation of (S)-2-(1-acryloylpiperidin-2-yl)-1-amino-4-(4-(thiazol-2-ylcarbamoyl)phenyl)-1H-imidazole-5-carboxamide

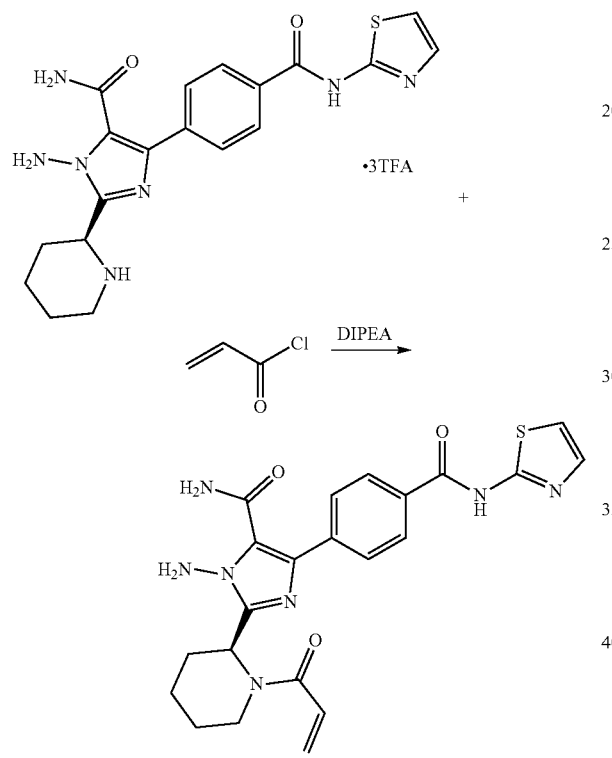

To the solution of 50 mg (0.09 mmol) of the product of Step C in dry dichloromethane (5 mL) was added diisopropylethylamine (587 µL, 0.59 mmol). After 5 min, acryloyl chloride (5.5 µL, 0.07 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×30 mL) with brine solution. The organic phase was dried over anhydrous Na₂SO₄, filtered and concentrated. The residue was purified by chromatography with dichloromethane and methanol (30:1) to give (S)-2-(1-acryloylpiperidin-2-yl)-1-amino-4-(4-(thiazol-2-ylcarbamoyl)phenyl)-1H-imidazole-5-carboxamide as an off-white solid (14 mg, 60%). $^1$H NMR (CDCl₃, 400 MHz) δ: 11.87 (s, 1H), 8.01 (d, J=8.1 Hz, 2H), 7.78 (d, J=7.9 Hz, 2H), 7.62 (s, 1H), 7.42 (d, J=3.3 Hz, 1H), 7.29 (s, 1H), 6.98 (d, J=3.5 Hz, 1H), 6.66-6.48 (m, 1H), 6.37-6.33 (m, 1H), 6.08 (s, 2H), 5.94-5.93 (m, 1H), 5.76 (d, J=10.6 Hz, 1H), 3.85 (d, J=13.0 Hz, 1H), 3.66 (t, J=12.0 Hz, 1H), 2.40-2.36 (m, 1H), 2.22-2.19 (m, 1H), 1.92-1.86 (m, 2H), 1.71-1.60 (m, 2H); $^{13}$C NMR (CDCl₃, 150 MHz) δ: 167.5, 165.2, 163.2, 160.1, 148.4, 141.6, 138.8, 137.4, 131.2, 129.7, 129.0, 128.0, 120.8, 115.4, 113.7, 44.8, 43.1, 27.9, 25.8, 19.7. MS (ESI, m/z): 466.1 [M+H]+.

Example 106: (S)-2-(1-acryloylpiperidin-2-yl)-1-amino-4-(4-((4-fluoropyridin-2-yl)carbamoyl)phenyl)-1H-imidazole-5-carboxamide

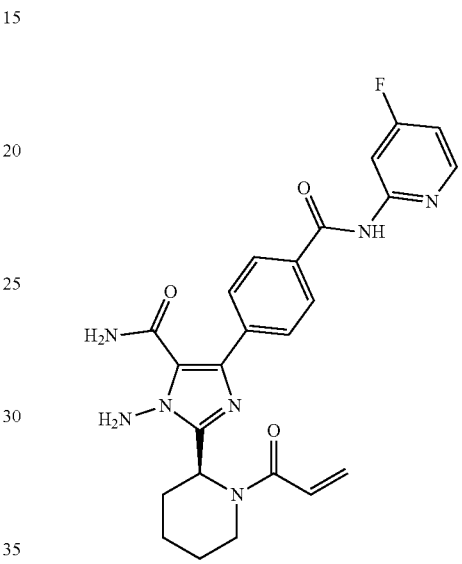

Step A: Preparation of tert-butyl (S)-2-(5-(ethoxycarbonyl)-4-(4-((4-fluoropyridin-2-yl)carbamoyl)phenyl)-1H-imidazol-2-yl)piperidine-1-carboxylate

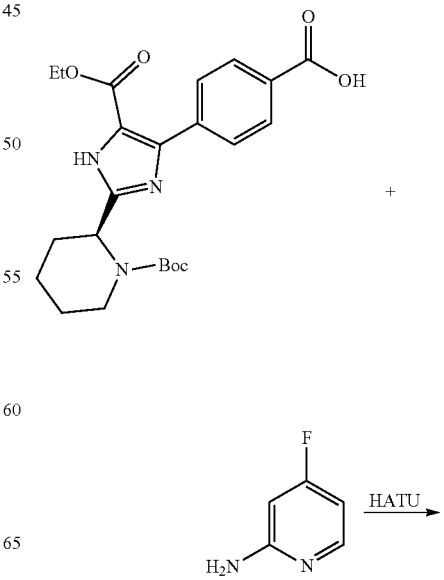

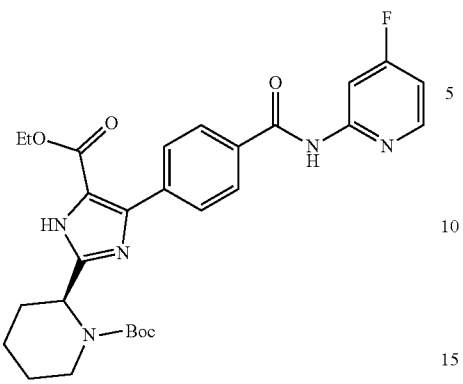

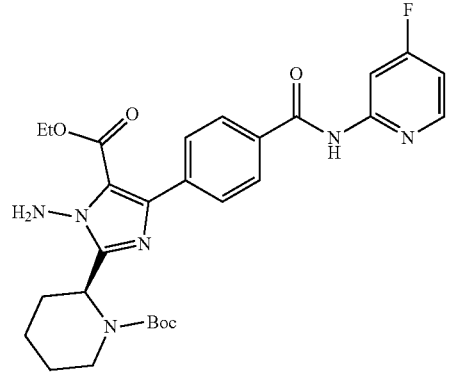

To the solution of 4.0 g (9.1 mmol) of the product of Step C of example 46 in dry N,N-Dimethylformamide (40 mL), HATU (4.15 g, 10.9 mmol), diisopropylethylamine (7.8 mL, 45 mmol) and 4-fluoropyridin-2-amine (2.2 g, 20 mmol) were added and stirred at 80° C. for 3 h. After the completion of the reaction (monitored by TLC), the mixture was quenched with brine and washed with ethyl acetate three times (3×100 mL). The combined organic layers were concentrated under reduced pressure and purified by flash chromatography with petroleum ether and ethyl acetate (2:1) to afford tert-butyl (S)-2-(5-(ethoxycarbonyl)-4-(4-((4-fluoropyridin-2-yl)carbamoyl)phenyl)-1H-imidazol-2-yl)piperidine-1-carboxylate as white solid (3.6 g, 73%). $^1$H NMR (CDCl$_3$, 400 MHz) δ: 10.23 (s, 1H), 9.12 (s, 1H), 8.22-8.13 (m, 4H), 7.95-7.91 (m, 2H), 6.78 (t, J=7.2 Hz, 1H), 5.39 (s, 1H), 4.31-4.24 (m, 2H), 3.99 (d, J=11.6 Hz, 1H), 2.49 (d, J=11.6 Hz, 1H), 1.88-1.63 (m, 6H), 1.48 (s, 9H), 1.28 (t, J=7.2 Hz, 3H). MS (ESI, m/z): 538.2 [M+H]$^+$ Step B: Preparation of tert-butyl (S)-2-(1-amino-5-(ethoxycarbonyl)-4-(4-((4-fluoropyridin-2-yl)carbamoyl)phenyl)-1H-imidazol-2-yl)piperidine-1-carboxylate To the solution of 3.6 g (6.7 mmol) of the product of Step A in anhydrous N,N-Dimethylformamide (40 mL), lithium hexamethyldisilazane (8.0 mL, 1 M solution in tetrahydrofuran) was slowly added at −10° C. After the mixture was stirred for 20 min, O-(diphenylphosphinyl) hydroxylamine (1.9 g, 8.0 mmol) was added at 0° C. and the resulting suspension was stirred at room temperature for 2 h (in cases where the reaction mixture became too viscous, additional N,N-Dimethylformamide was added). The mixture was quenched with brine and washed with ethyl acetate three times (3×100 mL). The combined organic fractions were dried with Na$_2$SO$_4$ and the solvent was removed under reduced pressure to afford the crude residue, which was subjected to column chromatography with petroleum ether and ethyl acetate (3:1) to afford tert-butyl (S)-2-(1-amino-5-(ethoxycarbonyl)-4-(4-((4-fluoropyridin-2-yl)carbamoyl)phenyl)-1H-imidazol-2-yl)piperidine-1-carboxylate as a white solid (1.4 g, 39%). $^1$H NMR (CDCl$_3$, 400 MHz) δ: 8.73 (s, 1H), 8.29-8.2 (m, 2H), 7.93 (d, J=8.0 Hz, 2H), 7.87 (d, J=8.0 Hz, 2H), 6.84 (t, J=6.8 Hz, 1H), 5.92 (s, 2H), 5.68 (d, J=4.8 Hz, 1H), 4.33-4.26 (m, 2H), 3.95 (d, J=13.2 Hz, 1H), 3.42 (td, J$_1$=2.8 Hz, J$_2$=12.8 Hz, 1H), 2.13-2.04 (m, 2H), 1.92-1.88 (m, 1H), 1.77-1.63 (m, 3H), 1.45 (s, 9H), 1.26 (t, J=7.6 Hz, 3H). MS (ESI, m/z): 553.2[M+H]$^+$ Step C: Preparation of (S)-1-amino-2-(1-(tert-butoxycarbonyl)piperidin-2-yl)-4-(4-((4-fluoropyridin-2-yl)carbamoyl)phenyl)-1H-imidazole-5-carboxylic acid

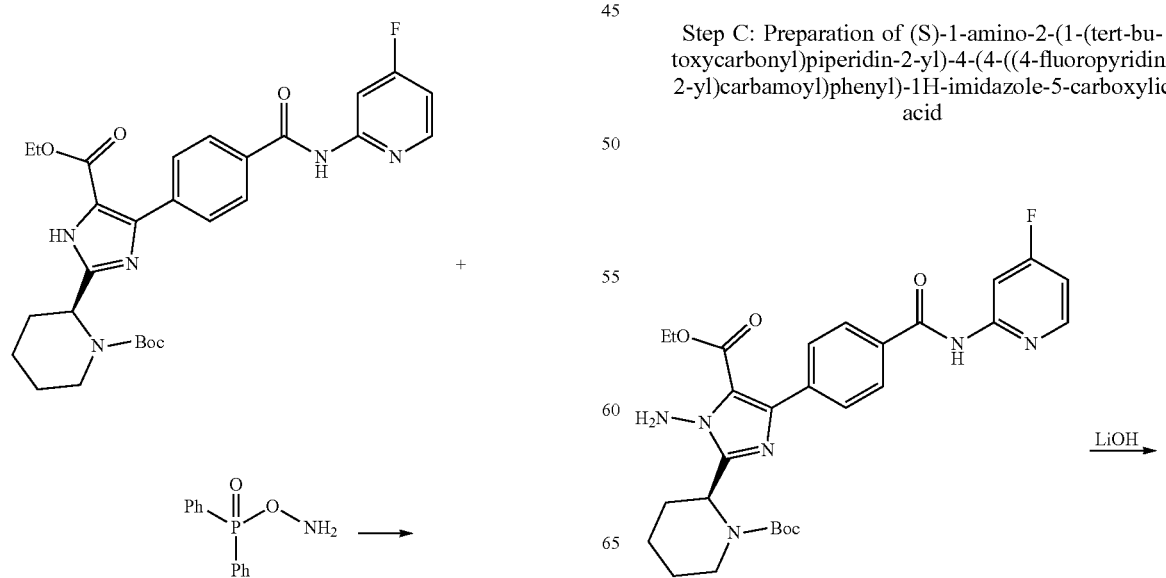

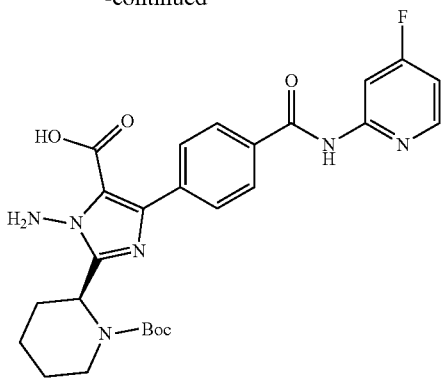

To the solution of 1.44 g (2.61 mmol) of the product of Step B in methanol (10 mL) was added 2 mol/L aqueous lithium hydroxide (6 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl) piperidin-2-yl)-4-(4-((4-fluoropyridin-2-yl)carbamoyl)phenyl)-1H-imidazole-5-carboxylic acid (1.1 g, 80%).

Step D: Preparation of tert-butyl (S)-2-(1-amino-5-carbamoyl-4-(4-((4-fluoropyridin-2-yl)carbamoyl) phenyl)-1H-imidazol-2-yl)piperidine-1-carboxylate

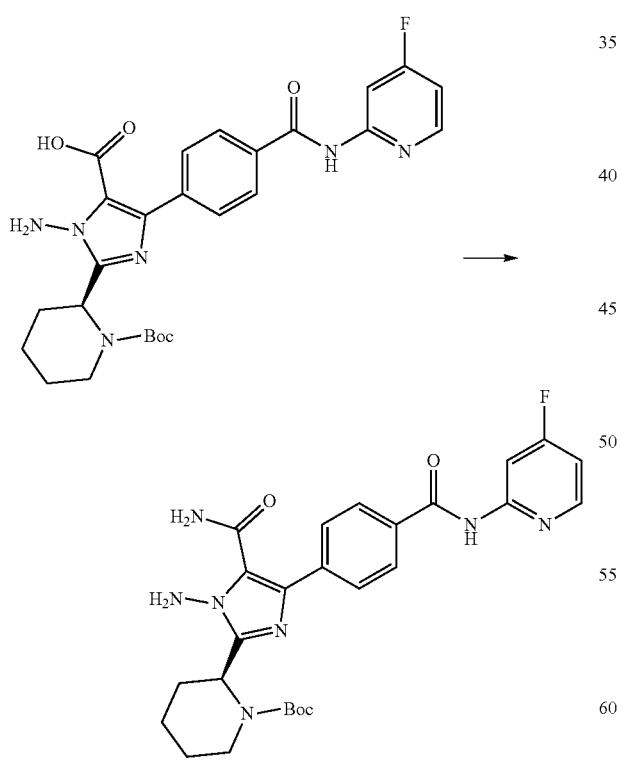

To the solution of 1.1 g (2.1 mmol) of the product of Step C in dry N,N-Dimethylformamide (10 mL) were added HATU (1.2 g, 3.1 mmol), diisopropylethylamine (1.1 mL, 6.3 mmol) and NH$_4$Cl (1.1 g, 21 mmol). The reaction mixture was stirred at room temperature for 2 h. The mixture was quenched with brine and washed with ethyl acetate three times (3×100 mL). The combined organic layers were concentrated under reduced pressure and purified by flash chromatography with dichloromethane and methanol (30:1) to afford tert-butyl (S)-2-(1-amino-5-carbamoyl-4-(4-((4-fluoropyridin-2-yl)carbamoyl)phenyl)-1H-imidazol-2-yl)piperidine-1-carboxylate as a white solid (0.5 g, 50%). $^1$H NMR (CDCl$_3$, 400 MHz) δ: 8.85 (s, 1H), 7.96 (d, J=8.0 Hz, 2H), 7.88 (d, J=8.0 Hz, 2H), 7.67 (d, J=8.0 Hz, 1H), 7.36 (d, J=8.0 Hz, 1H), 6.84 (t, J=5.6 Hz, 1H), 6.07 (s, 2H), 6.01 (s, 1H), 5.64 (d, J=4.8 Hz, 1H), 5.46 (s, 1H), 3.94 (d, J=13.2 Hz, 1H), 3.35-3.25 (m, 1H), 2.15 (d, J=13.2 Hz, 2H), 1.93-1.87 (m, 2H), 1.54-1.51 (m, 2H), 1.46 (s, 9H). MS (ESI, m/z): 524.2 [M+H]$^+$.

Step E: Preparation of (S)-1-amino-4-(4-((4-fluoropyridin-2-yl)carbamoyl)phenyl)-2-(piperidin-2-yl)-1H-imidazole-5-carboxamide

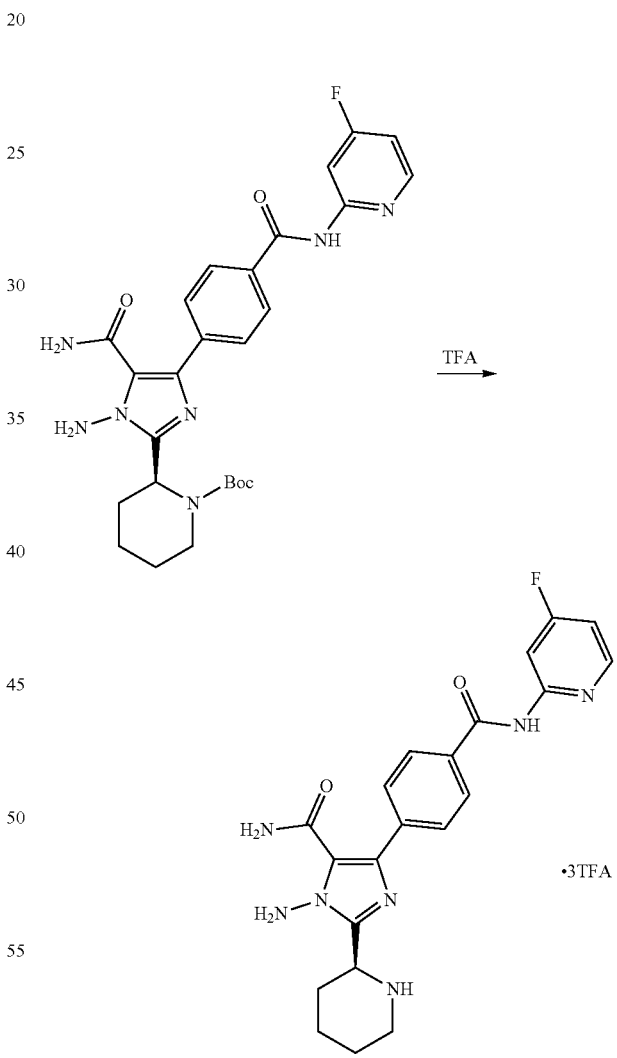

To the solution of 180 mg (0.34 mmol) of the product of Step D in dichloromethane (5 mL) was added trifluoroacetic acid (2.1 mL). The mixture was stirred at room temperature for 1 h and then concentrated to afford (S)-1-amino-4-(4-((4-fluoropyridin-2-yl)carbamoyl)phenyl)-2-(piperidin-2-yl)-1H-imidazole-5-carboxamide as a light yellow oil. MS (ESI, m/z): 424.2 [M+H]$^+$.

Step F: Preparation of (S)-2-(1-acryloylpiperidin-2-yl)-1-amino-4-(4-((4-fluoropyridin-2-yl)carbamoyl)phenyl)-1H-imidazole-5-carboxamide

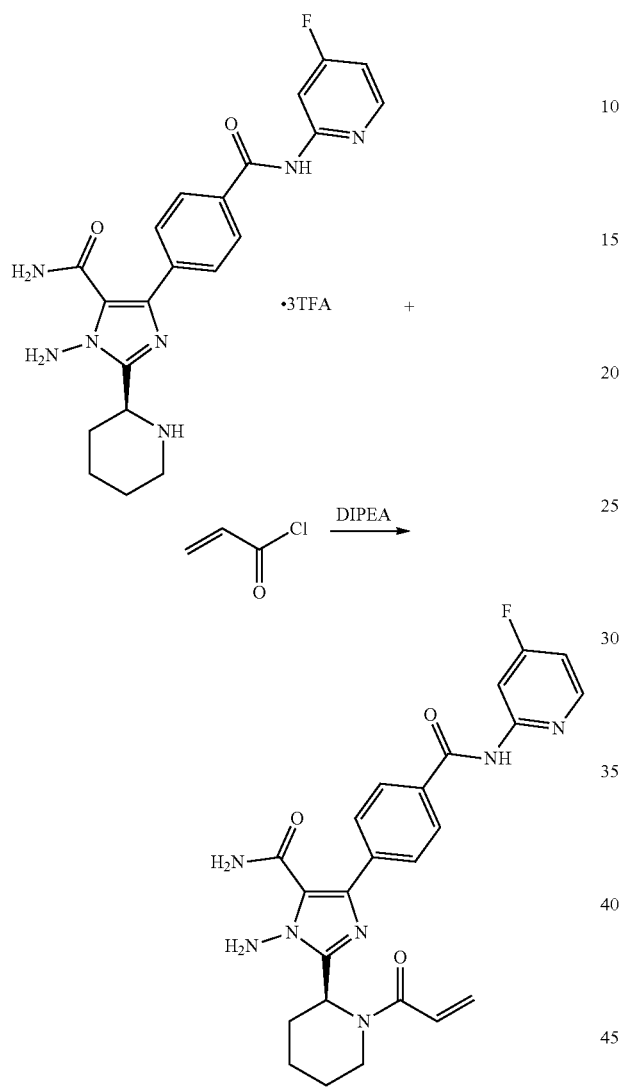

To the solution of 143.8 mg (0.34 mmol) of the product of Step E in dry dichloromethane (5 mL) was added diisopropylethylamine (356 µL, 2.1 mmol). After 5 min, acryloyl chloride (25 µL, 0.31 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous Na$_2$SO$_4$, filtered and concentrated. The residue was purified by chromatography with dichloromethane and methanol (30:1) to give (S)-2-(1-acryloylpiperidin-2-yl)-1-amino-4-(4-((4-fluoropyridin-2-yl)carbamoyl)phenyl)-1H-imidazole-5-carboxamide as an off-white solid (95 mg, 64%). $^1$H NMR (CDCl$_3$, 600 MHz) δ: 9.36 (s, 1H), 8.23-8.21 (m, 1H), 8.19 (dd, J$_1$=2.4 Hz, J$_2$=11.4 Hz, 1H), 7.88 (d, J=7.8 Hz, 2H), 7.79 (d, J=7.2 Hz, 2H), 7.21 (s, 1H), 6.81-6.80 (m, 1H), 6.61-6.56 (m, 1H), 6.40-6.37 (m, 1H), 6.31-6.27 (m, 3H), 6.00-5.94 (m, 1H), 5.71 (d, J=10.2 Hz, 1H), 3.84-3.82 (m, 1H), 3.71-3.66 (m, 1H), 2.42-2.40 (m, 1H), 2.19-2.17 (m, 1H), 1.92-1.85 (m, 2H), 1.72-1.69 (m, 1H), 1.62-1.60 (m, 1H); $^{13}$C NMR (CDCl$_3$, 150 MHz) δ: 170.1 (d, J=258.0 Hz), 167.3, 166.1, 162.7, 154.2 (d, J=2.0 Hz), 149.9 (d, J=9.0 Hz), 148.3, 141.3, 138.6, 133.2, 129.7, 128.8, 127.8, 127.4, 120.2, 108.2 (d, J=18.0 Hz), 102.4 (d, J=22.5 Hz), 44.4, 42.98, 28.0, 25.8, 19.7. MS (ESI, m/z): 478.2 [M+H]$^+$.

Example 107: (S)-2-(1-acryloylpiperidin-2-yl)-1-amino-4-(4-((5-fluoro-4-methylpyridin-2-yl)carbamoyl)phenyl)-1H-imidazole-5-carboxamide

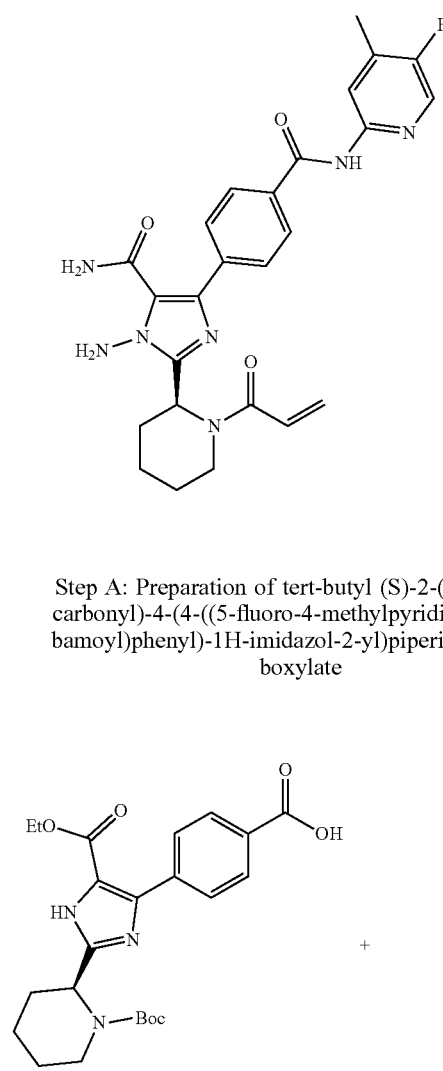

Step A: Preparation of tert-butyl (S)-2-(5-(ethoxycarbonyl)-4-(4-((5-fluoro-4-methylpyridin-2-yl)carbamoyl)phenyl)-1H-imidazol-2-yl)piperidine-1-carboxylate

369
-continued

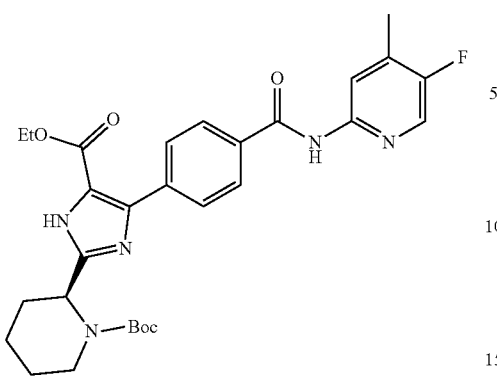

To the solution of 2.0 g (4.5 mmol) of the product of Step C of example 46 in dry N,N-Dimethylformamide (20 mL), HATU (2.0 g, 5.4 mmol), diisopropylethylamine (3.8 mL, 22 mmol) and 5-fluoro-4-methylpyridin-2-amine (1.3 g, 9.9 mmol) were added and stirred at 80° C. for 3 h. After the completion of the reaction (monitored by TLC), the mixture was quenched with brine and washed with ethyl acetate three times (3×100 mL). The combined organic layers were concentrated under reduced pressure and purified by flash chromatography with petroleum ether and ethyl acetate (2:1) to afford (S)-2-(5-(ethoxycarbonyl)-4-(4-((5-fluoro-4-methylpyridin-2-yl)carbamoyl)phenyl)-1H-imidazol-2-yl)piperidine-1-carboxylate as white solid (1.6 g, 63%). $^1$H NMR (CDCl$_3$, 400 MHz) δ: 10.09 (s, 1H), 8.65 (s, 1H), 8.31 (d, J=5.6 Hz, 1H), 8.16 (d, J=8.4 Hz, 2H), 8.04 (s, 1H), 7.93 (d, J=8.4 Hz, 2H), 5.40 (d, J=4.0 Hz, 1H), 4.34-4.31 (m, 2H), 4.01 (d, J=11.6 Hz, 1H), 2.53 (d, J=12.8 Hz, 1H), 2.36 (s, 3H), 2.04 (t, J=14.4 Hz, 2H), 1.93 (t, J=13.2 Hz, 1H), 1.85-1.81 (m, 1H), 1.75 (t, J=8.8 Hz, 1H), 1.66 (d, J=10.8 Hz, 1H), 1.51 (s, 9H), 1.32 (t, J=7.2 Hz, 3H). MS (ESI, m/z): 552.3 [M+H]$^+$.

Step B: Preparation of tert-butyl (S)-2-(1-amino-5-(ethoxycarbonyl)-4-(4-((5-fluoro-4-methylpyridin-2-yl)carbamoyl)phenyl)-1H-imidazol-2-yl)piperidine-1-carboxylate

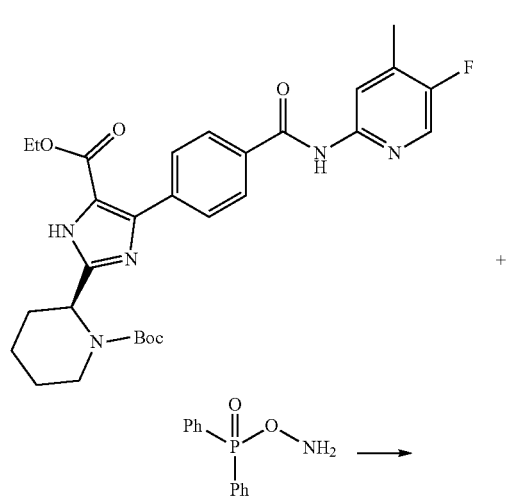

370
-continued

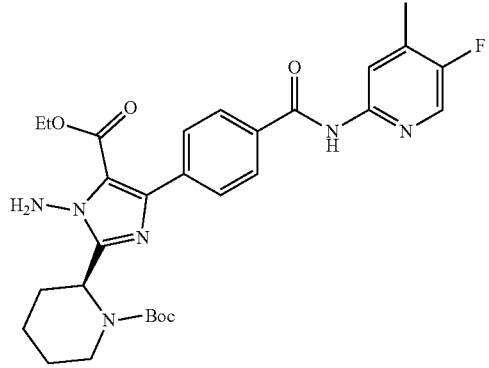

To the solution of 1.6 g (2.9 mmol) of the product of Step A in anhydrous N,N-Dimethylformamide (10 mL), lithium hexamethyldisilazane (3.4 mL, 1 M solution in tetrahydrofuran) was slowly added at −10° C. After the mixture was stirred for 20 min, O-(diphenylphosphinyl) hydroxylamine (0.8 g, 3.4 mmol) was added at 0° C. and the resulting suspension was stirred at room temperature for 2 h (in cases where the reaction mixture became too viscous, additional N,N-Dimethylformamide was added). The mixture was quenched with brine and washed with ethyl acetate three times (3×100 mL). The combined organic fractions were dried with Na$_2$SO$_4$ and the solvent was removed under reduced pressure to afford the crude residue, which was subjected to column chromatography with petroleum ether and ethyl acetate (3:1) to afford (S)-2-(1-amino-5-(ethoxycarbonyl)-4-(4-((5-fluoro-4-methylpyridin-2-yl)carbamoyl) phenyl)-1H-imidazol-2-yl)piperidine-1-carboxylate as a white solid (0.5 g, 30%). $^1$H NMR (CDCl$_3$, 400 MHz) δ: 8.59 (s, 1H), 8.32 (d, J=6.0 Hz, 1H), 8.04 (s, 1H), 7.91 (d, J=8.0 Hz, 2H), 7.85 (d, J=8.4 Hz, 2H), 5.92 (s, 2H), 5.68 (d, J=5.6 Hz, 1H), 4.33-4.25 (m, 2H), 3.95 (d, J=12.8 Hz, 1H), 3.45-3.38 (m, 1H), 2.12-2.02 (m, 2H), 1.93-1.84 (m, 1H), 1.75 (d, J=16.8 Hz, 1H), 1.66-1.50 (m, 2H), 1.44 (s, 9H), 1.25 (t, J=7.2 Hz, 3H). MS (ESI, m/z): 567.3 [M+H]$^+$.

Step C: Preparation of (S)-1-amino-2-(1-(tert-butoxycarbonyl)piperidin-2-yl)-4-(4-((5-fluoro-4-methylpyridin-2-yl)carbamoyl)phenyl)-1H-imidazole-5-carboxylic acid

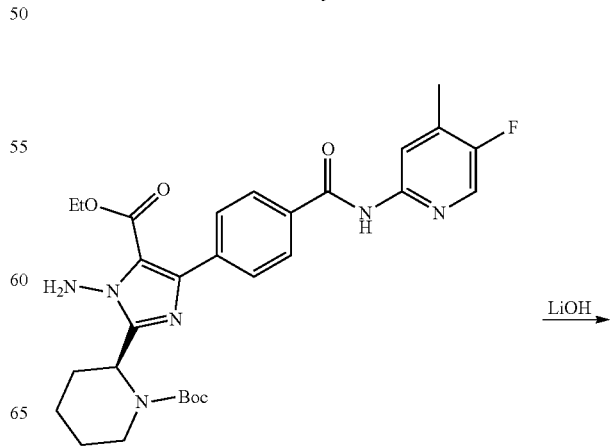

-continued

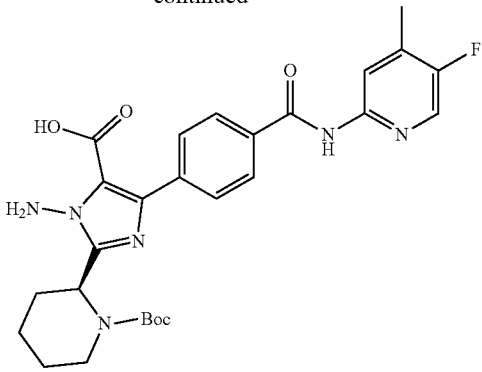

To the solution of 0.49 g (0.87 mmol) of the product of Step B in methanol (10 mL) was added 2 mol/L aqueous lithium hydroxide (4 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl) piperidin-2-yl)-4-(4-((5-fluoro-4-methylpyridin-2-yl)carbamoyl)phenyl)-1H-imidazole-5-carboxylic acid (0.48 g, 99%).

Step D: Preparation of tert-butyl (S)-2-(1-amino-5-carbamoyl-4-(4-((5-fluoro-4-methylpyridin-2-yl) carbamoyl)phenyl)-1H-imidazol-2-yl)piperidine-1-carboxylate

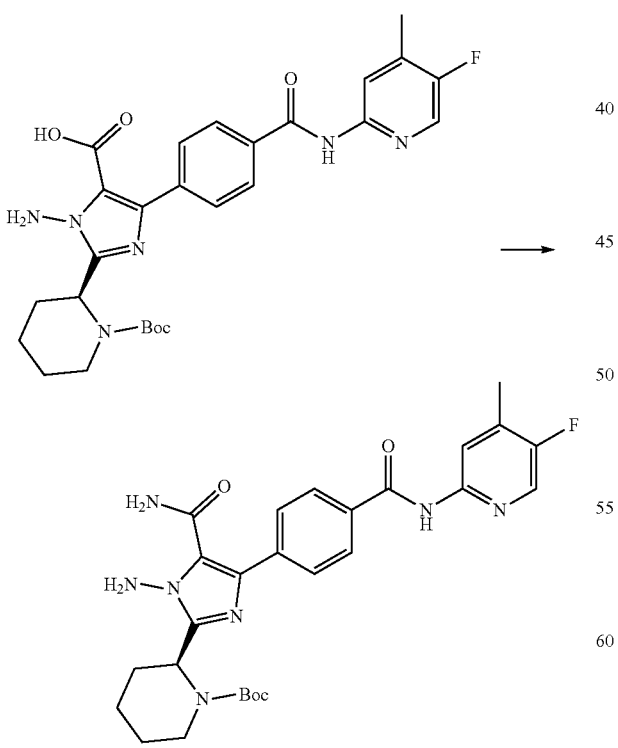

To the solution of 0.48 g (0.9 mmol) of the product of Step C in dry N,N-Dimethylformamide (5 mL) were added HATU (0.5 g, 1.3 mmol), diisopropylethylamine (0.5 mL, 2.6 mmol) and NH₄Cl (0.5 g, 8.9 mmol). The reaction mixture was stirred at room temperature for 2 h. The mixture was quenched with brine and washed with ethyl acetate three times (3×100 mL). The combined organic layers were concentrated under reduced pressure and purified by flash chromatography with dichloromethane and methanol (30:1) to afford tert-butyl (S)-2-(1-amino-5-carbamoyl-4-(4-((5-fluoro-4-methylpyridin-2-yl)carbamoyl)phenyl)-1H-imidazol-2-yl)piperidine-1-carboxylate as a white solid (0.3 g, 71%). MS (ESI, m/z): 538.3 [M+H]⁺.

Step E: Preparation of (S)-1-amino-4-(4-((5-fluoro-4-methylpyridin-2-yl)carbamoyl)phenyl)-2-(piperidin-2-yl)-1H-imidazole-5-carboxamide

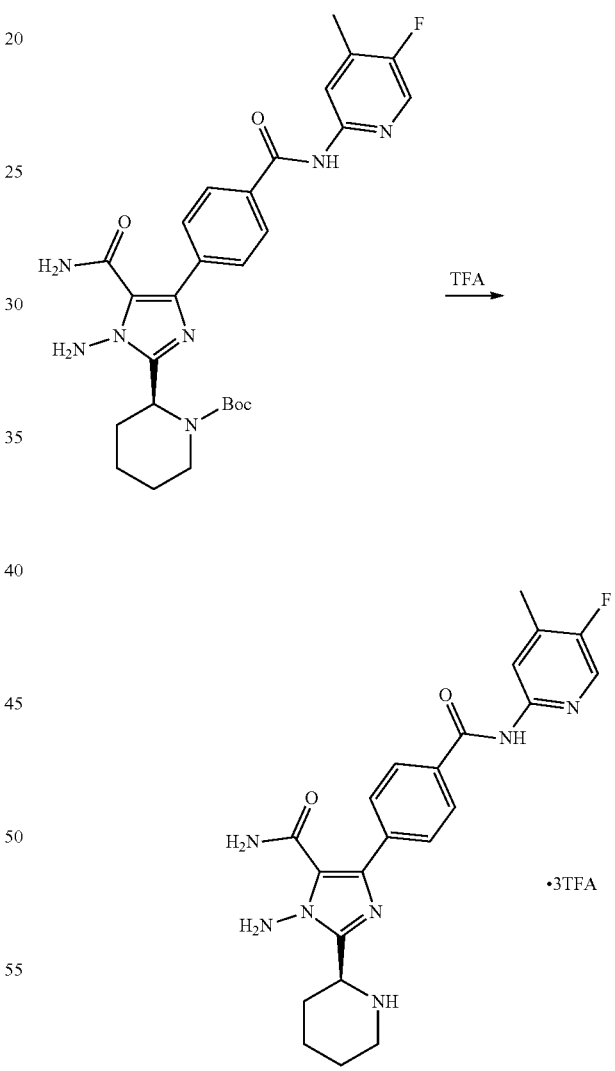

To the solution of 123 mg (0.22 mmol) of the product of Step D in dichloromethane (2 mL) was added trifluoroacetic acid (1.3 mL). The mixture was stirred at room temperature for 1 h and then concentrated to afford (S)-1-amino-4-(4-((5-fluoro-4-methylpyridin-2-yl)carbamoyl)phenyl)-2-(piperidin-2-yl)-1H-imidazole-5-carboxamide as a light yellow oil. MS (ESI, m/z): 438.2 [M+H]⁺.

Step F: Preparation of (S)-2-(1-acryloylpiperidin-2-yl)-1-amino-4-(4-((5-fluoro-4-methylpyridin-2-yl)carbamoyl)phenyl)-1H-imidazole-5-carboxamide

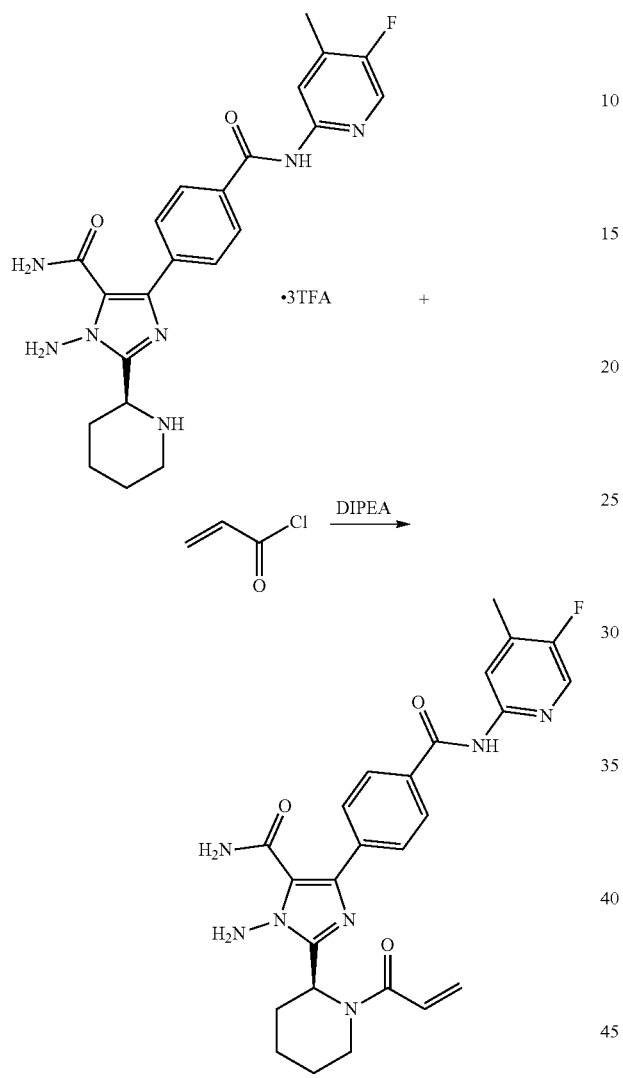

To the solution of 96.1 mg (0.22 mmol) of the product of Step E in dry dichloromethane (5 mL) was added diisopropylethylamine (236.7 μL, 1.37 mmol). After 5 min, acryloyl chloride (16.7 μL, 0.21 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to give (S)-2-(1-acryloylpiperidin-2-yl)-1-amino-4-(4-((5-fluoro-4-methylpyridin-2-yl)carbamoyl)phenyl)-1H-imidazole-5-carboxamide as an off-white solid (86 mg, 80%). $^1$H NMR ($CDCl_3$, 400 MHz) δ: 9.26 (s, 1H), 8.25 (d, J=5.6 Hz, 1H), 7.97 (s, 1H), 7.81 (d, J=7.6 Hz, 2H), 7.70 (d, J=7.6 Hz, 2H), 7.31 (s, 1H), 6.67 (s, 1H), 6.60-6.54 (m, 1H), 6.31-6.25 (m, 3H), 6.02-5.92 (m, 1H), 5.69 (d, J=10.4 Hz, 1H), 3.81 (d, J=12.0 Hz, 1H), 3.71-3.65 (m, 1H), 2.40-2.38 (m, 1H), 2.33 (s, 3H), 2.18 (d, J=13.2 Hz, 1H), 1.94-1.83 (m, 2H), 1.71-1.58 (m, 2H); $^{13}$C NMR ($CDCl_3$, 150 MHz) δ: 167.2, 165.7, 162.8, 155.9 (d, J=247.5 Hz), 148.3, 147.8, 141.3, 138.3, 136.7 (d, J=15.0 Hz), 134.5 (d, J=27.0 Hz), 133.3, 129.5, 128.7, 127.8, 127.2, 120.1, 116.7, 44.4, 43.0, 28.0, 25.8, 19.6, 14.9 (d, J=3.0 Hz). MS (ESI, m/z): 492.2 $[M+H]^+$.

Example 108: (S)-1-amino-2-(1-(but-2-ynoyl)piperidin-2-yl)-4-(4-((5-fluoro-4-methylpyridin-2-yl)carbamoyl)phenyl)-1H-imidazole-5-carboxamide

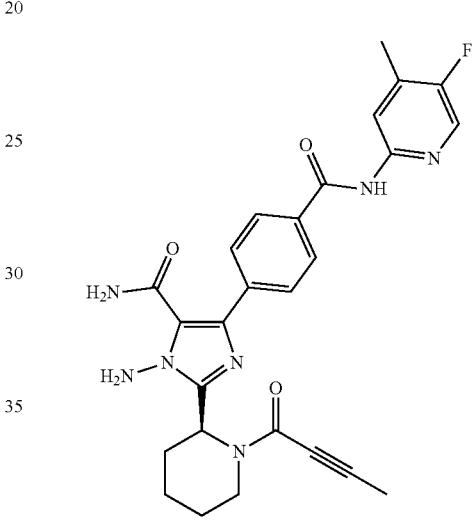

Preparation of (S)-1-amino-2-(1-(but-2-ynoyl)piperidin-2-yl)-4-(4-((5-fluoro-4-methylpyridin-2-yl)carbamoyl)phenyl)-1H-imidazole-5-carboxamide

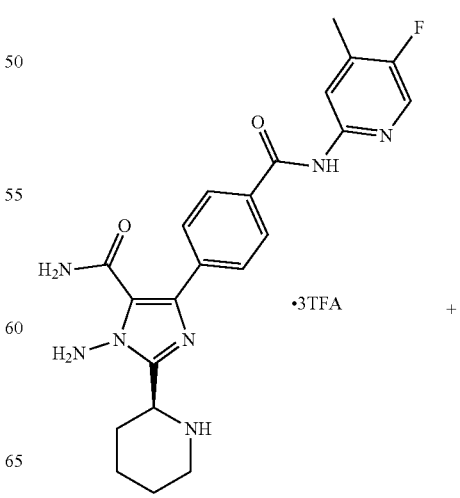

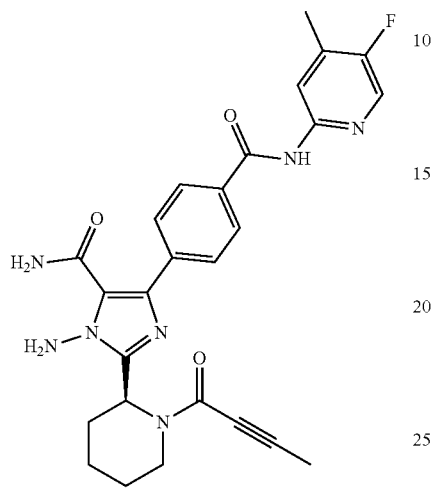

To the solution of 223 mg (0.51 mmol) of the product of Step E of example 107 in dry N,N-Dimethylformamide (7 mL) was added triethylamine (308 mg, 3.06 mmol). After 5 min, but-2-ynoic acid (37.6 mg, 0.45 mmol) and HATU (289 mg, 0.76 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (25:1) to give (S)-1-amino-2-(1-(but-2-ynoyl)piperidin-2-yl)-4-(4-((5-fluoro-4-methylpyridin-2-yl)carbamoyl)phenyl)-1H-imidazole-5-carboxamide as an off-white solid (154 mg, 60%). $^1$H NMR (CDCl$_3$, 400 MHz) δ: 8.85 (s, 1H), 8.29 (d, J=5.6 Hz, 1H), 8.03 (s, 1H), 7.91 (d, J=8.0 Hz, 2H), 7.82 (d, J=8.0 Hz, 2H), 6.90 (s, 1H), 6.14 (s, 2H), 6.01 (s, 1H), 5.94 (d, J=5.2 Hz, 1H), 4.28 (d, J=12.8 Hz, 1H), 3.65 (td, $J_1$=2.8 Hz, $J_2$=13.2 Hz, 1H), 2.36 (s, 3H), 2.17 (d, J=14.8 Hz, 1H), 2.01 (s, 3H), 1.89-1.86 (m, 2H), 1.73-1.70 (m, 2H), 1.63-1.59 (m, 1H); $^{13}$C NMR (CDCl$_3$, 150 MHz) δ: 165.5, 162.6, 156.0 (d, J=247.5 Hz), 155.0, 148.0, 147.7, 141.2, 138.4, 136.7 (d, J=16.5 Hz), 134.6 (d, J=27.0 Hz), 133.6, 129.7, 127.4, 120.0, 116.6, 91.0, 73.0, 44.5, 43.8, 27.8, 25.7, 19.8, 14.9 (d, J=3.0 Hz), 4.3. MS (ESI, m/z): 504.2 [M+H]$^+$.

Example 109: (S)-2-(1-acryloylpiperidin-2-yl)-1-amino-4-(4-((4-(4-chlorophenyl)pyridin-2-yl)carbamoyl)phenyl)-1H-imidazole-5-carboxamide

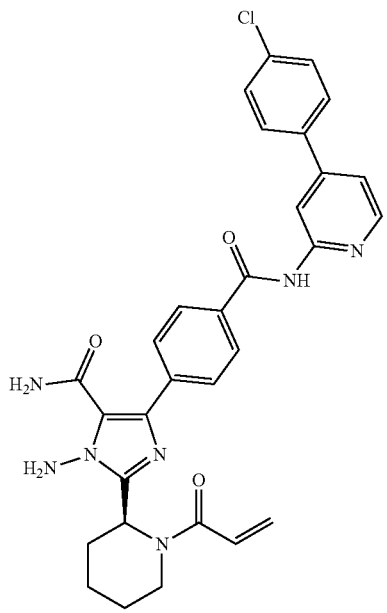 [SMILES: C=CC(=O)N1CCCC[C@H]1c1nc(-c2ccc(C(=O)Nc3cc(-c4ccc(Cl)cc4)ccn3)cc2)c(C(N)=O)n1N]

Step A: Preparation of tert-butyl (S)-2-(4-(4-((4-(4-chlorophenyl)pyridin-2-yl)carbamoyl)phenyl)-5-(ethoxycarbonyl)-1H-imidazol-2-yl)piperidine-1-carboxylate

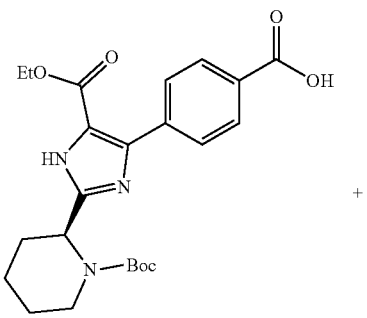

+

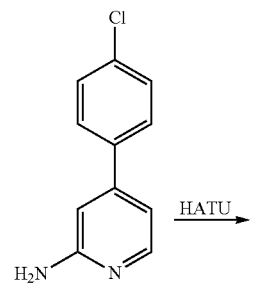

-continued

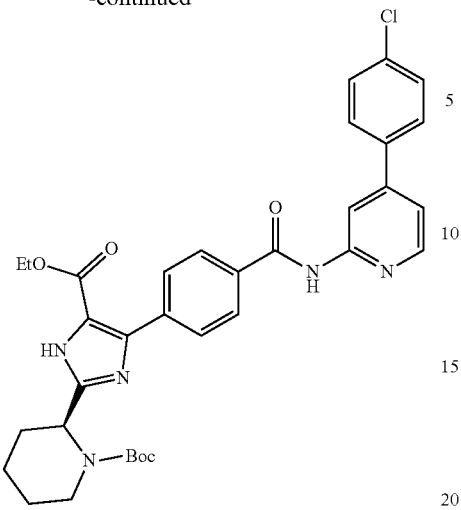

To the solution of 2.0 g (4.5 mmol) of the product of Step C of example 46 in dry N,N-Dimethylformamide (20 mL), HATU (2.0 g, 5.4 mmol), diisopropylethylamine (3.8 mL, 22 mmol) and 4-(4-chlorophenyl)pyridin-2-amine (1.4 g, 6.7 mmol) were added and stirred at 80° C. for 3 h. After the completion of the reaction (monitored by TLC), the mixture was quenched with brine and washed with ethyl acetate three times (3×100 mL). The combined organic layers were concentrated under reduced pressure and purified by flash chromatography with petroleum ether and ethyl acetate (2:1) to afford tert-butyl (S)-2-(4-(4-((4-(4-chlorophenyl)pyridin-2-yl)carbamoyl)phenyl)-5-(ethoxycarbonyl)-1H-imidazol-2-yl)piperidine-1-carboxylate as white solid (1.5 g, 52%). MS (ESI, m/z): 630.2 [M+H]⁺.

Step B: Preparation of tert-butyl (S)-2-(1-amino-4-(4-((4-(4-chlorophenyl)pyridin-2-yl)carbamoyl)phenyl)-5-(ethoxycarbonyl)-1H-imidazol-2-yl)piperidine-1-carboxylate

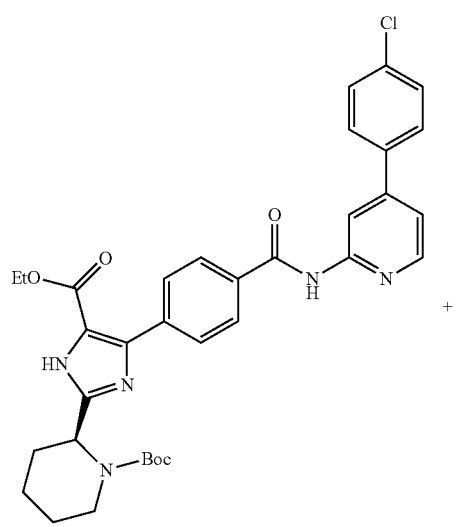

+

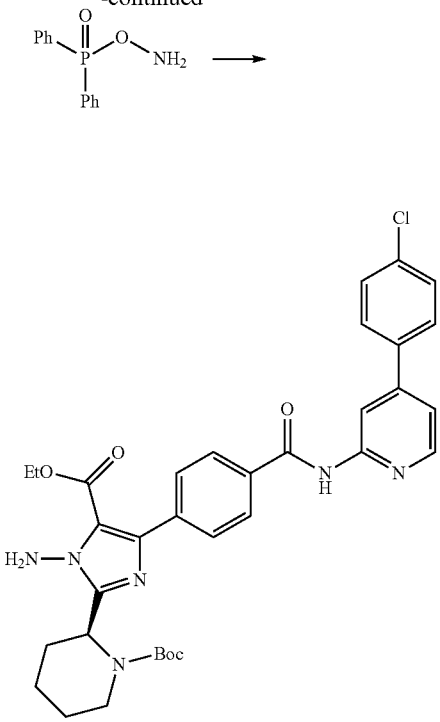

To the solution of 2.7 g (4.4 mmol) of the product of Step A in anhydrous N,N-Dimethylformamide (30 mL), lithium hexamethyldisilazane (5.3 mL, 1 M solution in tetrahydrofuran) was slowly added at −10° C. After the mixture was stirred for 20 min, O-(diphenylphosphinyl) hydroxylamine (1.2 g, 5.2 mmol) was added at 0° C. and the resulting suspension was stirred at room temperature for 2 h (in cases where the reaction mixture became too viscous, additional N,N-Dimethylformamide was added). The mixture was quenched with brine and washed with ethyl acetate three times (3×100 mL). The combined organic fractions were dried with Na₂SO₄ and the solvent was removed under reduced pressure to afford the crude residue, which was subjected to column chromatography with petroleum ether and ethyl acetate (3:1) to afford tert-butyl (S)-2-(1-amino-4-(4-((4-(4-chlorophenyl)pyridin-2-yl)carbamoyl)phenyl)-5-(ethoxycarbonyl)-1H-imidazol-2-yl)piperidine-1-carboxylate as a white solid (1.4 g, 50%). $^1$H NMR (CDCl₃, 400 MHz) δ: 8.79 (s, 1H), 8.69 (s, 1H), 8.34 (d, J=5.2 Hz, 1H), 7.96 (d, J=8.4 Hz, 2H), 7.87 (d, J=8.4 Hz, 2H), 7.66 (d, J=8.4 Hz, 2H), 7.46 (d, J=8.4 Hz, 2H), 7.28 (d, J=1.6 Hz, 1H), 2.93 (s, 2H), 5.68 (d, J=4.8 Hz, 1H), 4.32-4.27 (m, 3H), 3.96 (d, J=12.4 Hz, 1H), 3.46-3.39 (m, 1H), 2.11 (d, J=12.4 Hz, 1H), 1.93-1.88 (m, 1H), 1.83-1.73 (m, 2H), 1.66-1.63 (m, 1H), 1.60-1.55 (m, 1H), 1.44 (s, 9H), 1.26 (t, J=7.2 Hz, 3H). MS (ESI, m/z): 645.3 [M+H]⁺.

Step C: Preparation of (S)-1-amino-2-(1-(tert-butoxycarbonyl)piperidin-2-yl)-4-(4-((4-(4-chlorophenyl)pyridin-2-yl)carbamoyl)phenyl)-1H-imidazole-5-carboxylic acid

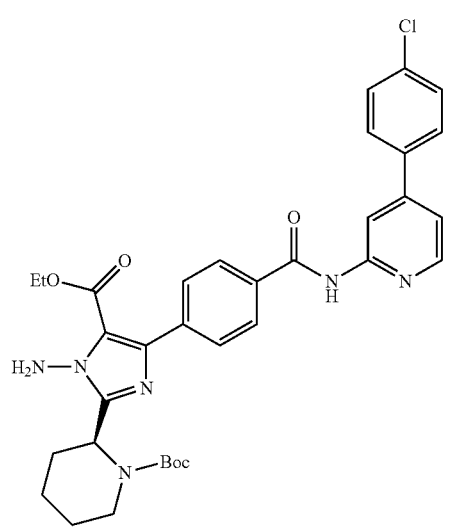

Step D: Preparation of tert-butyl (S)-2-(1-amino-5-carbamoyl-4-(4-((4-(4-chlorophenyl)pyridin-2-yl)carbamoyl)phenyl)-1H-imidazol-2-yl)piperidine-1-carboxylate

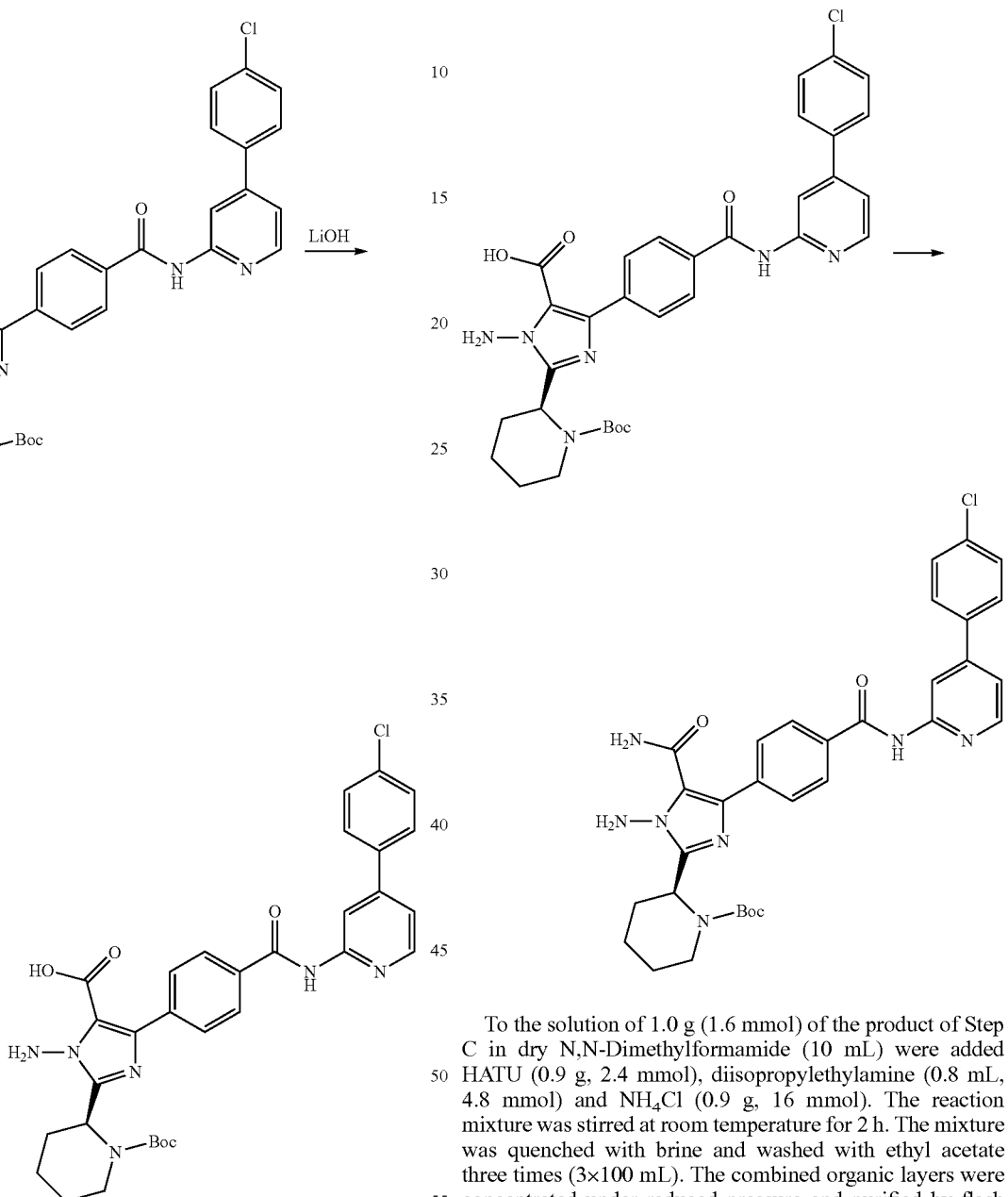

To the solution of 0.2 g (0.3 mmol) of the product of Step B in methanol (3 mL) was added 2 mol/L aqueous lithium hydroxide (6 mL) and stirred at room temperature for 2 h. The reaction mixture was evaporated and diluted with water (10 mL) and acidified with aqueous HCl till pH 3. The mixture was washed with ethyl acetate three times (3×10 mL). The white precipitate was isolated by filtration and dried to afford (S)-1-amino-2-(1-(tert-butoxycarbonyl)piperidin-2-yl)-4-(4-((4-(4-chlorophenyl)pyridin-2-yl)carbamoyl)phenyl)-1H-imidazole-5-carboxylic acid (0.18 g, 99%).

To the solution of 1.0 g (1.6 mmol) of the product of Step C in dry N,N-Dimethylformamide (10 mL) were added HATU (0.9 g, 2.4 mmol), diisopropylethylamine (0.8 mL, 4.8 mmol) and $NH_4Cl$ (0.9 g, 16 mmol). The reaction mixture was stirred at room temperature for 2 h. The mixture was quenched with brine and washed with ethyl acetate three times (3×100 mL). The combined organic layers were concentrated under reduced pressure and purified by flash chromatography with dichloromethane and methanol (50:1) to afford tert-butyl (S)-2-(1-amino-5-carbamoyl-4-(4-((4-(4-chlorophenyl)pyridin-2-yl)carbamoyl)phenyl)-1H-imidazol-2-yl)piperidine-1-carboxylate as a white solid (0.7 g, 71%). $^1$H NMR ($CDCl_3$, 400 MHz) δ: 8.94 (s, 1H), 8.66 (s, 1H), 8.34 (d, J=5.2 Hz, 1H), 7.96 (d, J=8.4 Hz, 2H), 7.86 (d, J=8.4 Hz, 2H), 7.66 (d, J=8.4 Hz, 2H), 7.45 (d, J=8.4 Hz, 2H), 7.27 (t, J=1.2 Hz, 1H), 6.83 (s, 1H), 6.02 (s, 2H), 5.91 (s, 1H), 5.60 (d, J=4.8 Hz, 1H), 3.93 (d, J=12.8 Hz, 1H), 3.28 (td, $J_1$=2.4 Hz, $J_2$=12.8 Hz, 1H), 2.28-2.13 (m, 2H), 1.94-1.88 (m, 1H), 1.68-1.64 (m, 1H), 1.55-1.50 (m, 2H), 1.46 (s, 9H). MS (ESI, m/z): 616.2 $[M+H]^+$.

381

Step E: Preparation of (S)-1-amino-4-(4-((4-(4-chlorophenyl)pyridin-2-yl)carbamoyl)phenyl)-2-(piperidin-2-yl)-1H-imidazole-5-carboxamide

382

Step F: Preparation of (S)-2-(1-acryloylpiperidin-2-yl)-1-amino-4-(4-((4-(4-chlorophenyl)pyridin-2-yl)carbamoyl)phenyl)-1H-imidazole-5-carboxamide

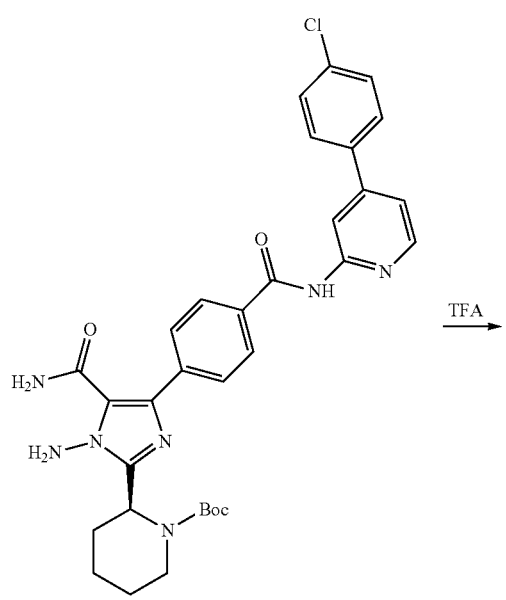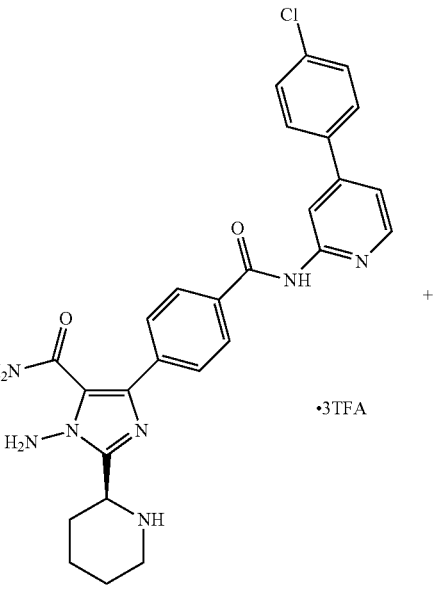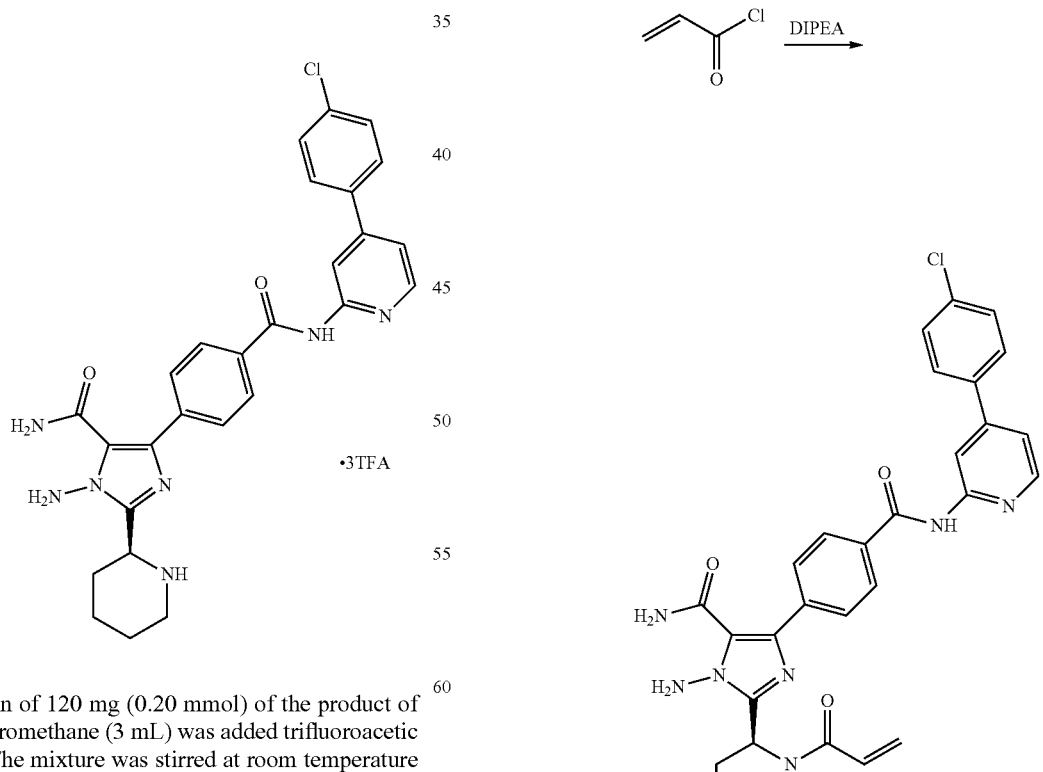

To the solution of 120 mg (0.20 mmol) of the product of Step D in dichloromethane (3 mL) was added trifluoroacetic acid (1.3 mL). The mixture was stirred at room temperature for 1 h and then concentrated to afford (S)-1-amino-4-(4-((4-(4-chlorophenyl)pyridin-2-yl)carbamoyl)phenyl)-2-(piperidin-2-yl)-1H-imidazole-5-carboxamide as a light yellow oil. MS (ESI, m/z): 516.2 [M+H]$^+$.

To the solution of 103 mg (0.2 mmol) of the product of Step E in dry dichloromethane (5 mL) was added diisopropylethylamine (202 μL, 1.17 mmol). After 5 min, acryloyl chloride (11 μL, 0.14 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to give (S)-2-(1-acryloylpiperidin-2-yl)-1-amino-4-(4-((4-(4-chlorophenyl)pyridin-2-yl)carbamoyl)phenyl)-1H-imidazole-5-carboxamide as an off-white solid (73 mg, 64%). $^1$H NMR (CDCl$_3$, 400 MHz) δ: 9.14 (s, 1H), 8.67 (s, 1H), 8.33 (d, J=5.2 Hz, 1H), 7.97 (d, J=8.0 Hz, 2H), 7.87 (d, J=7.2 Hz, 2H), 7.65 (d, J=8.8 Hz, 2H), 7.45 (d, J=8.4 Hz, 2H), 7.27 (s, 1H), 7.14 (s, 1H), 6.63-6.56 (m, 1H), 6.34-6.27 (m, 3H), 6.08-6.04 (m, 1H), 5.98-5.97 (m, 1H), 5.73 (d, J=10.4 Hz, 1H), 3.85-3.82 (m, 1H), 3.72-3.65 (m, 1H), 2.46-2.43 (m, 1H), 2.22-2.18 (m, 1H), 1.97-1.86 (m, 2H), 1.73-1.70 (m, 1H), 1.63-1.60 (m, 1H); $^{13}$C NMR (CDCl$_3$, 150 MHz) δ: 167.3, 165.8, 162.5, 152.5, 150.1, 148.2, 148.1, 138.6, 136.6, 135.7, 133.5, 129.8, 129.4, 128.8, 128.7, 127.8, 127.4, 119.9, 118.0, 112.1, 110.9, 44.4, 43.0, 28.0, 25.8, 19.7. MS (ESI, m/z): 570.2 [M+H]$^+$.

Example 110: (S)-1-amino-2-(1-(but-2-ynoyl)piperidin-2-yl)-4-(4-((4-(4-chlorophenyl)pyridin-2-yl)carbamoyl)phenyl)-1H-imidazole-5-carboxamide Preparation of (S)-1-amino-2-(1-(but-2-ynoyl)piperidin-2-yl)-4-(4-((4-(4-chlorophenyl)pyridin-2-yl)carbamoyl)phenyl)-1H-imidazole-5-carboxamide

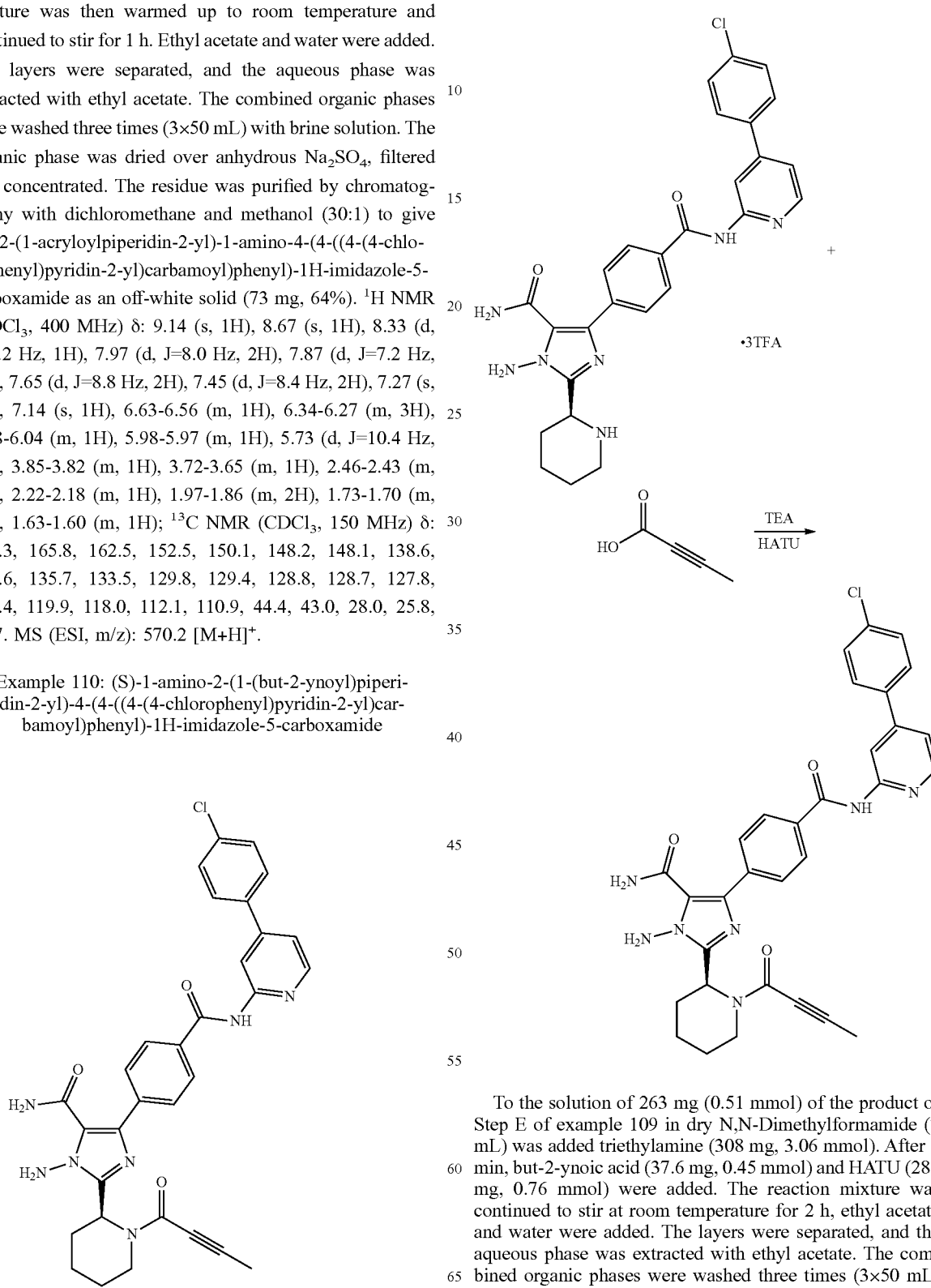

To the solution of 263 mg (0.51 mmol) of the product of Step E of example 109 in dry N,N-Dimethylformamide (7 mL) was added triethylamine (308 mg, 3.06 mmol). After 5 min, but-2-ynoic acid (37.6 mg, 0.45 mmol) and HATU (289 mg, 0.76 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (26:1) to give (S)-1-amino-2-(1-(but-2-ynoyl)piperidin-2-yl)-4-(4-((4-(4-chlorophenyl)pyridin-2-yl)carbamoyl)phenyl)-1H-imidazole-5-carboxamide as an off-white solid (178 mg, 60%). $^1$H NMR (CDCl$_3$, 600 MHz) δ: 9.00 (s, 1H), 8.67 (s, 1H), 8.34 (d, J=1.8 Hz, 1H), 7.97 (d, J=7.8 Hz, 2H), 7.86 (d, J=7.8 Hz, 2H), 7.66 (d, J=7.2 Hz, 2H), 7.45 (d, J=7.8 Hz, 2H), 7.28 (d, J=4.8 Hz, 1H), 6.88 (s, 1H), 6.15 (s, 2H), 5.95 (d, J=5.4 Hz, 1H), 5.91 (s, 1H), 4.28 (d, J=12.6 Hz, 1H), 3.66 (t, J=13.2 Hz, 1H), 2.43-2.36 (m, 1H), 2.18 (d, J=13.8 Hz, 1H), 2.02 (s, 3H), 1.89-1.87 (m, 2H), 1.73-1.71 (m, 1H), 1.64-1.60 (m, 1H); $^{13}$C NMR (DMSO-d6, 150 MHz) δ: 165.8, 162.4, 153.1, 148.7, 147.8, 147.4, 137.8, 136.4, 135.0, 134.2, 132.0, 129.3, 128.7, 128.0, 127.9, 126.7, 125.6, 117.4, 111.9, 91.9, 73.2, 43.8, 40.1, 27.9, 25.4, 19.3, 3.4. MS (ESI, m/z): 582.1 [M+H]$^+$.

Example 111: (S)-2-(1-acryloylpiperidin-2-yl)-1-amino-4-(4-((4-(4-cyanophenyl)pyridin-2-yl)carbamoyl)phenyl)-1H-imidazole-5-carboxamide

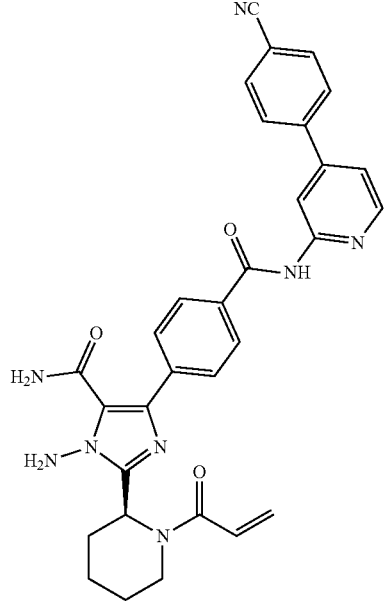

Step A: Preparation of tert-butyl (S)-2-(4-(4-((4-(4-cyanophenyl)pyridin-2-yl)carbamoyl)phenyl)-5-(ethoxycarbonyl)-1H-imidazol-2-yl)piperidine-1-carboxylate

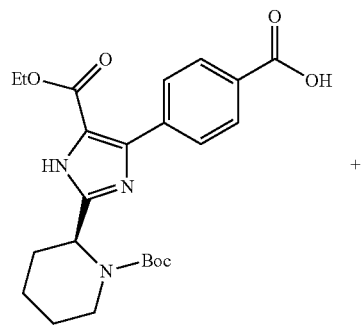

+

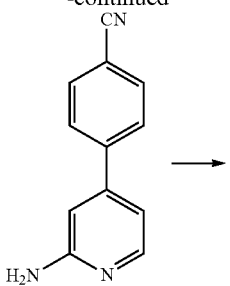

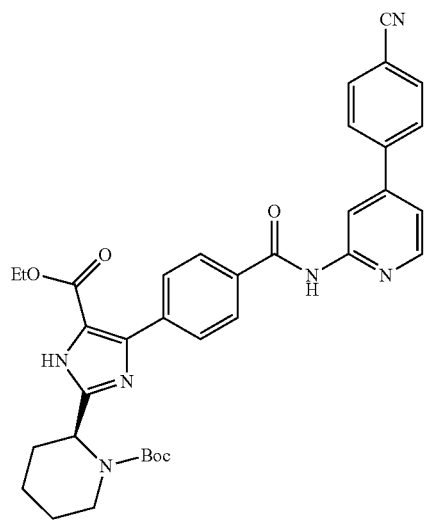

To the solution of 2.0 g (4.5 mmol) of the product of Step C of example 46 in dry N,N-Dimethylformamide (20 mL), HATU (2.0 g, 5.4 mmol), diisopropylethylamine (3.8 mL, 22 mmol) and 4-(2-aminopyridin-4-yl)benzonitrile (1.3 g, 6.7 mmol) were added and stirred at 80° C. for 3 h. After the completion of the reaction (monitored by TLC), the mixture was quenched with brine and washed with ethyl acetate three times (3×100 mL). The combined organic layers were concentrated under reduced pressure and purified by flash chromatography with petroleum ether and ethyl acetate (2:1) to afford tert-butyl (S)-2-(4-(4-((4-(4-cyanophenyl)pyridin-2-yl)carbamoyl)phenyl)-5-(ethoxycarbonyl)-1H-imidazol-2-yl)piperidine-1-carboxylate as white solid (1.5 g, 52%). $^1$H NMR (CDCl$_3$, 400 MHz) δ: 10.01 (s, 1H), 8.81 (s, 1H), 8.73 (s, 1H), 8.40 (d, J=5.2 Hz, 1H), 8.20 (d, J=8.4 Hz, 2H), 7.98 (d, J=8.4 Hz, 2H), 7.82 (d, J=8.4 Hz, 2H), 7.78 (d, J=8.0 Hz, 2H), 7.30-7.28 (m, 1H), 5.41 (d, J=4.0 Hz, 1H), 4.36-4.31 (m, 2H), 4.02 (d, J=10.0 Hz, 1H), 2.79-2.73 (m, 1H), 2.55 (d, J=12.4 Hz, 1H), 1.93-1.74, (m, 4H), 1.76 (d, J=11.6 Hz, 1H), 1.53 (s, 9H), 1.50 (s, 1H), 1.34 (t, J=7.2 Hz, 3H). MS (ESI, m/z): 621.3 [M+H]$^+$.

Step B: Preparation of tert-butyl (S)-2-(1-amino-4-(4-((4-(4-cyanophenyl)pyridin-2-yl)carbamoyl)phenyl)-5-(ethoxycarbonyl)-1H-imidazol-2-yl)piperidine-1-carboxylate

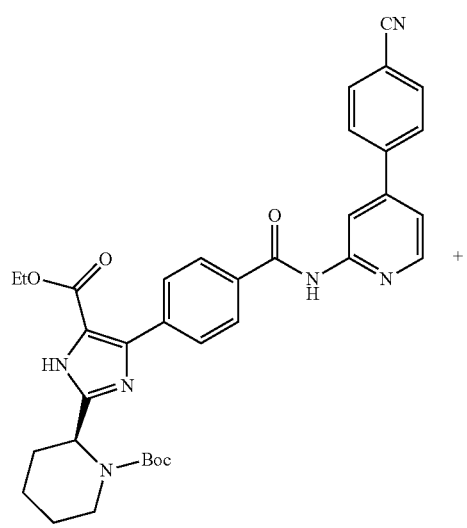

5-(ethoxycarbonyl)-1H-imidazol-2-yl)piperidine-1-carboxylate as a white solid (1.3 g, 48%). $^1$H NMR (CDCl$_3$, 600 MHz) δ: 8.80 (s, 1H), 8.72 (s, 1H), 8.40 (d, J=5.4 Hz, 1H), 7.96-7.95 (m, 2H), 7.89-7.87 (m, 2H), 7.83-7.81 (m, 2H), 7.79-7.78 (m, 2H), 7.30-7.28 (m, 1H), 5.94 (s, 2H), 5.68 (d, J=4.8 Hz, 1H), 4.33-4.27 (m, 2H), 3.95 (d, J=12.6 Hz, 1H), 3.42 (td, J$_1$=3.0 Hz, J$_2$=13.2 Hz, 1H), 2.12-2.01 (m, 2H), 1.91-1.88 (m, 1H), 1.75 (d, J=12.0 Hz, 1H), 1.66-1.64 (m, 1H), 1.55-1.51 (m, 1H), 1.44 (s, 9H), 1.26 (t, J=7.2 Hz, 3H). MS (ESI, m/z): 636.3 [M+H]$^+$.

Step C: Preparation of (S)-1-amino-2-(1-(tert-butoxycarbonyl)piperidin-2-yl)-4-(4-((4-(4-cyanophenyl)pyridin-2-yl)carbamoyl)phenyl)-1H-imidazole-5-carboxylic acid

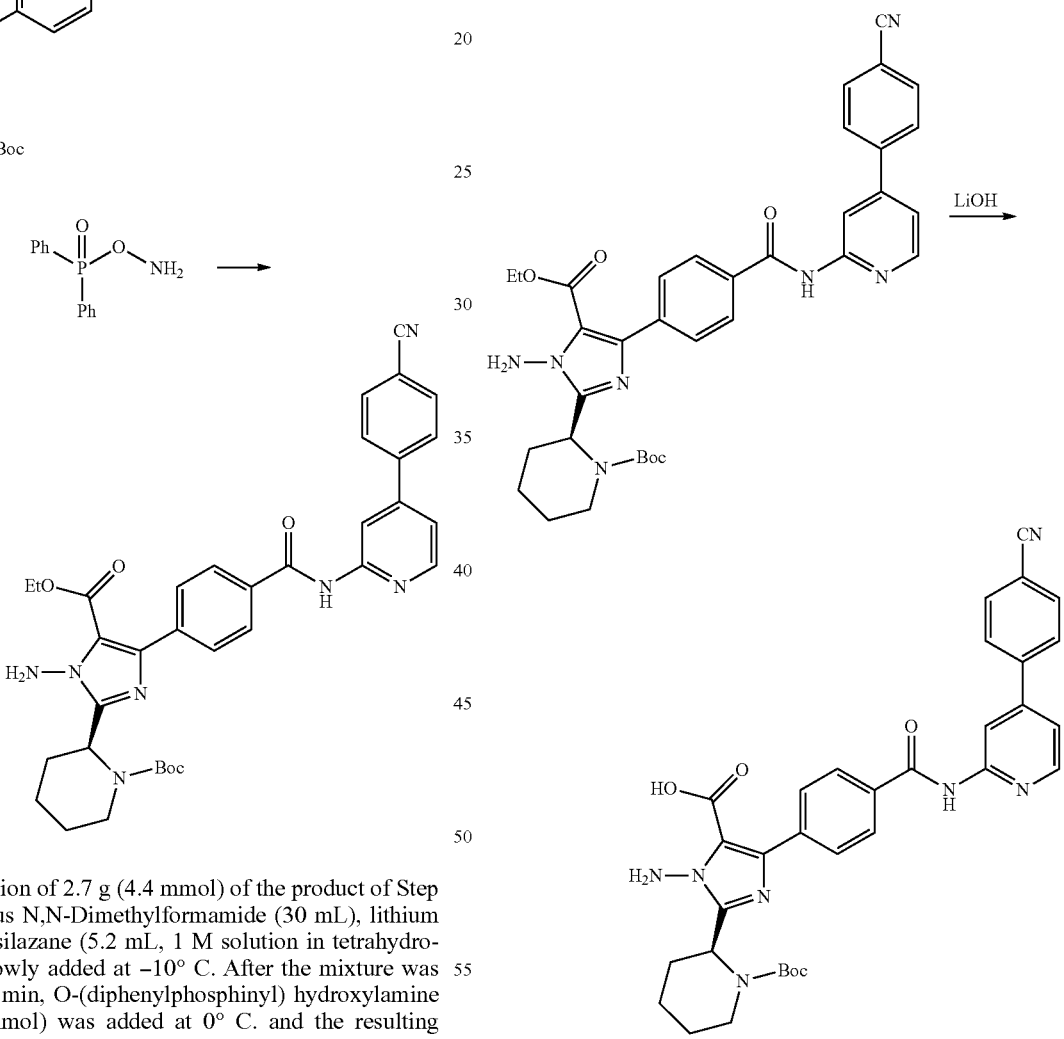

To the solution of 2.7 g (4.4 mmol) of the product of Step A in anhydrous N,N-Dimethylformamide (30 mL), lithium hexamethyldisilazane (5.2 mL, 1 M solution in tetrahydrofuran) was slowly added at −10° C. After the mixture was stirred for 20 min, O-(diphenylphosphinyl) hydroxylamine (1.2 g, 5.2 mmol) was added at 0° C. and the resulting suspension was stirred at room temperature for 2 h (in cases where the reaction mixture became too viscous, additional N,N-Dimethylformamide was added). The mixture was quenched with brine and washed with ethyl acetate three times (3×100 mL). The combined organic fractions were dried with Na$_2$SO$_4$ and the solvent was removed under reduced pressure to afford the crude residue, which was subjected to column chromatography with petroleum ether and ethyl acetate (3:1) to afford tert-butyl (S)-2-(1-amino-4-(4-((4-(4-cyanophenyl)pyridin-2-yl)carbamoyl)phenyl)-

To the solution of 1.47 g (2.3 mmol) of the product of Step B in methanol (15 mL) was added 2 mol/L aqueous lithium hydroxide (12 mL) and stirred at room temperature for 2 h. The reaction mixture was evaporated and diluted with water (100 mL) and acidified with aqueous HCl till pH 3. The mixture was washed with ethyl acetate three times (3×100 mL). The white precipitate was isolated by filtration and dried to afford (S)-1-amino-2-(1-(tert-butoxycarbonyl)piperidin-2-yl)-4-(4-((4-(4-cyanophenyl)pyridin-2-yl)carbamoyl)phenyl)-1H-imidazole-5-carboxylic acid (1.3 g, 90%).

Step D: Preparation of tert-butyl (S)-2-(1-amino-5-carbamoyl-4-(4-((4-(4-cyanophenyl)pyridin-2-yl)carbamoyl)phenyl)-1H-imidazol-2-yl)piperidine-1-carboxylate

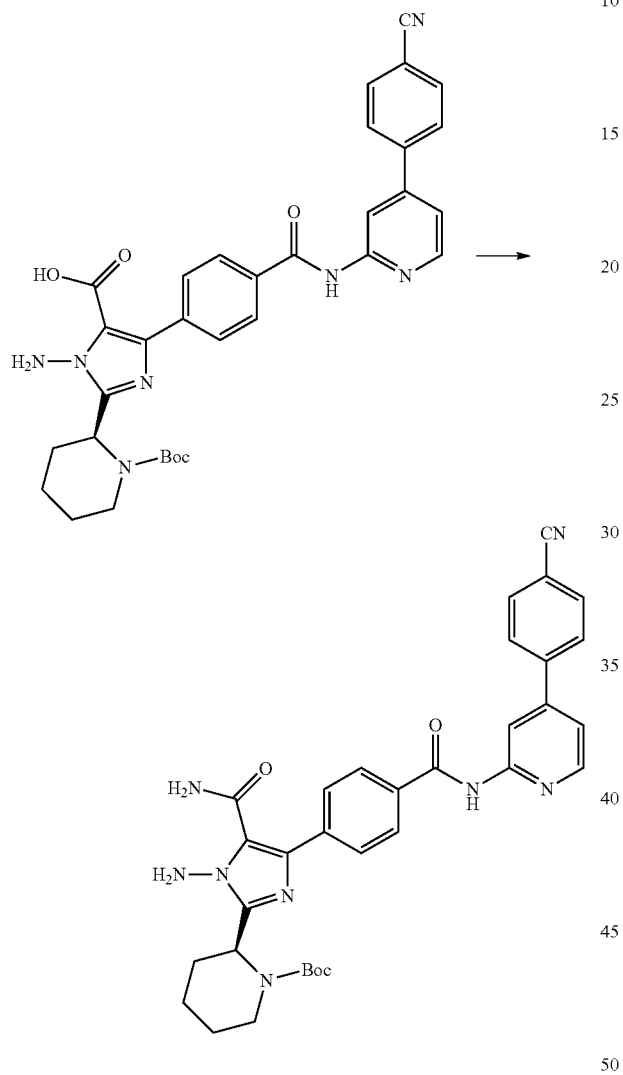

To the solution of 0.3 g (0.4 mmol) of the product of Step C in dry N,N-Dimethylformamide (5 mL) were added HATU (0.2 g, 0.6 mmol), diisopropylethylamine (0.2 mL, 1.3 mmol) and NH₄Cl (0.2 g, 4.1 mmol). The reaction mixture was stirred at room temperature for 2 h. The mixture was quenched with brine and washed with ethyl acetate three times (3×30 mL). The combined organic layers were concentrated under reduced pressure and purified by flash chromatography with dichloromethane and methanol (30:1) to afford tert-butyl (S)-2-(1-amino-5-carbamoyl-4-(4-((4-(4-cyanophenyl)pyridin-2-yl)carbamoyl)phenyl)-1H-imidazol-2-yl)piperidine-1-carboxylate as a white solid (0.13 g, 53%). ¹H NMR (CDCl₃, 400 MHz) δ: 8.95 (s, 1H), 8.69 (s, 1H), 8.40 (d, J=5.2 Hz, 1H), 7.96 (d, J=8.4 Hz, 2H), 7.88 (d, J=8.4 Hz, 2H), 7.83-7.76 (m, 4H), 7.30-7.28 (m, 1H), 6.13-6.02 (m, 3H), 5.88 (s, 1H), 5.59 (d, J=4.8 Hz, 1H), 3.93 (d, J=12.4 Hz, 1H), 3.26 (td, J₁=2.8 Hz, J₂=13.2 Hz, 1H), 2.26 (d, J=12.0 Hz, 1H), 2.14 (d, J=12.8 Hz, 1H), 1.93-1.88 (m, 1H), 1.69-1.65 (m, 1H), 1.55-1.47 (m, 2H), 1.46 (s, 9H). MS (ESI, m/z): 607.3[M+H]⁺.

Step E: Preparation of (S)-1-amino-4-(4-((4-(4-cyanophenyl)pyridin-2-yl)carbamoyl)phenyl)-2-(piperidin-2-yl)-1H-imidazole-5-carboxamide

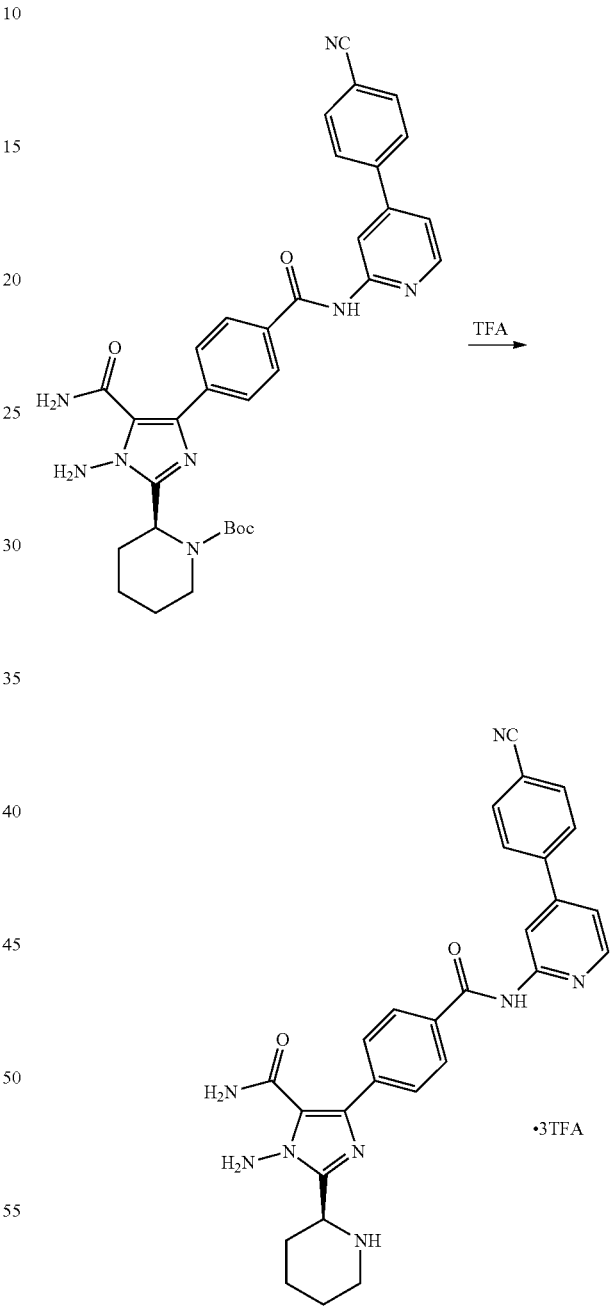

To the solution of 134 mg (0.22 mmol) of the product of Step D in dichloromethane (3 mL) was added trifluoroacetic acid (1.3 mL). The mixture was stirred at room temperature for 1 h and then concentrated to afford (S)-1-amino-4-(4-((4-(4-cyanophenyl)pyridin-2-yl)carbamoyl)phenyl)-2-(piperidin-2-yl)-1H-imidazole-5-carboxamide as a light yellow oil. MS (ESI, m/z): 507.2 [M+H]⁺.

Step F: Preparation of (S)-2-(1-acryloylpiperidin-2-yl)-1-amino-4-(4-((4-(4-cyanophenyl)pyridin-2-yl)carbamoyl)phenyl)-1H-imidazole-5-carboxamide

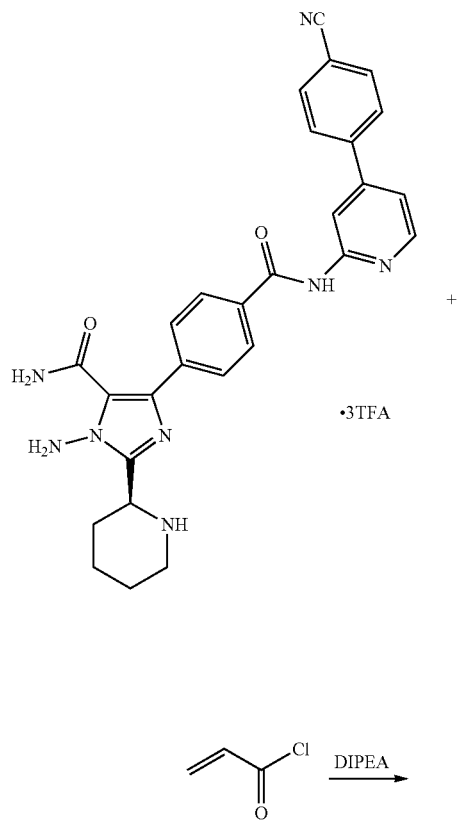

To the solution of 111.3 mg (0.22 mmol) of the product of Step E in dry dichloromethane (5 mL) was added diisopropylethylamine (227.5 μL, 1.32 mmol). After 5 min, acryloyl chloride (12.5 μL, 0.15 mmol) was added at 0° C. The reaction mixture was then warmed up to room temperature and continued to stir for 1 h. Ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to give (S)-2-(1-acryloylpiperidin-2-yl)-1-amino-4-(4-((4-(4-cyanophenyl)pyridin-2-yl)carbamoyl)phenyl)-1H-imidazole-5-carboxamide as an off-white solid (81 mg, 66%). $^1$H NMR (CDCl$_3$, 400 MHz) δ: 9.25 (s, 1H), 8.67 (s, 1H), 8.38 (d, J=5.2 Hz, 1H), 7.93 (d, J=8.0 Hz, 2H), 7.84 (d, J=7.6 Hz, 2H), 7.80 (d, J=8.4 Hz, 2H), 7.76 (d, J=8.4 Hz, 2H), 7.34 (s, 1H), 7.27 (s, 1H), 6.59 (dd, J$_1$=10.8 Hz, J$_2$=16.4 Hz, 1H), 6.33-6.27 (m, 4H), 6.00-5.96 (m, 1H), 5.73 (d, J=10.8 Hz, 1H), 3.83 (d, J=12.4 Hz, 1H), 3.67 (t, J=12.8 Hz, 1H), 2.46-2.43 (m, 1H), 2.20-2.17 (m, 1H), 1.93-1.86 (m, 2H), 1.73-1.70 (m, 1H), 1.63-1.60 (m, 1H); $^{13}$C NMR (CDCl$_3$, 150 MHz) δ: 167.3, 166.0, 162.6, 152.8, 149.0, 148.6, 148.3, 142.7, 141.4, 138.6, 133.3, 132.9, 129.8, 128.8, 128.1, 127.8, 127.4, 120.1, 118.6, 118.0, 113.0, 112.4, 44.4, 43.0, 28.0, 25.8, 19.7. MS (ESI, m/z): 561.2 [M+H]$^+$.

Example 112: (S)-1-amino-2-(1-(but-2-ynoyl)piperidin-2-yl)-4-(4-((4-(4-cyanophenyl)pyridin-2-yl)carbamoyl)phenyl)-1H-imidazole-5-carboxamide

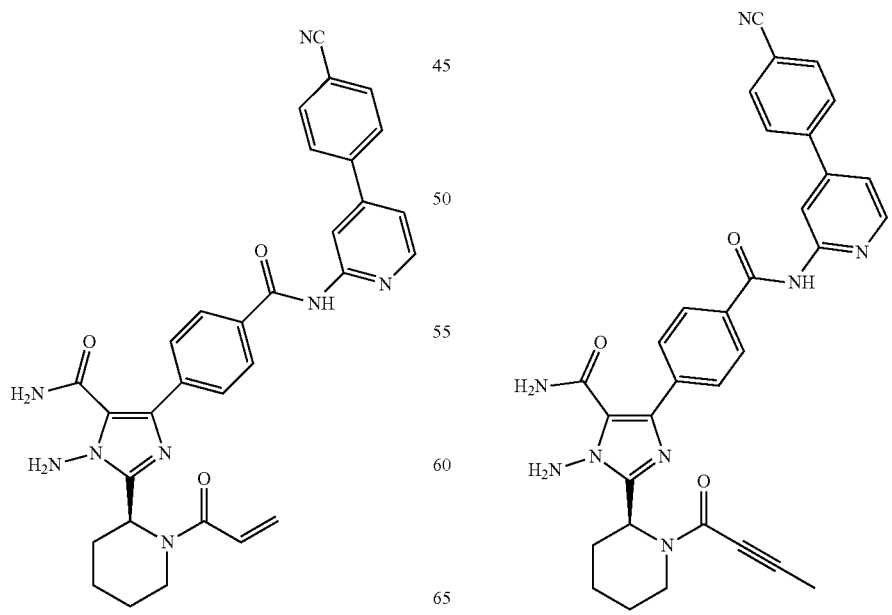

Preparation of (S)-1-amino-2-(1-(but-2-ynoyl)piperidin-2-yl)-4-(4-((4-(4-cyanophenyl)pyridin-2-yl)carbamoyl)phenyl)-1H-imidazole-5-carboxamide

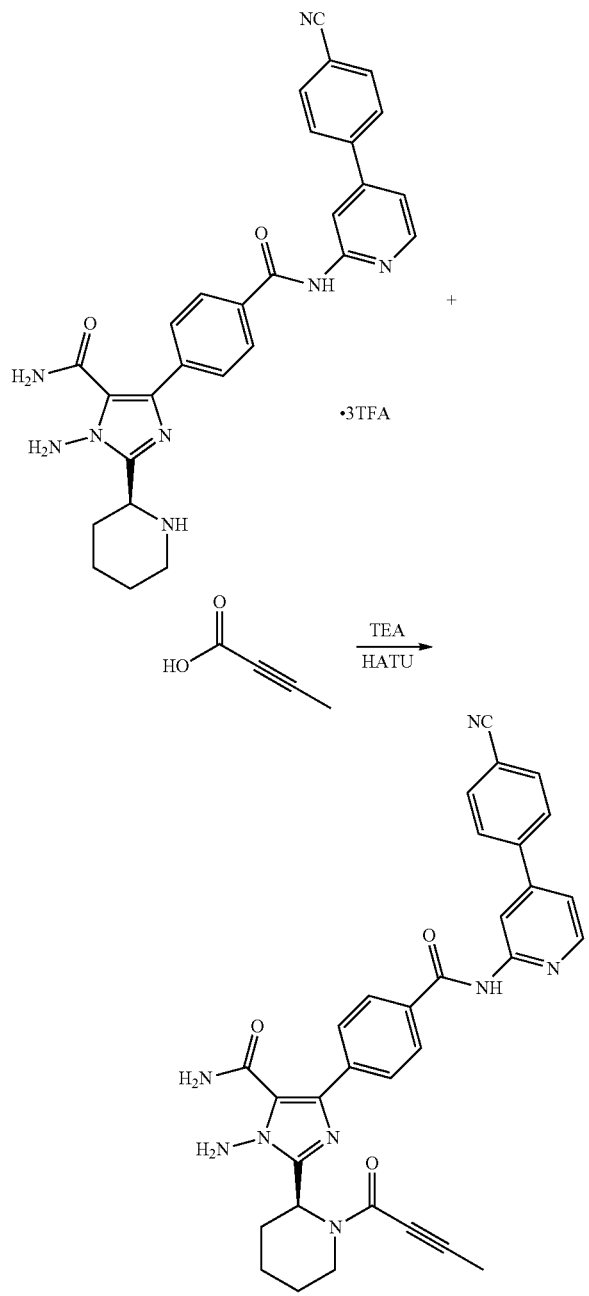

To the solution of 258 mg (0.51 mmol) of the product of Step E of example 111 in dry N,N-Dimethylformamide (7 mL) was added triethylamine (308 mg, 3.06 mmol). After 5 min, but-2-ynoic acid (37.6 mg, 0.45 mmol) and HATU (289 mg, 0.76 mmol) were added. The reaction mixture was continued to stir at room temperature for 2 h, ethyl acetate and water were added. The layers were separated, and the aqueous phase was extracted with ethyl acetate. The combined organic phases were washed three times (3×50 mL) with brine solution. The organic phase was dried over anhydrous $Na_2SO_4$, filtered and concentrated. The residue was purified by chromatography with dichloromethane and methanol (30:1) to give (S)-1-amino-2-(1-(but-2-ynoyl)piperidin-2-yl)-4-(4-((4-(4-cyanophenyl)pyridin-2-yl)carbamoyl)phenyl)-1H-imidazole-5-carboxamide as an off-white solid (175 mg, 60%). $^1$H NMR (CDCl$_3$, 600 MHz) δ: 9.00 (s, 1H), 8.70 (s, 1H), 8.41 (d, J=4.2 Hz, 1H), 7.97 (d, J=7.8 Hz, 2H), 7.88 (d, J=7.8 Hz, 2H), 7.82 (d, J=7.8 Hz, 2H), 7.78 (d, J=7.8 Hz, 2H), 7.29 (d, J=5.4 Hz, 1H), 6.99 (s, 1H), 6.14 (s, 2H), 5.94 (d, J=6.0 Hz, 1H), 5.87 (s, 1H), 4.28 (d, J=13.2 Hz, 1H), 3.64 (t, J=13.2 Hz, 1H), 2.44-2.38 (s, 1H), 2.18 (d, J=13.8 Hz, 1H), 2.02 (s, 3H), 1.89-1.88 (m, 2H), 1.74-1.72 (m, 2H); $^{13}$C NMR (CDCl$_3$, 150 MHz) δ: 165.8, 162.4, 155.1, 152.7, 149.1, 148.7, 148.0, 142.8, 141.3, 138.7, 133.4, 133.0, 129.9, 128.1, 127.4, 120.1, 118.6, 118.1, 113.1, 112.4, 91.1, 73.0, 44.5, 43.8, 27.8, 25.7, 19.9, 4.3. MS (ESI, m/z): 573.2 [M+H]$^+$.

Example 113

BTK inhibition Assay and selectivity Assay The assay was conducted either a by a third party (Reaction Biology Corporation, PA, USA) or in house.

a) Reagent and Procedure by Reaction Biology Corporation:

Base Reaction buffer; 20 mM Hepes (pH 7.5), 10 mM MgCl$_2$, 1 mM EGTA, 0.02%. Brij35, 0.02 mg/ml BSA, 0.1 mM Na$_3$VO$_4$, 2 mM DTT, 1% DMSO. Required cofactors were added individually to each kinase reaction. Compound handling: testing compounds were dissolved in 100% DMSO to specific concentration. The serial dilution was conducted by Integra Viaflo Assist in DMSO.

Reaction Procedure:

The substrate was prepared in freshly prepared reaction buffer of above and required cofactors were added to the substrate solution. The kinase was delivered to the substrate solution and the mixture was gently mixed. Testing compounds in 100% DMSO was added to the kinase reaction mixture by Acoustic technology (Echo550; nanoliter range) and the new mixture was incubated for 20 min at room temperature. Then $^{33}$P-ATP (Specific activity 10 μCi/μl) was added to the reaction mixture to initiate the reaction and the mixture was incubated for 2 hours at room temperature. The radioactivity was detected by filter-binding method and the kinase activity data was expressed as the percent of remaining kinase activity in test sample compared to vehicle (dimethyl sulfoxide) reaction. IC$_{50}$ values and curve fits were obtained using Prism (GraphPad Software). The result is outlined in Table-I b) In House Procedure for BTK, BMX, EGFR and ITK:

Kinase inhibitory activities of compounds were evaluated using the Enzyme-linked immunosorbent assay (ELISA). The kinase enzyme of BTK, BMX, EGFR and ITK were purchased from Carna Bioscience (Kobe, Japan). A total of 10 ng/mL antiphosphotyrosine (PY713) antibody (abcam, Cambridge Science Park, UK) was precoated in 96-well ELISA plates. The kinase enzymes in each reaction well were set to BTK (101.25 ng/mL), BMX (90 ng/mL), EGFR (90 ng/mL) or ITK (120 ng/mL) and incubated with indicated drugs in 1× reaction buffer (50 mmol/L HEPES pH 7.4, 20 mmol/L MgCl$_2$, 0.1 mmol/L MnCl$_2$, 1 mmol/L DTT) containing 20 μmol/L (the final concentration of substrate in ITK reaction was 30 μmol/L) substrate (NH$_2$-ETVY-SEVRK-biotin) at 25° C. for 1 h. Then, a total of 3 μmol/L ATP was added and the reaction was continued for 2 h. The products of reaction were transferred into 96-well ELISA plates containing antibody and incubated at 25° C. for 30 min. After incubation, the wells were washed with PBS and then incubated with horseradish peroxidase (HRP)-conjugated streptavidin. The wells were visualized using 3,3',5,5'-tetramethylbenzidine (TMB), and chromogenic reaction was ended with 2 mol/L H$_2$SO$_4$, the absorbance was read with a multimode plate reader (PerkinElmer, USA) at 450 nm. IC$_{50}$ values and curve fits were obtained using Prism (GraphPad Software). (Table I-IV)

TABLE I

BTK inhibition of representative compounds

| Example No. | BTK (IC$_{50}$, nM) |
|---|---|
| 1 | 131[a], 176[b] |
| 7 | 85[a] |
| 9 | 5920[a] |
| 10 | 78.96[b] |
| 17 | 24.4[a], 30.3[b] |
| 18 | 7,200[a], 3083[b] |
| 19 | 212[b] |
| 26 | 12.5[a], 18.4[b] |
| 27 | 2055[b] |
| 28 | 72.9[b] |
| 33 | 13.5[a], |
| 34 | 1,669[b] |
| 35 | 33[b] |
| 37 | 2,210[a] |
| 38 | 1038[b] |
| 39 | 3,846[b] |
| 40 | 70.56[b] |
| 41 | 1,678[b] |
| 42 | 48.04[b] |
| 43 | 577.1[b] |
| 44 | 121.7[b] |
| 45 | 58.16[b] |
| 46 | 44.6[a], 13.14[b] |
| 50 | 99.95[b] |
| 53 | 18.1[b] |
| 58 | 58.1[b] |
| 59 | 1,274[b] |
| 60 | 43.93[b] |
| 61 | 18.38[b] |
| 64 | 129.3[b] |
| 65 | 5.06[b] |
| 66 | 16.4[b] |
| 67 | 9.12[b] |
| 68 | 79.64[b] |
| 69 | 70.74[b] |
| 70 | 2,890[b] |
| 71 | 55.1[a], 22.59[b] |
| 72 | 10.1[a], 11.23[b] |
| 73 | 9.68[a] |
| 77 | 17.9[b] |
| 78 | 6,565[b] |
| 79 | 1,720[b] |
| 81 | 11[a] |
| 82 | 45.56[b] |
| 84 | 3.46[b] |
| 85 | 7.29[b] |
| 86 | 29.19[a] |
| 87 | 4.375[a] |
| 88 | 22.64[a] |
| 89 | 6.116[a] |
| 90 | 10.66[a] |
| 91 | 4.972[a] |
| 92 | 14.69[a] |
| 93 | 14.6[a] |
| 94 | 225.6[b] |
| 95 | 85.6[b] |
| 96 | 19.2[b] |

TABLE I-continued

BTK inhibition of representative compounds

| Example No. | BTK (IC$_{50}$, nM) |
|---|---|
| 97 | 9.22[b] |
| 98 | 19.36[b] |
| 99 | 2.78[b] |
| 100 | 9.99[b] |
| 101 | 210.9[b] |
| 102 | 2283[b] |
| 103 | 175.5[b] |
| 104 | 459.2[b] |
| 105 | 18.66[a] |
| 106 | 15.0[b] |
| 107 | 44.5[b] |
| 108 | 120.7[b] |
| 109 | 1.9[b] |
| 110 | 14.8[b] |
| 111 | 10.6[b] |
| 112 | 22.8[b] |

Notice:
[a]From Reaction Biology Corporation;
[b]From in house procedure.

TABLE II

The selectivity of representative compounds for BTK and BMX

| Example No. | BTK (IC$_{50}$, nM) | BMX (IC$_{50}$, nM) | Selectivity ratio |
|---|---|---|---|
| 84 | 3.46 | 114.2 | 33.0 |
| 85 | 7.29 | 789 | 108.2 |
| 90 | 10.66 | 226.3 | 21.2 |
| 92 | 14.69 | 153.7 | 10.5 |
| 98 | 19.36 | 1080 | 55.8 |

TABLE III

The selectivity of representative compounds for BTK and ITK

| Example No. | BTK (IC$_{50}$, nM) | ITK (IC$_{50}$, nM) | Selectivity ratio |
|---|---|---|---|
| 84 | 3.46 | 607.6 | 175.6 |
| 85 | 7.29 | 30000 | 4115 |
| 90 | 10.66 | 532.1 | 49.9 |
| 92 | 14.69 | 33124 | 2255 |
| 98 | 19.36 | 16456 | 850 |

TABLE IV

The selectivity of representative compounds for BTK and EGFR

| Example No. | BTK (IC$_{50}$, nM) | EGFR (IC$_{50}$, nM) | Selectivity ratio |
|---|---|---|---|
| 84 | 3.46 | 155.7 | 45 |
| 85 | 7.29 | 11802 | 1619 |
| 90 | 10.66 | 4678 | 439 |
| 92 | 14.69 | 1090 | 74 |
| 98 | 19.36 | 3984 | 206 |

Example 114

In-Vitro Antitumor Activity Assay

Method: Reagent and procedure by Hefei PreceDo pharmaceuticals Co. Ltd.

Cell antiproliferative activity was evaluated by the CellTiter-Glo (Promega, USA) assay. Make 1000× compounds solution in DMSO, add 1 μl 1000× compounds to 49 μl growth medium to make 20× compounds. Dilute cell suspensions in growth medium to desired density and 95 μl were taken to 96-well plate. Add 5 μl 20× compounds into 96-well plate according to the plate map. Final DMSO concentration in each well was 0.1%. Then the cell was incubated at 37° C., 5% $CO_2$ for 72 h. Equilibrate the assay plate to room temperature before measurement. Add 20 μl of CellTiter-Glo© Reagent into each well. Mix contents for 2 minutes on an orbital shaker to induce cell lysis. Incubate at room temperature for 10 minutes to stabilize luminescent signal. Record luminescence using EnVision Multilabel Reader (PerkinElmer). Cell viability (CV %) was calculated relative to vehicle (DMSO) treated control wells using following formula: Cell viability (%)=(RLU compound−RLU blank)/(RLU control−RLU blank)*100%. The IC50 values were calculated using GraphPad Prism 6.0 software, fitting to a 4-parameter equation to generate concentration response curves. All assays were conducted with three parallel samples and three repetitions.

TABLE V in-vitro antitumor activity of representative compounds

| Example No. | TMD-8 ($IC_{50}$ nM) |
|---|---|
| 84 | 24.5 |
| 85 | 54.3 |
| 90 | 35.1 |
| 92 | 90.8 |
| 98 | 37.0 |
| 72 | 19.0 |

Example 115

Rat Pharmacokinetic Assay
Method: Reagent and Procedure by Hefei PreceDo Pharmaceuticals Co. Ltd.

Male Sprague-Dawley rats with 6-8 weeks of age were purchased from Beijing Vital River Laboratory Animal Technology Co., Ltd. Rats were randomly assigned with three rats per group. A single dose of compound 84 or 85 was administered by tail vein injection in iv group. In po group, compound 84 or 85 was orally. Blood samples (~0.25 mL) were obtained by orbital venous plexus at 2 min (iv only), 5 min, 15 min, 1 h, 2 h, 4 h, 6 h, 8 h, 12 h and 24 h (po only) post dose. After centrifuged at 4000 rpm for 10 min at 4° C., plasma was collected and stored at −20° C. until determine by LC-MS/MS.

As shown in Table VI, 84 showed a favorable PK profile. After intravenous at a dose of 5 mg/kg, the half-life ($t_{1/2}$) and mean clearance rate (CL) of 84 were 1.32 h and 13.4 mL/min/kg, respectively. Meanwhile, the compound showed relatively high exposure $C_{max}$ (501 ng/mL), AUC (1996 h ng/mL) and acceptable bioavailability (32.4%) following oral administration at the same dose.

TABLE VI

PK Profile of Compound 84 in Rats

| | iv (5 mg/kg)[a] | | | po (5 mg/kg)[b] | | | |
|---|---|---|---|---|---|---|---|
| Compd. | $T_{1/2}$ (h) | CL (mL/min/kg) | $V_d$ (L/kg) | $T_{1/2}$ (h) | $C_{max}$ (ng/mL) | AUC (h · ng/mL) | F (%) |
| 84 | 1.32 | 13.4 | 1.50 | 1.35 | 501 | 1996 | 32.4 |

[a]Dosed using 5 mg/kg solution (20% water, 80% PEG400). [b]Dosed using 5 mg/kg solution (20% water, 80% PEG400), n = 3.

The PK properties of compound 85 was evaluated in rats following intravenous (1 mg/kg) and oral (10 mg/kg). As shown in Table 8, 85 exhibited an impressive PK profile. It showed half-life $t_{1/2}$ (2.74 h), AUC (3247 h ng/mL) and bioavailability (90.6%) after oral administration.

TABLE VII

PK Profile of Compound 85 in Rats

| | iv (1 mg/kg)[a] | | | po (10 mg/kg)[b] | | | |
|---|---|---|---|---|---|---|---|
| Compd. | $T_{1/2}$ (h) | CL (mL/min/kg) | $V_d$ (L/kg) | $T_{1/2}$ (h) | $C_{max}$ (ng/mL) | AUC (h · ng/mL) | F (%) |
| 85 | 1.97 | 50.0 | 8.62 | 2.74 | 723 | 3247 | 90.6 |

[a]Dosed using 1 mg/kg solution (20% water, 80% PEG400). [b]Dosed using 10 mg/kg solution (20% water, 80% PEG400), n = 3.

What is claimed is:
1. A compound represented by Formula I, or a pharmaceutically acceptable salt, active metabolite, tautomer, stereoisomer, or prodrug thereof,

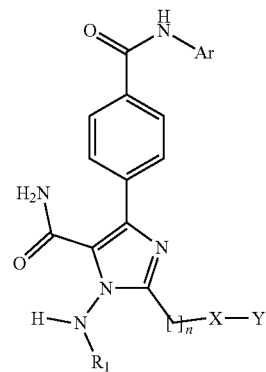

wherein
$R_1$ is selected from the group consisting of H, $C_{1-6}$ alkyl, and $R_5C(O)$, where $R_5$ is independently selected from the group consisting of $C_{1-6}$ alkyl and $C_{1-6}$ alkoxy;
Ar is selected from heteroaryl or heteroaryl substituted with a substituent selected from the group consisting of halogen, cyano, $C_{1-6}$ alkyl, $C_{1-6}$ alkoxy, $C_6$ or $C_{10}$ aryl, and $C_6$ or $C_{10}$ aryl substituted with a substituent selected from the group consisting of halogen, cyano, $C_{1-6}$ alkyl optionally substituted with halogen, hydroxyl or $C_{1-6}$ alkoxy;
n is an integer selected from 0 and 1;
X is a 4-8 membered nitrogen-containing heterocyclyl where the heterocyclyl is substituted on a nitrogen with Y; or a nitrogen-containing spiral heterocyclyl where the spiral heterocyclyl is substituted on a nitrogen with Y;
Y is selected from the group consisting of —CN, —C(=O)P, —S(=O)P and —S(=$O_2$)P; where P is selected from

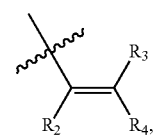

-continued

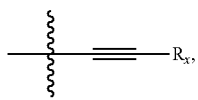

and

Rx is selected from the group consisting of H, halogen, cyano, $C_{1-6}$ alkyl, $C_{1-6}$ alkyl substituted with halogen, $C_{1-6}$ alkoxy, $C_{3-6}$ cycloalkyl, phenyl and $-(CH_2)_m NR_6R_7$;

R2 is selected from the group consisting of hydrogen, halogen, cyano, $C_{1-6}$ alkyl, $C_{1-6}$ alkyl substituted by substituents selected from the group consisting of F, hydroxyl and $C_{1-6}$ alkoxy; $C_{3-6}$ cycloalkyl and $C_{3-6}$ cycloalkyl substituted with F;

R3 and R4 are independently selected from the group consisting of hydrogen; halogen; cyano; $C_6$ or $C_{10}$ aryl; heteroaryl; $C_{1-6}$ alkyl; $C_{1-6}$ alkyl substituted with $C_{1-6}$ alkoxy, $NR_6R_7$, halogen, hydroxyl, $C_6$ or $C_{10}$ aryl, and heteroaryl; $C_{3-6}$ cycloalkyl; $C_{3-6}$ cycloalkyl substituted with halogen; $C_{2-6}$ alkenyl; and $C_{2-6}$ alkenyl substituted with a subtituent selected from the group consisting of $C_{1-6}$ alkoxy, $NR_6R_7$, halogen, hydroxyl, $C_6$ or $C_{10}$ aryl and heteroaryl;

R6 and R7 are each independently selected from hydrogen, $C_{1-6}$ alkyl or together with the nitrogen they substitute form a 4-6 membered heterocyclyl;

m is an integer selected from 1 to 3.

2. The compound of claim 1, wherein $R_1$ is H or $C_{1-6}$ alkyl.

3. The compound of claim 2, wherein $R_1$ is H or methyl.

4. The compound of claim 1, wherein Ar is represented by a formula selected from the group consisting of:

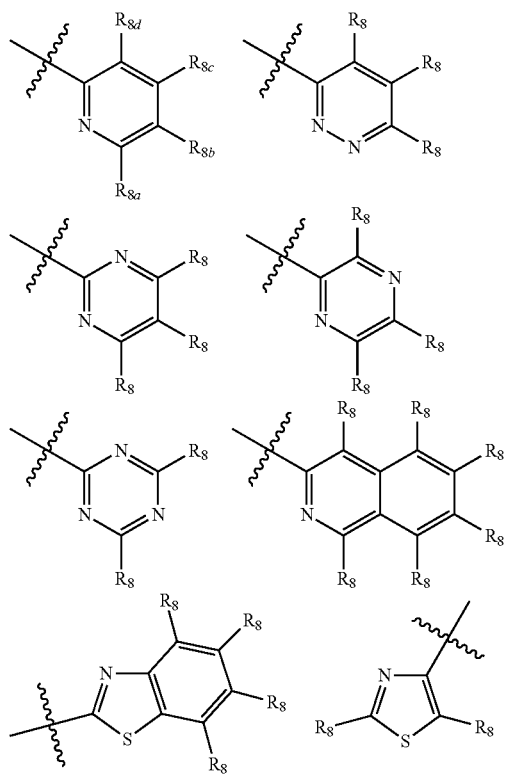

-continued

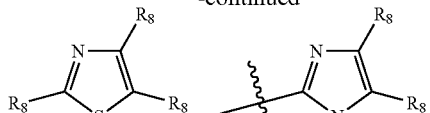

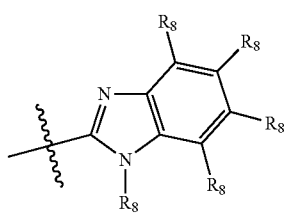

wherein $R_8$ are different or same, and independently selected from the group consisting of H; $C_{1-6}$ alkyl; $C_{1-6}$ alkyl substituted with halogen; $C_{1-6}$ alkoxy; halogen; $C_6$ or $C_{10}$ aryl; $C_6$ or $C_{10}$ aryl substituted with a substituent selected from a group consisting of halogen, $C_{1-6}$ alkyl, $C_{1-6}$ alkoxy, cyano, and trifluloromethyl; heteroaryl; and cyano;

$R_{8a}$, $R_{8b}$, $R_{8c}$ and $R_{8d}$ are independently selected from the group consisting of H; $C_{1-6}$ alkyl;

$C_{1-6}$ alkyl substituted with halogen; $C_{1-6}$ alkoxy; halogen; $C_6$ or $C_{10}$ aryl; $C_6$ or $C_{10}$ aryl substituted with a substituent selected from a group consisting of halogen, $C_{1-6}$ alkyl, $C_{1-6}$ alkoxy, cyano, and trifluloromethyl; heteroaryl; and cyano.

5. The compound of claim 1, wherein Ar is represented by the following formula:

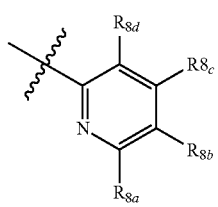

wherein, $R_{8a}$ is hydrogen;

$R_{8b}$ is hydrogen, $C_{1-6}$ alkyl, or halogen;

$R_{8c}$ is selected from the group consisting of H; $C_{1-6}$ alkyl; $C_{1-6}$ alkyl substituted with halogen; $C_{1-6}$ alkoxy; halogen; $C_6$ or $C_{10}$ aryl; $C_6$ or $C_{10}$ aryl substituted with halogen or cyano; and cyano; and $R_{8d}$ is hydrogen.

6. The compound of claim 1, wherein Ar is represented by the following formula:

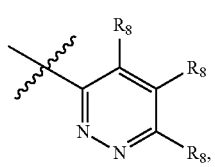

-continued

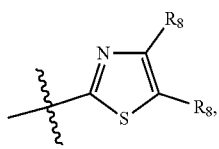

wherein, $R_8$ is hydrogen.

7. The compound of claim 1, wherein Ar is represented by the following formula:

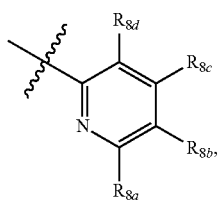

wherein, $R_{8a}$ is H;

$R_{8b}$ is independently selected from H, Cl or $CH_3$;

$R_{8c}$ is independently selected from the group consisting of H, $CH_3$, $CH_2CH_3$, $OCH_3$, F, Cl, Br, I, cyano, $CF_3$, isopropyl, phenyl, phenyl substituted with substituents selected from the group consisting of halogen and cyano; and $R_{8d}$ is H.

8. The compound of claim 1, wherein X is selected from the group consisting of:

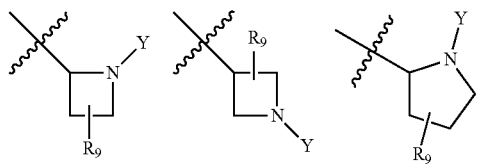

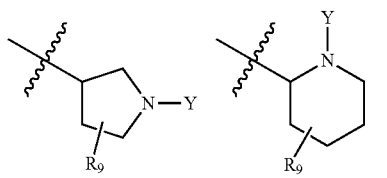

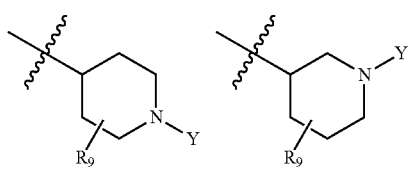

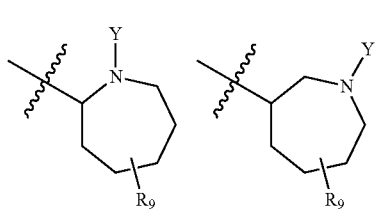

-continued

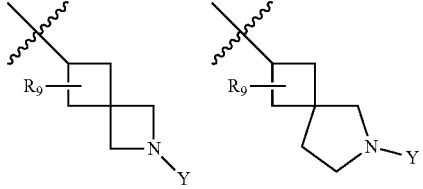

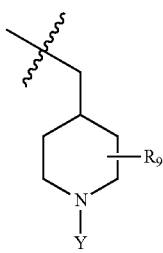

wherein, $R_9$ is selected from H, F, $C_{1-6}$ alkyl, $C_{1-6}$ alkyl substituted with halogen, $C_{1-6}$ alkoxy and $NR_6R_7$; and $R_9$ substitute one or more positions; or $R_9$ may form a double bond in the ring, or form a 4-6 member ring fused with the ring $R_9$ substitute;

$R_6$ and $R_7$ are defined as claim 1.

9. The compound of claim 1, wherein, $R_2$ is selected from the group consisting of H, halogen, cyano, $C_{1-6}$ alkyl, and $C_{1-6}$ alkyl substituted with F;

$R_3$ is selected from hydrogen or $C_{1-6}$ alkyl;

$R_4$ is selected from the group consisting of hydrogen, $C_6$ or $C_{10}$ aryl, $C_{3-6}$ cycloalkyl, $C_{1-6}$ alkyl, and $C_{1-6}$ alkyl substituted with F; and Rx is selected from the group consisting of H, $C_{3-6}$ cycloalkyl, $C_{1-6}$ alkyl, and $C_{1-6}$ alkyl substituted with F.

10. The compound of claim 1, wherein, $R_2$ is independently selected from the group consisting of H, F, cyano, $CH_3$ and $CF_3$;

$R_3$ is selected from hydrogen or methyl; and $R_4$ is selected from the group consisting of hydrogen, phenyl, cyclopropy, methyl, ethyl, isopropyl, tert-butyl, and trifluoromethyl; or Rx is selected from the group consisting of H, methyl, and cyclopropyl.

11. The compound of claim 9, wherein X is

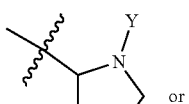 or

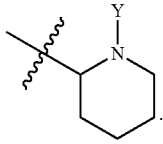

12. The compound of claim 1, wherein X is

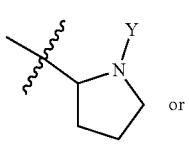 or

-continued

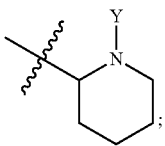

wherein Y is —C(=O)P,
P is

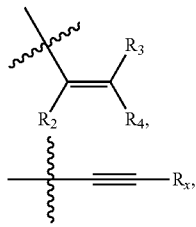

wherein,
R₂ is independently selected from the group consisting of H, F, cyano and CF₃;
R₃ is hydrogen;
R₄ is independently selected from the group consisting of H, cyclopropyl, methyl, and trifluoromethyl;
Rx is selected from the group consisting of H, methyl, and cyclopropyl;
n is 0.

13. The compound of claim 1, wherein in formula I, Ar is represented by

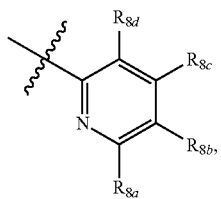

wherein,
R$_{8a}$, R$_{8b}$ and R$_{8d}$ are hydrogen;
R$_{8c}$ is independently selected from Cl, I, CF₃ or phenyl substituted with F;
X is

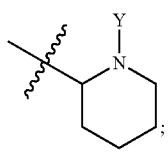

Y is —C(=O)P, and P is

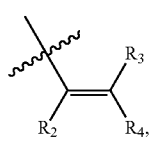

-continued

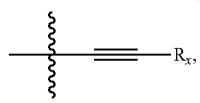

wherein,
R₂ is hydrogen;
R₃ is hydrogen;
R₄ is independently selected from the group consisting of H and trifluoromethyl;
Rx is selected from the group consisting of H and methyl;
n is 0; and
R₁ is hydrogen.

14. A pharmaceutical composition comprising a compound, a pharmaceutically acceptable salt, active metabolite, tautomer, stereoisomer, or prodrug thereof as claimed in claim 1, and a pharmaceutically acceptable carrier.

15. A method of preventing or treating a subject suffering from or at risk of BTK mediated disease or condition, comprising administering to said subject an effective amount of a compound of claim 1 or a pharmaceutically acceptable salt, active metabolite, tautomer, stereoisomer, or prodrug thereof.

16. A method of preventing or treating a subject suffering from or at risk of a disease or disorder selected from the group consisting of an autoimmune disease, inflammatory disease, cancer, allergy, diffused large B cell lymphoma, follicular lymphoma, chronic lymphocytic leukemia, mantel cell lymphoma, splenic marginal zone lymphoma, large B cell lymphoma, lupus erythematosus, rheumatoid arthritis, Crohn's disease, psoriasis, multiple sclerosis, asthma etc., comprising administering to said subject an effective amount of a compound of claim 1 or a pharmaceutically acceptable salt, active metabolite, tautomer, stereoisomer, or prodrug thereof.

17. The method of claim 16, wherein the subject is a mammal.

18. A compound of claim 1, which is selected from the following, or a pharmaceutically acceptable salt, active metabolite, tautomer, stereoisomer, or prodrug thereof:
(S)-2-(1-acryloylpyrrolidin-2-yl)-1-amino-4-(4-(pyridin-2-ylcarbamoyl)phenyl)-1H-imidazole-5-carboxamide
(S)-1-amino-2-(1-methacryloylpyrrolidin-2-yl)-4-(4-(pyridin-2-ylcarbamoyl)phenyl)-1H-imidazole-5-carboxamide
(S)-1-amino-2-(1-(3-methylbut-2-enoyl)pyrrolidin-2-yl)-4-(4-(pyridin-2-ylcarbamoyl)phenyl)-1H-imidazole-5-carboxamide
(S,E)-1-amino-2-(1-(but-2-enoyl)pyrrolidin-2-yl)-4-(4-(pyridin-2-ylcarbamoyl)phenyl)-1H-imidazole-5-carboxamide
(S)-1-amino-2-(1-(2-cyano-3-cyclopropylacryloyl)pyrrolidin-2-yl)-4-(4-(pyridin-2-ylcarbamoyl)phenyl)-1H-imidazole-5-carboxamide
(S,E)-1-amino-2-(1-(pent-2-enoyl)pyrrolidin-2-yl)-4-(4-(pyridin-2-ylcarbamoyl)phenyl)-1H-imidazole-5-carboxamide
(S)-1-amino-2-(1-propioloylpyrrolidin-2-yl)-4-(4-(pyridin-2-ylcarbamoyl)phenyl)-1H-imidazole-5-carboxamide
(S)-1-amino-2-(1-(but-2-ynoyl)pyrrolidin-2-yl)-4-(4-(pyridin-2-ylcarbamoyl)phenyl)-1H-imidazole-5-carboxamide (S)-1-amino-2-(1-cyanopyrrolidin-2-yl)-4-(4-(pyridin-2-ylcarbamoyl)phenyl)-1H-imidazole-5-carboxamide (S)-2-(1-acryloylpyrrolidin-2-yl)-1-amino-4-(4-((4-methylpyridin-2-yl)carbamoyl)phenyl)-1H-imidazole-5-carboxamide (S)-1-amino-2-(1-methacryloylpyrrolidin-2-yl)-4-(4-((4-methylpyridin-2-yl)carbamoyl)phenyl)-1H-imidazole-5-carboxamide (S)-1-amino-2-(1-(3-methylbut-2-enoyl)pyrrolidin-2-yl)-4-(4-((4-methylpyridin-2-yl)carbamoyl)phenyl)-1H-imidazole-5-carboxamide (S,E)-1-amino-2-(1-(but-2-enoyl)pyrrolidin-2-yl)-4-(4-((4-methyl-pyridin-2-yl)carbamoyl)phenyl)-1H-imidazole-5-carboxamide (S, E)-1-amino-2-(1-(2-cyano-3-cyclopropylacryloyl)pyrrolidin-2-yl)-4-(4-((4-methylpyridin-2-yl)carbamoyl)phenyl)-1H-imidazole-5-carboxamide (S, E)-1-amino-2-(1-(2-cyano-4-methylpent-2-enoyl)pyrrolidin-2-yl)-4-(4-((4-methylpyridin-2-yl)carbamoyl)phenyl)-1H-imidazole-5-carboxamide (S,E)-1-amino-4-(4-((4-methylpyridin-2-yl)carbamoyl)phenyl)-2-(1-(pent-2-enoyl)pyrrolidin-2-yl)-1H-imidazole-5-carboxamide (S)-1-amino-4-(4-((4-methylpyridin-2-yl)carbamoyl)phenyl)-2-(1-propioloylpyrrolidin-2-yl)-1H-imidazole-5-carboxamide (S)-1-amino-2-(1-(but-2-ynoyl)pyrrolidin-2-yl)-4-(4-((4-methylpyridin-2-yl)carbamoyl)phenyl)-1H-imidazole-5-carboxamide (S)-2-(1-acryloylpyrrolidin-2-yl)-1-amino-4-(4-((5-methylpyridin-2-yl)carbamoyl)phenyl)-1H-imidazole-5-carboxamide (S)-1-amino-2-(1-methacryloylpyrrolidin-2-yl)-4-(4-((5-methylpyridin-2-yl)carbamoyl)phenyl)-1H-imidazole-5-carboxamide (S)-1-amino-2-(1-(3-methylbut-2-enoyl)pyrrolidin-2-yl)-4-(4-((5-methylpyridin-2-yl)carbamoyl)phenyl)-1H-imidazole-5-carboxamide (S,E)-1-amino-2-(1-(but-2-enoyl)pyrrolidin-2-yl)-4-(4-((5-methylpyridin-2-yl)carbamoyl)phenyl)-1H-imidazole-5-carboxamide (S, E)-1-amino-2-(1-(2-cyano-3-cyclopropylacryloyl)pyrrolidin-2-yl)-4-(4-((5-methylpyridin-2-yl)carbamoyl)phenyl)-1H-imidazole-5-carboxamide (S, E)-1-amino-2-(1-(2-cyano-4,4-dimethylpent-2-enoyl)pyrrolidin-2-yl)-4-(4-((5-methylpyridin-2-yl)carbamoyl)phenyl)-1H-imidazole-5-carboxamide (S,E)-1-amino-4-(4-((5-methylpyridin-2-yl)carbamoyl)phenyl)-2-(1-(pent-2-enoyl)pyrrolidin-2-yl)-1H-imidazole-5-carboxamide (S)-1-amino-4-(4-((5-methylpyridin-2-yl)carbamoyl)phenyl)-2-(1-propioloylpyrrolidin-2-yl)-1H-imidazole-5-carboxamide (S)-1-amino-2-(1-(but-2-ynoyl)pyrrolidin-2-yl)-4-(4-((5-methylpyridin-2-yl)carbamoyl)phenyl)-1H-imidazole-5-carboxamide (S)-2-(1-acryloylpyrrolidin-2-yl)-1-amino-4-(4-((4-methoxypyridin-2-yl)carbamoyl)phenyl)-1H-imidazole-5-carboxamide (S)-1-amino-2-(1-methacryloylpyrrolidin-2-yl)-4-(4-((4-methoxypyridin-2-yl)carbamoyl)phenyl)-1H-imidazole-5-carboxamide (S)-1-amino-4-(4-((4-methoxypyridin-2-yl)carbamoyl)phenyl)-2-(1-(3-methylbut-2-enoyl)pyrrolidin-2-yl)-1H-imidazole-5-carboxamide (S,E)-1-amino-2-(1-(but-2-enoyl)pyrrolidin-2-yl)-4-(4-((4-methoxypyridin-2-yl)carbamoyl)phenyl)-1H-imidazole-5-carboxamide (S,E)-1-amino-4-(4-((4-methoxypyridin-2-yl)carbamoyl)phenyl)-2-(1-(pent-2-enoyl)pyrrolidin-2-yl)-1H-imidazole-5-carboxamide (S)-1-amino-4-(4-((4-methoxypyridin-2-yl)carbamoyl)phenyl)-2-(1-propioloylpyrrolidin-2-yl)-1H-imidazole-5-carboxamide (S)-1-amino-2-(1-(but-2-ynoyl)pyrrolidin-2-yl)-4-(4-((4-methoxypyridin-2-yl)carbamoyl)phenyl)-1H-imidazole-5-carboxamide (S)-2-(1-acryloylpyrrolidin-2-yl)-1-amino-4-(4-((4-ethylpyridin-2-yl)carbamoyl)phenyl)-1H-imidazole-5-carboxamide (S)-1-amino-4-(4-((4-ethylpyridin-2-yl)carbamoyl)phenyl)-2-(1-methacryloylpyrrolidin-2-yl)-1H-imidazole-5-carboxamide (S)-1-amino-4-(4-((4-ethylpyridin-2-yl)carbamoyl)phenyl)-2-(1-(3-methylbut-2-enoyl)pyrrolidin-2-yl)-1H-imidazole-5-carboxamide (S)-1-amino-2-(1-(but-2-ynoyl)pyrrolidin-2-yl)-4-(4-((4-ethylpyridin-2-yl)carbamoyl)phenyl)-1H-imidazole-5-carboxamide (S)-1-amino-2-(1-cyanopyrrolidin-2-yl)-4-(4-((4-ethylpyridin-2-yl)carbamoyl)phenyl)-1H-imidazole-5-carboxamide (S)-2-(1-acryloylpyrrolidin-2-yl)-1-amino-4-(4-((4-fluoropyridin-2-yl)carbamoyl)phenyl)-1H-imidazole-5-carboxamide (S)-1-amino-2-(1-(but-2-ynoyl)pyrrolidin-2-yl)-4-(4-((4-fluoropyridin-2-yl)carbamoyl)phenyl)-1H-imidazole-5-carboxamide (S)-2-(1-acryloylpyrrolidin-2-yl)-1-amino-4-(4-((4-(trifluoromethyl) pyridin-2-yl)carbamoyl)phenyl)-1H-imidazole-5-carboxamide (S)-1-amino-2-(1-(but-2-ynoyl)pyrrolidin-2-yl)-4-(4-((4-(trifluoromethyl) pyridin-2-yl)carbamoyl)phenyl)-1H-imidazole-5-carboxamide (S)-2-(1-acryloylpyrrolidin-2-yl)-1-amino-4-(4-((4-isopropylpyridin-2-yl)carbamoyl)phenyl)-1H-imidazole-5-carboxamide (S)-2-(1-acryloylpyrrolidin-2-yl)-1-(methylamino)-4-(4-((4-methylpyridin-2-yl)carbamoyl)phenyl)-1H-imidazole-5-carboxamide (S)-2-(1-acryloylpiperidin-2-yl)-1-amino-4-(4-(pyridin-2-ylcarbamoyl)phenyl)-1H-imidazole-5-carboxamide (S)-1-amino-2-(1-methacryloylpiperidin-2-yl)-4-(4-(pyridin-2-ylcarbamoyl)phenyl)-1H-imidazole-5-carboxamide (S,E)-1-amino-2-(1-(but-2-enoyl) piperidin-2-yl)-4-(4-(pyridin-2-ylcarbamoyl)phenyl)-1H-imidazole-5-carboxamide (S)-1-amino-2-(1-(3-methylbut-2-enoyl) piperidin-2-yl)-4-(4-(pyridin-2-ylcarbamoyl)phenyl)-1H-imidazole-5-carboxamide (S)-1-amino-2-(1-(but-2-ynoyl) piperidin-2-yl)-4-(4-(pyridin-2-ylcarbamoyl)phenyl)-1H-imidazole-5-carboxamide (S,E)-1-amino-2-(1-(pent-2-enoyl) piperidin-2-yl)-4-(4-(pyridin-2-ylcarbamoyl)phenyl)-1H-imidazole-5-carboxamide (S,E)-1-amino-2-(1-(2-cyano-3-cyclopropylacryloyl) piperidin-2-yl)-4-(4-(pyridin-2-ylcarbamoyl)phenyl)-1H-imidazole-5-carboxamide (S)-2-(1-acryloylpiperidin-2-yl)-1-amino-4-(4-((4-methylpyridin-2-yl)carbamoyl)phenyl)-1H-imidazole-5-carboxamide (S)-1-amino-2-(1-methacryloylpiperidin-2-yl)-4-(4-((4-methylpyridin-2-yl)carbamoyl)phenyl)-1H-imidazole-5-carboxamide (S,E)-1-amino-2-(1-(but-2-enoyl) piperidin-2-yl)-4-(4-((4-methylpyridin-2-yl)carbamoyl)phenyl)-1H-imidazole-5-carboxamide (S)-1-amino-2-(1-(3-methylbut-2-enoyl) piperidin-2-yl)-4-(4-((4-methylpyridin-2-yl)carbamoyl)phenyl)-1H-imidazole-5-carboxamide (S, E)-1-amino-2-(1-cinnamoylpiperidin-2-yl)-4-(4-((4-methylpyridin-2-yl)carbamoyl)phenyl)-1H-imidazole-5-carboxamide (S)-1-amino-2-(1-(but-2-ynoyl) piperidin-2-yl)-4-(4-((4-methylpyridin-2-yl)carbamoyl)phenyl)-1H-imidazole-5-carboxamide (S)-1-amino-2-(1-(2-fluoroacryloyl) piperidin-2-yl)-4-(4-((4-methylpyridin-2-yl)carbamoyl)phenyl)-1H-imidazole-5-carboxamide (S,E)-1-amino-4-(4-((4-methylpyridin-2-yl)carbamoyl)phenyl)-2-(1-(4,4,4-trifluorobut-2-enoyl) piperidin-2-yl)-1H-imidazole-5-carboxamide (S)-2-(1-acryloylpiperidin-2-yl)-1-amino-4-(4-((5-methylpyridin-2-yl)carbamoyl)phenyl)-1H-imidazole-5-carboxamide (S)-1-amino-2-(1-methacryloylpiperidin-2-yl)-4-(4-((5-methylpyridin-2-yl)carbamoyl)phenyl)-1H-imidazole-5-carboxamide (S)-1-amino-2-(1-(3-methylbut-2-enoyl) piperidin-2-yl)-4-(4-((5-methylpyridin-2-yl)carbamoyl)phenyl)-1H-imidazole-5-carboxamide (S)-1-amino-2-(1-(but-2-ynoyl) piperidin-2-yl)-4-(4-((5-methylpyridin-2-yl)carbamoyl)phenyl)-1H-imidazole-5-carboxamide (S)-2-(1-acryloylpiperidin-2-yl)-1-amino-4-(4-((4-phenylpyridin-2-yl)carbamoyl)phenyl)-1H-imidazole-5-carboxamide (S)-1-amino-2-(1-(but-2-ynoyl) piperidin-2-yl)-4-(4-((4-phenylpyridin-2-yl)carbamoyl)phenyl)-1H-imidazole-5-carboxamide (S)-2-(1-acryloylpiperidin-2-yl)-1-amino-4-(4-((4-methoxypyridin-2-yl)carbamoyl)phenyl)-1H-imidazole-5-carboxamide (S)-1-amino-2-(1-(but-2-ynoyl) piperidin-2-yl)-4-(4-((4-methoxy-pyridin-2-yl)carbamoyl)phenyl)-1H-imidazole-5-carboxamide (S,E)-1-amino-4-(4-((4-methoxypyridin-2-yl)carbamoyl)phenyl)-2-(1-(4,4,4-trifluorobut-2-enoyl) piperidin-2-yl)-1H-imidazole-5-carboxamide (S)-1-amino-2-(1-(2-fluoroacryloyl) piperidin-2-yl)-4-(4-((4-methoxy-pyridin-2-yl)carbamoyl)phenyl)-1H-imidazole-5-carboxamide (S)-2-(1-acryloylpiperidin-2-yl)-1-amino-4-(4-((4-isopropylpyridin-2-yl)carbamoyl)phenyl)-1H-imidazole-5-carboxamide (S)-2-(1-acryloylpiperidin-2-yl)-1-amino-4-(4-((4-chloropyridin-2-yl)carbamoyl)phenyl)-1H-imidazole-5-carboxamide (S)-2-(1-acryloylpiperidin-2-yl)-1-amino-4-(4-((4-ethylpyridin-2-yl)carbamoyl)phenyl)-1H-imidazole-5-carboxamide (S)-1-amino-4-(4-((4-ethylpyridin-2-yl)carbamoyl)phenyl)-2-(1-methacryloylpiperidin-2-yl)-1H-imidazole-5-carboxamide (S,E)-1-amino-2-(1-(but-2-enoyl) piperidin-2-yl)-4-(4-((4-ethylpyridin-2-yl)carbamoyl)phenyl)-1H-imidazole-5-carboxamide (S)-1-amino-4-(4-((4-ethylpyridin-2-yl)carbamoyl)phenyl)-2-(1-(3-methylbut-2-enoyl) piperidin-2-yl)-1H-imidazole-5-carboxamide (S)-1-amino-2-(1-(but-2-ynoyl) piperidin-2-yl)-4-(4-((4-ethylpyridin-2-yl)carbamoyl)phenyl)-1H-imidazole-5-carboxamide (S,E)-1-amino-2-(1-(2-cyano-3-cyclopropylacryloyl) piperidin-2-yl)-4-(4-((4-ethylpyridin-2-yl)carbamoyl)phenyl)-1H-imidazole-5-carboxamide (S,E)-1-amino-2-(1-(2-cyano-4-methylpent-2-enoyl) piperidin-2-yl)-4-(4-((4-ethylpyridin-2-yl)carbamoyl)phenyl)-1H-imidazole-5-carboxamide (S,E)-1-amino-4-(4-((4-ethylpyridin-2-yl)carbamoyl)phenyl)-2-(1-(pent-2-enoyl) piperidin-2-yl)-1H-imidazole-5-carboxamide (S)-2-(1-acryloylpiperidin-2-yl)-4-(4-((4-ethylpyridin-2-yl)carbamoyl)phenyl)-1-(methylamino)-1H-imidazole-5-carboxamide (S)-1-amino-2-(1-(but-2-ynoyl) piperidin-2-yl)-4-(4-((4-cyanopyridin-2-yl)carbamoyl)phenyl)-1H-imidazole-5-carboxamide (S)-2-(1-acryloylpiperidin-2-yl)-1-amino-4-(4-((4-cyanopyridin-2-yl)carbamoyl)phenyl)-1H-imidazole-5-carboxamide (S)-2-(1-acryloylpiperidin-2-yl)-1-amino-4-(4-((4-(trifluoromethyl) pyridin-2-yl)carbamoyl)phenyl)-1H-imidazole-5-carboxamide (S)-1-amino-2-(1-(but-2-ynoyl) piperidin-2-yl)-4-(4-((4-(trifluoromethyl) pyridin-2-yl)carbamoyl)phenyl)-1H-imidazole-5-carboxamide (S)-2-(1-acryloylpiperidin-2-yl)-1-amino-4-(4-((5-chloropyridin-2-yl)carbamoyl)phenyl)-1H-imidazole-5-carboxamide (S)-2-(1-acryloylpiperidin-2-yl)-1-amino-4-(4-((4-bromopyridin-2-yl)carbamoyl)phenyl)-1H-imidazole-5-carboxamide (S)-1-amino-4-(4-((4-bromopyridin-2-yl)carbamoyl)phenyl)-2-(1-(but-2-ynoyl) piperidin-2-yl)-1H-imidazole-5-carboxamide (S)-2-(1-acryloylpiperidin-2-yl)-1-amino-4-(4-((4-iodopyridin-2-yl)carbamoyl)phenyl)-1H-imidazole-5-carboxamide (S)-1-amino-2-(1-(but-2-ynoyl) piperidin-2-yl)-4-(4-((4-iodopyridin-2-yl)carbamoyl)phenyl)-1H-imidazole-5-carboxamide (S)-2-(1-acryloylpiperidin-2-yl)-1-amino-4-(4-((4-(4-fluorophenyl)pyridin-2-yl)carbamoyl)phenyl)-1H-imidazole-5-carboxamide (S)-1-amino-2-(1-(but-2-ynoyl) piperidin-2-yl)-4-(4-((4-(4-fluorophenyl)pyridin-2-yl)carbamoyl)phenyl)-1H-imidazole-5-carboxamide (R)-2-(1-acryloylpiperidin-3-yl)-1-amino-4-(4-((4-ethylpyridin-2-yl)carbamoyl)phenyl)-1H-imidazole-5-carboxamide 2-(1-acryloylazepan-2-yl)-1-amino-4-(4-((4-ethylpyridin-2-yl)carbamoyl)phenyl)-1H-imidazole-5-carboxamide 2-(2-acryloyl-2-azaspiro [3.3]heptan-6-yl)-1-amino-4-(4-((4-ethylpyridin-2-yl)carbamoyl)phenyl)-1H-imidazole-5-carboxamide (S)-1-amino-4-(4-((4-methylpyridin-2-yl)carbamoyl)phenyl)-2-(1-propioloylpiperidin-2-yl)-1H-imidazole-5-carboxamide (S)-1-amino-4-(4-((4-methoxypyridin-2-yl)carbamoyl) phenyl)-2-(1-propioloylpiperidin-2-yl)-1H-imidazole-5-carboxamide (S)-1-amino-2-(1-(but-2-ynoyl) piperidin-2-yl)-4-(4-((4-chloropyridin-2-yl)carbamoyl)phenyl)-1H-imidazole-5-carboxamide (S)-1-amino-4-(4-((4-chloropyridin-2-yl)carbamoyl)phenyl)-2-(1-propioloylpiperidin-2-yl)-1H-imidazole-5-carboxamide (S)-1-amino-4-(4-((4-ethylpyridin-2-yl)carbamoyl)phenyl)-2-(1-propioloylpiperidin-2-yl)-1H-imidazole-5-carboxamide (S)-2-(1-acryloylpiperidin-2-yl)-1-amino-4-(4-(pyridazin-3-ylcarbamoyl)phenyl)-1H-imidazole-5-carboxamide (S)-1-amino-2-(1-(but-2-ynoyl) piperidin-2-yl)-4-(4-(pyridazin-3-ylcarbamoyl)phenyl)-1H-imidazole-5-carboxamide 2-((1-acryloylpiperidin-4-yl)methyl)-1-amino-4-(4-(pyridin-2-ylcarbamoyl)phenyl)-1H-imidazole-5-carboxamide 1-amino-2-((1-(but-2-ynoyl) piperidin-4-yl)methyl)-4-(4-(pyridin-2-ylcarbamoyl)phenyl)-1H-imidazole-5-carboxamide (S)-2-(1-acryloylpiperidin-2-yl)-1-amino-4-(4-(thiazol-2-ylcarbamoyl)phenyl)-1H-imidazole-5-carboxamide (S)-2-(1-acryloylpiperidin-2-yl)-1-amino-4-(4-((4-fluoropyridin-2-yl)carbamoyl)phenyl)-1H-imidazole-5-carboxamide (S)-2-(1-acryloylpiperidin-2-yl)-1-amino-4-(4-((5-fluoro-4-methylpyridin-2-yl)carbamoyl)phenyl)-1H-imidazole-5-carboxamide (S)-1-amino-2-(1-(but-2-ynoyl) piperidin-2-yl)-4-(4-((5-fluoro-4-methylpyridin-2-yl)carbamoyl)phenyl)-1H-imidazole-5-carboxamide (S)-2-(1-acryloylpiperidin-2-yl)-1-amino-4-(4-((4-(4-chlorophenyl)pyridin-2-yl)carbamoyl)phenyl)-1H-imidazole-5-carboxamide (S)-1-amino-2-(1-(but-2-ynoyl) piperidin-2-yl)-4-(4-((4-(4-chlorophenyl)pyridin-2-yl)carbamoyl)phenyl)-1H-imidazole-5-carboxamide (S)-2-(1-acryloylpiperidin-2-yl)-1-amino-4-(4-((4-(4-cyanophenyl)pyridin-2-yl)carbamoyl)phenyl)-1H-imidazole-5-carboxamide (S)-1-amino-2-(1-(but-2-ynoyl) piperidin-2-yl)-4-(4-((4-(4-cyanophenyl)pyridin-2-yl)carbamoyl)phenyl)-1H-imidazole-5-carboxamide.

\* \* \* \* \*